United States Patent
Buysse et al.

(10) Patent No.: US 9,708,288 B2
(45) Date of Patent: *Jul. 18, 2017

(54) PESTICIDAL COMPOSITIONS AND PROCESSES RELATED THERETO

(71) Applicant: Dow AgroSciences LLC, Indianapolis, IN (US)

(72) Inventors: Ann M. Buysse, Carmel, IN (US); Noormohamed M. Niyaz, Indianapolis, IN (US); David A. Demeter, Fishers, IN (US); Yu Zhang, Carmel, IN (US); Martin J. Walsh, Carmel, IN (US); Asako Kubota, Indianapolis, IN (US); Ricky Hunter, Westfield, IN (US); Tony K. Trullinger, Westfield, IN (US); Christian T. Lowe, Westfield, IN (US); Daniel I. Knueppel, Zionsville, IN (US); Akshay Patny, Waltham, MA (US); Negar Garizi, Westfield, IN (US); Paul Renee LePlae, Jr., Brownsburg, IN (US); Frank J. Wessels, Indianapolis, IN (US); Ronald Ross, Jr., Zionsville, IN (US); Carl DeAmicis, Indianapolis, IN (US); Peter Borromeo, Fishers, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 89 days.

This patent is subject to a terminal disclaimer.

(21) Appl. No.: 14/474,362

(22) Filed: Sep. 2, 2014

(65) Prior Publication Data
US 2016/0060245 A1 Mar. 3, 2016
US 2016/0159766 A9 Jun. 9, 2016

Related U.S. Application Data

(63) Continuation of application No. 13/788,850, filed on Mar. 7, 2013, now Pat. No. 8,901,153.

(60) Provisional application No. 61/639,274, filed on Apr. 27, 2012.

(51) Int. Cl.
| | | |
|---|---|---|
| *A61K 9/48* | (2006.01) |
| *A61K 9/50* | (2006.01) |
| *A01N 25/00* | (2006.01) |
| *A01N 43/40* | (2006.01) |
| *A01N 43/56* | (2006.01) |
| *A61K 31/44* | (2006.01) |
| *A61K 31/4406* | (2006.01) |
| *A61K 31/4427* | (2006.01) |
| *C07D 401/04* | (2006.01) |
| *A01N 47/36* | (2006.01) |
| *A01N 47/18* | (2006.01) |
| *C07D 405/14* | (2006.01) |
| *C07D 401/14* | (2006.01) |
| *A01N 43/653* | (2006.01) |
| *C07D 417/14* | (2006.01) |
| *A01N 43/78* | (2006.01) |
| *C07D 413/14* | (2006.01) |
| *A01N 43/76* | (2006.01) |
| *A01N 43/80* | (2006.01) |
| *C07D 409/14* | (2006.01) |
| *C07D 403/04* | (2006.01) |
| *A01N 43/84* | (2006.01) |

(52) U.S. Cl.
CPC .......... *C07D 401/04* (2013.01); *A01N 43/56* (2013.01); *A01N 43/653* (2013.01); *A01N 43/76* (2013.01); *A01N 43/78* (2013.01); *A01N 43/80* (2013.01); *A01N 43/84* (2013.01); *A01N 47/18* (2013.01); *A01N 47/36* (2013.01); *C07D 401/14* (2013.01); *C07D 403/04* (2013.01); *C07D 405/14* (2013.01); *C07D 409/14* (2013.01); *C07D 413/14* (2013.01); *C07D 417/14* (2013.01)

(58) Field of Classification Search
CPC ..... C07D 401/04; C07D 403/04; A01N 43/56
See application file for complete search history.

(56) References Cited

U.S. PATENT DOCUMENTS

| | | |
|---|---|---|
| 4,080,457 A | 3/1978 | Harrison et al. |
| 4,260,765 A | 4/1981 | Harrison et al. |
| 4,536,506 A | 8/1985 | Marcoux et al. |

(Continued)

FOREIGN PATENT DOCUMENTS

| | | |
|---|---|---|
| EP | 0097323 A2 | 1/1984 |
| EP | 0205024 A2 | 12/1986 |

(Continued)

OTHER PUBLICATIONS

Friedman, Michael et al. "Structure activity optimization of 6H-pyrollo[2,3-e][1,2,4]triazolo[4,3-a]pyrazines as Jak1 kinase inhibitors" Bioorganic & Medicinal Chemistry Letters 25, 4399-4404 (2015).

(Continued)

*Primary Examiner* — Alton Pryor
(74) *Attorney, Agent, or Firm* — Carl D. Corvin

(57) ABSTRACT

This document discloses molecules having the following formula ("Formula One"):

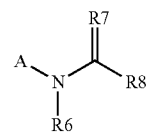

and processes related thereto.

32 Claims, No Drawings

(56) References Cited

U.S. PATENT DOCUMENTS

| | | |
|---|---|---|
| 5,556,873 A | 9/1996 | Huang et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony |
| 5,869,681 A | 2/1999 | Muller et al. |
| 6,218,418 B1 | 4/2001 | Pevarello et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 7,192,906 B2 | 3/2007 | Hirohara et al. |
| 7,196,104 B2 | 3/2007 | Askew, Jr. et al. |
| 7,319,108 B2 | 1/2008 | Schwink et al. |
| 7,774,978 B2 | 8/2010 | Ding et al. |
| 7,803,832 B2 | 9/2010 | Critcher et al. |
| 7,910,606 B2 | 3/2011 | Nazare et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2* | 12/2014 | Buysse et al. .......... A01N 43/78 514/341 |
| 9,144,241 B2* | 9/2015 | Gomez et al. .......... A01N 25/26 |
| 9,155,304 B2* | 10/2015 | Gomez et al. .......... A01N 43/56 |
| 9,282,739 B2* | 3/2016 | Buysse et al. .......... A01N 43/56 |
| 9,282,740 B2* | 3/2016 | Gomez et al. .......... A01N 43/56 |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0160857 A1 | 7/2006 | Buettelmann et al. |
| 2006/0160875 A1 | 7/2006 | Gaines et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0075956 A1 | 3/2010 | Critcher et al. |
| 2010/0130474 A1 | 5/2010 | Bothmann et al. |
| 2010/0204164 A1 | 8/2010 | Crouse et al. |
| 2010/0292253 A1 | 11/2010 | Trullinger et al. |
| 2010/0305200 A1 | 12/2010 | Veliclebi et al. |
| 2011/0021771 A1 | 1/2011 | Mallais et al. |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0220453 A1 | 8/2012 | Lowe et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324735 A1 | 12/2013 | Ross, Jr. et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0057785 A1 | 2/2014 | Parker et al. |
| 2014/0213448 A1 | 7/2014 | Buysse et al. |
| 2015/0072859 A1* | 3/2015 | Niyaz et al. .......... A01N 43/78 504/100 |
| 2015/0111737 A1* | 4/2015 | Gomez et al. .......... A01N 43/56 |
| 2015/0111738 A1* | 4/2015 | Gomez et al. .......... A01N 57/16 |
| 2015/0111739 A1* | 4/2015 | Gomez .......... A01N 43/56 504/103 |
| 2015/0111740 A1* | 4/2015 | Gomez et al. .......... A01N 43/56 |
| 2015/0111741 A1* | 4/2015 | Gomez et al. .......... A01N 43/88 |
| 2015/0111742 A1* | 4/2015 | Gomez et al. .......... A01N 53/00 |
| 2015/0111743 A1* | 4/2015 | Gomez et al. .......... A01N 43/56 |
| 2015/0111744 A1* | 4/2015 | Gomez .......... A01N 43/40 504/103 |
| 2015/0111745 A1* | 4/2015 | Gomez .......... A01N 43/90 504/103 |
| 2015/0264929 A1* | 9/2015 | Gomez .......... A01N 43/90 504/103 |
| 2015/0335022 A1* | 11/2015 | Buysse et al. .......... A01N 47/36 |

FOREIGN PATENT DOCUMENTS

| | | |
|---|---|---|
| EP | 0248315 A2 | 12/1987 |
| EP | 0425948 A2 | 5/1991 |
| EP | 1273582 A1 | 1/2003 |
| EP | 1321463 A1 | 6/2003 |
| EP | 1329160 A2 | 7/2003 |
| JP | 1987-153273 A | 7/1987 |
| JP | 1988-174905 A | 7/1988 |
| JP | 1989-226815 A | 9/1989 |
| JP | 2003-212864 A | 7/2003 |
| JP | 2003-313103 A | 11/2003 |
| JP | 2004-051628 A | 2/2004 |
| JP | 2004-292703 A | 10/2004 |
| JP | 2012-188418 A | 10/2012 |
| JP | 2013-075871 A | 4/2013 |
| JP | 2013-082699 A | 5/2013 |
| JP | 2013-082704 A | 5/2013 |
| JP | 2013-107867 A | 6/2013 |
| JP | 2013-129651 A | 7/2013 |
| JP | 2013-129653 A | 7/2013 |
| WO | WO 2006/033005 A1 | 0/0000 |
| WO | WO 94/13644 A1 | 6/1994 |
| WO | WO 97/36897 A1 | 10/1997 |
| WO | WO 98/49166 A1 | 11/1998 |
| WO | WO 00/35919 A2 | 6/2000 |
| WO | WO 01/34127 A1 | 5/2001 |
| WO | WO 01/90078 A1 | 11/2001 |
| WO | WO 02/083111 A2 | 10/2002 |
| WO | WO 03/008405 A1 | 1/2003 |
| WO | WO 03/072102 A1 | 9/2003 |
| WO | WO 2004/041813 A1 | 5/2004 |
| WO | WO 2005/070925 A1 | 8/2005 |
| WO | WO 2005/074875 A2 | 8/2005 |
| WO | WO 2006/023462 A1 | 3/2006 |
| WO | WO 2006/046593 A1 | 5/2006 |
| WO | WO 2006/103045 A1 | 10/2006 |
| WO | WO 2007/005838 A2 | 1/2007 |
| WO | WO 2007/087427 A2 | 8/2007 |
| WO | WO 2007/098826 A2 | 9/2007 |
| WO | WO 2008/005457 A2 | 1/2008 |
| WO | WO 2008/079277 A1 | 7/2008 |
| WO | WO 2008/090382 A1 | 7/2008 |
| WO | WO 2011/045224 A1 | 10/2009 |
| WO | WO 2009/149858 A1 | 12/2009 |
| WO | WO 2010/006713 A2 | 1/2010 |
| WO | WO 2010/009290 A1 | 1/2010 |
| WO | WO 2010/012442 A2 | 2/2010 |
| WO | WO 2010/048207 | 4/2010 |
| WO | WO 2010/060379 | 6/2010 |
| WO | WO 2010/075376 | 7/2010 |
| WO | WO 2010/129497 A1 | 11/2010 |
| WO | WO 2010/133336 A1 | 11/2010 |
| WO | WO 2010/146236 A1 | 12/2010 |
| WO | WO 2011/003065 A2 | 1/2011 |
| WO | WO 2011/043371 A1 | 4/2011 |

(56) References Cited

FOREIGN PATENT DOCUMENTS

| | | |
|---|---|---|
| WO | WO 2011/045240 A1 | 4/2011 |
| WO | WO 2011/091153 A1 | 7/2011 |
| WO | WO 2011/101229 A1 | 8/2011 |
| WO | WO 2011/126903 A2 | 10/2011 |
| WO | WO 2011/128304 A1 | 10/2011 |
| WO | WO 2011/134964 | 11/2011 |
| WO | WO 2011/138285 | 11/2011 |
| WO | WO 2011/163518 | 12/2011 |
| WO | WO 2012/000896 | 1/2012 |
| WO | WO 2012/004217 | 1/2012 |
| WO | WO 2012/007500 | 1/2012 |
| WO | WO 2010/033360 A1 | 3/2012 |
| WO | WO 2012/035011 | 3/2012 |
| WO | PCT-US2011-058578 | 4/2012 |
| WO | WO 2012/052412 | 4/2012 |
| WO | WO 2012/061290 | 5/2012 |
| WO | WO 2012/070114 | 5/2012 |
| WO | WO 2012/102387 | 8/2012 |
| WO | WO 2012/108511 A1 | 8/2012 |
| WO | PCT-US2011-058578 | 12/2012 |
| WO | WO 2012/168361 A1 | 12/2012 |
| WO | WO 2013/000931 A1 | 1/2013 |
| WO | WO 2013/010946 A2 | 1/2013 |
| WO | WO 2013/010947 A2 | 1/2013 |
| WO | PCT-US2013-029615 | 5/2013 |
| WO | WO 2013/062980 A1 | 5/2013 |
| WO | WO 2013/156431 A1 | 10/2013 |
| WO | WO 2013/156433 A1 | 10/2013 |

OTHER PUBLICATIONS

Stellwegen, J.C. and Uehling, D.E. et al. "Development of potent B-RafV600E inhibitors containing an arylsulfonamide headgroup" Bioorganic & Medicinal Chemistry Letters 21, 4436-4440 (2011).

Nordhoff, S. et al. "Discovery of β-homophenylalanine based pyrrolidin-2-ylmethyl amides and sulfonamides as highly potent and selective inhibitors of dipeptidyl peptidase IV" Bioorganic & Medicinal Chemistry Letters 19, 4201-4203 (2009).

* cited by examiner

PESTICIDAL COMPOSITIONS AND PROCESSES RELATED THERETO

CROSS REFERENCES TO RELATED APPLICATIONS

This application is a continuation of U.S. non-provisional application Ser. No. 13/788,850, which was filed on Mar. 7, 2013, which claims priority from, and benefit of, U.S. provisional application Ser. No. 61/639,274, which was filed on Apr. 27, 2012. The entire contents of these applications is hereby incorporated by reference into this application.

FIELD OF THE DISCLOSURE

This disclosure is related to the field of processes to produce molecules that are useful as pesticides (e.g., acaricides, insecticides, molluscicides, and nematicides), such molecules, and processes of using such molecules to control pests.

BACKGROUND

Pests cause millions of human deaths around the world each year. Furthermore, there are more than ten thousand species of pests that cause losses in agriculture. The worldwide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, $(C_3)$alkyl which represents n-propyl and isopropyl), $(C_4)$alkyl which represents n-butyl, sec-butyl, isobutyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"$(C_x-C_y)$" where the subscripts "x" and "y" are integers such as 1, 2, or 3, means the range of carbon atoms for a substituent—for example, $(C_1-C_4)$alkyl means methyl, ethyl, n-propyl, isopropyl, n-butyl, sec-butyl, isobutyl, and tert-butyl, each individually.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following

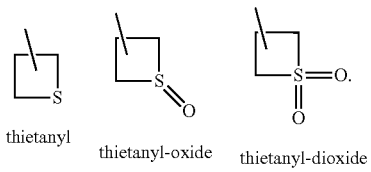

thietanyl  thietanyl-oxide  thietanyl-dioxide

DETAILED DESCRIPTION

This document discloses molecules having the following formula ("Formula One"):

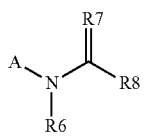

wherein
(a) A is either

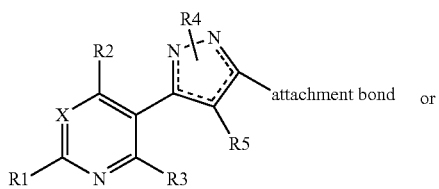

A1

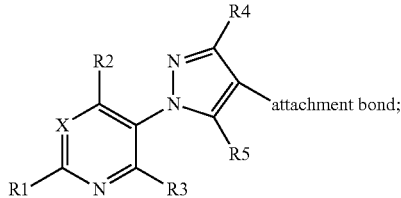

A2

(b) R1 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, S(O)$_n$R9, S(O)$_n$OR9, S(O)$_n$N(R9)$_2$, or R9S(O)$_n$R9,
wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(c) R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(d) R3 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(e) when A is
(1) A1 then A1 is either
(a) A11

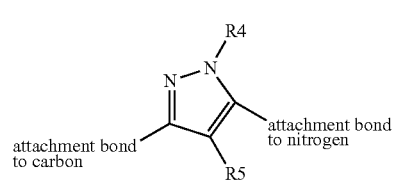

A11 where R4 is H, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, C(=X1)R9, C(=X1)OR9, C(=X1)N(R9)$_2$, N(R9)$_2$, N(R9)C(=X1)R9, S(O)$_n$OR9, or R9S(O)$_n$R9,
wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9), or (b) A12

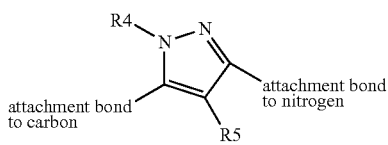

A12 where R4 is a $C_1$-$C_6$ alkyl, (2) A2 then R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(f) R5 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(g)

(1) when A is A1 then R6 is R11, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl) S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9, wherein each said R6 (except R11), which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9aryl, (each of which that can be substituted, may optionally be substituted with R9), optionally R6 (except R11) and R8 can be connected in a cyclic arrangement, where optionally such arrangement can have one or more heteroatoms selected from O, S, or, N, in the cyclic structure connecting R6 and R8, and (2) when A is A2 then R6 is R11, H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl) S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9, wherein each said R6 (except R11), which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9aryl, (each of which that can be substituted, may optionally be substituted with R9), optionally R6 (except R11) and R8 can be connected in a cyclic arrangement, where optionally such arrangement can have one or more heteroatoms selected from O, S, or N, in the cyclic structure connecting R6 and R8;

(h) R7 is O, S, NR9, or NOR9;

(i) R8 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, or R9S(O)$_n$(NZ)R9, wherein each said R8, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, N(R9)S(O)$_n$R9, oxo, OR9, S(O)$_n$OR9, R9S(O)$_n$R9, S(O)$_n$R9, $C_6$-$C_{20}$ aryl, or $C_1$-$C_{20}$ heterocyclyl, (each of which that can be substituted, may optionally be substituted with R9)

alternatively R8 is R13-S(O)$_n$—R13 wherein each R13 is independently selected from substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted S(O)$_n$$C_1$-$C_6$ alkyl, substituted or unsubstituted N($C_1$-$C_6$alkyl)$_2$, wherein each said substituted alkyl, substituted alkenyl, substituted alkoxy, substituted alkenyloxy, substituted cycloalkyl, substituted cycloalkenyl, substituted aryl, substituted heterocyclyl, has one or more substituents independently selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, O$C_1$-$C_6$ alkyl, O$C_1$-$C_6$ haloalkyl, S(O)$_n$$C_1$-$C_6$alkyl, S(O)$_n$O$C_1$-$C_6$ alkyl, $C_6$-$C_{20}$ aryl, or $C_1$-$C_{20}$ heterocyclyl, $C_2$-$C_6$ alkynyl, $C_1$-$C_6$ alkoxy, N(R9)S(O)$_n$R9, OR9, N(R9)$_2$, R9OR9, R9N(R9)$_2$, R9C(=X1)R9, R9C(=X1)N(R9)$_2$, N(R9)C(=X1)R9, R9N(R9)C(=X1)R9, S(O)$_n$OR9, R9C(=X1)OR9, R9OC(=X1)R9, R9S(O)$_n$R9, S(O)$_n$R9, oxo, (each of which that can be substituted, may optionally be substituted with R9);

(j) R9 is (each independently) H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted S(O)$_n$$C_1$-$C_6$ alkyl, substituted or unsubstituted N($C_1$-$C_6$alkyl)$_2$, wherein each said R9, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, O$C_1$-$C_6$ alkyl, O$C_1$-$C_6$ haloalkyl, S(O)$_n$$C_1$-$C_6$alkyl, S(O)$_n$O$C_1$-$C_6$ alkyl, $C_6$-$C_{20}$ aryl, or $C_1$-$C_{20}$ heterocyclyl;

(k) n is 0, 1, or 2;

(l) X is N or CR$_{n1}$ where R$_{n1}$ is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$R9, S(O)$_n$OR9, or R9S(O)$_n$R9, wherein each said R$_{n1}$ which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(m) X1 is (each independently) O or S;

(n) X2 is (each independently) O, S, =NR9, or =NOR9;

(o) Z is CN, NO$_2$, $C_1$-$C_6$ alkyl(R9), C(=X1)N(R9)$_2$;

(p) R11 is Q$_1$(C≡C)R12, wherein Q$_1$ is a bond, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ cycloalkyl, substituted or unsubstituted $C_2$-$C_{10}$ cycloalkoxy, substituted or unsubstituted $C_1$-$C_6$ alkylOR9, substituted or unsubstituted $C_1$-$C_6$ alkylS(O)$_n$R9, substituted or unsubstituted $C_1$-$C_6$ alkylS(O)$_n$(=NR9), substituted or unsubstituted $C_1$-$C_6$ alkylN(R9) (where (C≡C) is attached directly to the N by a bond), substituted or unsubstituted $C_1$-$C_6$ alkylN(R9)$_2$, substituted or unsubstituted $C_2$-$C_6$ alkenyloxy, substituted or unsubstituted $C_3$-$C_{10}$ cycloalkenyl, substituted or unsubstituted $C_0$-$C_6$ alkylC(=R7)$C_0$-$C_6$ alkylR9, substituted or unsubstituted $C_0$-$C_6$ alkylC(=R7)OR9, substituted or unsubstituted $C_1$-$C_6$ alkylO$C_0$-$C_6$ alkylC(=R7)R9, substituted or unsubstituted $C_1$-$C_6$ alkylN(R9)(C(=R7)R9), substituted or unsubstituted $C_1$-$C_6$ alkylN(R9)(C(=R7)OR9), substituted or unsubstituted $C_0$-$C_6$ alkyl C(=R7)$C_0$-$C_6$ alkylN(R9) (where (C≡C) is attached directly to the N by a bond), substituted or unsubstituted $C_0$-$C_6$alkylC(=R7)$C_0$-$C_6$ alkylN(R9)$_2$, OR9, S(O)$_n$R9, N(R9)R9, substituted or unsubstituted $C_6$-$C_{20}$ aryl, substituted or unsubstituted $C_1$-$C_{20}$ heterocyclyl, wherein each said Q$_1$, which is substituted, has one or more substituents selected from F, Cl, Br, I, CN, NO$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, SR9, S(O)$_n$R9, S(O)$_n$OR9, $C_6$-$C_{20}$ aryl, or $C_1$-$C_{20}$ heterocyclyl, R9aryl, $C_1$-$C_6$alkylOR9, $C_1$-$C_6$alkylS(O)$_n$R9, (each of which that can be substituted, may optionally be substituted with R9)

optionally Q$_1$ and R8 can be connected in a cyclic arrangement, where optionally such arrangement can have one or more heteroatoms selected from O, S, or N, in the cyclic structure connecting Q$_1$ and R8;

(q) R12 is Q$_1$ (except where Q$_1$ is a bond), F, Cl, Br, I, Si(R9)$_3$ (where each R9 is independently selected), or R9; and (r) with the following provisos (1) that R6 and R8 cannot both be C(=O)CH$_3$, (2) that when A1 is A11 then R6 and R8 together do not form fused ring systems, (3) that R6 and R8 are not linked in a cyclic arrangement with only —CH$_2$—, (4) that when A is A2 then R5 is not C(=O)OH, (5) that when A is A2 and R6 is H then R8 is not a —($C_1$-$C_6$ alkyl)-O-(substituted aryl), and (6) that when A is A2 then R6 is not —($C_1$alkyl)(substituted aryl).

In another embodiment of this invention A is A1.

In another embodiment of this invention A is A2.

In another embodiment of this invention R1 is H.

In another embodiment of this invention R2 is H.

In another embodiment of this invention R3 is selected from H, or substituted or unsubstituted $C_1$-$C_6$ alkyl.

In another embodiment of this invention R3 is selected from H or CH$_3$.

In another embodiment of the invention when A is A1 then A1 is A11.

In another embodiment of the invention when A is A1, and A1 is A11, then R4 is selected from H, or substituted or unsubstituted $C_1$-$C_6$ alkyl, or substituted or unsubstituted $C_6$-$C_{20}$ aryl.

In another embodiment of the invention when A is A1, and A1 is A11 then R4 is selected from $CH_3$, $CH(CH_3)_2$, or phenyl.

In another embodiment of the invention when A is A1, and A1 is A12, then R4 is $CH_3$.

In another embodiment of this invention when A is A2 then R4 is selected from H, or substituted or unsubstituted $C_1$-$C_6$ alkyl, substituted or unsubstituted $C_2$-$C_6$ alkenyl, substituted or unsubstituted $C_3$-$C_{10}$ cycloalkyl, substituted or unsubstituted $C_6$-$C_{20}$ aryl, wherein each said R4, which is substituted, has one or more substituents selected from F, Cl, Br, or I.

In another embodiment of this invention when A is A2 then R4 is H or $C_1$-$C_6$ alkyl.

In another embodiment of this invention when A is A2 then R4 is H, $CH_3$, $CH_2CH_3$, $CH=CH_2$, cyclopropyl, $CH_2Cl$, $CF_3$, or phenyl.

In another embodiment of this invention when A is A2 then R4 is Br or Cl.

In another embodiment of this invention R5 is H, F, Cl, Br, I, or substituted or unsubstituted $C_1$-$C_6$ alkyl, substituted or unsubstituted $C_1$-$C_6$ alkoxy.

In another embodiment of this invention R5 is H, $OCH_2CH_3$, F, Cl, Br, or $CH_3$.

In another embodiment of this invention, when A is A1 then R6 is substituted or unsubstituted $C_1$-$C_6$ alkyl.

In another embodiment of this invention when A is A2 then R6 is selected from is substituted or unsubstituted $C_1$-$C_6$ alkyl, substituted or unsubstituted $C_2$-$C_6$ alkenyl, substituted or unsubstituted $C_3$-$C_{10}$ cycloalkyl, C(=X1)R9, C(=X1)X2R9, R9X2R9, C(=O)($C_1$-$C_6$ alkyl)S(O)$_n$($C_1$-$C_6$ alkyl), ($C_1$-$C_6$ alkyl)OC(=O)($C_6$-$C_{20}$ aryl), ($C_1$-$C_6$ alkyl) OC(=O)($C_1$-$C_6$ alkyl), or R9X2C(=X1)X2R9.

In another embodiment of this invention when A is A2 then R6 and R8 are connected in a cyclic arrangement, where optionally such arrangement can have one or more heteroatoms selected from O, S, or, N, in the cyclic structure connecting R6 and R8.

In another embodiment of this invention R6 is $C_1$-$C_6$ alkyl, or $C_1$-$C_6$ alkyl-phenyl.

In another embodiment of this invention R6 is H, $CH_3$, $CH_2CH_3$, $CH_2CH_2CH_3$, $CH(CH_3)_2$, $CH_2$phenyl, $CH_2CH(CH_3)_2$, $CH_2$cyclopropyl, C(=O)$CH_2CH_2SCH_3$, C(=O) OC($CH_3$)$_3$, $CH_2CH=CH_2$, C(=O)O$CH_2CH_3$, C(=O)CH($CH_3$)$CH_2SCH_3$, cyclopropyl, $CD_3$, $CH_2$OC(=O)phenyl, C(=O)$CH_3$, C(=O)CH($CH_3$)$_2$, $CH_2$OC(=O)CH($CH_3$)$_2$, $CH_2$OC(=O)$CH_3$, C(=O)phenyl, $CH_2OCH_3$, $CH_2$OC (=O)$CH_2OCH_2CH_3$, $CH_2CH_2OCH_3$, $CH_2$OC(=O)OCH ($CH_3$)$_2$, $CH_2CH_2OCH_2OCH_3$, $CH_2CH_2OCH_3$, $CH_2CH_2$OC (=O)$CH_3$, $CH_2CN$.

In another embodiment of this invention R6 is methyl or ethyl.

In another embodiment of this invention R7 is O or S.

In another embodiment of this invention R8 is selected from substituted or unsubstituted $C_1$-$C_6$ alkyl, substituted or unsubstituted $C_2$-$C_6$ alkenyl, substituted or unsubstituted $C_3$-$C_{10}$ cycloalkyl, substituted or unsubstituted $C_6$-$C_{20}$ aryl, substituted or unsubstituted $C_1$-$C_{20}$ heterocyclyl, R9C (=X1)OR9, SR9, S(O)$_n$OR9, R9S(O)$_n$R9, or R9S(O)$_n$(NZ) R9.

In another embodiment of this invention R8 is CH($CH_3$) $CH_2SCH_3$, CH($CH_3$)$_2$, C($CH_3$)$_2CH_2SCH_3$, $CH_2CH_2SCH_3$, $CH_2CF_3$, $CH_2CH_2$C(=O)O$CH_3$, N(H)(CH$_2$CH$_2$SCH$_3$), $OCH_2CH_2SCH_3$, CH($CH_2SCH_3$)($CH_2$phenyl), thiazolyl, oxazolyl, isothiazolyl, substituted-furanyl, $CH_3$, C($CH_3$)$_3$, phenyl, $CH_2CH_2OCH_3$, pyridyl, $CH_2$CH(CH$_3$)SCH$_3$, OC($CH_3$)$_3$, C($CH_3$)$_2CH_2SCH_3$, CH($CH_3$)CH($CH_3$)SCH$_3$, CH($CH_3$)$CF_3$, $CH_2CH_2$-thienyl, CH($CH_3$)$SCF_3$, $CH_2CH_2Cl$, $CH_2CH_2CH_2CF_3$, $CH_2CH_2$S(=O)CH$_3$, CH($CH_3$)CH$_2$S(=O)CH$_3$, $CH_2CH_2$S(=O)$_2CH_3$, CH($CH_3$) CH$_2$S(=O)$_2CH_3$, NCH$_2$CH$_3$, N(H)(CH$_2$CH$_2$CH$_3$), C(CH$_3$) =C(H)(CH$_3$), N(H)(CH$_2$CH=CH$_2$), $CH_2CH(CF_3)SCH_3$, CH(CF$_3$)CH$_2SCH_3$, thietanyl, $CH_2CH(CF_3)_2$, $CH_2CH_2$CF (OCF$_3$)CF$_3$, $CH_2CH_2$CF(CF$_3$)CF$_3$, CF(CH$_3$)$_2$, CH(CH$_3$) phenyl-Cl, CH(CH$_3$)phenyl-F, CH(CH$_3$)phenyl-OCF$_3$, $CH_2$N(CH$_3$)(S(=O)$_2$N(CH$_3$)$_2$), CH(CH$_3$)OCH$_2$CH$_2$SCH$_3$, CH(CH$_3$)OCH$_2$CH$_2$OCH$_3$, $OCH_3$, CH(CH$_3$)SCH$_3$, $CH_2SCH_3$, N(H)CH$_3$, CH(Br)CH$_2$Br, or CH(CH$_3$) $CH_2SCD_3$.

In another more preferred embodiment of this invention R8 is preferably R13-S(O)$_n$—R13 wherein each R13 is independently selected from substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted S(O)$_n$$C_1$-$C_6$ alkyl, substituted or unsubstituted N($C_1$-$C_6$alkyl)$_2$, wherein each said substituted alkyl, substituted alkenyl, substituted alkoxy, substituted alkenyloxy, substituted cycloalkyl, substituted cycloalkenyl, substituted aryl, substituted heterocyclyl, has one or more substituents independently selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, O$C_1$-$C_6$ alkyl, O$C_1$-$C_6$ haloalkyl, S(O)$_n$$C_1$-$C_6$alkyl, S(O)$_n$O$C_1$-$C_6$ alkyl, $C_6$-$C_{20}$ aryl, or $C_1$-$C_{20}$ heterocyclyl, $C_2$-$C_6$ alkynyl, $C_1$-$C_6$ alkoxy, N(R9)S (O)$_n$R9, OR9, N(R9)$_2$, R9OR9, R9N(R9)$_2$, R9C(=X1)R9, R9C(=X1)N(R9)$_2$, N(R9)C(=X1)R9, R9N(R9)C(=X1) R9, S(O)$_n$OR9, R9C(=X1)OR9, R9OC(=X1)R9, R9S(O)$_n$R9, S(O)$_n$R9, oxo, (each of which that can be substituted, may optionally be substituted with R9).

In another embodiment of this invention R8 is (substituted or unsubstituted $C_1$-$C_6$ alkyl)-S(O)$_n$-(substituted or unsubstituted $C_1$-$C_6$ alkyl) wherein said substituents on said substituted alkyls are independently selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$cycloalkyl, $C_3$-$C_{10}$ cycloalkenyl, $C_3$-$C_{10}$ halocycloalkyl, $C_3$-$C_{10}$ halocycloalkenyl, O$C_1$-$C_6$ alkyl, O$C_1$-$C_6$ haloalkyl, S(O)$_n$$C_1$-$C_6$alkyl, S(O)$_n$O$C_1$-$C_6$ alkyl, $C_6$-$C_{20}$ aryl, or $C_1$-$C_{20}$ heterocyclyl, $C_2$-$C_6$ alkynyl, $C_1$-$C_6$ alkoxy, N(R9)S(O)$_n$R9, OR9, N(R9)$_2$, R9OR9, R9N(R9)$_2$, R9C (=X1)R9, R9C(=X1)N(R9)$_2$, N(R9)C(=X1)R9, R9N (R9)C(=X1)R9, S(O)$_n$OR9, R9C(=X1)OR9, R9OC (=X1)R9, R9S(O)$_n$R9, S(O)$_n$R9, oxo, (each of which that can be substituted, may optionally be substituted with R9).

In another embodiment of this invention R8 is selected from CH(CH$_3$)SCH$_2$CF$_3$, CH$_2$CH$_2$SCH$_2$CF$_3$, CH$_2$SCH$_2$CF$_3$, CH$_2$SCHClCF$_3$, CH(CH$_2$CH$_3$)SCH$_2$CF$_3$, CH(CH$_3$)SCH$_2$CHF$_2$, CH(CH$_3$)SCH$_2$CH$_2$F, CH$_2$CH$_2$SCH$_2$CH$_2$F, CH(CH$_3$)S(=O)$_2$CH$_2$CF$_3$, CH(CH$_3$)S (=O)CH$_2$CF$_3$, CH(CH$_3$)CH$_2$SCF$_3$, CH(CH$_3$)CH$_2$SCF$_3$, CH(CH$_3$)SCH$_2$CH$_2$CF$_3$, and CH$_2$CH$_2$SCH$_2$CH$_2$CF$_3$.

In another embodiment of this invention R8 is (substituted or unsubstituted $C_1$-$C_6$ alkyl)-S(O)$_n$-(substituted or unsubstituted $C_1$-$C_6$ alkyl)-(substituted or unsubstituted $C_3$-$C_{10}$ cycloalkyl) wherein said substituents on said substituted alkyls and said substituted cycloalkyls are independently selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6$alkyl, $S(O)_nOC_1$-$C_6$ alkyl, $C_6$-$C_{20}$ aryl, or $C_1$-$C_{20}$ heterocyclyl, $C_2$-$C_6$ alkynyl, $C_1$-$C_6$ alkoxy, N(R9)S(O)$_n$R9, OR9, N(R9)$_2$, R9OR9, R9N(R9)$_2$, R9C(=X1)R9, R9C(=X1)N(R9)$_2$, N(R9)C(=X1)R9, R9N(R9)C(=X1)R9, S(O)$_n$OR9, R9C(=X1)OR9, R9OC(=X1)R9, R9S(O)$_n$R9, S(O)$_n$R9, oxo, (each of which that can be substituted, may optionally be substituted with R9).

In another embodiment of this invention R8 is selected from CH(CH$_3$)CH$_2$SCH$_2$(2,2 difluorocyclopropyl), CH$_2$CH$_2$SCH$_2$(2,2 difluorocyclopropyl), CH$_2$CH$_2$S(=O) CH$_2$(2,2 difluorocyclopropyl), CH$_2$CH$_2$S(=O)$_2$ CH$_2$CH$_2$ (2,2 difluorocyclopropyl), and CH$_2$CH(CF$_3$)SCH$_2$(2,2 difluorocyclopropyl).

In another embodiment of this invention R8 is (substituted or unsubstituted $C_1$-$C_6$ alkyl)-S(O)$_n$-(substituted or unsubstituted $C_2$-$C_6$ alkenyl) wherein said substituents on said substituted alkyls and substituted alkenyls are independently selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6$alkyl, $S(O)_nOC_1$-$C_6$ alkyl, $C_6$-$C_{20}$ aryl, or $C_1$-$C_{20}$ heterocyclyl, $C_2$-$C_6$ alkynyl, $C_1$-$C_6$ alkoxy, N(R9)S(O)$_n$R9, OR9, N(R9)$_2$, R9OR9, R9N(R9)$_2$, R9C(=X1)R9, R9C(=X1)N(R9)$_2$, N(R9)C(=X1)R9, R9N(R9)C(=X1)R9, S(O)$_n$OR9, R9C(=X1)OR9, R9OC(=X1)R9, R9S(O)$_n$R9, S(O)$_n$R9, oxo, (each of which that can be substituted, may optionally be substituted with R9).

In another embodiment of this invention R8 is selected from CH$_2$CH$_2$SCH$_2$CH=CCl$_2$, CH2SCH2CH=CCl$_2$, CH(CH3)SCH2CH=CCl$_2$, CH(CH3)SCH=CHF, CH$_2$CH$_2$S(=O)CH$_2$CH$_2$CF$_3$, and CH$_2$CH$_2$S(=O)$_2$ CH$_2$CH$_2$CF$_3$.

In another embodiment of this invention X is CR$_{n1}$ where R$_{n1}$ is H or halo.

In another embodiment of this invention X is CR$_{n1}$ where R$_{n1}$ is H or F.

In another embodiment of this invention X1 is O.

In another embodiment of this invention X2 is O.

In another embodiment of this invention R11 is substituted or unsubstituted $C_1$-$C_6$ alkylC=CR12.

In another embodiment of this invention R11 is CH$_2$C=CH.

The molecules of Formula One will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

The following schemes illustrate approaches to generating aminopyrazoles. In step a of Scheme I, treatment of a 3-acetopyridine or a 5-acetopyrimidine of Formula II, wherein R1, R2, R3 and X are as previously defined, with carbon disulfide and iodomethane in the presence of a base such as sodium hydride and in a solvent such as dimethyl sulfoxide provides the compound of Formula III. In step b of Scheme I, the compound of Formula III can be treated with an amine or amine hydrochloride, in the presence of a base, such as triethylamine, in a solvent such as ethyl alcohol to afford the compound of Formula IV, wherein R1, R2, R3, R6 and X are as previously defined. The compound of Formula IV can be transformed into the aminopyrazole of Formula Va where R5=H as in step c of Scheme I and as in Peruncheralathan, S. et al. *J. Org. Chem.* 2005, 70, 9644-9647, by reaction with a hydrazine, such as methylhydrazine, in a polar protic solvent such as ethyl alcohol.

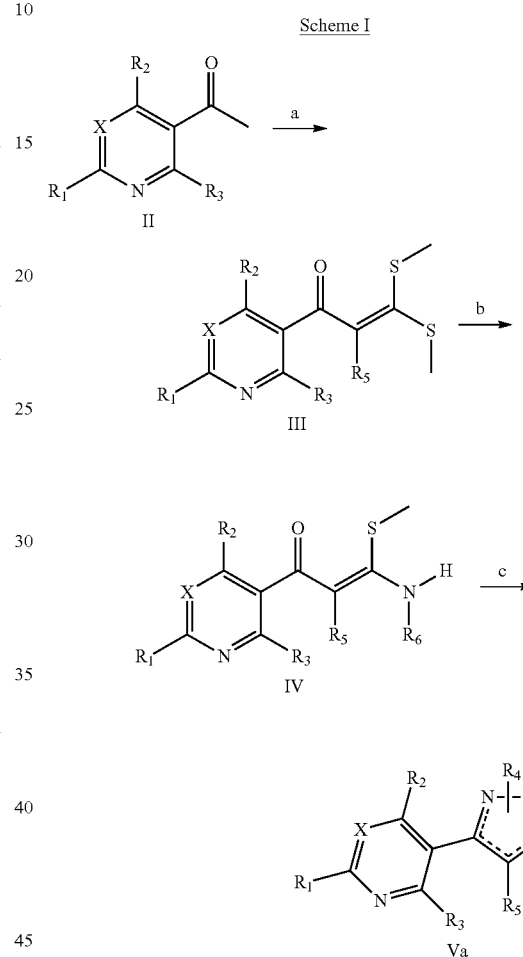

Scheme I

Another approach to aminopyrazoles is illustrated in Scheme II. In step a, the nitrile of Formula VI wherein X, R1, R2 and R3 are as previously defined and R5 is hydrogen, is condensed as in Dhananjay, B. Kendre et al. *J. Het Chem* 2008, 45, (5), 1281-86 with hydrazine of Formula VII, such as methylhydrazine to give a mixture of aminopyrazoles of Formula Vb, wherein R5 and R6=H, both of whose components were isolated.

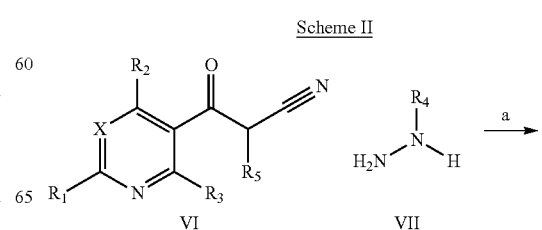

Scheme II

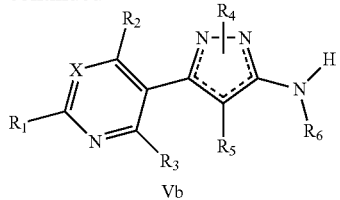

Vb

Preparation of aminopyrazoles such as those of Formula XIIa is demonstrated in Scheme III. The compound of Formula X in step a and as in Cristau, Henri-Jean et al. *Eur. J. Org. Chem.* 2004, 695-709 can be prepared through the N-arylation of a pyrazole of Formula IX with an appropriate aryl halide of Formula VIIIa where Q is bromo in the presence of a base such as cesium carbonate, a copper catalyst such as copper (II) oxide and a ligand such as salicylaldoxime in a polar aprotic solvent such as acetonitrile. Compounds of Formula IX, as shown in Scheme III, wherein R4=Cl and R5=H, can be prepared as in Pelcman, B. et al WO 2007/045868 A1. Nitration of the pyridylpyrazole of Formula X as in step b of Scheme III and as in Khan, Misbanul Ain et al. *J. Heterocyclic Chem.* 1981, 18, 9-14 by reaction with nitric acid and sulfuric acid gave compounds of Formula XIa. Reduction of the nitro functionality of compounds of Formula XIa in the presence of hydrogen with a catalyst such as 5% Pd/C in a polar aprotic solvent such as tetrahydrofuran gave the amine of Formula XIIa, as shown in step c in Scheme III. Reduction of the nitro functionality of compounds of Formula XIa, wherein R1, R2, R3, R4 and X are as previously defined and R5=H, in the presence of hydrogen with a catalyst such as 10% Pd/C in a polar protic solvent such as ethanol gave the amine of Formula XIIa, wherein R5=H, as well as the amine of Formula XIIa, wherein R5=OEt, as shown in step d of Scheme III. Compounds of Formula XIa, wherein R1, R2, R3, R5 and X are as previously defined and R4=Cl, can be reduced in the presence of a reducing agent such as iron in a mixture of polar protic solvents such as acetic acid, water, and ethanol to give amines of Formula XIIa, wherein R1, R2, R3, R5 and X are as previously defined R4=Cl, as shown in step e of Scheme III. Compounds of Formula XIa, wherein R1, R2, R3, R5 and X are as previously defined and R4=Cl, can be allowed to react under Suzuki coupling conditions with a boronic acid such as phenylboronic acid in the presence of a catalyst such as palladium tetrakis, a base such as 2M aqueous potassium carbonate, and in a mixed solvent system such as ethanol and toluene to provide cross-coupled pyrazoles of Formula XIb, as shown in step f of Scheme III.

Scheme III

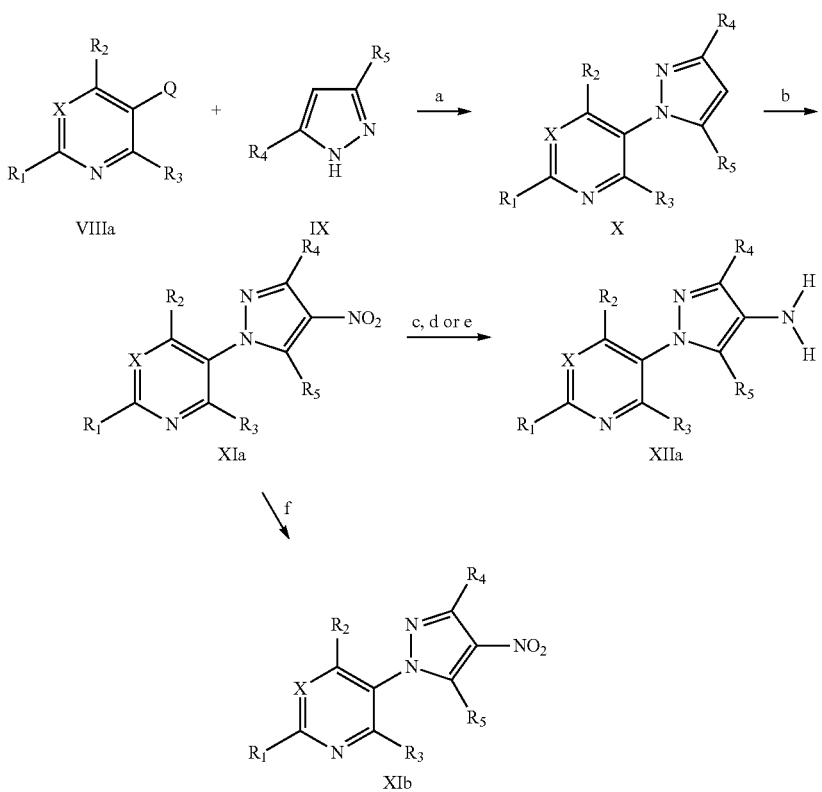

In step a of Scheme IV, the compounds of Formula XIIb can be treated with triethylorthoformate and an acid such as trifluoroacetic acid. Subsequent addition of a reducing agent such as sodium borohydride in a polar protic solvent such as ethanol gave a compound of Formula XIIIa, wherein R6=methyl.

In step b of Scheme IV, the compound of Formula XIIb can be treated with acetone in a solvent such as isopropyl acetate, an acid such as trifluoroacetic acid and sodium triacetoxyborohydride to give compounds of Formula XIIIa, wherein R6=isopropyl.

In step c of Scheme IV, the compounds of Formula XIIb can be acylated with an acid chloride such as acetyl chloride in a polar aprotic solvent such as dichloromethane using the conditions described in Scheme V. Reduction of the amide with a reducing agent such as lithium aluminum hydride in a polar aprotic solvent such tetrahydrofuran gives compounds of Formula XIIIa, wherein R6=ethyl.

Alternatively, in step d of Scheme IV, the compounds of Formula XIIb can be treated with benzotriazole and an aldehyde in ethanol followed by reduction using, for example, sodium borohydride, to afford compounds of Formula XIIIa. In step e of Scheme IV, the compounds of Formula XIIb can be treated with an aldehyde such as propionaldehyde and sodium triacetoxyborohydride in a polar aprotic solvent such as dichloromethane to give compounds of Formula XIIIa, wherein R6=propyl. As in step f, acylation of compounds of Formula XIIIa in Scheme IV using the conditions described in Scheme IX affords compounds of Formula Ia, wherein R1, R2, R3, R4, R5, R6, R8 and X are as previously defined.

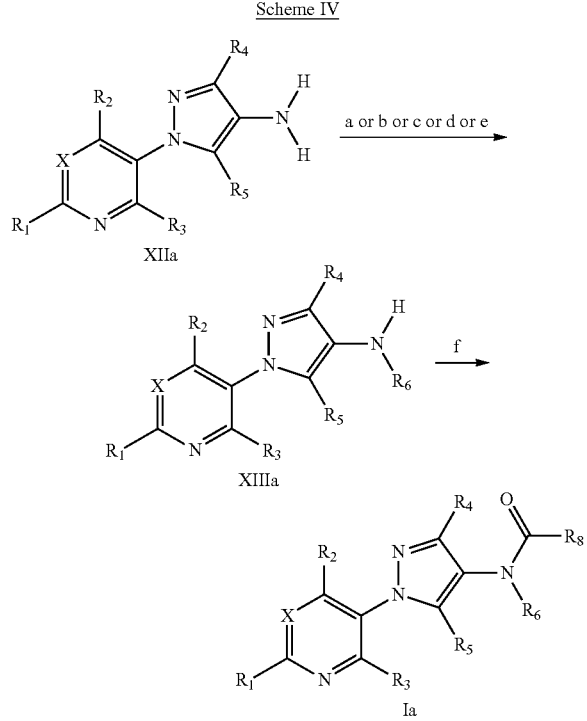

Scheme IV

In step a of Scheme V, the compounds of Formula Vc, wherein R1, R2, R3, R4, R5 and R6 and X are as previously defined, can be treated with an acid chloride of Formula XIV, in the presence of a base such as triethylamine or N,N-dimethylaminopyridine in a polar aprotic solvent such as dichloroethane (DCE) to yield compounds of Formula Ib, wherein R8 is as previously defined. Additionally, when R6=H the 2° amide may be subsequently alkylated in step b of Scheme V with an alkyl halide such as iodoethane, in the presence of a base such as sodium hydride and a polar aprotic solvent such as N,N-dimethylformamide (DMF) to yield the desired compounds of Formula Ib. The acid chlorides used in the acylation reactions herein are either commercially available or can be synthesized by those skilled in the art.

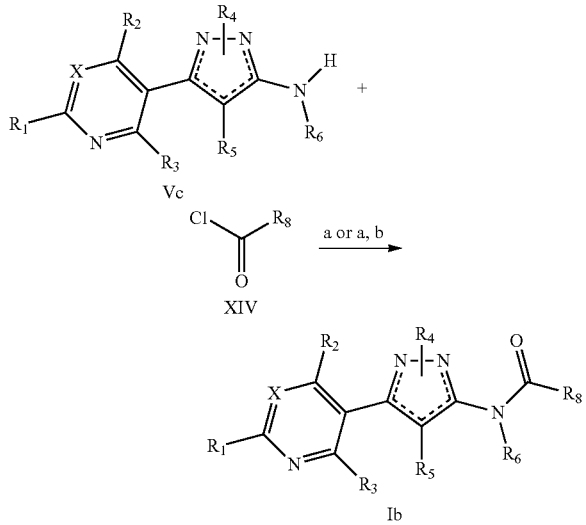

Scheme V

In step a of Scheme VI and as in Sammelson et al. *Bioorg. Med. Chem.* 2004, 12, 3345-3355, the aminopyrazoles of Formula Vd, wherein R1, R2, R3, R4, R6 and X are as previously defined and R5=H, can be halogenated with a halogen source such as N-chlorosuccinimide or N-bromosuccinimide in a polar aprotic solvent such as acetonitrile to provide the R5-substituted pyrazole. In step b, acylation of this compound using the conditions described in Scheme V affords the compound of Formula Ic, wherein R1, R2, R3, R4, R5, R6, R8 and X are as previously defined.

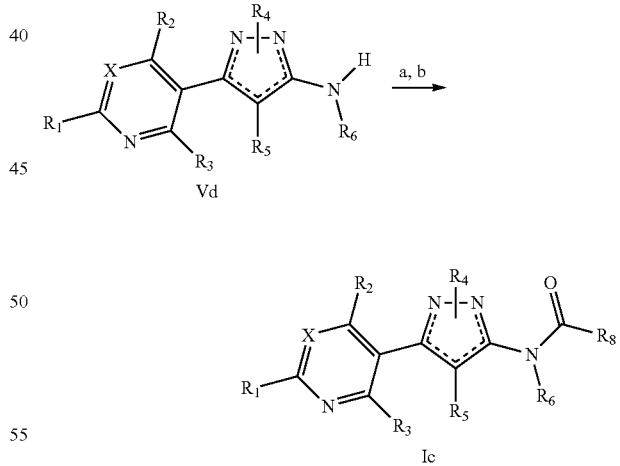

Scheme VI

In step a of Scheme VII, ureas and carbamates are made from the aminopyrazoles of Formula Ve. Compounds of Formula Ve, wherein X, R1, R2, R3, R4, R5 and R6 are as previously defined are allowed to react with phosgene to provide the intermediate carbamoyl chloride which is subsequently treated with an amine, as shown in step b, or alcohol, as shown in step c, respectively, to generate a urea of Formula Id or a carbamate of Formula Ie, respectively, wherein R9 is as previously defined.

Scheme VII

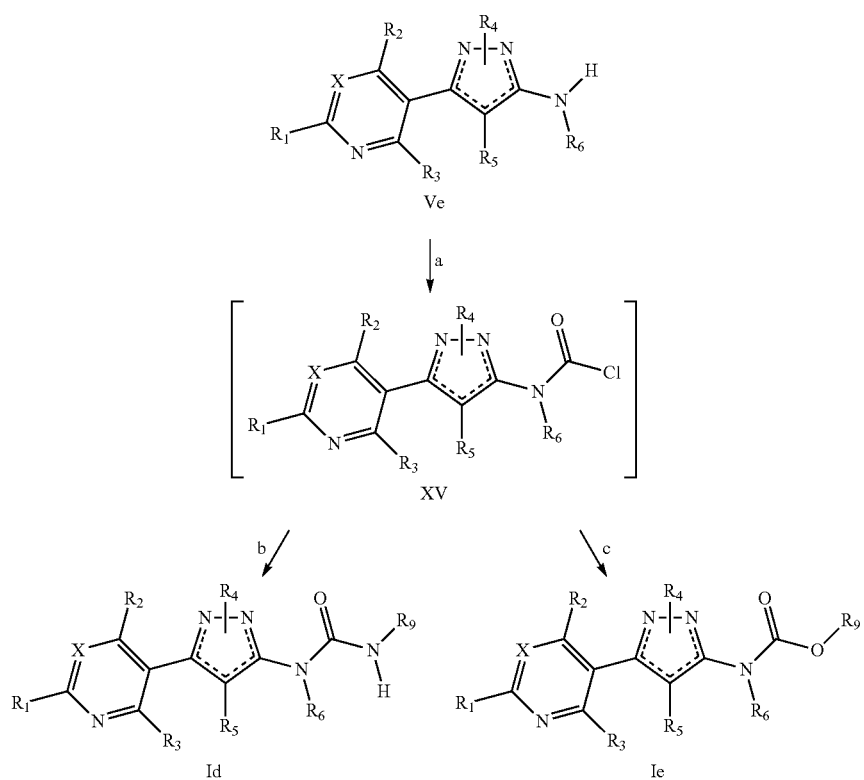

In step a of Scheme VIII, compounds of Formula XIIc, wherein X, R1, R2, R3, R4 and R5 are as previously defined, can be treated with di-tert-butyl dicarbonate (Boc₂O) and a base such as triethylamine in a polar aprotic solvent such as dichloromethane (DCM) to yield compounds of Formula XVIa. Treatment of the carbamate functionality with an alkyl halide such as iodomethane or Boc-anhydride in the presence of a base such as sodium hydride and in a polar aprotic solvent such as DMF yields carbamates of Formula XVII, as shown in step b of Scheme VIII, wherein R6 is as previously defined, except where R6 is hydrogen. The Boc-group can be removed under conditions that are well-known in the art, such as under acidic conditions such as trifluoroacetic acid (TFA) in a polar aprotic solvent like dichloromethane to give compounds of Formula XIIIb as in step c.

Scheme VIII

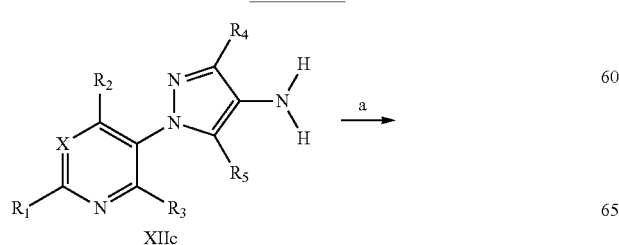

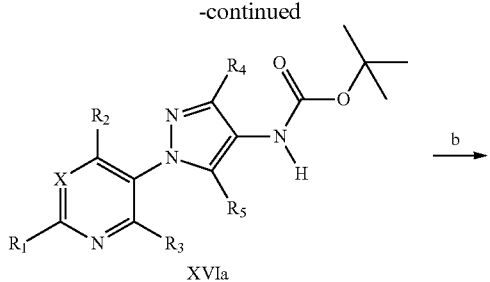

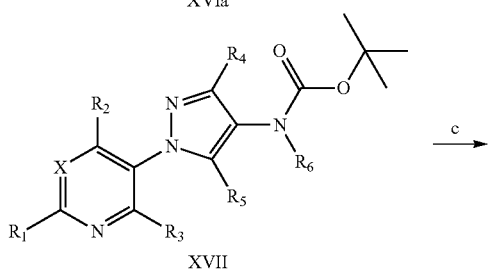

In steps a, b and c of Scheme IX, compounds of Formula XIIIc, wherein X, R1, R2, R3, R4, R5 and R6 are as previously defined, can be treated with a compound of Formula XVIII, wherein R8 is as previously defined and R10 is either OH, OR9 or O(C=O)OR9, to yield compounds of Formula Id. When R10=OH, compounds of Formula XIIIc can be converted to compounds of Formula Id in the presence of a coupling reagent such as 1-(3-dimethylaminopropyl)-3-ethylcarbodiimide hydrochloride (EDC.HCl) and a base such as N,N-dimethylaminopyridine (DMAP) in a polar aprotic solvent such as dichloroethane (DCE), as shown in step a. When R10=OR9, compounds of Formula XIIIc can be converted to compounds of Formula Id in the presence of 2,3,4,6,7,8-hexahydro-1H-pyrimido[1,2-a]pyrimidine in a polar aprotic solvent such as 1,4-dioxane under elevated temperature, as shown in step b. When R10=O(C=O)OR9, compounds of Formula XIIIc can be converted to compounds of Formula Id in a polar aprotic solvent such as dichloromethane (DCM), as shown in step c. Acylation of amides of Formula Id, when R6=H, with an acid chloride in the presence of a base such as diisopropyl ethylamine in a polar aprotic solvent such as dichloroethane (DCE) yields imides of Formula Ie, as shown in step d. Furthermore, alkylation of amides of Formula Id, when R6=H, with an alkyl halide or alkyl sulfonate in the presence of a base such as sodium hydride in a polar aprotic solvent such as N,N-dimethylformamide (DMF) yields alkylated amides of Formula Ie, as shown in step e. Halogenation of compounds of Formula Id, wherein R1, R2, R3, R4, R6, R8 and X are as previously defined and R5=H, with a halogen source such as N-bromosuccinimide in a polar aprotic solvent such as DCE or a halogen source such as N-chlorosuccinimide in a polar aprotic solvent such as DCE or acetonitrile or a halogen source such as Selectfluor® in a mixture of polar aprotic solvents such as acetonitrile and DMF give halogenated pyrazoles of Formula Ie, wherein R5=halogen, as shown in step f of Scheme IX. Amides of Formula Id can be converted to thioamides of Formula If in the presence of a thionating agent such as Lawesson's reagent in a polar aprotic solvent such as dichloroethane (DCE), as shown in step g.

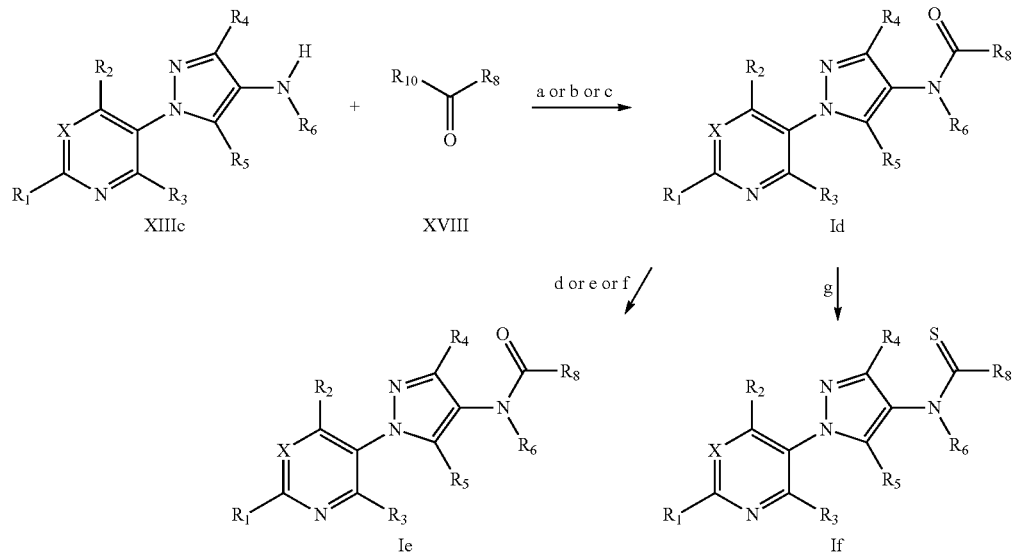

Scheme IX

In step a of Scheme X, compounds of Formula XIIId, wherein X, R1, R2, R3, R4, R5 and R6 are as previously defined, can be treated with compounds of Formula XIX, wherein R8 is as previously defined, in a polar aprotic solvent such as dichloroethane (DCE) to yield compounds of Formula XX. Additionally, when R6=H and R8 contains a halogen, compounds of Formula XX can be treated with a base, such as sodium hydride, in a polar aprotic solvent, such as THF, to yield compounds of Formula XXI, where m is an integer selected from 1, 2, 3, 4, 5, or 6, as shown in step b of Scheme X.

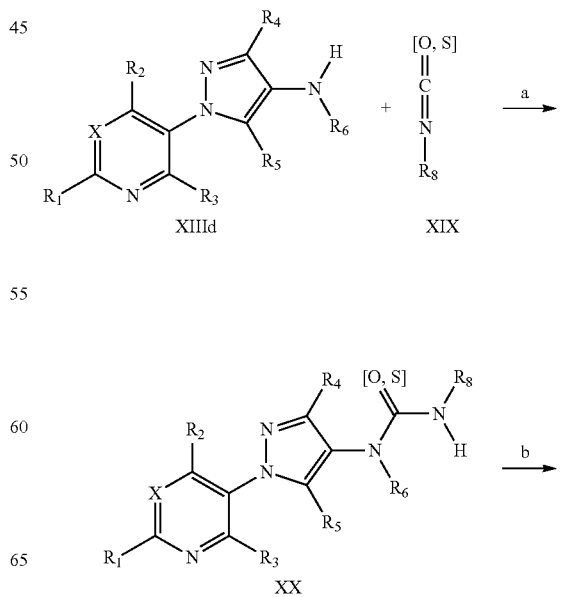

Scheme X

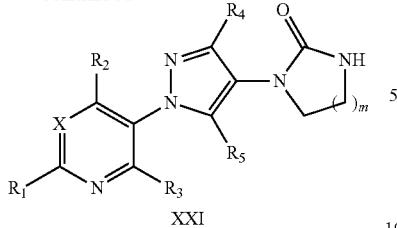

XXI

Oxidation of the sulfide to the sulfoxide or sulfone is accomplished as in Scheme XI where (~S~) can be any sulfide previously defined within the scope of R8 of this invention. The sulfide of Formula XXIIa, wherein X, R1, R2, R3, R4, R5 and R6 are as previously defined, is treated with an oxidant such as sodium perborate tetrahydrate in a polar protic solvent such as glacial acetic acid to give the sulfoxide of Formula XXIII as in step a of Scheme XI. Alternatively, the sulfide of Formula XXIIa can be oxidized with an oxidant such as hydrogen peroxide in a polar protic solvent such as hexafluoroisopropanol to give the sulfoxide of Formula XXIII as in step d of Scheme XI. The sulfoxide of Formula XXIII can be further oxidized to the sulfone of Formula XXIV by sodium perborate tetrahydrate in a polar protic solvent such as glacial acetic acid as in step c of Scheme XI. Alternatively, the sulfone of Formula XXIV can be generated in a one-step procedure from the sulfide of Formula XXIIa by using the aforementioned conditions with >2 equivalents of sodium perborate tetrahydrate, as in step b of Scheme XI.

such as potassium carbonate in a protic polar solvent system such as ethanol and water as in step b of Scheme XII.

Scheme XII

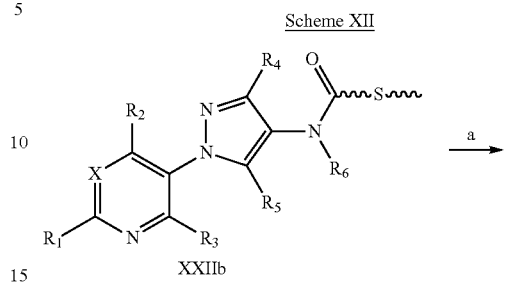

XXIIb

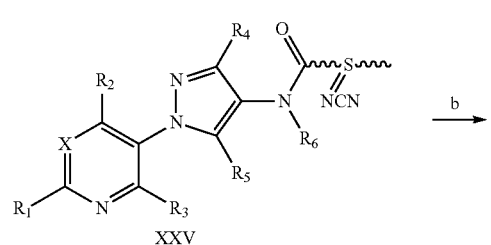

XXV

Scheme XI

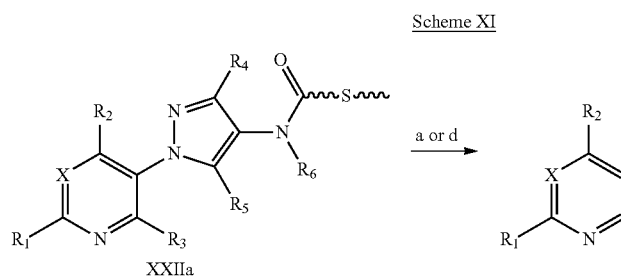

XXIIa            XXIII

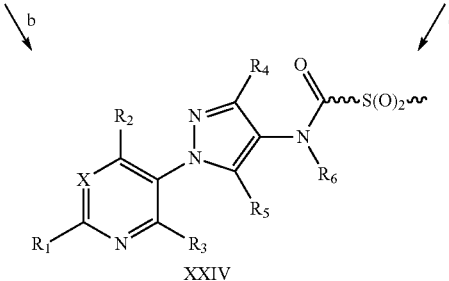

XXIV

Oxidation of the sulfide to the sulfoximine is accomplished as in Scheme XII where (~S~) can be any sulfide previously defined within the scope of R8 of this invention. The sulfide of Formula XXIIb, wherein X, R1, R2, R3, R4, R5 and R6 are as previously defined, is oxidized as in step a with iodobenzene diacetate in the presence of cyanamide in a polar aprotic solvent such as methylene chloride (DCM) to give the sulfilimine of the Formula XXV. The sulfilimine of Formula XXV may be further oxidized to the sulfoximine of Formula XXVI with an oxidant such as meta-Chloroperoxybenzoic acid ("mCPBA") in the presence of a base -continued

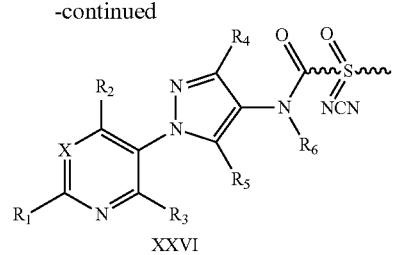

XXVI

Iodination of the pyrazole of Formula Xb as in step a of Scheme XIII and as in Potapov, A. et al. *Russ. J. Org. Chem.* 2006, 42, 1368-1373 was accomplished by reaction with an iodinating agent such as iodine in the presence of acids such as iodic acid and sulfuric acid in a polar protic solvent such as acetic acid gives compounds of Formula XXVII. In step b of Scheme XIII and as in Wang, D. et al. *Adv. Synth. Catal.* 2009, 351, 1722-1726, aminopyrazoles of Formula XIIIe can be prepared from iodopyrazoles of Formula XXVII through cross coupling reactions with an appropriate amine in the presence of a base such as cesium carbonate, a copper catalyst such as copper (I) bromide, and a ligand such as 1-(5,6,7,8-tetrahydroquinolin-8-yl)ethanone in a polar aprotic solvent such as DMSO.

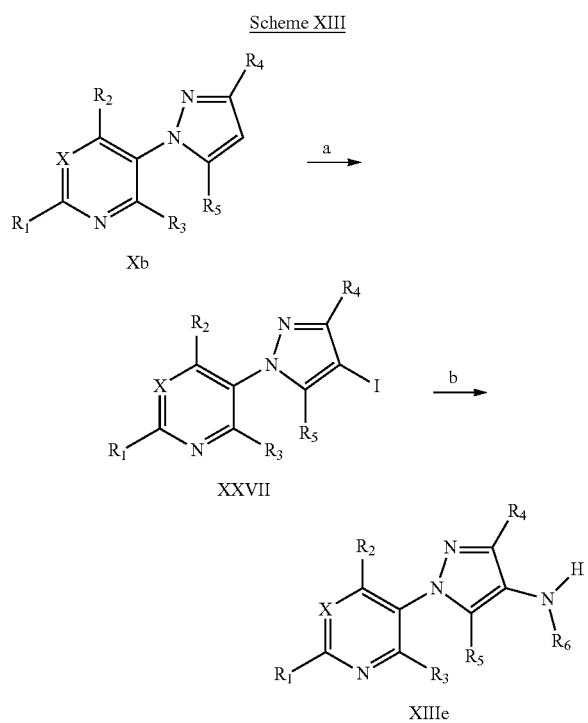

In step a of the Scheme XIV, compounds of the formula XXIX, wherein R4 is Cl, R5 is H and X$^-$ represents Cl$^-$, can be prepared according to the methods described in *Acta. Pharm. Suec.* 22, 147-156 (1985) by Tolf, Bo-Ragnar and Dahlbom, R. In a similar manner, compounds of the Formula XXIX, wherein R4 is Br, X$^-$ represents Br$^-$ and R5 is as defined previously, can be prepared by treating compounds of the Formula XXVIII with hydrogen gas in the presence of a metal catalyst such as 5% Pd on alumina and a solution of 50% aqueous HBr in a solvent such as ethanol. Alternatively, in step a of Scheme XIV, compounds of the Formula XXIX, wherein R4 is Cl or Br, X$^-$ represents Cl$^-$ or Br$^-$ and R5 is as defined previously, can be prepared by treating compounds of the Formula XXVIII, wherein R5 is as defined previously, with a hydrosilane such as triethyl silane in the presence of a metal catalyst such as 5% Pd on alumina and an acid such as HCl or HBr, respectively, in a solvent such as ethanol.

In step b of the Scheme XIV, compounds of the Formula XXX, wherein R4 is Cl or Br and R5 is as defined previously, can be prepared by treating the compounds of the Formula XXIX, wherein R4 is Cl or Br, X$^-$ represents Cl$^-$ or Br$^-$ and R5 is as defined previously, with di-tert-butyl dicarbonate (Boc$_2$O) in the presence of a mixture of solvents such as THF and water and a base such as sodium bicarbonate.

In step c of the Scheme XIV, compounds of the Formula XVIa, wherein X, R1, R2, R3 and R5 are as defined previously and R4 is Cl or Br, preferably Cl can be obtained by treating compounds of the Formula XXX, wherein R4 is Cl or Br and R5 is as defined previously, preferably H, with compounds of the Formula VIIIb, wherein X, R1, R2 and R3 are as defined previously and Q is iodo, in the presence of a catalytic amount of copper salt such as CuCl$_2$, a ligand such as an ethane-1,2-diamine derivative such as N$^1$,N$^2$-dimethylethane-1,2-diamine and a base such as K$_3$PO$_4$ in a polar aprotic solvent such as acetonitrile at a suitable temperature.

In step c pyrazoles of Formula XXX are coupled with compounds of the Formula VIIIb, preferably 3-iodo pyridine, in the presence of a metal catalyst, such as CuCl$_2$, and a diamine ligand such as N$^1$,N$^2$-dimethylethane-1,2-diamine, and an inorganic base, such as K$_3$PO$_4$. The reaction is carried out in a polar aprotic solvent such as acetonitrile. The reaction is conducted at a temperature from about 60° C. to about 82° C. and preferably from about 75° C. to 82° C. Approximately, a 1:1.2 molar ratio of pyrazoles of Formula XXX to heterocyclyl iodide of Formula VIIIb may be used, however, a molar ratios of about 5:1 to about 1:5 may also be used. The reaction is conducted at about atmospheric pressure, however, higher or lower pressures can be used.

The Boc-group of compounds of Formula XVIa can be removed under conditions that are well-known in the art such as under acidic conditions such as TFA in a polar aprotic solvent such as dichloromethane to give compounds of Formula XIId, as shown in step d of Scheme XIV.

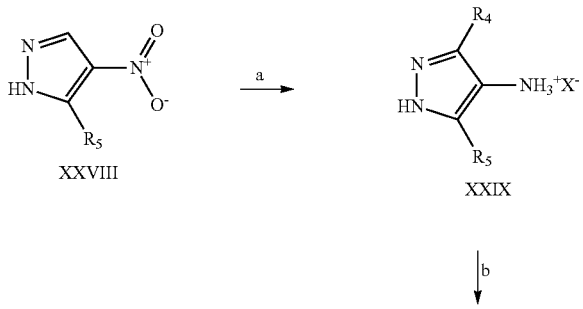

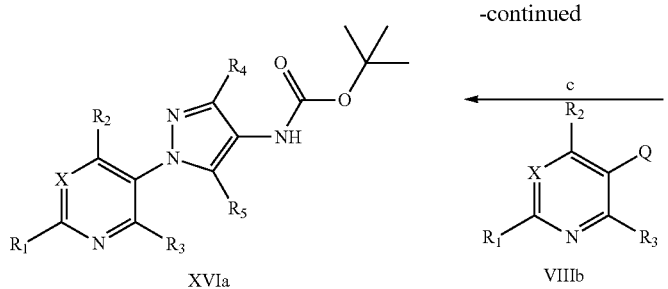

XVIa

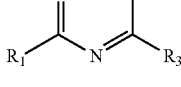

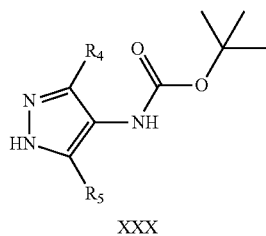

XXX

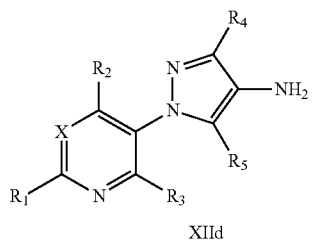

XIId

Bromopyrazoles of Formula XXXI, wherein R1, R2, R3, R5, R8 and X are as previously defined, can be allowed to react under Suzuki coupling conditions with a boronic ester such as vinylboronic acid pinacol ester or cyclopropylboronic acid pinacol ester in the presence of a catalyst such as palladium tetrakis, a base such as 2 M aqueous potassium carbonate, and in a mixed solvent system such as ethanol and toluene to provide compounds of Formula XXXII, as shown in step a of Scheme XV.

Scheme XV

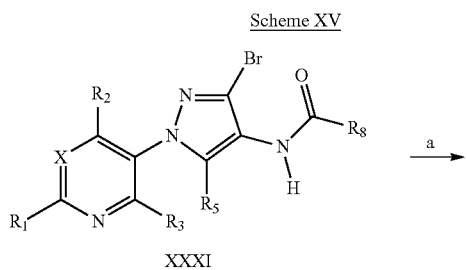

XXXI

-continued

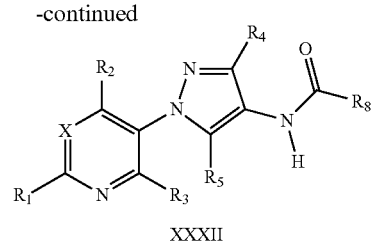

XXXII

The vinyl group of compounds of Formula XXXIII, wherein R1, R2, R3, R5, R6, R8 and X are as previously defined, can be reduced in the presence of hydrogen with a catalyst such as 10% Pd/C in a polar protic solvent such methanol to give compounds of Formula XXXIV, as shown in step a of Scheme XVI. Oxidation of the vinyl group of compounds of Formula XXXIII using an oxidant such as osmium tetroxide in the presence of sodium periodate in mixture of a polar protic solvent such as water and a polar aprotic solvent such as THF gave compounds of Formula XXXV, as shown in step b of Scheme XVI. Reduction of the aldehyde of compounds of Formula XXXV, as shown in step c of Scheme XVI, with a reducing agent such as sodium borohydride in a polar protic solvent such as methanol gave the corresponding alcohol of Formula XXXVI. Treatment of compounds of Formula XXXVI with a chlorinating agent such as thionyl chloride in a polar aprotic solvent such as dichloromethane gave compounds of Formula XXXVII, as shown in step d of Scheme XVI.

Scheme XVI

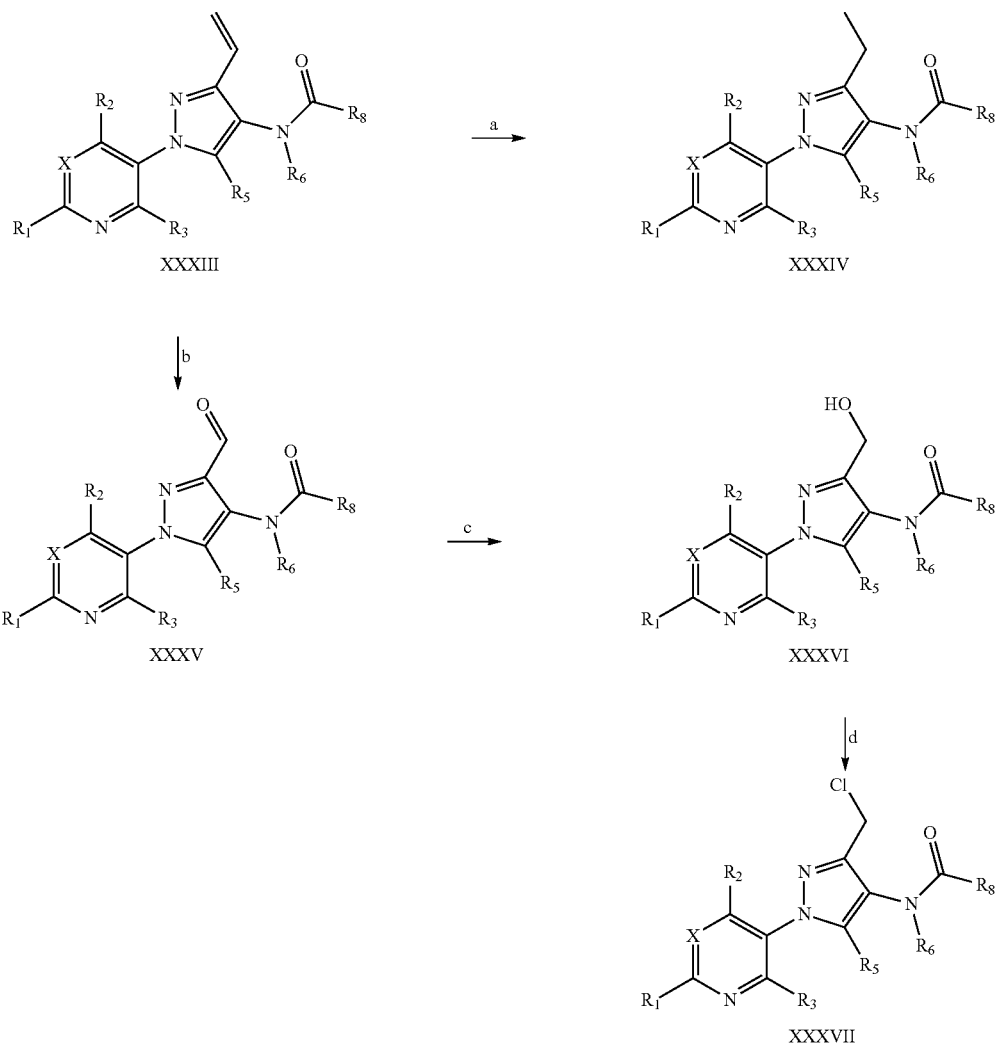

In step a of Scheme XVII, an α,β-unsaturated acid XXXVIII can be treated with a nucleophile such as sodium thiomethoxide in a polar protic solvent such as methanol to give acid XXXIX.

Scheme XVII

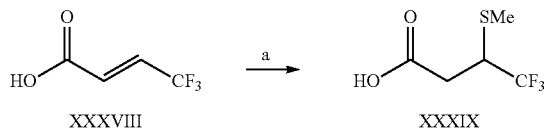

In Step a of the Scheme XVIII, treatment of the compounds of Formula Ig, where A is A2, R7 is O and R8 is tert-butoxy with a reagent such as propargyl bromide in the presence of a base such as sodium hydride and in a polar aprotic solvent such as DMF yields compounds of Formula Ih, wherein R6=R11.

Scheme XVIII

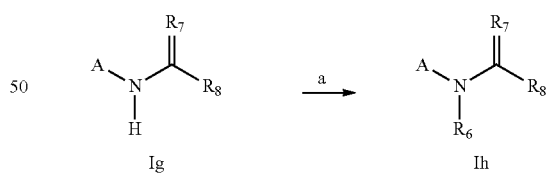

In step a of Scheme XIX, compounds of Formula XL, wherein X, R1, R2, R3, R4, R5 and R6 are as previously defined, can be treated with an acid of Formula XLI, wherein R8 is as previously defined, in the presence of a coupling reagent, such as 1-(3-dimethylaminopropyl)-3-ethylcarbodiimide hydrochloride (EDC.HCl), and a base, such as N,N-dimethylaminopyridine (DMAP), in a polar aprotic solvent, such as dichloromethane (DCM), to yield compounds of Formula XLII. In step b, compounds of the Formula XLII can be treated with a base, such as sodium methoxide, in a polar solvent such as THF, followed by an alkyl halide R9-Hal to give the compounds of the Formula XLIII.

Scheme XIX

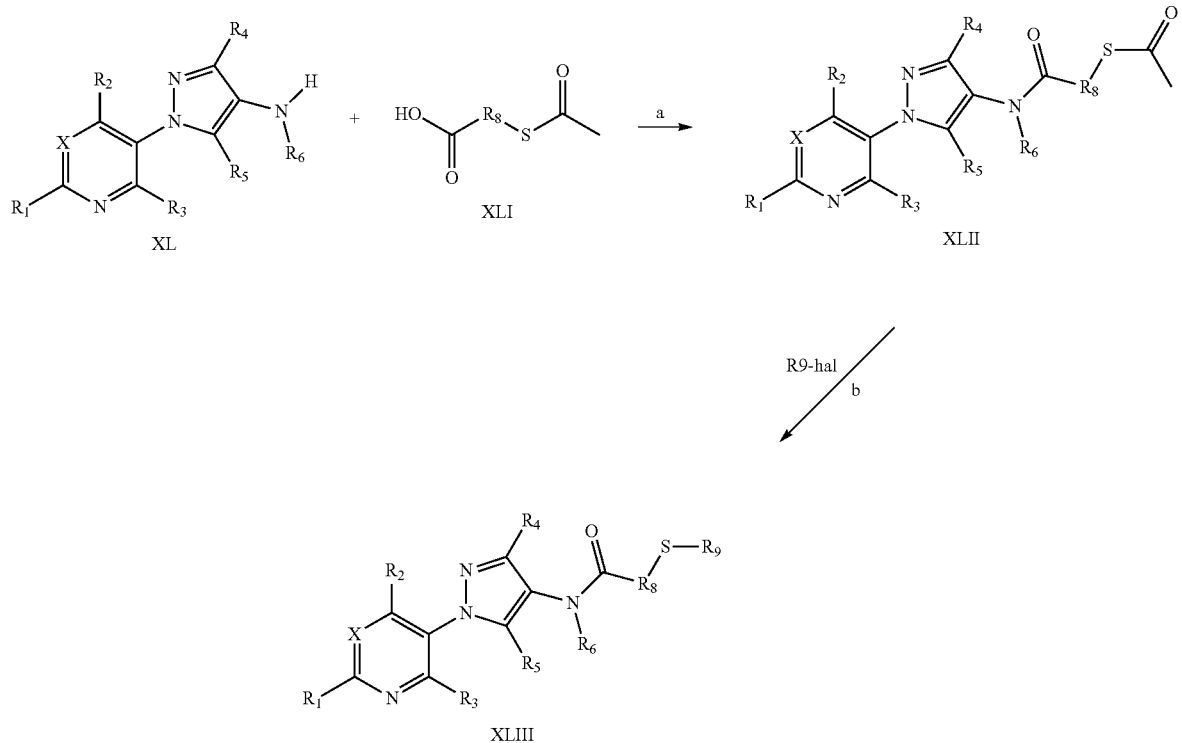

Alternatively, in step a of Scheme XX, compounds of the Formula XL or the corresponding HCl salt, wherein X, R1, R2, R3, R4, R5, and R6 are as previously defined, can be coupled to acids of the formula XLIV, wherein R8 is as previously defined, in the presence of a coupling reagent, such as 1-(3-dimethylaminopropyl)-3-ethylcarbodiimide hydrochloride (EDC.HCl), and a base, such as N,N-dimethylaminopyridine, in a polar aprotic solvent, such as dichloromethane, to yield compounds of the Formula XLV, wherein X, R1, R2, R3, R4, R5, R6 and R8 are as previously defined. In step b of Scheme XX, compounds of the Formula XLV, wherein X, R1, R2, R3, R4, R5, R6 and R8 are as previously defined and Tr represents trityl (triphenylmethyl), can be treated with an acid, such as 2,2,2-trifluoroacetic acid, in the presence of a trialkyl silane, such as triethyl silane, in a polar aprotic solvent, such as methylene chloride, to remove the trityl group to give thiols of the Formula XLVI, wherein X, R1, R2, R3, R4, R5, R6 and R8 are as previously defined. In step c of Scheme XX, thiols of the Formula XLVI, wherein X, R1, R2, R3, R4, R5, R6 and R8 are as previously defined, can be treated with a base, such as sodium hydride, in a polar aprotic solvent such as tetrahydrofuran, or cesium carbonate in acetonitrile, or DBU in dimethylformamide, and an electrophile (R9-Hal), such as 2-(bromomethyl)-1,1-difluorocyclopropane, in tetrahydrofuran, to give compounds of the Formula XLVII. Alternatively, the modified conditions described by Pustovit and coworkers (*Synthesis* 2010, 7, 1159-1165) could be employed in the transformation of XLVI to XLVII.

Scheme XX

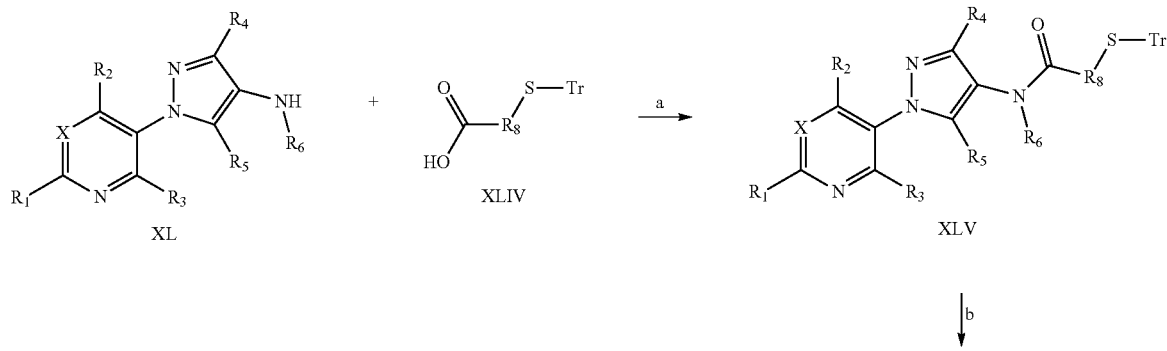

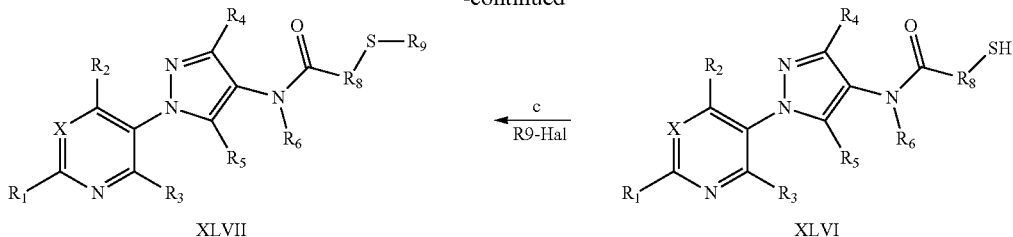

Alternatively, in step a of the Scheme XXI, compounds of the Formula XL or the corresponding HCl salt, wherein X, R1, R2, R3, R4, R5, and R6 are as previously defined, can be coupled to acids of the Formula XLVIII, wherein R9 is as previously defined, in the presence of a coupling reagent such as EDC.HCl and a base such as DMAP in a polar aprotic solvent such as DMF to yield compounds of Formula XLIX, where in X, R1, R2, R3, R4, R5, R6 and R9 are as previously defined. In step b of the Scheme XXI, compounds of the Formula XLIX, wherein X, R1, R2, R3, R4, R5, R6 and R9 are as previously defined, can be treated with a thio acid salt, such as potassium thioacetate, at an elevated temperature (about 50° C.) in a solvent, such as DMSO, to give compounds of the Formula L, wherein X, R1, R2, R3, R4, R5, R6 and R9 are as previously defined. In step c of the Scheme XXI, compounds of the Formula L, wherein X, R1, R2, R3, R4, R5, R6 and R9 are as previously defined, can be treated with an equimolar amount of a base, such as sodium methoxide, prepared from mixing sodium hydride, and methanol, followed by an electrophile (R9-Halo), such as 2-(bromomethyl)-1,1-difluorocyclopropane, in a solvent, such as tetrahydrofuran, to give compounds of the Formula LI.

In step a of Scheme XXII, compounds of the Formula XL, wherein X, R1, R2, R3, R4, R5, R6, and halo are as previously defined, can be treated with an acid chloride of Formula LII in the presence of a base, such as triethylamine or diisopropylethylamine in a polar aprotic solvent, such as DCE, to yield compounds of the Formula LIII, wherein R8 is either a substituted or unsubstituted alkyl chain. In step b, compounds of the Formula LIII can be treated with potassium thioacetate to provide compounds of Formula LIV after heating (about 60° C.) in a polar aprotic solvent, such as acetone. As indicated in step c, a one-pot methanolysis/alkylation sequence can be achieved via treatment of compounds of the Formula LIV with one equivalent of a base, such as sodium methoxide (NaOMe) in a polar aprotic solvent, such as tetrahydrofuran (THF). An alkyl sulfonate or alkyl halide, such as 2-iodo-1,1,1-trifluoroethane, can then be added to the reaction mixture to deliver compounds of the Formula LV, wherein R9 is as previously defined. In step d compounds of the Formula LV may be obtained from compounds of the Formula LIII via treatment with an alkyl thiol such as 2,2,2-trifluoroethanethiol at elevated temperatures (about 50° C.) in a polar aprotic solvent, such as THF, in the presence of sodium iodide and a base, such as diisopropylethylamine. Alternatively, in step f treating com- Scheme XXI

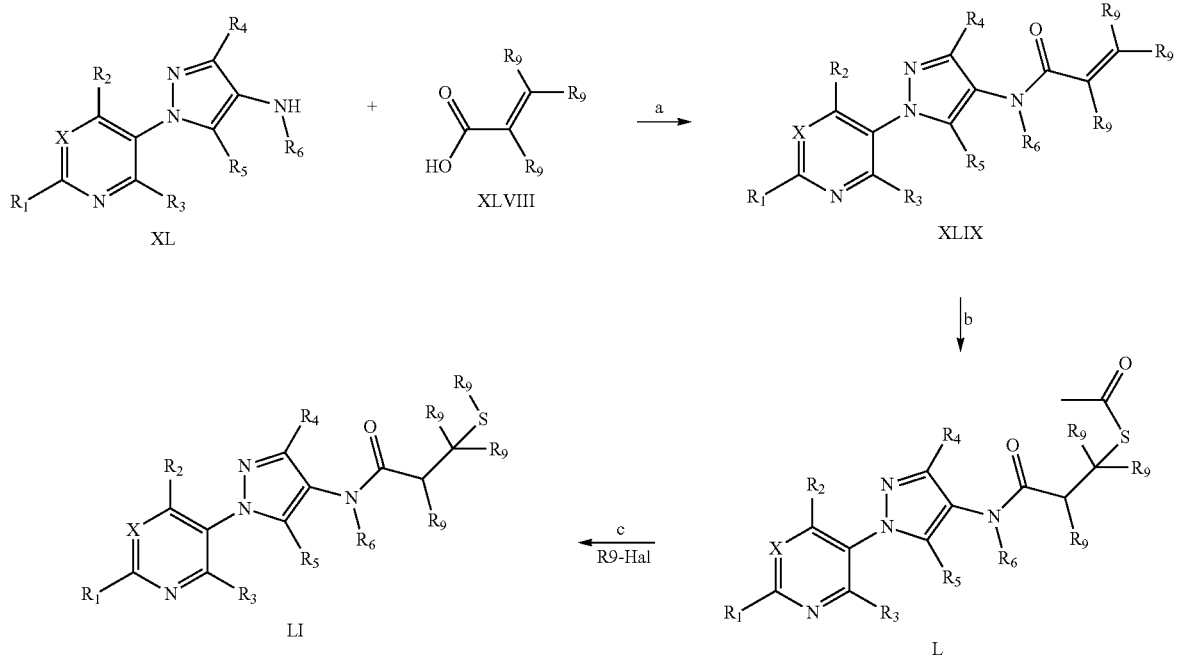

pounds of Formula LIII with an alkyl thiol, such as sodium methanethiolate, in a polar aprotic solvent, such as DMSO, at elevated temperatures (about 50° C.) will afford compounds of Formula LV. As demonstrated in step e, when compounds of the Formula LIV are treated with two or more equivalents of a base, such as NaOMe, followed by a 1,2,2-trihaloalkyl compound, such as 2-bromo-1,1-difluoroethane, compounds of Formula LVI are obtained.

defined, can be treated with a base, such as aqueous 2M lithium hydroxide, in a polar protic solvent, such as methanol, to give compounds of Formula 23.2. Then in step b, compounds of Formula 23.2 can be treated with a base, such as sodium hydride in a polar aprotic solvent, such as tetrahydrofuran, followed by an electrophile, such as an

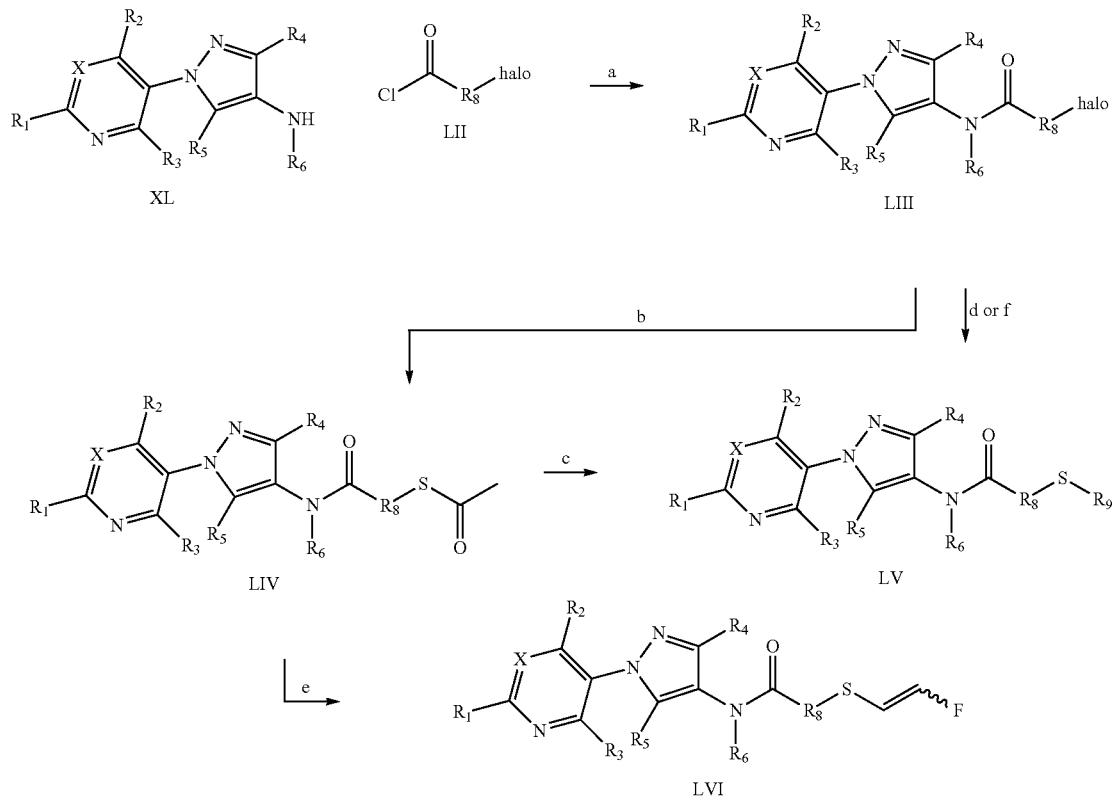

Scheme XXII

In step a of Scheme 23, compounds of Formula 23.1, wherein X, R1, R2, R3, R4, R5, R6 and R8 are as previously alkyl halide or sulfonyl halide, to afford compounds of Formula 23.3.

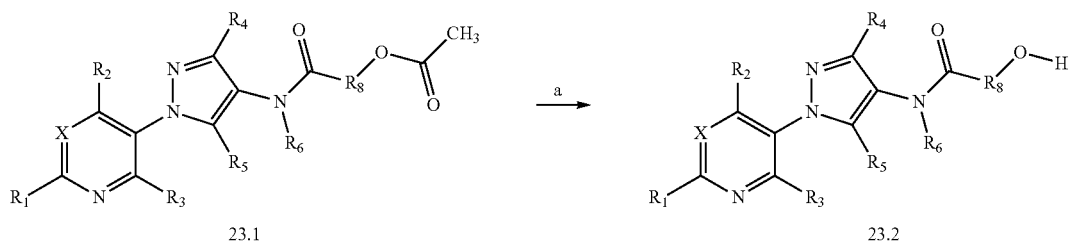

Scheme 23

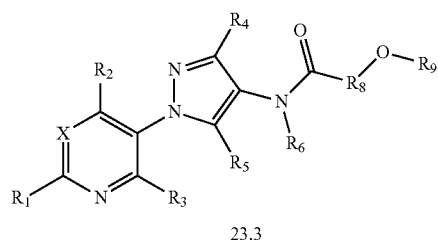

23.3

In step a of Scheme 24, compounds of Formula 24.1, where X, R1, R2, R3, R4, R5, R8 and halo are as previously defined, and R6=H, can be treated with a base such as sodium hydride, in a polar aprotic solvent, such as tetrahydrofuran (THF), to yield compounds of Formula 24.2 where m is an integer selected from 0, 1,2,3, 4, 5, or 6. In step b of Scheme 24, compounds of Formula 24.2 can be treated with a base, such as triethylamine, and silylation reagents, such as trimethylsilyl trifluoromethanesulfonate and dimethylmethylideneammonium iodide (Eschenmoser's salt) in a polar aprotic solvent, such as dichloromethane (DCM), to yield compounds of Formula 24.3. In step c of Scheme 24, compounds of Formula 24.3 can be treated with a base, such as potassium hydroxide, and a nucleophile, such as S,S-dimethyl carbonodithioate, in water and a polar aprotic solvent such as tetrahydrofuran (THF) to yield compounds of Formula 24.4, wherein X, R1, R2, R3, R4, R5, R9 and m are as previously defined.

Scheme 25

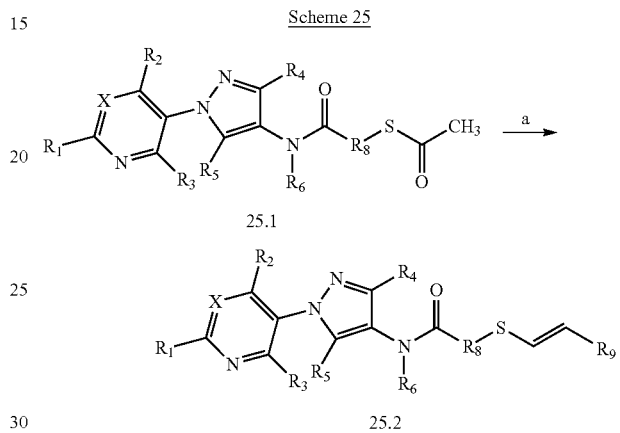

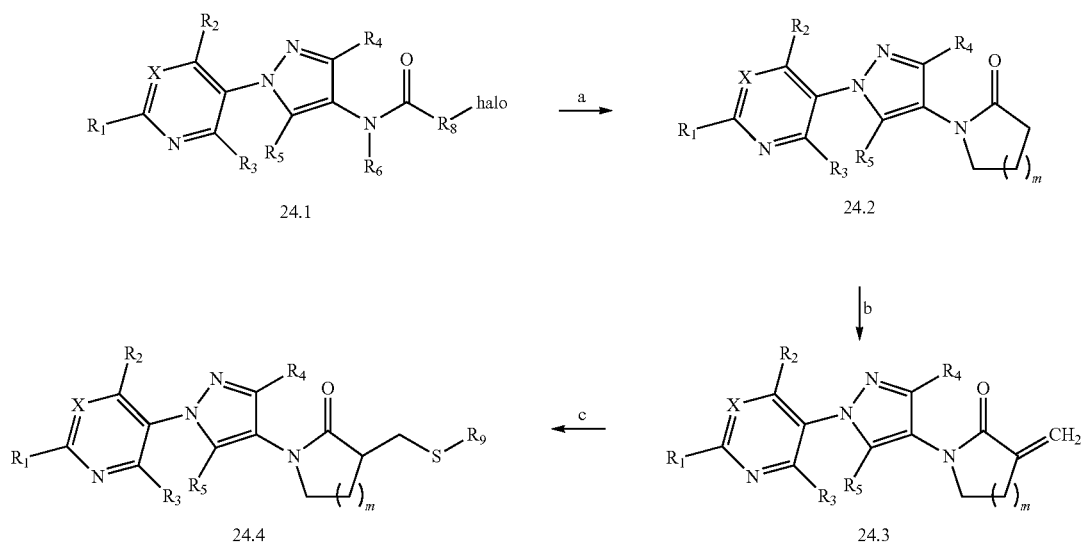

A route to compounds of Formula 25.2 is described in Scheme 25. As demonstrated in step a, when compounds of the Formula 25.1, wherein X, R1, R2, R3, R4, R5, R6 and R8 are as previously defined, are treated with two or more equivalents of a base, such as sodium methoxide, followed by a 1,2-dihaloalkyl compound, such as 1-fluoro-2-iodoethane, in a solvent, such as tetrahydrofuran (THF), compounds of Formula 25.2, wherein R9 is as previously defined, are obtained.

An alternative route to vinyl sulfides is described in step a of Scheme 26. This route utilizes conditions developed by Kao and Lee (*Org. Lett.* 2011, 13, 5204-5207) in which thiols of the Formula 26.1, wherein X, R1, R2, R3, R4, R5, R6 and R8 are as previously defined, are coupled with a vinyl halide, such as (E)-1-bromo-3,3,3-trifluoroprop-1-ene, in the presence of a catalyst, such as copper(I) oxide, a base, such as potassium hydroxide, and a solvent, such as dioxane, at elevated temperatures to afford products of Formula 26.2, wherein R9 is as previously defined.

Scheme 26

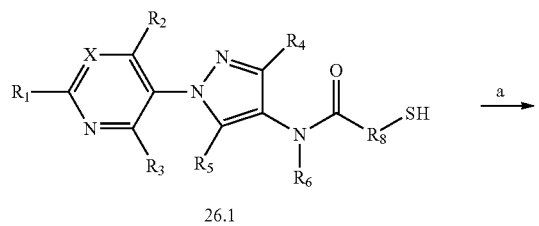

26.1

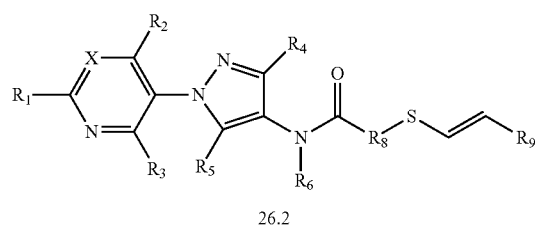

26.2

In step a of Scheme 27, an acrylamide of Formula 27.1, wherein X, R1, R2, R3, R4, R5, and R6 are as previously defined, is reacted with a sulfonamide of Formula 27.2, wherein R9 is as previously defined, in the presence of a base, such as potassium carbonate, at elevated temperatures in a polar aprotic solvent, such as dimethylformamide (DMF), to deliver compounds of Formula 27.3. This product can then be treated with a base, such as sodium hydride, and an alkyl halide, such as 2-bromoacetonitrile, in a polar aprotic solvent, such as tetrahydrofuran (THF), to provide compounds of the Formula 27.4, as demonstrated in step b.

When compounds of the Formula 28.1, wherein X, R1, R2, R3, R4, R5, R6, R8 and halo are as previously defined, are treated with amines of the Formula 28.2, wherein R9 is as previously defined, at elevated temperatures in a polar protic solvent, such as methanol, compounds of the Formula 28.3 can be obtained, as demonstrated in step a of Scheme 28. Compounds of the Formula 28.3 may be treated with a sulfonyl chloride, such as methanesulfonyl chloride, in the presence of a base, such as diisopropylethylamine, and a polar aprotic solvent, such as dichloromethane (DCM), to afford products of the Formula 28.4, as shown in step b. As demonstrated in step c, when compounds of the Formula 28.3 are treated with an alkyl halide, such as 3-bromo-1,1,1-trifluoropropane, at elevated temperatures and in the presence of a base, such as potassium carbonate, and a polar aprotic solvent, such as dimethylformamide (DMF), compounds of the Formula 28.5 may be obtained. Alternatively, compounds of Formula 28.3 may be prepared via a two step process as described in steps d and e of Scheme 28. Compounds of Formula 28.6 can be converted to compounds of Formula 28.8 when treated with compounds of Formula 28.7 in the presence of a coupling reagent such as 1-(3-dimethylaminopropyl)-3-ethylcarbodiimide hydrochloride (EDC.HCl) and a base such as N,N-dimethylaminopyridine (DMAP) in a polar aprotic solvent such as dichloroethane (DCE), as shown in step d. The Boc-group can be removed under conditions that are well-known in the art, such as under acidic conditions such as trifluoroacetic acid (TFA) in a polar aprotic solvent like dichloromethane to give compounds of Formula 28.3 as in step e.

Scheme 27

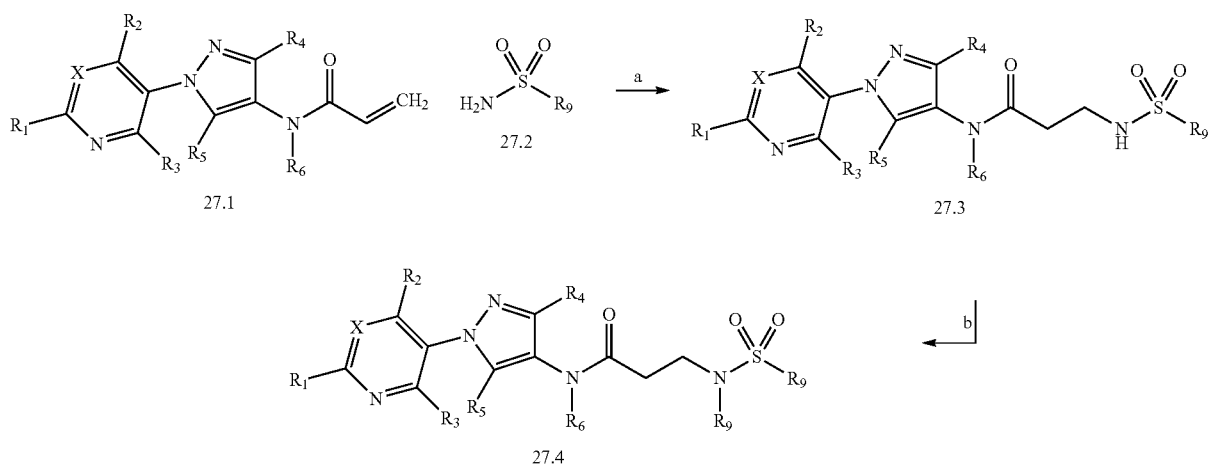

Scheme 28

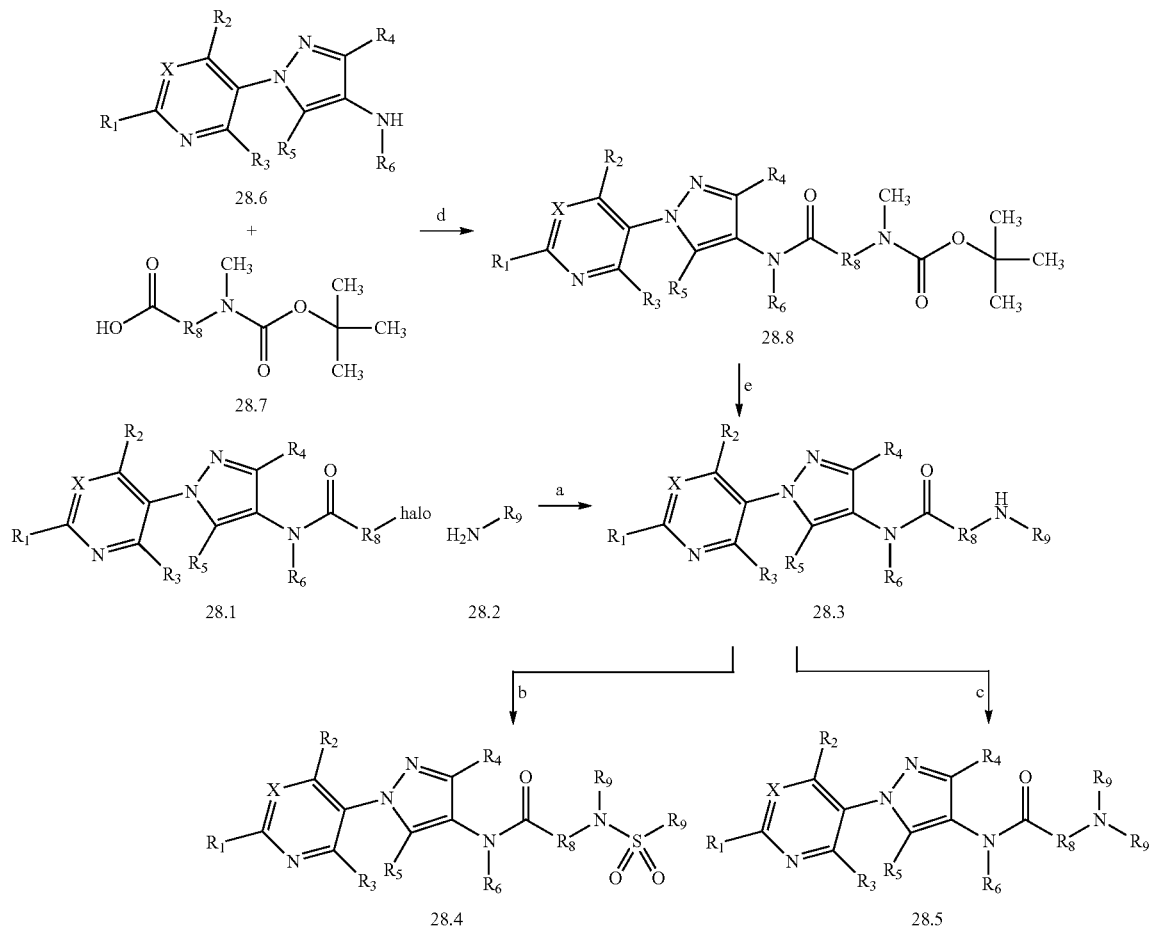

In step a of Scheme 29, compounds of Formula 29.1, wherein X, R1, R2, R3, R4, R5, R6 and R8 are as previously defined, can be reacted with either a cyclic or acyclic enone, such as but-3-ene-2-one, under the conditions described by Chakraborti (*Org. Lett.* 2006, 8, 2433-2436) to deliver compounds of the Formula 29.2, wherein R9 is as previously defined. These products may then be subjected to a fluorinating reagent, such as Deoxo-Fluor®, and an initiator, such as ethanol, in a polar aprotic solvent, such as dichloromethane (DCM), to deliver compounds of the Formula 29.3, as described in step b.

Scheme 29

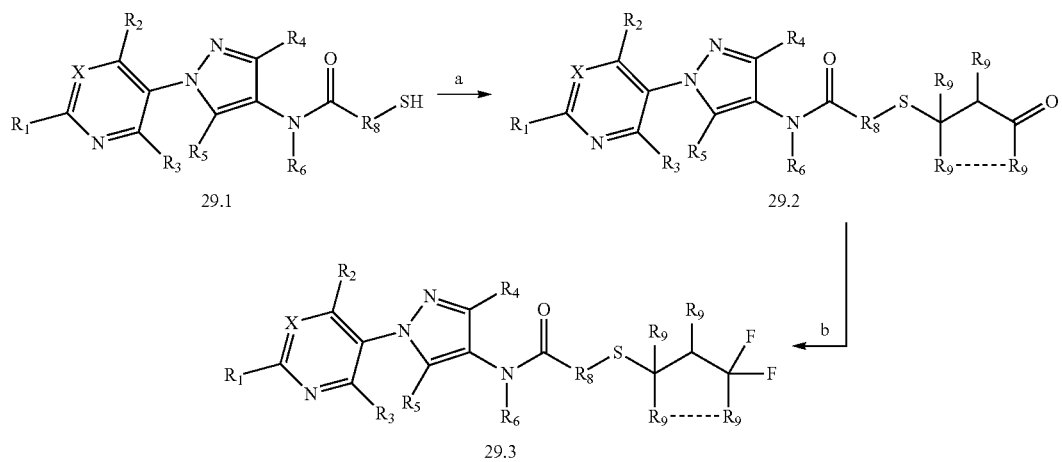

Step a of Scheme 30 depicts the hydrolysis of compounds of the Formula 30.1, wherein X, R1, R2, R3, R4, R5, R6, R8, and R9 are as previously defined, via treatment with an acid, such as aqueous hydrochloric acid, in a solvent, such as THF, to afford an intermediate aldehyde of the Formula 30.2. Compounds of the Formula 30.2 can be immediately reacted with a fluorinating reagent, such as Deoxo-Fluor®, in the presence of an initiator, such as ethanol, and a solvent, such as tetrahydrofuran (THF), to provide products of the Formula 30.3.

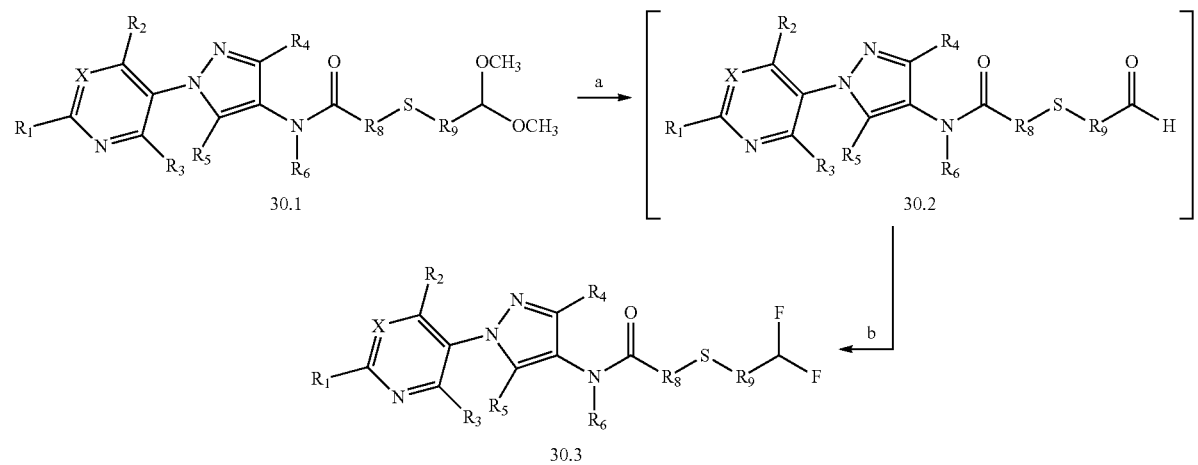

Scheme 30

In Scheme 31, compounds of the Formula 31.1, wherein R9 is as previously defined, are converted to compounds of the Formula 31.2 via the procedure described in Dmowski (*J. Fluor. Chem.*, 2007, 128, 997-1006), as shown in step a. Compounds of Formula 31.2 may then be subjected to conditions described in step b, in which a reaction with a thioate salt in a solvent, such as dimethylformamide (DMF), provides compounds of the Formula 31.3, wherein W is aryl or alkyl. As indicated in step c, a one-pot deprotection/alkylation sequence can be achieved via treatment of compounds of the Formula 31.3 with one equivalent of a base, such as sodium methoxide (NaOMe), in a polar aprotic solvent, such as tetrahydrofuran (THF). A compound of the Formula 31.4, wherein X, R1, R2, R3, R4, R5, R6, R8 and halo are as previously defined, may then be added to the reaction mixture to afford compounds of the Formula 31.5.

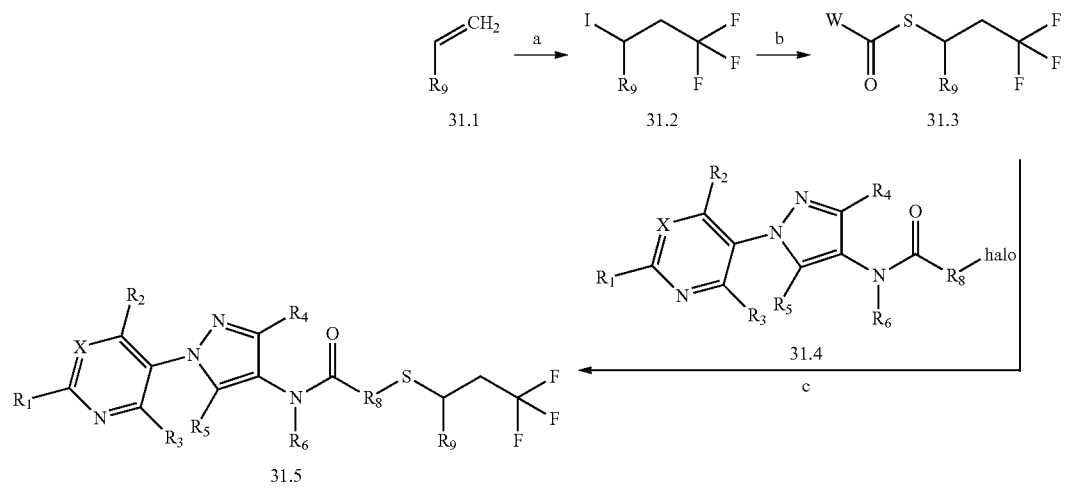

Scheme 31

In Scheme 32, a neat mixture of an olefin of the Formula 32.1, where n is an integer selected from 0, 1, 2, 3, 4, or 5, and trimethylsilyl 2,2-difluoro-2-(fluorosulfonyl)acetate can be heated in the presence of sodium fluoride to deliver a substituted difluorocyclopropane of the Formula 32.2, as indicated in step a. In step b, this product was treated with tetrabutylammonium fluoride (TBAF) in tetrahydrofuran (THF) to afford an intermediate homoallylic alcohol of the Formula 32.3. This alcohol was not isolated, but rather immediately treated with p-toluenesulfonyl chloride in the presence of pyridine and dichloromethane to afford a tosylate of the Formula 32.4, as shown in step c.

Scheme 33

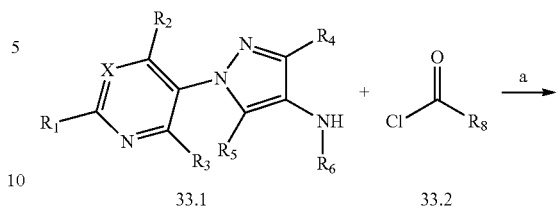

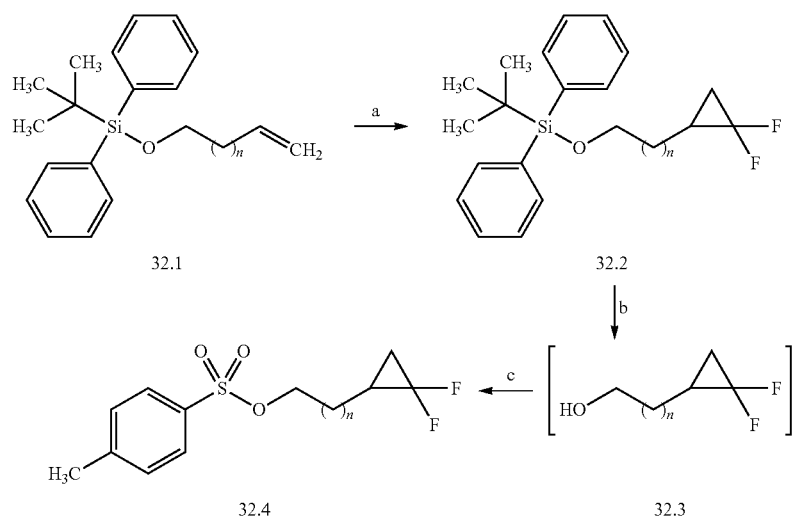

Scheme 32

Compounds of the Formula 33.1, wherein X, R1, R2, R3, R4, R5, and R6 are as previously defined, where X is preferably carbon, R1, R2, R3, and R5 are hydrogen and R4 is chloro, may be coupled with an acid chloride of the Formula 33.2, wherein R8 is as previously defined, in the presence of a base, such as pyridine, diisopropylethylamine, or N,N-dimethylaminopyridine (DMAP), and a solvent, such as 1,2-dichloroethane or methylene chloride, to afford products of the Formula 33.3, as depicted in step a of Scheme 33.

In step a of Scheme 33 amines of Formula 33.1 are coupled with acid chlorides of Formula 33.2 in the presence of a base, or combination of bases such as pyridine, N,N-dimethylaminopyridine, or diisopropylethylamine. The reaction is carried out in a halogenated solvent such as 1,2-dichloroethane or methylene chloride. The reaction is conducted at a temperature from 0° C. to 80° C. and preferably from about 0° C. to 23° C. Approximately, a 1:1 molar ratio of the amine of formula 33.1 to acid chloride of Formula 33.2 may be used, however, molar ratios of about 5:1 to about 1:5 may also be used. The reaction is conducted at about atmospheric pressure, however, higher or lower pressures can be used.

-continued

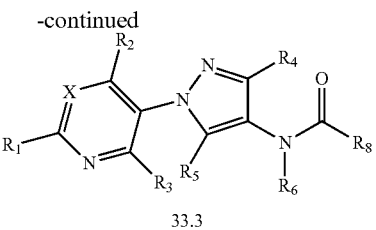

In step a of Scheme 34, the compounds of Formula 34.1, wherein R1, R2, R3, R4, R5 and R6 and X are as previously defined, can be treated with an acid of Formula 34.2, wherein R8 is as previously defined, in the presence of N,N'-dicyclohexylcarbodiimide (DCC), and a base, such as N,N-dimethylaminopyridine (DMAP), in a solvent, such as diethyl ether (Et$_2$O), to yield compounds of Formula 34.3.

Scheme 34

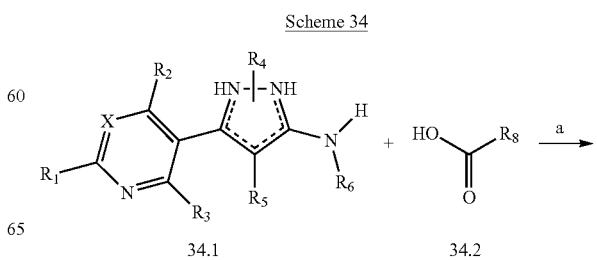

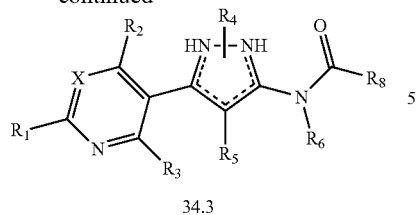

34.3

In step a of Scheme 35, aminopyrazoles of Formula 35.1, wherein X, R1, R2, R3, R4, R5 and R6 are as previously defined, can be treated with phosgene and N,N-dimethylaminopyridine (DMAP) at about 80° C. in a polar aprotic solvent such as dichloroethane (DCE). Subsequently, treatment with an amine, as shown in step b, or an alcohol, as shown in step c, or a thiol, as shown in step d, generates a urea of Formula 35.2, a carbamate of Formula 35.3, or a carbamothioate of Formula 35.4, wherein R9 is as previously defined, respectively.

Scheme 35

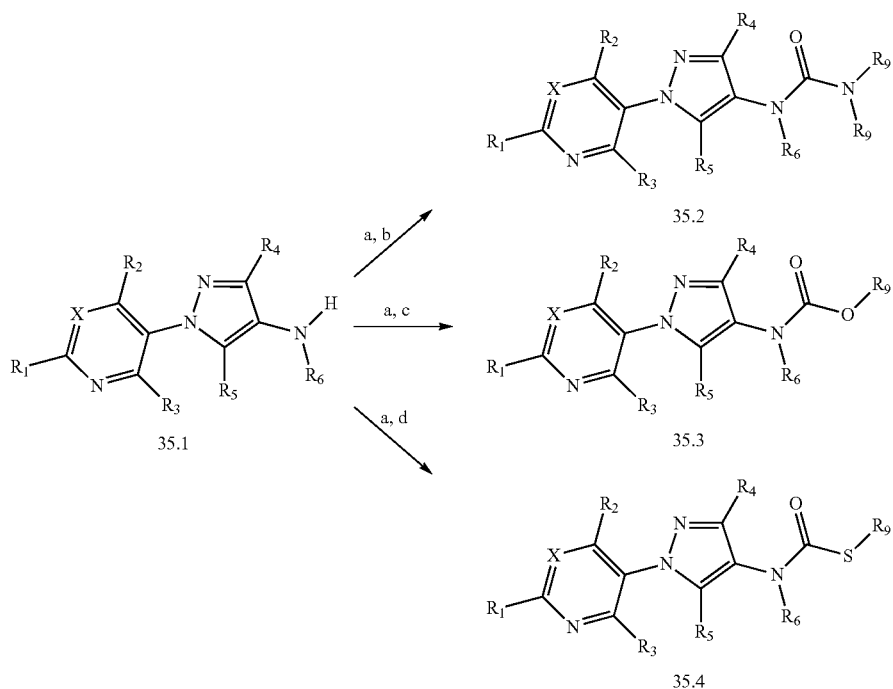

In step a of Scheme 36, compounds of Formula 36.1, wherein X, R1, R2 and R3 are as previously defined, can be treated with a base such as triethylamine, carbon disulfide and a sulfonyl chloride such as 4-methylbenzene-1-sulfonyl chloride in a polar aprotic solvent such as tetrahydrofuran (THF) to yield compounds of Formula 36.2. In step b of Scheme 36, oxazolidin-2-one can be treated with an equimolar amount of a base, such as sodium hydride followed by compounds of Formula 36.2, in a polar aprotic solvent such as dimethylformamide (DMF) to give compounds of the Formula 36.3. Additionally, the product of step b, (previous to work-up) can be treated with an electrophile such as iodomethane to give compounds of Formula 36.4 as demonstrated in step c of Scheme 36.

Scheme 36

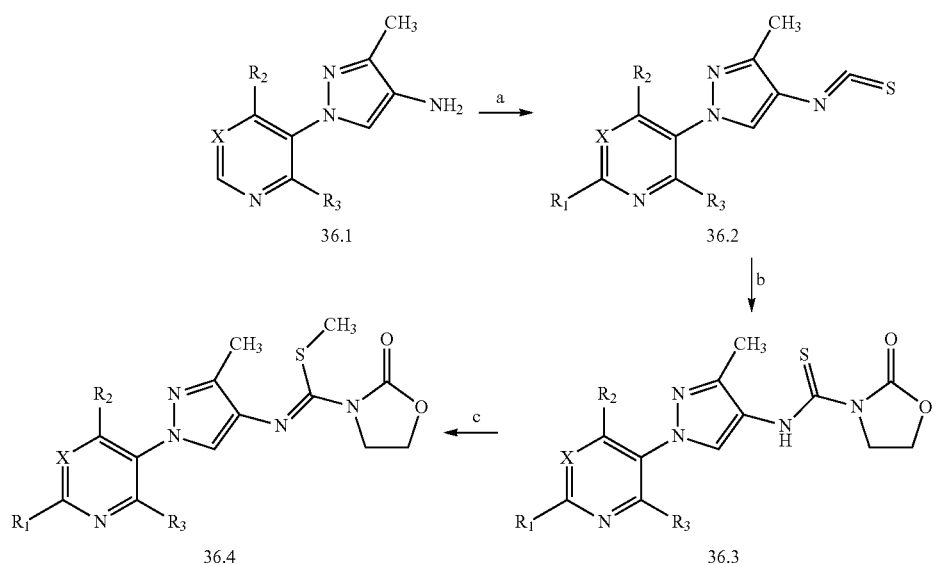

In step a of Scheme 37, ureas of Formula 37.1, wherein R1, R2, R3, R4, R5, R6, R8, and X are as previously defined, can be reacted with a base such as lithium bis(trimethylsilyl)amide in a polar aprotic solvent such as THF followed by an acyl chloride such as pivaloyl chloride to yield acylated ureas of Formula 37.2, wherein R1, R2, R3, R4, R5, R6, R8, are as previously defined, can be reacted with a base such as lithium bis(trimethylsilyl)amide in a polar aprotic solvent such as THF followed by a sulfonyl chloride such as methanesulfonyl chloride to yield sulfonylated ureas of Formula 37.3, wherein R1, R2, R3, R4, R5, R6, R8, and X are as previously defined.

Scheme 37

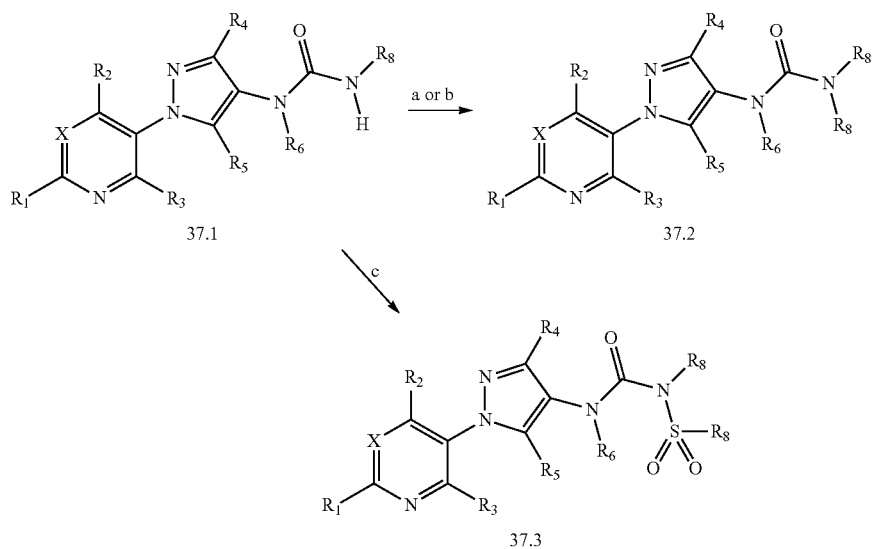

and X are as previously defined. In step b of Scheme 37, ureas of Formula 37.1, wherein R1, R2, R3, R4, R5, R6, R8, and X are as previously defined, can be reacted with a base such as lithium bis(trimethylsilyl)amide in a polar aprotic solvent such as THF followed by an alkyl halide such as (chloromethyl)(methyl)sulfane to yield alkylated ureas of Formula 37.2, wherein R1, R2, R3, R4, R5, R6, R8, and X are as previously defined. In step c of Scheme 37, ureas of Formula 37.1, wherein R1, R2, R3, R4, R5, R6, R8, and X In step a of Scheme 38, amines of Formula 38.1, wherein R6 is H or Me, can be reacted with an electrophile of Formula 38.2, wherein R8 and R9 are as previously defined, such as naphthalen-2-ylmethyl 3-(methylthio)propanimidothioate hydrobromide in a polar protic solvent such as ethanol followed by exposure to a base such as MP-Carbonate in a polar protic solvent such as methanol to give amidines of Formula 38.3, wherein R6 is H or Me, and R8 and R9 are as previously defined.

Scheme 38

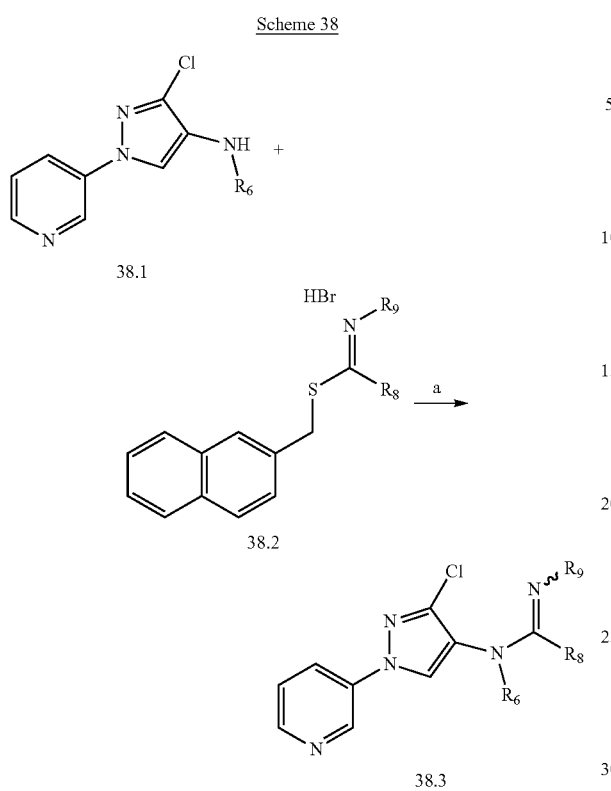

In step a of the Scheme 39, compounds of the Formula 39.1, wherein X, R1, R2, R3, R4, R5, R6 and R8 are as previously defined, can be treated with alcohols of the Formula 39.2, wherein R9 is as previously defined, in the presence of a base such as sodium hydride or potassium tert-butoxide in a polar aprotic solvent such as THF at appropriate temperatures, to give the corresponding ethers of the Formula 39.3. Alternatively, in step b of Scheme 39, thioethers of the Formula 39.5 can be obtained by treating compounds of the Formula 39.1, wherein X, R1, R2, R3, R4, R5, R6 and R8 are as previously defined, with thiols of the Formula 39.4, wherein R9 is as previously defined, in the presence of a base such as sodium hydride in an aprotic solvent such as THF.

In Scheme 40, compounds of the Formula 40.1, wherein X, R1, R2, R3, R4, R5, R6 and R8 are as previously defined, can be treated according to the conditions of Estrada et. al. (*Synlett*, 2011, 2387-2891), to give the corresponding sulfonamides of the Formula 40.2, wherein R9 is as previously defined with the proviso that at least one of the R9 is not H.

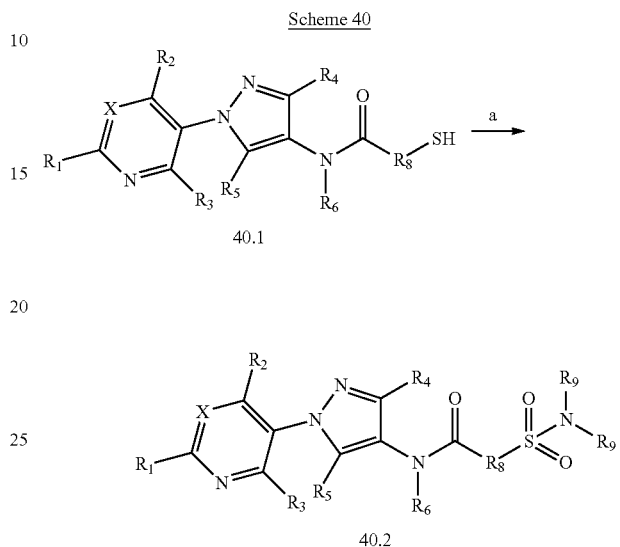

In step a of Scheme 41, compounds of the Formula 41.1, wherein X, R1, R2, R3, R4, R5 and R6 are as previously defined, can be coupled to acids of the Formula 41.2, wherein R8 and R9 are as previously defined, in the presence of a coupling reagent such as EDC.HCl and a base such as DMAP in an aprotic solvent such as dichloromethane to give phosphonates of the Formula 41.3. In step b of Scheme 41, phosphonates of the Formula 41.3, wherein X, R1, R2, R3, R4, R5, R6, R8 and R9 are as previously defined, can be treated with carbonyl compounds of the Formula 41.4, where R9 is as previously defined in the presence of a base such as sodium hydride in an aprotic solvent such as THF to give the corresponding alkenes of the Formula 41.5.

Scheme 39

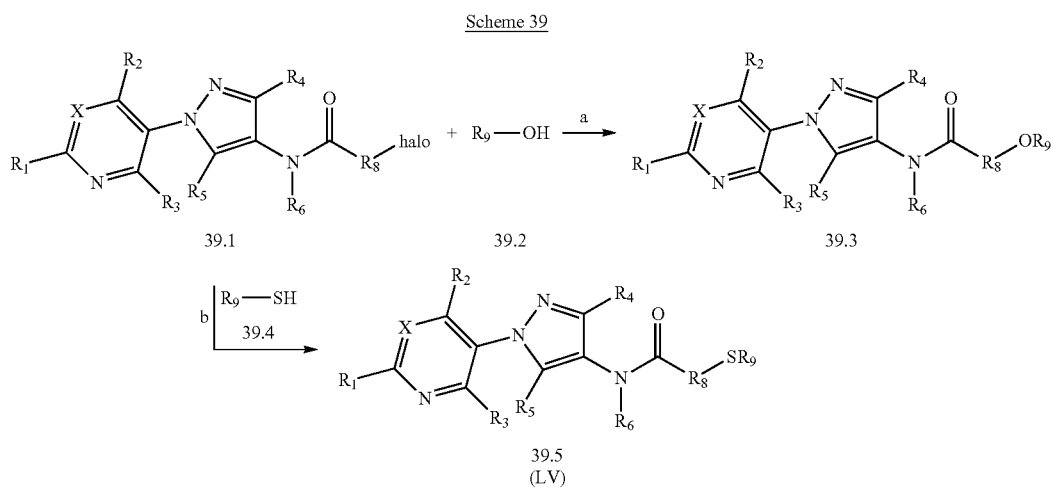

Scheme 41

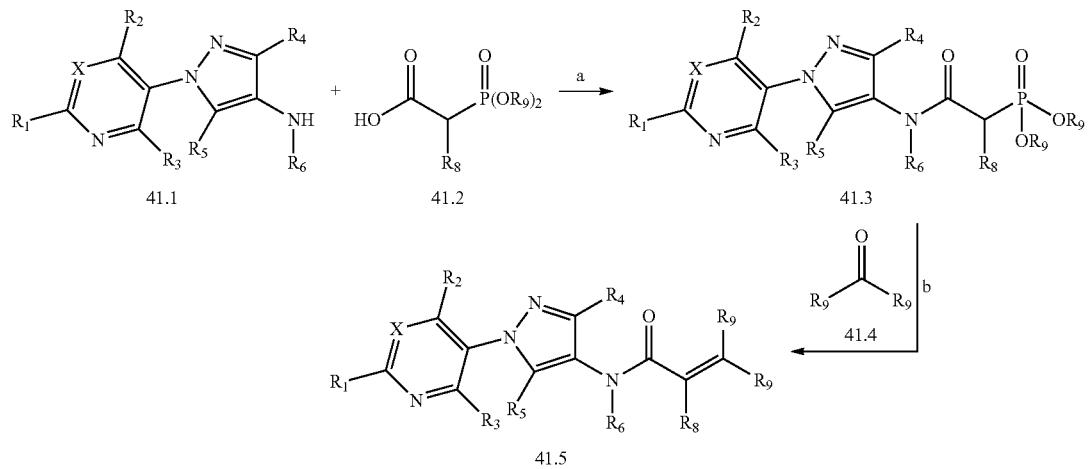

In step a of the Scheme 42, compounds of the Formula 42.1, wherein X, R1, R2, R3, R4, and R5, are as previously defined, can be treated with trifluoroacetic anhydride in the presence of a base such as triethylamine in an aprotic solvent such as dichloromethane to give amides of the Formula 42.2, where X, R1, R2, R3, R4, and R5, are as previously defined. In step b of Scheme 42, amides of the Formula 42.2, wherein X, R1, R2, R3, R4, and R5, are as previously defined, can be treated with an alkylating agent such as iodomethane in the presence of a base such as potassium tert-butoxide in a solvent such as THF to afford compounds of the Formula 42.3. In step c of the Scheme 42 amides of the Formula 42.3, wherein X, R1, R2, R3, R4, and R5, are as previously defined can be treated under basic conditions such as potassium carbonate and methanol to give the corresponding amines of the Formula 42.4.

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable Scheme 42

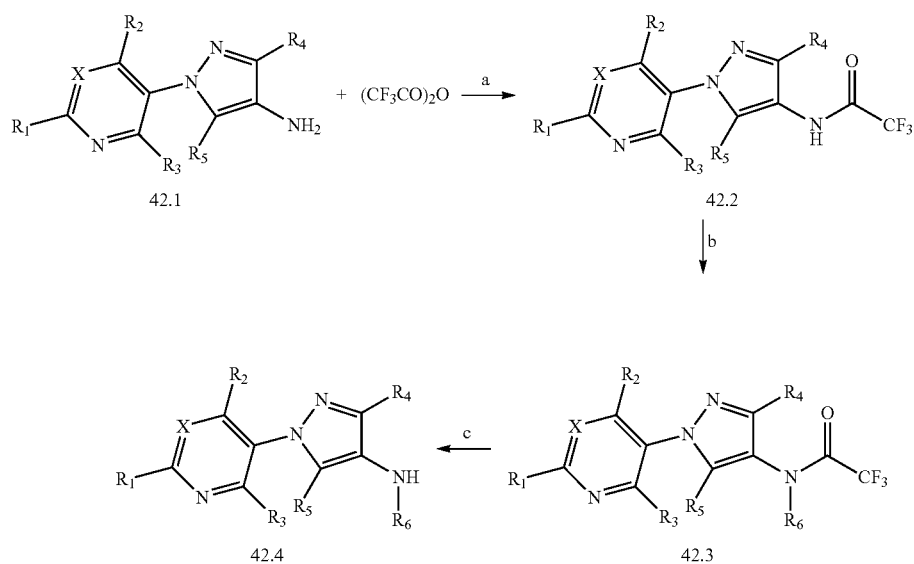

to name a molecule, the molecule is named using conventional naming rules. All NMR shifts are in ppm (δ) and were recorded at 300, 400 or 600 MHz unless otherwise stated. Examples using "room temperature" were conducted in climate controlled laboratories with temperatures ranging from about 20° C. to about 24° C.

Example 1, Step 1: Preparation of 3,3-bis-methylsulfanyl-1-pyridin-3-yl-propenone

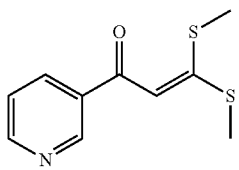

To a room-temperature suspension of sodium hydride (NaH, 60% suspension in mineral oil; 4.13 g, 86 mmol) in dry dimethyl sulfoxide (DMSO, 60 mL) under an atmosphere of nitrogen ($N_2$) was added 3-acetylpyridine (5.00 g, 41.3 mmol) dropwise over 30 minutes (min). The mixture was stirred for an additional 30 minutes at the same temperature. Carbon disulfide ($CS_2$; 3.27 g, 43 mmol) was added dropwise with vigorous stirring followed by iodomethane (12.21 g, 86 mmol) dropwise over a period of 45 min. Stirring was continued for an additional 18 hours (h) under $N_2$. The reaction was quenched with cold water ($H_2O$, 50 mL). The dark solid was filtered and washed with ice-cold ethyl alcohol (EtOH) until the washings were colorless. The off-white solid product was dried under vacuum at 60° C. to provide 3,3-bis-methylsulfanyl-1-pyridin-3-yl-propenone as a brown solid (4.8 g, 51%): $^1$H NMR (300 MHz, CDCl$_3$) δ 9.13 (d, J=1.8 Hz, 1H), 8.72 (dd, J=4.8, 1.6 Hz, 1H), 8.23 (ddd, J=7.9, 2, 2 Hz, 1H), 7.40 (dd, J=7.9, 4.8 Hz, 1H), 6.73 (s, 1H), 2.58 (d, J=9.4 Hz, 6H); MS m/z 226.2 (M+1).

1-(5-fluoropyridin-3-yl)-3,3-bis(methylthio)prop-2-en-1-one was prepared as described in Example 1, Step 1: mp 150-152° C.; $^1$H NMR (400 MHz, CDCl$_3$) δ 8.93 (t, J=1.6 Hz, 1H), 8.58 (d, J=2.8 Hz, 1H), 7.94 (ddd, J=8.9, 2.8, 1.7 Hz, 1H), 6.69 (s, 1H), 2.60 (s, 3H), 2.57 (s, 3H).

Example 1, Step 2: Preparation of (Z)-3-methyl-amino-3-methylsulfanyl-1-pyridin-3-yl-propenone

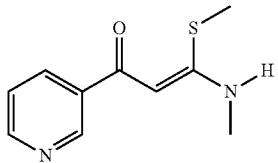

A solution of 3,3-bis-methylsulfanyl-1-pyridin-3-yl-propenone (18.6 g, 82.5 mmol) in absolute alcohol (400 mL) under $N_2$ was treated with methylamine hydrochloride (27.86 g, 412 mmol) followed by triethylamine (Et$_3$N; 58.5 mL, 412 mmol). The mixture was heated to reflux for 3 h, cooled to room temperature and concentrated under reduced pressure. The solid residue was dissolved in ethyl acetate (EtOAc; 150 mL). The solution was washed with $H_2O$ (2×50 mL) and brine (50 mL), dried over Na$_2$SO$_4$, concentrated under reduced pressure and purified by silica gel chromatography eluting with 10% EtOAc in petroleum ether to yield (Z)-3-methylamino-3-methylsulfanyl-1-pyridin-3-yl-propenone as a pale yellow solid (8.6 g, 50%): $^1$H NMR (300 MHz, CDCl$_3$) δ 11.8 (br s, 1H), 9.06 (s, 1H); 8.67 (d, J=3.9 Hz, 1H), 8.26 (d, J=8.0 Hz 1H), 7.46 (dd, J=7.6, 4.9 Hz 1H), 5.62 (s, 1H), 3.10 (d, J=5.2 Hz, 3H), 2.52 (s, 3H); MS (m/z) 209.2 [M+1].

(Z)-3-(ethylamino)-3(methylthio)-1-(pyridin-3-yl)prop-2-en-1-one was prepared as described in Example 1, Step 2: $^1$H NMR (400 MHz, CDCl$_3$) δ 11.81 (bs, 1H), 9.04 (dd, J=2.2, 0.7 Hz, 1H), 8.64 (dd, J=4.8, 1.7 Hz, 1H), 8.29-7.98 (m, 1H), 7.35 (ddd, J=7.9, 4.8, 0.9 Hz, 1H), 3.45 (q, J=7.2, 5.6 Hz, 2H), 2.50 (s, 3H), 1.35 (t, J=7.2 Hz, 3H).

(Z)-3-(cyclopropylmethyl)amino-3(methylthio)-1-(pyridin-3-yl)prop-2-en-1-one was prepared as described in Example 1, Step 2: $^1$H NMR (400 MHz, CDCl$_3$) δ 9.00 (s, 1H), 9.05 (dd, J=2.2, 0.7 Hz, 1H), 8.64 (dd, J=4.8, 1.7 Hz, 1H), 8.16 (dt, J=7.9, 2.0 Hz, 1H), 7.35 (ddd, J=7.9, 4.8, 0.8 Hz, 1H), 5.62 (s, 1H), 3.27 (dd, J=7.0, 5.5 Hz, 2H), 2.50 (s, 3H), 1.20-1.07 (m, 1H), 0.73-0.49 (m, 2H), 0.41-0.17 (m, 2H).

Example 1, Step 3: Preparation of methyl-(2-methyl-5-pyridin-3-pyrazol-3-yl)-amine

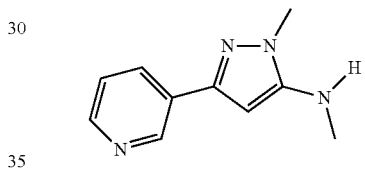

A solution of (Z)-3-methylamino-3-methylsulfanyl-1-pyridin-3-yl-propenone (3.00 g, 14 mmol) and methylhydrazine (729 mg, 15.4 mmol) in absolute EtOH (64 mL) was stirred at reflux for 18 h under $N_2$, cooled to room temperature and evaporated under reduced pressure. The residue was dissolved in EtOAc (50 mL), and the organic layer was washed with $H_2O$ (2×30 mL) and brine (30 mL), dried over Na$_2$SO$_4$, concentrated under reduced pressure and purified using silica gel chromatography eluting with a gradient of 0-1% EtOH in EtOAc to yield two regioisomers in a 1:2 ratio, with the major regioisomer as a brown solid (1.0 g, 27%): $^1$H NMR (300 MHz, CDCl$_3$) δ 8.97 (d, J=1.3 Hz, 1H), 8.51 (dd, J=3.6, 1.0 Hz, 1H), 8.07 (ddd, J=5.9, 1.4, 1.4 Hz, 1H), 7.30 (dd, J=5.9, 3.6 Hz, 1H), 5.82 (s, 1H), 3.69 (s, 3H), 2.93 (s, 3H); MS (m/z) 188.6 [M+1].

1-Ethyl-N-methyl-3-(pyridin-3-yl)-1H-pyrazol-5-amine was prepared as described in Example 1, Step 3: ESIMS m/z 204 ([M+2H]).

N-ethyl-1-methyl-3-(pyridin-3-yl)-1H-pyrazol-5-amine was prepared as described in Example 1, Step 3: ESIMS m/z 203 ([M+H]).

N-methyl-1-phenyl-3-(pyridin-3-yl)-1H-pyrazol-5-amine was prepared as described in Example 1, Step 3: ESIMS m/z 252 ([M+2H]).

N-(cyclopropylmethyl)-1-methyl-3-(pyridin-3-yl)-1H-pyrazol-5-amine was prepared as described in Example 1, Step 3: ESIMS m/z 230 ([M+2H]).

1-Isopropyl-N-methyl-3-(pyridin-3-yl)-1H-pyrazol-5-amine was prepared as described in Example 1, Step 3: $^1$H NMR (300 MHz, CDCl$_3$) δ 8.53 (s, 1H), 8.06-7.90 (m, J=7.2 Hz, 2H), 7.13 (dd, J=7.9, 5.6 Hz, 1H), 5.33 (s, 1H), 3.70 (bs, 1H), 3.65 (dt, J=13.2, 6.6 Hz, 1H), 2.31 (s, 3H), 0.88 (d, J=6.6 Hz, 6H); ESIMS m/z 217 ([M+H]).

3-(5-Fluoropyridin-3-yl)-N, 1-dimethyl-1H-pyrazol-5-amine was prepared as described in Example 1, Step 3: $^1$H NMR (300 MHz, CDCl$_3$) δ 8.28 (s, 1H), 7.87 (t, J=1.3 Hz, 1H), 7.60 (m, 1H), 6.66 (s, 1H), 5.28 (bs, 2H), 3.12 (s, 3H), 2.34 (s, 3H); ESIMS m/z 206 ([M+H])

Example 2: Preparation of (4-chloro-2-methyl-5-pyridin-3-yl-2H-pyrazol-3-yl)-methylamine

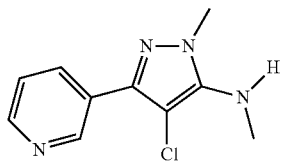

A mixture of methyl-(2-methyl-5-pyridin-3-yl-2H-pyrazol-3-yl)-amine (0.35 g, 1.8 mmol) and N-chlorosuccinimide (0.273 g, 2 mmol) was combined in acetonitrile (3 mL), stirred at room temperature for 30 minutes, concentrated under reduced pressure and purified using silica gel chromatography eluting with a gradient of EtOAc in hexanes to yield the title compound as a yellow oil (0.096 g, 23%): IR (thin film) 1581.6 cm$^{-1}$; $^1$H NMR (400 MHz, CDCl$_3$) δ 9.12 (d, J=1.5 Hz, 1H), 8.57 (dd, J=4.8, 1.3 Hz, 1H), 8.15 (ddd, J=7.8, 2.0, 2.0 Hz, 1H), 7.33 (dd, J=8.1, 5.1 Hz, 1H), 3.80 (s, 3H), 2.91 (d, J=5.8 Hz, 3H); ESIMS (m/z) 225.6 [M+2].

The reaction also gave 4-chloro-2-methyl-5-pyridin-3-yl-2H-pyrazol-3-ylamine as a green gum (0.046 g, 13%): IR (thin film) 1720.5 cm$^{-1}$; $^1$H NMR (CDCl$_3$, 400 MHz) δ 9.13 (br s, 1H), 8.57 (br s, 1H), 8.16 (dt, J=8.0, 2.0 Hz, 1H), 7.33 (dd, J=7.8, 4.8 Hz, 1H), 3.76 (s, 3H); ESIMS (m/z) 207.0 [M−1].

Example 3: Preparation of 2,N-dimethyl-N-(2-methyl-5-pyridin-3-yl-2H-pyrazol-3-yl)-3-methylsulfanyl-propionamide (Compound 1)

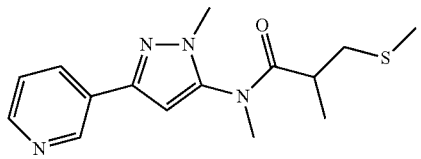 [SMILES: CSCC(C)C(=O)N(C)c1cc(-c2cccnc2)nn1C]

To a solution of methyl-(2-methyl-5-pyridin-3-yl-2H-pyrazol-3-yl)-amine (150 mg, 0.8 mmol) under N$_2$ in ice-cold dichloroethane (DCE; 2 mL) was added dropwise via pipette a solution of 2-methyl-3-methylsulfanyl-propionyl-chloride (146 mg, 0.9 mmol) in DCE (1.5 mL). After stirring for 10 minutes (min), a solution of 4-N,N-dimethylaminopyridine (DMAP; 107 mg, 0.9 mmol) in DCE (2 mL) was added dropwise. The ice bath was removed after 30 min, and the mixture was stirred at room temperature for 90 min and then at reflux for 14 h. The mixture was concentrated under reduced pressure and was purified by silica gel chromatography eluting with a gradient of EtOAc in hexane. The product, 2,N-dimethyl-N-(2-methyl-5-pyridin-3-yl-2H-pyrazol-3-yl)-3-methylsulfanyl-propionamide, was isolated as a yellow semi-solid (44 mg, 24%): $^1$H NMR (400 MHz, CDCl$_3$) δ 9.00 (s, 1H), 8.58 (s, 1H), 8.08 (br d, J=7.0 Hz, 1H), 7.35 (br dd, J=7.3, 4.8 Hz, 1H), 6.58 (br s, 0.5H), 6.49 (br s, 0.5H), 3.89-3.79 (m, 3H), 3.25 (s, 3H), 2.96-2.80 (m, 1H), 2.42-2.40 (m, 1H), 2.02-1.99 (m, 3H), 2.62 (m, 1H), 1.15 (d, J=6.0 Hz, 3H); MS (m/z) 305.0 [M+1].

Compounds 2-6, 9-10, 12, 18-21, 24-33, 477, 487, 509, 520, 556-557, 562-568 were made from the appropriate amines in accordance with the procedures disclosed in Example 3.

Example 4: Preparation of 1-methyl-1-(2-methyl-5-pyridin-3-yl-2H-pyrazol-3-yl)-3-(2-methylsulfanyl-ethyl)-urea (Compound 7)

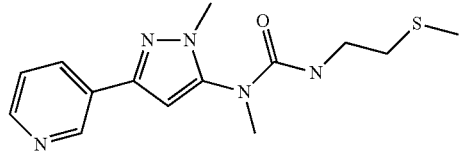 [SMILES: CSCCNC(=O)N(C)c1cc(-c2cccnc2)nn1C]

To a solution of methyl-(2-methyl-5-pyridin-3-yl-2H-pyrazol-3-yl)-amine (150 mg, 0.8 mmol) in ice-cold DCE (2 mL) under N$_2$ was added a solution of phosgene in toluene (20%, 0.43 mL, 0.88 mmol). The ice bath was removed after 30 min, and the mixture was stirred at room temperature for 1 h and at reflux for 2 h. The mixture was cooled to room temperature and then more phosgene (0.86 mL, 1.76 mmol) was added. The mixture was stirred at reflux for 90 min and then cooled in an ice bath. To this was added a solution of 2-methylthioethylamine (80 mg, 0.88 mmol) in DCE (2 mL). The ice bath was removed after 10 min, and the reaction mixture was stirred at reflux for 14 h, cooled, and diluted with DCE (30 mL). The diluted reaction mixture was washed with saturated NaHCO$_3$ (20 mL), dried over MgSO$_4$, adsorbed onto silica gel and purified using silica gel chromatography eluting with a gradient of methanol in dichloromethane to afford 1-methyl-1-(2-methyl-5-pyridin-3-yl-2H-pyrazol-3-yl)-3-(2-methylsulfanyl-ethyl)-urea as a yellow gum (14 mg, 6%): $^1$H NMR (400 MHz, CDCl$_3$) δ 8.99 (d, J=1.5 Hz, 1H), 8.57 (dd, J=4.8, 1.5 Hz, 1H), 8.08 (ddd, J=8.1, 2.1, 2.1 Hz, 1H), 7.34 (dd, J=7.9, 4.8 Hz, 1H), 6.52 (s, 1H), 4.88 (br t, J=5.5 Hz, 1H), 3.80 (s, 3H), 3.41 (q, J=6.3 Hz, 2H), 3.24 (s, 3H), 2.61 (t, J=6.3 Hz, 2H), 2.06 (s, 3H); ESIMS (m/z) 292.2 [M+2].

Compound 8 was made in accordance with the procedures disclosed in Example 4 using 2-(methylthio)ethanol in place of 2-methylthioethylamine.

Example 5: Preparation of 1-methyl-5-(pyridin-3-yl)-1H-pyrazol-3-amine and 1-methyl-3-(pyridin-3-yl)-1H-pyrazol-5-amine

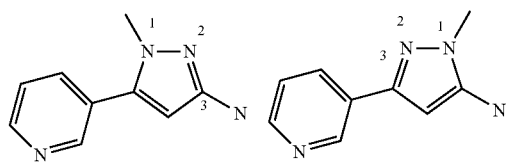

To ethanol (8.53 mL) was added 3-oxo-3-(pyridin-3-yl)propanenitrile (0.82 g, 5.61 mmol) and methylhydrazine (0.25 g, 5.61 mmol) and stirred at reflux for 2 hours. The reaction was cooled to room temperature and concentrated to dryness. The crude material was purified by silica gel chromatography by eluting with 0-20% MeOH/dichloromethane to yield two products—1-methyl-5-(pyridin-3-yl)-1H-pyrazol-3-amine (0.060 g; 6.14%): $^1$H NMR (300 MHz, CDCl$_3$) δ 8.72 (s, 1H), 8.53 (d, 1H), 7.76-7.63 (m, 1H), 7.43-7.33 (m, 1H), 5.75 (s, 1H), 3.76-3.57 (m, 5H) and 1-methyl-3-(pyridin-3-yl)-1H-pyrazol-5-amine (0.150 g, 15.35%): $^1$H NMR (300 MHz, CDCl$_3$) δ 8.88 (s, 1H), 8.48 (d, 1H), 7.99 (d, 1H), 7.38-7.07 (m, 1H), 585 (s, 1H), 3.80-3.59 (m, 5H).

Example 6, Step 1: Preparation of 3-pyrazol-1-yl-pyridine

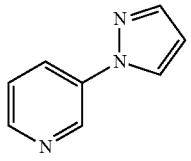 [SMILES: c1cncc(-n2cccn2)c1]

To a solution of 3-bromopyridine (5 g, 0.031 mol) in 50 ml of acetonitrile were added pyrazole (2.6 g, 0.038 mol), Cs$_2$CO$_3$ (16.5 g, 0.050 mol), Cu$_2$O (0.226 g, 0.0016 mol), and salicylaldoxime (0.867 g, 0.006 mol) under N$_2$ atmosphere. The reaction mass was refluxed for 24 hrs at 80° C. The reaction mass was concentrated and the crude was purified by column chromatography using ethyl acetate and hexane (1:1) to afford the pyrazolyl pyridine as a dark brown liquid (2 g, 43%): $^1$H NMR (400 MHz, CDCl$_3$) δ 8.99 (d, J=2.8 Hz, 1H), 8.48 (dd, J=4.8, 1.2 Hz, 1H), 8.11-8.08 (m, 1H), 7.99 (d, J=1.2 Hz, 1H), 7.78 (d, J=1.2 Hz, 1H), 7.38-7.35 (m, 1H), 6.53 (t, J=1.2 Hz, 1H); MS (m/z) 146 [M+1].

3-(3-chloro-1H-pyrazol-1-yl)pyridine was prepared as in Example 6, Step 1: mp 98-106° C.; $^1$H NMR (400 MHz, CDCl$_3$) δ 8.93 (d, J=2.6 Hz, 1H), 8.57 (dd, J=4.8, 1.4 Hz, 1H), 8.03 (ddd, J=8.3, 2.7, 1.5 Hz, 1H), 7.90 (d, J=2.5 Hz, 1H), 7.42 (ddd, J=8.3, 4.8, 0.7 Hz, 1H), 6.46 (d, J=2.5 Hz, 1H); $^{13}$C (DMSO-d$_6$) 148, 142, 140, 136, 131, 126, 125, 108.

2-methyl-3-(3-methyl-1H-pyrazol-1-yl)pyridine was prepared as in Example 6, Step 1: $^1$H NMR (400 MHz, CDCl$_3$) δ 8.53 (d, J=4.7 Hz, 1H), 7.67 (d, J=7.9 Hz, 1H), 7.54 (t, J=8.0 Hz, 1H), 7.27-7.19 (m, 1H), 6.27 (d, J=1.4 Hz, 1H), 2.53 (s, 3H), 2.38 (s, 3H).

3-(3-(Trifluoromethyl)-1H-pyrazol-1-yl)pyridine was prepared from the appropriate starting materials as described in Example 6, Step 1: mp 59.0-61.0° C.; $^1$H NMR (400 MHz, CDCl$_3$) δ 9.00 (s, 1H), 8.70-8.59 (m, 1H), 8.11 (ddd, J=8.3, 2.7, 1.5 Hz, 1H), 8.05-7.98 (m, 1H), 7.46 (dd, J=8.3, 4.8 Hz, 1H), 6.79 (d, J=2.4 Hz, 1H); EIMS m/z 213.

3-Fluoro-5-(3-methyl-1H-pyrazol-1-yl)pyridine was prepared from the appropriate starting materials as described in Example 6, Step 1: mp 70.0-72.0° C.; $^1$H NMR (400 MHz, CDCl$_3$) δ 8.76-8.73 (m, 1H), 8.37-8.33 (m, 1H), 7.88-7.85 (m, 1H), 7.84-7.79 (m, 1H), 6.34-6.29 (m, 1H), 2.37 (s, 3H); EIMS m/z 177.

3-(3-Chloro-1H-pyrazol-1-yl)-5-fluoropyridine was prepared from the appropriate starting materials as described in Example 6, Step 1: mp 77.0-82.0° C.; $^1$H NMR (400 MHz, CDCl$_3$) δ 8.75 (d, J=1.8 Hz, 1H), 8.43 (d, J=2.3 Hz, 1H), 7.92 (d, J=2.6 Hz, 1H), 7.84 (dt, J=9.3, 2.4 Hz, 1H), 6.48 (d, J=2.6 Hz, 1H); EIMS m/z 198.

3-(3-methyl-1H-pyrazol-1-yl)pyridine was prepared as described in Example 6, Step 1: $^1$H NMR (400 MHz, CDCl$_3$) δ 8.94 (bs, 1H), 8.51 (d, J=3.9 Hz, 1H), 8.02 (ddd, J=8.3, 2.6, 1.5 Hz, 1H), 7.90-7.79 (m, 1H), 7.39 (dd, J=8.2, 5.1 Hz, 1H), 6.30 (d, J=2.4 Hz, 1H), 2.39 (s, 3H).

3-(5-methyl-1H-pyrazol-1-yl)pyridine was prepared as in Example 6, Step 1: $^1$H NMR (400 MHz, CDCl$_3$) δ 8.77 (d, J=2.5 Hz, 1H), 8.65 (dd, J=4.8, 1.5 Hz, 1H), 7.84 (ddd, J=8.2, 2.5, 1.5 Hz, 1H), 7.63 (d, J=1.6 Hz, 1H), 7.44 (ddd, J=8.2, 4.8, 0.7 Hz, 1H), 6.225 (dd, J=1.6, 0.7 Hz, 1H), 2.40 (s, 3H).

Example 6, Step 2: Preparation of 3-(4-nitro-pyrazol-1-yl)-pyridine

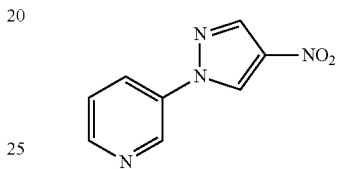

3-Pyrazol-1-yl-pyridine (2 g, 0.032 mol) was dissolved in concentrated H$_2$SO$_4$ (32 mL 0.598 mmol) and cooled at −5° C. using an ice bath. To the reaction mass, a 1:1 mixture of concentrated HNO$_3$ (30 mL, 0.673 mmol) and concentrated H$_2$SO$_4$ (30 ml, 15 Vol.) was added dropwise over a period of 30 min. Cooling was discontinued and the reaction mixture was stirred at room temperature overnight. After the reaction was complete, the mixture was poured over crushed ice and neutralized with saturated NaHCO$_3$, filtered, washed with water and dried to furnish the nitro pyrazole as pale yellow solid (1.8 g, 68%): $^1$H NMR (400 MHz, DMSO-d$_6$) δ 9.03 (d, J=2.8 Hz, 1H); 8.70 (dd, J=4.8, 1.6 Hz, 1H), 8.69 (s, 1H), 8.33 (s, 1H), 8.11-8.08 (m, 1H), 7.51 (dd, J=8.4, 4.8 Hz, 1H); MS (m/z) 191 [M+1].

3-(3-chloro-4-nitro-1H-pyrazol-1-yl)pyridine was prepared as in Example 6, Step 2: mp 139-142° C., $^1$H NMR (400 MHz, CDCl$_3$) δ 9.01 (d, J=2.0 Hz, 1H), 8.73 (d, J=4.9 Hz, 2H), 8.08 (ddd, J=8.3, 2.5, 1.3 Hz, 1H), 7.52 (dd, J=8.3, 4.8 Hz, 1H), EIMS m/z 224.

3-(5-methyl-4-nitro-1H-pyrazol-1-yl)pyridine was prepared as in Example 6, Step 2: $^1$H NMR (400 MHz, CDCl$_3$) δ 8.81-8.71 (m, 2H), 8.32 (s, 1H), 7.83 (ddd, J=8.2, 2.5, 1.6 Hz, 1H), 7.54 (dd, J=8.2, 4.8 Hz, 1H), 2.72 (s, 3H).

2-methyl-3-(3-methyl-4-nitro-1H-pyrazol-1-yl)pyridine was prepared as in Example 6, Step 2: $^1$H NMR (400 MHz, d$_6$-DMSO) δ 14.01 (s, 1H), 9.37 (d, J=4.0 Hz, 1H), 8.69 (t, J=17.3 Hz, 1H), 8.21 (dd, J=7.7, 4.8 Hz, 1H), 2.29 (s, 3H), 2.20 (s, 3H); $^{13}$C 154, 150, 146, 135, 134.9, 134.8, 134.3, 122, 21, 14; EIMS m/z 218.

3-(3-methyl-4-nitro-1H-pyrazol-1-yl)pyridine was prepared as in Example 6, Step 2: mp 122-124° C.; $^1$H NMR (400 MHz, CDCl$_3$) δ 9.01 (d, J=2.5 Hz, 1H), 8.77-8.56 (m, 2H), 8.07 (ddd, J=8.3, 2.7, 1.5 Hz, 1H), 7.56-7.37 (m, 1H), 2.66 (s, 3H); EIMS m/z 208.

3-Fluoro-5-(3-methyl-4-nitro-1H-pyrazol-1-yl)pyridine was prepared from the appropriate starting material as described in Example 6, Step 2: mp 90.0-92.0° C.; $^1$H NMR (400 MHz, CDCl$_3$) δ 8.82 (d, J=2.0 Hz, 1H), 8.69 (s, 1H), 8.54 (d, J=2.5 Hz, 1H), 7.89 (dt, J=8.9, 2.4 Hz, 1H), 2.66 (s, 3H); EIMS m/z 222.

3-(4-Nitro-3-(trifluoromethyl)-1H-pyrazol-1-yl)pyridine was prepared from the appropriate starting material as described in Example 6, Step 2: mp 121.0-123.0° C.; $^1$H NMR (400 MHz, CDCl$_3$) δ 9.04 (d, J=2.5 Hz, 1H), 8.79 (s, 1H), 8.77 (d, J=0.9 Hz, 1H), 8.13 (ddd, J=8.3, 2.7, 1.4 Hz, 1H), 7.55 (dt, J=10.8, 5.4 Hz, 1H); EIMS m/z 258.

3-(3-Chloro-4-nitro-1H-pyrazol-1-yl)-5-fluoropyridine was prepared from the appropriate starting material as described in Example 6, Step 2: mp 109.5-111.0° C.; $^1$H NMR (400 MHz, CDCl$_3$) δ 8.83 (d, J=2.1 Hz, 1H), 8.75 (s, 1H), 8.60 (d, J=2.4 Hz, 1H), 7.89 (dt, J=8.6, 2.4 Hz, 1H); EIMS m/z 242.

3-(3-Bromo-4-nitro-1H-pyrazol-1-yl)pyridine was prepared from the appropriate starting material as described in Example 6, Step 2: mp 139.0-141.0° C.; $^1$H NMR (400 MHz, CDCl$_3$) δ 9.01 (d, J=2.5 Hz, 1H), 8.73 (dd, J=4.7, 1.1 Hz, 1H), 8.71 (s, 1H), 8.15-8.00 (m, 1H), 7.52 (dd, J=8.3, 4.8 Hz, 1H); ESIMS m/z 271 ([M+2]$^+$).

Example 6, Step 3: Preparation of 1-pyridin-3-yl-1H-pyrazol-4-ylamine

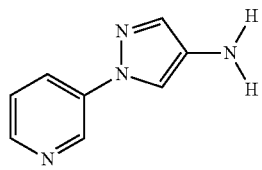 [SMILES: Nc1cnn(-c2cccnc2)c1]

To a solution of 3-(4-nitro-pyrazol-1-yl)-pyridine (1.8 g, 0.009 mol) in dry THF (18 mL) was added 5% Pd/C (180 mg) under nitrogen atmosphere. The mixture was then stirred under hydrogen atmosphere until the reaction was complete. The reaction mixture was filtered through a pad of celite, and concentrated to dryness to give an impure dark brown solid (1.76 g): $^1$H NMR (400 MHz, DMSO-d$_6$) δ 8.89 (dd, J=2.8. 0.4 Hz, 1H); 8.48 (dd, J=4.8, 1.2 Hz, 1H), 7.99-7.96 (m, 1H), 7.54 (d, J=1.2 Hz, 1H), 7.45 (d, J=0.4 Hz, 1H), 7.38-7.35 (m, 1H), 4.81 (bs 1H); ESIMS (m/z) 161 [M+1].

5-methyl-1-(pyridin-3-yl)-1H-pyrazol-4-amine was prepared as in Example 6, Step 3: $^1$H NMR (400 MHz, CDCl$_3$) δ 8.74 (d, J=2.3 Hz, 1H), 8.63-8.50 (m, 1H), 7.81 (ddd, J=8.2, 2.5, 1.5 Hz, 1H), 7.46-7.33 (m, 2H), 2.64 (bs, 1H), 2.29 (s, 3H); $^{13}$C (DMSO-d$_6$) 147, 144, 137, 133, 130, 129, 124, 123, 10; EIMS m/z 174

3-methyl-1-(pyrimidin-5-yl)-1H-pyrazol-4-amine was prepared as in Example 6, Step 3: mp 211-215° C.; $^1$H NMR (400 MHz, CDCl$_3$) δ 9.10-8.87 (m, 3H), 7.51 (s, 1H), 3.24 (bs, 2H), 2.29 (s, 3H); ESIMS m/z 176 ([M+H]).

3-chloro-1-(pyrimidin-5-yl)-1H-pyrazol-4-amine was prepared as in Example 6, Step 3: mp 146-148° C.; $^1$H NMR (400 MHz, CDCl$_3$) δ 9.07 (s, 1H), 9.02 (s, 2H), 7.52 (s, 1H), 3.45 (s, 2H); ESIMS m/z 196 ([M+H]).

Example 7: Preparation of methyl-(1-pyridin-3-yl-1H-pyrazol-4-yl)-amine

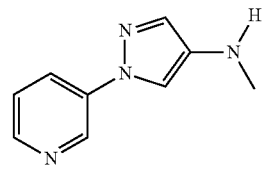

Method A:
To a 25 ml round bottom flask containing 1-pyridin-3-yl-1H-pyrazol-4-ylamine (1.76 g, 0.011 mol) in ethanol (26.4 mL) was added benzotriazole (1.31 g, 0.011 mol). The reaction was cooled at 0° C.-10° C. and formaldehyde (0.36 mL, 0.0121 mol) was added slowly and kept for 30 min at this temperature. The reaction was filtered and concentrated to dryness. The crude material (2.56 g, 0.009 mol) was dissolved in dry tetrahydrofuran (25.6 mL), cooled to 0° C. and sodium borohydride (0.326 g, 0.00882 mol.) was added over 15 min. The reaction was warmed to room temperature and stirred for 2 hours. The reaction was poured into water and extracted using dichloromethane, the organic layer was dried over anhydrous Na$_2$SO$_4$ and concentrated to dryness. Purified the crude material by silica gel chromatography eluting with 20% methanol/chloroform to afford the desired product as a brown solid (0.610 g, 32%): $^1$H NMR (400 MHz, d$_6$-DMSO) δ 8.92 (d, J=2.4 Hz, 1H), 8.47 (dd, J=4.8, 1.6 Hz, 1H), 8.01-7.98 (m, 1H), 7.45 (s, 1H), 7.30 (s, 1H), 7.37 (dd, J=8.0, 4.4 Hz, 1H), 2.84 (s, 3H); ESIMS m/z 175 ([M+1]).

Method B:
1-pyridin-3-yl-1H-pyrazol-4-ylamine (1.0 g, 6.2 mmol) was dissolved in triethyl orthoformate (5 mL, 30 mmol) and to that was added trifluoroacetic acid (3-4 drops). The reaction mixture was refluxed at 120° C. for 3 hours and was then concentrated. The crude was dissolved in ethanol (5 ml), cooled to 0° C. and treated with sodium borohydride (0.6 g, 15.7 mmol). After warming to room temperature, the mixture was refluxed for 3 hours. The mixture was concentrated and the residue was suspended between water and diethyl ether. The diethyl ether layer was separated and concentrated to dryness. The crude material was purified by silica gel chromatography, eluting with 5% methanol/chloroform to afford the desired product as a pale yellow solid (0.3 g, 27%): mp 65-67° C.; $^1$H NMR (300 MHz, CDCl$_3$) δ 8.91 (bs, 1H), 8.46 (d, J=4.5 Hz, 1H), 7.99 (d, J=8.3 Hz, 1H), 7.43 (s, 1H), 7.41 (s, 1H), 7.36 (dd, J=8.3, 4.7 Hz, 1H), 2.86 (d, J=12.4 Hz, 3H); ESIMS m/z 175 ([M+1]).

Example 8: Preparation of ethyl-(1-pyridin-3-yl-1H-pyrazol-4-yl)-amine

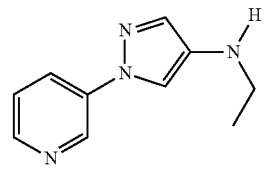

Method A:

To 1-pyridin-3-yl-1H-pyrazol-4-ylamine (0.5 g, 3.12 mmol) in dichloromethane (5 mL) was added acetyl chloride (0.28 g, 3.75 mmol) followed by DMAP (0.57 g, 4.68 mmol) and stirred at room temperature for 3 hours. The reaction mixture was concentrated and purified by silica gel column chromatography. The recovered material was dissolved in tetrahydrofuran (5 mL) and lithium aluminum hydride (0.23 g, 6.25 mmol) was added and stirred at room temperature for 12 hours. The reaction was quenched with saturated $Na_2SO_4$ and filtered through celite. The filtrate was collected and concentrated to dryness. The crude material was purified by silica gel column chromatography eluting with 0-5% methanol/chloroform and resubjected to silica gel chromatography, eluting with 0-100% ethyl acetate/hexanes) to give the desired product (0.080 g, 14%): $^1$H NMR (400 MHz, $CDCl_3$) δ 8.90 (d, J=2.7 Hz, 1H), 8.46 (dd, J=4.7, 1.3 Hz, 1H), 7.98 (ddd, J=8.3, 2.6, 1.5 Hz, 1H), 7.41 (dt, J=13.3, 6.6 Hz, 2H), 7.36 (ddd, J=8.3, 4.7, 0.7 Hz, 1H), 3.10 (q, J=7.1 Hz, 2H), 1.27 (t, 3H).

Method B:

To a solution of tert-butyl ethyl(1-(pyridin-3-yl)-1H-pyrazol-4-yl)carbamate (3.4 g, 11.79 mmol) in dichloromethane (4.54 mL) was added trifluoroacetic acid (9 mL), and the reaction mixture was stirred for 1 hour at room temperature. Toluene was added and the reaction was concentrated to near dryness. The reaction was poured into a separatory funnel and carefully quenched with saturated aqueous $NaHCO_3$ and extracted with dichloroethane.

The organic layer was dried ($MgSO_4$), filtered and concentrated to dryness. The crude product was purified by silica gel chromatography (0-10% MeOH/dichloromethane) to give the desired product as a pale yellow oil (2.10 g, 95%): $^1$H NMR (400 MHz, $CDCl_3$) δ 8.90 (dd, J=1.8, 0.8 Hz, 1H), 8.51-8.39 (m, 1H), 7.97 (ddt, J=8.3, 2.7, 1.3 Hz, 1H), 7.41 (d, J=0.8 Hz, 2H), 7.38-7.30 (m, 1H), 3.21-2.93 (m, 2H), 1.34-1.19 (m, 3H).

3-chloro-N-ethyl-1-(pyridin-3-yl)-1H-pyrazol-4-amine was prepared as described in Example 8, Method B: $^1$H NMR (400 MHz, $CDCl_3$) δ 8.87 (d, J=2.5 Hz, 1H), 8.47 (dd, J=4.7, 1.2 Hz, 1H), 7.96 (ddd, J=8.4, 2.6, 1.4 Hz, 1H), 7.38-7.32 (m, 2H), 3.11 (q, J=7.1 Hz, 2H), 2.97 (bs, 1H), 1.31 (t, J=7.1 Hz, 3H).

3-chloro-N-methyl-1-(pyridin-3-yl)-1H-pyrazol-4-amine was prepared as in Example 8, Method B: mp 108-118 C; $^1$H NMR (400 MHz, $CDCl_3$) δ 8.88 (d, J=2.4 Hz, 1H), 8.48 (dd, J=4.7, 1.4 Hz, 1H), 7.96 (ddd, J=8.3, 2.7, 1.4 Hz, 1H), 7.41-7.29 (m, 2H), 2.87 (s, 3H); EIMS m/z 208.

N,3-dimethyl-1-(pyridin-3-yl)-1H-pyrazol-4-amine was prepared as in Example 8, Method B: $^1$H NMR (400 MHz, $CDCl_3$) δ 9.03-8.73 (m, 1H), 8.41 (dd, J=4.7, 1.4 Hz, 1H), 7.95 (ddd, J=8.4, 2.7, 1.4 Hz, 1H), 7.42-7.27 (m, 2H), 2.85 (s, 4H), 2.25 (s, 3H); EIMS m/z 189

3-chloro-N-(cylopropylmethyl)-1-(pyridin-3-yl)-1H-pyrazol-4-amine was prepared as in Example 8, Method B: $^1$H NMR (400 MHz, $CDCl_3$) δ 8.86 (d, J=2.5 Hz, 1H), 8.47 (dd, J=4.7, 1.4 Hz, 1H), 8.03-7.89 (m, 1H), 7.40-7.29 (m, 2H), 3.21 (s, 1H), 2.91 (d, J=4.4 Hz, 2H), 1.18-1.02 (m, 1H), 0.65-0.45 (m, 2H), 0.41-0.12 (m, 2H).

3-chloro-N-propyl-1-(pyridin-3-yl)-1H-pyrazol-4-amine was prepared as in Example 8, Method B: $^1$H NMR (400 MHz, $CDCl_3$) δ 8.86 (d, J=2.6 Hz, 1H), 8.47 (dd, J=4.7, 1.4 Hz, 1H), 8.01-7.89 (m, 1H), 7.42-7.27 (m, 2H), 3.23-2.84 (m, 3H), 1.77-1.59 (m, 2H), 1.03 (t, J=7.4 Hz, 3H).

1-(5-Fluoropyridin-3-yl)-N, 3-dimethyl-1H-pyrazol-4-amine was prepared from the appropriate Boc-amine as described in Example 8, Method B: mp 142.0-143.5° C.; $^1$H NMR (400 MHz, $CDCl_3$) δ 8.67 (s, 1H), 8.26 (d, J=2.3 Hz, 1H), 7.73 (dt, J=10.0, 2.4 Hz, 1H), 7.27 (s, 1H), 2.92-2.81 (m, 4H), 2.24 (s, 3H); ESIMS m/z 207 ([M+H]$^+$).

N-ethyl-1-(5-fluoropyridin-3-yl)-3-methyl-1H-pyrazol-4-amine was prepared from the appropriate Boc-amine as described in Example 8, Method B: mp 85.0-86.0° C.; $^1$H NMR (400 MHz, $CDCl_3$) δ 8.66 (s, 1H), 8.25 (d, J=2.5 Hz, 1H), 7.72 (dt, J=10.0, 2.3 Hz, 1H), 7.27 (s, 1H), 3.07 (q, J=7.1 Hz, 2H), 2.71 (s, 1H), 2.25 (s, 3H), 1.30 (t, J=7.1 Hz, 3H); ESIMS m/z 221 ([M+H]$^+$).

3-Methyl-N-propyl-1-(pyridin-3-yl)-1H-pyrazol-4-amine was prepared from the appropriate Boc-amine as described in Example 8, Method B: mp 65.0-67.0° C.; $^1$H NMR (400 MHz, $CDCl_3$) δ 8.86 (d, J=2.4 Hz, 1H), 8.40 (dd, J=4.7, 1.4 Hz, 1H), 7.94 (ddd, J=8.3, 2.7, 1.5 Hz, 1H), 7.35-7.28 (m, 2H), 3.00 (t, J=7.1 Hz, 2H), 2.26 (s, 3H), 1.76-1.58 (m, 2H), 1.03 (t, J=7.4 Hz, 3H); ESIMS m/z 217 ([M+H]$^+$).

N-(cyclopropylmethyl)-3-methyl-1-(pyridin-3-yl)-1H-pyrazol-4-amine was prepared from the appropriate Boc-amine as described in Example 8, Method B: mp 73.0-75.0° C.; $^1$H NMR (400 MHz, $CDCl_3$) δ 8.86 (d, J=2.4 Hz, 1H), 8.40 (dd, J=4.7, 1.3 Hz, 1H), 7.94 (ddd, J=8.3, 2.6, 1.5 Hz, 1H), 7.35-7.28 (m, 2H), 2.87 (d, J=6.9 Hz, 2H), 2.75 (s, 1H), 2.28 (s, 3H), 1.22-1.05 (m, 1H), 0.63-0.56 (m, 2H), 0.26 (q, J=4.7 Hz, 2H); ESIMS m/z 229 ([M+H]$^+$).

N-isopropyl-3-methyl-1-(pyridin-3-yl)-1H-pyrazol-4-amine was prepared from the appropriate Boc-amine as described in Example 8, Method B: IR (thin film) 3303 cm$^{-1}$; $^1$H NMR (400 MHz, $CDCl_3$) δ 8.86 (d, J=2.3 Hz, 1H), 8.41 (dd, J=4.7, 1.4 Hz, 1H), 7.94 (ddd, J=8.3, 2.7, 1.5 Hz, 1H), 7.36-7.28 (m, 2H), 3.30 (hept, J=6.3 Hz, 1H), 2.25 (s, 3H), 1.24 (d, J=6.3 Hz, 6H); EIMS m/z 216.

5-Ethoxy-1-(5-fluoropyridin-3-yl)-N,3-dimethyl-1H-pyrazol-4-amine was prepared from the appropriate Boc-amine as described in Example 8, Method B: IR (thin film) 3340 cm$^{-1}$; $^1$H NMR (400 MHz, $CDCl_3$) δ 8.91 (s, 1H), 8.31 (d, J=2.5 Hz, 1H), 7.88-7.80 (m, 1H), 4.24 (q, J=7.1 Hz, 2H), 2.79 (s, 3H), 2.24 (s, 3H), 1.36 (t, J=7.1 Hz, 3H); EIMS m/z 250.

5-Bromo-N-methyl-1-(pyridin-3-yl)-1H-pyrazol-4-amine was prepared from the appropriate Boc-amine as described in Example 8, Method B: mp 77.0-79.0° C.; $^1$H NMR (400 MHz, $CDCl_3$) δ 8.90 (d, J=2.0 Hz, 1H), 8.63 (d, J=3.9 Hz, 1H), 7.93 (ddd, J=8.2, 2.4, 1.5 Hz, 1H), 7.51 (s, 1H), 7.43 (dd, J=8.2, 4.8 Hz, 1H), 4.49 (s, 1H), 2.91 (s, 3H); ESIMS m/z 255 ([M+2]$^+$).

5-Fluoro-N, 3-dimethyl-1-(pyridin-3-yl)-1H-pyrazol-4-amine was prepared from the appropriate Boc-amine as described in Example 8, Method B: $^1$H NMR (400 MHz, $CDCl_3$) δ 8.91 (t, J=2.1 Hz, 1H), 8.50 (dd, J=4.8, 1.5 Hz, 1H), 7.93 (ddt, J=8.3, 2.8, 1.5 Hz, 1H), 7.37 (ddd, J=8.3, 4.8, 0.7 Hz, 1H), 2.86 (d, J=1.6 Hz, 3H), 2.43 (s, 2H), 2.24 (s, 3H); EIMS m/z 206.

5-Bromo-N, 3-dimethyl-1-(pyridin-3-yl)-1H-pyrazol-4-amine was prepared from the appropriate Boc-amine as described in Example 8, Method B: $^1$H NMR (400 MHz, $CDCl_3$) δ 8.86 (dd, J=2.5, 0.5 Hz, 1H), 8.59 (dd, J=4.8, 1.5 Hz, 1H), 7.88 (ddd, J=8.2, 2.6, 1.5 Hz, 1H), 7.40 (ddd, J=8.2, 4.8, 0.7 Hz, 1H), 2.85 (s, 3H), 2.69 (s, 1H), 2.35 (s, 3H); ESIMS m/z 268 ([M+H]$^+$).

5-Chloro-N, 3-dimethyl-1-(pyridin-3-yl)-1H-pyrazol-4-amine was prepared from the appropriate Boc-amine as described in Example 8, Method B: $^1$H NMR (400 MHz, $CDCl_3$) δ 8.87 (d, J=2.3 Hz, 1H), 8.59 (dd, J=4.8, 1.3 Hz, 1H), 7.90 (ddd, J=8.2, 2.6, 1.5 Hz, 1H), 7.40 (ddd, J=8.2, 4.8, 0.6 Hz, 1H), 2.87 (s, 3H), 2.45-2.19 (m, 4H); EIMS m/z 223.

3-Chloro-1-(5-fluoropyridin-3-yl)-N-methyl-1H-pyrazol-4-amine was prepared from the appropriate Boc-amine as described in Example 8, Method B: mp 117.5-119.0° C.; $^1$H NMR (400 MHz, CDCl$_3$) δ 8.68 (d, J=1.1 Hz, 1H), 8.33 (d, J=2.5 Hz, 1H), 7.75 (dt, J=9.6, 2.4 Hz, 1H), 7.31 (s, 1H), 3.14 (s, 1H), 2.87 (s, 3H); ESIMS m/z 227 ([M]$^+$).

3-Chloro-N-ethyl-1-(5-fluoropyridin-3-yl)-1H-pyrazol-4-amine amine was prepared from the appropriate Boc-amine as described in Example 8, Method B: $^1$H NMR (400 MHz, CDCl$_3$) δ 8.70-8.63 (m, 1H), 8.32 (d, J=2.4 Hz, 1H), 7.74 (dt, J=9.7, 2.4 Hz, 1H), 7.31 (s, 1H), 3.11 (q, J=7.2 Hz, 2H), 1.31 (t, J=7.1 Hz, 3H).

1-(5-Fluoropyridin-3-yl)-N-methyl-3-vinyl-1H-pyrazol-4-amine was prepared from the appropriate Boc-amine as described in Example 8, Method B: 105.0-107.0° C.; $^1$H NMR (400 MHz, CDCl$_3$) δ 8.72 (s, 1H), 8.31 (d, J=2.5 Hz, 1H), 7.81 (dt, J=9.8, 2.4 Hz, 1H), 7.33 (s, 1H), 6.75 (dd, J=18.0, 11.6 Hz, 1H), 5.83 (dd, J=18.0, 1.1 Hz, 1H), 5.46 (dd, J=11.6, 1.1 Hz, 1H), 2.86 (s, 3H); ESIMS m/z 219 ([M+H]$^+$).

3-Cyclopropyl-1-(5-fluoropyridin-3-yl)-N-methyl-1H-pyrazol-4-amine was prepared from the appropriate Boc-amine as described in Example 8, Method B: mp 118.0-119.5° C.; $^1$H NMR (400 MHz, CDCl$_3$) δ 8.66-8.58 (m, 1H), 8.23 (d, J=2.5 Hz, 1H), 7.75-7.68 (m, 1H), 7.25 (s, 1H), 3.09 (s, 1H), 2.86 (s, 3H), 1.78-1.63 (m, 1H), 0.99-0.90 (m, 4H); ESIMS m/z 233 ([M+H]$^+$).

3-Chloro-1-(pyridin-3-yl)-1H-pyrazol-4-amine was prepared from the appropriate Boc-amine as described in Example 8, Method B: mp 137.9-139.9; $^1$H NMR (400 MHz, CDCl$_3$) δ 8.84 (d, J=2.4 Hz, 1H), 8.50 (dd, J=4.7, 1.4 Hz, 1H), 7.95 (ddd, J=8.3, 2.7, 1.5 Hz, 1H), 7.52 (s, 1H), 7.37 (ddd, J=8.4, 4.7, 0.7 Hz, 1H), 3.18 (s, 2H); ESIMS m/z 196 ([M+H]$^+$).

2-((3-Chloro-1-(pyridin-3-yl)-1H-pyrazol-4-yl)amino)acetonitrile was prepared from tert-butyl(3-chloro-1-(pyridin-3-yl)-1H-pyrazol-4-yl)(cyanomethyl)carbamate as in Example 8, Method B: mp 141-143° C.; $^1$H NMR (300 MHz, CDCl$_3$) δ 8.91 (d, J=2.7 Hz, 1H), 8.54 (dd, J=5.1, 1.8 Hz, 1H), 7.97 (m, 1H), 7.62 (s, 1H), 7.38 (dd, J=12.0, 7.5 Hz, 1H), 4.97 (d, J=6.9 Hz, 2H), 3.52 (m, 1H); EIMS m/z 235 ([M+1]$^+$).

N-3-dimethyl-1-(pyrimidin-5-yl)-1H-pyrazol-4-amine was prepared as in Example 8, Method B: mp 139-143° C.; $^1$H NMR (400 MHz, CDCl$_3$) δ 9.02 (s, 2H), 9.00 (s, 1H), 7.30 (s, 1H), 2.87 (d, J=11.5 Hz, 3H), 2.27 (s, 3H); ESIMS m/z 190 ([M+H]).

3-chloro-N-methyl-1-(pyrimidin-5-yl)1-1H-pyrazol-4-amine was prepared as in Example 8, Method B: mp 111-114° C.; $^1$H NMR (400 MHz, CDCl$_3$) δ 9.09-9.04 (m, 1H), 9.02 (s, 2H), 7.30 (s, 1H), 3.14 (bs, 1H), 2.88 (s, 3H); ESIMS m/z 196 ([M+H]).

1-(5-Fluoro-3-pyridyl)-3-methyl-N-(trideuteriomethyl)pyrazol-4-amine was prepared from compound 380 using the procedure as described in Example 8, method B: mp 146-148° C.; $^1$H NMR (400 MHz, CDCl$_3$) δ 8.67 (s, 1H), 8.25 (d, J=2.5 Hz, 1H), 7.73 (dt, J=10.0, 2.3 Hz, 1H), 7.27 (s, 1H), 2.87 (s, 1H), 2.24 (s, 3H); ESIMS m/z 210 ([M+H]$^+$); IR (Thin film) 1599 cm$^{-1}$.

3-Chloro-1-(3-pyridyl)-N-(trideuteriomethyl)pyrazol-4-amine was prepared from compound 381 using the procedure as described in Example 8, method B: mp 104-106° C.; $^1$H NMR (400 MHz, CDCl$_3$) δ 8.87 (d, J=1.9 Hz, 1H), 8.47 (d, J=4.7 Hz, 1H), 8.00-7.90 (m, 1H), 7.40-7.30 (m, 2H), 3.10 (s, 1H); ESIMS m/z 212 ([M+H]$^+$); IR (Thin film) 1579 cm$^{-1}$.

3-Chloro-N-(cyclopropylmethyl)-1-(pyridin-3-yl)-1H-pyrazol-4-amine was prepared from compound 361 using the procedure as described in Example 8, method B: mp 82-83° C.; $^1$H NMR (400 MHz, CDCl$_3$) δ 8.86 (d, J=2.5 Hz, 1H), 8.47 (dd, J=4.7, 1.3 Hz, 1H), 7.95 (ddd, J=8.4, 2.7, 1.5 Hz, 1H), 7.38-7.32 (m, 2H), 3.22 (s, 1H), 2.90 (d, J=6.9 Hz, 2H), 1.23-1.06 (m, 1H), 0.65-0.53 (m, 2H), 0.31-0.19 (m, 2H); ESIMS m/z 249 ([M+H]$^+$);

3-Chloro-N-propyl-1-(pyridin-3-yl)-1H-pyrazol-4-amine was prepared from compound 360 using the procedure as described in Example 8, method B: mp 92-94° C.; $^1$H NMR (400 MHz, CDCl$_3$) δ 8.86 (d, J=2.6 Hz, 1H), 8.47 (dd, J=4.7, 1.4 Hz, 1H), 7.95 (ddd, J=8.3, 2.7, 1.5 Hz, 1H), 7.35 (ddd, J=8.4, 4.7, 0.6 Hz, 1H), 7.33 (s, 1H), 3.22-2.94 (m, 3H), 1.75-1.52 (m, 2H), 1.02 (t, J=7.4 Hz, 3H); ESIMS m/z 237 ([M+H]$^+$).

3-Chloro-1-(pyridin-3-yl)-N-(4,4,4-trifluorobutyl)-1H-pyrazol-4-amine was prepared from the appropriate Boc-amine as described in Example 8, Method B: IR (thin film) 3416, 3089 cm$^{-1}$; $^1$H NMR (400 MHz, CDCl$_3$) δ 8.86 (d, J=2.5 Hz, 1H), 8.48 (dd, J=4.7, 1.3 Hz, 1H), 7.95 (ddd, J=8.3, 2.7, 1.4 Hz, 1H), 7.42-7.31 (multiple peaks, 2H), 3.16 (dd, J=13.0, 6.5 Hz, 2H), 3.08 (d, J=5.6 Hz, 1H), 2.35-2.18 (m, 2H), 2.00-1.86 (m, 2H); ESIMS m/z 307 ([M+2H]$^+$).

3-Chloro-1-(pyridin-3-yl)-N-(5,5,5-trifluoropentyl)-1H-pyrazol-4-amine was prepared from the appropriate Boc-amine as described in Example 8, Method B: IR (thin film) 3087 cm$^{-1}$; $^1$H NMR (400 MHz, CDCl$_3$) δ 8.86 (d, J=2.5 Hz, 1H), 8.48 (dd, J=4.7, 1.4 Hz, 1H), 7.96 (ddd, J=8.3, 2.7, 1.5 Hz, 1H), 7.36 (ddd, J=8.3, 4.8, 0.6 Hz, 1H), 7.34 (s, 1H), 3.10 (s, 2H), 3.04 (s, 1H), 2.30-1.98 (m, 2H), 1.84-1.69 (multiple peaks, 4H); $^{19}$F NMR (376 MHz, CDCl$_3$) δ-66.28; ESIMS m/z 320 ([M+2H]$^+$).

3-Chloro-N-(4-fluorobutyl)-1-(pyridin-3-yl)-1H-pyrazol-4-amine was prepared from the appropriate Boc-amine as described in Example 8, Method B: mp 82-83° C.; IR (thin film) 3348, 3086 cm$^{-1}$; $^1$H NMR (400 MHz, CDCl$_3$) δ 8.86 (d, J=2.5 Hz, 1H), 8.47 (dd, J=4.7, 1.4 Hz, 1H), 7.95 (ddd, J=8.3, 2.7, 1.5 Hz, 1H), 7.38-7.33 (multiple peaks, 2H), 4.58 (t, J=5.7 Hz, 1H), 4.50-4.42 (m, 1H), 3.11 (multiple peaks, 3H), 1.90-1.76 (multiple peaks, 4H); ESIMS m/z 269 ([M+H]$^+$).

3-Chloro-N-isopropyl-1-(pyridin-3-yl)-1H-pyrazol-4-amine was prepared from the appropriate Boc-amine as described in Example 8, Method B: IR (thin film) 3318, 1583 cm$^{-1}$; $^1$H NMR (400 MHz, CDCl$_3$) δ 8.86 (d, J=2.7 Hz, 1H), 8.47 (dd, J=4.7, 1.4 Hz, 1H), 7.96 (ddd, J=8.4, 2.7, 1.5 Hz, 1H), 7.36 (ddd, J=8.3, 4.8, 0.7 Hz, 1H), 7.31 (s, 1H), 2.87 (d, J=6.8 Hz, 2H), 1.92 (dq, J=13.4, 6.7 Hz, 1H), 1.02 (d, J=6.7 Hz, 6H); ESIMS m/z 251 ([M+H]$^+$).

3-Chloro-N-(2-methoxyethyl)-1-(pyridin-3-yl)-1H-pyrazol-4-amine was prepared from the appropriate Boc-amine as described in Example 8, Method B: IR (thin film) 3364, 1485 cm$^{-1}$; $^1$H NMR (400 MHz, CDCl$_3$) δ 8.86 (dd, J=2.7, 0.7 Hz, 1H), 8.48 (dd, J=4.7, 1.5 Hz, 1H), 7.96 (ddd, J=8.4, 2.7, 1.5 Hz, 1H), 7.38 (s, 1H), 7.38-7.34 (m, 1H), 3.68-3.59 (m, 2H), 3.49 (s, 1H), 3.42 (s, 3H), 3.24 (d, J=7.3 Hz, 2H); ESIMS m/z 253 ([M+H]$^+$).

3-Chloro-N-((2,2-difluorocyclopropyl)methyl)-1-(pyridin-3-yl)-1H-pyrazol-4-amine was prepared from the appropriate Boc-amine as described in Example 8, Method B: $^1$H NMR (400 MHz, CDCl$_3$) δ 8.87 (d, J=2.6 Hz, 1H), 8.49 (dd, J=4.7, 1.5 Hz, 1H), 7.96 (ddd, J=8.4, 2.7, 1.4 Hz, 1H), 7.41 (s, 1H), 7.37 (ddd, J=8.3, 4.7, 0.7 Hz, 1H), 3.19 (td, J=15.5, 13.0, 6.8 Hz, 2H), 2.00-1.84 (m, 1H), 1.55 (m, 1H), 1.26 (s, 1H), 1.23-1.11 (m, 1H); ¹⁹F NMR (376 MHz, CDCl₃) δ-128.61 (d, J=159.5 Hz), −143.58 (d, J=160.0 Hz); ESIMS m/z 285 ([M+H]⁺).

3-Chloro-N-(3-fluoropropyl)-1-(pyridin-3-yl)-1H-pyrazol-4-amine was prepared from the appropriate Boc-amine as described in Example 8, Method B: IR (thin film) 3359 cm⁻¹; ¹H NMR (400 MHz, CDCl₃) δ 8.87 (d, J=2.7 Hz, 1H), 8.48 (dd, J=4.7, 1.4 Hz, 1H), 7.95 (ddd, J=8.3, 2.6, 1.4 Hz, 1H), 7.39-7.34 (multiple peaks, 2H), 4.63 (dt, J=47.2, 5.6 Hz, 2H), 3.25 (t, J=6.7 Hz, 2H), 3.18 (br s, 1H), 2.17-1.92 (m, 2H); ESIMS m/z 255 ([M+H]⁺).

N-allyl-3-chloro-1-(pyridin-3-yl)-1H-pyrazol-4-amine was prepared from the appropriate Boc-amine as described in Example 8, Method B: IR (thin film) 3291 cm⁻¹; ¹H NMR (400 MHz, CDCl₃) δ 8.85 (d, J=2.6 Hz, 1H), 8.48 (dd, J=4.8, 1.5 Hz, 1H), 7.95 (ddd, J=8.3, 2.7, 1.4 Hz, 1H), 7.38-7.35 (m, 1H), 7.34 (s, 1H), 5.97 (ddt, J=17.3, 10.6, 5.5 Hz, 1H), 5.34 (dq, J=17.2, 1.6 Hz, 1H), 5.23 (dq, J=10.3, 1.5 Hz, 1H), 3.73 (dt, J=5.5, 1.6 Hz, 2H), 3.25 (s, 1H); ESIMS m/z 235 ([M+H]⁺).

2-((3-Chloro-1-(pyridin-3-yl)-1H-pyrazol-4-yl)amino) ethyl acetate was prepared from the appropriate Boc-amine as described in Example 8, Method B: IR (thin film) 3361, 1733 cm⁻¹; ¹H NMR (400 MHz, CDCl₃) δ 8.87 (s, 1H), 8.49 (d, J=4.7 Hz, 1H), 7.96 (ddd, J=8.3, 2.7, 1.4 Hz, 1H), 7.43 (s, 1H), 7.37 (dd, J=8.4, 4.7 Hz, 1H), 4.30 (dd, J=5.9, 4.8 Hz, 2H), 3.34 (t, J=5.5 Hz, 2H), 2.12 (s, 3H), 1.59 (s, 1H); ESIMS m/z 281 ([M+H]⁺).

3-Chloro-N-(2-fluoroethyl)-1-(pyridin-3-yl)-1H-pyrazol-4-amine was prepared from the appropriate Boc-amine as described in Example 8, Method B: IR (thin film) 3369 cm⁻¹; ¹H NMR (400 MHz, CDCl₃) δ 8.86 (d, J=2.7 Hz, 1H), 8.49 (dd, J=4.7, 1.4 Hz, 1H), 7.96 (ddd, J=8.3, 2.7, 1.5 Hz, 1H), 7.40 (s, 1H), 7.37 (dd, J=8.3, 4.7 Hz, 1H), 4.82-4.53 (m, 2H), 3.54-3.27 (multiple peaks, 3H); ESIMS m/z 241 ([M+H]⁺).

3-Chloro-1-(pyridin-3-yl)-N-(2-(pyrrolidin-1-yl)ethyl)-1H-pyrazol-4-amine was prepared from the appropriate Boc-amine as described in Example 8, Method B: ESIMS m/z 292 ([M+H]⁺).

3-Chloro-N-(2,2-difluoroethyl)-1-(pyridin-3-yl)-1H-pyrazol-4-amine was prepared from the appropriate Boc-amine as described in Example 8, Method B: IR (thin film) 3295 cm⁻¹; ¹H NMR (400 MHz, CDCl₃) δ 8.87 (dd, J=2.8, 0.7 Hz, 1H), 8.51 (dd, J=4.7, 1.4 Hz, 1H), 7.95 (ddd, J=8.4, 2.7, 1.5 Hz, 1H), 7.45 (s, 1H), 7.37 (ddd, J=8.5, 4.7, 0.8 Hz, 1H), 5.96 (tt, J=55.9, 4.1 Hz, 1H), 3.69-3.26 (multiple peaks, 3H); ¹⁹F NMR (376 MHz, CDCl₃) δ-122.15; ESIMS m/z 259 ([M+H]⁺).

3-Chloro-1-(pyridin-3-yl)-N-(2,2,2-trifluoroethyl)-1H-pyrazol-4-amine was prepared from the appropriate Boc-amine as described in Example 8, Method B: IR (thin film) 3309 cm⁻¹; ¹H NMR (400 MHz, CDCl₃) δ 8.92-8.85 (m, 1H), 8.52 (dd, J=4.8, 1.4 Hz, 1H), 7.98 (ddd, J=8.4, 2.7, 1.5 Hz, 1H), 7.47 (s, 1H), 7.40 (ddd, J=8.4, 4.8, 0.7 Hz, 1H), 3.68 (q, J=8.9 Hz, 2H), 3.49 (s, 1H); ¹⁹F NMR (376 MHz, CDCl₃) δ-72.29; ESIMS m/z 277 ([M+H]⁺).

3-Chloro-N-(2-chloroethyl)-1-(pyridin-3-yl)-1H-pyrazol-4-amine was prepared from the appropriate Boc-amine as described in Example 8, Method B: IR (thin film) 3354 cm⁻¹; ¹H NMR (400 MHz, CDCl₃) δ 8.86 (dd, J=2.7, 0.7 Hz, 1H), 8.50 (dd, J=4.8, 1.5 Hz, 1H), 7.96 (ddd, J=8.3, 2.7, 1.4 Hz, 1H), 7.40 (s, 1H), 7.37 (ddd, J=8.5, 4.8, 0.8 Hz, 1H), 3.76 (dd, J=6.0, 5.4 Hz, 2H), 3.54 (s, 1H), 3.43 (t, J=5.7 Hz, 2H); ESIMS m/z 257 ([M+H]⁺).

3-Chloro-1-(pyridin-3-yl)-N-(3,3,3-trifluoropropyl)-1H-pyrazol-4-amine was prepared from the appropriate Boc-amine as described in Example 8, Method B: IR (thin film) 3366, 3081 cm⁻¹; ¹H NMR (400 MHz, CDCl₃) δ 8.87 (dd, J=2.6, 0.7 Hz, 1H), 8.50 (dd, J=4.7, 1.4 Hz, 1H), 7.96 (ddd, J=8.3, 2.7, 1.4 Hz, 1H), 7.40-7.35 (multiple peaks, 2H), 3.38 (q, J=6.8 Hz, 2H), 3.22 (t, J=6.7 Hz, 1H), 2.48 (qt, J=10.7, 7.0 Hz, 2H); ¹⁹F NMR (376 MHz, CDCl₃) δ-64.99; ESIMS m/z 291 ([M+H]⁺).

N-(but-2-yn-1-yl)-3-chloro-1-(pyridin-3-yl)-1H-pyrazol-4-amine was prepared from the appropriate Boc-amine as described in Example 8, Method B: IR (thin film) 3249, 3122 cm⁻¹; ¹H NMR (400 MHz, CDCl₃) δ 8.89 (dd, J=2.7, 0.7 Hz, 1H), 8.49 (dd, J=4.8, 1.5 Hz, 1H), 7.98 (ddd, J=8.3, 2.7, 1.5 Hz, 1H), 7.50 (s, 1H), 7.37 (ddd, J=8.4, 4.8, 0.8 Hz, 1H), 3.93-3.68 (m, 2H), 3.33 (s, 1H), 1.83 (t, J=2.4 Hz, 3H); ESIMS m/z 247 ([M+H]⁺).

3-Chloro-N-isobutyl-1-(pyridin-3-yl)-1H-pyrazol-4-amine was prepared as in Example 8, Method B: ¹H NMR (400 MHz, CDCl₃) δ 8.86 (d, J=2.5 Hz, 1H), 8.47 (dd, J=4.7, 1.3 Hz, 1H), 7.95 (ddd, J=8.4, 2.7, 1.5 Hz, 1H), 7.35 (ddd, J=8.3, 4.7, 0.6 Hz, 1H), 7.31 (s, 1H), 3.11 (bs, 1H), 2.87 (t, J=6.5 Hz, 2H), 1.93 (dp, J=13.4, 6.7 Hz, 1H), 1.01 (d, J=6.7 Hz, 6H).

Example 9: Preparation of isopropyl-(1-pyridin-3-yl-1H-pyrazol-4-yl)-amine

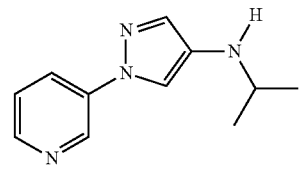

1-pyridin-3-yl-1H-pyrazol-4-ylamine (0.6 g, 3.7 mmol) was dissolved in isopropyl acetate (8.5 mL). To the mixture, acetone (0.261 g, 4.5 mmol), trifluoroacetic acid (0.855 g, 7.5 mmol) and sodium triacetoxyborohydride (0.945 g, 4.5 mmol) were added. The reaction was stirred under nitrogen at room temperature for 4.5 hours and then quenched with 10% sodium hydroxide solution until the pH reached ~9. The layers were separated, and the aqueous phase was extracted with ethyl acetate. The organic extracts were combined, dried over sodium sulfate and concentrated to dryness. The crude material was purified by silica gel chromatography (gradient elution of 5% methanol/dichloromethane) to give the title compound as an off white solid (0.35 g, 46%): mp 105-107° C.; ¹H NMR (300 MHz, CDCl₃) δ 8.82 (d, J=2.2 Hz, 1H), 8.63 (dd, J=4.8, 1.5 Hz, 1H), 8.13 (d, J=1.8 Hz, 1H), 8.03 (d, J=2.7 Hz, 1H), 7.94-7.77 (m, 1H), 7.38 (dt, J=15.2, 7.6 Hz, 1H), 6.99 (t, 1H), 3.72 (m, 1H), 1.30 (t, J=10.0 Hz, 6H). ESIMS 214 m/z (M+1).

Example 10: Preparation of propyl-(1-pyridin-3-yl-1H-pyrazol-4-yl-amine

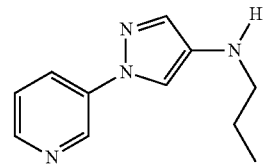

To 1-pyridin-3-yl-1H-pyrazol-4-ylamine (0.5 g, 3.12 mmol) in dichloromethane (5 mL) was added propionaldehyde (0.18 g, 3.12 mmol) and sodium triacetoxy borohydride (0.99 g, 4.68 mmol) and stirred at room temperature for 16 hours. The reaction was taken up in dichloromethane and was washed with water and brine. The organic layer was dried (MgSO₄), filtered and concentrated to dryness. The crude material was purified by silica gel chromatography eluting with 0-5% MeOH/Dichloromethane and resubjected in 0-100% ethylacetate/hexanes) to give the title compound as a dark oil (0.05 g, 7%): $^1$H NMR (300 MHz, CDCl$_3$) δ 8.92 (d, J=2.6 Hz, 1H), 8.48 (dd, J=4.7, 1.4 Hz, 1H), 8.00 (ddd, J=8.3, 2.7, 1.5 Hz, 1H), 7.47-7.40 (m, 2H), 7.37 (dd, J=8.3, 4.7 Hz, 1H), 3.04 (t, J=7.1 Hz, 3H), 1.92-1.46 (m, 2H), 1.03 (t, J=7.4 Hz, 3H).

Example 11: Preparation of N-methyl-N-(1-pyridin-3-yl-1H-pyrazol-4-yl)-isobutyramide (Compound 42)

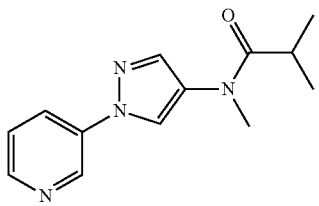 [SMILES: CC(C)C(=O)N(C)c1cnn(-c2cccnc2)c1]

A solution of isobutyryl chloride (0.138 g, 1.3 mmol) in dichloroethane (1 mL) was pipetted at a dropwise rate into an ice-cold suspension of methyl-(1-pyridin-3-yl-1H-pyrazol-4-yl)-amine (0.15 g, 0.86 mmol) in dichloroethane (5 mL), stirred for 10 minutes and then treated at a dropwise rate with a solution of 4-N,N-dimethylaminopyridine (0.11 g, 0.9 mmol) in dichloroethane (1.5 mL). The cooling bath was removed after 30 minutes, stirred under nitrogen at room temperature for 14 hours, diluted with dichloroethane (40 mL), washed with water (30 mL), brine (10 mL), dried over MgSO₄ and purified by reversed phase column chromatography to give a yellowish gum (0.114 g, 54%) $^1$H NMR (300 MHz, CDCl$_3$) δ 9.01-8.93 (m, 1H), 8.67 (s, 0.4H), 8.61 (d, J=4.2 Hz, 0.6H), 8.54 (d, 0.4H), 8.08-8.02 (m, 1H), 7.96 (s, 0.6H), 7.80 (s, 0.4H), 7.70 (s, 0.6H), 7.47-7.37 (m, 1H), 3.49 (s, 1.2H), 3.26 (s, 2.8H), 3.06-2.98 (m, 0.4H), 2.86-2.70 (m, 0.6H), 1.25 (d, J=6.1 Hz, 2.4H), 1.09 (d, J=6.6 Hz, 3.6H). ESIMS m/z 245 ([M+1]).

Compounds 32-41, 43-52, 54-56, 59-61, 66, 73-75, 77-79, 82-85, 93-100, 113, 117-129, 131-134, 139-140, 142-144, 148, 160, 163, 173-175, 184-186, 197-198, 202, 208, 215-217, 252-253, 277, 282-285, 287-290, 314-316, 347, 350-351, 353-355, 365-367, 370, 388, 395, 399-403, 407, 409, 415-418, 444-449, 452-463, 465, 467-469, 496-498, 506-507, 512, 525-527, 569, 577, 581 and 592 were made from the appropriate amines in accordance with the procedures disclosed in Example 11.

Example 12: Preparation of 4,4,4-trifluoro-2-methyl-N-(1-(pyridin-3-yl)-1H-pyrazol-4-yl)butanamide (Compound 65)

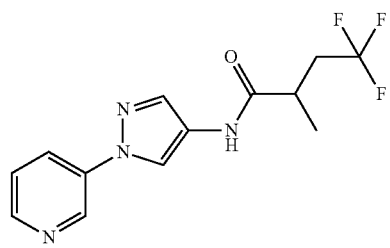 [SMILES: CC(CC(F)(F)F)C(=O)Nc1cnn(-c2cccnc2)c1]

To a solution of 1-(pyridin-3-yl)-1H-pyrazol-4-amine (0.150 g, 0.93 mmol) in dichloroethane (1.8 mL) was added 4,4,4-trifluoro-2-methylbutanoic acid (0.14 g, 0.93 mmol) and 4-N,N-dimethylaminopyridine (0.23 g, 1.87 mmol) followed by 1-(3-dimethylaminopropyl)-3-ethylcarbodiimide hydrochloride (0.36 g, 1.87 mmol). The reaction stirred at room temperature overnight. The reaction mixture was concentrated and the crude product was purified by silica gel chromatography eluting with 0-5% MeOH/dichloromethane to give a white solid (0.15 g, 55%); mp 140-145° C.; $^1$H NMR (400 MHz, CDCl$_3$) δ 9.00 (d, J=2.4 Hz, 1H), 8.62-8.47 (m, 2H), 8.01 (ddd, J=8.3, 2.7, 1.5 Hz, 1H), 7.68 (s, 1H), 7.53 (bs, 1H), 7.40 (ddd, J=8.3, 4.8, 0.6 Hz, 1H), 2.92-2.61 (m, 2H), 2.32-2.05 (m, 1H), 1.38 (d, J=6.6 Hz, 3H); ESIMS m/z 300 ([M+2]).

Compounds 53, 58, 62-63, 72, 76, 80-81, 107-108, 136-138, 147, 151-159, 164-168, 176-179, 187-196, 201, 203-207, 209-214, 220, 224-249, 251, 259-275, 286, 292-296, 303-313, 323-326, 341-344, 356-359, 371, 378-379, 382, 384, 419-426, 439-443, 455, 458-461, 464, 466, 476, 486, 490-493, 505, 508, 517, 528-529, 536-537, 539-541, 544-545, 549-554, 572-577, 578, 579 and 580 were prepared from the appropriate amines in accordance with the procedures disclosed in Example 12.

Example 13: Preparation of tert-butyl 1-(pyridin-3-yl)-1H-pyrazol-4-ylcarbamate (Compound 57)

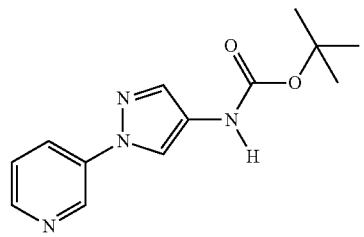 [SMILES: CC(C)(C)OC(=O)Nc1cnn(-c2cccnc2)c1]

Method A:
To a solution of 1-(pyridin-3-yl)-1H-pyrazol-4-amine (3 g, 18.73 mmol) in dichloromethane (33.4 mL) was added triethylamine (3.13 mL, 7.68 mmol) and BOC-anhydride (4.5 g, 20.60 mmol). The resulting solution was stirred at room temperature overnight. The reaction mixture was partitioned between ethyl acetate and water. The organic portion was dried (MgSO₄), filtered and concentrated to dryness. The crude product was purified by silica gel chromatography eluting with 0-100% ethyl acetate/hexanes to yield a white solid (2.0 g, 41%); mp 108-112° C.; ¹H NMR (400 MHz, CDCl₃) δ 9.02 (d, J=2.2 Hz, 1H), 8.51 (t, J=8.7 Hz, 1H), 8.37 (s, 1H), 8.30 (s, 1H), 7.98 (ddd, J=8.3, 2.4, 1.3 Hz, 1H), 7.68 (s, 1H), 7.36 (dd, J=8.2, 4.8 Hz, 1H), 1.52 (s, 9H); ESIMS m/z 261 ([M+1]).

Compounds 64 and 130 were prepared in accordance with the procedures disclosed in Example 13, Method A.

Method B:

To a solution of 1-(pyridin-3-yl)-1H-pyrazol-4-amine (0.1 g, 0.624 mmol) and di-tert-butyl dicarbonate (0.161 mL, 0.693 mmol) in tetrahydrofuran (1.890 mL) and water (0.568 mL) was added dropwise saturated aqueous sodium bicarbonate (0.572 mL, 0.687 mmol). The reaction was stirred at room temperature overnight. The reaction was diluted with water and extracted with ethyl acetate. The combined organic phases were concentrate to give tert-butyl 1-(pyridin-3-yl)-1H-pyrazol-4-ylcarbamate (135 mg, 0.519 mmol, 83%), for which the analytical data was consistent with that reported in Example 13, Method A.

Compounds 150, 172, 223, and 317 were prepared in accordance with the procedures disclosed in Example 13, Method B. Compound 172 and 317 was also prepared in accordance with the procedures disclosed in Example 17. These compounds, as well as, certain other compounds, were made by alternative methods further illustrating certain embodiments.

Example 14: Preparation of tert-butyl methyl(1-(pyridin-3-yl)-1H-pyrazol-4-yl)carbamate (Compound 67)

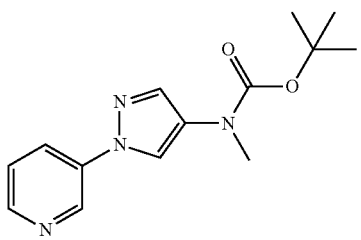 [SMILES: CN(C(=O)OC(C)(C)C)c1cnn(-c2cccnc2)c1]

To a solution of tert-butyl 1-(pyridin-3-yl)-1H-pyrazol-4-ylcarbamate (1.6 g, 6.15 mmol) in DMF (30.7 mL) at 0° C. was added sodium hydride (0.34 g, 8.61 mmol, 60% dispersion in mineral oil) in one portion and the suspension was stirred for 30 minutes. The ice bath was removed and stirred for an additional 30 minutes. Iodomethane (0.46 mL, 7.38 mmol) was added in one portion and stirred overnight at room temperature. Water and ethyl acetate were added and the resulting biphasic mixture was separated. The aqueous layer was extracted one time with ethyl acetate. The combined organic extracts were washed with brine, dried (MgSO₄), filtered and concentrated to dryness. The crude product was purified by silica gel chromatography eluting with 0-35% ethyl acetate/hexanes to yield a light yellow semi-solid (0.85 g, 50%): IR (KBr) 1703 cm⁻¹; ¹H NMR (400 MHz, CDCl₃) δ 8.98 (s, 1H), 8.52 (d, J=3.8 Hz, 1H), 8.32 (s, 0.5H), 8.13-7.97 (m, 1H), 7.84 (s, 0.5H), 7.74 (s, 1H), 7.39 (dd, J=8.0, 4.8 Hz, 1H), 3.30 (s, 3H), 1.56 (s, 9H); ESIMS m/z 275 ([M+H]).

Compounds 68, 86-92, 105-106, 114-116, 141, 149, 161-162, 199-200, 254, 258, 291, 332, 352, 360-361, 380-381, 414, 430-431, 450, 457, 474-475, 485, 488, 510-511, 515, 523, and 590 were prepared from the appropriate amides in accordance with the procedures disclosed in Example 14.

Tert-butyl methyl(3-methyl-1-(pyridin-3-yl)-1H-pyrazol-4-yl)carbamate was prepared as in Example 14: ¹H NMR (400 MHz, CDCl₃) δ 8.91 (d, J=2.5 Hz, 1H), 8.51 (dd, J=4.7, 1.3 Hz, 1H), 8.00 (ddd, J=8.3, 2.4, 1.4 Hz, 1H), 7.83 (s, 1H), 7.38 (dd, J=8.3, 4.7 Hz, 1H), 3.20 (s, 3H), 2.22 (s, 3H), 1.60-1.30 (m, 9H).

Example 15: Preparation of N-ethyl-N-(1-methyl-3-(pyridin-3-yl)-1H-pyrazol-5-yl)isobutyramide (Compound 23)

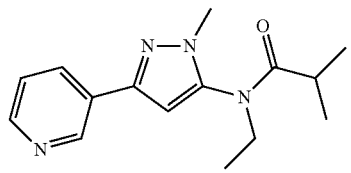 [SMILES: CCN(C(=O)C(C)C)c1cc(-c2cccnc2)nn1C]

To a solution of N-(1-methyl-3-(pyridine-3-yl)-1H-pyrazol-5-yl)isobutyramide (0.08 g, 0.33 mmol) in DMF (0.66 mL) at 0° C. was added sodium hydride (0.016 g, 0.39 mmol, 60% dispersion in mineral oil) in one portion and the suspension was stirred for 30 minutes. The ice bath was removed and stirred for an additional 30 minutes. Iodoethane (0.06 g, 0.39 mmol) was added in one portion and stirred overnight at room temperature. Water and ethyl acetate were added and the resulting biphasic mixture was separated. The aqueous layer was extracted one time with ethyl acetate. The combined organic extracts were washed with brine, dried (MgSO₄), filtered and concentrated to dryness. The crude product was purified by silica gel chromatography to give the title compound as a clear oil (27.5 mg, 30%): ¹H NMR (300 MHz, CDCl₃) δ 9.00 (bs, 1H), 8.57 (s, 1H), 8.09 (dd, J=7.9 Hz, 1H), 7.34 (dd, 1H), 6.48 (s, 1H), 4.00 (m, 1H), 3.76 (s, 3H), 3.36 (m, 1H), 2.33 (m, 1H), 1.17 (t, J=7.1 Hz, 3H), 1.08 (t, J=6.7 Hz, 6H); ESIMS m/z 273 (M+H).

Compound 22 was prepared in accordance with the procedures disclosed in Example 15.

Example 16: Preparation of 5-bromo-1H-pyrazol-4-amine, HBr

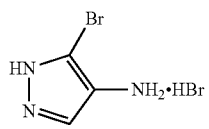

A mixture of 4-nitro-1H-pyrazole (10 g, 88 mmol) and 5% palladium on Al₂O₃ (1 g) in a mixture of ethanol (150 mL) and 50% aqueous HBr (50 mL) was shaken in a Par apparatus under hydrogen (10 psi) for 36 h. The mixture was filtered and the catalyst washed with ethanol. The filtrate was concentrated in vacuo to give a white solid. This solid was suspended in 10 mL of ethanol. After swirling the flask for 5 min, diethyl ether was added to complete the crystallization. The solid was filtered, was washed with ether and dried under high vacuum to afford 5-bromo-1H-pyrazol-4-amine, HBr (18.1 g, 84% yield) as a white solid: mp 248° C. dec; ¹H NMR (400 MHz, DMSO-d₆) δ 11.47 (s, 1H), 10.00 (s, 1H), 7.79 (s, 1H).

Example 17: Preparation of tert-butyl(3-chloro-1-(pyridin-3-yl)-1H-pyrazol-4-yl)carbamate (Compound 172)

Example 17, Step 1: Preparation of 3-chloro-1H-pyrazol-4-amine hydrochloride

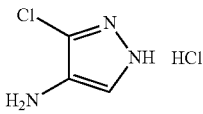

Into a 2 L three-necked round bottom flask affixed with an overhead stirrer, a temperature probe, an addition funnel, and a nitrogen inlet were added ethanol (600 mL) and 4-nitro-1H-pyrazole (50.6 g, 447 mmol). To this solution was added, in one portion, conc. HCl (368 mL) (note: rapid exotherm from 15° C. to 39° C.) and the resulting mixture was purged with nitrogen for 5 minutes. Palladium on alumina (5% w/w) (2.6 g, Alfa, black solid) was added to the mixture and stirred at room temperature while triethylsilane (208 g, 1789 mmol) was added drop-wise over 4 h. The reaction, which started to slowly exotherm from 35° C. to 55° C. over 2.0 h, was stirred for a total of 16 h and vacuum filtered through a plug of Celite® to give a biphasic mixture. The mixture was transferred to a separatory funnel, the bottom aqueous layer was collected and rotary evaporated (60° C., 50 mmHg) to dryness with the aid of acetonitrile (3×350 mL). The resulting yellow solid was suspended in acetonitrile (150 mL) and allowed to stand for 2 h at room temperature followed by 1 h at 0° C. in the refrigerator. The solids were filtered and washed with acetonitrile (100 mL) to afford the titled compound 3-chloro-1H-pyrazol-4-amine hydrochloride (84 g, 97% yield, 80% purity) as a white solid: mp 190-193° C.; $^1$H NMR (400 MHz, DMSO-d$_6$) δ 10.46-10.24 (bs, 2H), 8.03 (s, 0.54H), 7.75 (s, 0.46H), 5.95 (bs, 1H)); $^{13}$C-NMR (101 MHz, DMSO) δ 128.24, 125.97, 116.71.

Example 17, Step 2: Preparation of tert-butyl(3-chloro-1H-pyrazol-4-yl)carbamate

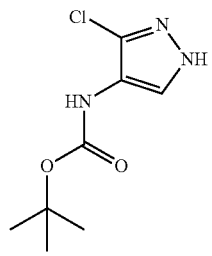

Into a 2 L round bottom flask was added 3-chloro-1H-pyrazol-4-amine hydrochloride (100 g, 649 mmol) and THF (500 mL). To this mixture were added di-tert-butyldicarbonate (156 g, 714 mmol) followed by sodium bicarbonate (120 g, 1429 mmol) and water (50.0 ml). The mixture was stirred for 16 h, diluted with water (500 mL) and ethyl acetate (500 mL) and transferred to a separatory funnel. This gave three layers; bottom—a white gelatinous precipitate, middle—light yellow aqueous, top—auburn organic. The phases were separated collecting the white gelatinous precipitate and the aqueous layer together. The aqueous was extracted with ethyl acetate (2×200 mL) and the ethyl acetate extracts were combined, washed with brine (200 mL), dried over anhydrous sodium sulfate, filtered and rotary evaporated to give an auburn thick oil (160 g). The thick oil was suspended in hexane (1000 mL) and stirred at 55° C. for 2 h. This gave a light brown suspension. The mixture was cooled to 0° C. and the solid collected by vacuum filtration and rinsed with hexane (2×10 mL). The sample was air dried to constant mass to afford (3-chloro-1H-pyrazol-4-yl)carbamate (102.97 g, 72% yield, 80% purity) as a light brown solid: mp 137-138° C.; $^1$H NMR (400 MHz, CDCl$_3$) δ 10.69 (s, 1H), 7.91 (s, 1H), 1.52 (s, 9H).

Example 17, Step 3: Preparation of tert-butyl(3-chloro-1-(pyridin-3-yl)-1H-pyrazol-4-yl)carbamate (Compound 172)

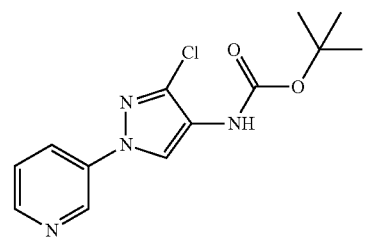 [SMILES: CC(C)(C)OC(=O)Nc1cn(-c2cccnc2)nc1Cl]

To a dry 2 L round bottom flask equipped with mechanical stirrer, nitrogen inlet, thermometer, and reflux condenser was charged the 3-iodopyridine (113.0 g, 551 mmol), (3-chloro-1H-pyrazol-4-yl)carbamate (100 g, 459 mmol), potassium phosphate (powdered in a mortar and pestle) (195 g, 919 mmol), and copper chloride (3.09, 22.97 mmol). Acetonitrile (1 L) followed by $N^1,N^2$-dimethylethane-1,2-diamine (101 g, 1149 mmol) were added and the mixture was heated to 81° C. for 4 hours. The mixture was cooled to room temperature and filtered through a bed of Celite®. The filtrate was transferred to a 4 L Erlenmeyer flask equipped with mechanical stirrer and diluted with water until the total volume was about 4 L. The mixture was stirred for 30 minutes at room temperature and the resulting solid was collected by vacuum filtration. The solid was washed with water and washed with water and oven dried for several days in vacuo at 40° C. to a constant weight to give tert-butyl(3-chloro-1-(pyridin-3-yl)-1H-pyrazol-4-yl)carbamate (117.8 g, 87% yield, 80% purity) as a tan solid: mp 140-143° C.; $^1$H NMR (400 MHz, CDCl$_3$) δ 8.96 (s, 1H), 8.53 (dd, J=4.7, 1.2 Hz, 1H), 8.36 (s, 1H), 7.98 (ddd, J=8.3, 2.7, 1.4 Hz, 1H), 7.38 (dd, J=8.3, 4.8 Hz, 1H), 6.37 (s, 1H), 1.54 (s, 9H); ESIMS (m/z) 338 ([M−t−Bu]$^+$), 220 ([M−O-t-Bu]$^-$).

Compound 172 was also prepared in accordance with the procedures disclosed in Example 13. Compound 317 was prepared in accordance with the procedures disclosed in Example 17 from tert-butyl(3-bromo-1H-pyrazol-4-yl)carbamate and also in accordance with the procedures disclosed in Example 13.

Example 18: Preparation of 3-(3-methyl-1H-pyrazol-1-yl)pyridine and 3-(5-methyl-1H-pyrazol-1-yl)pyridine

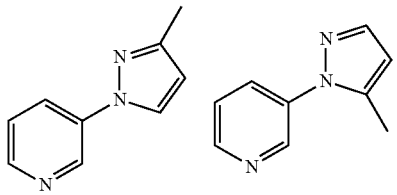

To a solution of 3-methyl-1H-pyrazole (10.99 g, 134 mmol) in N,N-dimethylformamide (100 ml) at 0° C. was added sodium hydride (3.71 g, 154 mmol, 60% dispersion). The reaction was stirred at 0° C. for 2 hours. 3-Fluoropyridine (10.0 g, 103 mmol) was added, and the reaction was stirred at 100° C. overnight. The reaction was cooled to room temperature and water was added slowly. The mixture was extracted with dichloromethane and the combined organic phases were washed with brine, concentrated and chromatographed (0-100% ethyl acetate/hexanes) to afford 3-(3-methyl-1H-pyrazol-1-yl)pyridine (8.4 g, 52.77 mmol, 51.2%) and 3-(5-methyl-1H-pyrazol-1-yl)pyridine (1.0 g, 6%). Analytical data of both products is consistent with that reported under Example 6, Step 1.

3-(3-Bromo-1H-pyrazol-1-yl)pyridine was prepared from 3-fluoropyridine and 3-bromopyrazole, which was made as in WO2008130021, as described Example 18: mp 89.5-92.5° C.; $^1$H NMR (400 MHz, CDCl$_3$) δ 8.94 (d, J=2.4 Hz, 1H), 8.62-8.49 (m, 1H), 8.03 (ddd, J=8.3, 2.7, 1.4 Hz, 1H), 7.87 (d, J=2.5 Hz, 1H), 7.42 (dd, J=8.2, 4.7 Hz, 1H), 6.54 (d, J=2.5 Hz, 1H); ESIMS m/z 224 ([M]$^+$).

Example 19, Preparation of 3-chloro-1-(5-fluoropyridin-3-yl)-1H-pyrazol-4-amine

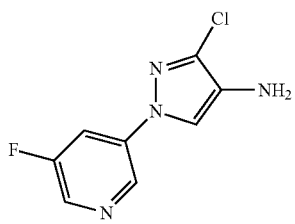 [SMILES: Nc1cn(-c2cncc(F)c2)nc1Cl]

To a stirred solution of 5-chloro-1H-pyrazol-4-amine, HCl (2 g, 12.99 mmol) and cesium carbonate (8.89 g, 27.3 mmol) in DMF (13 mL) was added 3,5-difluoropyridine (1.794 g, 15.58 mmol) and the mixture heated at 70° C. for 12 h. The mixture was cooled to room temperature and filtered. The solids were washed with copious amount of ethyl acetate. The filtrates was washed with brine, dried over anhydrous MgSO$_4$ and concentrated in vacuo to give a brown solid. This solid was dissolved in ethyl acetate and the resulting solution was saturated with hexanes to precipitate 3-chloro-1-(5-fluoropyridin-3-yl)-1H-pyrazol-4-amine (2.31 g, 10.32 mmol, 79% yield) as a brown solid: $^1$H NMR (400 MHz, DMSO-d$_6$) δ 8.89-8.82 (m, 1H), 8.45 (d, J=2.5 Hz, 1H), 8.07 (d, J=10.4 Hz, 1H), 7.94 (s, 1H), 4.51 (s, 2H); EIMS (m/z) 213 ([M+1]$^+$).

3-Bromo-1-(5-fluoropyridin-3-yl)-1H-pyrazol-4-amine was prepared from the corresponding pyrazole as described in Example 19: mp 164-165° C.; $^1$H NMR (400 MHz, CDCl$_3$) δ 8.65 (d, J=1.7 Hz, 1H), 8.36 (d, J=2.5 Hz, 1H), 7.76 (dd, J=5.9, 3.6 Hz, 1H), 7.48 (s, 1H), 3.22 (s, 2H). $^{13}$C NMR (101 MHz, CDCl$_3$) δ 160.87, 158.30, 135.36, 135.13, 134.39, 134.35, 131.16, 123.31, 114.02, 112.77, 112.54; EIMS (m/z) 258 ([M+1]$^+$).

Example 20: Preparation of 1-(5-fluoropyridin-3-yl)-3-methyl-1H-pyrazol-4-amine

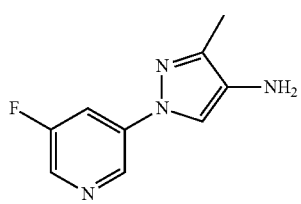

To a solution of 3-fluoro-5-(3-methyl-4-nitro-1H-pyrazol-1-yl)pyridine (3.133 g, 14.10 mmol) in ethanol (28.2 ml) was added ethyl acetate until all of the starting material went into solution. The solution was degassed and 10% palladium on carbon (0.750 g, 0.705 mmol) was added and the reaction was stirred in a parr hydrogenator at 40 psi for 3 hours. The solution was filtered through celite with ethyl acetate and concentrated to give 1-(5-fluoropyridin-3-yl)-3-methyl-1H-pyrazol-4-amine (2.000 g, 10.41 mmol, 73.8%) as a brown solid: mp 136.0-138.0° C.; $^1$H NMR (400 MHz, CDCl$_3$) δ 8.67-8.59 (m, 1H), 8.27 (d, J=2.5 Hz, 1H), 7.73 (dt, J=9.9, 2.3 Hz, 1H), 7.45 (s, 1H), 3.01 (s, 2H), 2.28 (s, 3H); EIMS m/z 192.

1-(Pyridin-3-yl)-3-(trifluoromethyl)-1H-pyrazol-4-amine was prepared from the appropriate nitropyrazole as described in Example 20: mp 112.5-115.0° C.; $^1$H NMR (400 MHz, CDCl$_3$) δ 8.89 (d, J=2.4 Hz, 1H), 8.57 (dd, J=4.7, 1.4 Hz, 1H), 8.03 (ddd, J=8.3, 2.7, 1.5 Hz, 1H), 7.56 (d, J=0.7 Hz, 1H), 7.41 (ddd, J=8.3, 4.8, 0.7 Hz, 1H), 3.47-3.31 (m, 2H); EIMS m/z 228.

Example 21: Preparation of 3-chloro-1-(pyridin-3-yl)-1H-pyrazol-4-amine

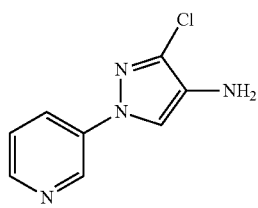 [SMILES: Nc1cn(-c2cccnc2)nc1Cl]

To 3-(3-chloro-4-nitro-1H-pyrazol-1-yl)pyridine (0.95 g, 4.23 mmol) in acetic acid (8.46 mL), ethanol (8.46 mL) and water (4.23 mL) was added iron powder (1.18 g, 21.15 mmol) and the reaction was stirred at room temperature for 30 minutes. To this was added carefully 2 M KOH and extracted with ethyl acetate. The ethyl acetate layers were combined, dried (MgSO$_4$), filtered and concentrated to dryness. The crude material was purified by silica gel chromatography (0-10% methanol/dichloromethane) to give the desired product as a white solid (0.66 g, 80%): ¹H NMR (400 MHz, CDCl₃) δ 8.84 (d, J=2.6 Hz, 1H), 8.49 (dd, J=4.7, 1.4 Hz, 1H), 7.95 (ddd, J=8.3, 2.7, 1.5 Hz, 1H), 7.53 (s, 1H), 7.37 (ddd, J=8.4, 4.7, 0.6 Hz, 1H), 3.17 (bs, 2H).

3-methyl-1-(2-methylpyridin-3-yl)-1H-pyrazol-4-amine was prepared as described in Example 21: ¹H NMR (400 MHz, CDCl₃) δ 8.48 (dd, J=4.8, 1.6 Hz, 1H), 7.62 (dd, J=8.0, 1.6 Hz, 1H), 7.23-7.18 (m, 2H), 2.91 (bs, 2H), 2.55 (s, 3H), 2.28 (s, 3H); EIMS m/z 188.

3-Phenyl-1-(pyridin-3-yl)-1H-pyrazol-4-amine was prepared from the appropriate nitropyrazole as described in Example 21: IR (thin film) 3324 cm⁻¹; ¹H NMR (400 MHz, CDCl₃) δ 8.94 (d, J=2.2 Hz, 1H), 8.47 (dd, J=4.7, 1.4 Hz, 1H), 8.07 (ddd, J=8.3, 2.7, 1.5 Hz, 1H), 7.87-7.80 (m, 2H), 7.60 (s, 1H), 7.50-7.44 (m, 2H), 7.40-7.34 (m, 2H), 3.86 (s, 2H); EIMS m/z 236.

3-Chloro-1-(5-fluoropyridin-3-yl)-1H-pyrazol-4-amine was prepared from the appropriate nitropyrazole as described in Example 21: mp 149.0-151.0° C.; ¹H NMR (400 MHz, CDCl₃) δ 8.65 (d, J=1.6 Hz, 1H), 8.35 (d, J=2.4 Hz, 1H), 7.75 (dt, J=9.5, 2.4 Hz, 1H), 7.51 (s, 1H), 3.21 (s, 2H); ESIMS m/z 213 ([M]⁺).

3-Bromo-1-(pyridin-3-yl)-1H-pyrazol-4-amine was prepared from the appropriate nitropyrazole as described in Example 21: mp 143.0-146.0° C.; ¹H NMR (400 MHz, CDCl₃) δ 8.85 (d, J=2.4 Hz, 1H), 8.50 (dd, J=4.7, 1.4 Hz, 1H), 7.96 (ddd, J=8.3, 2.7, 1.5 Hz, 1H), 7.49 (s, 1H), 7.37 (ddd, J=8.4, 4.7, 0.7 Hz, 1H), 3.21 (s, 2H); ESIMS m/z 241 ([M+2]⁺)

Example 22: Preparation of tert-butyl(5-methyl-1-(pyridin-3-yl)-1H-pyrazol-4-yl)carbamate (Compound 281)

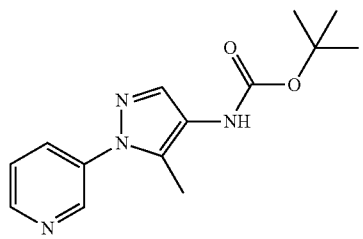 [SMILES: Cc1c(NC(=O)OC(C)(C)C)cnn1-c1cccnc1]

To a solution of (E)-tert-butyl 1-(dimethylamino)-3-oxobut-1-en-2-ylcarbamate (0.59 g, 2.58 mmol) in ethanol (2.5 mL) was added 3-hydrazinylpyridine, 2HCl (0.470 g, 2.58 mmol). The reaction mixture was stirred at ambient temperature for 16 hours. The reaction mixture was concentrated and purified using silica gel chromatography (0-100% ethyl acetate/hexanes) to yield the title compound as an orange foam (0.235 g, 30%): IR (thin film) 3268, 2978 and 1698 cm⁻¹; ¹H NMR (400 MHz, CDCl₃) δ 8.75 (dd, J=2.5, 0.5 Hz, 1H), 8.62 (dd, J=4.8, 1.5 Hz, 1H), 7.82 (ddd, J=8.2, 2.6, 1.5 Hz, 1H), 7.78 (s, 1H), 7.43 (ddd, J=8.1, 4.8, 0.6 Hz, 1H), 6.04 (s, 1H), 2.29 (s, 3H), 1.52 (s, 9H); ESIMS m/z 275 ([M+H]⁺), 273 ([M−H]⁻).

Example 23: Preparation of tert-butyl 1-(5-fluoropyridin-3-yl)-3-methyl-1H-pyrazol-4-ylcarbamate (Compound 111) and tert-butyl 5-ethoxy-1-(5-fluoropyridin-3-yl)-3-methyl-1H-pyrazol-4-ylcarbamate (Compound 112)

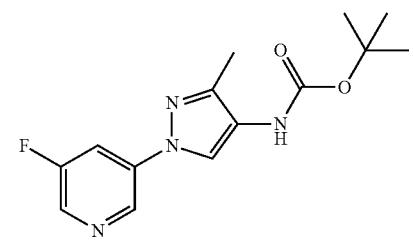

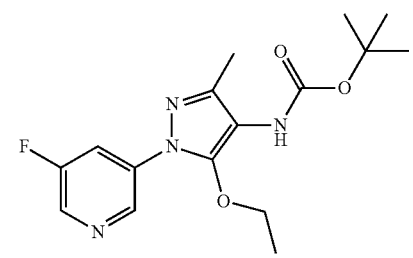

To a solution of 3-fluoro-5-(3-methyl-4-nitro-1H-pyrazol-1-yl)pyridine (3.133 g, 14.10 mmol) in ethanol (28.2 ml) was added ethyl acetate until all of the starting material went into solution. The solution was degassed and 10% palladium on carbon (0.750 g, 0.705 mmol) was added and the reaction was stirred in a parr hydrogenator at 40 psi for 3 hours. The solution was filtered through celite with ethyl acetate and the solvent was removed under reduced pressure. The residue was dissolved in tetrahydrofuran (32.0 ml) and water (9.61 ml). Di-tert-butyl dicarbonate (2.52 g, 11.55 mmol) was added followed by saturated aqueous sodium bicarbonate (9.54 ml, 11.45 mmol). The reaction was stirred at room temperature overnight, diluted with water and extracted with ethyl acetate. The combined organic phases were concentrated and chromatographed (0-100% ethyl acetate/hexanes) to give tert-butyl 1-(5-fluoropyridin-3-yl)-3-methyl-1H-pyrazol-4-ylcarbamate (1.673 g, 5.72 mmol, 41.0%) as a yellow solid and the tert-butyl 5-ethoxy-1-(5-fluoropyridin-3-yl)-3-methyl-1H-pyrazol-4-ylcarbamate (0.250 g, 0.74 mmol, 5.2%) as a brown oil:

Tert-butyl 1-(5-fluoropyridin-3-yl)-3-methyl-1H-pyrazol-4-ylcarbamate (Compound 111): mp 131.5-133.0° C.; ¹H NMR (400 MHz, CDCl₃) δ 8.75 (s, 1H), 8.32 (d, J=2.5 Hz, 1H), 8.28 (s, 1H), 7.77 (dt, J=9.7, 2.4 Hz, 1H), 6.15 (s, 1H), 2.29 (s, 3H), 1.54 (s, 9H); ESIMS m/z 293 ([M+H]⁺).

Tert-butyl 5-ethoxy-1-(5-fluoropyridin-3-yl)-3-methyl-1H-pyrazol-4-ylcarbamate (Compound 112): IR (thin film) 1698 cm⁻¹; ¹H NMR (400 MHz, CDCl₃) δ 8.88 (s, 1H), 8.34 (d, J=2.5 Hz, 1H), 7.83 (d, J=9.9 Hz, 1H), 5.99 (s, 1H), 4.37 (q, J=7.0 Hz, 2H), 2.17 (s, 3H), 1.50 (s, 9H), 1.37 (t, J=7.1 Hz, 3H); ESIMS m/z 337 ([M+H]⁺).

Example 24: Preparation of Bis tert-t-butyl(1-(pyridin-3-yl)-1H-pyrazol-4-yl)carbamate (Compound 595)

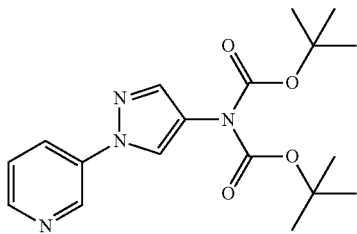 [SMILES: CC(C)(C)OC(=O)N(C(=O)OC(C)(C)C)c1cnn(-c2cccnc2)c1]

To a solution of tert-butyl(1-(pyridin-3-yl)-1H-pyrazol-4-yl)carbamate (2.00 g, 7.68 mmol) in dry THF (21.95 mL) at 0° C. was added 60% sodium hydride (0.33 g, 8.45 mmol) in one portion and stirred at that temperature for 30 minutes. To this was then added Boc-Anhydride (1.84 g, 8.45 mmol) in one portion and stirred for 5 minutes at 0° C. The water bath was removed and the reaction was warmed to room temperature and stirred at additional 30 minutes. The reaction was quenched with water and extracted with ethyl acetate. The ethyl acetate layers were combined, dried (MgSO$_4$), filtered and concentrated to dryness. The crude material was purified by silica gel chromatography (0-100% ethyl acetate/hexanes) to give the desired product as a white solid (2.0 g, 72%): $^1$H NMR (400 MHz, CDCl$_3$) δ 9.12-8.86 (m, 1H), 8.55 (dd, J=4.7, 1.4 Hz, 1H), 8.04 (ddd, J=8.3, 2.7, 1.5 Hz, 1H), 8.01 (d, J=0.5 Hz, 1H), 7.84-7.65 (m, 1H), 7.41 (ddd, J=8.3, 4.8, 0.7 Hz, 1H), 1.51 (s, 18H).

Example 25: Preparation of 3-chloro-1-(pyridin-3-yl)-1H-pyrazol-4-amine (Compound 516)

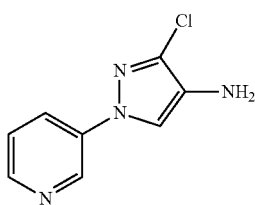 [SMILES: Nc1cn(-c2cccnc2)nc1Cl]

To tert-butyl(3-chloro-1-(pyridin-3-yl)-1H-pyrazol-4-yl) carbamate (2 g, 6.79 mmol) in dichloromethane (6.79 ml) was added trifluoroacetic acid (6.79 ml) and the mixture was left stirring at room temperature for 2 hours. Toluene (12 mL) was added and the reaction was concentrated to near dryness. The mixture was poured into a separatory funnel containing saturated aqueous sodium bicarbonated and was extracted with dichloromethane. The combined organic layers were concentrated to give 3-chloro-1-(pyridin-3-yl)-1H-pyrazol-4-amine (0.954 g, 4.90 mmol, 72.2%) as a white solid: mp 137.9-139.9° C.; $^1$H NMR (400 MHz, CDCl$_3$) δ 8.84 (d, J=2.4 Hz, 1H), 8.50 (dd, J=4.7, 1.4 Hz, 1H), 7.95 (ddd, J=8.3, 2.7, 1.5 Hz, 1H), 7.52 (s, 1H), 7.37 (ddd, J=8.4, 4.7, 0.7 Hz, 1H), 3.18 (s, 2H); ESIMS m/z 196 ([M+H]$^+$).

Example 26: Preparation of N-allyl-1-(5-fluoropyridin-3-yl)-3-methyl-1H-pyrazol-4-amine hydrochloride

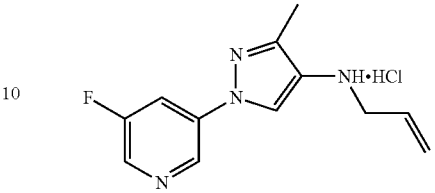

To a solution of tert-butyl allyl(1-(5-fluoropyridin-3-yl)-3-methyl-1H-pyrazol-4-yl)carbamate (908 mg, 2.73 mmol) in dioxane (5 mL) was added HCl (1M in ether) (13.65 mL, 13.65 mmol) and the mixture stirred at room temperature for 48 h. The resulting white solid was filtered, washed with ether and dried under vacuum to give N-allyl-1-(5-fluoropyridin-3-yl)-3-methyl-1H-pyrazol-4-amine, HCl (688 mg, 94% yield) as a white solid: mp 189-190° C.; $^1$H NMR (400 MHz, CDCl$_3$) δ 8.79-8.68 (m, 1H), 8.32-8.26 (m, 1H), 8.23 (s, 1H), 7.98-7.86 (m, 1H), 5.86-5.68 (m, 1H), 5.28-5.17 (m, 1H), 5.17-5.03 (m, 1H), 3.59 (d, J=6.2 Hz, 2H), 2.11 (s, 3H); EIMS (m/z) 233 ([M+1]$^+$).

N-Allyl-3-chloro-1-(pyridin-3-yl)-1H-pyrazol-4-amine, HCl was prepared as described in Example 26 from tert-butyl allyl(3-chloro-1-(pyridin-3-yl)-1H-pyrazol-4-yl)carbamate: mp 172-174° C.; $^1$H NMR (400 MHz, CDCl$_3$) δ 9.20 (d, J=2.5 Hz, 1H), 8.65 (dd, J=5.3, 1.1 Hz, 1H), 8.61 (ddd, J=8.6, 2.5, 1.1 Hz, 1H), 8.24 (s, 1H), 7.93 (dd, J=8.6, 5.3 Hz, 1H), 3.66 (dt, J=5.5, 1.3 Hz, 2H); EIMS (m/z) 235 ([M+1]$^+$).

N-Allyl-3-methyl-1-(pyridin-3-yl)-1H-pyrazol-4-amine, HCl was prepared as described in Example 26 from tert-butyl allyl(3-methyl-1-(pyridin-3-yl)-1H-pyrazol-4-yl): mp 195-197° C.; $^1$H NMR (400 MHz, DMSO-d$_6$) δ 9.12 (d, J=2.4 Hz, 1H), 8.58 (dd, J=5.0, 1.2 Hz, 1H), 8.48 (s, 1H), 8.43 (d, J=9.7 Hz, 1H), 7.77 (dd, J=8.4, 5.0 Hz, 1H), 6.04-5.92 (m, 1H), 5.44 (dd, J=17.2, 1.4 Hz, 1H), 5.32 (d, J=9.4 Hz, 1H), 3.81 (d, J=6.2 Hz, 2H); EIMS (m/z) 249 ([M−1]$^+$).

3-Bromo-1-(5-fluoropyridin-3-yl)-N-methyl-1H-pyrazol-4-amine, HCl was prepared as described in Example 26 from tert-butyl 3-bromo-1-(5-fluoropyridin-3-yl)-1H-pyrazol-4-yl(methyl)carbamate: mp 167-168° C.; $^1$H NMR (400 MHz, CDCl$_3$) δ 8.93 (s, 1H), 8.50 (d, J=2.5 Hz, 1H), 8.23 (s, 1H), 8.14 (dt, J=10.4, 2.3 Hz, 1H), 2.73 (s, 3H).

3-Bromo-N-methyl-1-(pyridin-3-yl)-1H-pyrazol-4-amine, HCl was prepared as described in Example 26 from tert-butyl(3-bromo-1-(pyridin-3-yl)-1H-pyrazol-4-yl)(methyl)carbamate (160 mg, 0.45 mmol) in dioxane (1 mL) was added 4M HCl: mp. 226-228° C.; $^1$H NMR (400 MHz, DMSO-d$_6$) δ 9.26-9.06 (d, J=2.6 Hz, 1H), 8.69-8.54 (m, 1H), 8.54-8.39 (d, J=8.0 Hz, 1H), 8.33-8.14 (s, 1H), 7.90-7.72 (m, 1H), 2.82-2.67 (s, 3H); EIMS (m/z) 253 ([M+1]$^+$), 255 ([M+2H]$^+$).

3-Bromo-N-ethyl-1-(pyridin-3-yl)-1H-pyrazol-4-amine, HCl was prepared as described in Example 26 from 3-bromo-N-ethyl-1-(pyridin-3-yl)-1H-pyrazol-4-amine, HCl: mp 216-217° C.; $^1$H NMR (400 MHz, DMSO-d$_6$) δ 10.66-10.05 (s, 3H), 9.28-9.20 (d, J=2.5 Hz, 1H), 8.74-8.67 (m, 1H), 8.67-8.56 (m, 3H), 7.96-7.84 (m, 1H), 3.21-3.14 (m, 2H), 1.29-1.22 (m, 3H); EIMS (m/z) 267 ([M+1]$^+$).

3-Chloro-N-(2-methoxyethyl)-1-(pyridin-3-yl)-1H-pyrazol-4-amine, HCl was prepared as described in Example 26 from tert-butyl(3-chloro-1-(pyridin-3-yl)-1H-pyrazol-4-yl)(2-methoxyethyl)carbamate, HCl: mp 157-158° C.; $^1$H NMR (400 MHz, DMSO) δ 9.22-9.14 (d, J=2.5 Hz, 1H), 8.70-8.65 (s, 1H), 8.65-8.59 (m, 1H), 8.38-8.33 (m, 1H), 8.00-7.89 (m, 1H), 3.59-3.50 (t, J=5.8 Hz, 2H), 3.32-3.27 (s, 3H), 3.22-3.14 (m, 2H); EIMS (m/z) 253 ([M+1]$^+$).

Example 27: Preparation of 3-chloro-N-ethyl-1-(pyridin-3-yl)-1H-pyrazol-4-amine hydrochloride

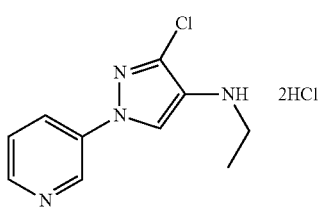

Into a 500 mL three-necked round bottom flask equipped with a magnetic stir bar was added a solution of tert-butyl (3-chloro-1-(pyridin-3-yl)-1H-pyrazol-4-yl)(ethyl)carbamate (21 g, 65.1 mmol) in 1,4-dioxane (35 mL). This pale yellow solution was placed into an ice bath and cooled to 1° C. A solution of 4M HCl/dioxane (65 mL, 260 mmol) was added in one portion. After stirring for 20 minutes, the ice bath was removed and the suspension was stirred further at ambient temperature for 16 hours. The reaction was diluted with 200 mL of ethyl ether and the solid was filtered and washed with ether and placed in a vacuum oven at 40° C. for 18 hours. The title compound was isolated as a pale yellow solid (18.2 g, 95%): $^1$H NMR (400 MHz, MeOD) δ 9.52 (d, J=2.5 Hz, 1H), 9.17 (s, 1H), 9.14 (ddd, J=8.7, 2.5, 1.1 Hz, 1H), 8.93 (ddd, J=5.7, 1.1, 0.6 Hz, 1H), 8.31 (ddd, J=8.7, 5.7, 0.5 Hz, 1H), 3.58 (q, J=7.3 Hz, 2H), 1.48 (t, J=7.3 Hz, 3H); ESIMS m/z 223 ([M+H]$^+$).

3-Chloro-N-methyl-1-(pyridin-3-yl)-1H-pyrazole-4-amine, 2HCl was prepared as described in Example 27: $^1$H NMR (400 MHz, MeOD) δ 9.28 (d, J=2.5 Hz, 1H), 8.86 (ddd, J=8.7, 2.5, 1.2 Hz, 1H), 8.79-8.75 (m, 1H), 8.62 (s, 1H), 8.19 (ddd, J=8.7, 5.6, 0.5 Hz, 1H), 3.06 (s, 3H); $^{13}$C NMR (101 MHz, MeOD) δ 141.42, 139.58, 137.76, 134.58, 134.11, 129.33, 127.55, 122.14, 35.62); ESIMS m/z 209 ([M+H]$^+$).

Example 28: Preparation of 3-(4-nitro-3-phenyl-1H-pyrazol-1-yl)pyridine

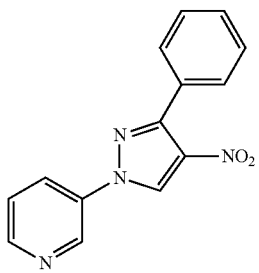 [SMILES: O=[N+]([O-])c1cn(-c2cccnc2)nc1-c1ccccc1]

To a suspension of phenylboronic acid (0.546 g, 4.47 mmol) in toluene (6.63 ml) was added 3-(3-chloro-4-nitro-1H-pyrazol-1-yl)pyridine (0.335 g, 1.492 mmol) followed by ethanol (3.31 ml) and 2 M aqueous potassium carbonate (1.492 ml, 2.98 mmol). The solution was degassed by applying vacuum and then purging with nitrogen (3 times). To the reaction mixture was added palladium tetrakis (0.086 g, 0.075 mmol) and the flask was heated at 110° C. under nitrogen for 16 hours. The aqueous layer was removed and the organic layer was concentrated. The crude product was purified via silica gel chromatography (0-100% ethyl acetate/hexanes) to give 3-(4-nitro-3-phenyl-1H-pyrazol-1-yl)pyridine (499 mg, 1.874 mmol, 80%) as a yellow solid: mp 144.0-146.0° C.; $^1$H NMR (400 MHz, CDCl$_3$) δ 9.09 (d, J=2.3 Hz, 1H), 8.82 (s, 1H), 8.71 (dd, J=4.8, 1.4 Hz, 1H), 8.16 (ddd, J=8.3, 2.7, 1.5 Hz, 1H), 7.82-7.74 (m, 2H), 7.55-7.48 (m, 4H); EIMS m/z 266.

Example 29: Preparation of 5-bromo-1-(pyridin-3-yl)-1H-pyrazol-4-yl(methyl)carbamate (Compound 110)

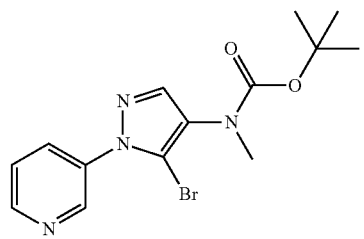 [SMILES: CN(C(=O)OC(C)(C)C)c1cnn(-c2cccnc2)c1Br]

To tert-butyl methyl(1-(pyridin-3-yl)-1H-pyrazol-4-yl)carbamate (0.200 g, 0.729 mmol) in dichloroethane (3.65 ml) was added 1-bromopyrrolidine-2,5-dione (0.260 g, 1.458 mmol) and the reaction was stirred overnight at 50° C. The reaction was concentrated, diluted with dichloromethane, and washed with water and saturated aqueous sodium thiosulfate. The organic phase was concentrated to give tert-butyl 5-bromo-1-(pyridin-3-yl)-1H-pyrazol-4-yl (methyl)carbamate (256 mg, 0.725 mmol, 99%) as a brown oil: IR (thin film) 1697 cm$^{-1}$; $^1$H NMR (400 MHz, CDCl$_3$) δ 8.89 (s, 1H), 8.68 (d, J=4.1 Hz, 1H), 7.93 (ddd, J=8.2, 2.5, 1.5 Hz, 1H), 7.69 (s, 1H), 7.46 (dd, J=8.1, 4.8 Hz, 1H), 3.22 (s, 3H), 1.44 (s, 9H); ESIMS m/z 352 ([M−H]$^−$).

Example 30: Preparation of Bis tert-t-butyl(5-chloro-1-(pyridin-3-yl)-1H-pyrazol-4-yl)carbamate (Compound 109)

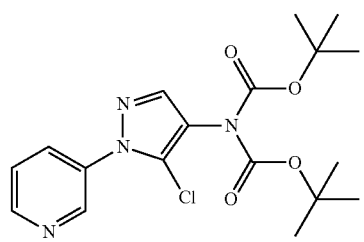 [SMILES: CC(C)(C)OC(=O)N(C(=O)OC(C)(C)C)c1cnn(-c2cccnc2)c1Cl]

To Bis tert-t-butyl(1-(pyridin-3-yl)-1H-pyrazol-4-yl)carbamate (1.30 g, 3.61 mmol) in acetonitrile (21.22 mL) was added N-chlorosuccinimide (0.96 g, 7.21 mmol) and the reaction was stirred at 45° C. for 48 hours. The reaction was cooled to room temperature and poured into water and extracted with dichloromethane. The dichloromethane layers were combined, poured through a phase separator to remove water and concentrated to dryness. The crude material was purified by silica gel chromatography (0-60% ethyl acetate/hexanes) to give the desired product as a yellow solid (0.90 g, 63%): mp 109-115° C.; $^1$H NMR (400 MHz, CDCl$_3$) δ 8.90 (d, J=2.3 Hz, 1H), 8.68 (dd, J=4.8, 1.5 Hz, 1H), 7.94 (ddd, J=8.2, 2.5, 1.5 Hz, 1H), 7.70 (s, 1H), 7.47 (dtd, J=11.0, 5.6, 5.5, 4.8 Hz, 1H), 1.49 (s, 18H); ESIMS m/z 395 ([M+H]$^+$).

Tert-butyl(5-chloro-3-methyl-1-(pyridin-3-yl)-1H-pyrazol-4-yl)(methyl)carbamate was prepared from the appropriate pyrazole in dichloroethane as the solvent as described in Example 30: ESIMS m/z 324 ([M+H]$^+$).

Compounds 110 (see also procedure in Example 29) and 146 were prepared from the appropriate pyrazoles using N-bromosuccinimide in accordance with the procedures disclosed in Example 30.

Tert-butyl 5-bromo-3-methyl-1-(pyridin-3-yl)-1H-pyrazol-4-yl(methyl)carbamate was prepared from the appropriate pyrazole in dichloroethane as described in Example 30: $^1$H NMR (400 MHz, CDCl$_3$) δ 8.88 (d, J=2.3 Hz, 1H), 8.69-8.60 (m, 1H), 7.96-7.86 (m, 1H), 7.48-7.39 (m, 1H), 3.18 (s, 3H), 2.26 (s, 3H), 1.60-1.36 (m, 9H); ESIMS m/z 368 ([M+H]$^+$).

Example 31: Preparation of bis tert-butyl(5-fluoro-1-(pyridin-3-yl)-1H-pyrazol-4-yl)carbamate (Compound 135)

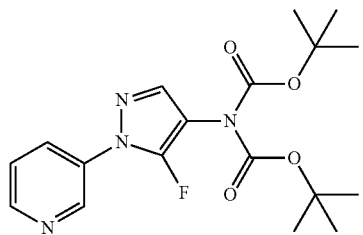 [SMILES: CC(C)(C)OC(=O)N(C(=O)OC(C)(C)C)c1cnn(-c2cccnc2)c1F]

To a solution of bis tert-t-butyl(1-(pyridin-3-yl)-1H-pyrazol-4-yl)carbamate (0.075 g, 0.208 mmol) in DMF (0.416 ml) and acetonitrile (0.416 ml) was added Selecfluor® (0.184 g, 0.520 mmol). The reaction was stirred at room temperature for one week. The reaction was concentrated, saturated aqueous ammonium chloride was added and the mixture was extracted with ethyl acetate. The combined organic phases were concentrated and chromatographed (0-100% ethyl acetate/hexanes) to give bis tert-butyl(5-fluoro-1-(pyridin-3-yl)-1H-pyrazol-4-yl)carbamate (16 mg, 0.042 mmol, 20.32%) as an off-white solid: $^1$H NMR (400 MHz, CDCl$_3$) δ 8.97 (t, J=2.0 Hz, 1H), 8.61 (dd, J=4.8, 1.4 Hz, 1H), 7.99 (ddt, J=8.3, 2.6, 1.3 Hz, 1H), 7.57 (d, J=2.5 Hz, 1H), 7.44 (ddd, J=8.3, 4.8, 0.6 Hz, 1H), 1.50 (s, 18H); ESIMS m/z 379 ([M+H]$^+$).

Tert-butyl(5-fluoro-3-methyl-1-(pyridin-3-yl)-1H-pyrazol-4-yl)(methyl)carbamate was prepared as described in Example 31: $^1$H NMR (400 MHz, CDCl$_3$) δ 8.94 (s, 1H), 8.57 (d, J=4.2 Hz, 1H), 7.96 (d, J=7.7 Hz, 1H), 7.41 (dd, J=7.9, 4.7 Hz, 1H), 3.17 (s, 3H), 2.23 (s, 3H), 1.58-1.40 (m, 9H); ESIMS m/z 307 ([M+H]$^+$).

Example 32: Preparation of N-cyclopropyl-3-methyl-1-(pyridin-3-yl)-1H-pyrazol-4-amine

Example 32, Step 1: Preparation of 3-(4-iodo-3-methyl-1H-pyrazol-1-yl)pyridine

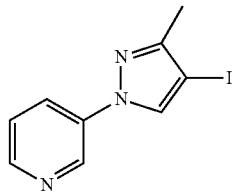

To a mixture of 3-(3-methyl-1H-pyrazol-1-yl)pyridine (6.7 g, 42.1 mmol), iodic acid (2.96 g, 16.84 mmol), and diiodine (8.55 g, 33.7 mmol) in acetic acid (60.1 ml) was added concentrated sulfur acid (3.74 ml, 21.04 mmol). The reaction mixture heated to 70° C. for 30 minutes. The reaction mixture was poured onto ice with sodium thiosulfate and was extracted with diethyl ether. The combined organic phases were washed with saturated aqueous sodium bicarbonate. The organic phases were then dried with magnesium sulfate, filtered and concentrated in vacuo. The solid residue was dissolved in dichloromethane, applied to a 80 g silica gel column, and eluted with 0-80% acetone in hexanes to afford 3-(4-iodo-3-methyl-1H-pyrazol-1-yl)pyridine (11.3 g, 35.7 mmol, 85%) as a white solid: mp 131° C.; $^1$H NMR (400 MHz, CDCl$_3$) δ 8.95-8.85 (m, 1H), 8.52 (dd, J=4.8, 1.4 Hz, 1H), 8.00-7.94 (m, 1H), 7.91 (s, 1H), 7.38 (ddd, J=8.3, 4.8, 0.7 Hz, 1H), 2.34 (s, 3H); EIMS m/z 285.

Example 32, Step 2: Preparation of N-cyclopropyl-3-methyl-1-(pyridin-3-yl)-1H-pyrazol-4-amine

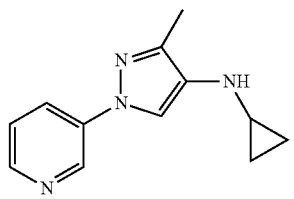 [SMILES: Cc1nn(-c2cccnc2)cc1NC1CC1]

To a solution of 3-(4-iodo-3-methyl-1H-pyrazol-1-yl)pyridine (2.0 g, 7.02 mmol) in dimethylsulfoxide (7.02 ml) was added 1-(5,6,7,8-tetrahydroquinolin-8-yl)ethanone (0.246 g, 1.403 mmol), cyclopropanamine (0.486 ml, 7.02 mmol), cesium carbonate (6.86 g, 21.05 mmol) and copper (I) bromide (0.101 g, 0.702 mmol). The reaction mixture was stirred at 35° C. for 2 days. The reaction mixture was diluted with water and extracted with dichloromethane. The combined organics were washed with brine, concentrated and chromatographed (0-100% ethyl acetate/hexanes) to give N-cyclopropyl-3-methyl-1-(pyridin-3-yl)-1H-pyrazol-4-amine (269 mg, 1.255 mmol, 17.90%) as a yellow solid: mp 104.0-107.0° C.; $^1$H NMR (400 MHz, CDCl$_3$) δ 8.89 (dd, J=2.7, 0.5 Hz, 1H), 8.41 (dd, J=4.7, 1.4 Hz, 1H), 7.96 (ddd, J=8.3, 2.7, 1.5 Hz, 1H), 7.51 (s, 1H), 7.33 (ddd, J=8.3, 4.7, 0.7 Hz, 1H), 3.42 (s, 1H), 2.53-2.42 (m, 1H), 2.22 (s, 3H), 0.72-0.65 (m, 2H), 0.60-0.53 (m, 2H); ESIMS m/z 215 ([M+H]$^+$).

3-Methyl-N-(3-(methylthio)propyl)-1-(pyridin-3-yl)-1H-pyrazol-4-amine was prepared as described in Example 32: IR (thin film) 3298 cm$^{-1}$; $^1$H NMR (400 MHz, CDCl$_3$) δ 8.87 (d, J=2.3 Hz, 1H), 8.40 (dd, J=4.7, 1.4 Hz, 1H), 7.93 (ddd, J=8.3, 2.7, 1.5 Hz, 1H), 7.35 (s, 1H), 7.34-7.29 (m, 1H), 3.16 (t, J=6.8 Hz, 2H), 2.89 (s, 1H), 2.64 (t, J=7.0 Hz, 2H), 2.25 (s, 3H), 2.13 (s, 3H), 1.95 (p, J=6.9 Hz, 2H); ESIMS m/z 263 ([M+H]$^+$).

3-Methyl-N-(2-methyl-3-(methylthio)propyl)-1-(pyridin-3-yl)-1H-pyrazol-4-amine was prepared as described in Example 32: IR (thin film) 3325 cm$^{-1}$; $^1$H NMR (400 MHz, CDCl$_3$) δ 8.86 (d, J=2.5 Hz, 1H), 8.40 (dd, J=4.7, 1.2 Hz, 1H), 7.93 (ddd, J=8.3, 2.7, 1.5 Hz, 1H), 7.35 (s, 1H), 7.32 (ddd, J=8.3, 4.7, 0.5 Hz, 1H), 3.12 (dd, J=11.5, 6.1 Hz, 1H), 2.94 (dd, J=11.9, 6.6 Hz, 1H), 2.62 (dd, J=12.9, 6.9 Hz, 1H), 2.52 (dd, J=12.9, 6.2 Hz, 1H), 2.26 (s, 3H), 2.14 (s, 3H), 2.12-2.02 (m, 1H), 1.11 (d, J=6.8 Hz, 3H); EIMS m/z 276.

Example 33: Preparation of tert-butyl(3-cyclopropyl-1-(5-fluoropyridin-3-yl)-1H-pyrazol-4-yl)carbamate (Compound 434) and tert-butyl(1-(5-fluoropyridin-3-yl)-1H-pyrazol-4-yl)carbamate (Compound 489)

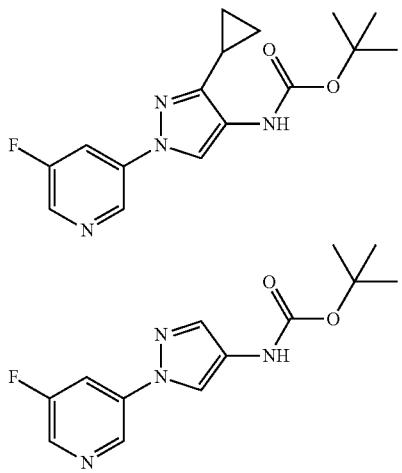

To a suspension of 2-cyclopropyl-4,4,5,5-tetramethyl-1,3,2-dioxaborolane (1.087 g, 6.47 mmol) in toluene (13.69 ml) was added tert-butyl(3-bromo-1-(5-fluoropyridin-3-yl)-1H-pyrazol-4-yl)carbamate (1.1 g, 3.08 mmol) followed by ethanol (6.84 ml) and 2 M aqueous potassium carbonate (3.08 mL, 6.16 mmol). The solution was degassed by applying vacuum and then purging with nitrogen (3 times). To the reaction mixture was added palladium tetrakis (0.178 g, 0.154 mmol) and the flask was heated at 100° C. under nitrogen for 36 hours. Water (5 mL) was added and the mixture was extracted with ethyl acetate. The combined organics were concentrated and chromatographed (0-100% ethyl acetate/hexanes) to give tert-butyl(3-cyclopropyl-1-(5-fluoropyridin-3-yl)-1H-pyrazol-4-yl)carbamate (705 mg, 2.215 mmol, 71.9% yield) as a yellow solid and tert-butyl (1-(5-fluoropyridin-3-yl)-1H-pyrazol-4-yl)carbamate (242 mg, 0.870 mmol, 28.2% yield) as a yellow solid.
tert-Butyl(3-cyclopropyl-1-(5-fluoropyridin-3-yl)-1H-pyrazol-4-yl)carbamate: mp 156.5-158.0; $^1$H NMR (400 MHz, CDCl$_3$) δ 8.73 (s, 1H), 8.30 (d, J=2.5 Hz, 1H), 8.27 (s, 1H), 7.76 (dt, J=9.8, 2.4 Hz, 1H), 6.43 (s, 1H), 1.55 (s, 9H), 1.01-0.91 (m, 4H); ESIMS m/z 319 ([M+H]$^+$).

(1-(5-Fluoropyridin-3-yl)-1H-pyrazol-4-yl)carbamate: mp 121.0-123.0° C.; $^1$H NMR (300 MHz, CDCl$_3$) δ 8.78 (s, 1H), 8.37 (s, 1H), 8.28 (s, 1H), 7.81 (d, J=9.6 Hz, 1H), 7.59 (s, 1H), 6.44 (s, 1H), 1.53 (s, 9H). ESIMS m/z 278 ([M]$^+$).

Compounds 340 and 404 were prepared as described in Example 33.

Example 34: Preparation of tert-butyl(3-ethyl-1-(5-fluoropyridin-3-yl)-1H-pyrazol-4-yl)(methyl)carbamate (Compound 408)

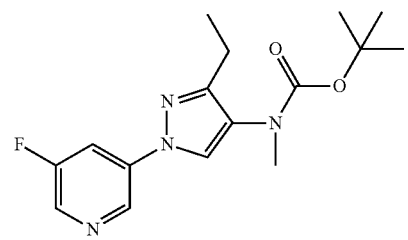 [SMILES: CCc1nn(-c2cncc(F)c2)cc1N(C)C(=O)OC(C)(C)C]

To a N$_2$-purged solution of tert-butyl(1-(5-fluoropyridin-3-yl)-3-vinyl-1H-pyrazol-4-yl)(methyl)carbamate (0.730 g, 2.293 mmol) in methanol (15.29 ml) was added 10% palladium on carbon (0.036 g, 0.339 mmol). The reaction was purged with hydrogen and run under 80 psi of hydrogen at room temperature for 60 hours. The reaction gave less than 20% conversion. The reaction mixture was filtered through celite, concentrated, and redissolved in ethyl acetate (4 mL) and transferred to a bomb. The reaction was heated at 50° C. at 600 psi of hydrogen for 20 hours. The reaction was only 50% complete. Methanol (1 mL) and 10% palladium on carbon (36 mg) were added, and the reaction was heated at 80° C. at 650 psi of hydrogen for 20 hours. The reaction was filtered through celite and concentrated to give tert-butyl(3-ethyl-1-(5-fluoropyridin-3-yl)-1H-pyrazol-4-yl)(methyl)carbamate (616 mg, 1.923 mmol, 84% yield) as yellow oil: IR (thin film) 1692 cm$^{-1}$; $^1$H NMR (300 MHz, CDCl$_3$) δ 8.71 (t, J=1.4 Hz, 1H), 8.35 (d, J=2.6 Hz, 1H), 7.83 (dt, J=9.5, 2.3 Hz, 2H), 3.18 (s, 3H), 2.65 (q, J=7.5 Hz, 2H), 1.44 (s, 9H), 1.25 (t, J=7.1 Hz, 3H); EIMS m/z 320.

Example 35: Preparation of N-(1-(5-fluoropyridin-3-yl)-3-formyl-1H-pyrazol-4-yl)isobutyramide (Compound 560)

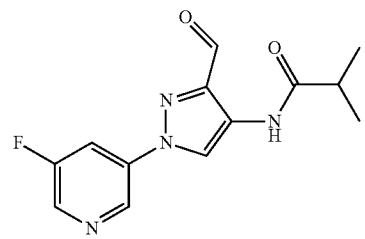 [SMILES: CC(C)C(=O)Nc1cn(-c2cncc(F)c2)nc1C=O]

To a solution of N-(1-(5-fluoropyridin-3-yl)-3-vinyl-1H-pyrazol-4-yl)isobutyramide (0.706 g, 2.57 mmol) in tetrahydrofuran (12.87 ml) and water (12.87 ml) was added osmium tetroxide (0.164 ml, 0.026 mmol). After 10 minutes at room temperature, sodium periodate (1.101 g, 5.15 mmol) was added in portions over 3 minutes and the resulting solution was stirred at room temperature. After 18 hours, the solution was poured into 10 mL water and was extracted with 3×10 mL dichloromethane. The combined organic layers were dried, concentrated and chromatographed (0-100% ethyl acetate/hexanes) to give N-(1-(5-fluoropyridin-3-yl)-3-formyl-1H-pyrazol-4-yl)isobutyramide (626 mg, 2.266 mmol, 88% yield) as a yellow solid: mp 140.0-142.0° C.; $^1$H NMR (300 MHz, CDCl$_3$) δ 10.12 (s, 1H), 9.14 (s, 1H), 8.90 (d, J=2.0 Hz, 1H), 8.82 (s, 1H), 8.51 (d, J=2.5 Hz, 1H), 7.92 (dt, J=9.2, 2.4 Hz, 1H), 2.65 (dt, J=13.8, 6.9 Hz, 1H), 1.31 (d, J=6.9 Hz, 6H); ESIMS m/z 277 ([M+H]$^+$).

Compound 369 was prepared in accordance with the procedures disclosed in Example 35.

Example 36: Preparation of N-(1-(5-fluoropyridin-3-yl)-3-(hydroxymethyl)-1H-pyrazol-4-yl)isobutyramide (Compound 435) and N-(1-(5-fluoropyridin-3-yl)-1H-pyrazol-4-yl)isobutyramide (Compound 436)

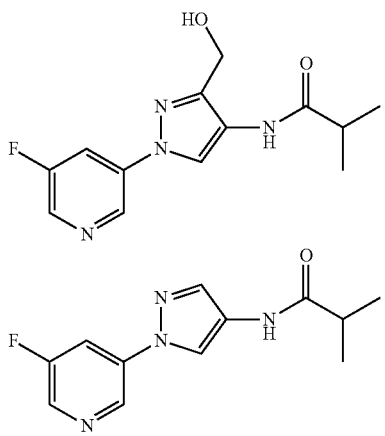

To a solution of N-(1-(5-fluoropyridin-3-yl)-3-formyl-1H-pyrazol-4-yl)isobutyramide (0.315 g, 1.140 mmol) in methanol (5.70 ml) at 0° C. was added sodium borohydride (0.086 g, 2.280 mmol). The reaction was stirred at 0° C. for 2 hours, and room temperature for 20 hours. 0.5 M HCl was added, the reaction was neutralized with saturated aqueous sodium bicarbonate, and the mixture was extracted with dichloromethane. The organic phases were concentrated and chromatographed (0-100% ethyl acetate/hexanes) to give N-(1-(5-fluoropyridin-3-yl)-3-(hydroxymethyl)-1H-pyrazol-4-yl)isobutyramide (180 mg, 0.647 mmol, 56.7%) as a white solid and N-(1-(5-fluoropyridin-3-yl)-1H-pyrazol-4-yl)isobutyramide (9 mg, 0.036 mmol, 3.18%) as a white solid.

N-(1-(5-fluoropyridin-3-yl)-3-(hydroxymethyl)-1H-pyrazol-4-yl)isobutyramide: mp 144.0-146.0° C.; $^1$H NMR (400 MHz, CDCl$_3$) δ 8.74 (d, J=1.1 Hz, 1H), 8.64 (s, 1H), 8.37-8.29 (m, 2H), 7.74 (dt, J=9.5, 2.3 Hz, 1H), 4.95 (d, J=3.0 Hz, 2H), 3.21-3.06 (m, 1H), 2.63-2.48 (m, 1H), 1.26 (d, J=6.9 Hz, 6H); ESIMS m/z 279 ([M+H]$^+$).

N-(1-(5-fluoropyridin-3-yl)-1H-pyrazol-4-yl)isobutyramide: IR (thin film) 1659 cm$^{-1}$; $^1$H NMR (400 MHz, CDCl$_3$) δ 8.79 (d, J=1.2 Hz, 1H), 8.60 (s, 1H), 8.38 (d, J=2.5 Hz, 1H), 7.81 (dt, J=9.5, 2.3 Hz, 1H), 7.68 (s, 1H), 7.54 (s, 1H), 2.63-2.51 (m, 1H), 1.28 (d, J=6.9 Hz, 6H); ESIMS m/z 249 ([M+H]$^+$).

Example 37: Preparation of N-(3-(chloromethyl)-1-(5-fluoropyridin-3-yl)-1H-pyrazol-4-yl)isobutyramide (Compound 561)

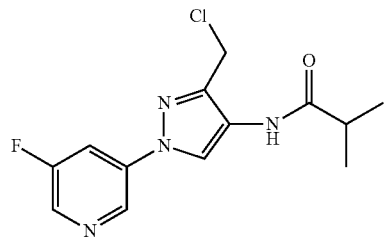 [SMILES: CC(C)C(=O)Nc1cn(-c2cncc(F)c2)nc1CCl]

To a solution of N-(1-(5-fluoropyridin-3-yl)-3-(hydroxymethyl)-1H-pyrazol-4-yl)isobutyramide (0.100 g, 0.359 mmol) in dichloromethane (3.59 ml) was added thionyl chloride (0.157 ml, 2.151 mmol). The reaction was stirred at room temperature for 2 hours. Saturated aqueous sodium bicarbonate was added, and the mixture was extracted with dichloromethane. The combined organic phases were washed with brine and concentrated to give N-(3-(chloromethyl)-1-(5-fluoropyridin-3-yl)-1H-pyrazol-4-yl)isobutyramide (100 mg, 0.337 mmol, 94% yield) as a white solid: mp 172.0-177.0° C.; $^1$H NMR (400 MHz, CDCl$_3$) δ 8.79 (s, 1H), 8.67 (s, 1H), 8.40 (s, 1H), 7.80 (dt, J=9.4, 2.3 Hz, 1H), 7.42 (s, 1H), 4.77 (s, 2H), 2.63 (hept, J=6.9 Hz, 1H), 1.30 (d, J=6.9 Hz, 6H); ESIMS m/z 298 ([M+H]$^+$).

Example 38: Preparation of N-(3-chloro-1-(pyridin-3-yl)-1H-pyrazol-4-yl)-N-ethyl-2-methoxyacetamide (Compound 512) (see also Example 11)

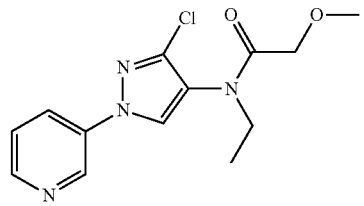 [SMILES: CCN(C(=O)COC)c1cn(-c2cccnc2)nc1Cl]

To a solution of 3-chloro-N-ethyl-1-(pyridin-3-yl)-1H-pyrazol-4-amine, 2HCl (0.130 g, 0.502 mmol) and in DCM (2.508 ml) was added N-ethyl-N-isopropylpropan-2-amine (0.257 ml, 1.505 mmol) followed by 2-methoxyacetyl chloride (0.109 g, 1.003 mmol) and the reaction mixture was stirred at ambient temperature for 16 hours. The reaction was quenched by the addition of saturated sodium bicarbonate. The organic layer was extracted with DCM. The organic layer was dried over sodium sulfate, filtered, concentrated and purified using silica gel chromatography (0-100% ethyl acetate/hexanes) to yield the title compound as a pale yellow oil (0.12 g, 77%): IR (thin film) 3514, 3091, 2978, 1676 cm$^{-1}$; $^1$H NMR (400 MHz, CDCl$_3$) δ 8.96 (d, J=2.4 Hz, 1H), 8.63 (d, J=3.8 Hz, 1H), 8.09-8.03 (m, 1H), 7.99 (s, 1H), 7.47 (dd, J=8.3, 4.8 Hz, 1H), 3.88 (s, 2H), 3.77-3.65 (m, 2H), 3.40 (s, 3H), 1.18 (t, J=7.2 Hz, 3H); ESIMS m/z 295 ([M+H]$^+$).

Compounds 71, 478, 481, 483-484, and 543 were prepared in accordance with the procedures disclosed in Example 38.

Example 39: Preparation of N-(3-chloro-1-(5-fluoropyridin-3-yl)-1H-pyrazol-4-yl)-N-ethyl-2-methyl-3-(methylthio)butanamide (Compound 182) and (Z)—N-(3-chloro-1-(5-fluoropyridin-3-yl)-1H-pyrazol-4-yl)-N-ethyl-2-methylbut-2-enamide (Compound 183)

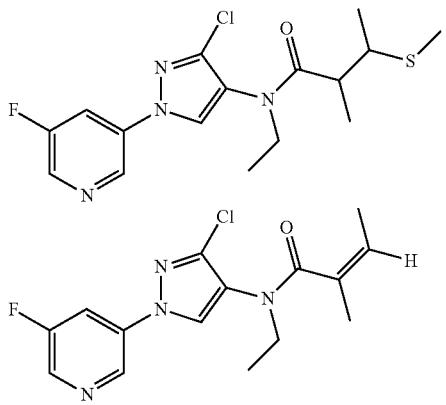

To a solution 2-methyl-3-(methylthio)butanoic acid (0.154 g, 1.039 mmol) in dichloromethane (1 mL) at room temperature was added 1 drop of dimethylformamide. Oxalyl dichloride (0.178 ml, 2.078 mmol) was added dropwise and the reaction was stirred at room temperature overnight. The solvent was removed under reduced pressure. The residue was redissolved in dichloromethane (1 mL) and the solvent was removed under reduced pressure. The residue was redissolved in dichloromethane (0.5 mL) and the solution was added to a solution of 3-chloro-N-ethyl-1-(5-fluoropyridin-3-yl)-1H-pyrazol-4-amine (0.100 g, 0.416 mmol) and 4-dimethylaminopyridine (0.254 g, 2.078 mmol) in dichloromethane (1.5 mL) and stirred at room temperature overnight. The solvent was removed under reduced pressure and the residue was purify by chromatography (0-100% ethyl acetate/hexanes) to give N-(3-chloro-1-(5-fluoropyridin-3-yl)-1H-pyrazol-4-yl)-N-ethyl-2-methyl-3-(methylthio)butanamide (34 mg, 0.092 mmol, 22.06%) as a faint yellow oil and (Z)—N-(3-chloro-1-(5-fluoropyridin-3-yl)-1H-pyrazol-4-yl)-N-ethyl-2-methylbut-2-enamide (38 mg, 0.118 mmol, 28.3% yield) as a yellow oil.

N-(3-chloro-1-(5-fluoropyridin-3-yl)-1H-pyrazol-4-yl)-N-ethyl-2-methyl-3-(methylthio)butanamide: IR (thin film) 1633 cm$^{-1}$; $^1$H NMR (400 MHz, CDCl$_3$) δ 8.79 (d, J=2.0 Hz, 0.66H), 8.77 (d, J=2.0 Hz, 0.33H), 8.50 (d, J=2.6 Hz, 0.33H), 8.49 (d, J=2.5 Hz, 0.66H), 8.08 (s, 0.66H), 7.95 (s, 0.33H), 7.92-7.81 (m, 1H), 4.03-3.46 (m, 2H), 3.03-2.78 (m, 1H), 2.59-2.33 (m, 1H), 2.04 (s, 2H), 2.02 (s, 1H), 1.32 (d, J=6.7 Hz, 1H), 1.27 (d, J=6.2 Hz, 1H), 1.23 (d, J=6.9 Hz, 2H), 1.18-1.12 (m, 5H); ESIMS m/z 371 ([M]$^+$).

(Z)—N-(3-chloro-1-(5-fluoropyridin-3-yl)-1H-pyrazol-4-yl)-N-ethyl-2-methylbut-2-enamide: $^1$H NMR (400 MHz, CDCl$_3$) δ 8.73 (d, J=2.0 Hz, 1H), 8.46 (d, J=2.4 Hz, 1H), 7.87 (d, J=4.9 Hz, 1H), 7.84 (dt, J=9.2, 2.4 Hz, 1H), 5.93-5.76 (m, 1H), 3.73 (q, J=7.1 Hz, 2H), 1.72 (s, 3H), 1.58 (dd, J=6.9, 0.9 Hz, 3H), 1.17 (t, J=7.1 Hz, 3H); ESIMS m/z 323 ([M]$^+$).

Compounds 70, 180-181, 389-392, 397-398, 405-406, 427-429, 432, 456, 482, 521-522, 532-534, 555, and 589 were prepared from the corresponding intermediates and starting materials in accordance with the procedures disclosed in Example 39.

Example 40: Preparation of N-(3-chloro-1-(pyridin-3-yl)-1H-pyrazol-4-yl)-N-methyl-2-(methylthio)acetamide (Compound 337)

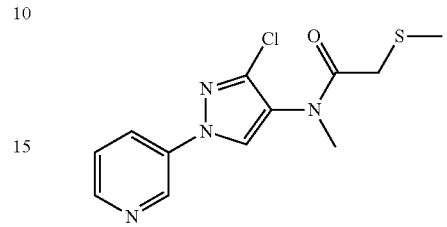

To an ice cold solution of 2-(methylthio)acetic acid (0.092 g, 0.863 mmol) in DCM (2 mL) was added N-ethyl-N-isopropylpropan-2-amine (0.111 g, 0.863 mmol) followed by isobutyl chloroformate (0.099 ml, 0.767 mmol). Stirring was continued for 10 minutes. Next, the mixed anhydride was added to a solution of 3-chloro-N-methyl-1-(pyridin-3-yl)-1H-pyrazol-4-amine (0.08 g, 0.383 mmol) in DCM (0.66 mL) and the reaction mixture was stirred at ambient temperature for 2 hours. The reaction mixture was concentrated and purified using reverse phase C-18 column chromatography (0-100% CH$_3$CN/H$_2$O) to yield the title compound as a pale yellow oil (0.075 g, 66%): $^1$H NMR (400 MHz, CDCl$_3$) δ 8.95 (d, J=2.5 Hz, 1H), 8.62 (dd, J=4.8, 1.4 Hz, 1H), 8.13 (s, 1H), 8.04 (ddd, J=8.3, 2.7, 1.4 Hz, 1H), 7.50-7.43 (m, 1H), 3.26 (s, 3H), 3.12 (s, 2H), 2.24 (s, 3H); $^{13}$C NMR (101 MHz, CDCl$_3$) δ 170.00, 148.61, 140.15, 140.03, 135.68, 126.56, 126.42, 125.33, 124.15, 37.16, 34.94, 16.22; ESIMS m/z 297 ([M+H]$^+$).

Compounds 335, 336, and 542 were prepared in accordance with the procedures disclosed in Example 40.

Example 41, Preparation of N-(3-chloro-1-(pyridin-3-yl)-1H-pyrazol-4-yl)-N-ethyl-2-methyl-3-oxobutanamide (Compound 499)

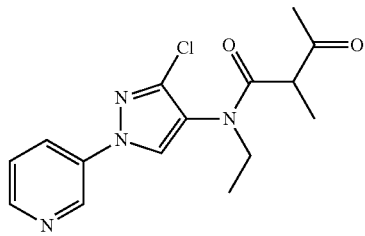 [SMILES: CCN(C(=O)C(C)C(C)=O)c1cn(-c2cccnc2)nc1Cl]

To a solution of 3-chloro-N-ethyl-1-(pyridin-3-yl)-1H-pyrazol-4-amine, HCl (259 mg, 1 mmol) and ethyl 2-methyl-3-oxobutanoate (144 mg, 1.000 mmol) in dioxane (1 mL) was added 2,3,4,6,7,8-hexahydro-1H-pyrimido[1,2-a]pyrimidine (181 mg, 1.30 mmol) and the mixture was heated in a microwave (CEM Discover) at 150° C. for 1.5 h, with external IR-sensor temperature monitoring from the bottom of the vessel. LCMS (ELSD) indicated a 40% conversion to the desired product. The mixture was diluted with ethyl acetate (50 ML) and saturated aqueous NH$_4$Cl (15 mL), and the organic phase was separated. The aqueous phase was extracted with ethyl acetate (20 mL) and the combined organic phase was washed with brine, dried over MgSO$_4$ and concentrated in vacuo to give an oily residue. This residue was purified on silica gel eluting with mixtures of ethyl acetate and hexanes to give N-(3-chloro-1-(pyridin-3-yl)-1H-pyrazol-4-yl)-N-ethyl-2-methyl-3-oxobutanamide (37 mg, 11% yield, 96% purity) as a colorless oil: $^1$H NMR (400 MHz, CDCl$_3$) δ 9.02-8.92 (dd, J=2.6, 0.8 Hz, 1H), 8.68-8.60 (dd, J=4.8, 1.5 Hz, 1H), 8.09-7.98 (m, 1H), 7.96-7.87 (s, 1H), 3.87-3.58 (d, J=3.0 Hz, 2H), 3.49-3.38 (m, 1H), 2.16-2.08 (s, 3H), 1.39-1.32 (d, J=7.0 Hz, 3H), 1.22-1.13 (m, 3H); EIMS (m/z) 321 ([M+1]$^+$), 319 ([M−1]$^−$).

Example 42: Preparation of N-(3-chloro-1-(pyridin-3-yl)-1H-pyrazol-4-yl)-N-ethylcyclopropanecarboxamide (Compound 538)

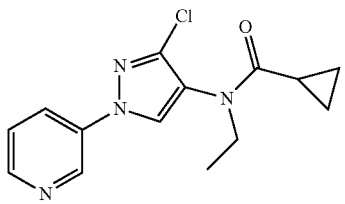 [SMILES: CCN(C(=O)C1CC1)c1cn(-c2cccnc2)nc1Cl]

To a solution of 3-chloro-N-ethyl-1-(pyridin-3-yl)-1H-pyrazol-4-amine monohydrochloride (0.10 g, 0.038 mmol) in dichloroethane (0.75 ml) was added cyclopropanecarboxylic acid (0.03 g, 0.38 mmol) and 4-N,N-dimethylaminopyridine (0.14 g, 1.15 mmol) followed by 1-(3-dimethylaminopropyl)-3-ethylcarbodiimide hydrochloride (0.14 g, 0.77 mmol). The reaction was stirred at room temperature overnight. The reaction mixture was concentrated to dryness and the crude product was purified by reverse phase silica gel chromatography eluting with 0-50% acetonitrile/water to give a white solid (0.03 g, 25%); mp 111-119° C.; $^1$H NMR (400 MHz, CDCl$_3$) δ 8.96 (d, J=2.5 Hz, 1H), 8.63-8.59 (m, 1H), 8.06 (ddd, J=8.3, 2.6, 1.4 Hz, 1H), 8.01 (s, 1H), 7.46 (dd, J=8.3, 4.7 Hz, 1H), 3.73 (q, J=7.2 Hz, 2H), 1.46 (ddd, J=12.6, 8.1, 4.7 Hz, 1H), 1.16 (t, J=7.2 Hz, 3H), 1.04 (t, J=3.7 Hz, 2H), 0.71 (dd, J=7.7, 3.0 Hz, 2H); ESIMS m/z 291 ([M+H]).

Compounds 69, 516, 524, 546, 558-559, 582-588, 593, and 594 were prepared from the appropriate acids in accordance with the procedures disclosed in Example 42.

Example 43: Preparation of N-(3-chloro-1-(pyridin-3-yl)-1H-pyrazol-4-yl)-2-methyl-3-(methylthio)-N-(3-(methylthio)propanoyl)propanamide (Compound 407)

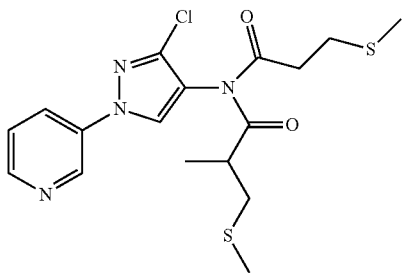 [SMILES: CSCCC(=O)N(C(=O)C(C)CSC)c1cn(-c2cccnc2)nc1Cl]

To a solution of N-(3-chloro-1-(pyridin-3-yl)-1H-pyrazol-4-yl)-3-(methylthio)propanamide (0.216 g, 0.728 mmol) in DCE (2.91 ml) in a 10 mL vial was added 2-methyl-3-(methylthio)propanoyl chloride (0.244 g, 1.601 mmol). The vial was capped and placed in a Biotage Initiator microwave reactor for 3 hours at 100° C., with external IR-sensor temperature monitoring from the side of the vessel. The crude mixture was concentrated and purified using reverse phase C-18 column chromatography (0-100% acetonitrile/water) to yield the title compound as a pale yellow oil (67 mg, 22%): IR (thin film) 2916 and 1714 cm$^{−1}$; $^1$H NMR (300 MHz, CDCl$_3$) δ 8.96-8.92 (d, J=2.7 Hz, 1H), 8.64-8.59 (dd, J=4.9, 1.4 Hz, 1H), 8.07-7.99 (m, 2H), 7.50-7.40 (dd, J=8.4, 4.8 Hz, 1H), 3.39-3.28 (m, 1H), 3.10-2.99 (td, J=7.2, 3.9 Hz, 2H), 2.96-2.86 (dd, J=13.2, 8.7 Hz, 1H), 2.86-2.79 (t, J=7.3 Hz, 2H), 2.58-2.48 (dd, J=13.1, 5.8 Hz, 1H), 2.14-2.12 (s, 3H), 2.09-2.06 (s, 3H), 1.30-1.26 (d, J=6.9 Hz, 3H); ESIMS m/z 413 ([M+H]$^+$).

Compounds 383, 410, 433, 437, 451, 470, 530 and 531 were prepared in accordance with the procedures disclosed in Example 43.

Example 44: Preparation of N-[3-chloro-1-(3-pyridyl)pyrazol-4-yl]-2,2-dideuterio-N-ethyl-3-methylsulfanyl-propanamide (Compound 393)

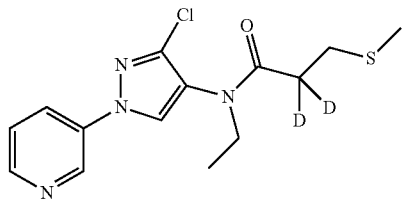 [SMILES: [2H]C([2H])(CSC)C(=O)N(CC)c1cn(-c2cccnc2)nc1Cl]

To a 7 mL vial was added 3-chloro-N-ethyl-1-(pyridin-3-yl)-1H-pyrazol-4-amine (111 mg, 0.5 mmol), 2,2-dideuterio-3-methylsulfanyl-propanoic acid (58.0 mg, 0.475 mmol) and followed by DCM (Volume: 2 mL). The solution was stirred at 0° C. Then the solution of DCC (0.500 mL, 0.500 mmol, 1.0 M in DCM) was added. The solution was allowed to warm up to 25° C. slowly and stirred at 25° C. overnight. White precipitate formed during the reaction. The crude reaction mixture was filtered through a cotton plug and purified by silica gel chromatography (0-100% EtOAc/hexane) to give N-[3-chloro-1-(3-pyridyl)pyrazol-4-yl]-2,2-dideuterio-N-ethyl-3-methylsulfanyl-propanamide (97 mg, 0.297 mmol, 59.4% yield) as a colorless oil: $^1$H NMR (400 MHz, CDCl$_3$) δ 8.96 (d, J=2.4 Hz, 1H), 8.63 (dd, J=4.6, 0.9 Hz, 1H), 8.06 (ddd, J=8.4, 2.7, 1.4 Hz, 1H), 7.98 (s, 1H), 7.52-7.40 (m, 1H), 3.72 (q, J=7.2 Hz, 2H), 2.78 (s, 2H), 2.06 (s, 3H), 1.17 (t, J=7.2 Hz, 3H); ESIMS m/z 327 ([M+H]$^+$); IR (Thin film) 1652 cm$^{−1}$.

Compounds 394, 396, and 471-473 were prepared from the corresponding intermediates and starting materials in accordance with the procedures disclosed in Example 44.

Example 45: Preparation of 1-ethyl-3-(3-methyl-1-(pyridin-3-yl)-1H-pyrazol-4-yl)urea (Compound 145)

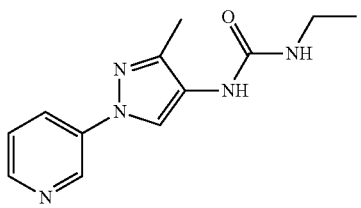 [SMILES: CCNC(=O)Nc1cn(-c2cccnc2)nc1C]

To a solution of 3-methyl-1-(pyridin-3-yl)-1H-pyrazol-4-amine (0.1 g, 0.574 mmol) in DCM (5.74 ml) was added ethyl isocyanate (0.041 g, 0.574 mmol) and the reaction mixture was stirred at ambient temperature for 40 minutes. The reaction mixture had turned from a clear solution to a suspension with white solid material. The reaction mixture was concentrated and purified using silica gel chromatography (0-20% MeOH/DCM) to yield the title compound as a white solid (0.135 g, 95%): mp 197-200° C.; $^1$H NMR (400 MHz, CDCl$_3$) δ 8.94 (d, J=2.3 Hz, 1H), 8.48-8.37 (m, 1H), 8.32 (s, 1H), 7.94 (d, J=8.3 Hz, 1H), 7.52 (br s, 1H), 7.41-7.25 (m, 1H), 5.79 (br s, 1H), 3.33-3.23 (m, 2H), 2.29 (d, J=2.9 Hz, 3H), 1.16 (dd, J=8.7, 5.7 Hz, 3H); ESIMS m/z 246 ([M+H]$^+$), 244 ([M−H]$^−$).

Compounds 169-171, 221-222, 255-257, 278-280, 297-302, 318-322, 334, 345, 348, 375-377, 385-387, and 411-413 were prepared in accordance with the procedures disclosed in Example 45.

1-(3-Chloro-1-(pyridin-3-yl)-1H-pyrazol-4-yl)-3-ethyl-1-methylthiourea (Compound Y2048) was prepared in accordance with the procedure disclosed in Example 45 using DMAP as a base, dioxane as a solvent, and heating the reaction in a microwave (CEM Discover®) with external IR-sensor temperature monitoring from the bottom of the vessel at 120° C. for 2 hours: white solid; mp 160.0-162.0° C.; $^1$H NMR (300 MHz, CDCl$_3$) δ 8.94 (d, J=2.6 Hz, 1H), 8.62 (dd, J=4.8, 1.4 Hz, 1H), 8.05-7.98 (m, 2H), 7.46 (dd, J=8.3, 4.7 Hz, 1H), 5.66 (s, 1H), 3.72-3.59 (m, 5H), 1.17 (t, J=7.2 Hz, 3H); ESIMS m/z 297 ([M+H]$^+$).

Example 46: Preparation of 3-butyl-1-(3-chloro-1-(pyridin-3-yl)-1H-pyrazol-4-yl)-1-ethylurea (Compound 500)

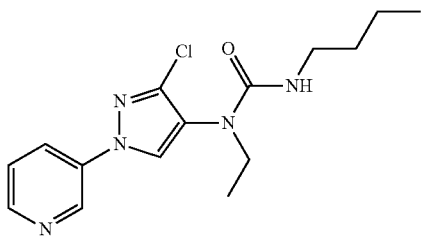 [SMILES: CCCCNC(=O)N(CC)c1cn(-c2cccnc2)nc1Cl]

To a solution of 3-chloro-N-ethyl-1-(pyridin-3-yl)-1H-pyrazol-4-amine, 2HCl (0.130 g, 0.502 mmol) in DCE (1.25 ml) was added N-ethyl-N-isopropylpropan-2-amine (0.21 mL, 1.255 mmol) followed by 1-isocyanatobutane (0.109 g, 1.104 mmol) and the reaction was stirred at ambient temperature for 16 hours. The reaction mixture was concentrated and purified using silica gel chromatography (0-20% MeOH/DCM) to yield the title compound as a beige solid (0.131 g, 77%): IR (thin film) 3326, 2959, 2931, 1648 cm$^{-1}$; $^1$H NMR (400 MHz, CDCl$_3$) δ 8.95 (s, 1H), 8.62 (d, J=4.0 Hz, 1H), 8.08-8.01 (m, 1H), 7.97 (s, 1H), 7.46 (dd, J=8.3, 4.7 Hz, 1H), 4.42-4.32 (m, 1H), 3.74-3.61 (m, 2H), 3.27-3.15 (m, 2H), 1.49-1.37 (m, 2H), 1.37-1.22 (m, 2H), 1.19-1.12 (m, 3H), 0.94-0.84 (m, 3H); ESIMS m/z 322 ([M+H]$^+$).

Compounds 479-480, 501-504, 513, 518 and 519 were prepared according to Example 46.

Example 47: Preparation of 1-(3-chloro-1-(pyridin-3-yl)-1H-pyrazol-4-yl)imidazolidin-2-one (Compound 374)

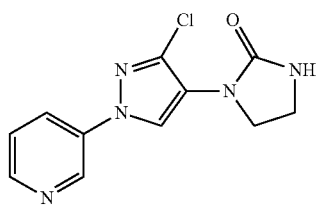 [SMILES: O=C1NCCN1c1cn(-c2cccnc2)nc1Cl]

To a solution of 1-(3-chloro-1-(pyridin-3-yl)-1H-pyrazol-4-yl)-3-(2-chloroethyl)urea (0.1 g, 0.333 mmol) in THF (6.66 ml) was added sodium hydride (8.00 mg, 0.333 mmol) and the reaction mixture was stirred at ambient temperature for 30 minutes. The reaction was quenched by the addition of a solution of saturated ammonium chloride and the product was extracted with ethyl acetate (2×). The combined organic layers were dried over sodium sulfate, filtered and concentrated. The product was a beige solid which was pure and did not need any further purification (63 mg, 72%): mp 167-170° C.; $^1$H NMR (400 MHz, CDCl$_3$) δ 8.96 (d, J=2.2 Hz, 1H), 8.56 (dd, J=4.7, 1.4 Hz, 1H), 8.33 (s, 1H), 7.99 (ddd, J=8.3, 2.7, 1.4 Hz, 1H), 7.40 (ddd, J=8.3, 4.8, 0.7 Hz, 1H), 5.00 (s, 1H), 4.14-4.07 (m, 2H), 3.68-3.58 (m, 2H); ESIMS m/z 264 ([M+H]$^+$).

Compound 349 was prepared in accordance with the procedures disclosed in Example 47.

Example 48: Preparation of S-tert-butyl(3-chloro-1-(pyridin-3-yl)-1H-pyrazol-4-yl)(ethyl)carbamothioate (Compound 514)

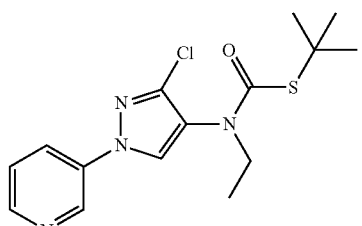

To a solution of 3-chloro-N-ethyl-1-(pyridin-3-yl)-1H-pyrazol-4-amine, 2HCl (0.13 g, 0.502 mmol) in DCM (2.508 ml) was added N-ethyl-N-isopropylpropan-2-amine (0.257 ml, 1.505 mmol) followed by S-tert-butyl carbonochloridothioate (0.153 g, 1.003 mmol). The reaction mixture was stirred at ambient temperature for 16 hours. The reaction was quenched by the addition of saturated sodium bicarbonate. The organic layer was extracted with DCM. The organic layer was dried over sodium sulfate, filtered, concentrated and purified using silica gel column chromatography (0-100% ethyl acetate/hexanes) to yield the title compound as a white solid (132 mg, 78%): mp 91-93° C.; $^1$H NMR (400 MHz, CDCl$_3$) δ 8.96 (d, J=2.5 Hz, 1H), 8.60 (dd, J=4.7, 1.4 Hz, 1H), 8.08-8.03 (m, 1H), 7.97 (s, 1H), 7.47-7.41 (m, 1H), 3.69 (q, J=7.2 Hz, 2H), 1.47 (s, 9H), 1.21-1.13 (m, 3H); ESIMS m/z 339 ([M+H]$^+$).

Compounds 333, 338, 339, 346, 368 and 373 were prepared in accordance with the procedures disclosed in Example 48.

Example 49: Preparation of N-(3-chloro-1-(pyridin-3-yl)-1H-pyrazol-4-yl)-N-ethyl-2-methyl-3-(methio) propanethioamide (Compound 364)

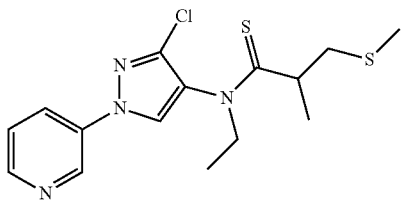 [SMILES: CCN(C(=S)C(C)CSC)c1cn(-c2cccnc2)nc1Cl]

To a microwave reaction vessel was added N-(3-chloro-1-(pyridin-3-yl)-1H-pyrazol-4-yl)-N-ethyl-2-methyl-3-(methio)propanamide (0.07 g, 0.22 mmol) in dichloroethane (1.87 mL) and Lawesson's reagent (0.05 g, 0.12 mmol). The vessel was capped and heated in a Biotage Initiator microwave reactor for 15 minutes at 130° C., with external IR-sensor temperature monitoring from the side of the vessel. The reaction was concentrated to dryness and the crude material was purified by silica gel chromatography (0-80% acetonitrile/water) to give the desired product as a yellow oil (0.33 g, 44%): IR (thin film) 1436 cm$^{-1}$; $^1$H NMR (400 MHz, CDCl$_3$) δ 8.97 (d, J=2.5 Hz, 1H), 8.77-8.52 (m, 1H), 8.11-7.89 (m, 2H), 7.60-7.38 (m, 1H), 4.62 (bs, 1H), 4.02 (bs, 1H), 3.21-2.46 (m, 3H), 2.01 (s, 3H), 1.35-1.15 (m, 6H); ESIMS m/z 355 ([M+H]$^+$).

Compounds 372, 438 and 548 were prepared in accordance with the procedures disclosed in Example 49.

N-methyl-3-(methylthio)propanethioamide was prepared in accordance with the procedure disclosed in Example 49 and isolated as a clear oil; $^1$H NMR (400 MHz, CDCl$_3$) δ 7.69 (s, 1H), 3.20 (d, J=4.8 Hz, 3H), 2.99-2.88 (m, 4H), 2.15 (s, 3H); ESIMS m/z 150 ([M+H]$^+$).

Example 50: Preparation of N-(3-chloro-1-(pyridin-3-yl)-1H-pyrazol-4-yl)-N-ethyl-4,4,4-trifluoro-3-(methylsulfinyl)butanamide (Compound 570)

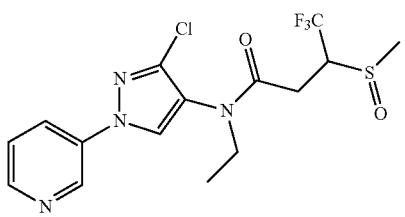 [SMILES: CCN(C(=O)CC(S(C)=O)C(F)(F)F)c1cn(-c2cccnc2)nc1Cl]

To a 20 mL vial was added N-(3-chloro-1-(pyridin-3-yl)-1H-pyrazol-4-yl)-N-ethyl-4,4,4-trifluoro-3-(methylthio)butanamide (82 mg, 0.209 mmol) and hexafluoroisopropanol (1.5 mL). Hydrogen peroxide (0.054 mL, 0.626 mmol, 35% solution in water) was added in one portion and the solution was stirred at room temperature. After 3 hours the reaction was quenched with saturated sodium sulfite solution and extracted with EtOAc (3×20 mL). The combined organic layers were dried over sodium sulfate, concentrated and purified by chromatography (0-10% MeOH/DCM) to give N-(3-chloro-1-(pyridin-3-yl)-1H-pyrazol-4-yl)-N-ethyl-4,4,4-trifluoro-3-(methylsulfinyl) butanamide (76 mg, 0.186 mmol, 89% yield) as white semi-solid: $^1$H NMR (400 MHz, CDCl$_3$) δ 8.98 (d, J=2.3 Hz, 1H), 8.63 (td, J=4.8, 2.4 Hz, 1H), 8.14-8.01 (m, 2H), 7.46 (ddd, J=8.3, 4.8, 0.7 Hz, 1H), 4.26 (dd, J=17.2, 8.4 Hz, 1H), 3.89-3.61 (m, 2H), 3.01 (dd, J=17.6, 8.2 Hz, 1H), 2.77 (s, 2H), 2.48 (dd, J=17.7, 3.3 Hz, 1H), 1.19 (t, J=7.2 Hz, 3H) (only one isomer shown); ESIMS m/z 409 ([M+H]$^+$); IR (Thin film) 1652 cm$^{-1}$.

Compound 571 was prepared from the corresponding intermediates and starting materials in accordance with the procedures disclosed in Example 50.

Example 51: Preparation of N-(3-chloro-1-(pyridin-3-yl)-1H-pyrazol-4-yl)-N-ethyl-3-(methylsulfinyl) propanamide (Compound 362)

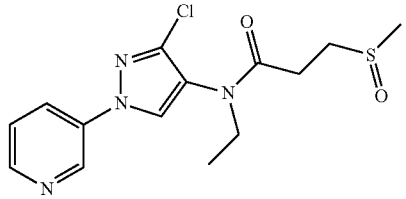 [SMILES: CCN(C(=O)CCS(C)=O)c1cn(-c2cccnc2)nc1Cl]

To N-(3-chloro-1-(pyridin-3-yl)-1H-pyrazol-4-yl)-N-ethyl-3-(methylthio)propanamide (0.08 g, 0.24 mmol) in glacial acetic acid (0.82 mL) was added sodium perborate tetrahydrate (0.05 g, 0.25 mmol), and the mixture was heated at 60° C. for 1 hour. The reaction mixture was carefully poured into a separatory funnel containing saturated aqueous NaHCO$_3$ resulting in gas evolution. When the gas evolution had ceased, ethyl acetate was added and the layers were separated. The aqueous layer was extracted twice with ethyl acetate, and all the organic layers were combined, dried over MgSO$_4$, filtered and concentrated under reduced pressure. The crude material was purified by silica gel chromatography (0-10% methanol/dichloromethane) to give the desired product as a clear oil (0.03 g, 40%): IR (thin film) 1655 cm$^{-1}$; $^1$H NMR (400 MHz, CDC$_{l3}$) δ 8.95 (t, J=9.2 Hz, 1H), 8.63 (dd, J=4.7, 1.4 Hz, 1H), 8.20-7.86 (m, 2H), 7.59-7.33 (m, 1H), 3.73 (ddt, J=20.5, 13.4, 6.8 Hz, 2H), 3.23-3.06 (m, 1H), 2.94-2.81 (m, 1H), 2.74-2.62 (m, 2H), 2.59 (s, 3H), 1.25-1.07 (m, 3H); ESIMS m/z 341 ([M+H]$^+$).

Compounds 101-102, 218, 328, 330, and 494 were prepared from the appropriate sulfides in accordance with the procedures disclosed in Example 51.

Example 52: Preparation of N-(3-chloro-1-(pyridin-3-yl)-1H-pyrazol-4-yl)-N-ethyl-3-(methylsulfonyl)propanamide (Compound 363)

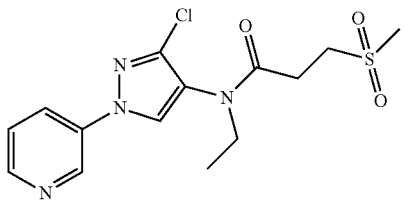 [SMILES: CCN(C(=O)CCS(C)(=O)=O)c1cn(-c2cccnc2)nc1Cl]

To N-(3-chloro-1-(pyridin-3-yl)-1H-pyrazol-4-yl)-N-ethyl-3-(methylthio)propanamide (0.08 g, 0.25 mmol) in glacial acetic acid (0.85 mL) was added sodium perborate tetrahydrate (0.11 g, 0.52 mmol), and the mixture was heated at 60° C. for 1 hour. The reaction mixture was carefully poured into a separatory funnel containing saturated aqueous NaHCO$_3$ resulting in gas evolution. When the gas evolution had ceased, ethyl acetate was added and the layers were separated. The aqueous layer was extracted twice with ethyl acetate, and all the organic layers were combined, dried over MgSO$_4$, filtered and concentrated under reduced pressure. The crude product was purified by silica gel column chromatography (0 to 10% methanol/dichloromethane) to give the desired product as a clear oil (0.04, 47%): (thin film) 1661 cm$^{-1}$; $^1$H NMR (400 MHz, CDCl$_3$) δ 8.95 (t, J=11.5 Hz, 1H), 8.64 (dd, J=4.8, 1.4 Hz, 1H), 8.17-7.96 (m, 2H), 7.59-7.39 (m, 1H), 3.73 (d, J=7.0 Hz, 2H), 3.44 (dd, J=22.5, 15.7 Hz, 2H), 2.96 (s, 3H), 2.71 (t, J=6.9 Hz, 2H), 1.18 (dd, J=8.8, 5.5 Hz, 3H); ESIMS m/z 357 ([M+H]$^+$).

Compounds 103, 104, 219, 329, 331 and 495 were prepared from the appropriate sulfides in accordance with the procedures disclosed in Example 52.

Example 53: Preparation of N-(3-methyl-1-(3-fluoropyridin-5-yl)-1H-pyrazol-4-yl)N-ethyl-2-methyl-(3-oxido-λ$^4$-sulfanylidenecyanamide)(methyl)propanamide (Compound 250)

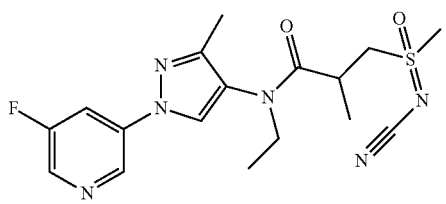 [SMILES: CCN(C(=O)C(C)CS(C)(=O)=NC#N)c1cn(-c2cncc(F)c2)nc1C]

To a solution of N-ethyl-N-(1-(5-fluoropyridin-3-yl)-3-methyl-1H-pyrazol-4-yl)-2-methyl-3-(methylthio)propanamide (0.30 g, 0.89 mmol) in dichloromethane (3.57 mL) at 0° C. was added cyanamide (0.07 g, 1.78 mmol) and iodobenzenediacetate (0.31 g, 0.98 mmol) and subsequently stirred at room temperature for 1 hour. The reaction was concentrated to dryness and the crude material was purified by silica gel column chromatography (10% methanol/ethyl acetate) to give the desired sulfilamine as a light yellow solid (0.28 g, 85%). To a solution of 70% mCPBA (0.25 g, 1.13 mmol) in ethanol (4.19 mL) at 0° C. was added a solution of potassium carbonate (0.31 g, 2.26 mmol) in water (4.19 mL) and stirred for 20 minutes after which a solution of sulfilamine (0.28 g, 0.75 mmol) in ethanol (4.19 mL) was added in one portion. The reaction was stirred for 1 hour at 0° C. The excess mCPBA was quenched with 10% sodium thiosulfite and the reaction was concentrated to dryness. The residue was purified by silica gel chromatography (0-10% methanol/dichloromethane) to give the desired product as a clear oil (0.16 g, 56%): IR (thin film) 1649 cm$^{-1}$; $^1$H NMR (400 MHz, CDCl$_3$) δ 8.80 (dd, J=43.8, 10.1 Hz, 1H), 8.51-8.36 (m, 1H), 8.11 (d, J=38.7 Hz, 1H), 7.96-7.77 (m, 1H), 4.32-3.92 (m, 2H), 3.49-3.11 (m, 6H), 2.32 (s, 3H), 1.27-1.05 (m, 6H); ESIMS m/z 393 ([M+H]$^+$).

Example 54: Preparation of N-ethyl-4,4,4-trifluoro-3-methoxy-N-(3-methyl-1-(pyridin-3-yl)-1H-pyrazol-4-yl)-3-(trifluoromethyl)butanamide (Compound 276)

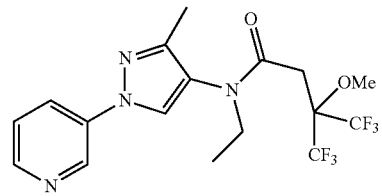 [SMILES: CCN(C(=O)CC(OC)(C(F)(F)F)C(F)(F)F)c1cn(-c2cccnc2)nc1C]

To a solution of N-ethyl-4,4,4-trifluoro-3-hydroxy-N-(3-methyl-1-(pyridin-3-yl)-1H-pyrazol-4-yl)-3-(trifluoromethyl)butanamide (184 mg, 0.448 mmol) in DMF (3 mL) stirring at 0° C. was added sodium hydride (26.9 mg, 0.673 mmol). The solution was stirred at 0° C. for 0.5 hour. Then iodomethane (0.034 mL, 0.538 mmol) was added and ice bath was removed and the mixture was stirred at 25° C. overnight. Reaction was worked up by slow addition of water and further diluted with 20 mL of water, then extracted with 4×20 mL of EtOAc. The combined organic layers were washed with water, dried over Na$_2$SO$_4$ and concentrated. Silica Gel chromatography (0-100% EtOAc/hexane) gave N-ethyl-4,4,4-trifluoro-3-methoxy-N-(3-methyl-1-(pyridin-3-yl)-1H-pyrazol-4-yl)-3-(trifluoromethyl)butanamide (52 mg, 0.123 mmol, 27.3% yield) as a white solid: mp=83-86° C.; $^1$H NMR (400 MHz, CDCl$_3$) δ 8.94 (d, J=2.5 Hz, 1H), 8.59 (dd, J=4.7, 1.3 Hz, 1H), 8.01 (ddd, J=8.3, 2.7, 1.5 Hz, 1H), 7.85 (s, 1H), 7.44 (ddd, J=8.3, 4.8, 0.6 Hz, 1H), 4.00 (brs, 1H), 3.73 (s, 3H), 3.39 (brs, 1H), 2.86 (s, 2H), 2.26 (s, 3H), 1.16 (t, J=7.1 Hz, 3H); ESIMS m/z 425 ([M+H]$^+$); IR (Thin film) 1664 cm$^{-1}$.

Compound 327 was prepared from the corresponding intermediates and starting materials in accordance with the procedures disclosed in Example 54.

Example 55: Step 1: Preparation of N-(2-((tert-butyldimethylsilyl)oxy)ethyl)-N-(3-chloro-1-(pyridin-3-yl)-1H-pyrazol-4-yl)-2-methyl-3-(methylthio)propanamide

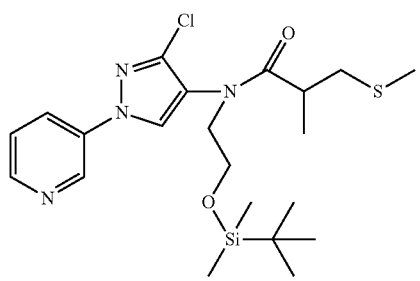 [SMILES: CSCC(C)C(=O)N(CCO[Si](C)(C)C(C)(C)C)c1cn(-c2cccnc2)nc1Cl]

A solution of N-(3-chloro-1-(pyridin-3-yl)-1H-pyrazol-4-yl)-2-methyl-3-(methylthio)propanamide (0.150 g, 0.483 mmol) in N,N-dimethylformamide (2.413 ml) was cooled to 0° C. Sodium hydride (0.039 g, 0.965 mmol, 60% dispersion) was added at and the reaction was stirred at 0° C. for 30 minutes. (2-Bromoethoxy)(tert-butyl)dimethylsilane (0.231 g, 0.965 mmol) was added, the ice bath was removed, and the reaction was stirred at room temperature for 2 hours. The reaction was heated at 65° C. for 1.5 hours and then cooled to room temperature. Brine was added and the mixture was extracted with dichloromethane. The combined organic phases were concentrated and chromatographed (0-100% ethyl acetate/hexanes) to give N-(2-((tert-butyldimethylsilyl)oxy)ethyl)-N-(3-chloro-1-(pyridin-3-yl)-1H-pyrazol-4-yl)-2-methyl-3-(methylthio)propanamide (0.120 g, 0.243 mmol, 50.4%) as an orange oil: IR (thin film) 1669 cm$^{-1}$; $^1$H NMR (400 MHz, CDCl$_3$) δ 8.88 (d, J=2.5 Hz, 1H), 8.55 (dd, J=4.7, 1.4 Hz, 1H), 8.05 (s, 1H), 7.98 (ddd, J=8.3, 2.6, 1.4 Hz, 1H), 7.41 (ddd, J=8.4, 4.8, 0.5 Hz, 1H), 4.35-3.06 (m, 4H), 2.86-2.73 (m, 1H), 2.73-2.59 (m, 1H), 2.41 (dd, J=12.8, 5.7 Hz, 1H), 1.94 (s, 3H), 1.11 (d, J=6.7 Hz, 3H), 0.80 (s, 9H), 0.00 (s, 3H), −0.01 (s, 3H); ESIMS m/z 470 ([M+H]$^+$).

Example 55: Step 2: Preparation of N-(3-chloro-1-(pyridin-3-yl)-1H-pyrazol-4-yl)-N-(2-hydroxyethyl)-2-methyl-3-(methylthio)propanamide (Compound 535)

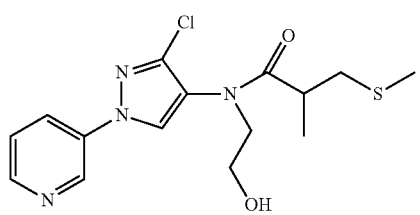 [SMILES: CSCC(C)C(=O)N(CCO)c1cn(-c2cccnc2)nc1Cl]

To a solution of N-(2-((tert-butyldimethylsilyl)oxy)ethyl)-N-(3-chloro-1-(pyridin-3-yl)-1H-pyrazol-4-yl)-2-methyl-3-(methylthio)propanamide (0.180 g, 0.384 mmol) in tetrahydrofuran (1.54 ml) was added tetrabutylammonium fluoride (0.201 g, 0.767 mmol) and the reaction was stirred at room temperature for 2 hours. Brine was added and the mixture was extracted with ethyl acetate. The combined organic phases were concentrated and chromatographed (0-100% water/acetonitrile) to give N-(3-chloro-1-(pyridin-3-yl)-1H-pyrazol-4-yl)-N-(2-hydroxyethyl)-2-methyl-3-(methylthio)propanamide as a white oil (0.081 g, 0.217 mmol, 56.5%): IR (thin film) 3423, 1654 cm$^{-1}$; $^1$H NMR (400 MHz, CDCl$_3$) δ 9.00 (d, J=2.5 Hz, 1H), 8.62 (dd, J=4.7, 1.2 Hz, 1H), 8.25 (s, 1H), 8.07 (ddd, J=8.3, 2.4, 1.3 Hz, 1H), 7.47 (dd, J=8.3, 4.7 Hz, 1H), 4.47-3.70 (m, 3H), 3.65-3.09 (m, 2H), 2.91-2.68 (m, 2H), 2.48 (dd, J=12.4, 5.0 Hz, 1H), 2.01 (s, 3H), 1.18 (d, J=6.5 Hz, 3H); ESIMS m/z 356 ([M+H]$^+$).

Example 56: Preparation of 2-(N-(3-chloro-1-(pyridin-3-yl)-1H-pyrazol-4-yl)-2-methyl-3-(methylthio)propanamido)ethyl acetate (Compound 547)

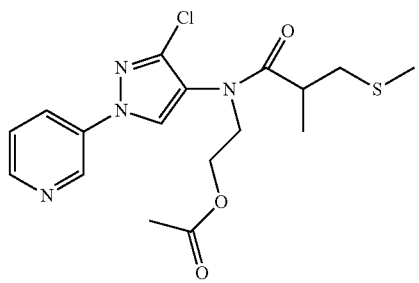 [SMILES: CSCC(C)C(=O)N(CCOC(C)=O)c1cn(-c2cccnc2)nc1Cl]

To a solution of N-(3-chloro-1-(pyridin-3-yl)-1H-pyrazol-4-yl)-N-(2-hydroxyethyl)-2-methyl-3-(methylthio)propanamide (0.045 g, 0.127 mmol) in dichloromethane (1.27 ml) was added N,N-dimethylpyridin-4-amine (0.023 g, 0.190 mmol) and triethylamine (0.019 g, 0.190 mmol) followed by acetyl chloride (0.015 g, 0.190 mmol). The reaction was stirred at room temperature overnight. Water was added and the mixture was extracted with dichloromethane. The combined organic phases were concentrated and chromatographed (0-100% ethyl acetate/hexanes) to give 2-(N-(3-chloro-1-(pyridin-3-yl)-1H-pyrazol-4-yl)-2-methyl-3-(methylthio)propanamido)ethyl acetate as a yellow oil (0.015 g, 0.034 mmol, 26.8%): IR (thin film) 1739, 1669 cm$^{-1}$; $^1$H NMR (400 MHz, CDCl$_3$) δ 8.97 (d, J=2.3 Hz, 1H), 8.64 (dd, J=4.7, 1.4 Hz, 1H), 8.15 (s, 1H), 8.04 (ddd, J=8.3, 2.7, 1.4 Hz, 1H), 7.47 (ddd, J=8.3, 4.8, 0.7 Hz, 1H), 4.50-3.40 (m, 4H), 2.84 (dd, J=12.7, 8.9 Hz, 1H), 2.78-2.63 (m, 1H), 2.46 (dd, J=12.7, 5.4 Hz, 1H), 2.03 (s, 3H), 2.01 (s, 3H), 1.16 (d, J=6.6 Hz, 3H); ESIMS m/z 398 ([M+H]$^+$).

Example 57: Preparation of 2,2-dideuterio-3-methylsulfanyl-propanoic acid

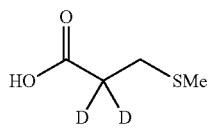

To a 100 mL round bottom flask was added 3-(methylthio)propanoic acid (3 g, 24.96 mmol), followed by D$_2$O (23 mL) and KOD (8.53 mL, 100 mmol) (40% wt solution in D$_2$O), the solution was heated to reflux overnight. NMR showed ca. 95% D at alpha-position. The reaction was cooled down and quenched with concentrated HCl until pH<2. White precipitate appeared in aqueous layer upon acidifying. Reaction mixture was extracted with 3×50 mL EtOAc, the combined organic layers were dried over Na$_2$SO$_4$, concentrated in vacuo to almost dryness. 100 mL hexane was added and the solution was concentrated again to give 2,2-dideuterio-3-methylsulfanyl-propanoic acid as a colorless oil (2.539 g, 20.78 mmol, 83%): IR (Thin film) 3430, 1704 cm$^{-1}$; $^1$H NMR (400 MHz, CDCl$_3$) δ 2.76 (s, 2H), 2.14 (s, 3H); $^{13}$C NMR (101 MHz, CDCl$_3$) δ 178.28, 38.14-28.55 (m), 28.55, 15.51; EIMS m/z 122.

2-Deuterio-2-methyl-3-methylsulfanyl-propanoic acid was prepared as described in Example 57 to afford a colorless oil (3.62 g, 26.8 mmol, 60.9%): IR (Thin film) 2975, 1701 cm$^{-1}$; $^1$H NMR (400 MHz, CDCl$_3$) δ 11.39-10.41 (brs, 1H), 2.88-2.79 (d, J=13.3 Hz, 1H), 2.61-2.53 (d, J=13.3 Hz, 1H), 2.16-2.09 (s, 3H), 1.32-1.25 (s, 3H); $^{13}$C NMR (101 MHz, CDCl$_3$) δ 181.74, 39.74-39.02 (m), 37.16, 16.50, 16.03; EIMS m/z 135.

Example 58: Preparation of 2-methyl-3-(trideuteriomethylsulfanyl)propanoic acid

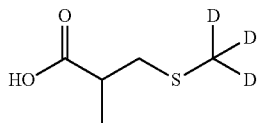

To a 50 mL round bottom flask was added 3-mercapto-2-methylpropanoic acid (5 g, 41.6 mmol), followed by MeOH (15 mL), the solution was stirred at 25° C. Potassium hydroxide (5.14 g, 92 mmol) was added slowly as the reaction is exothermic. Iodomethane-d$_3$ (6.63 g, 45.8 mmol) was added slowly and then the reaction mixture was heated at 65° C. overnight. The reaction was worked up by addition of 2 N HCl until the mixture was acidic. It was then extracted with EtOAc (4×50 mL) and the combined organic layers were dried over Na$_2$SO$_4$, concentrated and purified with flash chromatography, eluted with 0-80% EtOAc/hexane to give 2-methyl-3-(trideuteriomethylsulfanyl)propanoic acid (4.534 g, 33.0 mmol, 79%) as colorless oil: IR (Thin film) 3446, 1704 cm$^{-1}$; $^1$H NMR (400 MHz, CDCl$_3$) δ 2.84 (dd, J=13.0, 7.1 Hz, 1H), 2.80-2.66 (m, 1H), 2.57 (dd, J=13.0, 6.6 Hz, 1H), 1.30 (d, J=7.0 Hz, 3H); EIMS m/z 137.

Example 59: Preparation of 2-hydroxy-3-(methylthio)propanoic acid

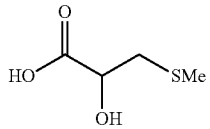

Sodium methanethiolate (4.50 g, 64.2 mmol) was added at 25° C. to a solution of 3-chloro-2-hydroxypropanoic acid (2 g, 16.06 mmol) in MeOH (120 mL). The reaction mixture was heated at reflux for 8 hours, then cooled to 25° C. The precipitate was removed by filtration and the filtrate was evaporated. The residue was acidified to pH 2 with 2 N HCl, extracted with EtOAc (3×30 mL), combined organic layers were dried with Na$_2$SO$_4$, concentrated to give 2-hydroxy-3-(methylthio)propanoic acid as a white solid, (1.898 g, 13.94 mmol, 87% yield): mp 55-59° C.; IR (Thin film) 2927, 1698 cm$^{-1}$; $^1$H NMR (400 MHz, CDCl$_3$) δ 6.33 (s, 3H), 4.48 (dd, J=6.3, 4.2 Hz, 1H), 3.02 (dd, J=14.2, 4.2 Hz, 1H), 2.90 (dd, J=14.2, 6.3 Hz, 1H), 2.20 (s, 3H); EIMS m/z 136.

Example 60: Preparation of 2-methoxy-3-(methylthio)propanoic acid

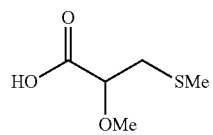

To a stirred solution of sodium hydride (0.176 g, 4.41 mmol) in DMF (5 mL) was added a solution of 2-hydroxy-3-(methylthio)propanoic acid (0.25 g, 1.836 mmol) in 1 mL DMF at 25° C. and stirred for 10 min. Vigorous bubbling was observed upon addition of NaH. Then iodomethane (0.126 mL, 2.020 mmol) was added and the solution was stirred at 25° C. overnight. The reaction was quenched by addition of 2 N HCl, extracted with 3×10 mL of EtOAc, the combined organic layers were washed with water (2×20 mL), concentrated and purified by column chromatography, eluted with 0-100% EtOAc/hexane, gave 2-methoxy-3-(methylthio)propanoic acid (126 mg, 0.839 mmol, 45.7% yield) as colorless oil: $^1$H NMR (400 MHz, CDCl$_3$) δ 9.10 (s, 1H), 4.03 (dd, J=6.9, 4.4 Hz, 1H), 3.51 (s, 3H), 2.98-2.93 (m, 1H), 2.86 (dd, J=14.1, 6.9 Hz, 1H), 2.21 (s, 3H); EIMS m/z 150.

Example 61: Preparation of 2-(acetylthiomethyl)-3,3,3-trifluoropropanoic acid

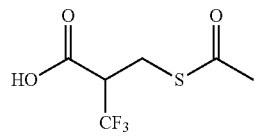

To a 50 mL round bottom flask was added 2-(trifluoromethyl)acrylic acid (6 g, 42.8 mmol), followed by thioacetic acid (4.59 ml, 64.3 mmol). The reaction was slightly exothermic. The mixture was then stirred at 25° C. overnight. NMR showed some starting material (~30%). One more equiv of thioacetic acid was added and the mixture was heated at 95° C. for 1 hour, then allowed to cool to room temperature. Mixture was purified by vacuum distillation at 2.1-2.5 mm Hg, fraction distilled at 80-85° C. was mostly thioacetic acid, fraction distilled at 100-110° C. was almost pure product, contaminated by a nonpolar impurity (by TLC). It was again purified by flash chromatography (0-20% MeOH/DCM), to give 2-(acetylthiomethyl)-3,3,3-trifluoropropanoic acid (7.78 g, 36.0 mmol, 84% yield) as colorless oil, which solidified under high vacuum to give a white solid: mp 28-30° C.; $^1$H NMR (400 MHz, CDCl$_3$) δ 7.52 (brs, 1H), 3.44 (dt, J=7.5, 3.5 Hz, 2H), 3.20 (dd, J=14.9, 11.1 Hz, 1H), 2.38 (s, 3H); $^{13}$C NMR (101 MHz, CDCl$_3$) δ 194.79, 171.14, 123.44 (q, J=281.6 Hz), 50.47 (q, J=27.9 Hz), 30.44, 24.69 (q, J=2.6 Hz); $^{19}$F NMR (376 MHz, CDCl$_3$) δ-67.82.

Example 62: Preparation of 3,3,3-trifluoro-2-(methylthiomethyl)propanoic acid

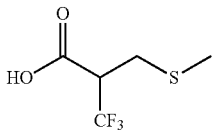

To a solution of 2-(acetylthiomethyl)-3,3,3-trifluoropropanoic acid (649 mg, 3 mmol) in MeOH (5 mL) stirring at 25° C. was added pellets of potassium hydroxide (421 mg, 7.50 mmol) in four portions over 5 minutes. Reaction was exothermic. Then MeI was added in once, the reaction mixture was then heated at 65° C. for 18 hours. The reaction was then cooled down and quenched with 2N HCl until acidic, and the aqueous layer extracted with chloroform (4×20 mL). Combined organic layer was dried, concentrated in vacuo, purified with flash chromatography (0-20% MeOH/DCM), to give 3,3,3-trifluoro-2-(methylthiomethyl)propanoic acid (410 mg, 2.179 mmol, 72.6% yield) as a light yellow oil: $^1$H NMR (400 MHz, CDCl$_3$) δ 10.95 (s, 1H), 3.49-3.37 (m, 1H), 3.02 (dd, J=13.8, 10.8 Hz, 1H), 2.90 (dd, J=13.8, 4.0 Hz, 1H), 2.18 (s, 3H); $^{13}$C NMR (101 MHz, CDCl$_3$) δ 172.04 (q, J=2.8 Hz), 123.55 (q, J=281.2 Hz), 50.89 (q, J=27.5 Hz), 29.62 (q, J=2.3 Hz), 15.85; $^{19}$F NMR (376 MHz, CDCl$_3$) δ-67.98.

Example 63: Preparation of 3-(methylthio)pentanoic acid

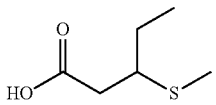

S,S-dimethyl carbonodithioate (1.467 g, 12.00 mmol) was added with vigorous stirring to a solution of (E)-pent-2-enoic acid (2.002 g, 20 mmol) in 30% KOH solution (prepared from potassium hydroxide (3.87 g, 69 mmol) and Water (10 mL)). The reaction mixture was slowly heated to 90° C. over a period of 20-30 min. Heating was continued for 3 hours before the reaction was cooled down to 25° C. and quenched slowly with HCl. The mixture was then extracted with DCM (3×30 mL), combined organic layer dried and concentrated to give 3-(methylthio)pentanoic acid (2.7 g, 18.22 mmol, 91% yield) as light orange oil: IR (Thin film) 2975, 1701 cm$^{-1}$; $^1$H NMR (400 MHz, CDCl$_3$) δ 2.92 (qd, J=7.3, 5.6 Hz, 1H), 2.63 (d, J=7.2 Hz, 2H), 2.08 (s, 3H), 1.75-1.51 (m, 2H), 1.03 (t, J=7.4 Hz, 3H); $^{13}$C NMR (101 MHz, CDCl$_3$) δ 178.14, 43.95, 39.78, 27.04, 12.95, 11.29; EIMS m/z 148.

4-methyl-3-(methylthio)pentanoic acid was prepared as described in Example 63 and isolated as a colorless oil: IR (Thin film) 2960, 1704 cm$^{-1}$; $^1$H NMR (400 MHz, CDCl$_3$) δ 2.88 (ddd, J=9.1, 5.4, 4.7 Hz, 1H), 2.68 (dd, J=16.0, 5.5 Hz, 1H), 2.55 (dd, J=16.0, 9.1 Hz, 1H), 2.13 (s, 3H), 2.01-1.90 (m, 1H), 1.03 (d, J=6.8 Hz, 3H), 0.99 (d, J=6.8 Hz, 3H); EIMS m/z 162.

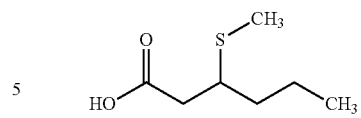

3-(Methylthio)hexanoic acid was prepared according to the procedure described in Example 63 and isolated as a colorless oil: IR (thin film) 2921, 1705 cm$^{-1}$; $^1$H NMR (400 MHz, CDCl$_3$) δ 10.72 (s, 1H), 3.06-2.92 (m, 1H), 2.63 (dd, J=7.2, 2.6 Hz, 2H), 2.08 (s, 3H), 1.66-1.37 (m, 4H), 0.94 (t, J=7.2 Hz, 3H); $^{13}$C NMR (101 MHz, CDCl$_3$) δ 178.19, 42.00, 40.20, 36.33, 20.05, 13.80, 12.86.

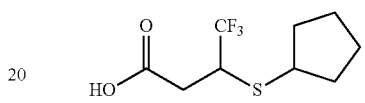

3-(Cyclopentylthio)-4,4,4-trifluorobutanoic acid was prepared according to the procedure described in Example 63 and isolated as a colorless oil: IR (thin film) 2959, 1714 cm$^{-1}$; $^1$H NMR (400 MHz, CDCl$_3$) δ 9.27 (s, 1H), 3.74-3.53 (m, 1H), 3.36 (p, J=6.9 Hz, 1H), 2.96 (dd, J=16.9, 3.9 Hz, 1H), 2.61 (dd, J=16.9, 10.6 Hz, 1H), 2.15-1.92 (m, 2H), 1.84-1.68 (m, 2H), 1.68-1.54 (m, 3H), 1.53-1.43 (m, 1H); EIMS m/z 242.

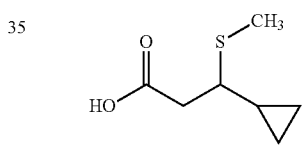

3-Cyclopropyl-3-(methylthio)propanoic acid was prepared according to the procedure described in Example 63 and isolated as a colorless oil: IR (thin film) 3002, 1703 cm$^{-1}$; $^1$H NMR (400 MHz, CDCl$_3$) δ 2.73 (dd, J=7.1, 2.2 Hz, 2H), 2.39 (dt, J=9.7, 7.1 Hz, 1H), 2.17 (s, 3H), 0.97 (dddd, J=14.6, 13.0, 6.5, 3.6 Hz, 1H), 0.74-0.52 (m, 2H), 0.43-0.35 (m, 1H), 0.35-0.26 (m, 1H); $^{13}$C NMR (101 MHz, CDCl$_3$) δ 177.60, 47.18, 40.66, 16.34, 13.61, 5.30, 4.91.

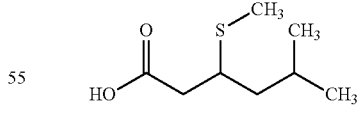

5-Methyl-3-(methylthio)hexanoic acid was prepared according to the procedure described in Example 63 and isolated as a light orange oil: IR (thin film) 2955, 1705 cm$^{-1}$; $^1$H NMR (400 MHz, CDCl$_3$) δ 3.12-2.96 (m, 1H), 2.70-2.53 (m, 2H), 2.07 (s, 3H), 1.91-1.78 (m, 1H), 1.49 (ddd, J=14.6, 9.1, 5.6 Hz, 1H), 1.38 (ddd, J=14.1, 8.4, 5.9 Hz, 1H), 0.93 (d, J=2.4 Hz, 3H), 0.92 (d, J=2.3 Hz, 3H); $^{13}$C NMR (101 MHz, CDCl$_3$) δ 178.07, 43.35, 40.53, 39.99, 25.45, 22.91, 21.83, 12.38.

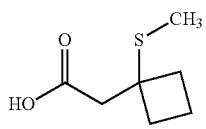

2-(1-(Methylthio)cyclobutyl)acetic acid was prepared according to the procedure described in Example 63 and isolated as a white crystalline solid: mp 43-46° C.; IR (thin film) 2955, 1691 cm$^{-1}$; $^1$H NMR (400 MHz, CDCl$_3$) δ 2.77 (s, 2H), 2.30 (tdd, J=5.4, 3.9, 2.2 Hz, 2H), 2.23-2.13 (m, 3H), 2.04 (s, 3H), 2.00-1.89 (m, 1H); $^{13}$C NMR (101 MHz, CDCl$_3$) δ 176.84, 47.08, 44.08, 33.27, 16.00, 11.72.

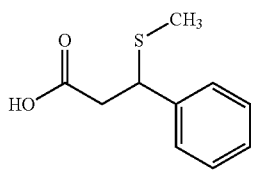

3-(Methylthio)-3-phenylpropanoic acid was prepared according to the procedure described in Example 63 and isolated as a white solid: mp 75-77° C.; IR (thin film) 2915, 1704 cm$^{-1}$; $^1$H NMR (400 MHz, CDCl$_3$) δ 7.35-7.29 (m, 4H), 7.29-7.20 (m, 1H), 4.17 (t, J=7.6 Hz, 1H), 2.93 (dd, J=7.6, 3.2 Hz, 2H), 1.91 (s, 3H); $^{13}$C NMR (101 MHz, CDCl$_3$) δ 176.98, 140.60, 128.61, 127.64, 127.56, 46.19, 40.70, 14.33.

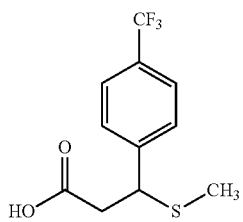 [SMILES: CSC(CC(=O)O)c1ccc(C(F)(F)F)cc1]

3-(Methylthio)-3-(4-(trifluoromethyl)phenyl)propanoic acid was prepared according to the procedure described in Example 63 and isolated as a white solid: mp 106-108° C.; IR (thin film) 2924, 1708 cm$^{-1}$; $^1$H NMR (400 MHz, CDCl$_3$) δ 7.59 (d, J=8.1 Hz, 2H), 7.45 (d, J=8.1 Hz, 2H), 4.21 (t, J=7.6 Hz, 1H), 2.95 (qd, J=16.3, 7.7 Hz, 2H), 1.92 (s, 3H); EIMS m/z (M−1) 263.

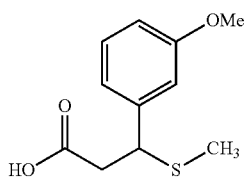

3-(3-Methoxyphenyl)-3-(methylthio)propanoic acid was prepared according to the procedure described in Example 63 and isolated as a white solid: mp 61-63° C.; IR (thin film) 2921, 1699 cm$^{-1}$; $^1$H NMR (400 MHz, CDCl$_3$) δ 7.28-7.17 (m, 1H), 6.94-6.86 (m, 2H), 6.79 (ddd, J=8.3, 2.5, 0.9 Hz, 1H), 4.14 (t, J=7.6 Hz, 1H), 3.80 (s, 3H), 2.92 (d, J=8.0 Hz, 2H), 1.92 (s, 3H); EIMS m/z 225.

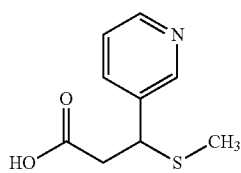

3-(Methylthio)-3-(pyridin-3-yl)propanoic acid was prepared according to the procedure described in Example 63 and isolated as a white semi-solid: IR (thin film) 3349, 1547 cm$^{-1}$; $^1$H NMR (400 MHz, CD$_3$OD) δ 8.54 (dd, J=2.3, 0.8 Hz, 1H), 8.39 (dd, J=4.9, 1.6 Hz, 1H), 7.90 (dt, J=7.9, 2.0 Hz, 1H), 7.41 (ddd, J=8.0, 4.9, 0.8 Hz, 1H), 4.26 (dd, J=9.2, 6.5 Hz, 1H), 2.81 (dd, J=14.7, 6.5 Hz, 1H), 2.71 (dd, J=14.8, 9.2 Hz, 1H), 1.94 (s, 3H); EIMS m/z 198.

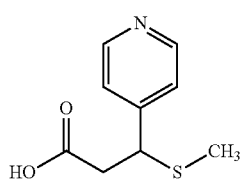

3-(Methylthio)-3-(pyridin-4-yl)propanoic acid was prepared according to the procedure described in Example 63 and isolated as a white solid: mp 187-189° C.; IR (thin film) 1692 cm$^{-1}$; $^1$H NMR (400 MHz, CD$_3$OD) δ 8.57-8.38 (m, 2H), 7.55-7.37 (m, 2H), 4.19 (dd, J=8.2, 7.3 Hz, 1H), 2.93 (dd, J=7.7, 2.8 Hz, 2H), 1.94 (s, 3H); EIMS m/z 198.

Example 64: Preparation of ethyl 1-(hydroxymethyl)cyclopropanecarboxylate

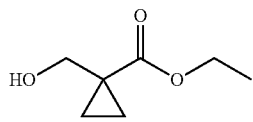

A 1M solution of lithium aluminum tri-tert-butoxyhydride in tetrahydrofuran (70.90 mL, 70.90 mmol) was added to a stirred solution of diethyl cyclopropane-1,1'-dicarboxylate (6 g, 32.20 mmol) in tetrahydrofuran (129 mL) at 23° C. The resulting solution was heated to 65° C. and stirred for 24 h. The cooled reaction mixture was diluted with a 10% solution of sodium bisulfate (275 mL) and extracted with ethyl acetate. The combined organic layers were dried (MgSO$_4$), filtered, and concentrated to dryness to give the desired product as a pale yellow oil (4.60, 91%): $^1$H NMR (300 MHz, CDCl$_3$) δ 4.16 (q, J=7 Hz, 2H), 3.62 (s, 2H), 2.60 (br s, 1H), 1.22-1.30 (m, 5H), 0.87 (dd, J=7, 4 Hz, 2H).

Example 65: Preparation of ethyl 1-((methylsulfonyloxy)methyl)cyclopropanecarboxylate

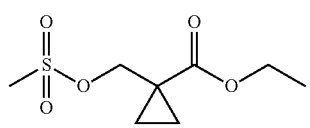

Triethylamine (5.57 mL, 40.00 mmol) and methanesulfonyl chloride (2.85 mL, 36.60 mmol) were sequentially added to a stirred solution of ethyl 1-(hydroxymethyl)cyclopropanecarboxylate (4.80 g, 33.30 mmol) in dichloromethane (83 mL) at 23° C. The resulting bright yellow solution was stirred at 23° C. for 20 h. The reaction mixture was diluted with water and extracted with dichloromethane. The combined organic layers were dried (MgSO$_4$), filtered, and concentrated to dryness to give the desired product as a brown oil (6.92 g, 94%): $^1$H NMR (300 MHz, CDCl$_3$) δ 4.33 (s, 2H), 4.16 (q, J=7 Hz, 2H), 3.08 (s, 3H), 1.43 (dd, J=7, 4 Hz, 2H), 1.26 (t, J=7 Hz, 3H), 1.04 (dd, J=7, 4 Hz, 2H).

Example 66: Preparation of ethyl 1-(methylthiomethyl)cyclopropanecarboxylate

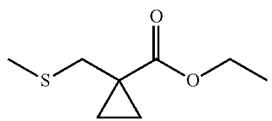

Sodium methanethiolate (4.36 g, 62.30 mmol) was added to a stirred solution of ethyl 1-((methylsulfonyloxy)methyl)cyclopropanecarboxylate (6.92 g, 31.10 mmol) in N,N-dimethylformamide (62.30 mL) at 23° C. The resulting brown suspension was stirred at 23° C. for 18 h. The reaction mixture was diluted with water and extracted with diethyl ether. The combined organic layers were dried (MgSO$_4$), filtered, and concentrated by rotary evaporation to afford the title compound as a brown oil (5.43 g, 100%): $^1$H NMR (300 MHz, CDCl$_3$) δ 4.14 (q, J=7 Hz, 2H), 2.83 (s, 2H), 2.16 (s, 3H), 1.31 (dd, J=7, 4 Hz, 2H), 1.25 (t, J=7 Hz, 3H), 0.89 (dd, J=7, 4 Hz, 2H).

Example 67: Preparation of 1-(methylthiomethyl)cyclopropanecarboxylic acid

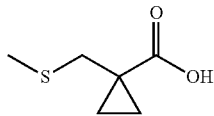

A 50% solution of sodium hydroxide (12.63 mL, 243 mmol) was added to a stirred solution of ethyl 1-(methylthiomethyl)cyclopropanecarboxylate (5.43 g, 31.20 mmol) in absolute ethanol (62.30 mL) at 23° C. The resulting solution was stirred at 23° C. for 20 h. The reaction mixture was diluted with a 0.5 M solution of sodium hydroxide and washed with dichloromethane. The aqueous layer was acidified to pH≈1 with concentrated hydrochloric acid and extracted with dichloromethane. The combined organic layers were dried (Na$_2$SO$_4$), filtered, and concentrated and concentrated to dryness to give the desired product as a light brown oil (2.10 g, 46%): $^1$H NMR (300 MHz, CDCl$_3$) δ 2.82 (s, 2H), 2.17 (s, 3H), 1.41 (dd, J=7, 4 Hz, 2H), 0.99 (dd, J=7, 4 Hz, 2H).

Example 68: Preparation of 2,2-dimethyl-3-(methylthio)propanoic acid

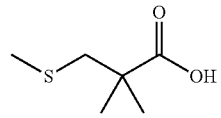

2,2-Dimethyl-3-(methylthio)propanoic acid can be prepared as demonstrated in the literature (reference Musker, W. K.; et al. *J. Org. Chem.* 1996, 51, 1026-1029). Sodium methanethiolate (1.0 g, 14 mmol, 2.0 equiv) was added to a stirred solution of 3-chloro-2,2-dimethylpropanoic acid (1.0 g, 7.2 mmol, 1.0 equiv) in N,N-dimethylformamide (3.7 mL) at 0° C. The resulting brown suspension was allowed to warm to 23° C. and stirred for 24 h. The reaction mixture was diluted with a saturated solution of sodium bicarbonate (300 mL) and washed with diethyl ether (3×75 mL). The aqueous layer was acidified to pH≈1 with concentrated hydrochloric acid and extracted with diethyl ether (3×75 mL). The combined organic layers were dried (sodium sulfate), gravity filtered, and concentrated to afford a colorless oil (1.2 g, 99% crude yield). $^1$H NMR (300 MHz, CDCl$_3$) δ 2.76 (s, 2H), 2.16 (s, 3H), 1.30 (s, 6H).

Example 69: Preparation of 4,4,4-trifluoro-3-(methylthio)butanoic acid

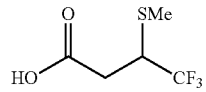

To a 100 mL round bottom flask was added (E)-4,4,4-trifluorobut-2-enoic acid (8 g, 57.1 mmol) and Methanol (24 mL), the solution was stirred in a water bath, then sodium methanethiolate (10.01 g, 143 mmol) was added in three portions. Vigorous bubbling was observed, the mixture was stirred at 25° C. overnight, NMR showed no more starting material. To the reaction mixture was added 2 N HCl until acidic. The mixture was extracted with chloroform (5×50 mL), combined organic layer was dried over Na$_2$SO$_4$, concentrated in vacuo and further dried under high vacuum until there was no weight loss to give 4,4,4-trifluoro-3-(methylthio)butanoic acid (10.68 g, 56.8 mmol, 99% yield) as a colorless oil: $^1$H NMR (400 MHz, CDCl$_3$) δ 10.88 (s, 1H), 3.53 (dqd, J=10.5, 8.3, 4.0 Hz, 1H), 2.96 (dd, J=16.9, 4.0 Hz, 1H), 2.65 (dd, J=16.9, 10.4 Hz, 1H), 2.29 (s, 3H); $^{13}$C NMR (101 MHz, CDCl$_3$) δ 175.78 (s), 126.61 (q, J$_{C-F}$=278.8 Hz), 44.99 (q, J$_{C-F}$=30.3 Hz), 34.12 (d, J$_{C-F}$=1.7 Hz), 15.95 (s); EIMS m/z 162.

Example 70: Preparation of 3-methyl-3-methylsulfanyl-butyric acid

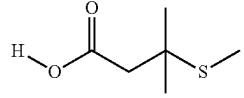

3-methyl-3-methylsulfanyl-butyric acid was made using the procedures disclosed in *J. Chem Soc Perkin* 1, 1992, 10, 1215-21).

Example 71: Preparation of 3-methylsulfanyl-butyric acid

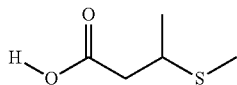

3-Methylsulfanyl-butyric acid was made using the procedures disclosed in *Synthetic Comm.*, 1985, 15 (7), 623-32.

Example 72: Preparation of tetrahydro-thiophene-3-carboxylic acid

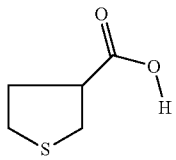

Tetrahydro-thiophene-3-carboxylic acid was made using the procedures disclosed in *Heterocycles*, 2007, 74, 397-409.

Example 73: Preparation of 2-methyl-3-methylsulfanyl-butyric acid

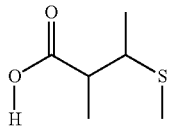

2-Methyl-3-methylsulfanyl-butyric acid was made as described in *J. Chem Soc Perkin* 1, 1992, 10, 1215-21.

Example 74: Preparation of (1S,2S)-2-(methylthio)cyclopropanecarboxylic acid

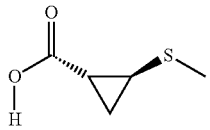

(1S,2S)-2-(Methylthio)cyclopropanecarboxylic acid was made using the procedures disclosed in *Synthetic Comm.*, 2003, 33 (5); 801-807.

Example 75: Preparation of 2-(2-(methylthio)ethoxy)propanoic acid

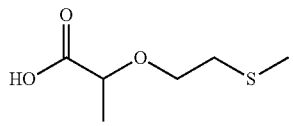

2-(2-(Methylthio)ethoxy)propanoic acid was made as described in WO 2007/064316 A1.

Example 76: Preparation of 2-((tetrahydrofuran-3-yl)oxy)propanoic acid

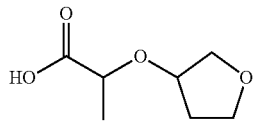

2-((Tetrahydrofuran-3-yl)oxy)propanoic acid was made as described in WO 2007/064316 A1.

Example 77: Preparation of tert-Butyl 1-(5-fluoropyridin-3-yl)-3-methyl-1H-pyrazol-4-yl(prop-2-ynyl)carbamate (Compound 601)

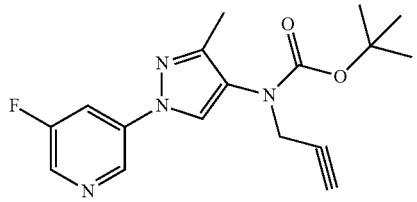 [SMILES: C#CCN(C(=O)OC(C)(C)C)c1cn(-c2cncc(F)c2)nc1C]

To an ice cold solution of tert-butyl 1-(5-fluoropyridin-3-yl)-3-methyl-1H-pyrazol-4-ylcarbamate (1200 mg, 4.11 mmol) in dry DMF (4 mL) under nitrogen was added 60% wt sodium hydride (197 mg, 4.93 mmol) and the mixture stirred for 10 min. 3-Bromoprop-1-yne (733 mg, 6.16 mmol) was then added and the mixture was stirred for additional 0.5 h at between 0-5° C. The mixture was allowed to warm to ambient temperature and then stirred for additional 3 h at room temperature. The brown reaction mixture poured into saturated aqueous NH$_4$Cl (20 mL), and diluted with ethyl acetate (50 mL). The organic phase was separated and the aqueous phase extracted with ethyl acetate (20 mL). The combined organic phase was washed with brine, dried over anhydrous MgSO$_4$, filtered, and concentrated in vacuo to give a brown oil. This oil was purified on silica gel eluting with mixtures of hexanes and ethyl acetate to give the title compound as a light yellow solid (1103 mg, 81%); mp 81-82° C.; $^1$H NMR (400 MHz, CDCl$_3$) δ 8.73 (s, 1H), 8.37 (d, J=2.5 Hz, 1H), 7.99 (s, 1H), 7.83 (dt, J=9.5, 2.2 Hz, 1H), 4.31 (s, 2H), 2.29 (t, J=2.4 Hz, 1H), 2.27 (s, 3H), 1.45 (s, 8H); ESIMS m/z 229.84 ([M]$^+$).

Compounds 596 and 606 were prepared in accordance with the procedure disclosed in Example 77 from the corresponding amine.

Example 78: Preparation of 1-(5-fluoropyridin-3-yl)-3-methyl-N-(prop-2-ynyl)-1H-pyrazol-4-amine, hydrochloride

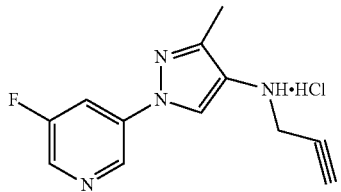

To a solution of tert-butyl 1-(5-fluoropyridin-3-yl)-3-methyl-1H-pyrazol-4-yl(prop-2-ynyl)carbamate (1.03 g, 3.11 mmol) in dioxane (5 mL) was added 4M HCl (3.9 mL, 15.5 mmol) indioxane. The mixture was stirred at room temperature for 48 h and the resulting white solid was filtered, washed with ether and dried under vacuum to give to give the title compound as a white solid (741 mg, 89%): mp 167-168° C.; $^1$H NMR (400 MHz, DMSO d$_6$) δ 8.92-8.85 (m, 1H), 8.42 (d, J=2.5 Hz, 1H), 8.15 (s, 1H), 8.12-8.02 (m, 1H), 3.85 (d, J=2.5 Hz, 2H), 3.27-3.19 (m, 1H), 2.22 (s, 3H); ESIMS m/z 230.4 ([M]$^+$).

3-Chloro-N-(prop-2-ynyl)-1-(pyridin-3-yl)-1H-pyrazol-4-amine, hydrochloride was prepared in accordance with the procedure disclosed in Example 78 from (Compound 606): mp 180-182° C.; $^1$H NMR (400 MHz, CDCl$_3$) δ 9.22 (d, J=2.5 Hz, 1H), 8.67 (dd, J=5.3, 1.0 Hz, 1H), 8.64 (ddd, J=8.6, 2.6, 1.2 Hz, 1H), 8.32 (s, 1H), 7.96 (dd, J=8.6, 5.3 Hz, 1H), 3.81 (d, J=2.4 Hz, 2H), 3.15 (t, J=2.4 Hz, 1H); ESIMS m/z 234 ([M+2]$^+$).

3-Methyl-N-(prop-2-yn-1-yl)-1-(pyridin-3-yl)-1H-pyrazol-4-amine, hydrochloride was prepared in accordance with the procedure disclosed in Example 78 from Compound 596: mp 161-163° C.; $^1$H NMR (400 MHz, DMSO-d$_6$) δ 8.46 (s, 1H), 8.05 (s, OH), 7.83 (d, J=5.9 Hz, 1H), 7.57 (s, 1H), 7.29 (dd, J=8.8, 5.6 Hz, 1H), 3.27 (d, J=2.5 Hz, 2H), 1.52 (s, 3H); EIMS m/z 213.1 ([M]$^+$).

Example 79: Preparation of N-(1-(5-Fluoropyridin-3-yl)-3-methyl-1H-pyrazol-4-yl)-3-(methylthio)-N-(prop-2-ynyl)propanamide (Compound 605)

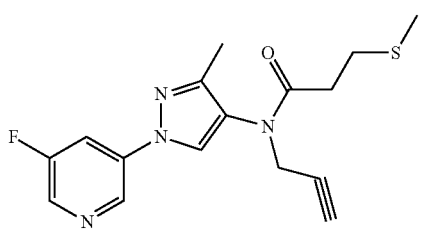 [SMILES: C#CCN(C(=O)CCSC)c1cn(-c2cncc(F)c2)nc1C]

To a stirred solution of 1-(5-fluoropyridin-3-yl)-3-methyl-N-(prop-2-yn-1-yl)-1H-pyrazol-4-amine, HCl (100 mg, 0.38 mmol) and N,N-dimethylpyridin-4-amine (115 mg, 0.94 mmol) in CH$_2$Cl$_2$ (2 mL) was added 2-methyl-3-(methylthio)propanoyl chloride (69 mg, 0.45 mmol) and the mixture stirred at room temperature for 24 h. The mixture was concentrated in vacuo to give a brown oil, which was purified on silica gel eluting with mixtures of ethyl acetate and hexanes to give the title compound as a colorless oil (80 mg, 61%): $^1$H NMR (400 MHz, CDCl$_3$) δ 8.77 (d, J=1.7 Hz, 1H), 8.43 (d, J=2.5 Hz, 1H), 8.05 (s, 1H), 7.86 (dt, J=9.4, 2.3 Hz, 1H), 4.49 (s, 1H), 2.88 (dd, J=12.8, 9.4 Hz, 1H), 2.74 (s, 1H), 2.45 (dd, J=12.9, 5.0 Hz, 1H), 2.34 (s, 3H), 2.24 (t, J=2.5 Hz, 1H), 2.02 (s, 3H), 1.14 (d, J=6.8 Hz, 3H); ESIMS m/z 347.5 ([M+H]$^+$).

Compounds 598, 599, 600, 602, 603, 607, 608 and 610 were prepared in accordance with the procedure disclosed in Example 79 from the corresponding amines.

Example 80: Preparation of N-(3-Chloro-1-(pyridin-3-yl)-1H-pyrazol-4-yl)-4,4,4-trifluoro-3-(methylthio)-N-(prop-2-yn-1-yl)butanamide (Compound 613)

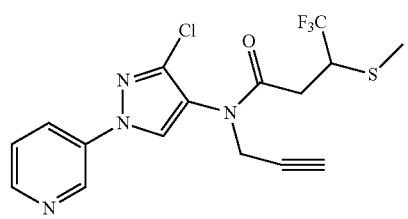 [SMILES: C#CCN(C(=O)CC(SC)C(F)(F)F)c1cn(-c2cccnc2)nc1Cl]

To a 7 mL vial was added 3-chloro-N-(prop-2-yn-1-yl)-1-(pyridin-3-yl)-1H-pyrazol-4-amine (140 mg, 0.6 mmol), N,N-dimethylpyridin-4-amine (249 mg, 2.040 mmol), N1-((ethylimino)methylene)-N3,N3-dimethylpropane-1,3-diamine hydrochloride (276 mg, 1.440 mmol) followed by 4,4,4-trifluoro-3-(methylthio)butanoic acid (158 mg, 0.840 mmol) and DCE (1.2 mL). The solution was stirred at 25° C. for 18 hours, the crude reaction mixture was concentrated and purified with silica gel chromatography (0-100% EtOAc/hexane) to give the title compound as a brown oil (237 mg, 0.588 mmol, 98%): (IR thin film) 1674 cm$^{-1}$; $^1$H NMR (400 MHz, CDCl$_3$) δ 8.97 (d, J=2.6 Hz, 1H), 8.64 (dd, J=4.7, 1.3 Hz, 1H), 8.13 (s, 1H), 8.07 (ddd, J=8.3, 2.7, 1.5 Hz, 1H), 7.48 (ddd, J=8.3, 4.8, 0.5 Hz, 1H), 4.39 (s, 2H), 3.76 (dqd, J=17.2, 8.6, 3.6 Hz, 1H), 2.67 (dd, J=16.6, 3.6 Hz, 1H), 2.46 (dd, J=16.5, 9.9 Hz, 1H), 2.29 (d, J=2.5 Hz, 4H); ESIMS m/z 403 ([M+H]$^+$).

Compounds 597, 604, 609, 614-616 were prepared in accordance with the procedure disclosed in Example 80.

Example 81: Preparation of 3-Chloro-N-(prop-2-ynyl)-1-(pyridin-3-yl)-1H-pyrazol-4-amine

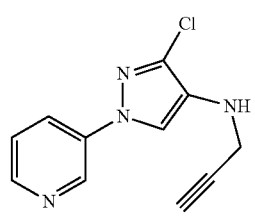 [SMILES: C#CCNc1cn(-c2cccnc2)nc1Cl]

To a solution of tert-butyl(3-chloro-1-(pyridin-3-yl)-1H-pyrazol-4-yl)(prop-2-yn-1-yl)carbamate (2.2 g, 6.61 mmol) in dichloromethane (8.3 ml) was added 2,2,2-trifluoroacetic acid (12.06 g, 106 mmol) and the reaction mixture was stirred at ambient temperature for 1 hour. The reaction was quenched by the addition of saturated sodium bicarbonate. The organic layer was extracted with dichloromethane (2×20 mL). The organic layers were combined and dried over sodium sulfate, filtered and concentrated without further purification to afford the title compound as a beige solid (1.5 g, 6.12 mmol, 93%): $^1$H NMR (400 MHz, CDCl$_3$) δ 8.89 (d, J=2.3 Hz, 1H), 8.50 (dd, J=4.7, 1.4 Hz, 1H), 8.01-7.93 (m, 1H), 7.54 (s, 1H), 7.37 (ddd, J=8.3, 4.8, 0.7 Hz, 1H), 3.90 (s, 2H), 3.38 (s, 1H), 2.44-2.09 (m, 1H); ESIMS m/z 233 ([M+H]$^+$).

Example 82: Preparation of N-(3-Chloro-1-(pyridin-3-yl)-1H-pyrazol-4-yl)-2-(methylthio)-N-(prop-2-yn-1-yl)propanamide (Compound 611)

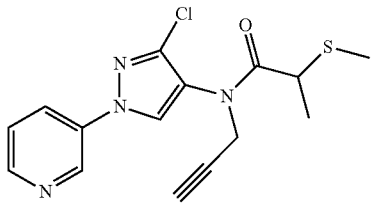 [SMILES: C#CCN(C(=O)C(C)SC)c1cn(-c2cccnc2)nc1Cl]

To a solution of 2-(methylthio)propanoic acid (0.36 g, 3.00 mmol) in dichloromethane (3 mL) was added oxalyl dichloride (0.29 ml, 3.31 mmol) followed by one drop of N,N-dimethylformamide. The reaction mixture was stirred for 30 minutes before all solvent was evaporated. The resulting residue was dissolved in dichloromethane (2 mL) and it was added to a pre-stirred solution of 3-chloro-N-(prop-2-yn-1-yl)-1-(pyridin-3-yl)-1H-pyrazol-4-amine (0.35 g, 1.50 mmol) and N-ethyl-N-isopropylpropan-2-amine (0.57 ml, 3.31 mmol) in dichloromethane (5.5 mL). The reaction mixture was stirred at ambient temperature for 16 hours. The reaction mixture was concentrated and the residue was purified using silica gel chromatography (0-100% ethyl acetate/hexanes) to afford the title compound as a yellow oil (432 mg, 1.23 mmol, 85%): $^1$H NMR (400 MHz, CDCl$_3$) δ 8.97 (d, J=2.5 Hz, 1H), 8.66-8.60 (m, 1H), 8.25 (s, 1H), 8.08-8.01 (m, 1H), 7.49-7.42 (m, 1H), 4.86 (s, 1H), 4.29-3.97 (m, 1H), 3.31 (d, J=6.5 Hz, 1H), 2.30-2.24 (m, 1H), 2.09 (s, 3H), 1.46 (d, J=6.9 Hz, 3H); $^{13}$C NMR (101 MHz, CDCl$_3$) δ 171.30, 148.66, 140.71, 140.18, 135.71, 127.87, 126.35, 124.11, 122.12, 78.53, 72.92, 53.39, 37.97, 16.42, 11.07; ESIMS m/z 335 ([M+H]$^+$).

Compound 612 was prepared in accordance with the procedure disclosed in Example 82.

Example 83: Preparation of N-(3-Chloro-1-(pyridin-3-yl)-1H-pyrazol-4-yl)-2-(methylsulfinyl)-N-(prop-2-yn-1-yl)propanamide (Compound 617)

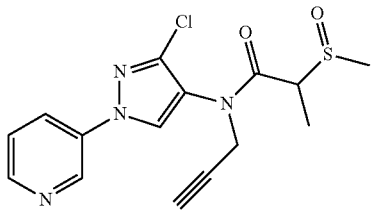 [SMILES: C#CCN(C(=O)C(C)S(C)=O)c1cn(-c2cccnc2)nc1Cl]

To a solution of N-(3-chloro-1-(pyridin-3-yl)-1H-pyrazol-4-yl)-2-(methylthio)-N-(prop-2-yn-1-yl)propanamide (0.1 g, 0.30 mmol) in hexafluoroisopropanol (2.0 ml) was added hydrogen peroxide (35 wt %, 0.08 ml, 0.90 mmol) and the reaction mixture was stirred vigorously at ambient temperature. The reaction was complete after 1 hour. The reaction was quenched with saturated sodium sulfite solution and the organic layer was extracted with ethyl acetate (3×20 mL). The combined organic layers were dried over sodium sulfate, filtered and concentrated. The residue was purified using silica gel chromatography (0-20% methanol/dichloromethane) to afford the title compound as an off-white foam (82 mg, 0.21 mmol, 78%): $^1$H NMR (400 MHz, CDCl$_3$) δ 8.98 (s, 1H), 8.65 (d, J=4.6 Hz, 1H), 8.23 (s, 1H), 8.11-7.97 (m, 1H), 7.51-7.41 (m, 1H), 4.88 (br s, 1H), 4.14 (br s, 1H), 2.64 (s, 1.2H), 2.55 (s, 1.8H), 2.33-2.27 (m, 1H), 1.47 (d, J=6.8 Hz, 3H); $^{13}$C NMR (101 MHz, CDCl$_3$) δ 168.11, 148.95, 148.78, 140.45, 140.33, 140.20, 135.56, 126.54, 124.10, 121.68, 121.58, 121.48, 77.69, 73.49, 38.60; ESIMS m/z 351 ([M+H]$^+$).

Example 84: Preparation of N-(3-Chloro-1-(pyridin-3-yl)-1H-pyrazol-4-yl)-2-(methylsulfonyl)-N-(prop-2-yn-1-yl)propanamide (Compound 618)

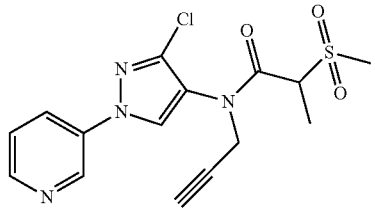 [SMILES: C#CCN(C(=O)C(C)S(C)(=O)=O)c1cn(-c2cccnc2)nc1Cl]

To a solution of N-(3-chloro-1-(pyridin-3-yl)-1H-pyrazol-4-yl)-2-(methylthio)-N-(prop-2-yn-1-yl)propanamide (0.10 g, 0.30 mmol) and acetic acid (2.0 ml). To this solution was added sodium perborate tetrahydrate (0.11 g, 0.74 mmol) and the vial was heated to 65° C. for 2 hours. The reaction mixture was cooled to ambient temperature and neutralized with saturated sodium bicarbonate. The organic layer was extracted with ethyl acetate (3×). The organic layers were combined, dried over sodium sulfate, filtered and concentrated. The residue was purified using silica gel chromatography (0-20% methanol/dichloromethane) to afford the title compound as a yellow foam (84 mg, 0.21 mmol, 73%): $^1$H NMR (400 MHz, CDCl$_3$) δ 9.00 (s, 1H), 8.65 (s, 1H), 8.29 (s, 1H), 8.03 (d, J=8.0 Hz, 1H), 7.54-7.39 (m, 1H), 4.89 (d, J=16.9 Hz, 1H), 4.20-4.08 (m, 1H), 4.07-3.92 (m, 1H), 3.01 (s, 3H), 2.34-2.29 (m, 1H), 1.67 (d, J=7.0 Hz, 3H); $^{13}$C NMR (101 MHz, CDCl$_3$) δ 166.97, 166.90, 148.77, 140.43, 140.24, 135.58, 129.36, 126.64, 124.14, 121.34, 73.80, 60.91, 38.78, 36.29, 13.97; ESIMS m/z 367 ([M+H]$^+$).

Example 85: Preparation of N-(3-chloro-1-(pyridin-3-yl)-1H-pyrazol-4-yl)-N-ethyl-2-methyl-3-(tritylthio)propanamide

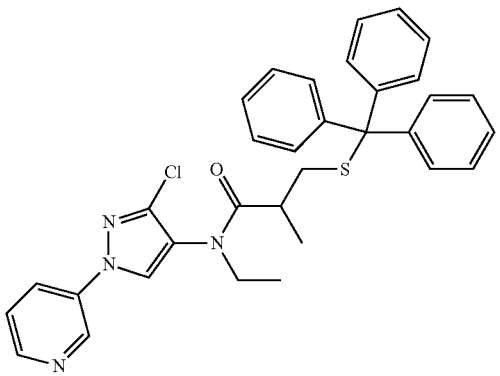 [SMILES: CCN(C(=O)C(C)CSC(c1ccccc1)(c1ccccc1)c1ccccc1)c1cn(-c2cccnc2)nc1Cl]

To a solution of N,N-dimethylpyridin-4-amine (2.60 g, 21.31 mmol), 2-methyl-3-(tritylthio)propanoic acid (4.41 g, 12.18 mmol) (prepared according to Ondetti, Miguel Angel et. al. DE 2703828) and N1-((ethylimino)methylene)-N3,N3-dimethylpropane-1,3-diamine hydrochloride (2.36 g, 15.22 mmol) in CH$_2$Cl$_2$ (20 mL) was added 3-chloro-N-ethyl-1-(pyridin-3-yl)-1H-pyrazol-4-amine, 2HCl (3.0 g, 10 mmol). The mixture was stirred at 0° C. for 2 hours, then at room temperature for additional 48 hours. The mixture was diluted with ethyl acetate (100 mL) and saturated aqueous NH$_4$Cl. The organic phase was separated, washed with brine, dried over MgSO$_4$ and concentrated in vacuo to give a light brown gum. This gum was purified on silica gel eluting with mixtures of ethyl acetate and hexanes to give the title molecule as a pink solid (2.97 g, 51%): mp 64-66° C.; $^1$H NMR (400 MHz, CDCl$_3$) δ 8.89 (d, J=2.7 Hz, 1H), 8.62 (dd, J=4.7, 1.4 Hz, 1H), 7.93-7.86 (m, 1H), 7.82 (s, 1H), 7.41 (dd, J=8.3, 4.7 Hz, 1H), 7.33-7.14 (m, 15H), 3.68 (d, J=47.9 Hz, 2H), 2.72 (dd, J=12.0, 8.8 Hz, 1H), 2.37-2.24 (m, 1H), 2.01 (dd, J=12.0, 5.2 Hz, 1H), 1.14 (t, J=7.2 Hz, 3H), 0.95 (d, J=6.7 Hz, 3H); ESIMS m/z 568 ([M+H]$^+$).

Example 86: Preparation of N-(3-chloro-1-(pyridin-3-yl)-1H-pyrazol-4-yl)-N-methyl-3-(tritylthio)propanamide

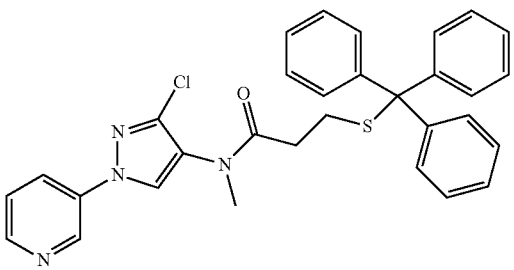 [SMILES: CN(C(=O)CCSC(c1ccccc1)(c1ccccc1)c1ccccc1)c1cn(-c2cccnc2)nc1Cl]

To a solution of 3-chloro-N-methyl-1-(pyridin-3-yl)-1H-pyrazol-4-amine, HCl (1.5 g, 6.12 mmol) in CH$_2$Cl$_2$ (10 mL) were added 3-(tritylthio)propanoic acid (2.35 g, 6.73 mmol) (prepared according to Ondetti, Miguel Angel et. al. DE 2703828). N,N-dimethylpyridin-4-amine (0.82 g, 6.73 mmol) and N1-((ethylimino)methylene)-N3,N3-dimethylpropane-1,3-diamine, HCl (1.76 g, 9.18 mmol), and the mixture was stirred at room temperature for 16 h.

The mixture was diluted with CH$_2$Cl$_2$ (100 mL) and water (50 mL) and the organic phase separated. The aqueous phase was extracted with ethyl acetate and the combined organic phase was washed with brine, dried over MgSO$_4$ and concentrated in vacuo to give the title molecule as a white powder (1.95 g, 59%): mp 62-64° C.; $^1$H NMR (400 MHz, CDCl$_3$) δ 8.91 (d, J=2.7 Hz, 1H), 8.67-8.61 (m, 1H), 8.06-7.96 (m, 1H), 7.81 (s, 1H), 7.49-7.46 (m, 1H), 7.25-7.45 (m, 15H), 3.17 (s, 3H), 2.56-2.46 (m, 2H), 2.09-1.97 (m, 2H); ESIMS m/z 540 ([M+H]$^+$).

Example 87: Preparation of N-(3-chloro-1-(pyridin-3-yl)-1H-pyrazol-4-yl)-3-mercapto-N-methylpropanamide

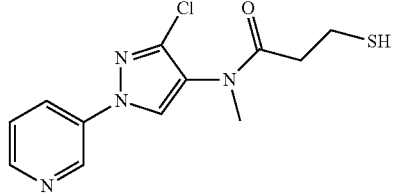 [SMILES: CN(C(=O)CCS)c1cn(-c2cccnc2)nc1Cl]

To a solution of N-(3-chloro-1-(pyridin-3-yl)-1H-pyrazol-4-yl)-N-methyl-3-(tritylthio)propanamide (1.300 g, 2.411 mmol) in CH$_2$Cl$_2$ (6.14 g, 72.3 mmol) were added triethylsilane (1.402 g, 12.06 mmol) followed by 2,2,2-trifluoroacetic acid (2.75 g, 24.11 mmol) at room temperature. The mixture was stirred for 1 hour and quenched with saturated aqueous NaHCO$_3$. The mixture was diluted with CH$_2$Cl$_2$ and the organic phase was separated. The aqueous phase was extracted with CH$_2$Cl$_2$ and the organic phases were combined, washed with brine dried over anhydrous MgSO$_4$ and concentrated in vacuo to give a light yellow oil. This oil was purified on silica gel eluting with ethyl acetate and hexanes to give the title molecule as a colorless oil (701 mg, 93%): IR (thin film) 3094, 2980, 1657, 1582 cm$^{-1}$; $^1$H NMR (400 MHz, CDCl$_3$) δ 8.95 (d, J=2.6 Hz, 1H), 8.63 (s, 1H), 8.06 (s, 1H), 8.04-7.96 (m, 1H), 7.52-7.42 (m, 1H), 3.26 (s, 3H), 2.85-2.73 (m, 2H), 2.56-2.48 (m, 2H).

The following molecules were made in accordance with the procedures disclosed in Example 87:

N-(3-chloro-1-(pyridin-3-yl)-1H-pyrazol-4-yl)-N-ethyl-3-mercatopropanamide

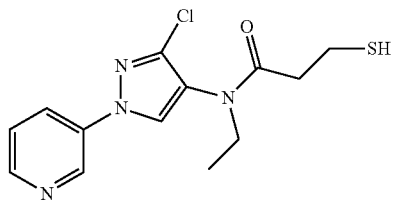 [SMILES: CCN(C(=O)CCS)c1cn(-c2cccnc2)nc1Cl]

The title molecule was isolated as a light brown gum (902 mg, 64%): IR (thin film) 3086, 2980, 2936, 2548, 1657 cm$^{-1}$; $^1$H NMR (400 MHz, CDCl$_3$) δ 8.96 (dd, J=2.7, 0.7 Hz, 1H), 8.63 (dd, J=4.8, 1.5 Hz, 1H), 8.06 (ddd, J=8.3, 2.7, 1.4 Hz, 1H), 7.97 (s, 1H), 7.47 (ddd, J=8.4, 4.7, 0.8 Hz, 1H), 3.72 (q, J=7.1 Hz, 2H), 2.79 (dt, J=8.5, 6.8 Hz, 2H), 2.49 (t, J=6.7 Hz, 2H), 1.67 (t, J=8.4 Hz, 1H), 1.17 (t, J=7.2 Hz, 3H); ESIMS m/z 311 ([M+H]$^+$), 309 ([M−H]$^−$).

N-(3-chloro-1-(pyridin-3-yl)-1H-pyrazol-4-yl)-N-ethyl-3-mercapto-2-methylpropanamide

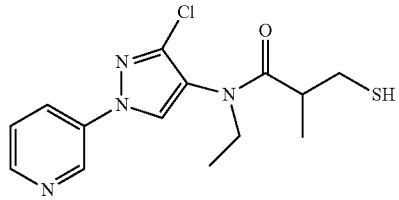 [SMILES: CCN(C(=O)C(C)CS)c1cn(-c2cccnc2)nc1Cl]

The title molecule was isolated as a colorless oil which solidified upon standing: mp 94-96° C.; $^1$H NMR (400 MHz, CDCl$_3$) δ 8.97 (dd, J=2.7, 0.7 Hz, 1H), 8.63 (dd, J=4.8, 1.5 Hz, 1H), 8.05 (ddd, J=8.3, 2.7, 1.5 Hz, 1H), 8.02 (s, 1H), 7.47 (ddd, J=8.3, 4.8, 0.8 Hz, 1H), 3.85 (m, 1H), 3.60 (m, 1H), 2.91 (ddd, J=13.2, 9.4, 8.1 Hz, 1H), 2.41 (ddd, J=13.2, 9.2, 4.9 Hz, 1H), 1.49 (dd, J=9.2, 8.2 Hz, 1H), 1.18 (t, J=7.2 Hz, 3H), 1.14 (d, J=6.7 Hz, 3H); ESIMS m/z 325 ([M+H]$^+$).

Example 88: Preparation of 3-(((2,2-difluorocyclopropyl)methyl)thio)propanoic acid

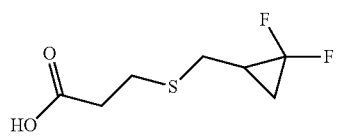 [SMILES: O=C(O)CCSCC1CC1(F)F]

Powdered potassium hydroxide (423 mg, 7.54 mmol) and 2-(bromomethyl)-1,1-difluorocyclopropane (657 mg, 3.84 mmol) were sequentially added to a stirred solution of 3-mercaptopropanoic acid (400 mg, 3.77 mmol) in methanol (2 mL) at room temperature. The resulting white suspension was stirred at 65° C. for 3 h and quenched with 1N aqueous HCl and diluted with ethyl acetate. The organic phase was separated and the aqueous phase extracted with ethyl acetate (2×50 mL). The combined organic extracts were dried over MgSO$_4$, filtered and concentrated in vacuo to give the title molecule as a colorless oil (652 mg, 84%): IR (KBr thin film) 3025, 2927, 2665, 2569, 1696 cm$^{-1}$; $^1$H NMR (400 MHz, CDCl$_3$) δ 2.85 (t, J=7.0 Hz, 2H), 2.82-2.56 (m, 4H), 1.88-1.72 (m, 1H), 1.53 (dddd, J=12.3, 11.2, 7.8, 4.5 Hz, 1H), 1.09 (dtd, J=13.1, 7.6, 3.7 Hz, 1H); ESIMS m/z 195.1 ([M−H]$^−$).

The following molecules were made in accordance with the procedures disclosed in Example 88:

4-(((2,2-Difluorocyclopropyl)methyl)thio)butanoic acid: $^1$H NMR (400 MHz, CDCl$_3$) δ 11.31 (s, 1H), 2.71-2.54 (m, 4H), 2.51 (t, J=7.2 Hz, 2H), 2.01-1.86 (m, 2H), 1.85-1.70 (m, 1H), 1.51 (dddd, J=12.3, 11.2, 7.8, 4.5 Hz, 1H), 1.07 (dtd, J=13.2, 7.6, 3.7 Hz, 1H); $^{13}$C NMR (101 MHz, CDCl$_3$) δ 179.6, 113.7 (dd, J=286.4, 283.4 Hz), 32.7, 30.7, 28.7 (d, J=4.6 Hz), 24.2, 22.8 (t, J=11.2 Hz), 16.6 (t, J=10.8 Hz); $^{19}$F NMR (376 MHz, CDCl$_3$) δ−128.12 (d, J=156.8 Hz), −142.77 (d, J=156.7 Hz).

4-((2,2,2-Trifluoroethyl)thio)butanoic acid: $^1$H NMR (400 MHz, DMSO-d$_6$) δ 3.47 (q, J=10.8 Hz, 2H), 2.72 (dd, J=7.8, 6.6 Hz, 2H), 2.32 (td, J=7.3, 4.5 Hz, 2H), 1.96-1.81 (m, 2H).

Example 89: Preparation of N-(3-chloro-1-(pyridin-3-yl)-1H-pyrazol-4-yl)-3-(((2,2-difluorocyclopropyl)methyl)thio)-N-ethylpropanamide (Molecule 626)

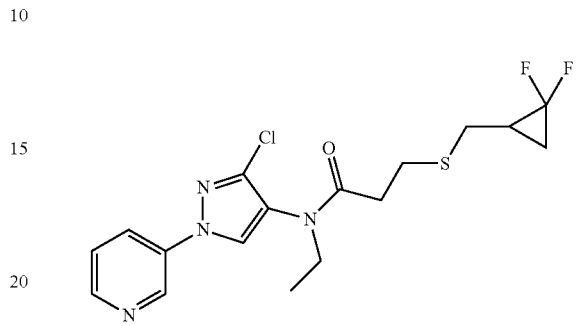

To a solution of N-(3-chloro-1-(pyridin-3-yl)-1H-pyrazol-4-yl)-N-ethyl-3-mercaptopropanamide (100 mg, 0.322 mmol) in THF (1 mL) was added sodium hydride (60% dispersion in oil, 13.5 mg, 0.34 mmol). The resulting mixture was stirred at room temperature for 10 min followed by addition of 2-(bromomethyl)-1,1-difluorocyclopropane (60 mg, 0.35 mmol). The mixture was stirred at room temperature for 24 h and diluted with saturated aqueous ammonium chloride and ethyl acetate. The organic phase was separated and the aqueous phase extracted with ethyl acetate (2×50 mL). The combined organic extracts were dried over MgSO$_4$, filtered and concentrated in vacuo to give a colorless oil. This oil was purified by chromatography eluting with mixtures of ethyl acetate and hexanes to give the title molecule as a colorless gum (101 mg, 78%): IR (thin film) 3092, 2975, 2931, 1659, 1584 cm$^{-1}$; $^1$H NMR (400 MHz, CDCl$_3$) δ 8.99-8.90 (m, 1H), 8.63 (dd, J=4.8, 1.5 Hz, 1H), 8.05 (ddd, J=8.3, 2.7, 1.5 Hz, 1H), 7.96 (s, 1H), 7.47 (ddd, J=8.3, 4.7, 0.7 Hz, 1H), 3.72 (q, J=7.2 Hz, 2H), 2.87 (t, J=7.3 Hz, 2H), 2.63-2.55 (m, 2H), 2.46 (t, J=7.3 Hz, 2H), 1.76 (ddq, J=13.2, 11.4, 7.5 Hz, 1H), 1.48 (dddd, J=12.3, 11.2, 7.8, 4.5 Hz, 1H), 1.17 (t, J=7.2 Hz, 3H), 1.04 (dtd, J=13.2, 7.6, 3.7 Hz, 1H); ESIMS m/z 400 ([M+H]$^+$).

Molecules 624, 625, 629, 633, 643 653 in Table 1 were made in accordance with the procedures disclosed in Example 89.

Example 90: Preparation of N-(3-chloro-1-(pyridin-3-yl)-1H-pyrazol-4-yl)-3-(((2,2-difluorocyclopropyl)methyl)sulfinyl)-N-ethylpropanamide (Molecule 627)

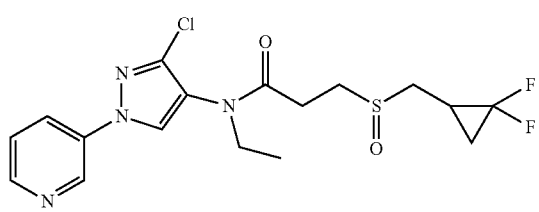 [SMILES: CCN(C(=O)CCS(=O)CC1CC1(F)F)c1cn(-c2cccnc2)nc1Cl]

To a solution of N-(3-chloro-1-(pyridin-3-yl)-1H-pyrazol-4-yl)-3-(((2,2-difluorocyclopropyl)methyl)thio)-N-ethylpropanamide (100 mg, 0.25 mmol) in acetic acid (5 ml, 0.25 mmol) was added sodium perborate tetrahydrate (38.4 mg, 0.25 mmol) and the mixture stirred at 50° C. for 1 hour. The mixture was cooled to room temperature, quenched with saturated aqueous sodium bicarbonate and then diluted with ethyl acetate. The organic phase was separated and the aqueous phase extracted with ethyl acetate. The combined organic phase was washed with brine, dried over MgSO₄ and concentrated in vacuo to give a colorless oil. This oil was purified on silica gel eluting with methanol and CH$_2$Cl$_2$ (0-10% gradient) to give the title molecule as a colorless gum (91 mg, 88%): IR (thin film) 3448, 3092, 2976, 2933, 1659, 1585, 1440, 1012 cm$^{-1}$; $^1$H NMR (400 MHz, CDCl$_3$) δ 8.97 (d, J=2.6 Hz, 1H), 8.63 (dd, J=4.8, 1.5 Hz, 1H), 8.04 (m, 2H), 7.46 (ddd, J=8.3, 4.8, 0.7 Hz, 1H), 3.72 (dq, J=13.8, 7.0 Hz, 2H), 3.16 (ddd, J=20.3, 13.9, 6.8 Hz, 1H), 3.00-2.79 (m, 3H), 2.69 (m, 2H), 2.13-1.85 (m, 1H), 1.77-1.62 (m, 1H), 1.41-1.21 (m, 1H), 1.18 (t, J=7.2 Hz, 3H); ESIMS m/z 417 ([M+H]$^+$).

Molecules 622, 630, 645 in Table 1 were made in accordance with the procedures disclosed in Example 90.

Example 91: Preparation of N-(3-chloro-1-(pyridin-3-yl)-1H-pyrazol-4-yl)-3-(((2,2-difluoro cyclopropyl)methyl)sulfonyl)-N-ethylpropanamide (Molecule 628)

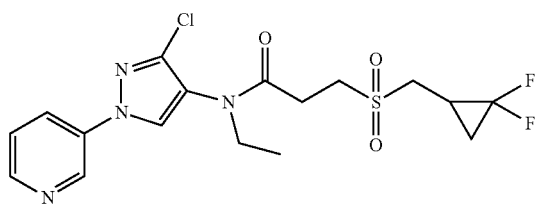 [SMILES: CCN(C(=O)CCS(=O)(=O)CC1CC1(F)F)c1cn(-c2cccnc2)nc1Cl]

To a solution of N-(3-chloro-1-(pyridin-3-yl)-1H-pyrazol-4-yl)-3-(((2,2-difluorocyclopropyl)methyl)thio)-N-ethylpropanamide (100 mg, 0.25 mmol) in acetic acid (5 ml, 0.25 mmol) was added sodium perborate tetrahydrate (77 mg, 0.499 mmol) and the mixture stirred at 50° C. for 1 hour. The mixture was cooled to room temperature, quenched with saturated aqueous sodium bicarbonate and then diluted with ethyl acetate. The organic phase was separated and the aqueous phase was extracted with ethyl acetate. The combined organic phase was washed with brine, dried over MgSO₄ and concentrated in vacuo to give a brown oil. This oil was purified on silica gel eluting with mixtures of ethyl acetate and hexanes to give the title molecule as a colorless gum (90 mg, 83%): IR (thin film) 3104, 2980, 2934, 1662, 1486, 1460 cm$^{-1}$; $^1$H NMR (400 MHz, CDCl$_3$) δ 9.00-8.90 (m, 1H), 8.64 (dd, J=4.7, 1.4 Hz, 1H), 8.09-8.00 (m, 2H), 7.47 (ddd, J=8.4, 4.8, 0.7 Hz, 1H), 3.72 (d, J=7.1 Hz, 2H), 3.43 (s, 2H), 3.30 (dd, J=14.7, 6.8 Hz, 1H), 3.11-3.00 (m, 1H), 2.72 (t, J=6.9 Hz, 2H), 2.13-1.96 (m, 1H), 1.73 (tdd, J=11.5, 8.3, 5.4 Hz, 1H), 1.45 (ddt, J=16.1, 8.0, 3.8 Hz, 1H), 1.18 (t, J=7.2 Hz, 3H); ESIMS m/z 433 ([M+H]$^+$).

Molecules 623, 631, 644 in Table 1 were made in accordance with the procedures disclosed in Example 91.

Example 92: Preparation of N-(3-chloro-1-(pyridin-3-yl)-1H-pyrazol-4-yl)-N-(cyclopropylmethyl)-3-(((2,2-difluorocyclopropyl)methyl)thio)propanamid (Molecule 632)

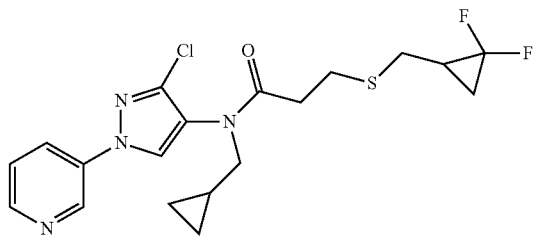 [SMILES: O=C(CCSCC1CC1(F)F)N(CC1CC1)c1cn(-c2cccnc2)nc1Cl]

To a solution of 3-chloro-N-(cyclopropylmethyl)-1-(pyridin-3-yl)-1H-pyrazol-4-amine (108 mg, 0.43 mmol), N,N-dimethylpyridin-4-amine (53 mg, 0.43 mmol) and 3-(((2,2-difluorocyclopropyl)methyl)thio)propanoic acid (85 mg, 0.43 mmol) in DMF (5 mL) was added N1-((ethylimino)methylene)-N3,N3-dimethylpropane-1,3-diamine hydrochloride (101 mg, 0.65 mmol). The resulting brown-yellow mixture was stirred at ambient temperature for 2 h. The mixture was diluted with saturated aqueous ammonium chloride and ethyl acetate. The organic phase was separated and the aqueous phase extracted with ethyl acetate (2×50 mL). The combined organic extracts were dried over MgSO₄, filtered and concentrated in vacuo to give the title molecule as a colorless oil (120 mg, 61%): IR (thin film) 3089, 3005, 2923, 1660 1584 cm$^{-1}$; $^1$H NMR (400 MHz, CDCl$_3$) δ 8.95 (d, J=2.6 Hz, 1H), 8.63 (dd, J=4.8, 1.5 Hz, 1H), 8.05 (ddd, J=8.3, 2.7, 1.5 Hz, 1H), 7.99 (s, 1H), 7.47 (ddd, J=8.3, 4.7, 0.7 Hz, 1H), 3.54 (s, 2H), 2.88 (t, J=7.3 Hz, 2H), 2.69-2.54 (m, 2H), 2.48 (t, J=7.3 Hz, 2H), 1.76 (ddt, J=18.7, 13.3, 7.4 Hz, 1H), 1.53-1.42 (m, 1H), 1.12-0.90 (m, 2H), 0.54-0.44 (m, 2H), 0.20 (dt, J=6.1, 4.6 Hz, 2H); ESIMS m/z 427 ([M+H]$^+$).

Molecule 646 in Table 1 was made in accordance with the procedures disclosed in Example 92.

Example 93: Preparation of (E)-N-(3-chloro-1-(pyridin-3-yl)-1H-pyrazol-4-yl)-N-ethyl-4,4,4-trifluorobut-2-enamide

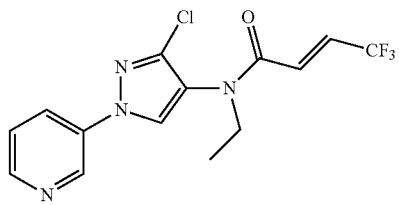 [SMILES: CCN(C(=O)/C=C/C(F)(F)F)c1cn(-c2cccnc2)nc1Cl]

To a solution of 3-chloro-N-ethyl-1-(pyridin-3-yl)-1H-pyrazol-4-amine, 2HCl (1.0 g, 3.38 mmol), N,N-dimethylpyridin-4-amine (827 mg, 6.77 mmol), and (E)-4,4,4-trifluorobut-2-enoic acid (474 mg, 3.38 mmol) in DMF (3 mL) was added N1-((ethylimino)methylene)-N3,N3-dimethylpropane-1,3-diamine, HCl (973 mg, 5.07 mmol). The resulting brown-yellow mixture was stirred at ambient temperature for 2 hours. The mixture was diluted with saturated aqueous NH₄Cl and ethyl acetate and saturated with NaCl. The organic phase was separated and the aqueous phase extracted with ethyl; acetate (22×5050 mL). The combined organic phase was dried over MgSO₄, filtered and concentrated in vacuo to give the title molecule as a light brown gum (901 mg, 73%): IR (thin film) 3093, 2978, 2937, 1681, 1649, 1585, 1114 cm$^{-1}$; $^1$H NMR (400 MHz, CDCl₃) δ 8.97 (d, J=2.7 Hz, 1H), 8.65 (dd, J=4.9, 1.4 Hz, 1H), 8.07 (ddd, J=8.3, 2.7, 1.5 Hz, 1H), 7.99 (s, 1H), 7.48 (dd, J=8.3, 4.8 Hz, 1H), 6.84 (dq, J=15.4, 6.8 Hz, 1H), 6.60-6.44 (m, 1H), 3.80 (q, J=7.2 Hz, 2H), 1.22 (t, J=7.2 Hz, 3H); ESIMS m/z 345 ([M+H]⁺).

Example 94: Preparation of S-(4-((3-chloro-1-(pyridin-3-yl)-1H-pyrazol-4-yl)(ethyl)amino)-1,1,1-trifluoro-4-oxobutan-2-yl) ethanethioate

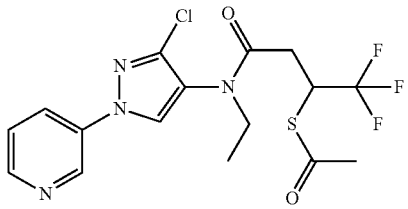 [SMILES: CCN(C(=O)CC(SC(C)=O)C(F)(F)F)c1cn(-c2cccnc2)nc1Cl]

To a solution of (E)-N-(3-chloro-1-(pyridin-3-yl)-1H-pyrazol-4-yl)-N-ethyl-4,4,4-trifluorobut-2-enamide (465 mg, 1.349 mmol) in dry DMSO (5 mL) was added potassium ethanethioacetate (616 mg, 5.40 mmol). The mixture was stirred at 50° C. for 96 hours under nitrogen. The mixture was quenched with saturated ammonium chloride and extracted twice with ethyl acetate. The combined organic phase was washed with brine, dried over MgSO₄, filtered and concentrated in vacuo to give a brown gum. Purification of this gum on silica gel eluting with mixtures of hexane and ethyl acetate gave the title molecule as a brown gum (265 mg, 44%): IR (thin film) 3099, 2976, 2936, 1708, 1666, 1585, 1102 cm$^{-1}$; $^1$H NMR (400 MHz, CDCl₃) δ 9.03-8.93 (m, 1H), 8.64 (dd, J=4.7, 1.5 Hz, 1H), 8.12-8.04 (m, 1H), 7.98 (s, 1H), 7.53-7.42 (m, 1H), 4.78 (dd, J=9.0, 4.4 Hz, 1H), 3.90-3.54 (m, 2H), 2.76 (dd, J=16.6, 4.4 Hz, 1H), 2.53 (dd, J=16.6, 9.4 Hz, 1H), 2.41 (s, 3H), 1.16 (t, J=7.2 Hz, 3H); ESIMS m/z 421 ([M+H]⁺).

Example 95: Preparation of N-(3-chloro-1-(pyridin-3-yl)-1H-pyrazol-4-yl)-3-(((2,2-difluorocyclopropyl)methyl)thio)-N-ethyl-4,4,4-trifluorobutanamide (Molecule 634)

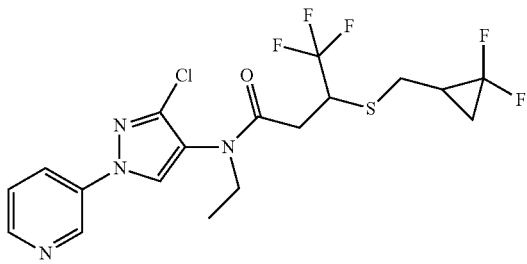 [SMILES: CCN(C(=O)CC(SCC1CC1(F)F)C(F)(F)F)c1cn(-c2cccnc2)nc1Cl]

To a solution of methanol (21.1 mg, 0.66 mmol) in THF (1 mL) was added sodium hydride (26.5 mg, 0.66 mmol, 60% oil suspension). The resulting mixture was stirred for 10 minutes at room temperature and S-(4-((3-chloro-1-(pyridin-3-yl)-1H-pyrazol-4-yl)(ethyl)amino)-1,1,1-trifluoro-4-oxobutan-2-yl) ethanethioate (266 mg, 0.63 mmol) in THF (1 mL) was added. After stirring for 30 minutes, 2-(bromomethyl)-1,1-difluorocyclopropane (130 mg, 0.76 mmol) was added. The mixture was stirred at room temperature for an additional 4 hours and diluted with saturated aqueous ammonium chloride and ethyl acetate. The organic phase was separated and the aqueous phase extracted with ethyl acetate (2×50 mL). The combined ethyl acetate extracts were dried over MgSO₄, filtered and concentrated in vacuo to give a colorless oil. Purification on silica gel eluting with ethyl acetate and hexanes gave the title molecule as a brown oil (89 mg, 30% yield): IR (thin film) 3097, 2978, 2937 1664, 1440 cm$^{-1}$; $^1$H NMR (400 MHz, CDCl₃) δ 8.96 (d, J=2.7 Hz, 1H), 8.64 (dd, J=4.8, 1.4 Hz, 1H), 8.06 (ddd, J=8.4, 2.8, 1.4 Hz, 1H), 7.98 (d, J=2.1 Hz, 1H), 7.47 (dd, J=8.3, 4.8 Hz, 1H), 3.94-3.84 (m, 1H), 3.75 (s, 2H), 2.97 (dd, J=13.4, 7.5 Hz, 0.55H), 2.85 (s, 1H), 2.79-2.65 (m, 0.45H), 2.60 (m, 1H), 2.43 (dt, J=16.3, 10.0 Hz, 1H), 1.89 (tt, J=12.2, 7.5 Hz, 1H), 1.63-1.49 (m, 1H), 1.23-1.13 (m, 4H); ESIMS m/z 469 ([M+H]⁺).

Example 96: Preparation of N-(3-chloro-1-(pyridin-3-yl)-1H-pyrazol-4-yl)-2-((cyclopropylmethyl)thio)-N-ethylpropanamide (Molecule 621)

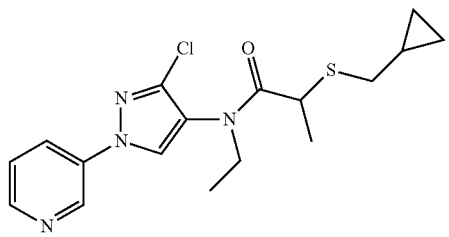 [SMILES: CCN(C(=O)C(C)SCC1CC1)c1cn(-c2cccnc2)nc1Cl]

To a solution of methanol (9.99 mg, 0.312 mmol) in THF (1 mL) was added sodium hydride (12.4 mg, 0.31 mmol, 60% oil suspension). The mixture was stirred at room temperature for 10 minutes and added S-(1-((3-chloro-1-(pyridin-3-yl)-1H-pyrazol-4-yl)(ethyl)amino)-1-oxopropan-2-yl) ethanethioate (100 mg, 0.28 mmol). After stirring the mixture for 30 min, (bromomethyl)cyclopropane (38 mg, 0.28 mmol) was added and the mixture stirred for additional 14 hours. The mixture was diluted with saturated aqueous ammonium chloride (5 mL) and ethyl acetate (15 mL), and the organic phase was separated. The aqueous phase was extracted with ethyl acetate (5 mL) and the combined organic phase was washed with brine, dried over MgSO₄ and concentrated in vacuo to give an oily residue. This residue was purified on silica gel eluting with mixtures of ethyl acetate and hexanes to give the title molecule as a colorless gum (31 mg, 30%): IR (thin film) 3081, 2972, 2930, 2871, 1655, 1438 cm$^{-1}$; $^1$H NMR (400 MHz, CDCl₃) δ 8.96 (d, J=2.8 Hz, 1H), 8.63 (dd, J=4.8, 1.4 Hz, 1H), 8.13 (s, 1H), 8.04 (ddt, J=8.3, 3.2, 1.6 Hz, 1H), 7.50-7.40 (m, 1H), 3.81 (bs, 1H), 3.59 (bs, 1H), 3.33 (d, J=7.4 Hz, 1H), 2.58-2.41 (m, 2H), 1.47 (d, J=6.9 Hz, 3H), 1.17 (td, J=7.1, 1.8 Hz, 3H), 0.84 (dt, J=10.3, 7.4, 3.7 Hz, 1H), 0.56-0.38 (m, 2H), 0.25-0.07 (m, 2H); ESIMS m/z 365 ([M+H]⁺).

Molecule 651 in Table 1 was made in accordance with the procedures disclosed in Example 96.

Example 97: Preparation of N-(3-chloro-1-(pyridin-3-yl)-1H-pyrazol-4-yl)-3-((cyclopropylmethyl)thio)-N-ethylpropanamide (Molecule 619)

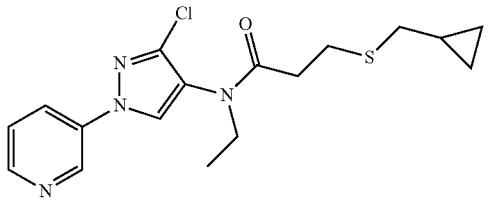 [SMILES: CCN(C(=O)CCSCC1CC1)c1cn(-c2cccnc2)nc1Cl]

To a solution of methanol (9.99 mg, 0.31 mmol) in DMSO (1 mL) was added sodium hydride (12.4 mg, 0.31 mmol). The mixture was stirred at room temperature for 10 minutes and added a solution of S-(3-((3-chloro-1-(pyridin-3-yl)-1H-pyrazol-4-yl)(ethyl)amino)-3-oxopropyl) ethanethioate (100 mg, 0.28 mmol). After stirring the mixture for 30 min, (bromomethyl)cyclopropane (38 mg, 0.28 mmol) was added and the mixture stirred for an additional 30 minutes. The mixture was diluted with saturated aqueous NH$_4$Cl and ethyl acetate and the organic phase separated. The aqueous phase was extracted with ethyl acetate and the combined organic phase was washed with brine, dried over MgSO$_4$ and concentrated in vacuo to give a light brown oil. This oil was purified on silica gel eluting with mixtures of hexanes and ethyl acetate to give the title molecule as a colorless gum (33 mg, 31%): IR (thin film) 3080, 2978, 2930, 1660, 1584 cm$^{-1}$; $^1$H NMR (400 MHz, CDCl$_3$) δ 8.95 (d, J=2.8 Hz, 1H), 8.63 (dd, J=4.7, 1.5 Hz, 1H), 8.12-8.01 (m, 1H), 7.98-7.92 (m, 1H), 7.53-7.40 (m, 1H), 3.78-3.62 (m, 2H), 2.95-2.84 (m, 2H), 2.51-2.38 (m, 4H), 1.20-1.11 (m, 3H), 0.94 (s, 1H), 0.60-0.34 (m, 2H), 0.24-0.09 (m, 2H); ESIMS m/z 365 ([M+H]$^+$).

Example 98: Preparation of N-(3-chloro-1-(pyridin-3-yl)-1H-pyrazol-4-yl)-2-((cyclopropylmethyl)thio)-N-ethylacetamide (Molecule 620)

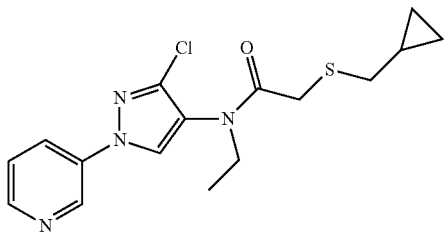 [SMILES: CCN(C(=O)CSCC1CC1)c1cn(-c2cccnc2)nc1Cl]

To a solution of methanol (10.4 mg, 0.32 mmol) in DMSO (1 mL) was added sodium hydride (13 mg, 0.32 mmol). The mixture was stirred at room temperature for 10 minutes and cooled to 0-5° C. and added a solution of S-(2-((3-chloro-1-(pyridin-3-yl)-1H-pyrazol-4-yl)(ethyl)amino)-2-oxoethyl) ethanethioate (100 mg, 0.29 mmol). After stirring the mixture for 30 min, (bromomethyl)cyclopropane (39 mg, 0.29 mmol) was added and the mixture stirred for additional 2 hours. The mixture was diluted with saturated aqueous ammonium chloride (5 mL) and ethyl acetate (15 mL), and the organic phase was separated. The aqueous phase was extracted with ethyl acetate (5 mL) and the combined organic phase was washed with brine, dried over MgSO$_4$ and concentrated in vacuo to give an oily residue. This residue was purified on silica gel eluting with ethyl acetate and hexanes to give the title molecule as a colorless gum (38 mg, 37%): IR (thin film) 3080, 2975, 2931, 1657, 1584 cm$^{-1}$; $^1$H NMR (400 MHz, CDCl$_3$) δ 8.96 (dd, J=2.7, 0.7 Hz, 1H), 8.63 (dd, J=4.8, 1.4 Hz, 1H), 8.08 (s, 1H), 8.04 (ddd, J=8.4, 2.8, 1.5 Hz, 1H), 7.46 (ddd, J=8.4, 4.7, 0.8 Hz, 1H), 3.6 (bs, 1H), 3.17 (s, 1H), 2.61 (d, J=7.1 Hz, 2H), 1.17 (t, J=7.2 Hz, 2H), 1.05-0.91 (m, 1H), 0.55 (dd, J=7.9, 1.5 Hz, 2H), 1.21-1.10 (m, 3H), 0.24 (dd, J=4.8, 1.4 Hz, 2H); ESIMS m/z 351 ([M+H]$^+$).

Molecule 650 in Table 1 was made in accordance with the procedures disclosed in Example 98.

Example 99: Preparation of N-(3-chloro-1-(pyridin-3-yl)-1H-pyrazol-4-yl)-3-((3,3-dichloroallyl)thio)-N-methylpropanamide (Molecule 649)

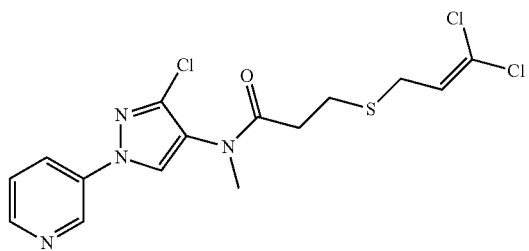 [SMILES: CN(C(=O)CCSCC=C(Cl)Cl)c1cn(-c2cccnc2)nc1Cl]

To a solution of N-(3-chloro-1-(pyridin-3-yl)-1H-pyrazol-4-yl)-3-mercapto-N-methylpropanamide (100 mg, 0.34 mmol) in DMSO (1 mL) was added sodium hydride (14.8 mg, 0.37 mmol). The mixture was stirred at room temperature for 10 min and cooled to 0-5° C. 1,1,3-Trichloroprop-1-ene (49.0 mg, 0.34 mmol) was added, and the mixture stirred for an additional 45 minutes. The mixture was diluted with saturated aqueous NH$_4$Cl and ethyl acetate and the organic phase was separated. The aqueous phase was extracted with ethyl acetate and the combined organic phase was washed with brine, dried over MgSO$_4$ and concentrated in vacuo to give a light brown oil. This oil was purified on silica gel eluting with mixtures of hexanes to give the title molecule as a colorless gum (60 mg, 43.9%): IR (thin film) 3078, 2926, 1659, 1583, 1458, 1437, 803 cm$^{-1}$; $^1$H NMR (400 MHz, CDCl$_3$) δ 8.94 (dd, J=2.7, 0.7 Hz, 1H), 8.63 (dd, J=4.8, 1.5 Hz, 1H), 8.04 (ddd, J=8.3, 2.7, 1.4 Hz, 1H), 7.98 (s, 1H), 7.47 (ddd, J=8.3, 4.7, 0.7 Hz, 1H), 5.30 (s, 1H), 3.51 (s, 2H), 3.25 (s, 3H), 2.87 (t, J=7.3 Hz, 2H), 2.52 (t, J=7.3 Hz, 2H); ESIMS m/z 406 ([M+2]$^+$), 403.7 ([M−1]$^−$).

Example 100: Preparation of 2-chloro-N-(3-chloro-1-(pyridin-3-yl)-1H-pyrazol-4-yl)-N-ethylpropanamide

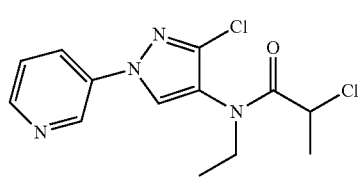 [SMILES: CCN(C(=O)C(C)Cl)c1cn(-c2cccnc2)nc1Cl]

To a solution of 3-chloro-N-ethyl-1-(pyridin-3-yl)-1H-pyrazol-4-amine (1.0 g, 4.49 mmol) in 1,2-dichloroethane (44.9 ml) at 0° C. were added diisopropylethylamine (0.941 ml, 5.39 mmol) and 2-chloropropanoyl chloride (0.436 ml, 4.49 mmol), sequentially. The reaction was allowed to warm to ambient temperature and was stirred for 1.5 hr. The reaction was quenched with the addition of aqueous NaHCO₃ and the layers were quickly separated. The aqueous layer was extracted with CH₂Cl₂ (3×50 mL) and the combined organics were dried over Na₂SO₄, filtered and concentrated in vacuo. The crude residue was purified via flash chromatography (30 to 100% EtOAc/Hex) to give the title molecule as a white solid (1.301 g, 93%): mp 94-105° C.; ¹H NMR (400 MHz, CDCl₃) δ 8.97 (d, J=2.7 Hz, 1H), 8.64 (dd, J=4.8, 1.5 Hz, 1H), 8.09 (s, 1H), 8.04 (ddd, J=8.4, 2.7, 1.5 Hz, 1H), 7.47 (dd, J=8.3, 4.8 Hz, 1H), 4.27 (q, J=6.5 Hz, 1H), 3.83 (s, 1H), 3.63 (s, 1H), 1.64 (d, J=6.5 Hz, 3H), 1.19 (t, J=7.2 Hz, 3H); ESIMS m/z 313 ([M+H]⁺).

The following molecules were made in accordance with the procedures disclosed in Example 100:

2-chloro-N-(3-chloro-1-(pyridin-3-yl)-1H-pyrazol-4-yl)-N-ethylbutanamide

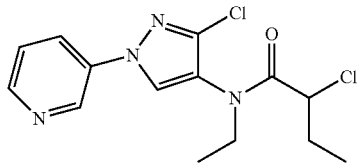 [SMILES: CCC(Cl)C(=O)N(CC)c1cn(-c2cccnc2)nc1Cl]

Mp 95-103° C.; ¹H NMR (400 MHz, CDCl₃) δ 8.98 (d, J=2.6 Hz, 1H), 8.64 (dd, J=4.8, 1.4 Hz, 1H), 8.08 (s, 1H), 8.05 (ddd, J=8.4, 2.7, 1.4 Hz, 1H), 7.47 (dd, J=8.3, 4.7 Hz, 1H), 3.99 (m, 1H), 3.86 (br. s, 1H), 3.60 (br. s, 1H), 2.13 (dt, J=14.6, 7.3 Hz, 1H), 1.91 (dt, J=14.5, 7.3 Hz, 1H), 1.19 (t, J=7.2 Hz, 3H), 0.97 (t, J=7.3 Hz, 3H); ESIMS m/z 327 ([M+H]⁺).

2-chloro-N-(3-chloro-1-(pyridin-3-yl)-1H-pyrazol-4-yl)-N-ethylacetamide (Compound Y2007)

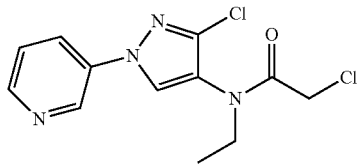

Due to observed decomposition when left at ambient temperatures overnight, the title molecule was immediately used in subsequent reactions: ¹H NMR (400 MHz, CDCl₃) δ 8.96 (d, J=2.6 Hz, 1H), 8.65 (dd, J=4.7, 1.3 Hz, 1H), 8.07-8.01 (m, 2H), 7.47 (dd, J=8.3, 4.7 Hz, 1H), 3.93 (s, 2H), 3.79-3.68 (bs, 2H), 1.19 (t, J=7.2 Hz, 3H).

N-(3-chloro-1-(pyridin-3-yl)-1H-pyrazol-4-yl)-2-((1-chloro-2,2,2-trifluoroethyl)thio)-N-ethylacetamide (Molecule 638)

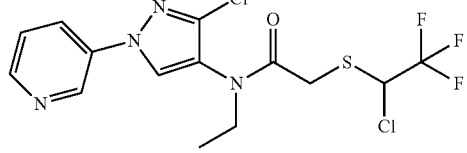

Supporting analytical data for the title molecule can be found in Table 2.

Example 101: Preparation of S-(1-((3-chloro-1-(pyridin-3-yl)-1H-pyrazol-4-yl)(ethyl)amino)-1-oxo-propan-2-yl) ethanethioate (Molecule 685)

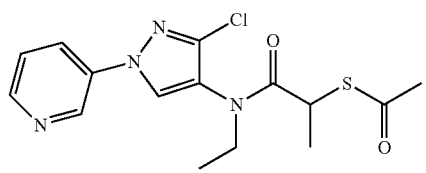 [SMILES: CCN(C(=O)C(C)SC(C)=O)c1cn(-c2cccnc2)nc1Cl]

To a solution of 2-chloro-N-(3-chloro-1-(pyridin-3-yl)-1H-pyrazol-4-yl)-N-ethylpropanamide (1.0 g, 3.19 mmol) in acetone (6.39 ml) was added potassium ethanethioate (0.438 g, 3.83 mmol). Reaction vessel was capped and heated to 60° C. for 1.5 h. The reaction was cooled and poured into a separatory funnel containing water (20 mL) and EtOAc (20 mL). The layers were separated and aqueous layer was extracted with EtOAc (3×20 mL). The combined organic extract was dried over anhydrous Na₂SO₄, filtered and concentrated in vacuo. The crude residue was purified (flash chromatography, 20 to 100% EtOAc/Hex) to give the title molecule as a brown, highly viscous oil (1.07 g, 90%).

The following molecules were made in accordance with the procedures disclosed in Example 101:

S-(1-((3-chloro-1-(pyridin-3-yl)-1H-pyrazol-4-yl)(ethyl)amino)-1-oxobutan-2-yl) ethanethioate

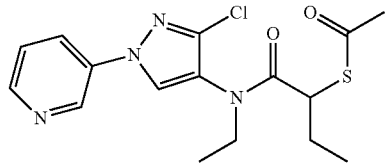 [SMILES: CCC(SC(C)=O)C(=O)N(CC)c1cn(-c2cccnc2)nc1Cl]

Mp 116-122° C.; ¹H NMR (400 MHz, CDCl₃) δ 8.97 (d, J=2.6 Hz, 1H), 8.63 (dd, J=4.8, 1.5 Hz, 1H), 8.13-7.99 (m, 2H), 7.46 (dd, J=8.3, 4.7 Hz, 1H), 4.14 (t, J=7.3 Hz, 1H), 3.85 (br. s, 1H), 3.57 (br. s, 1H), 2.27 (s, 3H), 1.98 (dt, J=14.2, 7.1 Hz, 1H), 1.74-1.62 (m, 1H), 1.16 (t, J=7.2 Hz, 3H), 0.92 (t, J=7.4 Hz, 3H); ESIMS m/z 367 ([M+H]⁺).

S-(2-((3-chloro-1-(pyridin-3-yl)-1H-pyrazol-4-yl)(ethyl)amino)-2-oxoethyl) ethanethioate (Molecule 694)

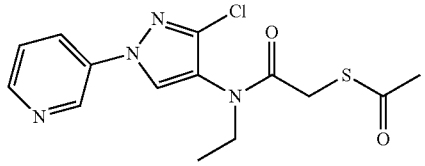 [SMILES: CCN(C(=O)CSC(C)=O)c1cn(-c2cccnc2)nc1Cl]

Mp 117-124° C.; $^1$H NMR (400 MHz, CDCl$_3$) δ 8.98 (dd, J=2.7, 0.7 Hz, 1H), 8.64 (dd, J=4.8, 1.5 Hz, 1H), 8.09 (s, 1H), 8.06 (ddd, J=8.3, 2.7, 1.5 Hz, 1H), 7.47 (ddd, J=8.3, 4.8, 0.7 Hz, 1H), 3.84-3.65 (m, 2H), 3.61 (s, 2H), 2.33 (s, 3H), 1.17 (t, J=7.2 Hz, 3H); ESIMS m/z 339 ([M+H]$^+$).

Example 102: Preparation of N-(3-chloro-1-(pyridin-3-yl)-1H-pyrazol-4-yl)-N-ethyl-2-((2,2,2-trifluoroethyl)thio)propanamide (Molecule 635)

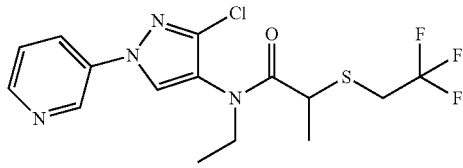 [SMILES: CCN(C(=O)C(C)SCC(F)(F)F)c1cn(-c2cccnc2)nc1Cl]

To a dry round-bottom flask under N$_2$ were added sodium hydride (0.018 g, 0.446 mmol) and THF (2.1 mL), followed by methanol (0.018 mL, 0.446 mmol). The reaction was allowed to stir at ambient temperature until cessation of hydrogen evolution was observed (~45 min). The reaction was then cooled at 0° C. and S-(1-((3-chloro-1-(pyridin-3-yl)-1H-pyrazol-4-yl)(ethyl)amino)-1-oxopropan-2-yl) ethanethioate (0.150 g, 0.425 mmol) in THF (2.1 mL) was added. The reaction was warmed to ambient temperature and stirred for 30 min. The reaction was again cooled at 0° C. and 1,1,1-trifluoro-2-iodoethane (0.063 ml, 0.638 mmol) in THF (2.1 mL) was added. The reaction was warmed to room temperature and stirred overnight. The reaction was diluted in EtOAc (20 mL) and quenched with H$_2$O (5 mL). The layers were separated and the aqueous layer was extracted with EtOAc (3×10 mL). The combined organic extracts were dried over Na$_2$SO$_4$, filtered and concentrated in vacuo to give a yellow oil. The crude product was purified via flash chromatography (0 to 75% CH$_2$Cl$_2$/EtOAc) to give the title molecule as an opaque, viscous oil (43 mg, 25%): IR (thin film) 1657 cm$^{-1}$; $^1$H NMR (400 MHz, CDCl$_3$) δ 8.96 (d, J=2.6 Hz, 1H), 8.64 (dd, J=4.8, 1.4 Hz, 1H), 8.14-7.96 (m, 2H), 7.47 (dd, J=8.3, 4.8 Hz, 1H), 3.82 (s, 1H), 3.59 (s, 1H), 3.44 (s, 1H), 3.25 (qd, J=10.2, 3.8 Hz, 2H), 1.48 (d, J=6.8 Hz, 3H), 1.17 (t, J=7.2 Hz, 3H); $^{19}$F NMR (376 MHz, CDCl$_3$) δ-66.16; ESIMS m/z 393 ([M+H]$^+$).

Molecules 637, 639-642, and 652 in Table 1 were made in accordance with the procedures disclosed in Example 102.

Example 103: Preparation of N-(3-chloro-1-(pyridin-3-yl)-1H-pyrazol-4-yl)-N-ethyl-2-((2-fluorovinyl)thio)propanamide (Molecule 654)

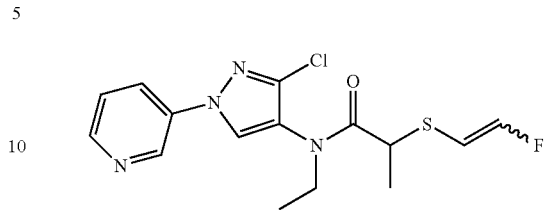

To a dry round-bottom flask under N$_2$ were added a 60% dispersion of NaH in mineral oil (0.043 g, 1.063 mmol) and THF (2.1 mL), followed by methanol (0.086 mL, 2.126 mmol). The reaction was allowed to stir at ambient temperature until cessation of hydrogen evolution was observed (~45 min). The reaction was then cooled at 0° C. and S-(1-((3-chloro-1-(pyridin-3-yl)-1H-pyrazol-4-yl)(ethyl)amino)-1-oxopropan-2-yl) ethanethioate (0.150 g, 0.425 mmol) in THF (2.1 mL) was added. Reaction was warmed to room temperature and stirred for 30 min. The reaction was again cooled at 0° C. and 2-bromo-1,1-difluoroethane (0.101 mL, 1.275 mmol) in THF (2.1 mL) was added. Reaction was warmed to room temperature and stirred overnight. LC-MS analysis indicated presence of two products, the major corresponding to the desired elimination product and the minor corresponding to the initial alkylation. Therefore, the reaction was cooled to 0° C. and transferred to a vial containing additional NaOMe (freshly prepared by mixing NaH (5.86 mg, 0.147 mmol) and MeOH (5.93 µL, 0.147 mmol) in THF (0.73 mL) at 0° C. After stirring an additional 18 h, reaction was diluted in EtOAc (5 mL) and quenched with H$_2$O (5 mL). Aqueous layer was extracted with EtOAc (3×10 mL) and the combined organic extracts were dried over Na$_2$SO$_4$, filtered, and concentrated in vacuo to give a yellow oil. The crude residue was purified via flash chromatography (25-80% EtOAc/Hex) to give an inseparable mixture of olefin isomers (~3:2, E/Z) as an opaque, viscous oil (15 mg, 10%): IR (thin film) 3091, 1656 cm$^{-1}$; $^1$H NMR (400 MHz, CDCl$_3$) δ 8.97 (m, 1H), 8.64 (dd, J=4.7, 1.4 Hz, 1H), 8.13 (s, 0.4H), 8.04 (m, 1.6H), 7.54-7.41 (m, 1H), 6.79 (dd, J=83.3, 11.0 Hz, 0.6H), 6.75 (dd, J=82.7, 4.3 Hz, 0.4H), 5.97 (dd, J=12.7, 11.0 Hz, 0.6H), 5.68 (dd, J=39.8, 4.3 Hz, 0.4H), 3.82 (br. s, 1H), 3.72-3.47 (m, 1H), 3.47-3.20 (m, 1H), 1.50 (d, J=6.9 Hz, 1.2H), 1.42 (d, J=6.8 Hz, 1.8H), 1.17 (m, 3H); ESIMS m/z 355 ([M+H]$^+$).

Example 104: Preparation of N-(3-chloro-1-(pyridin-3-yl)-1H-pyrazol-4-yl)-N-ethyl-3-((2,2,2-trifluoroethyl)thio)propanamide (Molecule 636)

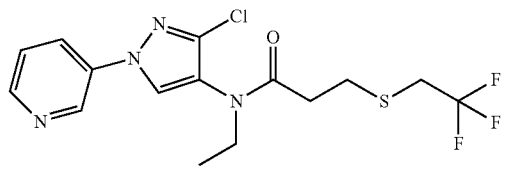 [SMILES: CCN(C(=O)CCSCC(F)(F)F)c1cn(-c2cccnc2)nc1Cl]

To a solution of 3-chloro-N-(3-chloro-1-(pyridin-3-yl)-1H-pyrazol-4-yl)-N-ethylpropanamide (100 mg, 0.32 mmol) in THF (0.3 mL) was added sodium iodide (4.7 mg, 0.032 mmol), 2,2,2-trifluoroethanethiol (148 mg, 1.3 mmol), and N,N-di-iso-propylethylamine (222 µl, 1.277 mmol). The reaction mixture was heated overnight at 50° C., diluted with DCM and washed with 5% KOH solution. The phases were separated, concentrated, and purified by silica gel chromatography eluting with 0-40% acetone in hexanes to afford the title molecule as a colorless oil (109 mg, 83%): $^1$H NMR (400 MHz, CDCl$_3$) δ 8.95 (d, J=2.4 Hz, 1H), 8.63 (dd, J=4.7, 1.4 Hz, 1H), 8.05 (ddd, J=8.3, 2.7, 1.4 Hz, 1H), 7.96 (d, J=7.1 Hz, 1H), 7.46 (ddd, J=8.3, 4.8, 0.6 Hz, 1H), 3.72 (q, J=7.1 Hz, 2H), 3.10 (q, J=10.0 Hz, 2H), 2.96 (t, J=7.0 Hz, 2H), 2.47 (t, J=7.0 Hz, 2H), 1.17 (t, J=7.2 Hz, 3H); $^{19}$F NMR (376 MHz, CDCl$_3$) δ-66.56 (s); ESIMS m/z 393 ([M+H]$^+$).

Example 105: Preparation of N-(3-chloro-1-(pyridin-3-yl)-1H-pyrazol-4-yl)-N,2-dimethyl-3-((trifluoromethyl)thio)propanamide (Molecule 647)

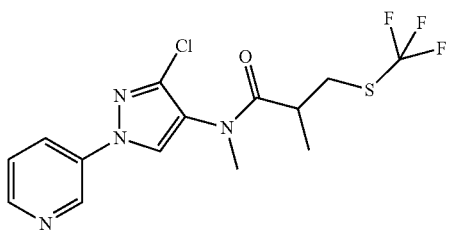 [SMILES: CC(CSC(F)(F)F)C(=O)N(C)c1cn(-c2cccnc2)nc1Cl]

To a solution of 2-methyl-3-((trifluoromethyl)thio)propanoic acid (0.200 g, 1.065 mmol) in DCM (1.0 mL) was added oxalyl dichloride (0.093 mL, 1.065 mmol) and 1 drop of DMF and stirred at ambient temperature for 1 hour (gas evolution was observed). The reaction mixture was concentrated and the crude acid chloride was dissolved in DCM (0.3 mL) which was subsequently added to a pre-stirred solution of 3-chloro-N-methyl-1-(pyridin-3-yl)-1H-pyrazol-4-amine dihydrochloride (0.100 g, 0.355 mmol) and N,N-dimethylpyridin-4-amine (0.130 g, 1.065 mmol) in DCM (1.0 mL) and stirred overnight at room temperature. The reaction mixture was diluted with saturated NaHCO$_3$ and extracted with DCM. The organic layer was dried over Na$_2$SO$_4$, filtered and concentrated. The crude material was purified via flash chromatography eluting with 0-100% EtOAc/hexanes to give the title molecule as a yellow oil (93 mg, 65.7%): IR (thin film) 1654 cm$^{-1}$; $^1$H NMR (400 MHz, CDCl$_3$) δ 8.96 (d, J=2.6 Hz, 1H), 8.64 (dd, J=4.7, 1.3 Hz, 1H), 8.08-8.00 (m, 1H), 7.98 (d, J=8.3 Hz, 1H), 7.51-7.44 (m, 1H), 4.07-3.36 (m, 2H), 3.25-3.11 (m, 1H), 2.94-2.77 (m, 2H), 1.22-1.15 (m, 6H); ESIMS m/z 394 ([M+H]$^+$).

Molecule 648 in Table 1 was made in accordance with the procedures disclosed in Example 105

Example 106: Preparation of N-methyl-N-(1-methyl-3-(pyridin-3-yl)-1H-pyrazol-5-yl)-3-((3,3,3-trifluoropropyl)thio)propanamide (Compound 1011)

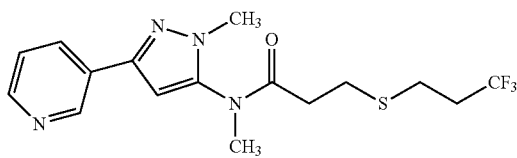 [SMILES: CN(C(=O)CCSCCC(F)(F)F)c1cc(-c2cccnc2)nn1C]

A solution of 3-((3,3,3-trifluoropropyl)thio)propanoic acid (75 mg, 0.372 mmol), DMAP (110 mg, 0.903 mmol), and N,1-dimethyl-3-(pyridin-3-yl)-1H-pyrazol-5-amine (50 mg, 0.266 mmol) in dry diethyl ether (886 µL) was cooled to 0° C. under N$_2$. N,N'-Dicyclohexylcarbodiimide (DCC) (132 mg, 0.638 mmol) was added and the reaction was warmed up to room temperature under N$_2$, then stirred at room temperature overnight. The reaction mixture was filtered using additional diethyl ether (0.5 mL) to remove salts and concentrated under reduced pressure. Purification by silica gel chromatography by eluting with 0-90% hexanes/EtOAc afforded the title compound as a clear oil (64 mg, 61%).

Example 107: Preparation of tert-butyl(3-chloro-1-(pyridin-3-yl)-1H-pyrazol-4-yl)(2-hydroxyethyl)carbamate (Compound Y2151)

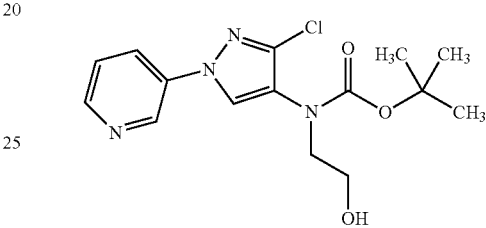

To a solution of 2-((tert-butoxycarbonyl)(3-chloro-1-(pyridin-3-yl)-1H-pyrazol-4-yl)amino)ethyl acetate (841 mg, 2.21 mmol) in MeOH (7.3 mL) was added potassium carbonate (305 mg, 2.21 mmol). The reaction was stirred at room temperature overnight. The reaction mixture was diluted with water (10 mL) and extracted with EtOAc (2×10 mL). The organic layer was washed with saturated aqueous NaHCO$_3$ (10 mL), dried over MgSO$_4$ and concentrated. Et$_2$O was added and the resulting precipitate was collected by filtration to afford the title compound as a white solid (249 mg, 32%).

Example 108: Preparation of 2-((tert-butoxycarbonyl)(3-chloro-1-(pyridin-3-yl)-1H-pyrazol-4-yl)amino)ethyl methanesulfonate

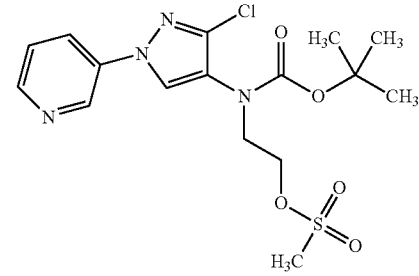 [SMILES: CC(C)(C)OC(=O)N(CCOS(C)(=O)=O)c1cn(-c2cccnc2)nc1Cl]

To a solution of tert-butyl(3-chloro-1-(pyridin-3-yl)-1H-pyrazol-4-yl)(2-hydroxyethyl)carbamate (574 mg, 1.69 mmol) in dry CH$_2$Cl$_2$ (4.0 mL), triethylamine (260 µl, 1.86 mmol) was added under N$_2$. Methanesulfonyl chloride (145 µl, 1.864 mmol) was added dropwise and the reaction was stirred at room temperature for 4 h. After the reaction was deemed complete by LCMS, the reaction mixture was diluted with CH$_2$Cl$_2$ (10 mL) and washed with water (2×10 mL) and brine (10 mL). The organic layer was dried and concentrated under reduced pressure. Purification by silica gel chromatography by eluting with 10-100% hexanes/EtOAc afforded the title compound as a colorless liquid (330 mg, 44%): $^1$H NMR (400 MHz, CDCl$_3$) δ 9.00 (s, 1H), 8.59 (dd, J=4.9, 1.5 Hz, 1H), 8.12 (s, 1H), 8.06 (ddd, J=8.4, 2.8, 1.3 Hz, 1H), 7.46 (dd, J=8.4, 4.7 Hz, 1H), 4.52-4.31 (m, 2H), 3.89 (t, J=5.1 Hz, 2H), 3.04 (s, 3H), 2.19 (s, 3H), 1.68-1.32 (m, 6H); ESIMS m/z 417 ([M+H]$^+$).

Example 109: Preparation of tert-butyl(3-chloro-1-(pyridin-3-yl)-1H-pyrazol-4-yl)(2-(pyrrolidin-1-yl)ethyl)carbamate (Compound Y2152)

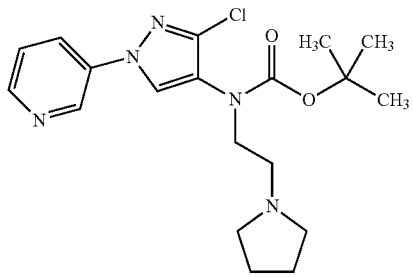 [SMILES: CC(C)(C)OC(=O)N(CCN1CCCC1)c1cn(-c2cccnc2)nc1Cl]

To a solution of 2-((tert-butoxycarbonyl)(3-chloro-1-(pyridin-3-yl)-1H-pyrazol-4-yl)amino)ethyl methanesulfonate (129 mg, 0.309 mmol) in dry DMF (884 al), triethylamine (51.8 µl, 0.371 mmol) and pyrrolidine (37.5 al, 0.449 mmol) was added under N$_2$. The reaction was then heated at 80° C. under N$_2$ overnight. After the reaction was deemed complete by LCMS, the reaction mixture was diluted with water (10 mL) and saturated aqueous NaHCO$_3$ (5 mL), then extracted with EtOAc (3×10 mL). The organic layer was dried over MgSO$_4$ and concentrated under reduced pressure. Purification by silica gel chromatography by eluting with 0-50% CH$_2$Cl$_2$/MeOH afforded the title compound as an off-white solid (65 mg, 51%).

Example 110: Preparation of N-(3-chloro-1-(pyridin-3-yl)-1H-pyrazol-4-yl)-N-(oxiran-2-ylmethyl)-3-((3,3,3-trifluoropropyl)thio)propanamide (Compound 928)

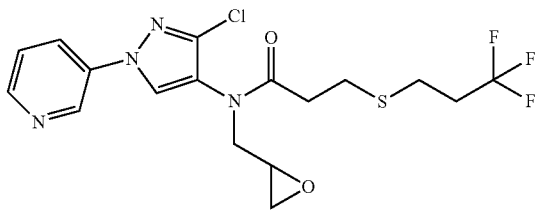 [SMILES: O=C(CCSCCC(F)(F)F)N(CC1CO1)c1cn(-c2cccnc2)nc1Cl]

A solution of N-(3-chloro-1-(pyridin-3-yl)-1H-pyrazol-4-yl)-3-((3,3,3-trifluoropropyl)thio)propanamide (109 mg, 0.288 mmol) in dry DMF (882 µl) was cooled to 0° C. in an ice bath under N$_2$. Sodium hydride (16.11 mg, 0.403 mmol, 60% dispersion in mineral oil) was carefully added and the reaction was stirred at 0° C. for 30 min. 2-(Bromomethyl) oxirane (47.6 µl, 0.576 mmol) was then added and stirred for 30 min at 0° C. The reaction was slowly warmed up to room temperature and stirred overnight under N$_2$. The reaction mixture was quenched with water (15 mL) and extracted with EtOAc (3×10 mL). The organic layer was dried over MgSO$_4$ and concentrated under reduced pressure. Purification by silica gel chromatography by eluting with 0-90% hexane/EtOAc afforded the title compound as an yellow oil (28 mg, 21%).

Example 111: Preparation of N-(3-chloro-1-(pyridin-3-yl)-1H-pyrazol-4-yl)-N-(ethylcarbamoyl)-3-((3,3,3-trifluoropropyl)thio)propanamide (Compound 988)

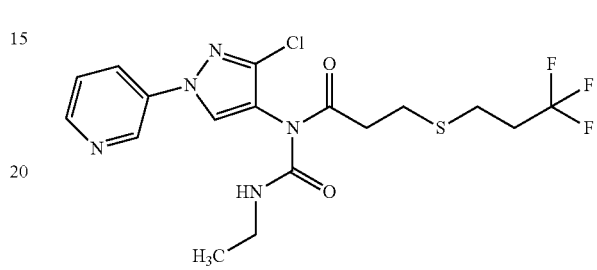

To a solution of N-(3-chloro-1-(pyridin-3-yl)-1H-pyrazol-4-yl)-3-((3,3,3-trifluoropropyl)thio)propanamide (106 mg, 0.280 mmol) in dry CH$_2$Cl$_2$ (1.8 mL), isocyanatoethane (44.3 µl, 0.560 mmol) was added. The reaction mixture was stirred at room temperature overnight then refluxed for 2 h. The solvent was switched to THF and another portion of isocyanatoethane (44.3 µl, 0.560 mmol) was added and refluxed for additional 2 h. Toluene (1.9 mL) was added along with another portion of isocyanatoethane (44.3 µl, 0.560 mmol) and the reaction was refluxed overnight. A small amount of product formation was observed by LCMS. The reaction mixture was poured into a 5 mL microwave vial with additional toluene (0.5 mL) and acetonitrile (0.5 mL) along with another portion of isocyanatoethane (44.3 µl, 0.560 mmol). The reaction was capped and placed on a Biotage® Initiator microwave reactor for total of 9 h at 120° C., then for 8 h at 125° C., with external IR-sensor temperature monitoring from the side of the vessel. The reaction mixture was concentrated under reduced pressure. Purification by silica gel chromatography by eluting with 0-10% CH$_2$Cl$_2$/MeOH and a subsequent purification eluting with 0-100% water/acetonitrile afforded the title compound as a white solid (36 mg, 27%). Reference: *J. Org. Chem.*, 1951, 16, 1879-1890.

Example 112: Preparation of 4-((3-chloro-1-(pyridin-3-yl)-1H-pyrazol-4-yl)(ethyl)amino)-4-oxobutanoic acid (Compound Y2187)

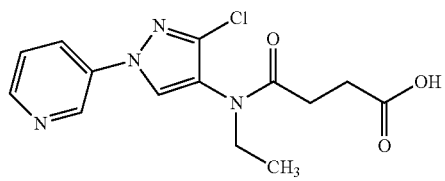 [SMILES: CCN(C(=O)CCC(=O)O)c1cn(-c2cccnc2)nc1Cl]

In a 100 mL round bottom flask (RBF), 3-chloro-N-ethyl-1-(pyridin-3-yl)-1H-pyrazol-4-amine (500 mg, 2.25 mmol), DMAP (27.4 mg, 0.225 mmol), triethylamine (0.469 mL, 3.37 mmol), and dihydrofuran-2,5-dione (449 mg, 4.49 mmol) was added with dichloroethane (22.5 mL). The reaction was heated at 60° C. under N₂ overnight. The reaction mixture was concentrated and purified by silica gel chromatography by eluting with 0-15% CH₂Cl₂/MeOH to afford the title compound as an off-white solid (635 mg, 86%).

Example 113: Preparation of S-(3,3,3-trifluoropropyl) 4-((3-chloro-1-(pyridin-3-yl)-1H-pyrazol-4-yl)(ethyl)amino)-4-oxobutanethioate (Compound 979)

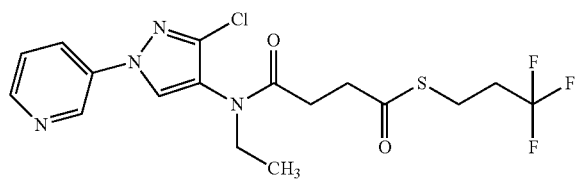

A solution of 4-((3-chloro-1-(pyridin-3-yl)-1H-pyrazol-4-yl)(ethyl)amino)-4-oxobutanoic acid (100 mg, 0.310 mmol), 3,3,3-trifluoropropane-1-thiol (42.0 µl, 0.387 mmol), and DMAP (3.79 mg, 0.031 mmol) in dry CH₂Cl₂ (620 µl) was cooled to 0° C. DCC (63.9 mg, 0.310 mmol) was added and the reaction was warmed up to room temperature under N₂, then stirred overnight. The reaction mixture was filtered using additional CH₂Cl₂ (1 mL) to remove salts and concentrated under reduced pressure. Purification by silica gel flash column chromatography eluting with 10-90% hexanes/EtOAc afforded the title compound as a slightly yellow clear viscous semi-solid (83 mg, 60%). Reference: *J. Am. Chem. Soc.*, 2009, 131, 14604-14605.

Example 114: Preparation of 3,3,3-trifluoropropyl 4-((3-chloro-1-(pyridin-3-yl)-1H-pyrazol-4-yl)(ethyl)amino)-4-oxobutanoate (Compound Y2154)

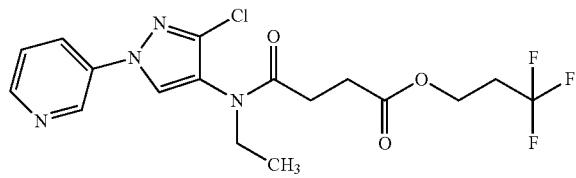 [SMILES: CCN(C(=O)CCC(=O)SCCC(F)(F)F)c1cn(-c2cccnc2)nc1Cl]

A solution of 4-((3-chloro-1-(pyridin-3-yl)-1H-pyrazol-4-yl)(ethyl)amino)-4-oxobutanoic acid (101 mg, 0.313 mmol), sodium bicarbonate (526 mg, 6.26 mmol), and 3-bromo-1,1,1-trifluoropropane (66.6 µl, 0.626 mmol) in DMF (1565 µl) was stirred at room temperature under N₂ overnight. The reaction was quenched with water (15 mL) and extracted with CH₂Cl₂ (3×10 mL). The organic layer was dried and concentrated under reduced pressure. Purification by silica gel chromatography by eluting with 0-100% hexanes/EtOAc afforded the title compound as a clear oil (36 mg, 26%). Reference: *Syn. Commun.*, 2008, 38, 54-71.

Example 115: Preparation of 2-((2,2,2-trifluoroethyl)thio)ethyl(3-chloro-1-(pyridin-3-yl)-1H-pyrazol-4-yl)(ethyl)carbamate (Compound 970)

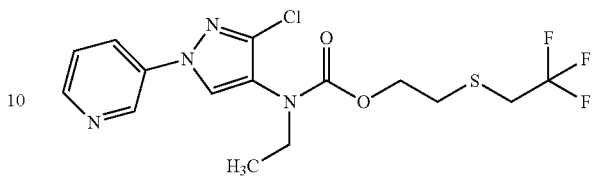

A solution of 3-chloro-N-ethyl-1-(pyridin-3-yl)-1H-pyrazol-4-amine (170 mg, 0.763 mmol) in dichloroethane (2 mL) was cooled to 0° C. Under N₂, phosgene (708 µl, 0.992 mmol, 15 wt % in toluene) was added and after 5 minutes N,N-dimethylpyridin-4-amine (196 mg, 1.603 mmol) was added in one portion. The ice bath was removed and the mixture was stirred at room temperature for 5 minutes and at 80° C. for 50 min. The mixture was cooled to room temperature and then 2-((2,2,2-trifluoroethyl)thio)ethanol (251 mg, 1.57 mmol) was added with CH₂Cl₂ (0.5 mL) followed by another portion of N,N-dimethylpyridin-4-amine (196 mg, 1.60 mmol). The reaction mixture was heated under N₂ at 80° C. for 2 h. The reaction mixture was diluted with CH₂Cl₂ (10 mL) and saturated aqueous NH₄Cl (10 mL). The organic layer was separated, dried, and concentrated. Purification by silica gel chromatography by eluting with 0-100% hexanes/EtOAc and a subsequent purification eluting with 0-100% water/acetonitrile afforded the title compound as a cloudy white oil (33 mg, 10%).

Example 116: Preparation of 1-(3-chloro-1-(pyridin-3-yl)-1H-pyrazol-4-yl)-1-ethyl-3-(((3,3,3-trifluoropropyl)thio)methyl)urea (Compound 990)

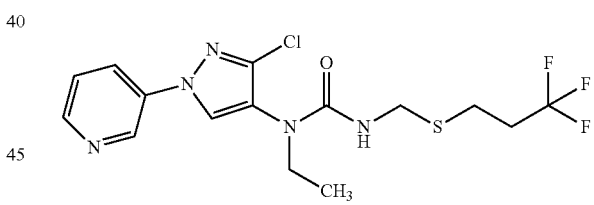

To a solution of 2-((3,3,3-trifluoropropyl)thio)acetic acid (696 mg, 3.70 mmol) in CH₂Cl₂ (7.40 mL), oxalyl chloride (1.619 mL, 18.49 mmol) was added along with a drop of DMF at room temperature. Once DMF was added, gas evolution was observed and continued for about 30 min. The reaction mixture was stirred at room temperature for total of 1 h then the solvent was removed under reduced pressure. Acetone (18.50 mL) was added to the concentrated material and the reaction was cooled to 0° C. in an ice bath. To that, a solution of sodium azide (265 mg, 4.07 mmol) in water (1 mL) was added dropwise. The reaction was stirred at 0° C. for 1 h. The reaction mixture was diluted with water (15 mL) and stirred at room temperature for 5 min. Dichloromethane (10 mL) was added and the organic layer was separated, dried, and concentrated under reduced pressure to afford 2-((3,3,3-trifluoropropyl)thio)acetyl azide as dark brown-green oil. Dry CH₂Cl₂ (4193 µl) was added to the crude azide and refluxed for 2 h. The reaction was cooled to room temperature and 3-chloro-N-ethyl-1-(pyridin-3-yl)-1H- pyrazol-4-amine (140 mg, 0.629 mmol) was added. The reaction was stirred overnight at room temperature. The reaction was concentrate under reduced pressure and purified by silica gel chromatography by eluting with 0-10% CH$_2$Cl$_2$/MeOH to afford title compound as a light brown solid (179 mg, 68%). Reference: *J. Org. Chem.*, 2003, 68, 9453-9455.

Example 117: Preparation of 3-(3-chloro-1-(pyridin-3-yl)-1H-pyrazol-4-yl)-5-(hydroxymethyl)oxazolidin-2-one (Compound Y2148)

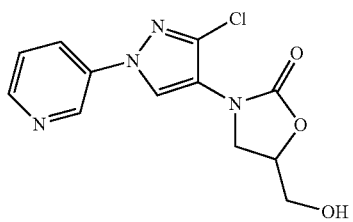 [SMILES: O=C1OC(CO)CN1c1cn(-c2cccnc2)nc1Cl]

To a solution of tert-butyl(3-chloro-1-(pyridin-3-yl)-1H-pyrazol-4-yl)(oxiran-2-ylmethyl)carbamate (321 mg, 0.915 mmol) in dry CH$_2$Cl$_2$ (915 µL), trifluoroacetic acid (915 µL) was added under N$_2$. The reaction mixture was stirred at room temperature for 90 min under N$_2$. The reaction mixture was diluted with toluene (10 mL) and concentrated under reduced pressure to almost dryness. EtOAc (5 mL) was added and the reaction was quenched with saturated aqueous NaHCO$_3$ (10 mL). The organic layer was separated and the aqueous layer was further extracted with EtOAc (3×5 mL), dried over MgSO$_4$, and concentrated under reduced pressure to afford the title compound as a white foam (134 mg, 47%).

Example 118: Preparation of N-((3-chloro-1-(pyridin-3-yl)-1H-pyrazol-4-yl)(ethyl)carbamoyl)-4-methoxybenzamide (Compound Y2189)

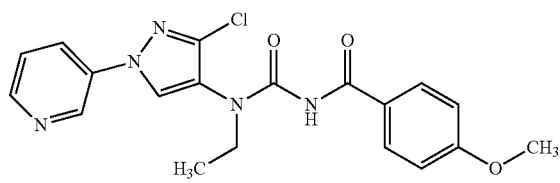 [SMILES: CCN(C(=O)NC(=O)c1ccc(OC)cc1)c1cn(-c2cccnc2)nc1Cl]

A solution of 4-methoxybenzamide (61.1 mg, 0.404 mmol) and oxalyl chloride (44.2 µl, 0.505 mmol) in DCE (1684 µl) was refluxed for 15 h under N$_2$. The reaction was cooled to room temperature and 3-chloro-N-ethyl-1-(pyridin-3-yl)-1H-pyrazol-4-amine (75 mg, 0.337 mmol) was added and stirred overnight at room temperature. The reaction mixture was diluted with saturated aqueous NaHCO$_3$ (5 mL) and CH$_2$Cl$_2$ (3 mL). The phases were separated and the aqueous layer was washed with CH$_2$Cl$_2$ (2×3 mL). The combined organic layer was dried and concentrated. Purification by silica gel chromatography eluting with 15-100% hexanes/EtOAc afforded the title compound as white solid (107 mg, 78%). Reference: *J. Org. Chem.*, 1963, 73, 1805.

Example 119: Preparation of 1-(3-chloro-1-(pyridin-3-yl)-1H-pyrazol-4-yl)-1-ethylurea (Compound Y2186)

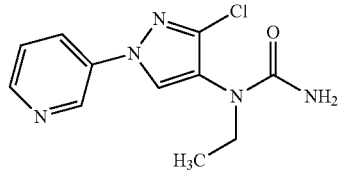 [SMILES: CCN(C(N)=O)c1cn(-c2cccnc2)nc1Cl]

A solution of N-((3-chloro-1-(pyridin-3-yl)-1H-pyrazol-4-yl)(ethyl)carbamoyl)benzamide (300 mg, 0.811 mmol) in dry MeOH (2028 µl) and 2 N aqueous NaOH (811 µl, 1.62 mmol) was heated at 65° C. for 3 h. The reaction mixture was cooled to room temperature and neutralized with 2 N aqueous HCl and concentrated under reduced pressure which produced yellow precipitate. The precipitate was collected by filtration, washed with hexanes (3 mL), and dried under vacuum to afford the title compound (109 mg, 48%).

Example 120: Preparation of N-ethyl-N-(3-methyl-1-(pyridin-3-yl)-1H-pyrazol-4-yl)-4-oxobutanamide (Compound Y2185)

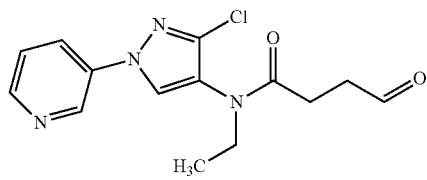 [SMILES: CCN(C(=O)CCC=O)c1cn(-c2cccnc2)nc1Cl]

A solution of N-(3-chloro-1-(pyridin-3-yl)-1H-pyrazol-4-yl)-N-ethyl-4-hydroxybutanamide (41 mg, 0.133 mmol) in dry CH$_2$Cl$_2$ (1328 µl) was cooled to 0° C. in an ice bath under N$_2$. Sodium bicarbonate (112 mg, 1.328 mmol) and Dess-Martin periodinane (64.8 mg, 0.153 mmol) was added and the reaction was warmed up to room temperature and stirred for 5 h. LCMS indicated no product formation so another portion of Dess-Martin periodinane (64.8 mg, 0.153 mmol) was added and stirred at room temperature overnight. The reaction mixture was diluted with saturated aqueous NaHCO$_3$ (5 mL) and extracted with CH$_2$Cl$_2$ (3×5 mL). The organic layer was dried, concentrated, and purified by silica gel chromatography eluting with 0-50% CH$_2$Cl$_2$/MeOH to afford the title compound as clear oil (21 mg, 46%).

Example 121: Preparation of 1,1,1-trifluoro-7,7-dimethoxyheptan-4-ol

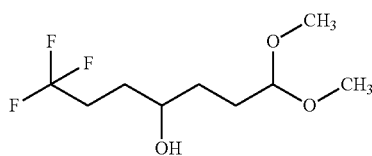

In an oven dried vial with a stir bar, magnesium (77 mg, 3.17 mmol) was added and the head space was purged with N₂. Dry THF (4957 µL) was added with a crystal of I₂ and heated with a heat gun until bubbles from Mg evolved. Slowly 3-bromo-1,1-dimethoxypropane (395 µL, 2.97 mmol) was added and heating continued with a heat gun until Mg was bubbling and the iodine color disappeared. The reaction mixture was refluxed for 1 h under N₂ to give a cloudy colorless solution. In a separate oven dried round bottom flask, 4,4,4-trifluorobutanal (208 µL, 1.983 mmol) was added with dry THF (10 mL, 0.2M) and cooled to 0° C. Room temperature Grignard reagent was added drop wise over 8 min and stirred at 0° C. for 30 min. The reaction was warmed up to room temperature and stirred for 1.5 h. The reaction was quenched with saturated aqueous NH₄Cl (15 mL) and extracted with CH₂Cl₂ (3×15 mL). The organic layer was dried, concentrated, and purified by silica gel chromatography eluting with 0-10% CH₂Cl₂/MeOH to afford the title product as 85% pure clear semi-solid (372 mg, 69%): IR (thin film) 3442 cm⁻¹; ¹H NMR (400 MHz, CDCl₃) δ 4.39 (t, J=5.2 Hz, 1H), 3.65 (tq, J=8.2, 3.9 Hz, 1H), 3.35 (d, J=0.7 Hz, 6H), 2.40 (dd, J=4.6, 0.7 Hz, 1H), 2.39-2.24 (m, 1H), 2.24-2.06 (m, 1H), 1.80-1.72 (m, 2H), 1.72-1.59 (multiple peaks, 3H), 1.52 (ddt, J=15.7, 14.2, 7.0 Hz, 1H); ¹⁹F NMR (376 MHz, CDCl₃) δ-66.37; HRMS-FAB (m/z) [M+Na]⁺ calcd for C₉H₁₇F₃NaO₃, 253.1022. found, 253.1025.

Example 122: Preparation of 7,7,7-trifluoro-4-oxoheptanoic acid

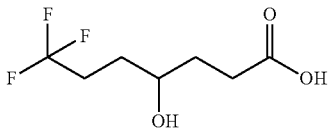 [SMILES: O=C(O)CCC(O)CCC(F)(F)F]

To a solution of 1,1,1-trifluoro-7,7-dimethoxyheptan-4-ol (372 mg, 1.616 mmol) in dry THF (10.8 mL), 1 N aqueous HCl (8079 µL, 8.08 mmol) was added at room temperature. The reaction mixture was stirred for 1 h then diluted with water (10 mL) and Et₂O (10 mL). The organic layer was separated and the aqueous layer was washed with Et₂O (2×10 mL). The combined organic layer was washed with saturated aqueous NaHCO₃ (10 mL), dried over MgSO₄, and concentrated. The concentrated crude material was dissolved in acetone (5 mL) and glacial acetic acid (0.5 mL). Then KMnO₄ (766 mg, 4.85 mmol) dissolved in water (10 mL) was added to the stirring solution drop wise and stirred at room temperature for 2.5 h. GCMS analysis showed incomplete conversion so more KMnO₄ (510 mg) was added and the reaction was left stirring overnight at room temperature. The reaction was diluted with AcOH (15 mL; 2 mL glacial AcOH in 13 mL water) and CH₂Cl₂ (10 mL). The organic layer was separated and the aqueous layer was extracted with CH₂Cl₂ (2×10 mL). The combined organic layer was washed with water (15 mL), dried, and concentrated. Purification by silica gel chromatography eluting with 0-10% CH₂Cl₂/MeOH afforded the title compound as white solid (66 mg, 15%): IR (thin film) 1715 cm⁻¹; ¹H NMR (400 MHz, CDCl₃) δ 2.81-2.72 (multiple peaks, 4H), 2.69 (ddd, J=6.8, 5.5, 1.2 Hz, 2H), 2.50-2.35 (m, 2H), 1.59 (br s, 1H); ¹⁹F NMR (376 MHz, CDCl₃) δ-66.66.

Example 123: Preparation of N-(3-chloro-1-(pyridin-3-yl)-1H-pyrazol-4-yl)-N-ethyl-7,7,7-trifluoro-4-oxoheptanamide (Compound Y2188)

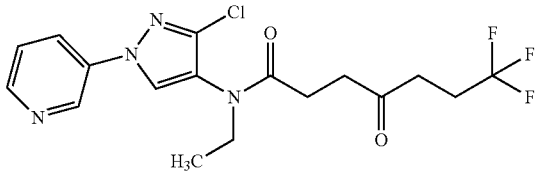 [SMILES: CCN(C(=O)CCC(=O)CCC(F)(F)F)c1cn(-c2cccnc2)nc1Cl]

A solution of 3-chloro-N-ethyl-1-(pyridin-3-yl)-1H-pyrazol-4-amine (62 mg, 0.278 mmol), 7,7,7-trifluoro-4-oxoheptanoic acid (66.2 mg, 0.334 mmol), and DMAP (51.0 mg, 0.418 mmol) in dry Et₂O (928 µL) was cooled to 0° C. in an ice bath under N₂. DCC (138 mg, 0.668 mmol) was added and the reaction was warmed up to room temperature slowly. The reaction was stirred under N₂ overnight at room temperature. A white precipitate was filtered off with Et₂O (1 mL) and the filtrate was concentrated. Purification by silica gel chromatography eluting with 0-75% hexanes/EtOAc afforded the title product as brown viscous oil (59 mg, 50%).

Example 124: Preparation of N-(3-chloro-1-(pyridin-3-yl)-1H-pyrazol-4-yl)-N-ethyl-2-hydroxypropanamide

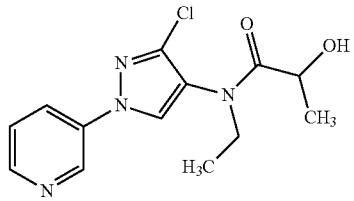 [SMILES: CCN(C(=O)C(C)O)c1cn(-c2cccnc2)nc1Cl]

To a solution of 1-((3-chloro-1-(pyridin-3-yl)-1H-pyrazol-4-yl)(ethyl)amino)-1-oxopropan-2-yl acetate (2.4 g, 7.1 mmol) in methanol (8.9 mL) and tetrahydrofuran (8.9 mL) was added 2M lithium hydroxide (7.1 mL, 14.2 mmol). The reaction mixture was stirred for 2 hours at 25° C. The reaction mixture pH was then made neutral by the addition of a 2M HCl. The mixture was extracted with ethyl acetate, and the organic portions were combined, dried over MgSO₄, filtered and concentrated in vacuo to afford the title compound as a white solid (1.85 g, 88%): mp 137-138° C.; ¹H NMR (400 MHz, DMSO) δ 9.08 (d, J=2.5 Hz, 1H), 8.98 (s, 1H), 8.58 (dd, J=4.7, 1.1 Hz, 1H), 8.23 (ddd, J=8.4, 2.6, 1.3 Hz, 1H), 7.59 (dd, J=8.3, 4.7 Hz, 1H), 4.97 (d, J=7.6 Hz, 1H), 4.08 (m, 1H), 3.57 (d, J=50.6 Hz, 2H), 1.10 (d, J=6.5 Hz, 3H), 1.07 (t, J=7.1 Hz, 3H); ESIMS m/z 295.6 ([M+H]⁺).

Example 125: 1-((3-chloro-1-(pyridin-3-yl)-1H-pyrazol-4-yl)(ethyl)amino)-1-oxopropan-2-yl methanesulfonate (Compound Y2008)

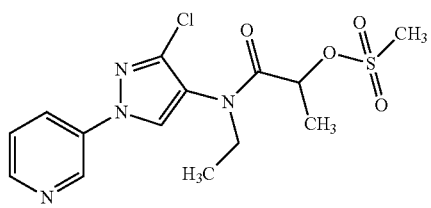 [SMILES: CCN(C(=O)C(C)OS(C)(=O)=O)c1cn(-c2cccnc2)nc1Cl]

To a solution of N-(3-chloro-1-(pyridin-3-yl)-1H-pyrazol-4-yl)-N-ethyl-2-hydroxypropanamide (100 mg, 0.34 mmol) in tetrahydrofuran (1.1 mL) was added sodium hydride (14.9 mg, 0.34 mmol). The mixture was stirred for 15 min and then methanesulfonyl chloride (58.3 mg, 0.51 mmol) was added. The reaction mixture was stirred for 16 hours, diluted with CH$_2$Cl$_2$, and washed with water. The phases were separated, dried, concentrated in vacuo and purified by silica gel chromatography eluting with 0-70% acetone in hexanes to afford the title compound as a light yellow oil (88 mg, 70%): IR (thin film) 2980, 2936, 1676 cm$^{-1}$; $^1$H NMR (400 MHz, CDCl$_3$) δ 9.00 (d, J=2.5 Hz, 1H), 8.64 (dd, J=4.8, 1.4 Hz, 1H), 8.12 (s, 1H), 8.02 (ddd, J=8.3, 2.7, 1.4 Hz, 1H), 7.46 (ddd, J=8.3, 4.8, 0.6 Hz, 1H), 5.17 (q, J=6.7 Hz, 1H), 3.71 (m, 2H), 3.13 (s, 3H), 1.50 (d, J=6.7 Hz, 3H), 1.19 (t, J=7.2 Hz, 3H); ESIMS m/z 373.6 ([M+H]$^+$).

Example 126: Preparation of N-(3-chloro-1-(pyridin-3-yl)-1H-pyrazol-4-yl)-3-((3,3-difluorocyclobutyl)thio)-N-ethylpropanamide (Compound 910)

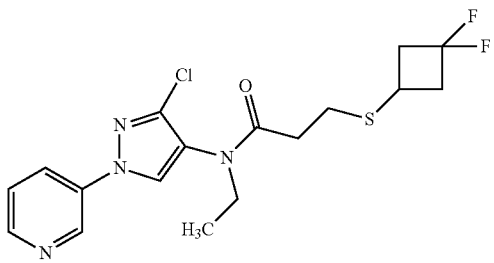 [SMILES: CCN(C(=O)CCSC1CC(F)(F)C1)c1cn(-c2cccnc2)nc1Cl]

N-(3-chloro-1-(pyridin-3-yl)-1H-pyrazol-4-yl)-N-ethyl-3-((3-oxocyclobutyl)thio)propanamide (100 mg, 0.264 mmol) was dissolved in CH$_2$Cl$_2$ (2 mL) and stirred at 0° C. Deoxofluor® (0.083 mL, 0.449 mmol) and EtOH (2.312 μl, 0.040 mmol) was added to the solution at 0° C. The resulting solution was warmed to 25° C. slowly and stirred at 25° C. After 4 hours, 1 more equivalent of Deoxofluor® (50 μL) and another 2.5 μL of EtOH was added. The reaction was worked up by slow addition of NaHCO$_3$ solution and stirred for 30 min at 25° C. The mixture was diluted with water (20 mL) and extracted with CH$_2$Cl$_2$ (3×20 mL). The combined organic layer was washed with 0.01 M HCl, dried over Na$_2$SO$_4$ and purified with silica gel chromatography (0-100% EtOAc/hexane) to give the title compound as a light yellow oil (19 mg, 18%).

Example 127: Preparation of N-(3-chloro-1-(pyridin-3-yl)-1H-pyrazol-4-yl)-N-ethyl-3-(vinylsulfinyl)propanamide (Compound 1004)

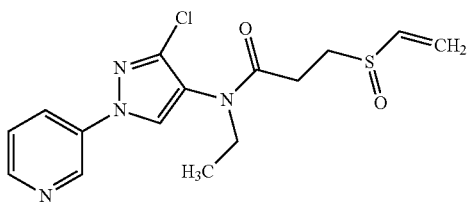 [SMILES: C=CS(=O)CCC(=O)N(CC)c1cn(-c2cccnc2)nc1Cl]

To a 7 mL vial was added N-(3-chloro-1-(pyridin-3-yl)-1H-pyrazol-4-yl)-N-ethyl-3-mercaptopropanamide (0.050 g, 0.161 mmol), 1,2-dibromoethane (0.907 g, 4.83 mmol) followed by 1,8-diazabicyclo[5.4.0]undec-7-ene (DBU) (0.024 g, 0.161 mmol). The solution was stirred at 25° C. overnight, then it was concentrated and re-dissolved in hexafluoroisopropanol (1 mL). Hydrogen peroxide (0.055 g, 0.483 mmol) was added and the solution was stirred at 25° C. for 2 hours, then worked up with sodium sulfite solution and extracted with CH$_2$Cl$_2$. The crude reaction mixture was purified by silica gel chromatography (0-10% MeOH/CH$_2$Cl$_2$) to give the title compound as a brown oil (33 mg, 58%).

Example 128: Preparation of 3-(N-carbamoyl-S-methylsulfonimidoyl)-N-(3-chloro-1-(pyridin-3-yl)-1H-pyrazol-4-yl)-N-ethylpropanamide (Compound Y2099)

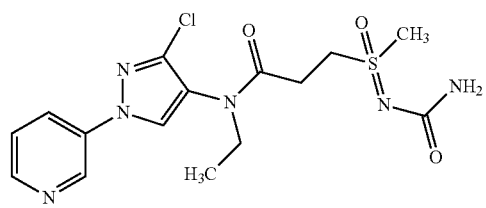 [SMILES: CCN(C(=O)CCS(C)(=O)=NC(N)=O)c1cn(-c2cccnc2)nc1Cl]

N-[3-chloro-1-(3-pyridyl)pyrazol-4-yl]-3-(N-cyano-S-methyl-sulfonimidoyl)-N-ethylpropanamide (320 mg, 0.840 mmol) was dissolved in conc. sulfuric acid (4 mL, 75 mmol) and stirred at 25° C. for 16 h. The solution was poured into a flask with ice and solid NaHCO$_3$ was added slowly until the aqueous layer was neutral. The aqueous layer was extracted with CH$_2$Cl$_2$ and the combined organic layers were dried over Na$_2$SO$_4$ and concentrated. The crude reaction mixture was purified by silica gel chromatography (0-10% MeOH/CH$_2$Cl$_2$) to give the title compound as white solid (135 mg, 40%).

Example 129: Preparation of 4-chloro-N-(3-chloro-1-(pyridin-3-yl)-1H-pyrazol-4-yl)butanamide (Compound Y2166)

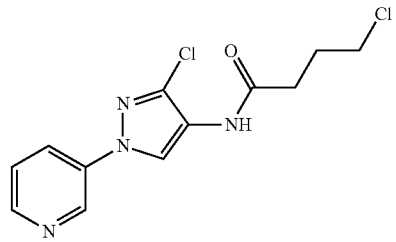 [SMILES: O=C(CCCCl)Nc1cn(-c2cccnc2)nc1Cl]

To a solution of 3-chloro-1-(pyridin-3-yl)-1H-pyrazol-4-amine (1.34 g, 6.89 mmol) in CH$_2$Cl$_2$ (11 mL) cooled to 0° C. was added triethylamine (1.439 mL, 10.33 mmol) and 4-chlorobutanoyl chloride (0.971 g, 6.89 mmol). The solution was allowed to slowly warm to 25° C. and stirred for 1 h. The reaction was diluted with water (20 mL) and extracted with CH$_2$Cl$_2$ (3×20 mL). The combined organic layers were dried, concentrated and purified with chromatography (0-100% EtOAc/hexane) to give the title compound as white solid (1.87 g, 91%).

Example 130: Preparation of 1-(3-chloro-1-(pyridin-3-yl)-1H-pyrazol-4-yl)pyrrolidin-2-one (Compound Y2167)

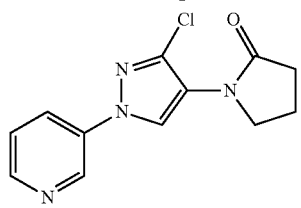

A solution of 4-chloro-N-(3-chloro-1-(pyridin-3-yl)-1H-pyrazol-4-yl)butanamide (1.82 g, 6.08 mmol) in THF (50 mL) was cooled to 0° C. NaH (0.280 g, 7.00 mmol) was added and the mixture was slowly warmed to 25° C. and stirred for 2 h. The mixture was diluted with water and extracted with CH$_2$Cl$_2$ (3×20 mL). The combined organic layers were dried, concentrated and purified with silica gel chromatography (0-10% MeOH/CH$_2$Cl$_2$) to give the title compound as yellow solid (1.70 g, 96%).

Example 131: Preparation of 1-(3-chloro-1-(pyridin-3-yl)-1H-pyrazol-4-yl)-3-methylenepyrrolidin-2-one (Compound Y2168)

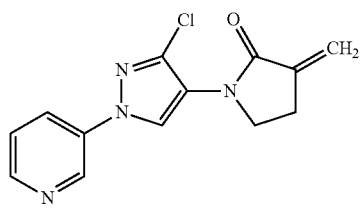 [SMILES: C=C1CCN(c2cn(-c3cccnc3)nc2Cl)C1=O]

A solution of 1-(3-chloro-1-(pyridin-3-yl)-1H-pyrazol-4-yl)pyrrolidin-2-one (1600 mg, 6.09 mmol) in CH$_2$Cl$_2$ (15 mL) was cooled to 0° C. Triethylamine (1.273 mL, 9.14 mmol) and trimethylsilyl trifluoromethanesulfonate (1.431 mL, 7.92 mmol) were added, and the resulting deep red solution was stirred at 0° C. for 45 min. Eschenmoser's salt (dimethylmethylideneammonium iodide)(1465 mg, 7.92 mmol) was then added and the solution was allowed to warm to 25° C. and stir overnight. The solution was diluted with CH$_2$Cl$_2$ (30 mL) and 1N HCl (30 mL) was added and the mixture was stirred for 10 min before it was neutralized with NaOH solution to pH=12. The mixture was extracted with CH$_2$Cl$_2$, and the combined organic layers were dried, concentrated and purified with silica gel chromatography (0-10% MeOH/CH$_2$Cl$_2$) to give the title compound as light yellow solid (866 mg, 52%).

Example 132: Preparation of 1-(3-chloro-1-(pyridin-3-yl)-1H-pyrazol-4-yl)-3-((methylthio)methyl)pyrrolidin-2-one (Compound 955)

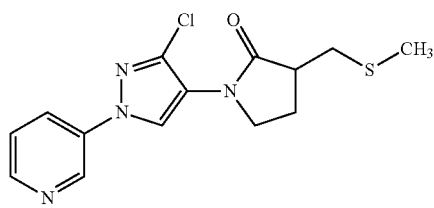 [SMILES: CSCC1CCN(c2cn(-c3cccnc3)nc2Cl)C1=O]

1-(3-chloro-1-(pyridin-3-yl)-1H-pyrazol-4-yl)-3-methylenepyrrolidin-2-one (400 mg, 1.46 mmol) was dissolved in THF (6 mL). Potassium hydroxide (384 mg, 5.82 mmol) dissolved in water (1 mL) was added to the mixture, followed by S,S-dimethyl carbonodithioate (125 mg, 1.019 mmol). The mixture was heated to reflux for 3 hours, then it was diluted with water (20 mL) and extracted with CH$_2$Cl$_2$ (3×20 mL). The combined organic layers were dried and concentrated, and the crude mixture was purified by silica gel chromatography (0-10% MeOH/CH$_2$Cl$_2$) to give the title compound as white solid (385 mg, 82%).

Example 133: Preparation of methyl 2-cyclobutylideneacetate

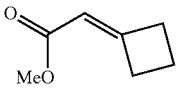

To a 250 mL round bottom flask was added methyl 2-(triphenylphosphoranylidene)acetate (12.04 g, 36 mmol) and benzene (90 mL). Cyclobutanone (5.05 g, 72.0 mmol) was added and the solution was heated to reflux for 2 days. The reaction was cooled and hexane (70 mL) was added. The white precipitate was filtered off and the solution was concentrated and purified by silica gel chromatography to give the title compound as a colorless oil (3.22 g, 71%): IR (thin film) 1714 cm$^{-1}$; $^1$H NMR (400 MHz, CDCl$_3$) δ 5.60 (t, J=2.3 Hz, 1H), 3.68 (s, 3H), 3.13 (dddd, J=9.0, 4.5, 2.2, 1.1 Hz, 2H), 2.90-2.76 (m, 2H), 2.09 (tt, J=11.4, 5.8 Hz, 2H); $^{13}$C NMR (101 MHz, CDCl$_3$) δ 167.92, 166.95, 111.93, 50.79, 33.71, 32.32, 17.62.

Example 134: Preparation of 2-cyclobutylideneacetic acid

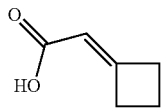

To a solution of methyl 2-cyclobutylideneacetate (100 mg, 0.793 mmol) in MeOH (1.00 mL) stirring at RT was added 2N LiOH solution (prepared from lithium hydroxide hydrate (100 mg, 2.378 mmol) and water (1 mL)). The mixture was stirred at 25° C. overnight, then it was worked up by addition of 2N HCl and extracted with CH$_2$Cl$_2$. The combined organic layer was dried to give a white solid, which was purified by silica gel chromatography (0-70% EtOAc/hexane) to give the title compound as a white solid (20 mg, 23%): IR (thin film) 2923, 1647 cm$^{-1}$; $^1$H NMR (400 MHz, CDCl$_3$) δ 10.89 (s, 1H), 5.60 (dd, J=4.3, 2.1 Hz, 1H), 3.38-3.02 (m, 2H), 2.97-2.71 (m, 2H), 2.10 (dq, J=15.9, 8.0 Hz, 2H); $^{13}$C NMR (101 MHz, CDCl$_3$) δ 172.35, 171.33, 112.13, 34.10, 32.58, 17.56.

Example 135: Preparation of 3-((3,3,3-trifluoropropyl)thio)propanoic acid

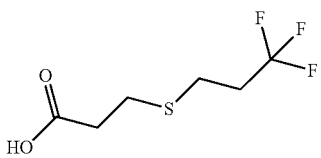 [SMILES: O=C(O)CCSCCC(F)(F)F]

3-Mercaptopropanoic acid (3.2 g, 30.1 mmol) was dissolved in MeOH (20 mL) and stirred at RT. Powdered potassium hydroxide (3.72 g, 66.3 mmol) was added to the solution, followed by 3-bromo-1,1,1-trifluoropropane (6.14 g, 34.7 mmol). The solution was then stirred at 65° C. for 3 h and then the reaction was quenched with 1N HCl until the pH of the solution was acidic. The mixture was extracted with $CH_2Cl_2$ (3×30 mL) and the combined organic phases were dried, concentrated and purified by silica gel chromatography (0-50% EtOAc/hexane) to give the title compound as colorless oil mixed with some white suspension (5.5 g, 90%): IR (thin film) 2936, 1708 $cm^{-1}$; $^1H$ NMR (300 MHz, $CDCl_3$) δ 2.86-2.78 (m, 2H), 2.78-2.58 (m, 4H), 2.52-2.25 (m, 2H); EIMS m/z 202.

Example 136: Preparation of N-[3-chloro-1-(3-pyridyl)pyrazol-4-yl]-3-[3-[[3-chloro-1-(3-pyridyl)pyrazol-4-yl]-methyl-amino]-3-oxo-propyl]sulfanyl-N-ethyl-2-methylpropanamide (Compound 790)

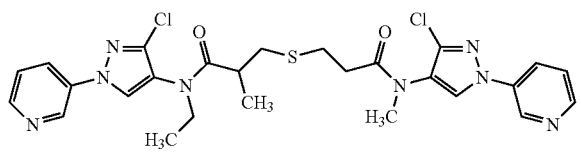 [SMILES: CCN(C(=O)C(C)CSCCC(=O)N(C)c1cn(-c2cccnc2)nc1Cl)c1cn(-c2cccnc2)nc1Cl]

To a solution of N-(3-chloro-1-(pyridin-3-yl)-1H-pyrazol-4-yl)-N-ethyl-2-methyl-3-mercatopropanamide (100 mg, 0.308 mmol) and 3-chloro-N-(3-chloro-1-(pyridin-3-yl)-1H-pyrazol-4yl)-N-methylpropanamide (100 mg, 0.334 mmol) in DMF (1 mL) was added sodium hydride (60% dispersion in oil, 15 mg, 0.375 mmol). The mixture was stirred at room temperature for 18 h and diluted with water and $CH_2Cl_2$. The organic phase was separated, dried over $Na_2SO_4$, filtered and concentrated in vacuo to give an orange oil. This oil was purified by chromatography eluting with mixtures of methanol and methylene chloride to give the title compound as a yellow oil (120 mg, 66%).

Example 137: Preparation of N-(3-chloro-1-(pyridin-3-yl)-1H-pyrazol-4-yl)-3-((2-((3-chloro-1-(pyridin-3-yl)-1H-pyrazol-4-yl)(methyl)amino)-2-oxo-ethyl)thio)-N-ethylpropanamide (Compound 789)

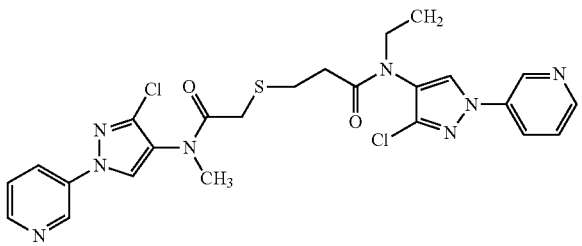 [SMILES: CCN(C(=O)CCSCC(=O)N(C)c1cn(-c2cccnc2)nc1Cl)c1cn(-c2cccnc2)nc1Cl]

To a solution of N-(3-chloro-1-(pyridin-3-yl)-1H-pyrazol-4-yl)-N-ethyl-3-mercaptopropanamide (100 mg, 0.322 mmol) in DMSO (1 mL) was added sodium hydride (60% dispersion in oil, 15 mg, 0.375 mmol). Freshly prepared 2-chloro-N-(3-chloro-1-(pyridin-3-yl)-1H-pyrazol-4-yl)-N-methylacetamide (150 mg, 0.526 mmol) was added and the mixture was left to stand for one hour with occasional swirling. The reaction mixture was diluted with saturated sodium bicarbonate and $Et_2O$. To the organic phase was added ammonia in MeOH (7 M, 1 mL, 1 mmol) followed by $Na_2SO_4$. After standing 10 minutes, the mixture was filtered and concentrated in vacuo to give an orange oil. The oil was purified by silica gel chromatography eluting with mixtures of methanol and $CH_2Cl_2$ to give the title molecule as an orange oil (120 mg, 66%).

Example 138: Preparation of tert-butyl((1R,4S)-4-((3-chloro-1-(pyridin-3-yl)-1H-pyrazol-4-yl)(methyl)carbamoyl)cyclopent-2-en-1-yl)carbamate

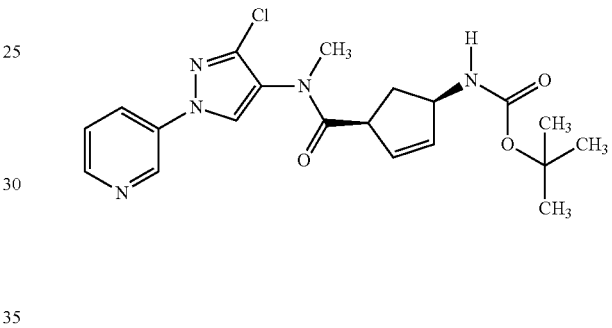

A solution of 3-chloro-N-methyl-1-(pyridin-3-yl)-1H-pyrazol-4-amine (200 mg, 0.96 mmol) in THF (10 mL) was cooled to −78° C. Lithium bis(trimethylsilyl)amide (1 mL, 1.00 mmol, 1M solution in hexane) was added and the solution was stirred at −78° C. for 15 minutes. A solution of (1R,4S)-tert-butyl 3-oxo-2-azabicyclo[2.2.1]hept-5-ene-2-carboxylate (201 mg, 0.96 mmol) dissolved in THF (3 mL) was added to the solution at −78° C. in one portion. After stirring for 1 hour at −78° C. the cooling bath was removed and the reaction warmed to 20° C. After stirring for an additional five minutes, acetic acid (0.1 mL) was added to the solution. The reaction mixture was concentrated and purified via silica gel chromatography utilizing a mobile phase of hexanes and ethyl acetate to give the title compound as a white solid (250 mg, 59%): $^1H$ NMR (400 MHz, $CDCl_3$) δ 9.01-8.93 (d, J=2.8 Hz, 1H), 8.66-8.60 (m, 1H), 8.11-8.02 (m, 2H), 7.52-7.42 (m, 1H), 5.93-5.85 (m, 1H), 5.72-5.66 (m, 1H), 5.53-5.44 (d, J=9.5 Hz, 1H), 4.80-4.67 (m, 1H), 3.58-3.47 (m, 1H), 3.30-3.21 (s, 3H), 2.35-2.22 (m, 1H), 1.90-1.80 (m, 1H), 1.51-1.34 (s, 9H); $^{13}C$ NMR (101 MHz, $CDCl_3$) δ 175.26, 155.23, 148.70, 140.31, 140.00, 135.61, 135.18, 130.99, 126.34, 125.92, 125.78, 124.12, 79.04, 55.69, 47.33, 37.49, 35.55, 28.45; ESIMS m/z 418 $[M+H]^+$, 416 ($[M−H]^-$).

Example 139: Preparation (1S,4R)-4-amino-N-(3-chloro-1-(pyridin-3-yl)-1H-pyrazol-4-yl)-N-methyl-cyclopent-2-enecarboxamide 2,2,2-trifluoroacetate

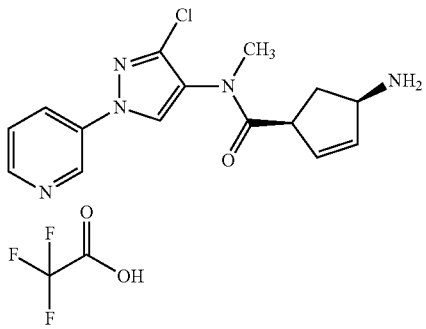

To a solution of tert-butyl((1R,4S)-4-((3-chloro-1-(pyridin-3-yl)-1H-pyrazol-4-yl)(methyl)carbamoyl)cyclopent-2-en-1-yl)carbamate (130 mg, 0.31 mmol) in $CH_2Cl_2$ (4 mL) was added trifluoroacetic acid (4 mL). The reaction was left to stand for 20 minutes with occasional swirling. The reaction mixture was concentrated in vacuo at 40° C. resulting in the isolation of the title compound as a clear oil (130 mg, 94%): $^1H$ NMR (400 MHz, $CD_3OD$) δ 9.02 (dd, J=2.7, 0.7 Hz, 1H), 8.70 (s, 1H), 8.54 (dd, J=5.0, 1.4 Hz, 1H), 8.30 (ddd, J=8.4, 2.7, 1.4 Hz, 1H), 7.63 (ddd, J=8.4, 5.0, 0.7 Hz, 1H), 6.09 (ddd, J=5.6, 2.7, 1.0 Hz, 1H), 5.92 (dt, J=5.6, 2.1 Hz, 1H), 4.16 (d, J=7.7 Hz, 1H), 3.80-3.72 (m, 1H), 2.98 (s, 3H), 2.29 (dt, J=14.3, 7.9 Hz, 1H), 2.01 (dt, J=14.3, 2.5 Hz, 1H); $^{13}C$ NMR (101 MHz, $CDCl_3$) δ 179.16, 163.52 (q, J=19 Hz), 145.04, 142.05, 141.15, 137.81, 136.71, 134.11, 134.06, 132.73, 131.26, 129.77, 119.49 (q, J=289 Hz) 59.80, 51.85, 40.50, 36.87; ESIMS m/z 318 ($[M+H]^+$).

Example 140: Preparation of (1S,4R)—N-(3-chloro-1-(pyridin-3-yl)-1H-pyrazol-4-yl)-N-methyl-4-(methylsulfonamido)cyclopent-2-enecarboxamide (Compound Y2054)

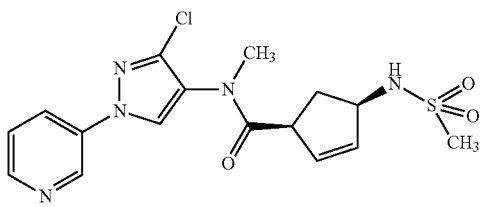 [SMILES: CN(C(=O)[C@@H]1C=C[C@H](NS(C)(=O)=O)C1)c1cn(-c2cccnc2)nc1Cl]

To a solution of (1S,4R)-4-amino-N-(3-chloro-1-(pyridin-3-yl)-1H-pyrazol-4-yl)-N-methylcyclopent-2-enecarboxamide 2,2,2-trifluoroacetate (541 mg, 1.25 mmol) dissolved in $CH_2Cl_2$ (15 mL) was added triethylamine (0.380 mg, 3.76 mmol) followed by methanesulfonyl chloride (215 mg, 1.88 mmol). After stirring for 24 hours the reaction was diluted with saturated aqueous sodium bicarbonate (15 mL) and the phases were separated. The organic layer was dried with anhydrous sodium sulfate, filtered, and concentrated. The resulting residue was purified by silica gel chromatography utilizing methanol and $CH_2Cl_2$ resulting in the isolation of the title compound as a white foam (319 mg, 64%).

Example 141: Preparation of (1S,3R)—N-(3-chloro-1-(pyridin-3-yl)-1H-pyrazol-4-yl)-N-methyl-3-(methylsulfonamido)cyclopentanecarboxamide (Compound Y2092)

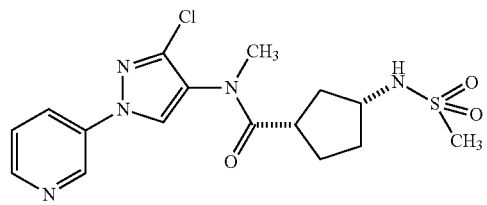

A solution of (1R,4S)-4-amino-N-(3-chloro-1-(pyridin-3-yl)-1H-pyrazol-4-yl)-N-methylcyclopent-2-enecarboxamide 2,2,2-trifluoroacetate (60 mg, 0.15 mmol) in methanol (1.5 mL) was passed through an H-Cube® continuous flow hydrogenator equipped with a 10% Pd/C cartridge (full $H_2$, 25° C., 1 mL/min flow rate). The resulting solution was concentrated and purified by silica gel chromatography utilizing methanol and $CH_2Cl_2$ as a mobile phase to provide the title compound as white solid (16 mg, 24%).

Example 142: Preparation of N-(3-chloro-1-(pyridin-3-yl)-1H-pyrazol-4-yl)-3-(1H-tetrazol-5-yl)-N-ethylpropanamide (Compound Y2178)

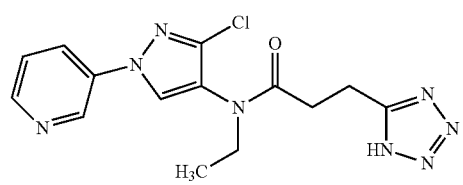 [SMILES: CCN(C(=O)CCc1nnn[nH]1)c1cn(-c2cccnc2)nc1Cl]

To a solution of N-(3-chloro-1-(pyridin-3-yl)-1H-pyrazol-4-yl)-3-cyano-N-ethylpropanamide (0.176 g, 0.579 mmol) in toluene (5.79 mL) at ambient temperature and under $N_2$ were added azidotrimethylsilane (0.154 mL, 1.159 mmol) and dibutylstannanone (0.014 g, 0.058 mmol). The reaction vessel was fitted with a condenser and heated to 110° C. The reaction was allowed to stir at the same temperature for 24 h at which point UPLC-MS analysis indicated nearly complete conversion to a product of the desired mass. The reaction was cooled, diluted (slowly) in MeOH (20 mL) and concentrated in vacuo to afford a dark brown oil. The residue was absorbed onto Celite and purified via reverse phase flash chromatography (0 to 100% $CH_3CN/H_2O$) to afford the desired product as a pale brown glassy solid (49 mg, 24%).

Example 143: Preparation of N-(3-chloro-1-(pyridin-3-yl)-1H-pyrazol-4-yl)-N-ethyl-3-((3,3,3-trifluoro-2-methylpropyl)thio)propanamide (Compound 919)

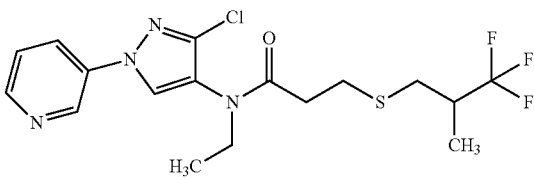 [SMILES: CCN(C(=O)CCSCC(C)C(F)(F)F)c1cn(-c2cccnc2)nc1Cl]

To a solution of N-(3-chloro-1-(pyridin-3-yl)-1H-pyrazol-4-yl)-N-ethyl-3-((2-(trifluoromethyl)allyl)thio)propanamide (0.056 g, 0.134 mmol) in DME (2.5 mL) and water (0.5 mL) were added 4-methylbenzenesulfonohydrazide (0.249 g, 1.337 mmol) and sodium acetate (0.110 g, 1.337 mmol). The reaction was heated to 90° C. and was stirred for 1.5 h. UPLC-MS analysis indicated ~30% conversion to a product of the desired mass. The reaction was stirred at 90° C. for an additional 1.5 h at which point UPLC-MS analysis indicated ~75% conversion to a product of the desired mass. The reaction was cooled and an additional 5 equivalents of both the hydrazide and sodium acetate were added. The reaction was again heated to 90° C. and stirred for an additional 2 h. UPLC-MS indicated only minor amount of starting material remaining. Therefore, an additional 5 equivalents of both hydrazide and sodium acetate were added. The reaction was stirred at 90° C. for additional 3 h. The reaction was cooled, diluted in EtOAc (10 mL) and washed with water (2×5 mL) and brine (1×5 mL). The organic layer was dried over $Na_2SO_4$, filtered and concentrated in vacuo to afford a yellow oil. The crude residue was purified via normal phase flash chromatography (0 to 100% EtOAc/$CH_2Cl_2$) to afford the desired product as a pale yellow oil (46 mg, 79%).

Example 144: Preparation of N-(3-chloro-1-(pyridin-3-yl)-1H-pyrazol-4-yl)-N-ethyl-2-(vinylthio)propanamide (Compound 787)

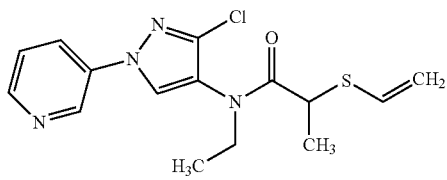 [SMILES: C=CSC(C)C(=O)N(CC)c1cn(-c2cccnc2)nc1Cl]

To a dry round bottom flask under $N_2$ were added sodium hydride (0.043 g, 1.063 mmol, 60% dispersion in mineral oil) and THF (2.126 mL), followed by methanol (0.086 mL, 2.126 mmol). The reaction was allowed to stir at ambient temperature until cessation of gas evolution was observed (~45 min). The reaction was then cooled to 0° C. and S-(1-((3-chloro-1-(pyridin-3-yl)-1H-pyrazol-4-yl)(ethyl)amino)-1-oxopropan-2-yl) ethanethioate (0.150 g, 0.425 mmol) in THF (2.126 mL) was added. The reaction was warmed to ambient temperature and stirred for 30 min. The reaction was again cooled to 0° C. and 1-fluoro-2-iodoethane (0.104 mL, 1.275 mmol) in THF (2.126 mL) was added. The reaction was warmed to ambient temperature and stirred overnight. The reaction was diluted in EtOAc (5 mL) and quenched with $H_2O$ (1 mL). The layers were separated and the aqueous layer was extracted with EtOAc (3×10 mL). The combined organic extracts were dried over $Na_2SO_4$, filtered and concentrated in vacuo to give a brown oil. The crude residue was purified via flash chromatography (25-80% EtOAc/Hexanes) to give the desired product as an opaque oil (29 mg, 20%).

Example 145: Preparation of (E)-N-(3-chloro-1-(pyridin-3-yl)-1H-pyrazol-4-yl)-N-ethyl-3-((3,3,3-trifluoroprop-1-en-1-yl)thio)propanamide (Compound 890)

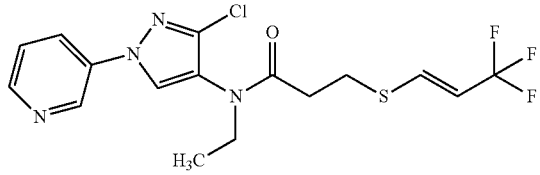 [SMILES: CCN(C(=O)CCS/C=C/C(F)(F)F)c1cn(-c2cccnc2)nc1Cl]

To an oven-dried microwave vial under $N_2$ were added dioxane (0.241 mL), $Cu_2O$ (3.45 mg, 0.024 mmol), KOH (0.0154 g, 0.965 mmol), (E)-1-bromo-3,3,3-trifluoroprop-1-ene (0.563 mL, 4.83 mmol), and N-(3-chloro-1-(pyridin-3-yl)-1H-pyrazol-4-yl)-N-ethyl-3-mercaptopropanamide (0.150 g, 0.483 mmol), sequentially. The reaction was capped and placed on a Biotage® Initiator microwave reactor for 3 h at 110° C., with external IR-sensor temperature monitoring from the side of the vessel. During this time, the reaction mixture went from a thick, yellow mixture to a black mixture. The heterogeneous mixture was cooled to room temperature and diluted with EtOAc (20 mL). The mixture was filtered through a pad of Celite (EtOAc wash) and the filtrate was concentrated in vacuo to give an dark brown oil. The crude residue was purified via normal phase flash chromatography (0 to 100% EtOAc/$CH_2Cl_2$) to afford the desired product as a pale yellow oil (71 mg, 35%). Reference: Kao, H.-L.; Lee, C.-F. *Org. Lett.* 2011, 13, 5204-5207.

Example 146: Preparation of N-(3-chloro-1-(pyridin-3-yl)-1H-pyrazol-4-yl)-N-ethyl-3-(methylsulfonamido)propanamide (Compound Y2145)

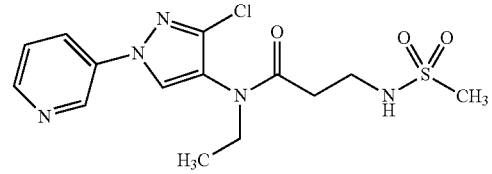 [SMILES: CCN(C(=O)CCNS(C)(=O)=O)c1cn(-c2cccnc2)nc1Cl]

To a solution of N-(3-chloro-1-(pyridin-3-yl)-1H-pyrazol-4-yl)-N-ethylacrylamide (0.538 g, 1.944 mmol) in DMF (19.44 mL) at ambient temperature were added $K_2CO_3$ (0.672 g, 4.86 mmol) and methanesulfonamide (0.277 g, 2.92 mmol). The reaction was fitted with a reflux condenser and heated to 80° C. After stirring for 1 h, the reaction was cooled to ambient temperature and diluted in EtOAc (50 mL) and water (50 mL). The layers were mixed vigorously for 2 min and then separated. The aqueous phase was extracted with EtOAc (3×50 mL) and the combined organic extracts were washed with brine (3×100 mL), dried over Na$_2$SO$_4$, filtered and concentrated in vacuo to afford a clear oil. The crude residue was purified via normal phase flash chromatography (0 to 30% MeOH/EtOAc) to afford the desired product as a clear semi-solid (524 mg, 69%).

Example 147: Preparation of N-(3-chloro-1-(pyridin-3-yl)-1H-pyrazol-4-yl)-3-(N-(cyanomethyl)methylsulfonamido)-N-methylpropanamide (Compound 803)

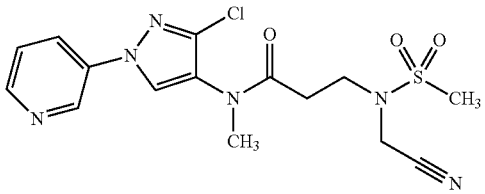 [SMILES: CN(C(=O)CCN(CC#N)S(C)(=O)=O)c1cn(-c2cccnc2)nc1Cl]

To a solution of N-(3-chloro-1-(pyridin-3-yl)-1H-pyrazol-4-yl)-N-methyl-3-(methylsulfonamido)propanamide (0.085 g, 0.238 mmol) in THF (2.376 mL) at 0° C. was added NaH (9.98 mg, 0.249 mmol, 60% dispersion in mineral oil). The reaction was allowed to stir for 10 min at which point 2-bromoacetonitrile (0.025 mL, 0.356 mmol) was added. The reaction was allowed to warm to room temperature and was stirred for 1 h. The reaction was quenched with the addition of water (5 mL) and was diluted in EtOAc (10 mL). The layers were separated and the aqueous layer was extracted with EtOAc (3×10 mL). The combined organic extracts were dried over Na$_2$SO$_4$, filtered and concentrated in vacuo. The crude residue was purified via flash chromatography (0 to 10% MeOH/CH$_2$Cl$_2$) to give the desired product as a pale yellow foam (86 mg, 87%).

Example 148: Preparation of N-(3-chloro-1-(pyridin-3-yl)-1H-pyrazol-4-yl)-N-ethyl-3-((3,3,3-trifluoropropyl)amino)propanamide

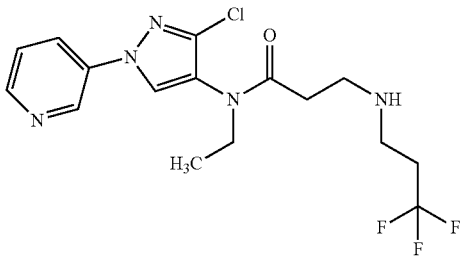 [SMILES: CCN(C(=O)CCNCCC(F)(F)F)c1cn(-c2cccnc2)nc1Cl]

To a microwave vial were added MeOH (2.0 mL), 3,3,3-trifluoropropan-1-amine (0.386 g, 3.42 mmol) and 3-chloro-N-(3-chloro-1-(pyridin-3-yl)-1H-pyrazol-4-yl)-N-ethylpropanamide (0.107 g, 0.342 mmol), sequentially. The reaction was capped and placed in a Biotage® Initiator microwave reactor for 3 h at 100° C., with external IR-sensor temperature monitoring from the side of the vessel. After cooling, the reaction was concentrated in vacuo and purified via normal phase flash chromatography (0 to 15% MeOH/EtOAc) to afford the desired product as an opaque viscous oil (127 mg, 94%): $^1$H NMR (400 MHz, CDCl$_3$) δ 8.94 (dd, J=2.8, 0.7 Hz, 1H), 8.63 (dd, J=4.7, 1.5 Hz, 1H), 8.04 (ddd, J=8.3, 2.7, 1.4 Hz, 1H), 7.95 (s, 1H), 7.46 (ddd, J=8.4, 4.8, 0.8 Hz, 1H), 3.71 (q, J=7.2 Hz, 2H), 2.93-2.80 (m, 4H), 2.35 (t, J=6.2 Hz, 2H), 2.28 (ddt, J=14.6, 7.3, 3.6 Hz, 2H), 1.16 (t, J=7.2 Hz, 3H); $^{19}$F NMR (376 MHz, CDCl$_3$) δ-65.13; ESIMS m/z 390 ([M+H]$^+$).

N-(3-chloro-1-(pyridin-3-yl)-1H-pyrazol-4-yl)-N-ethyl-3-(methylamino)propanamide was prepared as in Example 148: $^1$H NMR (400 MHz, CDCl$_3$) δ 9.01 (d, J=2.6 Hz, 1H), 8.61 (dd, J=4.8, 1.4 Hz, 1H), 8.23 (s, 1H), 8.06 (ddd, J=8.3, 2.7, 1.4 Hz, 1H), 7.45 (dd, J=8.3, 4.8 Hz, 1H), 7.24 (s, 1H), 3.68 (q, J=7.2 Hz, 2H), 3.14 (t, J=6.1 Hz, 2H), 2.71-2.56 (m, 5H), 1.14 (t, J=7.2 Hz, 3H); $^{13}$C NMR (101 MHz, CDCl$_3$) δ 172.1, 148.6, 140.8, 140.1, 135.6, 126.6, 126.3, 124.1, 123.8, 47.1, 43.8, 36.1, 33.5, 13.1; ESIMS m/z 308 ([M+H]$^+$).

N-(3-chloro-1-(pyridin-3-yl)-1H-pyrazol-4-yl)-N-ethyl-3-((4,4,4-trifluorobutyl)amino)propanamide was prepared as in Example 148: $^1$H NMR (400 MHz, CDCl$_3$) δ 9.04 (d, J=2.7 Hz, 1H), 8.61 (dd, J=4.7, 1.5 Hz, 1H), 8.36 (s, 1H), 8.08 (ddd, J=8.4, 2.8, 1.5 Hz, 1H), 7.45 (ddd, J=8.4, 4.8, 0.7 Hz, 1H), 3.69 (q, J=7.2 Hz, 2H), 3.18 (t, J=6.0 Hz, 2H), 3.02 (t, J=7.7 Hz, 3H), 2.75 (t, J=6.0 Hz, 2H), 2.25 (tdt, J=16.1, 10.6, 5.5 Hz, 2H), 2.14-1.98 (m, 2H), 1.16 (t, J=7.2 Hz, 3H); $^{19}$F NMR (376 MHz, CDCl$_3$) δ-66.03; ESIMS m/z 404 ([M+H]$^+$).

N-(3-chloro-1-(pyridin-3-yl)-1H-pyrazol-4-yl)-N-ethyl-3-(ethylamino)propanamide was prepared as in Example 148: $^1$H NMR (400 MHz, CDCl$_3$) δ 9.05 (s, 1H), 8.61 (s, 1H), 8.41 (dd, J=7.6, 2.1 Hz, 1H), 8.09 (dd, J=8.3, 1.4 Hz, 1H), 7.44 (dd, J=8.4, 4.8 Hz, 1H), 3.83-3.59 (m, 2H), 3.21 (t, J=6.0 Hz, 2H), 3.14-2.97 (m, 2H), 2.86 (s, 2H), 1.52-1.32 (m, 3H), 1.23-1.06 (m, 3H); $^{13}$C NMR (101 MHz, CDCl$_3$) δ 170.7, 148.5, 140.5, 140.0, 135.6, 128.1, 126.4, 124.0, 122.4, 44.0, 43.3, 43.3, 30.1, 12.8, 11.4; ESIMS m/z 322 ([M+H]$^+$).

N-(3-chloro-1-(pyridin-3-yl)-1H-pyrazol-4-yl)-N-ethyl-3-(phenylamino)propanamide was prepared as in Example 148: $^1$H NMR (400 MHz, CDCl$_3$) δ 8.81 (d, J=2.7 Hz, 1H), 8.60 (dd, J=4.8, 1.4 Hz, 1H), 7.89 (ddd, J=8.3, 2.7, 1.5 Hz, 1H), 7.54 (s, 1H), 7.42 (ddd, J=8.3, 4.8, 0.8 Hz, 1H), 7.17-7.05 (m, 2H), 6.64 (tt, J=7.3, 1.1 Hz, 1H), 6.59-6.49 (m, 2H), 4.22 (s, 1H), 3.70 (dt, J=14.8, 7.4 Hz, 2H), 3.48 (t, J=6.0 Hz, 2H), 2.45 (t, J=6.2 Hz, 2H), 1.14 (t, J=7.1 Hz, 3H); ESIMS m/z 370 ([M+H]$^+$).

Example 149: Preparation of N-(3-chloro-1-(pyridin-3-yl)-1H-pyrazol-4-yl)-N-ethyl-3-(N-(3,3,3-trifluoropropyl)methylsulfonamido)propanamide (Compound 978)

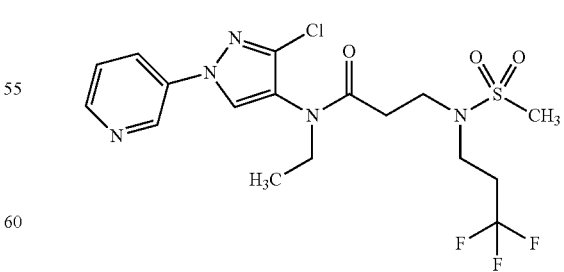

To a solution of N-(3-chloro-1-(pyridin-3-yl)-1H-pyrazol-4-yl)-N-ethyl-3-((3,3,3-trifluoropropyl)amino)propanamide (0.085 g, 0.218 mmol) in CH$_2$Cl$_2$ (2.181 mL) at ambient temperature and under N$_2$ were added diisopropylethylamine (0.152 mL, 0.872 mmol) and methanesulfonyl chloride (0.025 mL, 0.327 mmol). The reaction was allowed to stir overnight after which the reaction was diluted in CH₂Cl₂ (5 mL) and water (3 mL). The phases were mixed and then separated by a phase separator. The organic layer was concentrated in vacuo to afford a dark orange oil. The crude product was purified via normal phase flash chromatography (0 to 100% EtOAc/CH₂Cl₂) to afford the desired product as a pale yellow, viscous oil (78 mg, 73%).

Example 150: Preparation of N-(3-chloro-1-(pyridin-3-yl)-1H-pyrazol-4-yl)-N-ethyl-3-(methyl(3,3,3-trifluoropropyl)amino)propanamide (Compound Y2146)

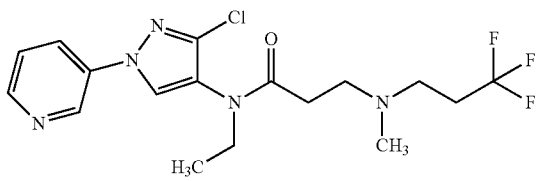 [SMILES: CCN(C(=O)CCN(C)CCC(F)(F)F)c1cn(-c2cccnc2)nc1Cl]

To a solution of N-(3-chloro-1-(pyridin-3-yl)-1H-pyrazol-4-yl)-N-ethyl-3-(methylamino)propanamide (0.139 g, 0.452 mmol) in DMF (4.52 mL) at ambient temperature were added K₂CO₃ (0.125 g, 0.903 mmol) and 3-bromo-1,1,1-trifluoropropane (0.060 mL, 0.565 mmol). The reaction was fitted with a condenser, heated to 70° C., and stirred overnight. UPLC-MS analysis indicated the presence of unreacted starting material. Therefore, an additional 3 equivalents of 3-bromo-1,1,1-trifluoropropane were added and reaction was left to stir at 70° C. for 3 h. UPLC-MS analysis indicated complete consumption of starting material and conversion to product of the desired mass. The reaction was cooled, diluted in EtOAc (20 mL) and filtered through a pad of Celite. The filtrate was then washed with half-saturated brine (3×20 mL), dried over Na₂SO₄, filtered and concentrated in vacuo. The crude residue was purified via normal phase flash chromatography (0 to 15% MeOH/CH₂Cl₂) to afford the desired product as a clear oil (84 mg, 44%).

Example 151: Preparation of N-(3-chloro-1-(pyridin-3-yl)-1H-pyrazol-4-yl)-N-ethyl-3-((3-oxobutyl)thio)propanamide (Compound 877)

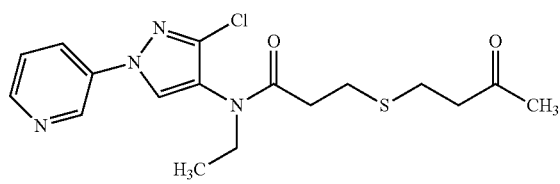 [SMILES: CCN(C(=O)CCSCCC(C)=O)c1cn(-c2cccnc2)nc1Cl]

To a solution of but-3-en-2-one (0.040 mL, 0.444 mmol) in water (0.370 mL) and dioxane (0.370 mL) was added N-(3-chloro-1-(pyridin-3-yl)-1H-pyrazol-4-yl)-N-ethyl-3-mercaptopropanamide (0.115 g, 0.370 mmol) at ambient temperature. The reaction was allowed to stir for 1 h at which point the reaction was diluted in CH₂Cl₂ and the mixture was stirred vigorously for 1 h. The mixture was then passed through a phase separator and the remaining aqueous phase was washed with CH₂Cl₂ (3×5 mL). The combined organic extracts were concentrated in vacuo to provide the desired product as an orange oil that was analytically pure by ¹H NMR and UPLC-MS analyses (140 mg, 94%). Reference: Khatik, G. L.; Kumar, R.; Chakraborti, A. K. *Org. Lett.* 2006, 8, 2433-2436.

Example 152: Preparation of N-(3-chloro-1-(pyridin-3-yl)-1H-pyrazol-4-yl)-3-((3,3-difluorobutyl)thio)-N-ethylpropanamide (Compound 889)

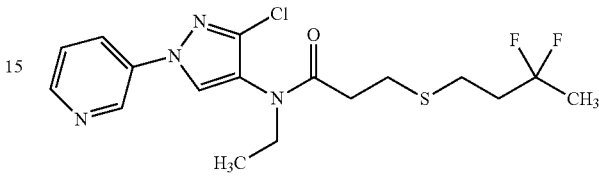

To a solution of N-(3-chloro-1-(pyridin-3-yl)-1H-pyrazol-4-yl)-N-ethyl-3-((3-oxobutyl)thio)propanamide (0.184 g, 0.483 mmol) in CH₂Cl₂ (4.83 mL) at 0° C. was added Deoxo-Fluor® (0.534 mL, 2.90 mmol) followed by EtOH (0.017 mL, 0.290 mmol). The reaction was stirred at ambient temperature for 48 h during which time the solution went from pale yellow to dark brown. The reaction was diluted in CH₂Cl₂ (10 mL) and quenched with the careful addition of NaHCO₃₍aq₎ (5 mL). The layers were separated and the aqueous phase was extracted with CH₂Cl₂ (3×10 mL). The combined organic extracts were dried over Na₂SO₄, filtered and concentrated in vacuo. The crude residue was purified via normal phase flash chromatography (0 to 100% EtOAc/CH₂Cl₂) to afford the desired product as a pale yellow oil (43 mg, 21%).

Example 153: Preparation of N-(3-chloro-1-(pyridin-3-yl)-1H-pyrazol-4-yl)-3-((3,3-difluoropropyl)thio)-N-ethylpropanamide (Compound 927)

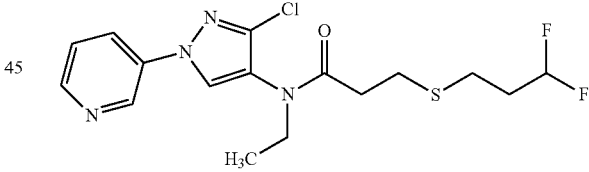

To a solution of N-(3-chloro-1-(pyridin-3-yl)-1H-pyrazol-4-yl)-3-((3,3-dimethoxypropyl)thio)-N-ethylpropanamide (0.307 g, 0.743 mmol) in THF (7.43 mL) was added a 1.0 M aqueous solution of HCl (7.43 mL, 7.43 mmol). The reaction was allowed to stir at ambient temperature for 1 h at which point TLC/UPLC-MS analysis indicated complete hydrolysis to the desired aldehyde product had occurred. The mixture was diluted in EtOAc (20 mL) and water (10 mL). The layers were mixed, separated, and the aqueous layer was extracted with EtOAc (3×20 mL). The combined organic extracts were washed with NaHCO₃ (1×25 mL), water (1×25 mL) and brine (1×25 mL) and then dried over Na₂SO₄, filtered and concentrated in vacuo. The crude product was dried via azeotropic distillation from toluene (3×10 mL) and then placed under N₂. To the flask was added CH₂Cl₂ (7.44 mL) and the solution was cooled to 0° C. Deoxo-Fluor® (0.686 mL, 3.72 mmol) and EtOH (4.34 µl, 0.074 mmol)

were added and the reaction was warmed to ambient temperature. After 18 h, the reaction was diluted in CH$_2$Cl$_2$ (10 mL) and quenched with the careful addition of NaHCO$_{3(aq)}$ (5 mL). The layers were separated and the aqueous phase was extracted with CH$_2$Cl$_2$ (3×10 mL). The combined organic extracts were dried over Na$_2$SO$_4$, filtered and concentrated in vacuo. The crude material was purified via normal phase flash chromatography (0 to 100% EtOAc/CH$_2$Cl$_2$) to afford the desired product as a pale yellow oil (151 mg, 50%).

Example 154: Preparation of 1,1,1-trifluoro-3-iodo-5-methylhexane

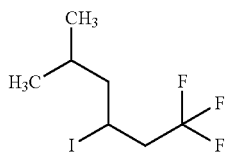

To a microwave vial equipped with a magnetic stir bar were added water (5.94 mL), acetonitrile (5.94 mL), sodium dithionite (0.569 g, 3.27 mmol), sodium bicarbonate (0.499 g, 5.94 mmol), and 4-methylpent-1-ene (0.379 mL, 2.97 mmol). The vessel was sealed with a microwave cap (crimped), cooled to −78° C. and evacuated under house vacuum. Next, trifluoroiodomethane (0.873 g, 4.46 mmol) (approximate) was condensed into the reaction vessel. After warming to ambient temperature, the reaction was stirred for 2.5 h. Prior to removing the cap, the reaction was vented with a needle and substantial gas evolution was observed. The reaction was then diluted in water (5 mL) and the mixture was extracted with Et$_2$O (3×20 mL) and the combined extracts were dried over MgSO$_4$, filtered and concentrated in vacuo to afford a clear oil (740 mg, 80%). Crude $^1$H NMR analysis indicated desired product to be of ~90% purity. Product was therefore used in subsequent reactions without further purification: $^1$H NMR (400 MHz, CDCl$_3$) δ 4.25-4.06 (m, 1H), 2.94 (dqd, J=15.5, 10.6, 6.1 Hz, 1H), 2.77 (dqd, J=15.5, 10.0, 7.5 Hz, 1H), 1.92-1.74 (m, 2H), 1.45-1.28 (m, 1H), 0.98 (d, J=6.5 Hz, 3H), 0.87 (d, J=6.5 Hz, 3H); $^{19}$F NMR (376 MHz, CDCl$_3$) δ-63.63. Reference: Ignatowska, J.; Dmowski, W. *J. Fluor. Chem.*, 2007, 128, 997-1006.

(4,4,4-trifluoro-2-iodobutyl)benzene was prepared as in Example 154: $^1$H NMR (400 MHz, CDCl$_3$) δ 7.41-7.27 (m, 3H), 7.23-7.16 (m, 2H), 4.33 (dq, J=8.2, 6.7 Hz, 1H), 3.31-3.15 (m, 2H), 2.96-2.72 (m, 2H); $^{19}$F NMR (376 MHz, CDCl$_3$) δ-63.63; EIMS m/z 314.

1-(4,4,4-trifluoro-2-iodobutyl)-1H-imidazole was prepared as in Example 154: $^1$H NMR (400 MHz, CDCl$_3$) δ 7.61 (t, J=1.1 Hz, 1H), 7.12 (t, J=1.1 Hz, 1H), 7.00 (t, J=1.4 Hz, 1H), 4.46-4.31 (m, 3H), 2.88-2.66 (m, 2H); $^{19}$F NMR (376 MHz, CDCl$_3$) δ-63.57; EIMS m/z 304.

1,1,1-trifluoro-3-iodopentane was prepared as in Example 154: $^1$H NMR (400 MHz, CDCl$_3$) δ 4.20 (tdd, J=7.9, 6.2, 4.4 Hz, 1H), 3.01-2.84 (m, 1H), 2.84-2.69 (m, 1H), 1.84-1.74 (m, 2H), 1.06 (t, J=7.1 Hz, 3H); $^{19}$F NMR (376 MHz, CDCl$_3$) δ-64.06; EIMS m/z 252.

Example 155: Preparation of S-(1,1,1-trifluoro-5-methylhexan-3-yl)benzothioate

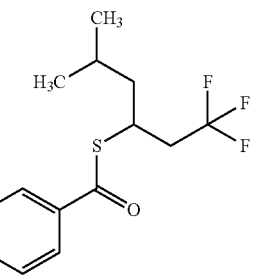

To a solution of 1,1,1-trifluoro-3-iodo-5-methylhexane (0.047 g, 0.168 mmol) in DMF (1.678 mL) at ambient temperature was added potassium benzothioate (0.035 g, 0.201 mmol). The reaction was allowed to stir for 18 h at which point the reaction was diluted in water (3 mL) and EtOAc (5 mL). The layers were mixed and then separated. The aqueous layer was extracted with EtOAc (3×5 mL) and the combined organic extracts were washed with water (1×10 mL) and half saturated brine (2×10 mL), dried over Na$_2$SO$_4$, filtered and concentrated in vacuo. Residue was purified via flash chromatography (0 to 30% EtOAc/Hexanes) to afford the desired product as a clear oil (37 mg, 68%): $^1$H NMR (400 MHz, CDCl$_3$) δ 7.99-7.92 (m, 2H), 7.62-7.55 (m, 1H), 7.50-7.41 (m, 2H), 4.10-3.95 (m, 1H), 2.73-2.56 (m, 1H), 2.56-2.40 (m, 1H), 1.94-1.73 (m, 1H), 1.73-1.61 (m, 2H), 0.97 (d, J=6.6 Hz, 3H), 0.94 (d, J=6.5 Hz, 3H); $^{19}$F NMR (376 MHz, CDCl$_3$) δ-62.89.

S-(4,4,4-trifluoro-1-phenylbutan-2-yl)benzothioate was prepared as in Example 155: $^1$H NMR (400 MHz, CDCl$_3$) δ 7.97-7.89 (m, 2H), 7.58 (ddt, J=7.9, 6.9, 1.3 Hz, 1H), 7.49-7.41 (m, 2H), 7.39-7.26 (m, 5H), 4.29-4.15 (m, 1H), 3.11 (d, J=7.2 Hz, 2H), 2.54 (qd, J=10.6, 6.6 Hz, 2H); $^{19}$F NMR (376 MHz, CDCl$_3$) δ-62.86; EIMS m/z 324.

S-(4,4,4-trifluoro-1-(1H-imidazol-1-yl)butan-2-yl)benzothioate was prepared as in Example 155: $^1$H NMR (400 MHz, CDCl$_3$) δ 7.98-7.89 (m, 2H), 7.68-7.60 (m, 1H), 7.56 (t, J=1.1 Hz, 1H), 7.53-7.45 (m, 2H), 7.11 (t, J=1.1 Hz, 1H), 7.05 (t, J=1.3 Hz, 1H), 4.42-4.18 (m, 3H), 2.64-2.39 (m, 2H); $^{19}$F NMR (376 MHz, CDCl$_3$) δ-62.98; EIMS m/z 314.

S-(1,1,1-trifluoropentan-3-yl)benzothioate was prepared as in Example 155: $^1$H NMR (400 MHz, CDCl$_3$) δ 8.02-7.91 (m, 2H), 7.64-7.55 (m, 1H), 7.51-7.40 (m, 2H), 4.06-3.90 (m, 1H), 2.70-2.41 (m, 2H), 2.02-1.86 (m, 1H), 1.86-1.71 (m, 1H), 1.05 (t, J=7.3 Hz, 3H); $^{19}$F NMR (376 MHz, CDCl$_3$) δ-63.32; EIMS m/z 262.

Example 156: Preparation of N-(3-chloro-1-(pyridin-3-yl)-1H-pyrazol-4-yl)-N-ethyl-3-((1,1,1-trifluoro-5-methylhexan-3-yl)thio)propanamide (Compound 1053)

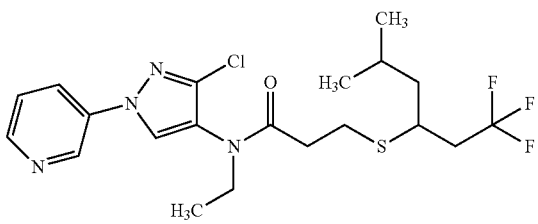 [SMILES: CCN(C(=O)CCSC(CC(C)C)CC(F)(F)F)c1cn(-c2cccnc2)nc1Cl]

To a suspension of NaH (60% in mineral oil, 0.012 g, 0.300 mmol) in THF (2.86 mL) at ambient temperature and under N$_2$ was added MeOH (0.058 mL, 1.429 mmol). The reaction became homogenous and gas evolution was observed. After stirring for 30 min, the reaction was cooled to 0° C. and a solution of S-(1,1,1-trifluoro-5-methylhexan-3-yl)benzothioate (0.083 g, 0.286 mmol) in THF (2 mL) was added slowly. The reaction was warmed to ambient temperature, stirred for 45 min, and then returned to 0° C. To the reaction was added a solution of 3-chloro-N-(3-chloro-1-(pyridin-3-yl)-1H-pyrazol-4-yl)-N-ethylpropanamide (0.090 g, 0.286 mmol) in THF (2 mL). The reaction was warmed to ambient temperature and stirred for 18 h. The reaction was diluted in EtOAc (20 mL) and water (10 mL). The layers were mixed and then separated. The aqueous layer was extracted with EtOAc (3×20 mL) and the combined organic extracts were dried over Na$_2$SO$_4$, filtered and concentrated in vacuo. The crude residue was purified via normal phase flash chromatography (0 to 100% EtOAc/CH$_2$Cl$_2$) to afford the desired product as a pale yellow oil (63 mg, 45%).

Example 157: Preparation of tert-butyl(2-(2,2-difluorocyclopropyl)ethoxy)diphenylsilane

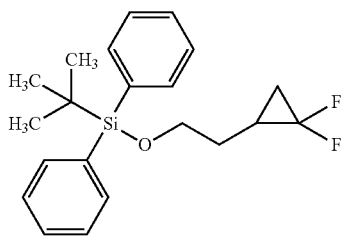 [SMILES: CC(C)(C)[Si](OCCC1CC1(F)F)(c1ccccc1)c1ccccc1]

To an oven-dried 3-neck round bottom flask equipped with reflux condenser and addition funnel under N$_2$ were added (but-3-en-1-yloxy)(tert-butyl)diphenylsilane (3.6 g, 11.59 mmol) and sodium fluoride (7.30 mg, 0.174 mmol) (For preparation of starting olefin, see: Waser, J.; Gaspar, B.; Nambu, H.; Carreira, E. M. *J. Am. Chem. Soc.* 2006, 128, 11693-11712). To the closed addition funnel was added trimethylsilyl 2,2-difluoro-2-(fluorosulfonyl)acetate (4.57 mL, 23.19 mmol). The reaction vessel and its contents were heated to 120° C. and the addition funnel was then opened to allow the sulfonyl fluoride to add over 1 h. Once the addition was complete, the reaction was allowed to continue stirring at 120° C. for 30 min. The reaction was cooled to ambient temperature, diluted in CH$_2$Cl$_2$ (50 mL) and washed with NaHCO$_{3(aq)}$ (2×50 mL). The organic phase was separated, dried over Na$_2$SO$_4$, filtered and concentrated in vacuo to provide a brown oil. The crude residue was purified via normal phase flash chromatography (0 to 15% CH$_2$Cl$_2$/Hexanes) to provide the desired product as a clear oil (3.07 g, 73%): $^1$H NMR (400 MHz, CDCl$_3$) δ 7.72-7.63 (m, 4H), 7.49-7.34 (m, 6H), 3.73 (t, J=6.0 Hz, 2H), 1.88-1.73 (m, 1H), 1.73-1.55 (m, 2H), 1.42-1.27 (m, 1H), 1.06 (s, 9H), 0.94-0.81 (m, 1H); $^{19}$F NMR (376 MHz, CDCl$_3$) δ-128.54 (d, J=156.2 Hz), -143.96 (d, J=155.5 Hz); $^{13}$C NMR (101 MHz, CDCl$_3$) δ 135.5, 133.7 (d, J=3.7 Hz), 129.6, 127.7, 114.5, 62.8, 30.0 (d, J=3.5 Hz), 26.8, 19.9 (t, J=10.9 Hz), 19.2, 15.9 (t, J=11.0 Hz).

Example 158: Preparation of 2-(2,2-difluorocyclopropyl)ethyl 4-methylbenzenesulfonate

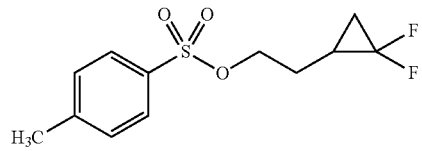 [SMILES: Cc1ccc(S(=O)(=O)OCCC2CC2(F)F)cc1]

To a solution of tert-butyl(2-(2,2-difluorocyclopropyl)ethoxy)diphenylsilane (0.386 g, 1.071 mmol) in THF (10.71 mL) at 0° C. was added a 1.0 M solution of TBAF (3.21 mL, 3.21 mmol) in THF. The reaction was warmed to ambient temperature and stirred for 3 h. The reaction was quenched with the addition of NH$_4$Cl$_{(aq)}$ (1 mL) and the mixture was partitioned between water (15 mL) and EtOAc (15 mL). The layers were mixed well and then separated. The aqueous layer was extracted with EtOAc (3×20 mL) and the combined organic extracts were dried over Na$_2$SO$_4$, filtered and concentrated in vacuo. The crude residue was then taken up in CH$_2$Cl$_2$ (7.15 mL). To the solution were then added pyridine (0.434 mL, 5.36 mmol) and p-toluenesulfonyl chloride (0.614 g, 3.22 mmol). The reaction was stirred at ambient temperature for 48 h at which point the reaction was partitioned between CH$_2$Cl$_2$ (50 mL) and water (25 mL). The layers were separated and the organic layer was washed with 1N HCl$_{(aq)}$ (20 mL), water (20 mL) and brine (20 mL). The organic layer was then dried over Na$_2$SO$_4$, filtered and concentrated in vacuo. The crude residue was purified via normal phase flash chromatography (0 to 50% EtOAc/Hexanes) to afford the desired product as a clear oil (142 mg, 46%, 2 steps): $^1$H NMR (400 MHz, CDCl$_3$) δ 7.89-7.71 (m, 2H), 7.42-7.29 (m, 2H), 4.20-3.96 (m, 2H), 2.46 (s, 3H), 1.92-1.81 (m, 1H), 1.81-1.69 (m, 1H), 1.63-1.48 (m, 1H), 1.39 (dddd, J=12.2, 11.2, 7.7, 4.3 Hz, 1H), 0.93 (dtd, J=13.0, 7.6, 3.5 Hz, 1H); $^{13}$C NMR (101 MHz, CDCl$_3$) δ 145.0, 132.9, 129.9, 127.9, 113.5 (t, J=282.4 Hz), 69.0 (d, J=2.2 Hz), 26.6 (d, J=4.3 Hz), 21.7, 18.9 (t, J=11.1 Hz), 15.9 (t, J=11.0 Hz); $^{19}$F NMR (376 MHz, CDCl$_3$) δ-129.09 (d, J=157.8 Hz), -144.18 (d, J=158.1 Hz).

Example 159: Preparation of N-(3-chloro-1-(pyridin-3-yl)-1H-pyrazol-4-yl)-N-methylacrylamide (Compound Y2098)

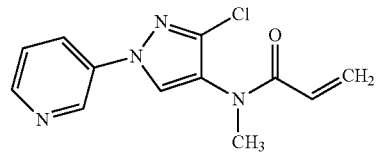 [SMILES: C=CC(=O)N(C)c1cn(-c2cccnc2)nc1Cl]

To a solution of 3-chloro-N-methyl-1-(pyridin-3-yl)-1H-pyrazol-4-amine (0.526 g, 2.52 mmol) in 1,2-dichloroethane (25.2 mL) at 0° C. were added diisopropylethylamine (0.484 mL, 2.77 mmol) and acryloyl chloride (0.205 mL, 2.52 mmol). The reaction was allowed to warm to ambient temperature and was stirred for 1 h. The reaction was quenched with the addition of NaHCO$_{3(aq)}$ and was diluted with CH$_2$Cl$_2$. The layers were separated and the aqueous layer was extracted with CH$_2$Cl$_2$. The combined organic extracts were dried over Na₂SO₄, filtered and concentrated in vacuo. The crude product was purified via flash chromatography (0 to 10% MeOH/CH₂Cl₂) to give the desired product as an orange solid (634 mg, 91%).

Example 160: Preparation of N-(3-chloro-1-(pyridin-3-yl)-1H-pyrazol-4-yl)-N-ethyl-3-((3,3,3-trifluoropropyl)thio)propanamide (Compound 653)

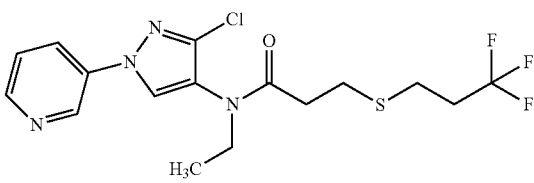 [SMILES: CCN(C(=O)CCSCCC(F)(F)F)c1cn(-c2cccnc2)nc1Cl]

To a solution of 3-chloro-N-ethyl-1-(pyridin-3-yl)-1H-pyrazol-4-amine (10 g, 44.9 mmol) in CH₂Cl₂ (100 mL) at 0° C. and under N₂ were added pyridine (5.45 mL, 67.4 mmol), 4-dimethylaminopyridine (DMAP) (2.74 g, 22.45 mmol), and 3-((3,3,3-trifluoropropyl)thio)propanoyl chloride (9.91 g, 44.9 mmol), sequentially. The reaction was warmed to ambient temperature and stirred for 1 h. The reaction was poured into water (100 mL) and the resulting mixture was stirred for 5 min. The mixture was transferred to a separatory funnel and the layers were separated. The aqueous phase was extracted with CH₂Cl₂ (3×50 mL) and the combined organic extracts were dried over Na₂SO₄, filtered and concentrated in vacuo. The crude product was purified via normal phase flash chromatography (0 to 100% EtOAc/CH₂Cl₂) to afford the desired product as a pale yellow solid (17.21 g, 89%).

Example 161: Preparation of N-(1-(5-fluoropyridin-3-yl)-3-methyl-1H-pyrazol-4-yl)-2-oxooxazolidine-3-carbothioamide (Compound Y2032)

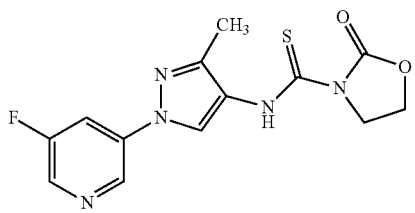 [SMILES: Cc1nn(-c2cncc(F)c2)cc1NC(=S)N1CCOC1=O]

To a solution of 1-(5-fluoropyridin-3-yl)-3-methyl-1H-pyrazol-4-amine (0.10 g, 0.52 mmol) and triethylamine (0.24 mL, 1.71 mmol) in dry THF (0.52 mL) was added carbon disulfide (0.03 mL, 0.52 mmol) via syringe over 15 minutes. After stirring for 1 hour, the mixture was cooled in an ice bath and 4-methylbenzene-1-sulfonyl chloride (0.11 g, 0.57 mmol) was added in one portion, stirred for 5 minutes at 0° C. and then warmed to 25° C. and stirred for 1 hour. The reaction mixture was quenched with 1N HCl and extracted with diethyl ether. The ether layers were combined, washed with water and half saturated aqueous sodium bicarbonate, dried (MgSO₄), filtered and concentrated to dryness to give the desired isothiocyanate (0.12 g, 98%). To a solution of oxazolidin-2-one (0.05 g, 0.61 mmol) dissolved in dry DMF (2.05 mL) was added sodium hydride (0.03 g, 0.61 mmol, 60% dispersion in mineral oil) in one portion and the suspension was stirred for 20 minutes. The reaction mixture was cooled to 0° C. and 3-fluoro-5-(4-isothiocyanato-3-methyl-1H-pyrazol-1-yl)pyridine (0.12 g, 0.51 mmol) was added in one portion in a minimum amount of dry DMF and stirred for 20 minutes. Water and ethyl acetate were added and the resulting biphasic mixture was separated and the aqueous layer was extracted one time with ethyl acetate. The combined organic extracts were washed with 1:1 hexanes/water, dried (MgSO₄), filtered and concentrated to dryness. The crude product was purified by silica gel chromatography eluting with 0-75% ethyl acetate/hexanes to give the desired product as a white solid (0.03 g, 18%).

Example 162: Preparation of 3-(4-isothiocyanato-3-methyl-1H-pyrazol-1-yl)pyridine

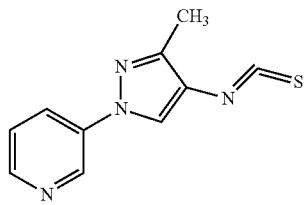

To a solution of 3-methyl-1-(pyridin-3-yl)-1H-pyrazol-4-amine (0.50 g, 2.87 mmol) and triethylamine (1.3 mL, 1.71 mmol) in dry THF (2.8 mL) was added carbon disulfide (0.17 mL, 2.87 mmol) via syringe over 15 minutes. After stirring for 1 hour, the mixture was cooled in an ice bath and 4-methylbenzene-1-sulfonyl chloride (0.60 g, 0.3.16 mmol) was added in one portion, stirred for 5 minutes at 0° C. and then warmed to 25° C. and stirred for 1 hour. The reaction mixture was quenched with 1N HCl and extracted with diethyl ether. The ether layers were combined, washed with water and half saturated aqueous NaHCO₃, dried (MgSO₄), filtered and concentrated to dryness. The crude material was purified by silica gel chromatography eluting with 0-100% ethyl acetate/hexanes to give the desired product as a light yellow solid (0.48 g, 78%): ¹H NMR (400 MHz, CDCl₃) δ 8.89 (d, J=2.6 Hz, 1H), 8.56 (dd, J=4.7, 1.4 Hz, 1H), 7.96 (ddd, J=8.3, 2.7, 1.5 Hz, 1H), 7.89 (s, 1H), 7.40 (ddd, J=8.3, 4.8, 0.7 Hz, 1H), 2.40 (s, 3H); ESIMS m/z 218 ([M+H]⁺).

Example 163: Preparation of N-(3-methyl-1-(pyridin-2-yl)-1H-pyrazol-4-yl)-2-oxooxazolidine-3-carbothioamide (Compound Y2034)

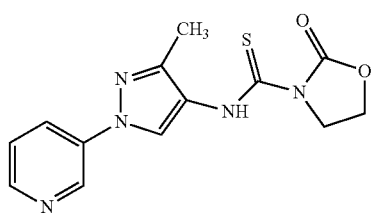 [SMILES: Cc1nn(-c2cccnc2)cc1NC(=S)N1CCOC1=O]

To a solution of oxazolidin-2-one (0.06 g, 0.66 mmol) dissolved in dry DMF (2.2 mL) was added sodium hydride (0.03 g, 0.67 mmol, 60% dispersion in mineral oil) in one portion and the suspension was stirred for 20 minutes. The reaction mixture was cooled to 0° C. and 3-(4-isothiocyanato-3-methyl-1H-pyrazol-1-yl)pyridine (0.12 g, 0.56 mmol) was added in one portion in a minimum amount of dry DMF and stirred for 20 minutes. Water and ethyl acetate were added and the resulting biphasic mixture was separated and the aqueous layer was extracted one time with ethyl acetate. The combined organic extracts were washed with 1:1 hexanes/water, dried (MgSO$_4$), filtered and concentrated to dryness. The crude product was purified by silica gel chromatography eluting with 0-75% ethyl acetate/hexanes to give the desired product as a white solid (0.07 g, 41%).

Example 164: Preparation of methyl N-(3-methyl-1-(pyridin-3-yl)-1H-pyrazol-4-yl)-2-oxooxazolidine-3-carbimidothioate (Compound Y2035)

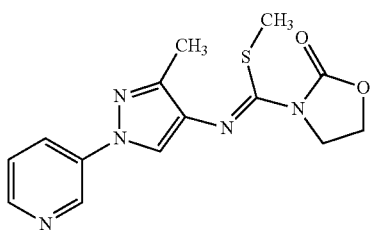 [SMILES: CS/C(=N\c1cn(-c2cccnc2)nc1C)N1CCOC1=O]

To a solution of oxazolidin-2-one (0.05 g, 0.66 mmol) dissolved in dry DMF (2.22 mL) was added sodium hydride (0.03 g, 0.66 mmol, 60% dispersion in mineral oil) in one portion and the suspension was stirred for 20 minutes. The reaction mixture was cooled to 0° C. and 3-(4-isothiocyanato-3-methyl-1H-pyrazol-1-yl)pyridine (0.12 g, 0.55 mmol) was added in one portion in a minimum amount of dry DMF and stirred for 20 minutes. Iodomethane (0.04 mL, 0.66 mmol) was added and the reaction was monitored by TLC. Aqueous ammonium chloride and 50% ethyl acetate/hexanes were added and the resulting biphasic mixture was separated and the organic extract washed with water and saturated aqueous sodium bicarbonate and concentrated to dryness. The crude product was purified by silica gel chromatography eluting with 0-10% methanol/CH$_2$Cl$_2$ to give the desired product as a light yellow solid (0.14 g, 82%).

Example 165: Preparation of N-acetyl-N-(3-chloro-1-(pyridin-3-yl)-1H-pyrazol-4-yl)cyclopropanecarboxamide (Compound Y2060)

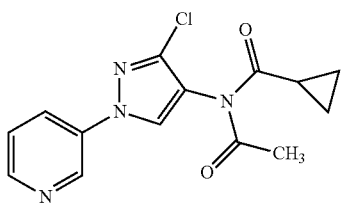 [SMILES: CC(=O)N(C(=O)C1CC1)c1cn(-c2cccnc2)nc1Cl]

To a solution of N-(3-chloro-1-(pyridin-3-yl)-1H-pyrazol-4-yl)cyclopropanecarboxamide (0.15 g, 0.57 mmol) in dichloroethane (2.5 mL) was added diisopropylethylamine (0.12 mL, 0.68 mmol) followed by acetyl chloride (0.54 g, 0.68 mmol) and the reaction was stirred at room temperature overnight. Saturated aqueous NaHCO$_3$ was added and the mixture was extracted with CH$_2$Cl$_2$. The combined organic phases were concentrated to dryness and purified by silica gel chromatography eluting with 0-100% ethyl acetate/hexanes to give the desired product as a white solid (10 mg, 6%).

Example 166: Preparation of S-methyl(3-chloro-5-(methylthio)-1-(pyridin-3-yl)-1H-pyrazol-4-yl)(ethyl)carbamothioate (Compound Y2076)

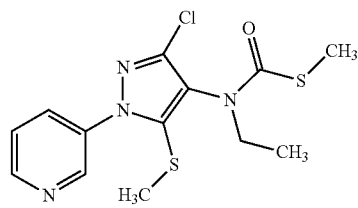 [SMILES: CCN(C(=O)SC)c1c(Cl)nn(-c2cccnc2)c1SC]

To a solution of THF (1.35 mL) and diisopropylethylamine (0.07 mL, 0.40 mmol) was added 2.5M n-butyllithium (0.16 mL, 0.40 mmol) and the reaction was stirred for 30 minutes. The reaction was cooled further to −78° C. and to this was added dropwise S-methyl(3-chloro-1-(pyridin-3-yl)-1H-pyrazol-4-yl)(ethyl)carbamothioate (0.10 g, 0.33 mmol) in a minimum amount of dry THF and stirred for 45 minutes. To this was then added 1,2-dimethyldisulfane (0.04 g, 0.37 mmol) and the reaction was stirred for additional 20 minutes. The reaction was poured into water and extracted with ethyl acetate. The ethyl acetate layers were combined, dried (MgSO$_4$), filtered and concentrated to dryness. The crude product was purified by silica gel chromatography eluting with 0-100% ethyl acetate/hexanes to give the desired product as a clear oil (53 mg, 46%).

Example 167: Preparation of N-(3-chloro-1-(pyridin-3-yl)-1H-pyrazol-4-yl)-N-ethyl-3-(3,3,3-trifluoropropyl)thio)propanamide (Compound 653)

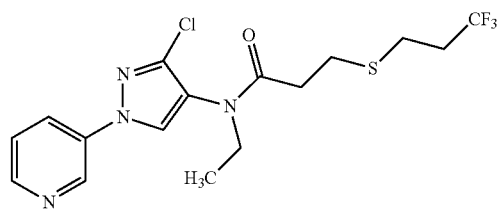 [SMILES: CCN(C(=O)CCSCCC(F)(F)F)c1cn(-c2cccnc2)nc1Cl]

To a solution of N-(3-chloro-1-(pyridin-3-yl)-1H-pyrazol-4-yl)-N-ethyl-3-mercaptopropanamide (0.10 g, 0.32 mmol) dissolved in dry THF (1.07 mL) and cooled in an ice bath was added sodium hydride (0.02 g, 0.34 mmol, 60% dispersion in mineral oil) in one portion and the reaction was stirred for 10 minutes. To this was added 3-bromo-1,1,1-trifluoropropane (0.06 g, 0.35 mmol) in one portion in a minimum amount of dry DMF and the reaction was stirred at room temperature for 2 hours. The reaction mixture was poured into water and extracted with ethyl acetate. The ethyl acetate layers were combined and concentrated to dryness. The crude product was purified by silica gel chromatography eluting with 0-75% ethyl acetate hexanes to give the desired product as a clear oil (83 mg, 63%).

Example 168: Preparation of tert-butyl(2-((3-chloro-1-(pyridin-3-yl)-1H-pyrazol-4-yl)(ethyl)amino)-2-oxoethyl)(methyl)carbamate

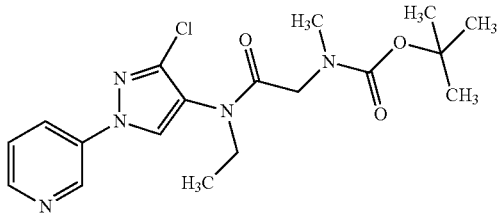 [SMILES: CCN(C(=O)CN(C)C(=O)OC(C)(C)C)c1cn(-c2cccnc2)nc1Cl]

To a solution of 3-chloro-N-ethyl-1-(pyridin-3-yl)-1H-pyrazol-4-amine (0.40 g, 1.79 mmol) in dichloroethane (3.59 mL) was added 2-((tert-butoxycarbonyl)(methyl)amino)acetic acid (0.37 g, 1.97 mmol), 4-N,N-dimethylaminopyridine (0.24 g, 1.97 mmol) and 1-(3-dimethylaminopropyl)-3-ethylcarbodiimide hydrochloride (0.51 g, 2.69 mmol) and the reaction was stirred overnight at room temperature. The reaction mixture was concentrated to dryness and the crude product was purified by silica gel chromatography eluting with 0-100% ethyl acetate/hexanes to give the desired product as a white semi solid (0.61 g, 87%): IR (thin film) 1673 cm$^{-1}$; $^1$H NMR (400 MHz, CDCl$_3$) δ 8.96 (d, J=2.4 Hz, 1H), 8.63 (dd, J=5.3 Hz, 1H), 8.11-7.86 (m, 2H), 7.51-7.36 (m, 1H), 3.92-3.57 (m, 4H), 2.96-2.81 (m, 3H), 1.50-1.37 (s, 9H), 1.20-1.11 (m, 3H); ESIMS m/z 394 ([M+H]$^+$).

The following molecules were made in accordance with the procedures disclosed in Example 168:

tert-Butyl(2-((3-chloro-1-(pyridin-3-yl)-1H-pyrazol-4-yl)(methyl)amino)-2-oxoethyl)(methyl)carbamate: $^1$H NMR (400 MHz, CDCl$_3$) δ 8.95 (d, J=2.5 Hz, 1H), 8.62 (d, J=4.8 Hz, 1H), 8.14-7.84 (m, 2H), 7.59-7.35 (m, 1H), 3.85 (d, J=25.9 Hz, 2H), 3.31-3.15 (m, 3H), 2.99-2.81 (m, 3H), 1.53-1.31 (s, 9H).

tert-Butyl(2-((3-chloro-1-(pyridin-3-yl)-1H-pyrazol-4-yl)(cyclopropylmethyl)amino)-2-oxoethyl)(methyl)carbamate: IR (thin film) 1675 cm$^{-1}$; $^1$H NMR (400 MHz, CDCl$_3$) δ 8.95 (bs, 1H), 8.63 (dd, J=5.1 Hz, 1H), 8.17-7.88 (m, 2H), 7.54-7.36 (m, 1H), 3.99-3.41 (m, 4H), 2.97-2.82 (m, 3H), 1.44 (s, 9H), 1.12-0.83 (m, 1H), 0.59-0.39 (m, 2H), 0.28-0.08 (m, 2H); ESIMS m/z 420 ([M+H]$^+$).

Example 169: Preparation of N-(3-chloro-1-pyridin-3-yl)-1H-pyrazol-4-yl)-N-ethyl-2-(methylamino)acetamide

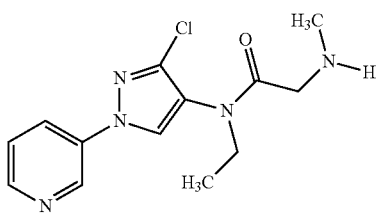 [SMILES: CCN(C(=O)CNC)c1cn(-c2cccnc2)nc1Cl]

To a solution of tert-butyl(2-((3-chloro-1-(pyridin-3-yl)-1H-pyrazol-4-yl)(ethyl)amino)-2-oxoethyl)(methyl)carbamate (0.57 g, 1.44 mmol) in CH$_2$Cl$_2$ (1.44 mL) was added trifluoroacetic acid (1.44 mL) and the reaction was stirred at room temperature for 1 hour. Toluene was added and the reaction was concentrated to near dryness. The mixture was poured into a separatory funnel containing saturated aqueous NaHCO$_3$ and was extracted with CH$_2$Cl$_2$. The CH$_2$Cl$_2$ layers were combined and concentrated to dryness. The crude product was purified by silica gel chromatography eluting with 0-15% methanol/CH$_2$Cl$_2$ to give the desired product as a yellow oil (0.31 g, 73%): IR (thin film) 1666 cm$^{-1}$; $^1$H NMR (400 MHz, CDCl$_3$) δ 8.98 (d, J=2.6 Hz, 1H), 8.63 (dd, J=4.7, 1.3 Hz, 1H), 8.06 (m, 2H), 7.47 (dd, J=8.3, 4.8 Hz, 1H), 3.72 (q, J=7.1 Hz, 2H), 3.30 (s, 2H), 2.48 (s, 3H), 1.17 (t, J=7.2 Hz, 3H); ESIMS m/z 294 ([M+H]$^+$).

The following compounds were made in accordance with the procedures disclosed in Example 169:

N-(3-Chloro-1-(pyridin-3-yl)-H-pyrazol-4-yl)-N-methyl-2-(methylamino)acetamide: IR (thin film) 1666 cm$^{-1}$; $^1$H NMR (400 MHz, CDCl$_3$) δ 8.96 (d, J=2.6 Hz, 1H), 8.64 (dd, J=4.8, 1.3 Hz, 1H), 8.11-7.94 (m, 2H), 7.47 (dd, J=8.4, 4.4 Hz, 1H), 3.30 (s, 2H), 3.27 (s, 3H), 2.47 (s, 3H); ESIMS m/z 280 ([M+H]$^+$).

N-(3-Chloro-1-(pyridin-3-yl)-1H-pyrazol-4-yl)-N-(cyclopropylmethyl)-2-(methylamino)acetamide: IR (thin film) 1667 cm$^{-1}$; $^1$H NMR (400 MHz, CDCl$_3$) δ 8.98 (d, J=2.6 Hz, 1H), 8.63 (dd, J=4.7, 1.3 Hz, 1H), 8.11 (s, 1H), 8.06 (ddd, J=8.3, 2.7, 1.4 Hz, 1H), 7.47 (dd, J=8.3, 4.8 Hz, 1H), 3.53 (bs, 2H), 3.27 (bs, 2H), 2.49 (s, 3H), 1.02-0.91 (m, 1H), 0.55-0.44 (m, 2H), 0.22-0.15 (m, 2H); ESIMS m/z 320 ([M+H]$^+$).

Example 170: Preparation of N-(3-chloro-1-(pyridin-3-yl)-1H-pyrazol-4-yl)-N-ethyl-2-(N-methylmethylsulfonamido)acetamide (Compound 800)

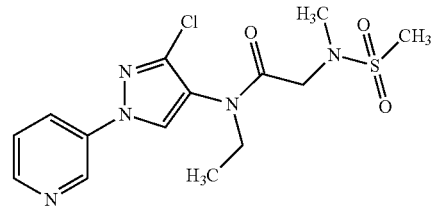 [SMILES: CCN(C(=O)CN(C)S(C)(=O)=O)c1cn(-c2cccnc2)nc1Cl]

To a solution of N-(3-chloro-1-(pyridin-3-yl)-1H-pyrazol-4-yl)-N-ethyl-2-(methylamino)acetamide (0.10 g, 0.34 mmol) in CH$_2$Cl$_2$ (0.68 mL) was added methanesulfonyl chloride (0.06 g, 0.51 mmol) followed by diisopropylethylamine (0.12 mL, 0.68 mmol) and the reaction was stirred overnight at room temperature. The reaction mixture was poured into saturated aqueous NaHCO$_3$ and extracted with CH$_2$Cl$_2$. The CH$_2$Cl$_2$ layers were combined and concentrated to dryness. The crude product was purified by silica gel chromatography eluting with 50-100% ethyl acetate/hexanes to give the desired product as a white semi-solid (81 mg, 64%).

Example 171: Preparation of N-(3-chloro-1-(pyridin-3-yl)-1H-pyrazol-4-yl)-N-ethyl-3-((3,3,3-trifluoropropyl)sulfinyl)propanamide (Compound 861)

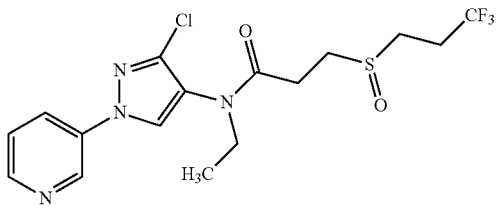 [SMILES: CCN(C(=O)CCS(=O)CCC(F)(F)F)c1cn(-c2cccnc2)nc1Cl]

Method A:

To N-(3-chloro-1-(pyridin-3-yl)-1H-pyrazol-4-yl)-N-ethyl-3-((3,3,3-trifluoropropyl)thio)propanamide (0.17 g, 0.43 mmol) in glacial acetic acid (4.35 mL) was added sodium perborate tetrahydrate (0.07 g, 0.45 mmol), and the mixture was heated at 55° C. for 1 hour. The reaction mixture was carefully poured into a separatory funnel containing saturated aqueous NaHCO₃ resulting in gas evolution. When the gas evolution had ceased, ethyl acetate was added and the layers were separated. The aqueous layer was extracted twice with ethyl acetate, and the organic layers were combined, dried over MgSO₄, filtered and concentrated under reduced pressure. The crude material was purified by silica gel chromatography eluting with 0-5% methanol/CH₂Cl₂ to give the desired product as a dark oil (60 mg, 33%).

Method B:

To a solution of N-(3-chloro-1-(pyridin-3-yl)-1H-pyrazol-4-yl)-N-ethyl-3-((3,3,3-trifluoropropyl)thio)propanamide (500 mg, 1.229 mmol) in hexafluoroisopropanol (5 mL) stirring at room temperature was added 30% hydrogen peroxide (523 mg, 4.92 mmol). The solution was stirred at room temperature for 15 min. It was quenched with saturated sodium sulfite solution and extracted with CH₂Cl₂. Silica gel chromatography (0-10% MeOH/CH₂Cl₂) gave the title compound as white semi-solid (495 mg, 95%).

Example 172: Preparation of N-(3-chloro-1-(pyridin-3-yl)-1H-pyrazol-4-yl)-N-ethyl-2-(methylamino)propanamide

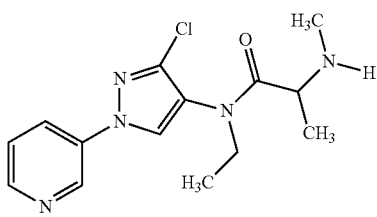 [SMILES: CCN(C(=O)C(C)NC)c1cn(-c2cccnc2)nc1Cl]

2-chloro-N-(3-chloro-1-(pyridin-3-yl)-1H-pyrazol-4-yl)-N-ethylpropanamide (0.51 g, 1.62 mmol) and methylamine (4.05 mL, 32.6 mmol, 33% in ethanol) were placed in a 25 mL vial on a Biotage® Initiator microwave reactor for 45 minutes at 100° C., with external IR-sensor temperature monitoring from the side of the vessel. The reaction was concentrated to dryness and purified by silica gel chromatography (0-10% methanol/CH₂Cl₂ to give the desired product as a yellow solid (0.21 g, 43%): ¹H NMR (400 MHz, CDCl₃) δ 8.96 (d, J=2.6 Hz, 1H), 8.64 (dd, J=4.7, 1.3 Hz, 1H), 8.06 (ddd, J=8.3, 2.7, 1.4 Hz, 1H), 7.98 (s, 1H), 7.47 (dd, J=8.3, 4.8 Hz, 1H), 3.93-3.57 (m, 2H), 3.25-3.11 (m, 1H), 2.34 (s, 3H), 1.21-1.17 (m, 6H).

The following compound was made in accordance with the procedures disclosed in Example 172:

N-(3-chloro-1-(pyridin-3-yl)-1H-pyrazol-4-yl)-N-ethyl-3-(methylamino)propanamide

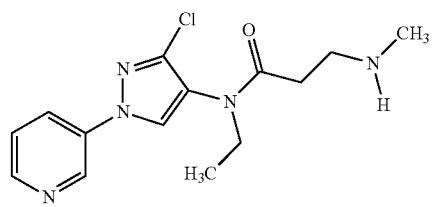

¹H NMR (400 MHz, Acetone) δ 9.12 (dd, J=6.7, 2.6 Hz, 1H), 8.90 (s, 1H), 8.58 (dd, J=4.7, 1.4 Hz, 1H), 8.25 (m, 1H), 7.56 (m, 1H), 3.67 (q, J=7.1 Hz, 2H), 3.01 (t, J=6.5 Hz, 2H), 2.66 (t, J=6.4 Hz, 2H), 2.50 (s, 3H), 1.12 (t, J=7.2 Hz, 3H); LC/MS (ESI) m/z 308.4 ([M+H]⁺); IR (KBr thin film) 3055, 2971, 2773, 1656 cm⁻¹.

Example 173: Preparation of N-(3-chloro-1-(pyridin-3-yl)-1H-pyrazol-4-yl)-N-ethyl-2-(2-methoxyethoxy)acetamide (Compound Y2195)

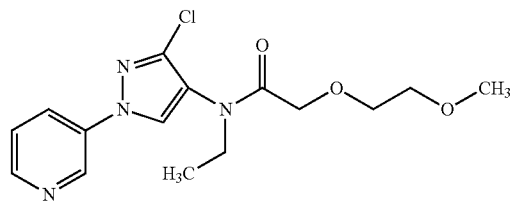 [SMILES: CCN(C(=O)COCCOC)c1cn(-c2cccnc2)nc1Cl]

To a stirred solution of 2-methoxyethanol (0.07 mL, 0.87 mmol) in THF (4 mL) at 0° C. was added sodium hydride (0.032 g, 0.80 mmol, 60% dispersion in oil). After stirring for 10 min 2-chloro-N-(3-chloro-1-(pyridin-3-yl)-1H-pyrazol-4-yl)-N-ethylacetamide (0.2 g, 0.7 mmol) was added in one portion. The reaction was stirred for 20 minutes then the reaction vessel was removed from the ice bath and allowed to warm to room temperature and was stirred overnight (ca 16 h), at which point the reaction was deemed complete by TLC. The reaction mixture was diluted with water and ethyl acetate and the layers were separated. The aqueous layer was extracted with ethyl acetate once. The combined organic layers were dried over MgSO₄, concentrated under reduced pressure, and purified by flash chromatography (SiO₂, 100-200 mesh; eluting with 0 to 20% methanol in CH₂Cl₂) to afford the title compound as a tan solid (0.045 g, 20%).

Example 174: Preparation of N-((3-chloro-1-(pyridin-3-yl)-1H-pyrazol-4-yl)(methyl)carbamoyl)-N-ethylpivalamide (Compound Y2082)

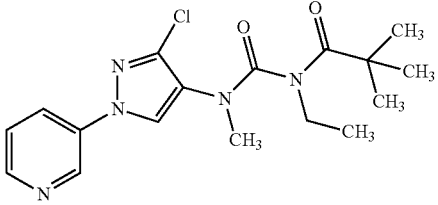 [SMILES: CCN(C(=O)N(C)c1cn(-c2cccnc2)nc1Cl)C(=O)C(C)(C)C]

To a solution of 1-(3-chloro-1-(pyridin-3-yl)-1H-pyrazol-4-yl)-3-ethyl-1-methylurea (0.075 g, 0.268 mmol) in THF (2.68 mL) at −78° C. was added 1 M lithium bis(trimethylsilyl)amide (LiHMDS) (0.282 mL, 0.282 mmol) in toluene. The reaction was stirred at −78° C. for 15 min and pivaloyl chloride (0.036 mL, 0.295 mmol) was added and the reaction was stirred at −78° C. for 10 min and room temperature for 30 min. Brine was added and the reaction was extracted with EtOAc. The combined organic phases were concentrated and purified by flash chromatography (0-15% MeOH/CH$_2$Cl$_2$) to give the title compound as a yellow oil (54 mg, 55%): IR (thin film) 2969, 1681 cm$^{-1}$; $^1$H NMR (400 MHz, CDCl$_3$) δ 8.93 (d, J=2.5 Hz, 1H), 8.61 (dd, J=4.7, 1.3 Hz, 1H), 8.06 (s, 1H), 8.00 (ddd, J=8.3, 2.6, 1.4 Hz, 1H), 7.44 (dd, J=8.3, 4.7 Hz, 1H), 3.58 (q, J=7.0 Hz, 2H), 3.35 (s, 3H), 1.25-1.13 (m, 12H); ESIMS m/z 365 ([M+H]$^+$).

Example 175: Preparation of N-(3-chloro-1-(pyridin-3-yl)-1H-pyrazol-4-yl)-3-(methylthio)propanimidamide (Compound 706)

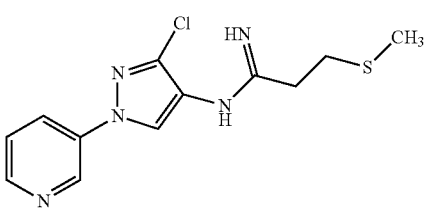 [SMILES: CSCCC(=N)Nc1cn(-c2cccnc2)nc1Cl]

To a solution of 3-chloro-1-(pyridin-3-yl)-1H-pyrazol-4-amine (0.058 g, 0.297 mmol) in EtOH (0.992 mL) was added naphthalen-2-ylmethyl 3-(methylthio)propanimidothioate hydrobromide (0.106 g, 0.297 mmol). The reaction was stirred at 0° C. for 1 hour. The solvent was removed under reduced pressure and water and Et$_2$O were added. The phases were separated and the aqueous phase was concentrated to give a crude mixture. The residue was dissolved in MeOH (1 mL) and MP-carbonate (0.281 g, 0.892 mmol) was added. The reaction was stirred at room temperature for 1 hour. The reaction was filtered, concentrated and purified by flash chromatography (0-15% MeOH/hexanes) to give the title compound as light brown solid (32 mg, 31%): mp 137° C.; $^1$H NMR (300 MHz, CDCl$_3$) δ 8.86 (d, J=2.6 Hz, 1H), 8.49 (dd, J=4.8, 1.2 Hz, 1H), 7.95 (ddd, J=8.3, 2.5, 1.3 Hz, 1H), 7.68 (s, 1H), 7.37 (dd, J=8.3, 4.8 Hz, 1H), 5.29 (br s, 2H), 3.02-2.73 (m, 2H), 2.64 (t, J=7.1 Hz, 2H), 2.18 (s, 3H); ESIMS m/z 297 ([M+H]$^+$).

Example 176: Preparation of naphthalen-2-ylmethyl 3-(methylthio)propanimidothioate hydrobromide

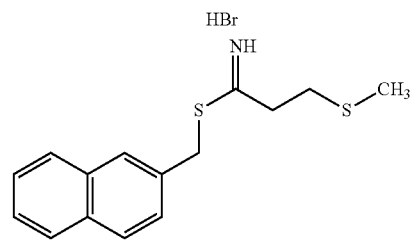 [SMILES: Br ; CSCCC(=N)SCc1ccc2ccccc2c1]

To a solution of 3-(methylthio)propanethioamide (0.062 g, 0.458 mmol) in CHCl$_3$ (1.146 mL) was added 2-(bromomethyl)naphthalene (0.101 g, 0.458 mmol). The mixture was heated at reflux for 1.5 hours. The reaction was cooled to room temperature, Et$_2$O was added and a precipitate formed. The solvent was removed under reduced pressure. Et$_2$O was added and subsequently decanted. The residual solid was dried under reduced pressure to give the title compound as a faint yellow solid (109 mg, 67%): $^1$H NMR (300 MHz, DMSO-d$_6$) δ 11.78 (br s, 1H), 8.00 (s, 1H), 7.98-7.85 (m, 3H), 7.59-7.49 (m, 3H), 4.74 (s, 2H), 3.10 (t, J=7.1 Hz, 2H), 2.84 (t, J=7.2 Hz, 2H), 2.08 (s, 3H). Reference: Shearer, B. G. et al. *Tetrahedron Letters* 1997, 38, 179-182.

Naphthalen-2-ylmethyl N-methyl-3-(methylthio)propanimidothioate hydrobromide was prepared in accordance with the procedure disclosed in Example 176 and isolated as an off-white semi-solid; $^1$H NMR (400 MHz, DMSO-d$_6$) δ 8.08 (s, 1H), 8.02-7.93 (m, 3H), 7.63-7.56 (m, 3H), 5.02 (s, 2H), 3.40-3.32 (m, 2H), 3.21 (s, 3H), 2.89-2.83 (m, 2H), 2.13 (s, 3H); ESIMS m/z 290 ([M+H]$^+$).

Naphthalen-2-ylmethyl N-methylethanimidothioate hydrobromide was prepared in accordance with the procedure disclosed in Example 176 and isolated as a white solid; $^1$H NMR (400 MHz, DMSO-d$_6$) δ 8.02 (s, 1H), 8.01-7.92 (m, 3H), 7.61-7.53 (m, 3H), 4.93 (s, 2H), 3.15 (d, J=1.1 Hz, 3H), 2.81 (d, J=1.1 Hz, 3H); ESIMS m/z 230 ([M+H]$^+$).

Naphthalen-2-ylmethyl ethanimidothioate hydrobromide was prepared as described in Shearer, B. G. et al. *Tetrahedron Letters* 1997, 38, 179-182.

Naphthalen-2-ylmethyl cyclopropanecarbimidothioate hydrobromide was prepared in accordance with the procedure disclosed in Example 176 and isolated as a yellow solid; $^1$H NMR (400 MHz, DMSO-d$_6$) δ 11.58 (s, 1H), 8.01 (s, 1H), 7.99-7.88 (m, 3H), 7.59-7.51 (m, 3H), 4.77 (s, 2H), 2.42-2.29 (m, 1H), 1.46-1.37 (m, 2H), 1.36-1.29 (m, 2H); ESIMS m/z 242 ([M+H]$^+$).

Example 177: Preparation of ethyl N-(3-chloro-1-(pyridin-3-yl)-1H-pyrazol-4-yl)-N'-ethyl-N-methylcarbamimidothioate (Compound Y2049)

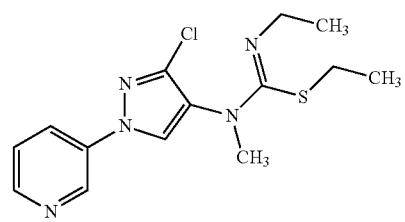 [SMILES: CC/N=C(\SCC)N(C)c1cn(-c2cccnc2)nc1Cl]

To a solution of 1-(3-chloro-1-(pyridin-3-yl)-1H-pyrazol-4-yl)-3-ethyl-1-methylthiourea (0.085 g, 0.287 mmol) in ethanol (1.916 mL) in a microwave vial was added iodoethane (0.028 mL, 0.345 mmol). The reaction was heated in a microwave (CEM Discover®) with external IR-sensor temperature monitoring from the bottom of the vessel at 80° C. for 6 hours. The reaction was concentrated and purified by flash chromatography (0-100% EtOAc/Hexanes) to give the title compound as a yellow oil (56 mg, 57%): IR (thin film) 3050, 2931, 1583 cm$^{-1}$; $^{1}$H NMR (300 MHz, CDCl$_3$) δ 9.05 (d, J=2.6 Hz, 1H), 8.91 (s, 1H), 8.59-8.48 (m, 1H), 8.13-8.04 (m, 1H), 7.40 (dd, J=8.4, 4.8 Hz, 1H), 3.81 (q, J=7.2 Hz, 2H), 3.73 (s, 3H), 2.95 (q, J=14.1, 7.0 Hz, 2H), 1.44-1.28 (m, 6H); ESIMS m/z 325 ([M+H]$^{+}$).

Example 178: Preparation of N-(3-chloro-1-(pyridin-3-yl)-1H-pyrazol-4-yl)-N-ethyl-3-(N-methyl-N-(3,3,3-trifluoropropyl)sulfamoyl)propanamide (Compound 965)

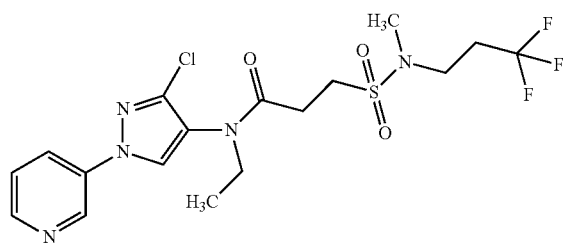 [SMILES: CCN(C(=O)CCS(=O)(=O)N(C)CCC(F)(F)F)c1cn(-c2cccnc2)nc1Cl]

To a stirred solution of N-(3-chloro-1-(pyridin-3-yl)-1H-pyrazol-4-yl)-N-ethyl-3-mercaptopropanamide (200 mg, 0.64 mmol), tetrabutylammonium chloride (715 mg, 2.57 mmol) and water (29 mg, 1.61 mmol) in acetonitrile (30 mL) at 0° C. was added 1-chloropyrrolidine-2,5-dione (258 mg, 1.93 mmol) in portions over 3 min. After stirring for 1 hour, 3,3,3-trifluoro-N-methylpropan-1-amine (82 mg, 0.64 mmol) was added and the reaction was stirred for additional 14 hours at room temperature. The mixture was filtered and concentrated in vacuo to give a brown residue. Purification of this residue on silica gel eluting with CH$_2$Cl$_2$ and methanol afforded the title compound as an off-white gum (71 mg, 22%).

Example 179: Preparation of N-(3-chloro-1-(pyridin-3-yl)-1H-pyrazol-4-yl)-3-((1-chloro-2,2,2-trifluoroethyl)thio)-N-ethylpropanamide (Compound 859)

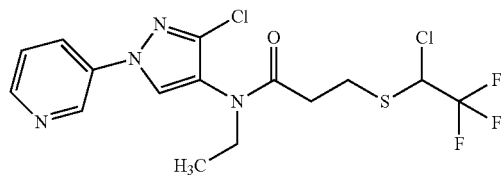 [SMILES: CCN(C(=O)CCSC(Cl)C(F)(F)F)c1cn(-c2cccnc2)nc1Cl]

To a suspension of N-(3-chloro-1-(pyridin-3-yl)-1H-pyrazol-4-yl)-N-ethyl-3-mercaptopropanamide (0.100 g, 0.322 mmol), sodium dithionite (0.070 g, 0.338 mmol) and sodium bicarbonate (0.028 g, 0.338 mmol) in DMSO (3.22 mL) at 40° C. was added 2-bromo-2-chloro-1,1,1-trifluoroethane (0.079 g, 0.402 mmol) dropwise. The reaction was stirred at the same temperature for 3 h after which the reaction was cooled, poured into water (10 mL) and extracted with EtOAc (3×20 mL). The combined organic extracts were washed with water (2×50 mL) and half-saturated brine (3×50 mL) and then dried over Na$_2$SO$_4$, filtered and concentrated in vacuo. The crude residue was purified via normal phase flash chromatography (0 to 100% EtOAc/CH$_2$Cl$_2$) to afford the desired product as a clear, viscous oil (111 mg, 77%). (Reference: Pustovit, et al., *Synthesis*, 2010, 7, 1159-1165).

Example 180: Preparation of N-(3-chloro-1-(pyridin-3-yl)-1H-pyrazol-4-yl)-N-ethyl-3-((3-(mesitylamino)-3-oxopropyl)thio)propanamide (Compound 1024)

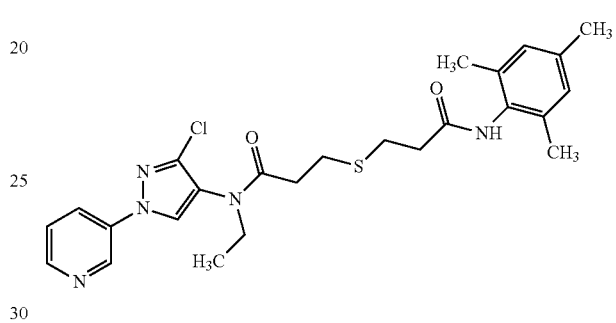

To a stirred solution of N-(3-chloro-1-(pyridin-3-yl)-1H-pyrazol-4-yl)-N-ethyl-3-mercaptopropanamide (0.20 g, 0.64 mmol) in acetonitrile (2.1 mL) was added 3-bromo-N-mesitylpropanamide (0.17 g, 0.64 mmol) and cesium carbonate (0.23 g, 0.70 mmol) and the reaction was stirred overnight at room temperature. The reaction was loaded directly onto celite and placed in a vacuum oven overnight at 25° C. The crude product was purified by silica gel chromatography eluting with 0-75% ethyl acetate/hexanes to give the desired product as a white semi-solid (226 mg, 53%).

Example 181: Preparation of two enantiomers of N-(3-chloro-1-(pyridin-3-yl)-1H-pyrazol-4-yl)-N-ethyl-3-((3,3,3-trifluoropropyl)sulfinyl)propanamide (Compounds 1028

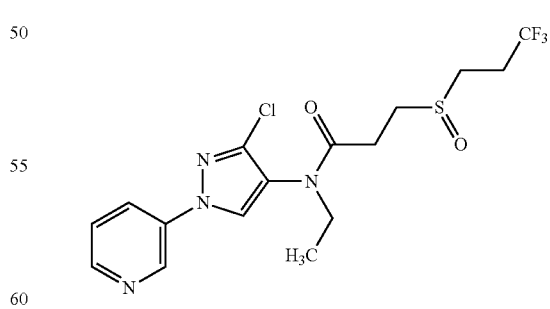

The two enantiomers of the title molecule were separated by chiral HPLC using a RegisCell™ semi-preparative column (25 cm×10.0 mm, 5 micron) using 0.1% TFA in hexane and isopropanol as the mobile phase (15 to 30% gradient IPA/hexane in 15 minutes, then hold to 20 minutes) with a flow rate of 15 mL/min at ambient temperature. Under these conditions compound 1028 was collected at a retention time of 6.0 min and possessed an optical rotation of $[\alpha]_D^{30}=+25.9$ (c 0.27% in CDCl$_3$). Compound 1029 was collected at a retention time of 7.5 min and possessed an optical rotation of $[\alpha]_D^{30}=-27.4$ (c 0.27% in CDCl$_3$). Characterization data for these molecules are listed in Table 2.

Example 182: Preparation of N-(3-chloro-1-(pyridin-3-yl)-1H-pyrazol-4-yl)-4,4,4-trifluoro-N-methyl-3-(methylsulfonyl)butanamide (Compound 714)

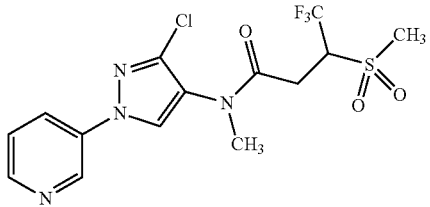 [SMILES: CN(C(=O)CC(C(F)(F)F)S(C)(=O)=O)c1cn(-c2cccnc2)nc1Cl]

To a 20 mL vial was added N-(3-chloro-1-(pyridin-3-yl)-1H-pyrazol-4-yl)-4,4,4-trifluoro-N-methyl-3-(methylsulfinyl)butanamide (130 mg, 0.329 mmol) and DCM (3 mL). m-CPBA (83 mg, 0.362 mmol) was added and the solution was stirred at room temperature for 3 hours. The reaction was quenched by the addition of sodium sulfite solution, extracted with DCM and concentrated. Purification with silica gel chromatography (0-100% EtOAc/hexane) afforded N-(3-chloro-1-(pyridin-3-yl)-1H-pyrazol-4-yl)-4,4,4-trifluoro-N-methyl-3-(methylsulfonyl)butanamide as a white solid (25 mg, 18%).

Example 183: Preparation of enantiomers of N-(3-chloro-1-(pyridin-3-yl)-1H-pyrazol-4-yl)-N-ethyl-2-methyl-3-(methylsulfinyl)propanamide (Compounds 804-807)

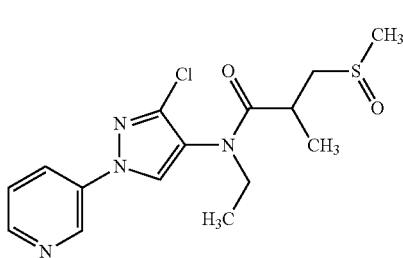 [SMILES: CCN(C(=O)C(C)CS(C)=O)c1cn(-c2cccnc2)nc1Cl]

The four stereoisomers of the title compound were separated by chiral HPLC using Chiralpak IC column (30×250 mm) using 0.2% TFA and 0.2% isopropylamine in hexane and isopropanol as the mobile phase (25% IPA in hexane) at ambient temperature. Under these conditions compound 804 was collected at a retention time of 8.4 minutes and possessed an optical rotation of $[\alpha]_D^{30}=-43.8$ (c 0.5% in CDCl$_3$). Compound 805 was collected at a retention time of 11.9 minutes and possessed an optical rotation of $[\alpha]_D^{30}=+48.2$ (c 0.5% in CDCl$_3$). Compound 806 was collected at a retention time of 16.4 minutes and possessed an optical rotation of $[\alpha]_D^{30}=+113.4$ (c 0.5% in CDCl$_3$). Compound 807 was collected at a retention time of 20.6 minutes and possessed an optical rotation of $[\alpha]_D^{30}=-93.0$ (c 0.5% in CDCl$_3$). Characterization data for these molecules are listed in Table 2.

Example 184: Preparation of 3-((3,3,3-trifluoropropyl)thio)propanoyl chloride

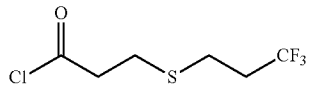 [SMILES: O=C(Cl)CCSCCC(F)(F)F]

A dry 5 L round bottom flask equipped with magnetic stirrer, nitrogen inlet, reflux condenser, and thermometer, was charged with 3-((3,3,3-trifluoropropyl)thio)propanoic acid (188 g, 883 mmol) in dichloromethane (3 L). Thionyl chloride (525 g, 321 mL, 4.42 mol) was then added dropwise over 50 minutes. The reaction mixture was heated to reflux (36° C.) for two hours, then cooled to ambient temperature. Concentration under vacuum on a rotary evaporator, followed by distillation (40 Torr, product collected from 123-127° C.) gave the title compound as a clear colorless liquid (177.3 g, 86%): $^1$H NMR (400 MHz, CDCl$_3$) δ 3.20 (t, J=7.1 Hz, 2H), 2.86 (t, J=7.1 Hz, 2H), 2.78-2.67 (m, 2H), 2.48-2.31 (m, 2H); $^{19}$F NMR (376 MHz, CDCl$_3$) δ-66.42, -66.43, -66.44, -66.44.

Example 185: Preparation of 3-chloro-1-(5-chloropyridin-3-yl)-1H-pyrazol-4-amine

To a solution of tert-butyl(3-chloro-1H-pyrazol-4-yl) carbamate (5 g, 22.97 mmol) in a mixture of DMF-H$_2$O (9:1) (40 mL) was added copper iodide (0.13 g, 0.69 mmol, 0.03 eq), cesium carbonate (14.97 g, 45.9 mmol), 8-hydroxy quinoline (0.33 g, 2.30 mmol) and 3-bromo-5-chloropyridine (5.29 g, 27.5 mmol). The mixture was heated at 140° C. under nitrogen for 11 hours. The reaction mixture was cooled to room temperature, quenched with ammonium hydroxide (15 mL), filtered through celite and the filtrate was extracted with ethyl acetate (3×50 mL). The combined organic layer was washed with brine (1×50 mL) dried over anhydrous Na$_2$SO$_4$, filtered, and evaporated to dryness under reduced pressure. The crude product was purified on silica gel using 0-100% ethyl acetate in hexane as eluent to give the title compound as dark brown amorphous solid (1.35 g, 26%): $^1$H NMR (400 MHz, DMSO-d$_6$) δ 8.93 (d, J=2.24 Hz, 1H), 8.48 (d, J=2.00 Hz, 1H), 8.25 (t, J=2.16 Hz, 1H), 7.96 (s, 1H), 4.52 (bs, 2H); ESIMS m/z 231 ([M+2H]$^+$).

The following molecules were made in accordance with the procedures disclosed in Example 185:

1-(5-Bromopyridin-3-yl)-3-chloro-1H-pyrazol-4-amine: ESIMS m/z 274 ([M+H]$^+$).

3-Chloro-1-(5-methoxypyridin-3-yl)-1H-pyrazol-4-amine: ESIMS m/z 225 ([M+H]$^+$).

3-Chloro-1-(5-methylpyridin-3-yl)-1H-pyrazol-4-amine: $^1$H NMR (400 MHz, DMSO-d$_6$, D$_2$O): δ 8.68 (s, 1H), 8.27 (s, 1H), 7.86 (d, J=5.64 Hz, 2H), 2.34 (s, 3H); ESIMS m/z 209 ([M+H]$^+$).

Example 186: Preparation of tert-butyl(3-chloro-1-(5-chloropyridin-3-yl)-1H-pyrazol-4-yl)carbamate

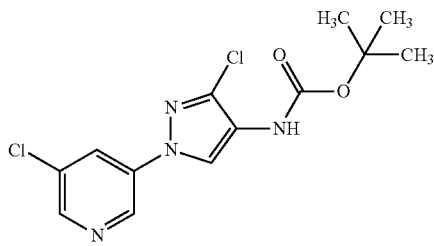 [SMILES: CC(C)(C)OC(=O)Nc1cn(-c2cncc(Cl)c2)nc1Cl]

To a solution of amine 3-chloro-1-(5-chloropyridin-3-yl)-1H-pyrazol-4-amine (1.00 g, 4.4 mmol) and triethylamine (666 mg, 6.6 mmol) in dry THF (10 mL) was added di-tert-butyl dicarbonate anhydride (960 mg, 4.62 mmol) over 30 minutes and the reaction was allowed to stir at room temperature for 18 hours. The reaction was diluted with water (10 mL) and extracted with ethyl acetate (50 mL×2). The organic phase was washed with brine (10 mL), dried over $Na_2SO_4$, and concentrated under reduced pressure. Purification by silica gel column chromatography using hexanes as an eluent afforded the titled compound (651 mg, 46%): ESIMS m/z 330 ([M+H]$^+$).

The following molecules were made in accordance with the procedures disclosed in Example 186:

tert-Butyl(1-(5-bromopyridin-3-yl)-3-chloro-1H-pyrazol-4-yl)carbamate: ESIMS m/z 372 ([M+H]$^+$).

tert-Butyl(3-chloro-1-(5-methylpyridin-3-yl)-1H-pyrazol-4-yl)carbamate: ESIMS m/z 309 ([M+H]$^+$).

Example 187: Preparation of tert-butyl(3-chloro-1-(5-chloropyridin-3-yl)-1H-pyrazol-4-yl)(methyl)carbamate

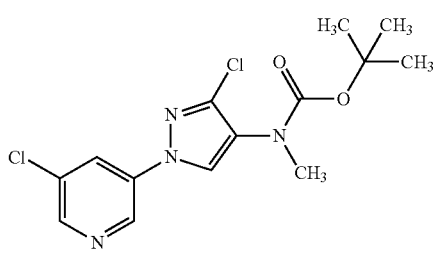 [SMILES: CN(C(=O)OC(C)(C)C)c1cn(-c2cncc(Cl)c2)nc1Cl]

To a solution of tert-butyl(3-chloro-1-(5-chloropyridin-3-yl)-1H-pyrazol-4-yl)carbamate (501 mg, 1.5 mmol) in dry THF (10 mL) was added potassium tert-butoxide (1.5 mL, 1 M solution in THF) and the reaction was stirred for 30 min. Methyl iodide (317 mg, 2.25 mmol) was added slowly at 0° C. and stirred for an additional 18 hours at room temperature. The mixture was quenched with saturated aqueous ammonium chloride and extracted with ethyl acetate (2×20 mL). The combined organic extract was washed with brine solution (1×20 mL), dried over $Na_2SO_4$ and evaporated to dryness under reduced pressure. The crude product was purified on silica gel using hexanes and ethyl acetate as eluent (0-10%) to give the title compound (220 mg, 42%): ESIMS m/z 345 ([M+H]$^+$).

The following molecules were made in accordance with the procedures disclosed in Example 187:

tert-Butyl(1-(5-bromopyridin-3-yl)-3-chloro-1H-pyrazol-4-yl)(methyl)carbamate: ESIMS m/z 387 ([M+H]$^+$).

tert-Butyl(3-chloro-1-(5-methylpyridin-3-yl)-1H-pyrazol-4-yl)(methyl)carbamate: ESIMS m/z 265 ([M–t–Bu]$^+$).

Example 188: Preparation of 3-chloro-1-(5-chloropyridin-3-yl)-N-methyl-1H-pyrazol-4-amine

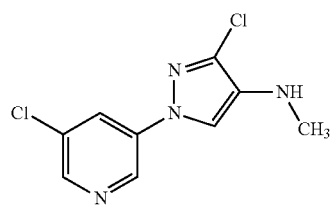

tert-Butyl(3-chloro-1-(5-chloropyridin-3-yl)-1H-pyrazol-4-yl)(methyl)carbamate (343 mg, 1 mmol, 1.0 eq) was dissolved in 1,4-dioxane (10 mL) and the solution was cooled to 0° C. A solution of HCl in dioxane (5 mL, 4 M) was added dropwise, and the mixture was stirred for 2 hours, then concentrated under reduced pressure. The residue was diluted with $CH_2Cl_2$ (50 mL), and the solution washed with aqueous sodium bicarbonate, water (10 mL) and brine (10 mL). The organic layer was dried over $Na_2SO_4$, and concentrated under reduced pressure to give the title compound (148 mg, 61%): ESMS m/z 244 ([M+H]$^+$).

The following molecule was made in accordance with the procedures disclosed in Example 188:

1-(5-Bromopyridin-3-yl)-3-chloro-N-methyl-1H-pyrazol-4-amine: ESIMS m/z 289 ([M+H]$^+$).

Example 189: Preparation of N-(3-chloro-1-(5-methoxypyridin-3-yl)-1H-pyrazol-4-yl)-2,2,2-trifluoroacetamide

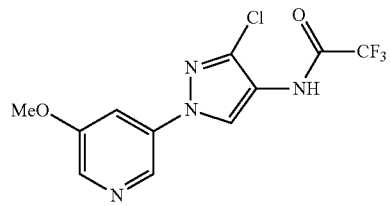 [SMILES: COc1cncc(-n2cc(NC(=O)C(F)(F)F)c(Cl)n2)c1]

To a solution of 3-chloro-1-(5-methoxypyridin-3-yl)-1H-pyrazol-4-amine (1.0 g, 4.46 mmol) and pyridine (530 mg, 6.69 mmol) in dry dichloromethane (10 mL) was added trifluoroacetic anhydride (1.0 eq) dropwise at 0° C. The reaction mixture was slowly warmed to room temperature and stirred for 4 hours. The reaction mixture was diluted with water (10 mL) and extracted with ethyl acetate (2×50 mL). The organic phase was washed with brine (10 mL), dried over $Na_2SO_4$ and concentrated under reduced pressure. The crude product was purified over silica eluting with hexanes and ethyl acetate to afford the title compound (700 mg, 49%): ESIMS m/z 321 ([M+H]$^+$).

Example 190: Preparation of N-(3-chloro-1-(5-methoxypyridin-3-yl)-1H-pyrazol-4-yl)-2,2,2-trifluoro-N-methylacetamide

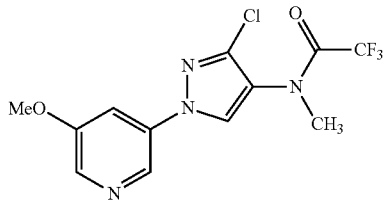 [SMILES: COc1cncc(-n2cc(N(C)C(=O)C(F)(F)F)c(Cl)n2)c1]

To a solution of N-(3-chloro-1-(5-methoxypyridin-3-yl)-1H-pyrazol-4-yl)-2,2,2-trifluoroacetamide (700 mg, 2.18 mmol) in dry THF (10 mL) was added potassium tert-butoxide (1 M solution in THF, 0.32 mL, 3.2 mmol) at 0° C. and the reaction was stirred for 30 min. Methyl iodide (466 mg, 3.28 mmol) was added slowly at 0° C. and the reaction was stirred for an additional 18 hours at room temperature. The reaction was quenched with saturated ammonium chloride solution and extracted with ethyl acetate (2×20 mL). The combined organic extract was washed with brine (1×20 mL), dried over $Na_2SO_4$ and evaporated to dryness under reduced pressure. The crude product was purified on silica eluting with hexanes and ethyl acetate (0-30%) to give the title compound (426 mg, 58% yield): ESIMS m/z 335 ([M+H]$^+$).

Example 191: Preparation of 3-chloro-1-(5-methoxypyridin-3-yl)-N-methyl-1H-pyrazol-4-amine

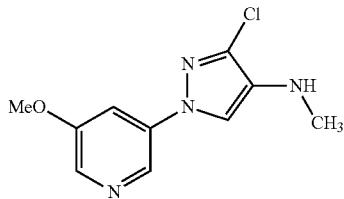 [SMILES: CNc1cn(-c2cncc(OC)c2)nc1Cl]

To a suspension of N-(3-chloro-1-(5-methoxypyridin-3-yl)-1H-pyrazol-4-yl)-2,2,2-trifluoro-N-methylacetamide (410 mg, 1.23 mmol) in methanol (10 mL) was added $K_2CO_3$ (254 mg, 1.8 mmol) and the mixture stirred at room temperature for 4 hours. The reaction was concentrated under reduced pressure and the residue suspended in dichloromethane (50 mL), and washed with water (10 mL) and brine (10 mL). The organic layer was dried over $Na_2SO_4$, and concentrated under reduced pressure to give the title compound (206 mg, 71%): ESIMS m/z 239 ([M+H]$^+$).

Example 192: Preparation of diethyl(2-((3-chloro-1-(pyridin-3-yl)-1H-pyrazol-4-yl)(ethyl)amino)-2-oxoethyl)phosphonate

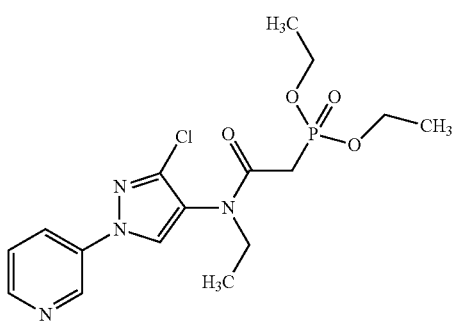 [SMILES: CCOP(=O)(CC(=O)N(CC)c1cn(-c2cccnc2)nc1Cl)OCC]

To a solution of 3-chloro-N-ethyl-1-(pyridin-3-yl)-1H-pyrazol-4-amine (2.00 g, 8.98 mmol), 2-(diethoxyphosphoryl)acetic acid (1.94 mg, 9.88 mmol) and N,N-dimethylpyridin-4-amine (2.20 g, 17.96 mmol) in dry DMF (10 mL) was added N'-((ethylimino)methylene)-$N^3$,$N^3$-dimethylpropane-1,3-diamine hydrochloride (2.58 g, 13.47 mmol), and the mixture was stirred at 0° C. for 2 hours. The mixture was diluted with water and extracted with ethyl acetate (75 mL×2). The combined organic extract was washed with saturated aqueous $NH_4Cl$, sat aqueous $NaHCO_3$ and brine, dried over $MgSO_4$, filtered and concentrated in vacuo to give a brown residue. This residue was purified on silica gel eluting with $CH_2Cl_2$ and methanol to give the title compound as a brown solid (2.62 g, 69%): mp 46-48° C.; $^1$H NMR (400 MHz, CDCl$_3$) δ 9.00 (dd, J=2.7, 0.7 Hz, 1H), 8.62 (dd, J=4.7, 1.4 Hz, 1H), 8.35 (s, 1H), 8.03 (ddd, J=8.3, 2.7, 1.5 Hz, 1H), 7.44 (ddd, J=8.3, 4.8, 0.8 Hz, 1H), 4.28-4.02 (m, 4H), 3.79 (m, 2H), 2.89 (d, J=22.0 Hz, 2H), 1.40-1.22 (m, 6H), 1.17 (t, J=7.2 Hz, 3H); ESIMS m/z 401 [(M+H)$^+$]399 [(M−H)$^−$].

Example 193: Preparation of (E)-N-(3-chloro-1-(pyridin-3-yl)-1H-pyrazol-4-yl)-N-ethyl-5,5,5-trifluoropent-2-enamide (Compound Y2177)

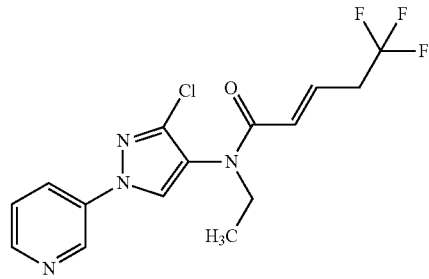 [SMILES: CCN(C(=O)/C=C/CC(F)(F)F)c1cn(-c2cccnc2)nc1Cl]

To a solution of diethyl(2-((3-chloro-1-(pyridin-3-yl)-1H-pyrazol-4-yl)(ethyl)amino)-2-oxoethyl)phosphonate (500 mg, 1.25 mmol) in THF (4 mL) was added sodium hydride (55 mg, 1.37 mmol, 60% wt. oil suspension) and the mixture stirred at 0° C. for 20 min. The mixture was cooled to −78° C. and 3,3,3-trifluoropropanal (210 mg, 1.87 mmol) was added and the reaction was stirred for 1 hour. The mixture was then warmed to room temperature and stirred at room temperature for 2 hours. Additional NaH (30 mg, 0.75 mmol, 60% wt. oil suspension) was added and the mixture stirred at room temperature for 0.5 h. The mixture was diluted with water and ethyl acetate and the organic phase separated, washed with brine, dried over $MgSO_4$ and concentrated in vacuo to give a brown oily residue. This residue was purified on silica gel eluting with $CH_2Cl_2$ and methanol to give the title compound as a light yellow gum (230 mg, 51%).

Example 194: Preparation of N-(3-chloro-1-(pyridin-3-yl)-1H-pyrazol-4-yl)-3-((3,3-difluoroallyl)thio)-N-ethylpropanamide (Compound 918)

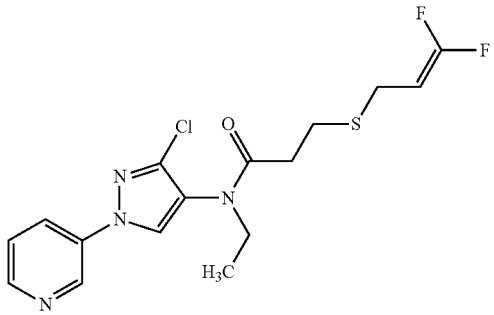 [SMILES: CCN(C(=O)CCSCC=C(F)F)c1cn(-c2cccnc2)nc1Cl]

To a solution of 3-((3-bromo-3,3-difluoropropyl)thio)-N-(3-chloro-1-(pyridin-3-yl)-1H-pyrazol-4-yl)-N-ethylpropanamide (100 mg, 0.21 mmol) in dioxane (1 mL) was added 2,3,4,6,7,8,9,10-octahydropyrimido[1,2-a]azepine (32 mg, 0.21 mmol) and the mixture stirred at 120° C. for 30 min in a Biotage® Initiator microwave reactor with external IR-sensor temperature monitoring from the side of the vessel. The mixture was diluted with ethyl acetate and then washed with saturated aqueous ammonium chloride and brine, dried over $MgSO_4$ and concentrated in vacuo to give a brown gum. This gum was purified on silica gel eluting with methylene chloride and methanol to give the title compound as a light yellow oil (76 mg, 92%).

Example 195: Preparation of 1-(3-chloro-1-(pyridin-3-yl)-1H-pyrazol-4-yl)-3-ethyl-1,3-dimethylurea (Compound Y2012)

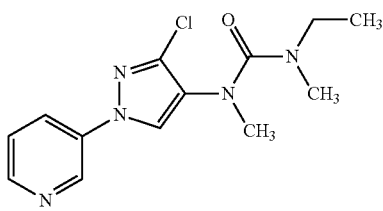 [SMILES: CCN(C)C(=O)N(C)c1cn(-c2cccnc2)nc1Cl]

To a solution of 3-chloro-N-methyl-1-(pyridin-3-yl)-1H-pyrazol-4-amine (0.100 g, 0.48 mmol) in $CH_2Cl_2$ (1.9 ml) was added N-ethyl-N-isopropylpropan-2-amine (0.21 ml, 1.20 mmol) followed by ethyl(methyl)carbamic chloride (0.117 g, 0.959 mmol) and the reaction mixture was stirred at ambient temperature for 2 hours. The reaction was quenched by the addition of saturated sodium bicarbonate. The aqueous layer was extracted with $CH_2Cl_2$. The combined organic layers were dried over sodium sulfate, filtered, concentrated in vacuo and purified via silica gel column chromatography (0-100% ethyl acetate/hexanes) to afford the title compound as a yellow oil (57 mg, 36%).

Example 196: Preparation of N-(3-chloro-1-(pyridin-3-yl)-1H-pyrazol-4-yl)-N-ethyl-2-(2,2,2-trifluoroethoxy)propanamide (Compound Y2001)

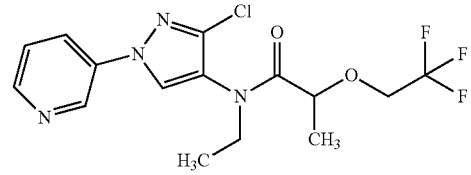 [SMILES: CCN(C(=O)C(C)OCC(F)(F)F)c1cn(-c2cccnc2)nc1Cl]

To a solution of 2,2,2-trifluoroethanol (128 mg, 1.3 mmol) in DMF (1.3 mL) was added sodium hydride (51.1 mg, 1.3 mmol). The reaction mixture was stirred for 30 min until the mixture became clear and no $H_2$ evolution was observed. To this solution was added 2-chloro-N-(3-chloro-1-(pyridin-3-yl)-1H-pyrazol-4-yl)-N-ethylpropanamide (200 mg, 0.64 mmol) and the reaction mixture was stirred at 50° C. overnight. The reaction mixture was diluted with $CH_2Cl_2$ and washed with water, the phases were separated with a Biotage® Phase separator and then concentrated. The residue was purified by silica gel chromatography eluting with 0-50% acetone in hexanes to afford the titled compound as a white solid (156 mg, 64%).

Example 197: Preparation of N-(3-chloro-1-(pyridin-3-yl)-1H-pyrazol-4-yl)-N-ethyl-2-((methylthio)methoxy)propanamide (Compound Y2199)

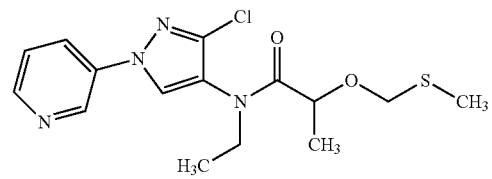 [SMILES: CCN(C(=O)C(C)OCSC)c1cn(-c2cccnc2)nc1Cl]

To a solution of N-(3-chloro-1-(pyridin-3-yl)-1H-pyrazol-4-yl)-N-ethyl-2-hydroxypropanamide (100 mg, 0.34 mmol) in THF (1.1 mL) was added sodium hydride (60% in mineral oil, 33.9 mg, 0.85 mmol). The mixture was stirred for 15 min and then (chloromethyl)(methyl)sulfane (33.6 µL, 0.41 mmol) was added. After stirring at ambient temp overnight the reaction mixture was diluted with $CH_2Cl_2$ and washed with water. The phases were separated and dried with a Biotage® Phases Separator© and concentrated in vacuo. The residue was purified by silica chromatography eluting with 0-70% acetone in hexanes to afford the titled compound as an off white solid (73 mg, 63%).

Example 198: Preparation of N-(3-chloro-1-(pyridin-3-yl)-1H-pyrazol-4-yl)-2,2-difluoro-N-methyl-2-(methylthio)acetamide (Compound Y2021)

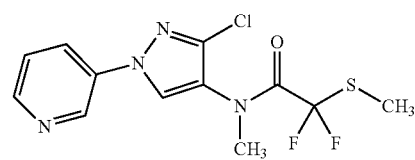 [SMILES: CSC(F)(F)C(=O)N(C)c1cn(-c2cccnc2)nc1Cl]

To a solution of 2-bromo-N-(3-chloro-1-(pyridin-3-yl)-1H-pyrazol-4-yl)-2,2-difluoro-N-methylacetamide (250 mg, 0.684 mmol) in DMSO (2.3 mL) was added methanethiol, sodium salt (96 mg, 1.37 mmol). The reaction mixture was heated to 50° C. for 3 h and then diluted with water and extracted with $CH_2Cl_2$. The organic phases were dried with $MgSO_4$, filtered and concentrated in vacuo. The residue was purified by silica gel chromatography eluting with 0-80% acetone in hexanes to afford the titled compound as a red oil (188 mg, 83%).

Example 199: Preparation of 3-chloro-N-ethyl-1-(pyridin-3-yl)-1H-pyrazol-4-amine To a 100 mL round bottom flask charged with 3-chloro-N-ethyl-1-(pyridin-3-yl)-1H-pyrazol-4-amine-bis HCl salt (2 g, 6.77 mmol) was added DCM (20 mL) and the suspension was stirred at room temperature. To this suspension was added saturated $NaHCO_3$ solution slowly until the bubbling stopped and the aqueous layer became basic. The mixture was loaded into a separatory funnel, the organic layer was separated and the aqueous layer was extracted with DCM (2×10 mL). The combined DCM layers were dried and concentrated to give the title compound as an off-white solid (1.41 g, 94%). Analytical data of 3-chloro-N-ethyl-1-(pyridin-3-yl)-1H-pyrazol-4-amine can be found in Example 8.

Example A: Bioassays on Green Peach APHID ("GPA") (*Myzus persicae*) (MYZUPE)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Certain molecules disclosed in this document were tested against GPA using procedures described in the following example. In the reporting of the results, "Table 3: GPA (MYZUPE) and sweetpotato whitefly-crawler (BEMITA) Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in $H_2O$ to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=$100*(X-Y)/X$ where

X=No. of live aphids on solvent check plants and

Y=No. of live aphids on treated plants

The results are indicated in the table entitled "Table 4. Biological Data for GPA (MYZUPE) and sweetpotato whitefly-crawler (BEMITA)" (See Table Section).

Example B: Insecticidal Test for Sweetpotato Whitefly-Crawler (*Bemisia tabaci*) (BEMITA) in Foliar Spray Assay Cotton plants grown in 3-inch pots, with 1 small (3-5 cm) true leaf, were used as test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbiss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in $H_2O$ to obtain a test solution at 200 ppm. A hand-held Devilbiss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula and presented in "Table 4. Biological Data for GPA (MYZUPE) and sweetpotato whitefly-crawler (BEMITA)" (see column "BEMITA"):

Corrected % Control=$100*(X-Y)/X$ where X=No. of live nymphs on solvent check plants Y=No. of live nymphs on treated plants Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{13}C$ or $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicambatrolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfenethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoproppotassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyrethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, niflurididide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benzenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;

17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidene-hydrazono)methyl)] phenyl mesylate; and
20. N-Ethyl-2,2-dichloro-1-methylcyclopropanecarboxamide-2-(2,6-dichloro-alpha, alpha, alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control— The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources.

Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta*

*australasiae, Periplaneta brunnea, Periplaneta fuliginosa, Pycnoscelus surinamensis,* and *Supella longipalpa.*

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertusfasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarvafrimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunc-* tella, *Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderiafurcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor*.

In another embodiment, the molecules of Formula One may be used to control pest of the Order Symphyla. A non-exhaustive list of particular sp. includes, but is not limited to, *Scutigerella immaculata*.

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis*.

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

TABLE 1
| Compound No. | Appearance | Structure | Prepared as in Example: |
|---|---|---|---|
| 1 | yellow gum | 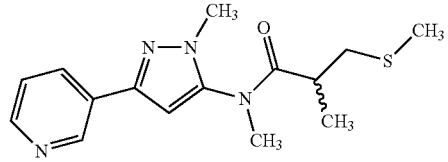 [SMILES: CSCC(C)C(=O)N(C)c1cc(-c2cccnc2)nn1C] | |
| 2 | yellow solid | 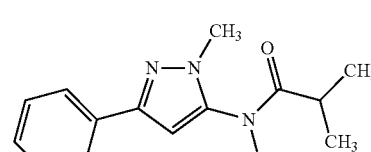 | |
| 3 | yellow gum | 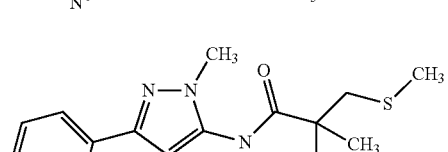 | |
| 4 | yellow oil | 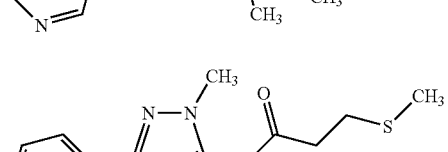 | |
| 5 | yellow oil | 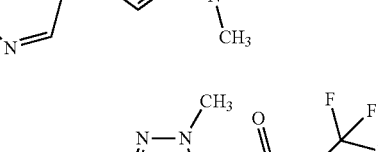 | |
| 6 | yellow gum | 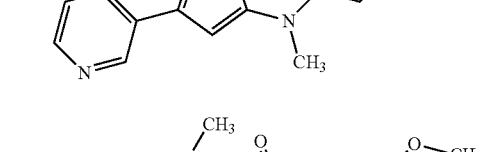 | |
| 7 | yellow gum | 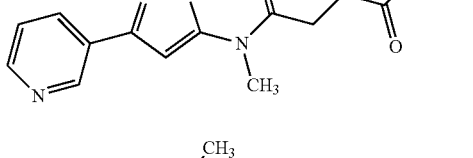 | |
| 8 | yellow gum | 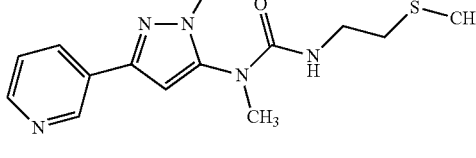 | |

TABLE 1-continued
Compound number, appearance, and structure
| Compound No. | Appearance | Structure | Prepared as in Example: |
|---|---|---|---|
| 9 | beige gum | 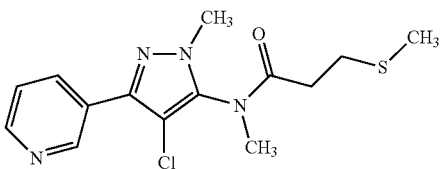 [SMILES: CSCCC(=O)N(C)c1c(Cl)c(-c2cccnc2)nn1C] | |
| 10 | colorless gum | 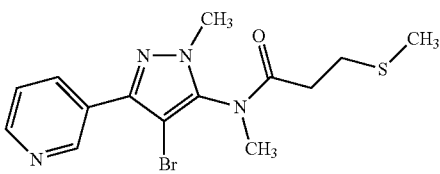 [SMILES: CSCCC(=O)N(C)c1c(Br)c(-c2cccnc2)nn1C] | |
| 12 | colorless glass | 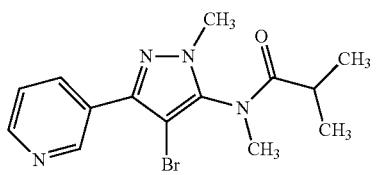 [SMILES: CC(C)C(=O)N(C)c1c(Br)c(-c2cccnc2)nn1C] | |
| 18 | Brown oil | 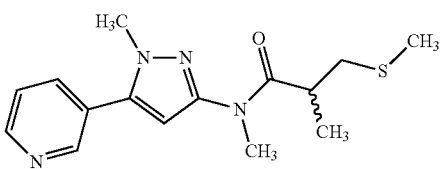 [SMILES: CSCC(C)C(=O)N(C)c1cc(-c2cccnc2)n(C)n1] | |
| 19 | Yellow oil | 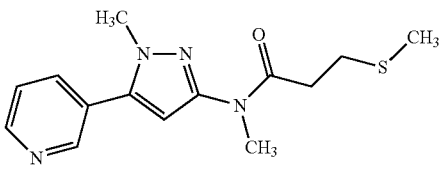 [SMILES: CSCCC(=O)N(C)c1cc(-c2cccnc2)n(C)n1] | |
| 20 | Yellow oil | 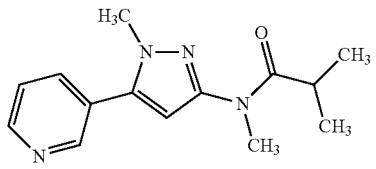 [SMILES: CC(C)C(=O)N(C)c1cc(-c2cccnc2)n(C)n1] | |
| 21 | Yellow oil | 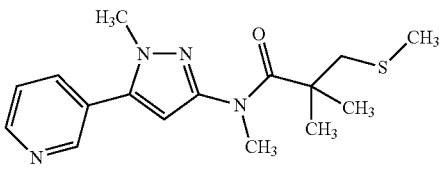 [SMILES: CSCC(C)(C)C(=O)N(C)c1cc(-c2cccnc2)n(C)n1] | |
| 22 | clear oil | 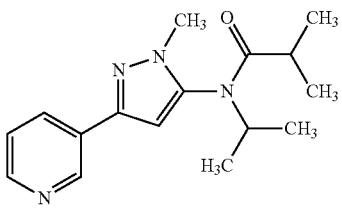 [SMILES: CC(C)C(=O)N(c1cc(-c2cccnc2)nn1C)C(C)C] | |

TABLE 1-continued

Compound number, appearance, and structure

| Compound No. | Appearance | Structure | Prepared as in Example: |
|---|---|---|---|
| 23 | clear oil | 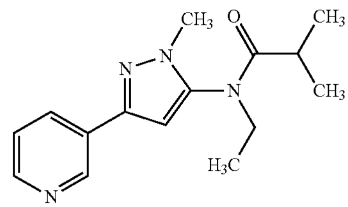 [SMILES: CCN(C(=O)C(C)C)c1cc(-c2cccnc2)nn1C] | |
| 24 | | 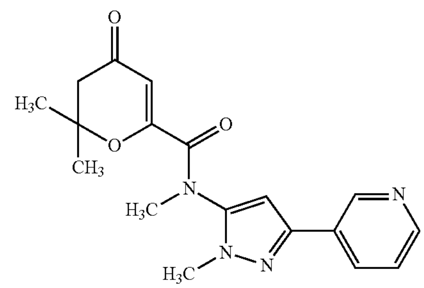 [SMILES: CN(C(=O)C1=CC(=O)CC(C)(C)O1)c1cc(-c2cccnc2)nn1C] | |
| 25 | | 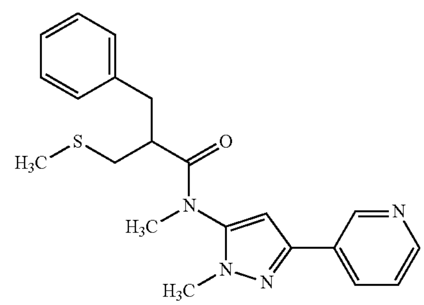 [SMILES: CSCC(Cc1ccccc1)C(=O)N(C)c1cc(-c2cccnc2)nn1C] | |
| 26 | | 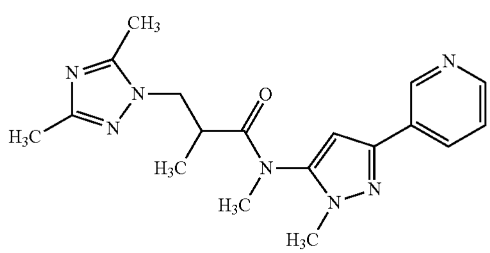 [SMILES: Cc1nc(C)n(CC(C)C(=O)N(C)c2cc(-c3cccnc3)nn2C)n1] | |
| 27 | | 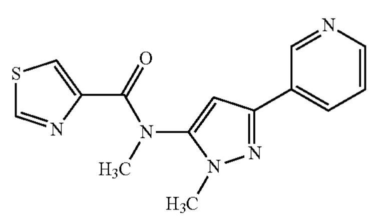 [SMILES: CN(C(=O)c1cscn1)c1cc(-c2cccnc2)nn1C] | |
| 28 | | 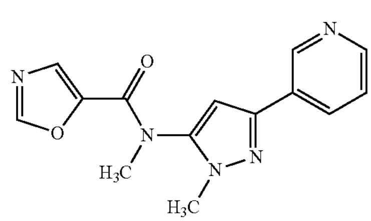 [SMILES: CN(C(=O)c1cnco1)c1cc(-c2cccnc2)nn1C] | |

TABLE 1-continued

Compound number, appearance, and structure

| Compound No. | Appearance | Structure | Prepared as in Example: |
|---|---|---|---|
| 29 | | 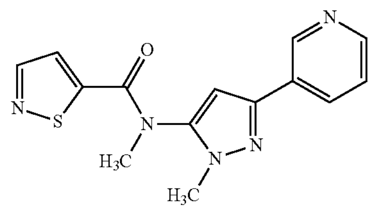 [SMILES: CN(C(=O)c1ccns1)c1cc(-c2cccnc2)nn1C] | |
| 30 | | 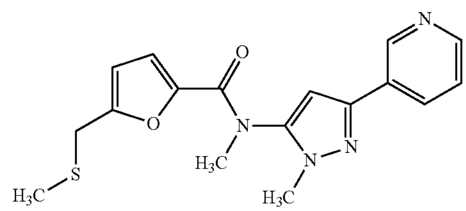 [SMILES: CSCc1ccc(C(=O)N(C)c2cc(-c3cccnc3)nn2C)o1] | |
| 31 | | 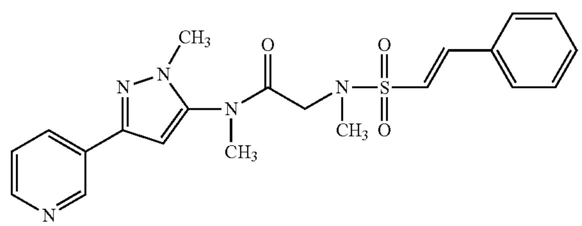 [SMILES: CN(C(=O)CN(C)S(=O)(=O)/C=C/c1ccccc1)c1cc(-c2cccnc2)nn1C] | |
| 32 | Gold syrup | 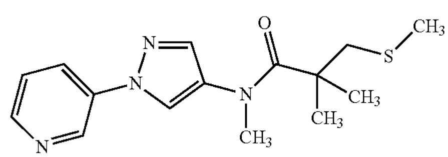 [SMILES: CSCC(C)(C)C(=O)N(C)c1cnn(-c2cccnc2)c1] | |
| 33 | Brown solid | 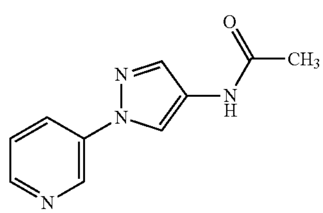 | |
| 34 | Off white solid | 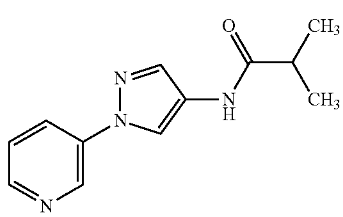 [SMILES: CC(C)C(=O)Nc1cnn(-c2cccnc2)c1] | |
| 35 | Off white solid | 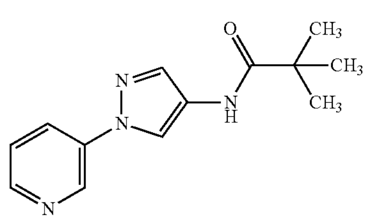 [SMILES: CC(C)(C)C(=O)Nc1cnn(-c2cccnc2)c1] | |

TABLE 1-continued

Compound number, appearance, and structure

| Compound No. | Appearance | Structure | Prepared as in Example: |
|---|---|---|---|
| 36 | Off white solid | 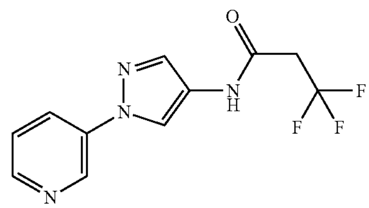 [SMILES: O=C(CC(F)(F)F)Nc1cnn(-c2cccnc2)c1] | |
| 37 | White solid | 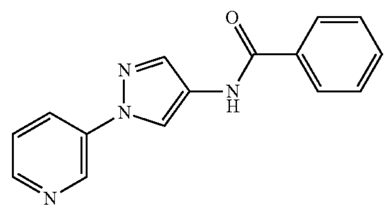 [SMILES: O=C(Nc1cnn(-c2cccnc2)c1)c1ccccc1] | |
| 38 | Off white solid | 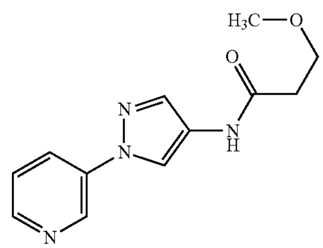 [SMILES: COCCC(=O)Nc1cnn(-c2cccnc2)c1] | |
| 39 | White solid | 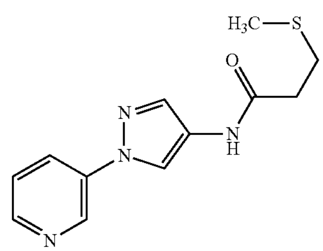 [SMILES: CSCCC(=O)Nc1cnn(-c2cccnc2)c1] | |
| 40 | Pale yellow solid | 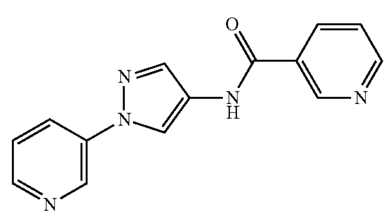 [SMILES: O=C(Nc1cnn(-c2cccnc2)c1)c1cccnc1] | |
| 41 | Brown thick mass | 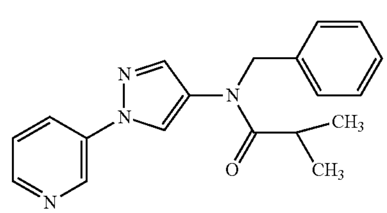 [SMILES: CC(C)C(=O)N(Cc1ccccc1)c1cnn(-c2cccnc2)c1] | |

TABLE 1-continued
Compound number, appearance, and structure
| Compound No. | Appearance | Structure | Prepared as in Example: |
|---|---|---|---|
| 42 | Pale yellow semi solid | 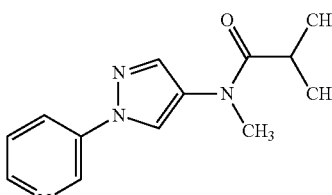 | |
| 43 | Pale yellow solid | 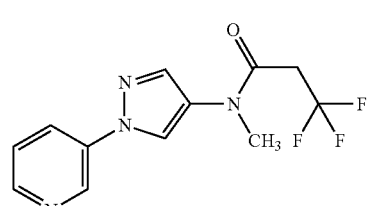 | |
| 44 | White solid | 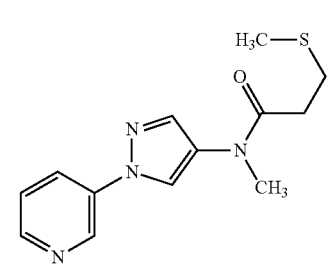 [SMILES: CSCCC(=O)N(C)c1cnn(-c2cccnc2)c1] | |
| 45 | Brown thick mass | 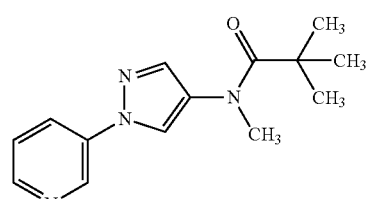 | |
| 46 | Pale yellow thick mass | 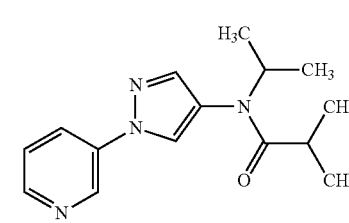 | |
| 47 | Pale yellow thick mass | 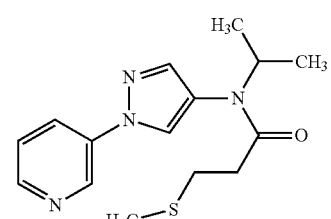 | |

TABLE 1-continued

Compound number, appearance, and structure

| Compound No. | Appearance | Structure | Prepared as in Example: |
|---|---|---|---|
| 48 | Pale green thick mass | 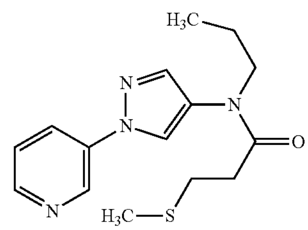 [SMILES: CCCN(C(=O)CCSC)c1cnn(-c2cccnc2)c1] | |
| 49 | Pale yellow solid | 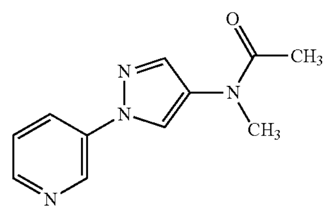 [SMILES: CC(=O)N(C)c1cnn(-c2cccnc2)c1] | |
| 50 | Brown thick mass | 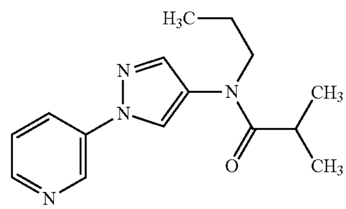 [SMILES: CCCN(C(=O)C(C)C)c1cnn(-c2cccnc2)c1] | |
| 51 | Pale yellow thick mass | 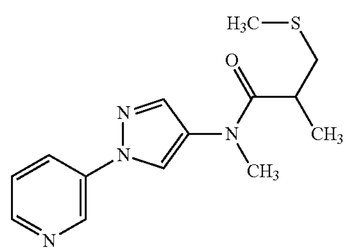 [SMILES: CSCC(C)C(=O)N(C)c1cnn(-c2cccnc2)c1] | |
| 52 | tan solid | 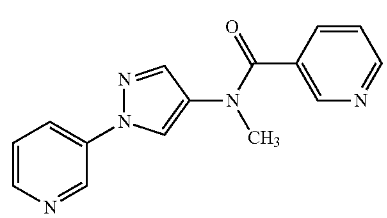 [SMILES: CN(C(=O)c1cccnc1)c1cnn(-c2cccnc2)c1] | |
| 53 | White Solid | 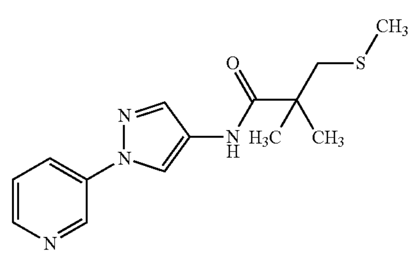 [SMILES: CSCC(C)(C)C(=O)Nc1cnn(-c2cccnc2)c1] | |

TABLE 1-continued

Compound number, appearance, and structure

| Compound No. | Appearance | Structure | Prepared as in Example: |
|---|---|---|---|
| 54 | Clear Oil | 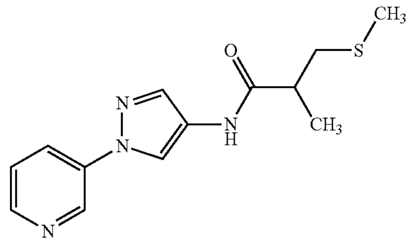 [SMILES: CSCC(C)C(=O)Nc1cnn(-c2cccnc2)c1] | |
| 55 | White Semi Solid | 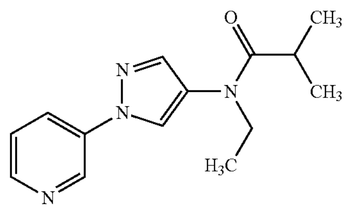 [SMILES: CCN(C(=O)C(C)C)c1cnn(-c2cccnc2)c1] | |
| 56 | Brown Solid | 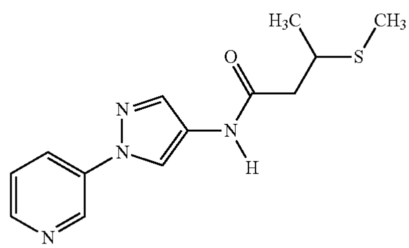 [SMILES: CSC(C)CC(=O)Nc1cnn(-c2cccnc2)c1] | |
| 57 | White Solid | 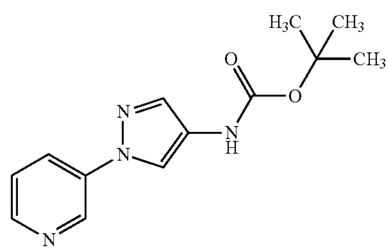 [SMILES: CC(C)(C)OC(=O)Nc1cnn(-c2cccnc2)c1] | |
| 58 | Clear Oil | 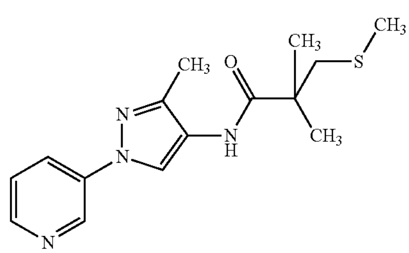 [SMILES: CSCC(C)(C)C(=O)Nc1cn(-c2cccnc2)nc1C] | |
| 59 | White Solid | 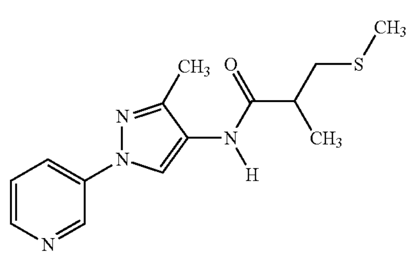 [SMILES: CSCC(C)C(=O)Nc1cn(-c2cccnc2)nc1C] | |

TABLE 1-continued

Compound number, appearance, and structure

| Compound No. | Appearance | Structure | Prepared as in Example: |
|---|---|---|---|
| 60 | White Solid | 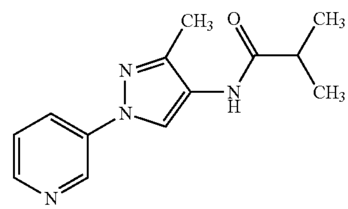 | |
| 61 | Light Yellow Solid | 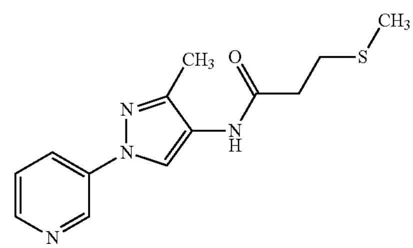 [SMILES: CSCCC(=O)Nc1cn(-c2cccnc2)nc1C] | |
| 62 | Clear Oil | 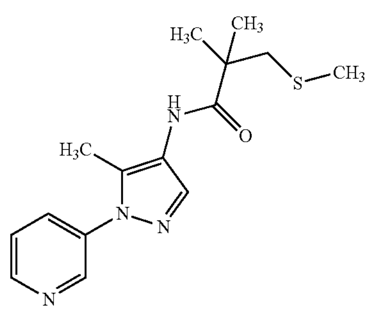 [SMILES: CSCC(C)(C)C(=O)Nc1cnn(-c2cccnc2)c1C] | |
| 63 | Light Yellow Solid | 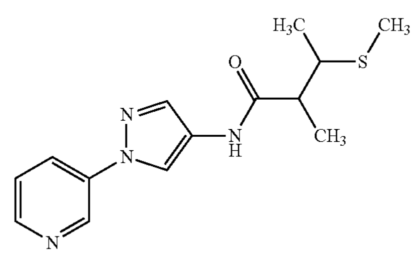 [SMILES: CSC(C)C(C)C(=O)Nc1cnn(-c2cccnc2)c1] | |
| 64 | White Solid | 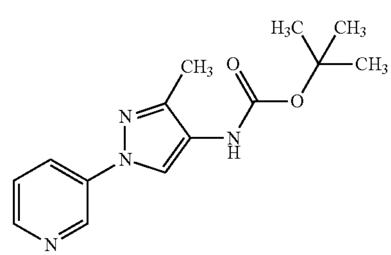 [SMILES: Cc1nn(-c2cccnc2)cc1NC(=O)OC(C)(C)C] | |
| 65 | White Solid | 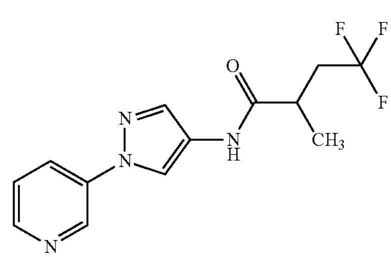 [SMILES: CC(CC(F)(F)F)C(=O)Nc1cnn(-c2cccnc2)c1] | |

TABLE 1-continued

Compound number, appearance, and structure

| Compound No. | Appearance | Structure | Prepared as in Example: |
|---|---|---|---|
| 66 | White Semi Solid | 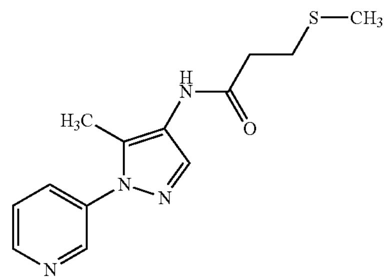 [SMILES: CSCCC(=O)Nc1cnn(-c2cccnc2)c1C] | |
| 67 | Yellow Semi Solid | 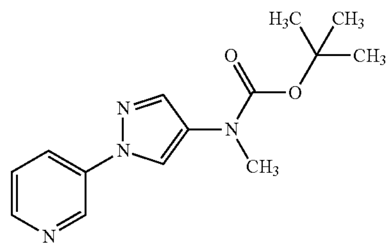 [SMILES: CN(C(=O)OC(C)(C)C)c1cnn(-c2cccnc2)c1] | |
| 68 | Clear Oil | 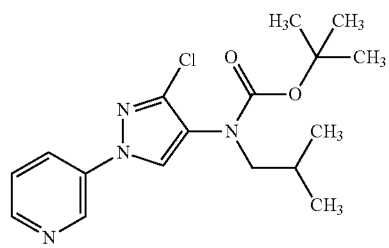 [SMILES: CC(C)CN(C(=O)OC(C)(C)C)c1cn(-c2cccnc2)nc1Cl] | |
| 69 | Dark Brown Oil | 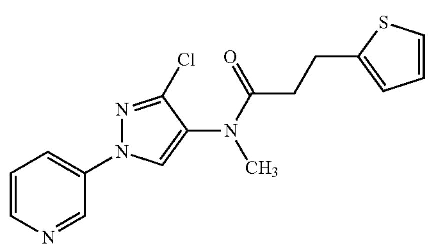 [SMILES: CN(C(=O)CCc1cccs1)c1cn(-c2cccnc2)nc1Cl] | |
| 70 | Viscous Pale Yellow Oil | 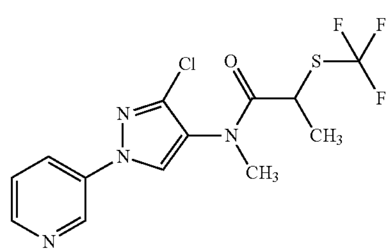 [SMILES: CC(SC(F)(F)F)C(=O)N(C)c1cn(-c2cccnc2)nc1Cl] | |
| 71 | White Solid | 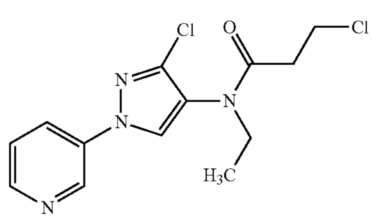 [SMILES: CCN(C(=O)CCCl)c1cn(-c2cccnc2)nc1Cl] | |

TABLE 1-continued

Compound number, appearance, and structure

| Compound No. | Appearance | Structure | Prepared as in Example: |
|---|---|---|---|
| 72 | White Semi Solid | 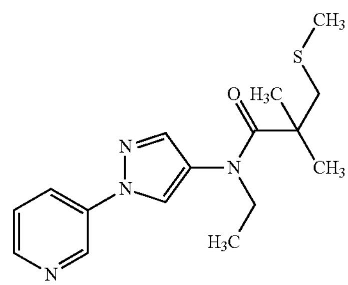 [SMILES: CCN(C(=O)C(C)(C)CSC)c1cnn(-c2cccnc2)c1] | |
| 73 | White Semi Solid | 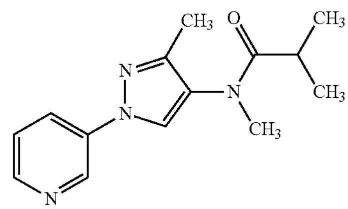 [SMILES: Cc1nn(-c2cccnc2)cc1N(C)C(=O)C(C)C] | |
| 74 | Clear Oil | 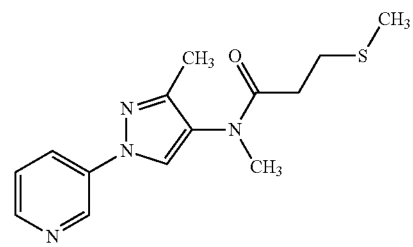 [SMILES: CSCCC(=O)N(C)c1cn(-c2cccnc2)nc1C] | |
| 75 | White Semi Solid | 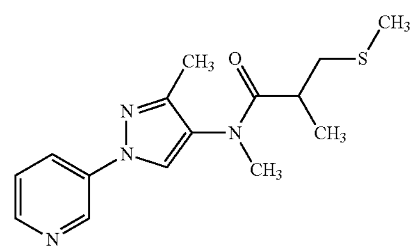 [SMILES: CSCC(C)C(=O)N(C)c1cn(-c2cccnc2)nc1C] | |
| 76 | Clear Oil | 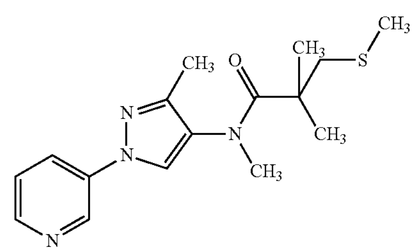 [SMILES: CSCC(C)(C)C(=O)N(C)c1cn(-c2cccnc2)nc1C] | |
| 77 | White Solid | 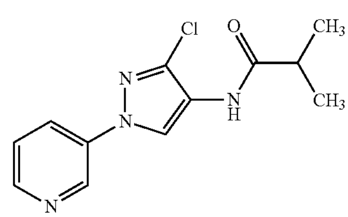 [SMILES: CC(C)C(=O)Nc1cn(-c2cccnc2)nc1Cl] | |

TABLE 1-continued
Compound number, appearance, and structure
| Compound No. | Appearance | Structure | Prepared as in Example: |
|---|---|---|---|
| 78 | White Solid | 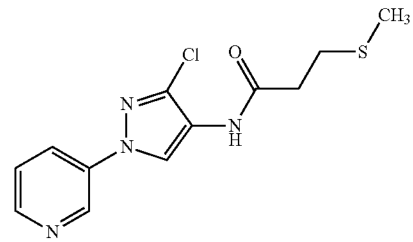 [SMILES: CSCCC(=O)Nc1cn(-c2cccnc2)nc1Cl] | |
| 79 | White Solid | 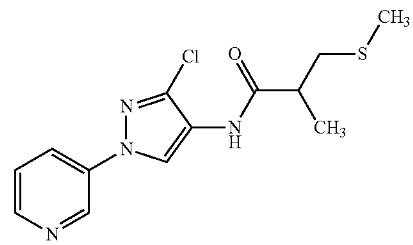 [SMILES: CSCC(C)C(=O)Nc1cn(-c2cccnc2)nc1Cl] | |
| 80 | White Solid | 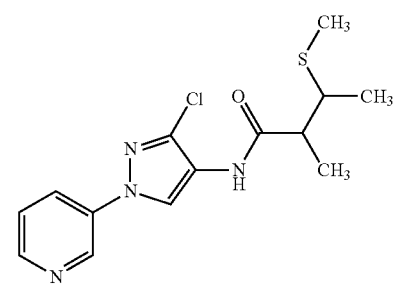 [SMILES: CSC(C)C(C)C(=O)Nc1cn(-c2cccnc2)nc1Cl] | |
| 81 | White Solid | 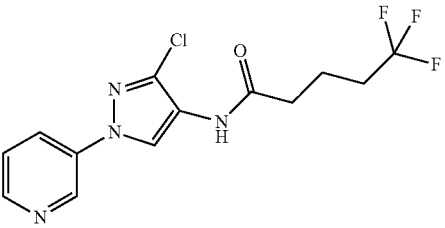 [SMILES: O=C(CCCC(F)(F)F)Nc1cn(-c2cccnc2)nc1Cl] | |
| 82 | White Solid | 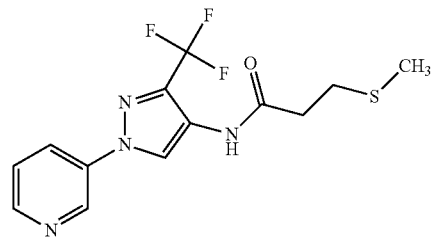 [SMILES: CSCCC(=O)Nc1cn(-c2cccnc2)nc1C(F)(F)F] | |
| 83 | White Solid | 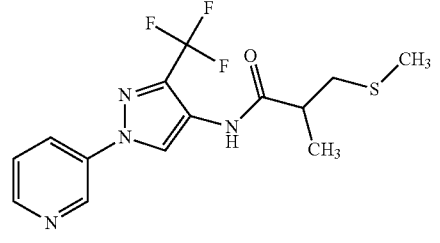 [SMILES: CSCC(C)C(=O)Nc1cn(-c2cccnc2)nc1C(F)(F)F] | |

TABLE 1-continued

Compound number, appearance, and structure

| Compound No. | Appearance | Structure | Prepared as in Example: |
|---|---|---|---|
| 84 | White Solid | 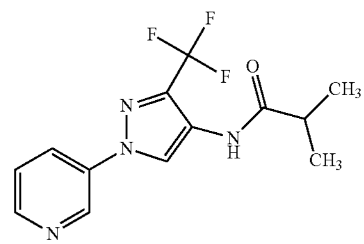 [SMILES: CC(C)C(=O)Nc1cn(-c2cccnc2)nc1C(F)(F)F] | |
| 85 | Off-White Solid | 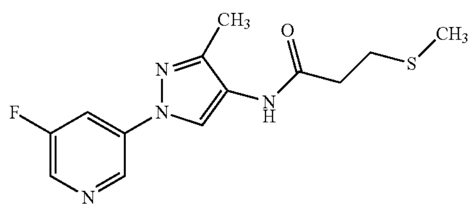 [SMILES: CSCCC(=O)Nc1cn(-c2cncc(F)c2)nc1C] | |
| 86 | Yellow Solid | 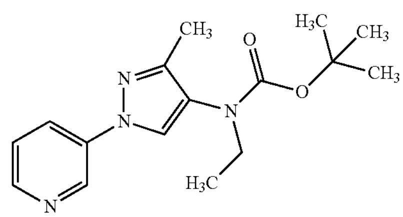 [SMILES: CCN(C(=O)OC(C)(C)C)c1cn(-c2cccnc2)nc1C] | |
| 87 | Yellow Solid | 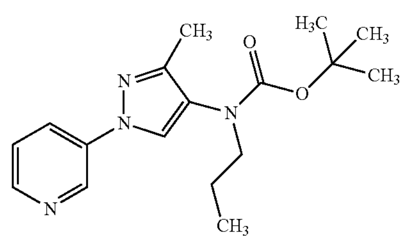 [SMILES: CCCN(C(=O)OC(C)(C)C)c1cn(-c2cccnc2)nc1C] | |
| 88 | White Solid | 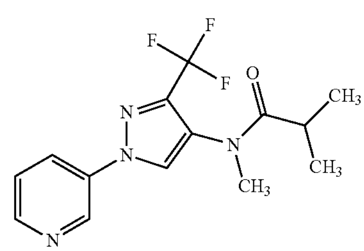 [SMILES: CC(C)C(=O)N(C)c1cn(-c2cccnc2)nc1C(F)(F)F] | |
| 89 | White Solid | 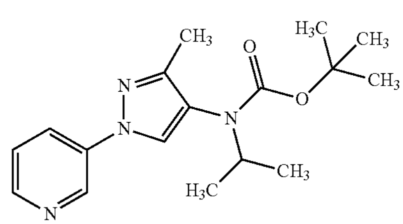 [SMILES: Cc1nn(-c2cccnc2)cc1N(C(=O)OC(C)(C)C)C(C)C] | |

TABLE 1-continued

Compound number, appearance, and structure

| Compound No. | Appearance | Structure | Prepared as in Example: |
|---|---|---|---|
| 90 | Clear Oil | 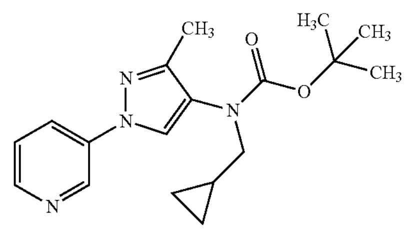 [SMILES: Cc1nn(-c2cccnc2)cc1N(CC1CC1)C(=O)OC(C)(C)C] | |
| 91 | Faint Yellow Oil | 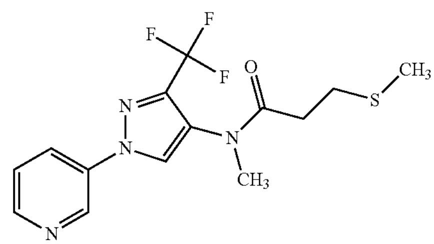 [SMILES: CSCCC(=O)N(C)c1cn(-c2cccnc2)nc1C(F)(F)F] | |
| 92 | Faint Yellow Oil | 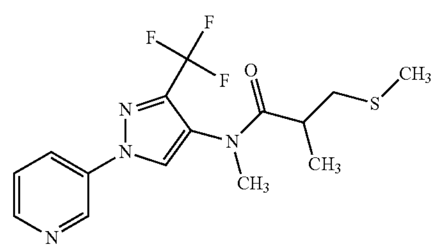 [SMILES: CSCC(C)C(=O)N(C)c1cn(-c2cccnc2)nc1C(F)(F)F] | |
| 93 | White Solid | 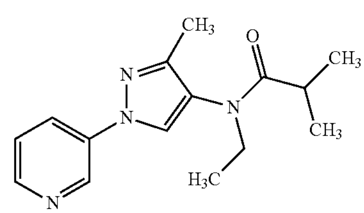 | |
| 94 | Clear Oil | 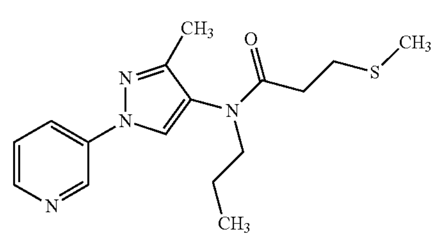 [SMILES: CCCN(C(=O)CCSC)c1cn(-c2cccnc2)nc1C] | |
| 95 | Clear Oil | 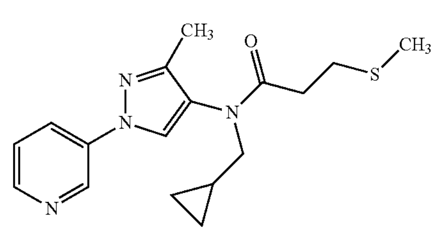 [SMILES: CSCCC(=O)N(CC1CC1)c1cn(-c2cccnc2)nc1C] | |

TABLE 1-continued
Compound number, appearance, and structure
| Compound No. | Appearance | Structure | Prepared as in Example: |
|---|---|---|---|
| 96 | Yellow Solid | 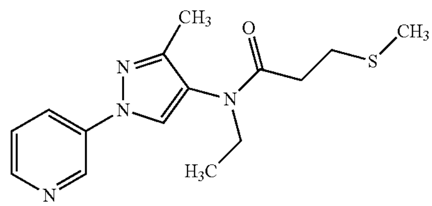 [SMILES: CCN(C(=O)CCSC)c1cn(-c2cccnc2)nc1C] | |
| 97 | Yellow Oil | 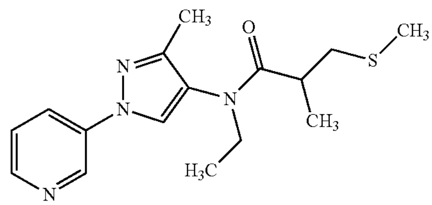 [SMILES: CCN(C(=O)C(C)CSC)c1cn(-c2cccnc2)nc1C] | |
| 98 | Yellow Oil | 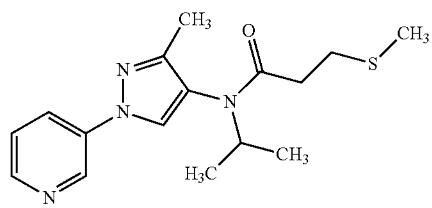 [SMILES: CSCCC(=O)N(c1cn(-c2cccnc2)nc1C)C(C)C] | |
| 99 | Yellow Solid | 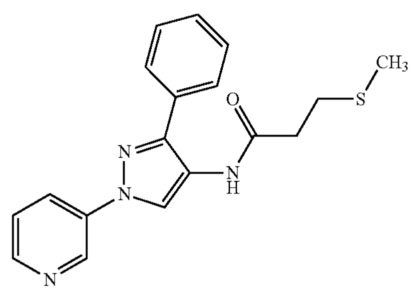 [SMILES: CSCCC(=O)Nc1cn(-c2cccnc2)nc1-c1ccccc1] | |
| 100 | Clear Oil | 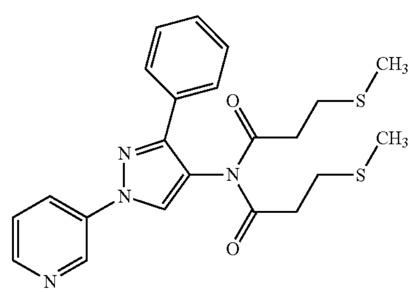 [SMILES: CSCCC(=O)N(C(=O)CCSC)c1cn(-c2cccnc2)nc1-c1ccccc1] | |
| 101 | Clear Oil | 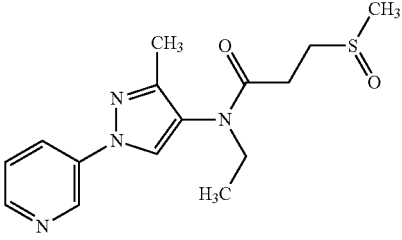 [SMILES: CCN(C(=O)CCS(C)=O)c1cn(-c2cccnc2)nc1C] | |

TABLE 1-continued

Compound number, appearance, and structure

| Compound No. | Appearance | Structure | Prepared as in Example: |
|---|---|---|---|
| 102 | Clear Oil | 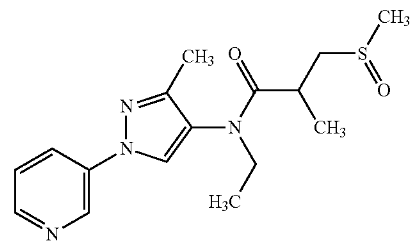 [SMILES: CCN(C(=O)C(C)CS(C)=O)c1cn(-c2cccnc2)nc1C] | |
| 103 | Clear Oil | 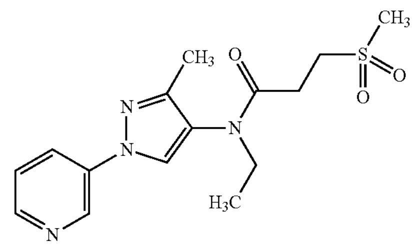 [SMILES: CCN(C(=O)CCS(C)(=O)=O)c1cn(-c2cccnc2)nc1C] | |
| 104 | Faint Yellow Oil | 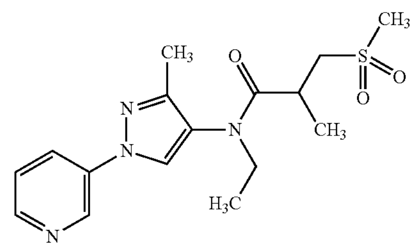 [SMILES: CCN(C(=O)C(C)CS(C)(=O)=O)c1cn(-c2cccnc2)nc1C] | |
| 105 | Off-White Solid | 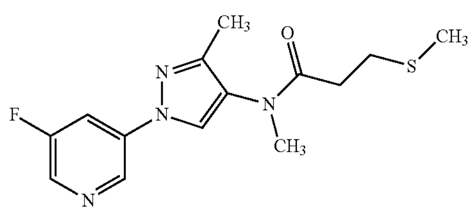 [SMILES: CSCCC(=O)N(C)c1cn(-c2cncc(F)c2)nc1C] | |
| 106 | Faint Yellow Oil | 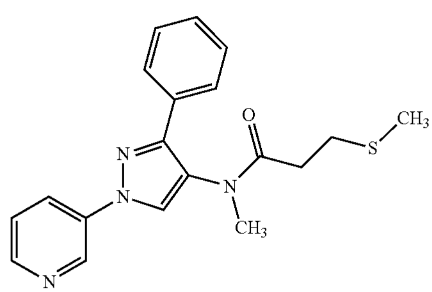 [SMILES: CSCCC(=O)N(C)c1cn(-c2cccnc2)nc1-c1ccccc1] | |
| 107 | White Solid | 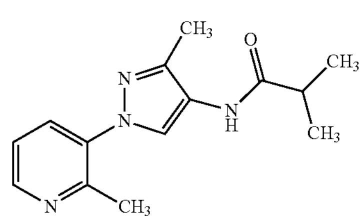 [SMILES: Cc1nn(-c2cccnc2C)cc1NC(=O)C(C)C] | |

TABLE 1-continued

Compound number, appearance, and structure

| Compound No. | Appearance | Structure | Prepared as in Example: |
|---|---|---|---|
| 108 | Clear Oil | 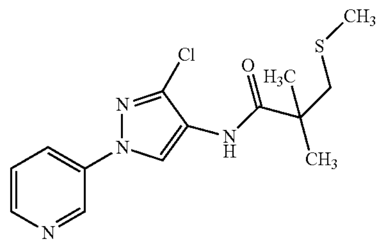 [SMILES: CSCC(C)(C)C(=O)Nc1cn(-c2cccnc2)nc1Cl] | |
| 109 | Yellow Solid | 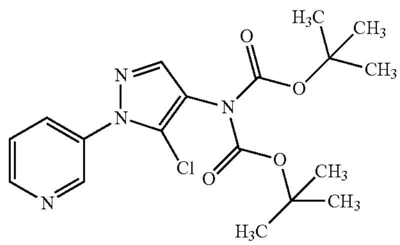 [SMILES: CC(C)(C)OC(=O)N(C(=O)OC(C)(C)C)c1cnn(-c2cccnc2)c1Cl] | |
| 110 | Brown Oil | 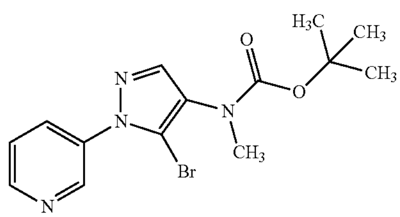 [SMILES: CN(C(=O)OC(C)(C)C)c1cnn(-c2cccnc2)c1Br] | |
| 111 | Yellow Solid | 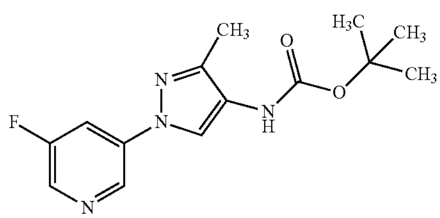 [SMILES: Cc1nn(-c2cncc(F)c2)cc1NC(=O)OC(C)(C)C] | |
| 112 | Brown Oil | 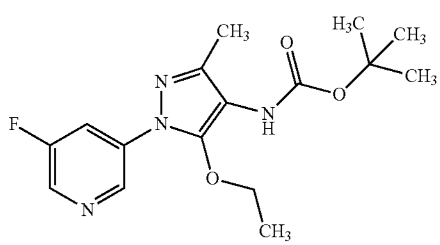 [SMILES: CCOc1c(NC(=O)OC(C)(C)C)c(C)nn1-c1cncc(F)c1] | |
| 113 | Yellow Oil | 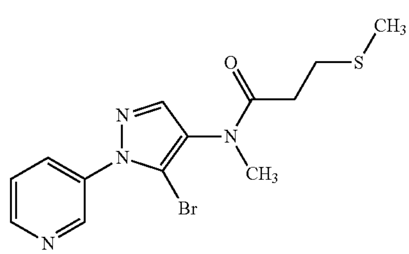 [SMILES: CSCCC(=O)N(C)c1cnn(-c2cccnc2)c1Br] | |

TABLE 1-continued
Compound number, appearance, and structure
| Compound No. | Appearance | Structure | Prepared as in Example: |
|---|---|---|---|
| 114 | Brown Oil | 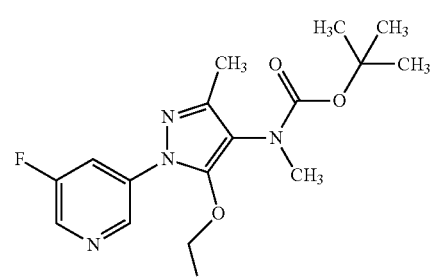 | |
| 115 | Light Brown Solid | 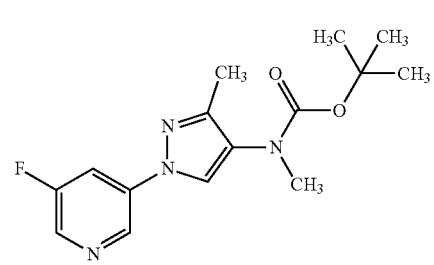 [SMILES: Cc1nn(-c2cncc(F)c2)cc1N(C)C(=O)OC(C)(C)C] | |
| 116 | Yellow Solid | 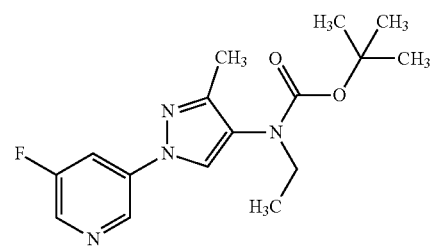 [SMILES: CCN(C(=O)OC(C)(C)C)c1cn(-c2cncc(F)c2)nc1C] | |
| 117 | Yellow Oil | 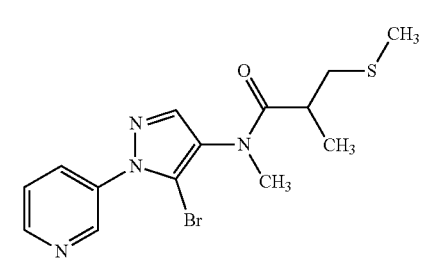 [SMILES: CSCC(C)C(=O)N(C)c1cnn(-c2cccnc2)c1Br] | |
| 118 | Brown Oil | 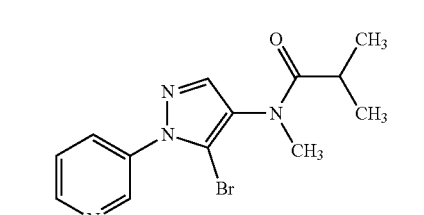 | |

TABLE 1-continued

Compound number, appearance, and structure

| Compound No. | Appearance | Structure | Prepared as in Example: |
|---|---|---|---|
| 119 | Brown Oil | 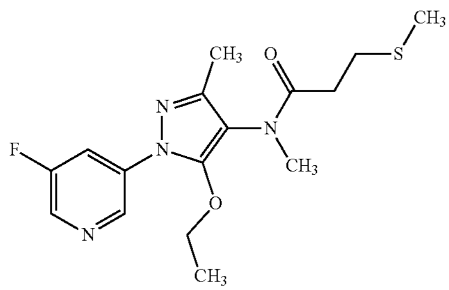 [SMILES: CCOc1c(N(C)C(=O)CCSC)c(C)nn1-c1cncc(F)c1] | |
| 120 | Brown Oil | 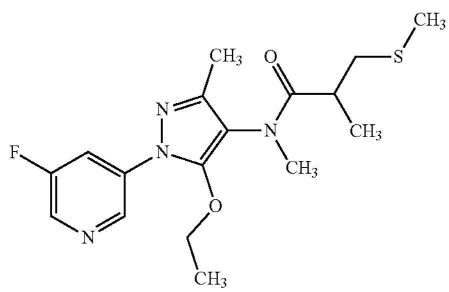 [SMILES: CCOc1c(N(C)C(=O)C(C)CSC)c(C)nn1-c1cncc(F)c1] | |
| 121 | Off-White Solid | 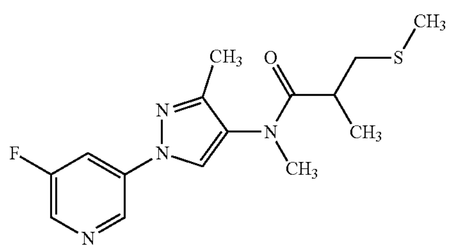 [SMILES: CSCC(C)C(=O)N(C)c1cn(-c2cncc(F)c2)nc1C] | |
| 122 | Faint Yellow Solid | 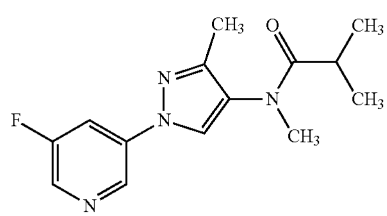 [SMILES: Cc1nn(-c2cncc(F)c2)cc1N(C)C(=O)C(C)C] | |
| 123 | Clear Oil | 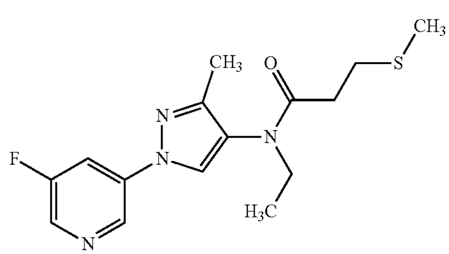 [SMILES: CCN(C(=O)CCSC)c1cn(-c2cncc(F)c2)nc1C] | |

TABLE 1-continued

Compound number, appearance, and structure

| Compound No. | Appearance | Structure | Prepared as in Example: |
|---|---|---|---|
| 124 | Yellow Solid | 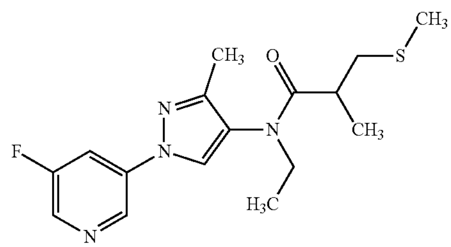 [SMILES: CCN(C(=O)C(C)CSC)c1cn(-c2cncc(F)c2)nc1C] | |
| 125 | White Solid | 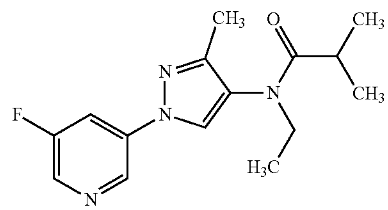 [SMILES: CCN(C(=O)C(C)C)c1cn(-c2cncc(F)c2)nc1C] | |
| 126 | Yellow Oil | 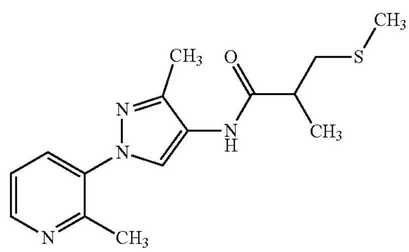 [SMILES: CSCC(C)C(=O)Nc1cn(-c2cccnc2C)nc1C] | |
| 127 | Yellow Oil | 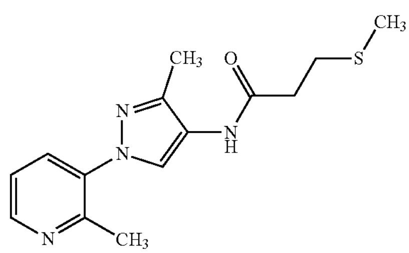 [SMILES: CSCCC(=O)Nc1cn(-c2cccnc2C)nc1C] | |
| 128 | Neon Yellow Oil | 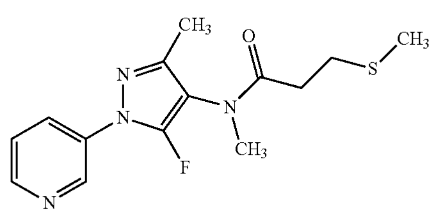 [SMILES: CSCCC(=O)N(C)c1c(C)nn(-c2cccnc2)c1F] | |
| 129 | Neon Yellow Oil | 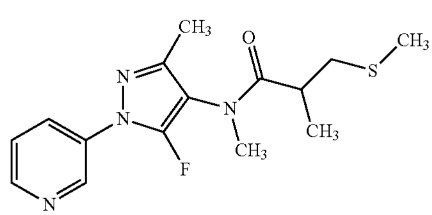 [SMILES: CSCC(C)C(=O)N(C)c1c(C)nn(-c2cccnc2)c1F] | |

TABLE 1-continued

Compound number, appearance, and structure

| Compound No. | Appearance | Structure | Prepared as in Example: |
|---|---|---|---|
| 130 | Pink Solid | 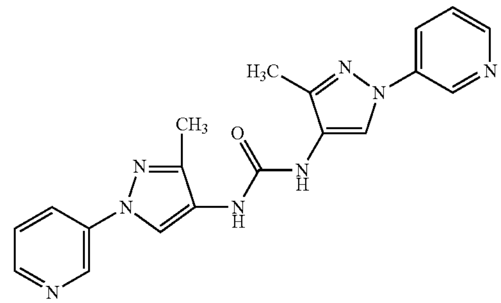 [SMILES: Cc1nn(-c2cccnc2)cc1NC(=O)Nc1cn(-c2cccnc2)nc1C] | |
| 131 | Red Oil | 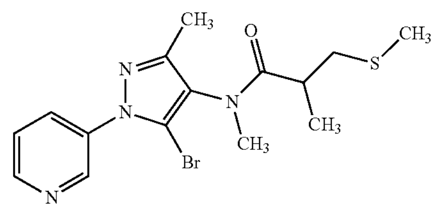 | |
| 132 | Yellow Oil | 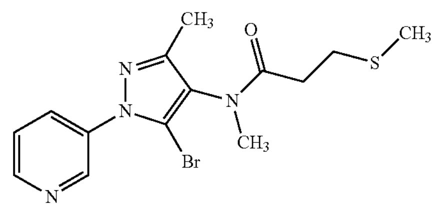 [SMILES: CSCCC(=O)N(C)c1c(C)nn(-c2cccnc2)c1Br] | |
| 133 | Yellow Oil | 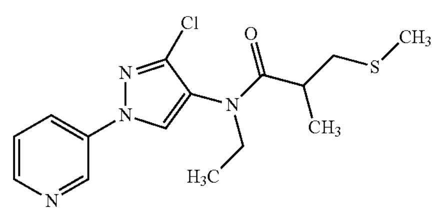 | |
| 134 | Clear Oil | 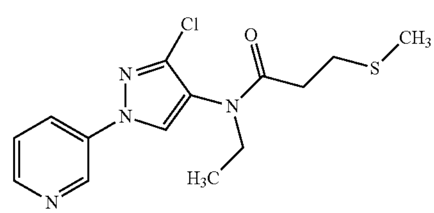 [SMILES: CCN(C(=O)CCSC)c1cn(-c2cccnc2)nc1Cl] | |
| 135 | Off-White Solid | 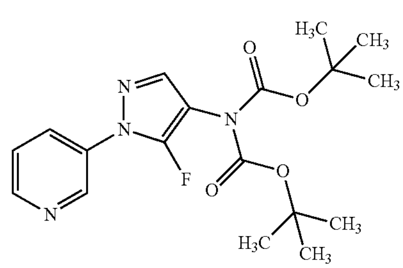 [SMILES: CC(C)(C)OC(=O)N(C(=O)OC(C)(C)C)c1cnn(-c2cccnc2)c1F] | |

TABLE 1-continued
Compound number, appearance, and structure
| Compound No. | Appearance | Structure | Prepared as in Example: |
|---|---|---|---|
| 136 | Yellow Oil | 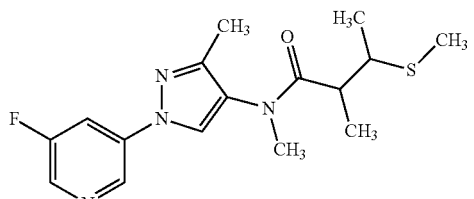 | |
| 137 | Yellow Oil | 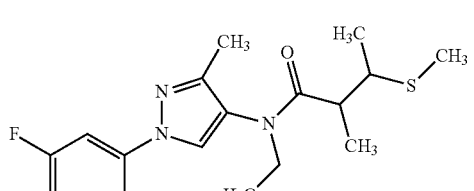 | |
| 138 | Yellow Oil | 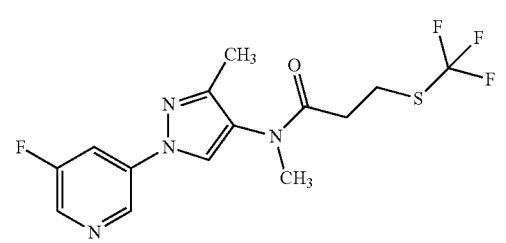 [SMILES: Cc1nn(-c2cncc(F)c2)cc1N(C)C(=O)CCSC(F)(F)F] | |
| 139 | Faint Yellow Oil | 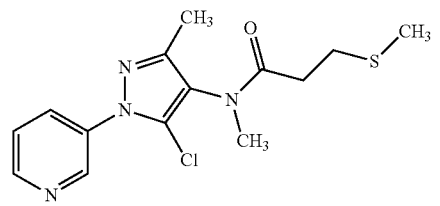 | |
| 140 | Faint Yellow | 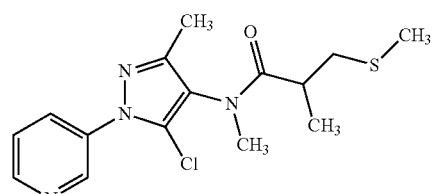 | |
| 141 | Light Yellow Solid | 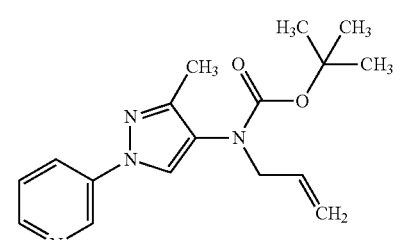 | |

TABLE 1-continued
Compound number, appearance, and structure
| Compound No. | Appearance | Structure | Prepared as in Example: |
|---|---|---|---|
| 142 | Clear Oil | 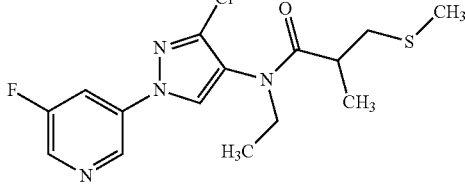 | |
| 143 | Colorless Oil | 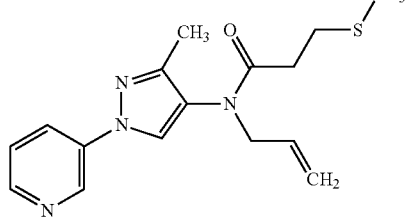 | |
| 144 | Colorless Oil | 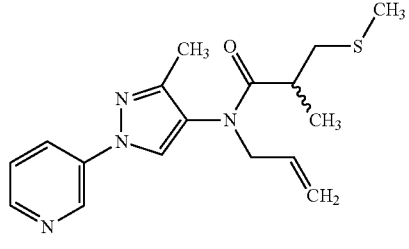 [SMILES: C=CCN(C(=O)C(C)CSC)c1cn(-c2cccnc2)nc1C] | |
| 145 | White Solid | 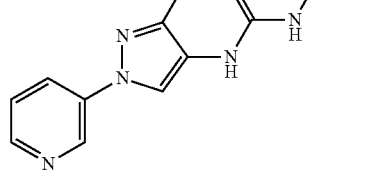 | |
| 146 | Gray Oil | 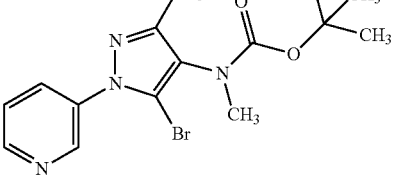 | |
| 147 | Colorless Oil | 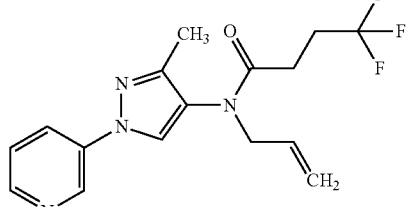 | |

TABLE 1-continued

Compound number, appearance, and structure

| Compound No. | Appearance | Structure | Prepared as in Example: |
|---|---|---|---|
| 148 | White Solid | 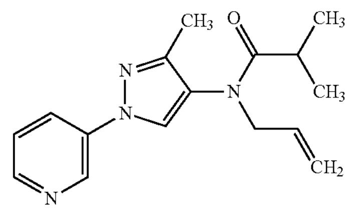 [SMILES: C=CCN(C(=O)C(C)C)c1cn(-c2cccnc2)nc1C] | |
| 149 | Yellow Solid | 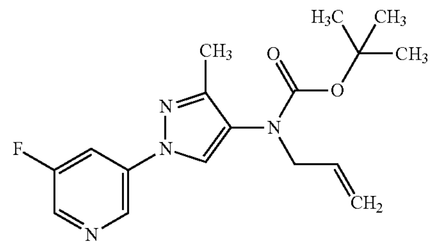 [SMILES: C=CCN(C(=O)OC(C)(C)C)c1cn(-c2cncc(F)c2)nc1C] | |
| 150 | White Solid | 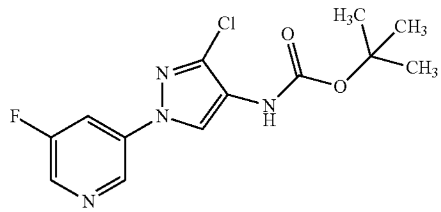 [SMILES: CC(C)(C)OC(=O)Nc1cn(-c2cncc(F)c2)nc1Cl] | |
| 151 | Clear Oil | 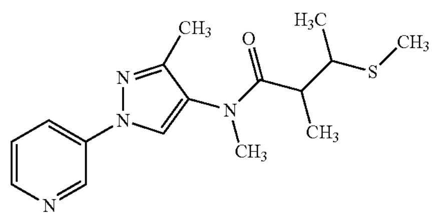 [SMILES: CSC(C)C(C)C(=O)N(C)c1cn(-c2cccnc2)nc1C] | |
| 152 | Clear Oil | 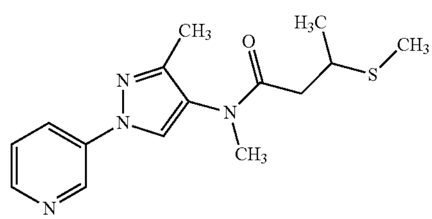 [SMILES: CSC(C)CC(=O)N(C)c1cn(-c2cccnc2)nc1C] | |
| 153 | White Solid | 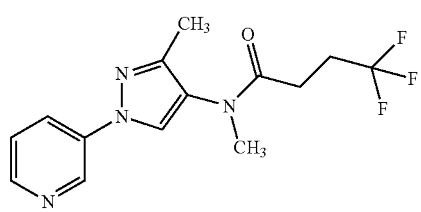 [SMILES: Cc1nn(-c2cccnc2)cc1N(C)C(=O)CCC(F)(F)F] | |

TABLE 1-continued

Compound number, appearance, and structure

| Compound No. | Appearance | Structure | Prepared as in Example: |
|---|---|---|---|
| 154 | Faint Orange Oil | 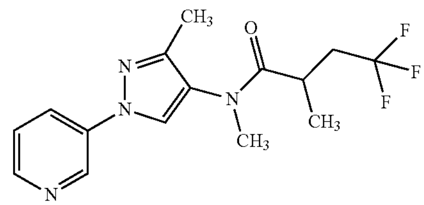 [SMILES: Cc1nn(-c2cccnc2)cc1N(C)C(=O)C(C)CC(F)(F)F] | |
| 155 | Clear Oil | 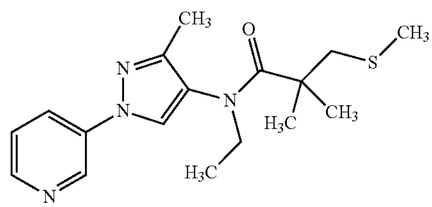 [SMILES: CCN(C(=O)C(C)(C)CSC)c1cn(-c2cccnc2)nc1C] | |
| 156 | Clear Oil | 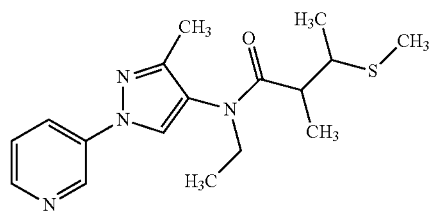 | |
| 157 | Clear Oil | 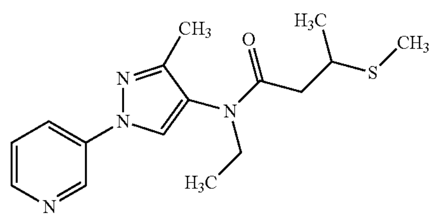 [SMILES: CCN(C(=O)CC(C)SC)c1cn(-c2cccnc2)nc1C] | |
| 158 | Clear Oil | 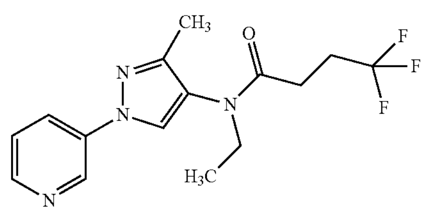 [SMILES: CCN(C(=O)CCC(F)(F)F)c1cn(-c2cccnc2)nc1C] | |
| 159 | Clear Oil | 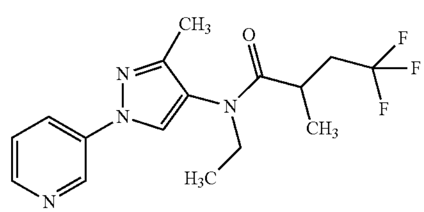 [SMILES: CCN(C(=O)C(C)CC(F)(F)F)c1cn(-c2cccnc2)nc1C] | |
| 160 | White Solid | 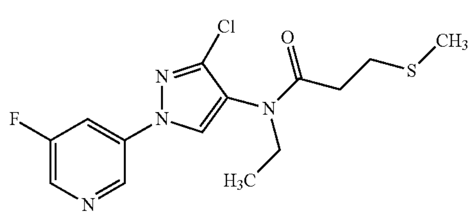 [SMILES: CCN(C(=O)CCSC)c1cn(-c2cncc(F)c2)nc1Cl] | |

TABLE 1-continued

Compound number, appearance, and structure

| Compound No. | Appearance | Structure | Prepared as in Example: |
|---|---|---|---|
| 161 | Brown Oil | 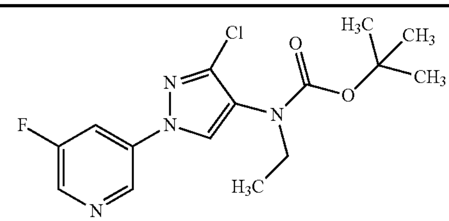 | |
| 162 | Light Brown Solid | 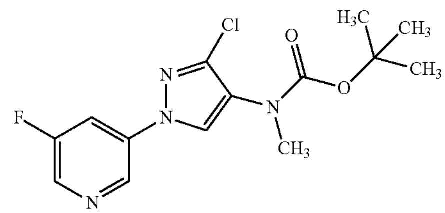 [SMILES: CN(C(=O)OC(C)(C)C)c1cn(-c2cncc(F)c2)nc1Cl] | |
| 163 | White Solid | 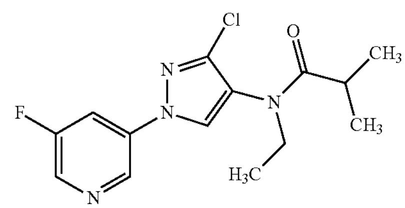 [SMILES: CCN(C(=O)C(C)C)c1cn(-c2cncc(F)c2)nc1Cl] | |
| 164 | White Solid | 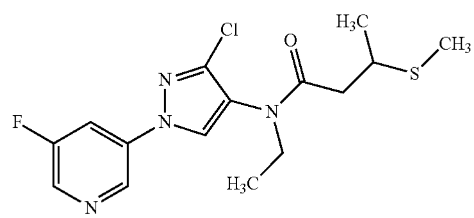 [SMILES: CCN(C(=O)CC(C)SC)c1cn(-c2cncc(F)c2)nc1Cl] | |
| 165 | White Solid | 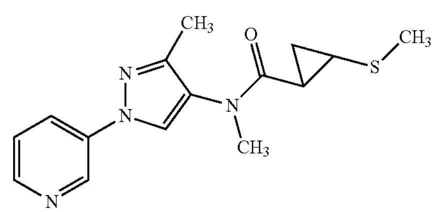 [SMILES: CSC1CC1C(=O)N(C)c1cn(-c2cccnc2)nc1C] | |
| 166 | Yellow Oil | 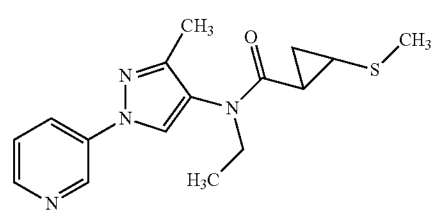 [SMILES: CCN(C(=O)C1CC1SC)c1cn(-c2cccnc2)nc1C] | |
| 167 | Grey Oil | 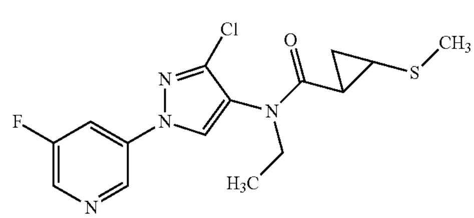 [SMILES: CCN(C(=O)C1CC1SC)c1cn(-c2cncc(F)c2)nc1Cl] | |

TABLE 1-continued

Compound number, appearance, and structure

| Compound No. | Appearance | Structure | Prepared as in Example: |
|---|---|---|---|
| 168 | Faint Purple Oil | 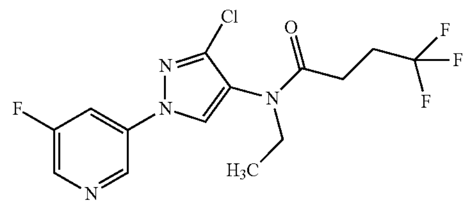 [SMILES: CCN(C(=O)CCC(F)(F)F)c1cn(-c2cncc(F)c2)nc1Cl] | |
| 169 | White Solid | 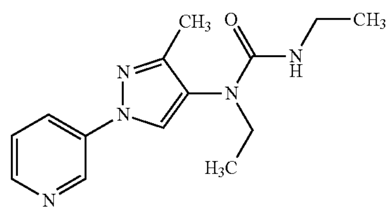 [SMILES: CCNC(=O)N(CC)c1cn(-c2cccnc2)nc1C] | |
| 170 | White Solid | 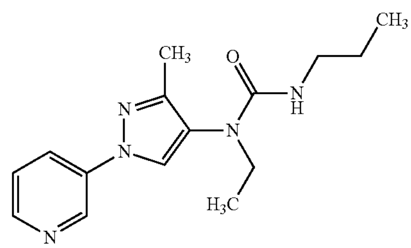 [SMILES: CCCNC(=O)N(CC)c1cn(-c2cccnc2)nc1C] | |
| 171 | White Solid | 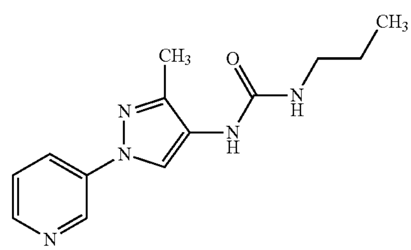 [SMILES: CCCNC(=O)Nc1cn(-c2cccnc2)nc1C] | |
| 172 | White Solid | 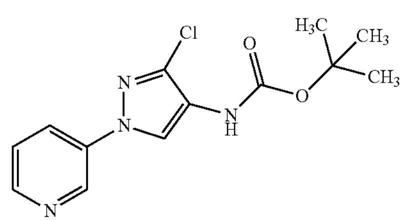 [SMILES: CC(C)(C)OC(=O)Nc1cn(-c2cccnc2)nc1Cl] | |
| 173 | White Solid | 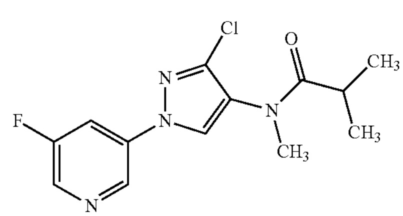 [SMILES: CC(C)C(=O)N(C)c1cn(-c2cncc(F)c2)nc1Cl] | |

TABLE 1-continued

Compound number, appearance, and structure

| Compound No. | Appearance | Structure | Prepared as in Example: |
|---|---|---|---|
| 174 | Clear Oil | 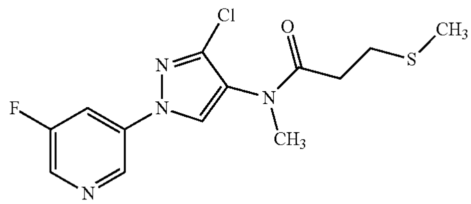 [SMILES: CSCCC(=O)N(C)c1cn(-c2cncc(F)c2)nc1Cl] | |
| 175 | White Solid | 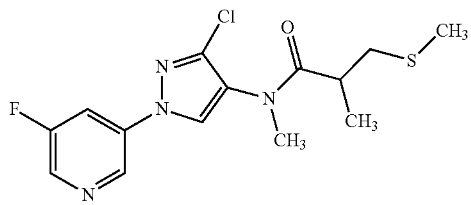 [SMILES: CSCC(C)C(=O)N(C)c1cn(-c2cncc(F)c2)nc1Cl] | |
| 176 | Yellow Oil | 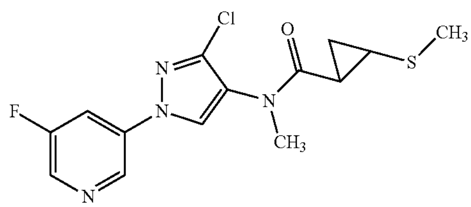 [SMILES: CSC1CC1C(=O)N(C)c1cn(-c2cncc(F)c2)nc1Cl] | |
| 177 | White Solid | 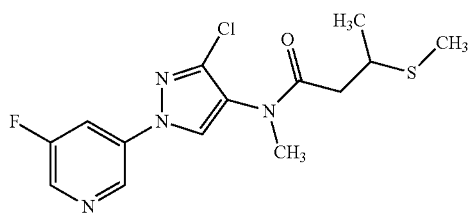 [SMILES: CSC(C)CC(=O)N(C)c1cn(-c2cncc(F)c2)nc1Cl] | |
| 178 | Yellow Oil | 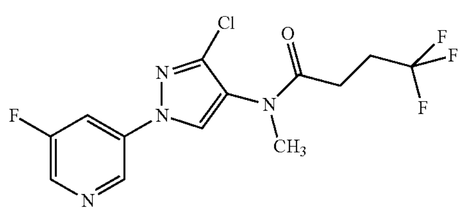 [SMILES: CN(C(=O)CCC(F)(F)F)c1cn(-c2cncc(F)c2)nc1Cl] | |
| 179 | White Solid | 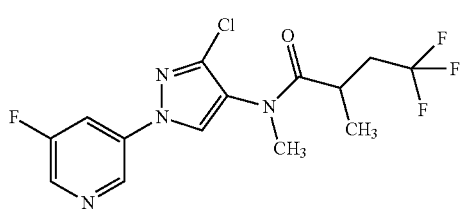 [SMILES: CC(CC(F)(F)F)C(=O)N(C)c1cn(-c2cncc(F)c2)nc1Cl] | |
| 180 | Yellow Solid | 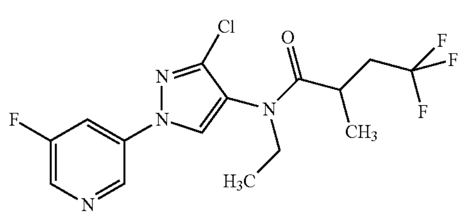 [SMILES: CCN(C(=O)C(C)CC(F)(F)F)c1cn(-c2cncc(F)c2)nc1Cl] | |

TABLE 1-continued
Compound number, appearance, and structure
| Compound No. | Appearance | Structure | Prepared as in Example: |
|---|---|---|---|
| 181 | Faint Yellow Oil | 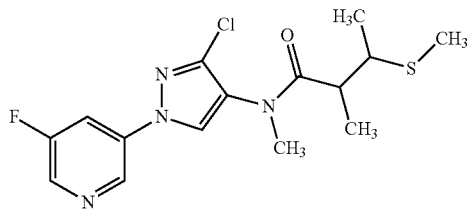 [SMILES: CSC(C)C(C)C(=O)N(C)c1cn(-c2cncc(F)c2)nc1Cl] | |
| 182 | Faint Yellow Oil | 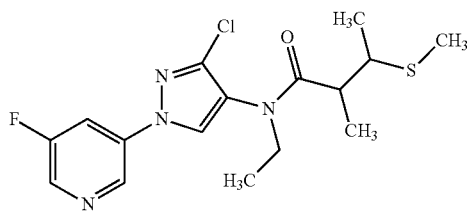 [SMILES: CCN(C(=O)C(C)C(C)SC)c1cn(-c2cncc(F)c2)nc1Cl] | |
| 183 | Yellow Oil | 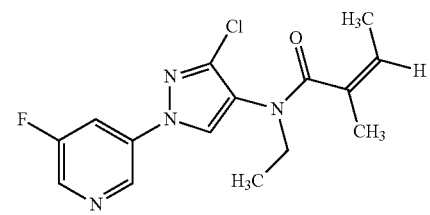 [SMILES: C/C=C(/C)C(=O)N(CC)c1cn(-c2cncc(F)c2)nc1Cl] | |
| 184 | Colorless Oil | 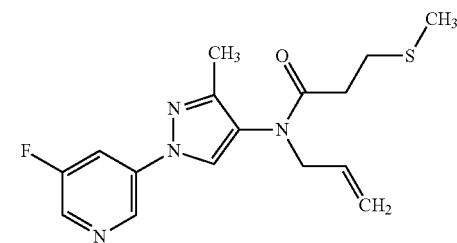 [SMILES: C=CCN(C(=O)CCSC)c1cn(-c2cncc(F)c2)nc1C] | |
| 185 | White Solid | 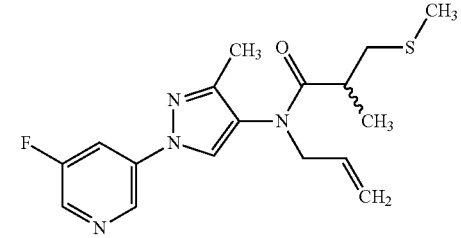 [SMILES: C=CCN(C(=O)C(C)CSC)c1cn(-c2cncc(F)c2)nc1C] | |
| 186 | White Solid | 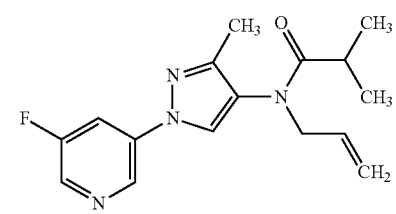 [SMILES: C=CCN(C(=O)C(C)C)c1cn(-c2cncc(F)c2)nc1C] | |

TABLE 1-continued

Compound number, appearance, and structure

| Compound No. | Appearance | Structure | Prepared as in Example: |
|---|---|---|---|
| 187 | Yellow Solid | 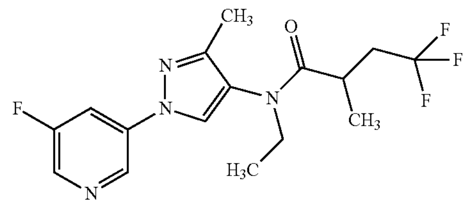 [SMILES: CCN(C(=O)C(C)CC(F)(F)F)c1cn(-c2cncc(F)c2)nc1C] | |
| 188 | Yellow Oil | 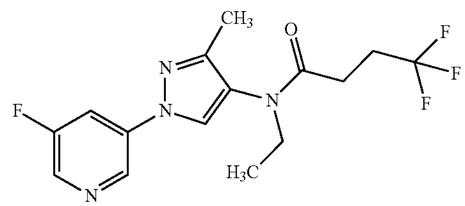 [SMILES: CCN(C(=O)CCC(F)(F)F)c1cn(-c2cncc(F)c2)nc1C] | |
| 189 | Yellow Oil | 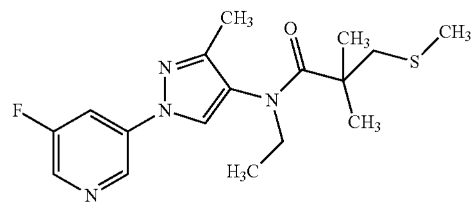 [SMILES: CCN(C(=O)C(C)(C)CSC)c1cn(-c2cncc(F)c2)nc1C] | |
| 190 | Yellow Oil | 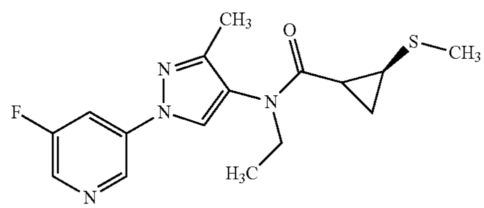 [SMILES: CCN(C(=O)C1C[C@@H]1SC)c1cn(-c2cncc(F)c2)nc1C] | |
| 191 | Yellow Oil | 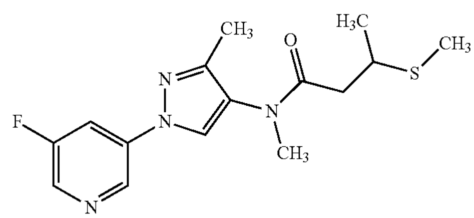 [SMILES: CSC(C)CC(=O)N(C)c1cn(-c2cncc(F)c2)nc1C] | |
| 192 | Yellow Oil | 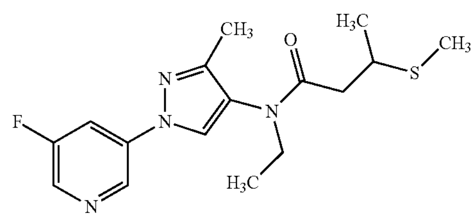 [SMILES: CCN(C(=O)CC(C)SC)c1cn(-c2cncc(F)c2)nc1C] | |
| 193 | Yellow Solid | 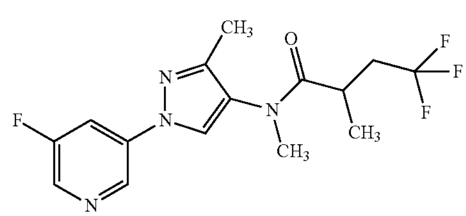 [SMILES: Cc1nn(-c2cncc(F)c2)cc1N(C)C(=O)C(C)CC(F)(F)F] | |

TABLE 1-continued
Compound number, appearance, and structure
| Compound No. | Appearance | Structure | Prepared as in Example: |
|---|---|---|---|
| 194 | White Solid | 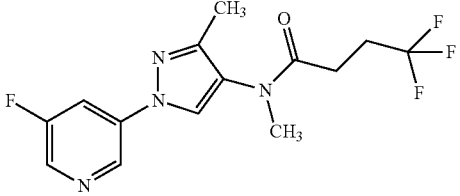 [SMILES: Cc1nn(-c2cncc(F)c2)cc1N(C)C(=O)CCC(F)(F)F] | |
| 195 | White Solid | 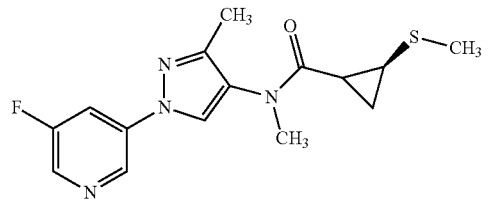 [SMILES: CS[C@H]1CC1C(=O)N(C)c1cn(-c2cncc(F)c2)nc1C] | |
| 196 | Tan Solid | 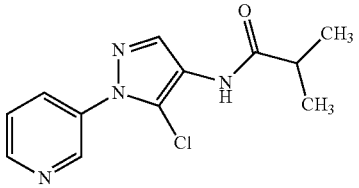 [SMILES: CC(C)C(=O)Nc1cnn(-c2cccnc2)c1Cl] | |
| 197 | White Solid | 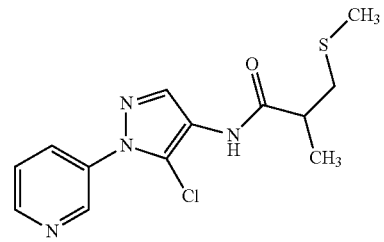 [SMILES: CSCC(C)C(=O)Nc1cnn(-c2cccnc2)c1Cl] | |
| 198 | Tan Solid | 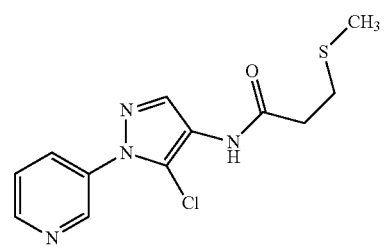 [SMILES: CSCCC(=O)Nc1cnn(-c2cccnc2)c1Cl] | |
| 199 | Gold Solid | 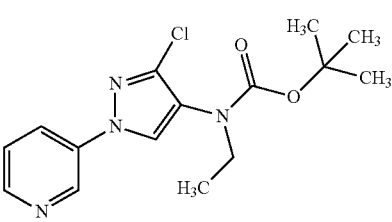 [SMILES: CCN(C(=O)OC(C)(C)C)c1cn(-c2cccnc2)nc1Cl] | |

TABLE 1-continued

Compound number, appearance, and structure

| Compound No. | Appearance | Structure | Prepared as in Example: |
|---|---|---|---|
| 200 | Yellow Oil | 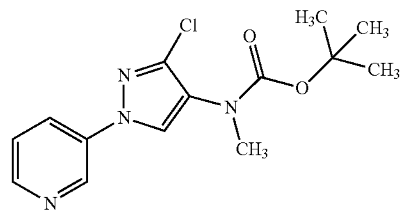 [SMILES: CN(C(=O)OC(C)(C)C)c1cn(-c2cccnc2)nc1Cl] | |
| 201 | Gold Oil | 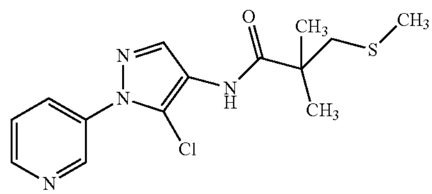 [SMILES: CSCC(C)(C)C(=O)Nc1cnn(-c2cccnc2)c1Cl] | |
| 202 | White Semi Solid | 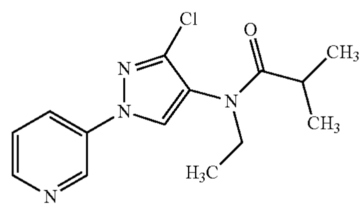 [SMILES: CCN(C(=O)C(C)C)c1cn(-c2cccnc2)nc1Cl] | |
| 203 | Yellow Oil | 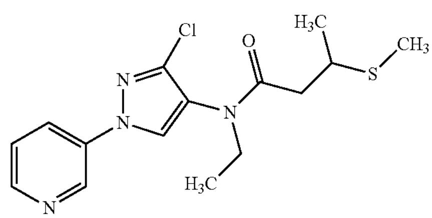 [SMILES: CCN(C(=O)CC(C)SC)c1cn(-c2cccnc2)nc1Cl] | |
| 204 | Yellow Oil | 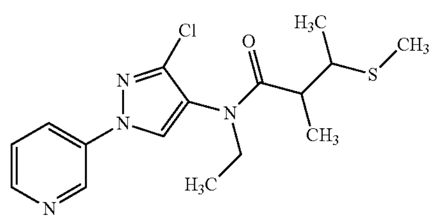 [SMILES: CCN(C(=O)C(C)C(C)SC)c1cn(-c2cccnc2)nc1Cl] | |
| 205 | Yellow Oil | AND Enantiomer | |
| 206 | Yellow Oil | 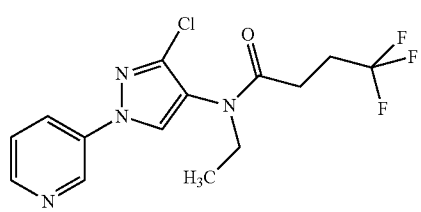 [SMILES: CCN(C(=O)CCC(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 207 | White Solid | 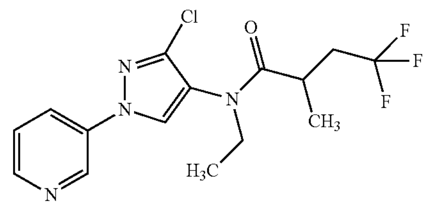 [SMILES: CCN(C(=O)C(C)CC(F)(F)F)c1cn(-c2cccnc2)nc1Cl] | |
| 208 | White Solid | 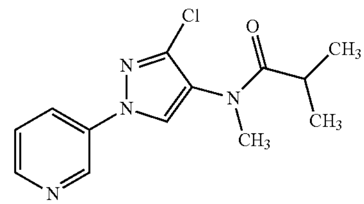 [SMILES: CC(C)C(=O)N(C)c1cn(-c2cccnc2)nc1Cl] | |
| 209 | Yellow Oil | 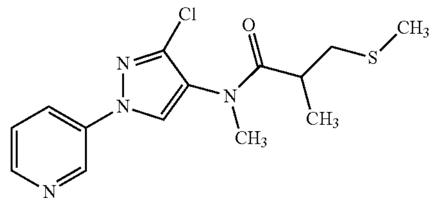 [SMILES: CSCC(C)C(=O)N(C)c1cn(-c2cccnc2)nc1Cl] | |
| 210 | Yellow Oil | 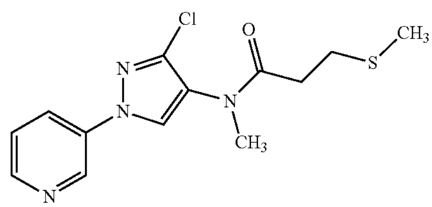 [SMILES: CSCCC(=O)N(C)c1cn(-c2cccnc2)nc1Cl] | |
| 211 | Yellow Oil | 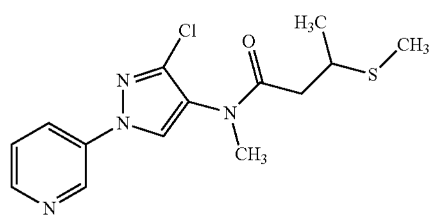 [SMILES: CSC(C)CC(=O)N(C)c1cn(-c2cccnc2)nc1Cl] | |
| 212 | Yellow Oil | 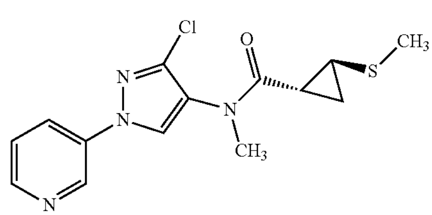 [SMILES: CS[C@H]1C[C@@H]1C(=O)N(C)c1cn(-c2cccnc2)nc1Cl] | |
| 213 | Yellow Oil | 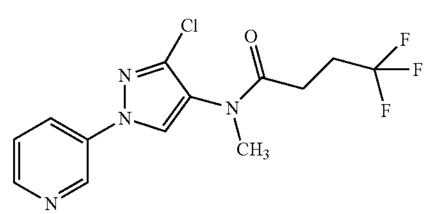 [SMILES: CN(C(=O)CCC(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 214 | Yellow Oil | 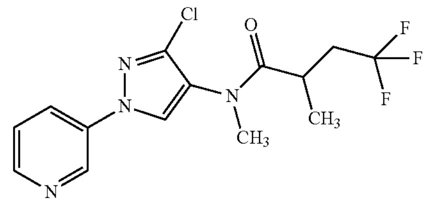 [SMILES: CC(CC(F)(F)F)C(=O)N(C)c1cn(-c2cccnc2)nc1Cl] | |
| 215 | Clear Oil | 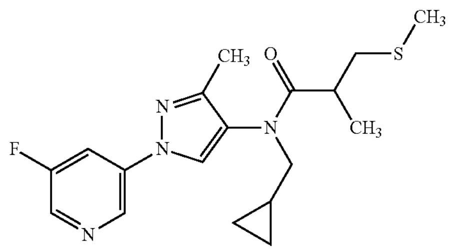 [SMILES: CSCC(C)C(=O)N(CC1CC1)c1cn(-c2cncc(F)c2)nc1C] | |
| 216 | Cream Colored Solid | 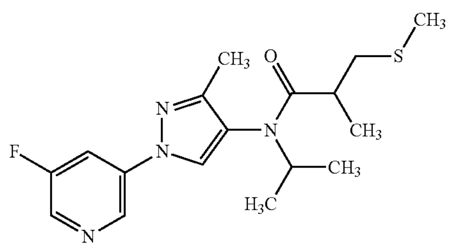 [SMILES: CSCC(C)C(=O)N(c1cn(-c2cncc(F)c2)nc1C)C(C)C] | |
| 217 | Clear Oil | 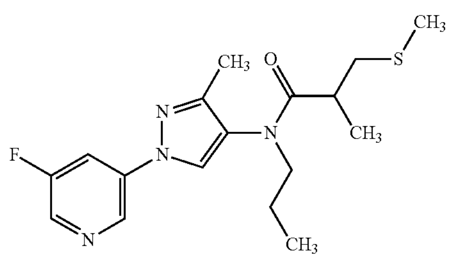 [SMILES: CCCN(C(=O)C(C)CSC)c1cn(-c2cncc(F)c2)nc1C] | |
| 218 | Clear Oil | 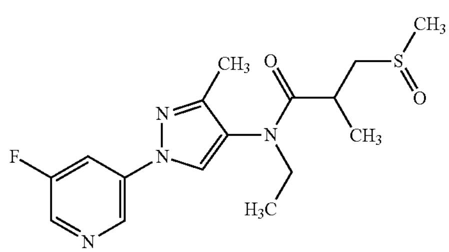 [SMILES: CCN(C(=O)C(C)CS(C)=O)c1cn(-c2cncc(F)c2)nc1C] | |
| 219 | Clear Oil | 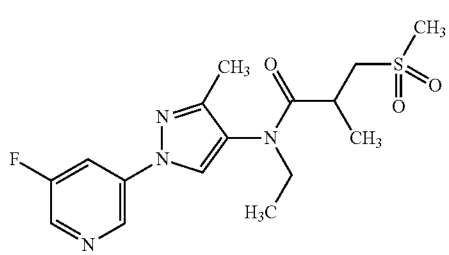 [SMILES: CCN(C(=O)C(C)CS(C)(=O)=O)c1cn(-c2cncc(F)c2)nc1C] | |

US 9,708,288 B2
267 268
TABLE 1-continued
Compound number, appearance, and structure
| Compound No. | Appearance | Structure | Prepared as in Example: |
|---|---|---|---|
| 220 | Yellow Oil | 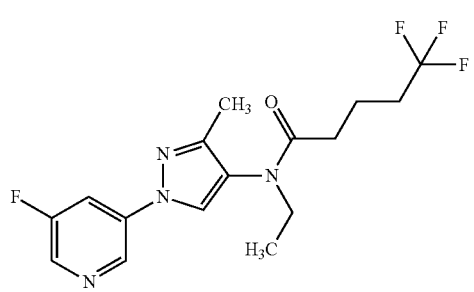 | |
| 221 | White Solid | 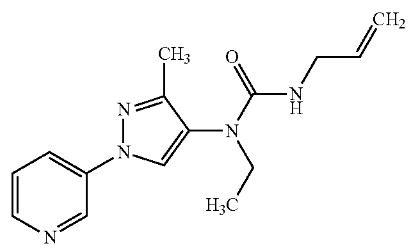 [SMILES: C=CCNC(=O)N(CC)c1cn(-c2cccnc2)nc1C] | |
| 222 | White Solid | 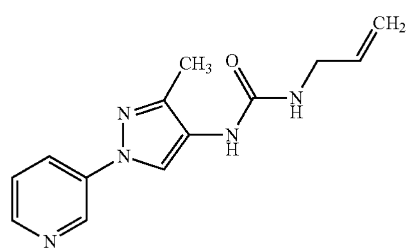 [SMILES: C=CCNC(=O)Nc1cn(-c2cccnc2)nc1C] | |
| 223 | White Solid | 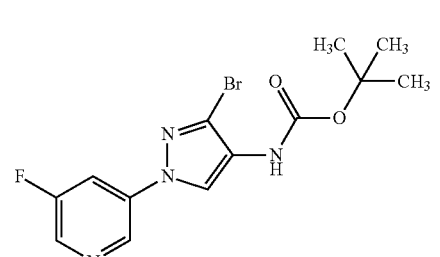 | |
| 224 | Colorless Oil | 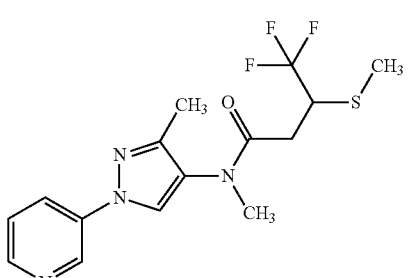 | |

TABLE 1-continued

Compound number, appearance, and structure

| Compound No. | Appearance | Structure | Prepared as in Example: |
|---|---|---|---|
| 225 | Light Yellow Oil | 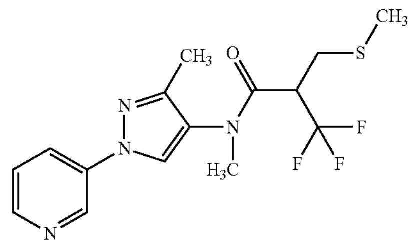 [SMILES: CSCC(C(=O)N(C)c1cn(-c2cccnc2)nc1C)C(F)(F)F] | |
| 226 | White Solid | 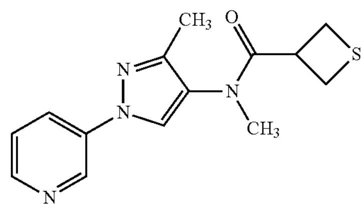 [SMILES: Cc1nn(-c2cccnc2)cc1N(C)C(=O)C1CSC1] | |
| 227 | White Solid | 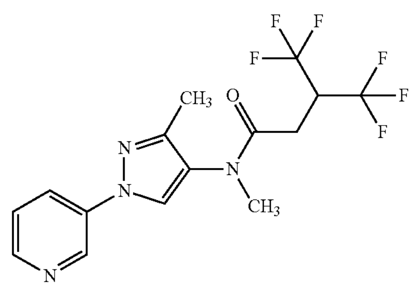 [SMILES: Cc1nn(-c2cccnc2)cc1N(C)C(=O)CC(C(F)(F)F)C(F)(F)F] | |
| 228 | Colorless Oil | 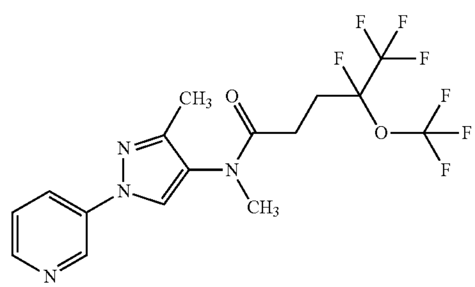 [SMILES: Cc1nn(-c2cccnc2)cc1N(C)C(=O)CCC(F)(OC(F)(F)F)C(F)(F)F] | |
| 229 | Colorless Oil | 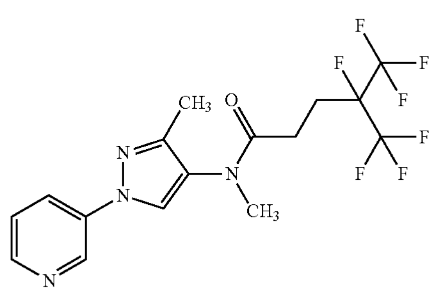 [SMILES: Cc1nn(-c2cccnc2)cc1N(C)C(=O)CCC(F)(C(F)(F)F)C(F)(F)F] | |
| 230 | Colorless Oil | 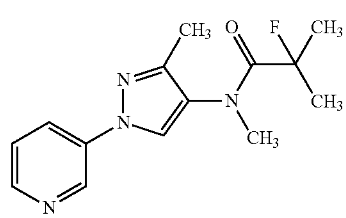 [SMILES: Cc1nn(-c2cccnc2)cc1N(C)C(=O)C(C)(C)F] | |

TABLE 1-continued

Compound number, appearance, and structure

| Compound No. | Appearance | Structure | Prepared as in Example: |
|---|---|---|---|
| 231 | Colorless Oil | 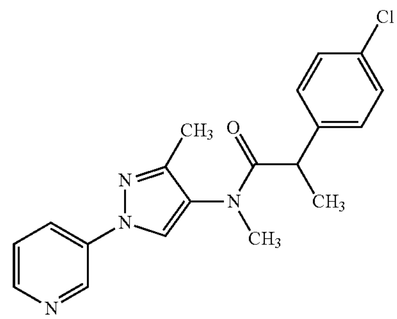 [SMILES: Cc1nn(-c2cccnc2)cc1N(C)C(=O)C(C)c1ccc(Cl)cc1] | |
| 232 | White Solid | 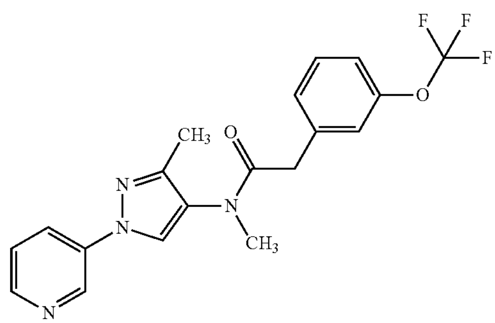 [SMILES: Cc1nn(-c2cccnc2)cc1N(C)C(=O)Cc1cccc(OC(F)(F)F)c1] | |
| 233 | White Solid | 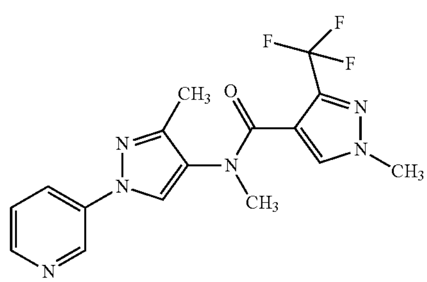 [SMILES: Cc1nn(-c2cccnc2)cc1N(C)C(=O)c1cn(C)nc1C(F)(F)F] | |
| 234 | White Solid | 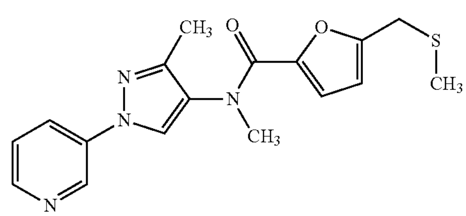 [SMILES: CSCc1ccc(C(=O)N(C)c2cn(-c3cccnc3)nc2C)o1] | |
| 235 | Colorless Oil | 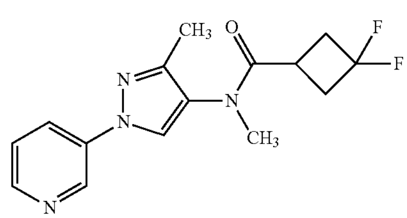 [SMILES: Cc1nn(-c2cccnc2)cc1N(C)C(=O)C1CC(F)(F)C1] | |

TABLE 1-continued

Compound number, appearance, and structure

| Compound No. | Appearance | Structure | Prepared as in Example: |
|---|---|---|---|
| 236 | Colorless Oil | 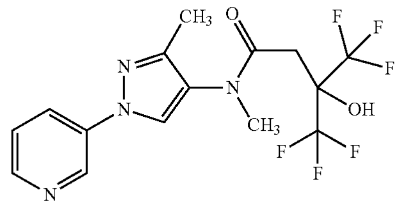 [SMILES: Cc1nn(-c2cccnc2)cc1N(C)C(=O)CC(O)(C(F)(F)F)C(F)(F)F] | |
| 237 | White Solid | 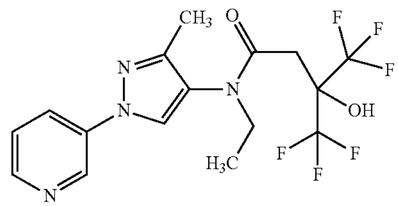 [SMILES: CCN(C(=O)CC(O)(C(F)(F)F)C(F)(F)F)c1cn(-c2cccnc2)nc1C] | |
| 238 | Colorless Oil | 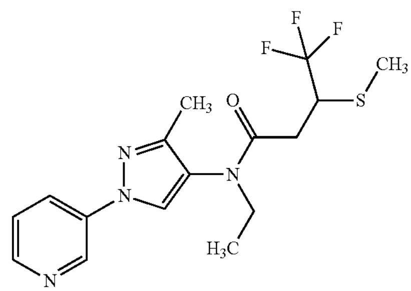 [SMILES: CCN(C(=O)CC(SC)C(F)(F)F)c1cn(-c2cccnc2)nc1C] | |
| 239 | Colorless Oil | 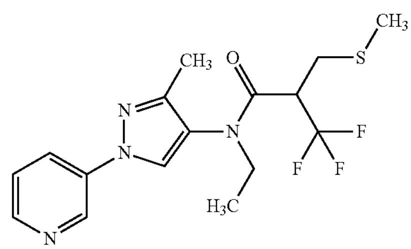 [SMILES: CCN(C(=O)C(CSC)C(F)(F)F)c1cn(-c2cccnc2)nc1C] | |
| 240 | White Solid | 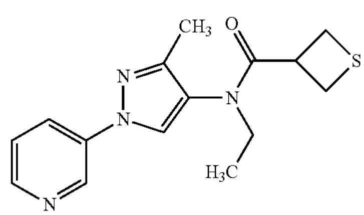 [SMILES: CCN(C(=O)C1CSC1)c1cn(-c2cccnc2)nc1C] | |
| 241 | Colorless Oil | 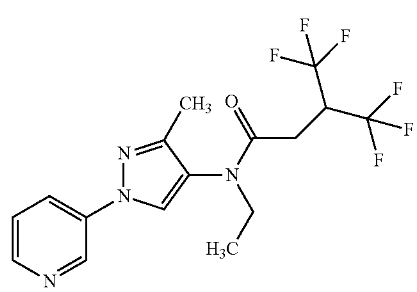 [SMILES: CCN(C(=O)CC(C(F)(F)F)C(F)(F)F)c1cn(-c2cccnc2)nc1C] | |

TABLE 1-continued

Compound number, appearance, and structure

| Compound No. | Appearance | Structure | Prepared as in Example: |
|---|---|---|---|
| 242 | Colorless Oil | 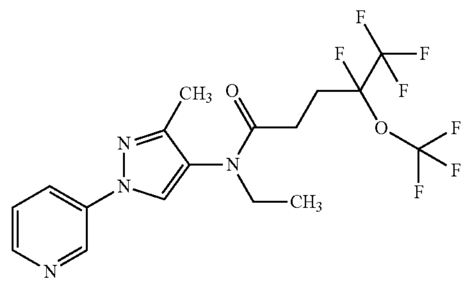 [SMILES: CCN(C(=O)CCC(F)(OC(F)(F)F)C(F)(F)F)c1cn(-c2cccnc2)nc1C] | |
| 243 | Colorless Oil | 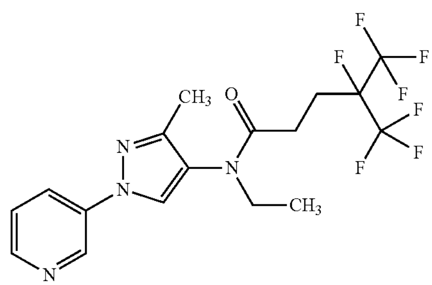 [SMILES: CCN(C(=O)CCC(F)(C(F)(F)F)C(F)(F)F)c1cn(-c2cccnc2)nc1C] | |
| 244 | White Solid | 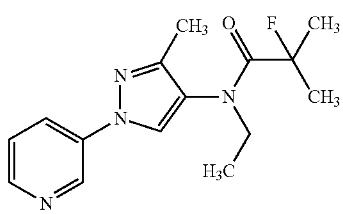 [SMILES: CCN(C(=O)C(C)(C)F)c1cn(-c2cccnc2)nc1C] | |
| 245 | White Solid | 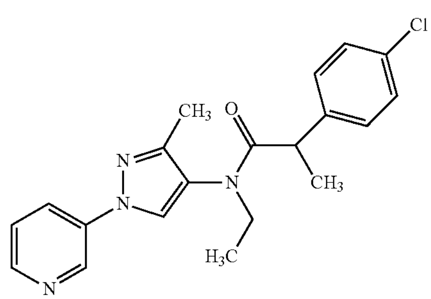 [SMILES: CCN(C(=O)C(C)c1ccc(Cl)cc1)c1cn(-c2cccnc2)nc1C] | |
| 246 | Colorless Oil | 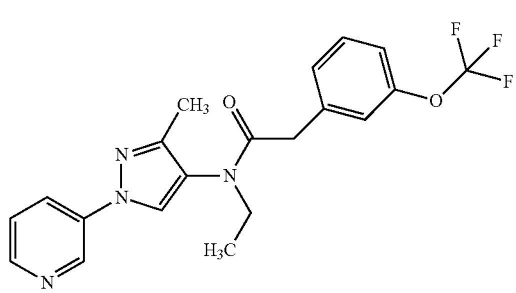 [SMILES: CCN(C(=O)Cc1cccc(OC(F)(F)F)c1)c1cn(-c2cccnc2)nc1C] | |

TABLE 1-continued

Compound number, appearance, and structure

| Compound No. | Appearance | Structure | Prepared as in Example: |
|---|---|---|---|
| 247 | White Solid | 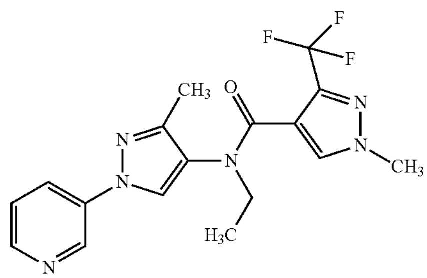 [SMILES: CCN(C(=O)c1cn(C)nc1C(F)(F)F)c1cn(-c2cccnc2)nc1C] | |
| 248 | Colorless Oil | 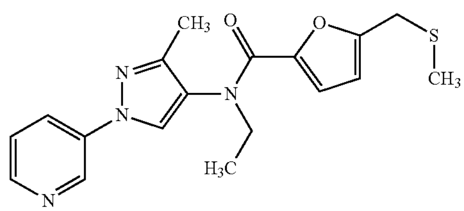 [SMILES: CCN(C(=O)c1ccc(CSC)o1)c1cn(-c2cccnc2)nc1C] | |
| 249 | White Solid | 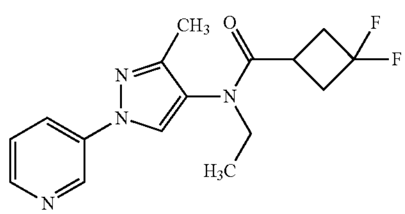 [SMILES: CCN(C(=O)C1CC(F)(F)C1)c1cn(-c2cccnc2)nc1C] | |
| 250 | Clear Oil | 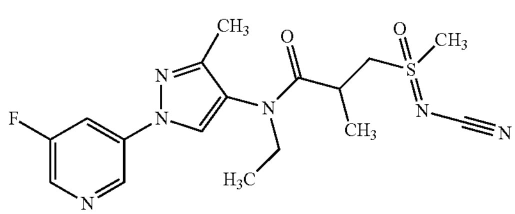 [SMILES: CCN(C(=O)C(C)CS(C)(=O)=NC#N)c1cn(-c2cncc(F)c2)nc1C] | |
| 251 | Brown Oil | 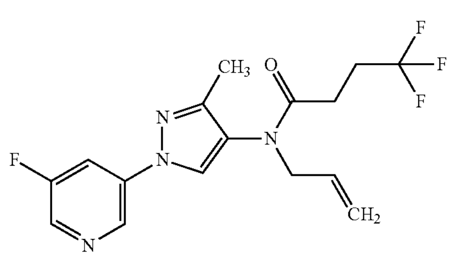 [SMILES: C=CCN(C(=O)CCC(F)(F)F)c1cn(-c2cncc(F)c2)nc1C] | |
| 252 | Off White Solid | 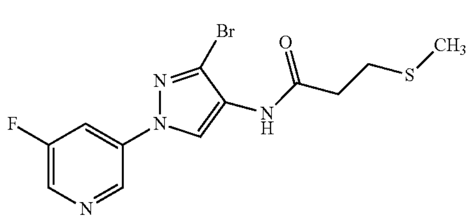 [SMILES: CSCCC(=O)Nc1cn(-c2cncc(F)c2)nc1Br] | |

TABLE 1-continued

Compound number, appearance, and structure

| Compound No. | Appearance | Structure | Prepared as in Example: |
|---|---|---|---|
| 253 | Off White Solid | 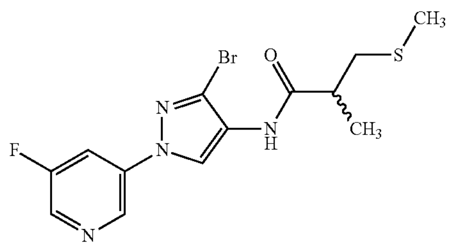 [SMILES: CSCC(C)C(=O)Nc1cn(-c2cncc(F)c2)nc1Br] | |
| 254 | Brown Solid | 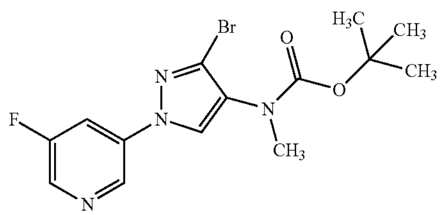 [SMILES: CN(C(=O)OC(C)(C)C)c1cn(-c2cncc(F)c2)nc1Br] | |
| 255 | White Solid | 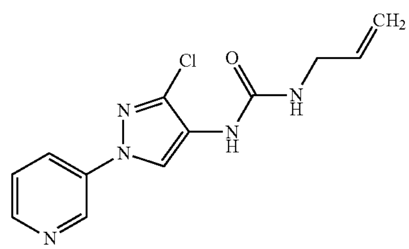 [SMILES: C=CCNC(=O)Nc1cn(-c2cccnc2)nc1Cl] | |
| 256 | White Solid | 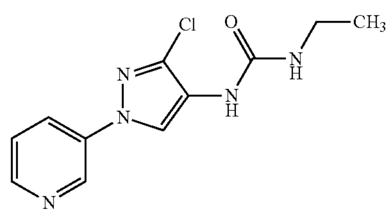 [SMILES: CCNC(=O)Nc1cn(-c2cccnc2)nc1Cl] | |
| 257 | White Solid | 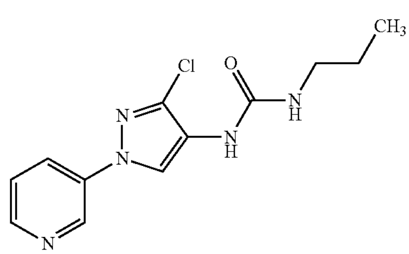 [SMILES: CCCNC(=O)Nc1cn(-c2cccnc2)nc1Cl] | |
| 258 | Brown Oil | 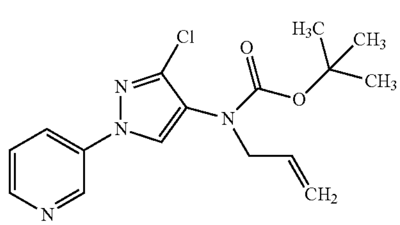 [SMILES: C=CCN(C(=O)OC(C)(C)C)c1cn(-c2cccnc2)nc1Cl] | |

TABLE 1-continued

Compound number, appearance, and structure

| Compound No. | Appearance | Structure | Prepared as in Example: |
|---|---|---|---|
| 259 | White Solid | 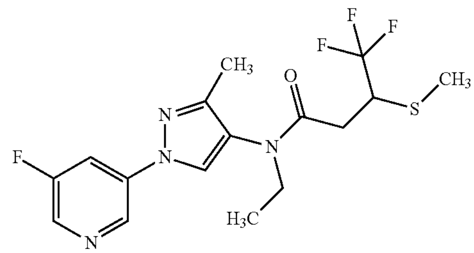 [SMILES: CCN(C(=O)CC(SC)C(F)(F)F)c1cn(-c2cncc(F)c2)nc1C] | |
| 260 | Colorless Oil | 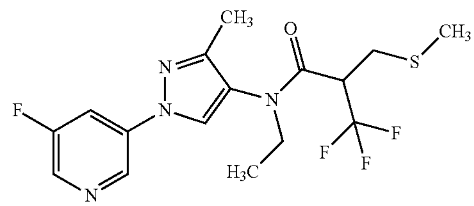 [SMILES: CCN(C(=O)C(CSC)C(F)(F)F)c1cn(-c2cncc(F)c2)nc1C] | |
| 261 | White Solid | 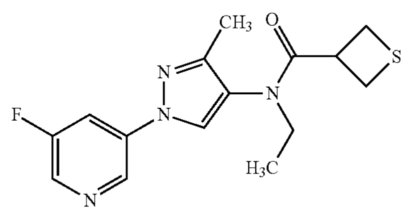 [SMILES: CCN(C(=O)C1CSC1)c1cn(-c2cncc(F)c2)nc1C] | |
| 262 | White Solid | 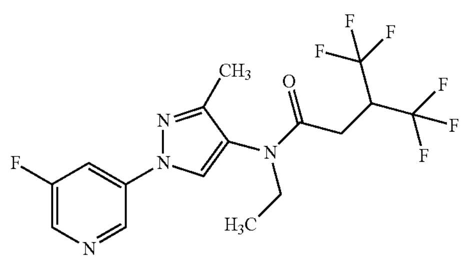 [SMILES: CCN(C(=O)CC(C(F)(F)F)C(F)(F)F)c1cn(-c2cncc(F)c2)nc1C] | |
| 263 | Colorless Oil | 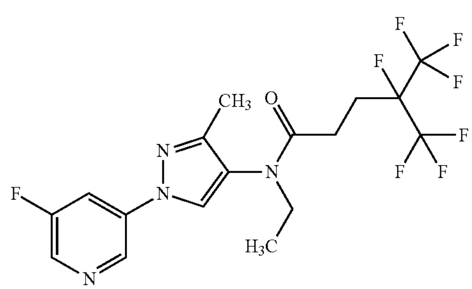 [SMILES: CCN(C(=O)CCC(F)(C(F)(F)F)C(F)(F)F)c1cn(-c2cncc(F)c2)nc1C] | |
| 264 | Colorless Oil | 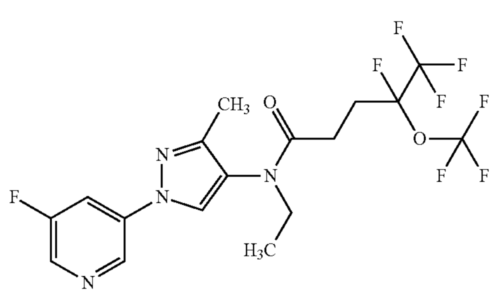 [SMILES: CCN(C(=O)CCC(F)(OC(F)(F)F)C(F)(F)F)c1cn(-c2cncc(F)c2)nc1C] | |

TABLE 1-continued

Compound number, appearance, and structure

| Compound No. | Appearance | Structure | Prepared as in Example: |
|---|---|---|---|
| 265 | White Solid | 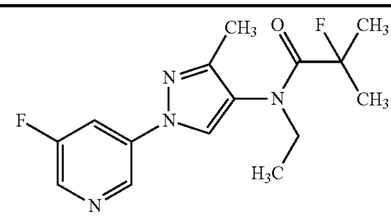 | |
| 266 | Colorless Semi-Solid | 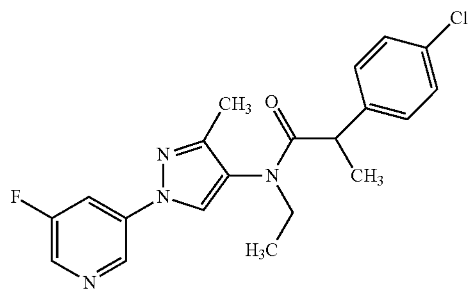 [SMILES: CCN(C(=O)C(C)c1ccc(Cl)cc1)c1cn(-c2cncc(F)c2)nc1C] | |
| 267 | Colorless Oil | 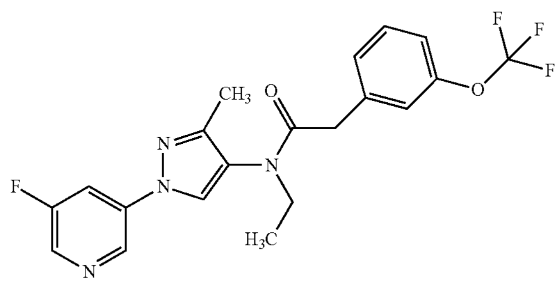 [SMILES: CCN(C(=O)Cc1cccc(OC(F)(F)F)c1)c1cn(-c2cncc(F)c2)nc1C] | |
| 268 | White Solid | 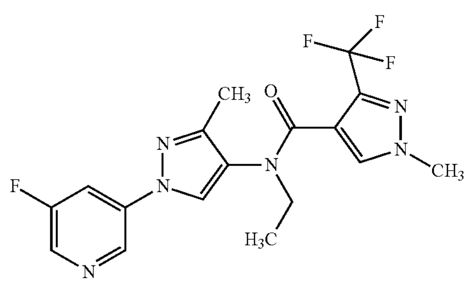 [SMILES: CCN(C(=O)c1cn(C)nc1C(F)(F)F)c1cn(-c2cncc(F)c2)nc1C] | |
| 269 | White Solid | 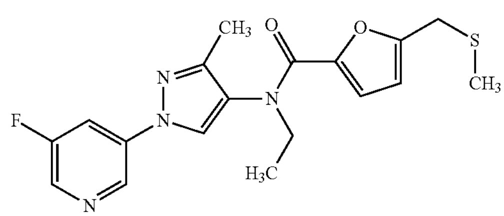 [SMILES: CCN(C(=O)c1ccc(CSC)o1)c1cn(-c2cncc(F)c2)nc1C] | |
| 270 | White Solid | 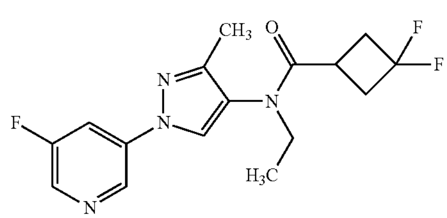 [SMILES: CCN(C(=O)C1CC(F)(F)C1)c1cn(-c2cncc(F)c2)nc1C] | |

TABLE 1-continued

Compound number, appearance, and structure

| Compound No. | Appearance | Structure | Prepared as in Example: |
|---|---|---|---|
| 271 | Colorless Oil | 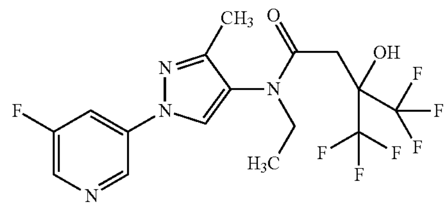 [SMILES: CCN(C(=O)CC(O)(C(F)(F)F)C(F)(F)F)c1cn(-c2cncc(F)c2)nc1C] | |
| 272 | White Solid | 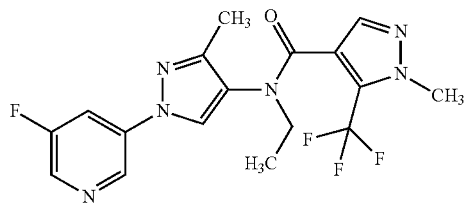 [SMILES: CCN(C(=O)c1cnn(C)c1C(F)(F)F)c1cn(-c2cncc(F)c2)nc1C] | |
| 273 | Colorless Oil | 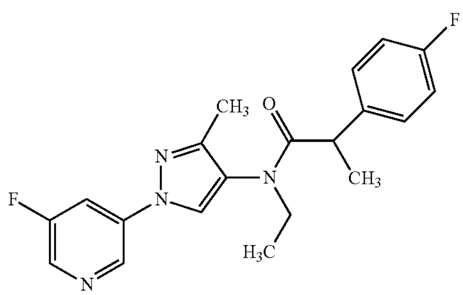 [SMILES: CCN(C(=O)C(C)c1ccc(F)cc1)c1cn(-c2cncc(F)c2)nc1C] | |
| 274 | Colorless Oil | 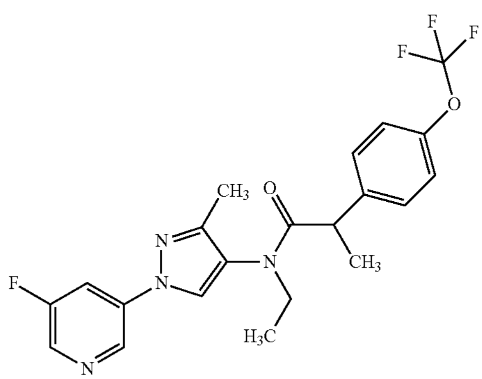 [SMILES: CCN(C(=O)C(C)c1ccc(OC(F)(F)F)cc1)c1cn(-c2cncc(F)c2)nc1C] | |
| 275 | White Solid | 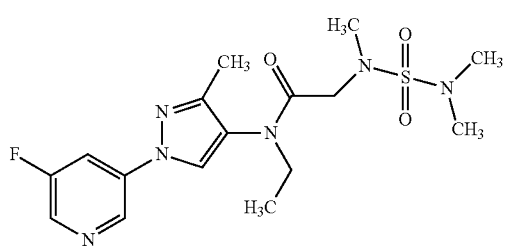 [SMILES: CCN(C(=O)CN(C)S(=O)(=O)N(C)C)c1cn(-c2cncc(F)c2)nc1C] | |

TABLE 1-continued
Compound number, appearance, and structure
| Compound No. | Appearance | Structure | Prepared as in Example: |
|---|---|---|---|
| 276 | White Solid | 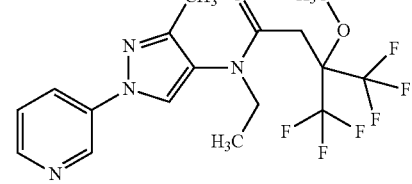 | |
| 277 | Brown Amorphous Solid | 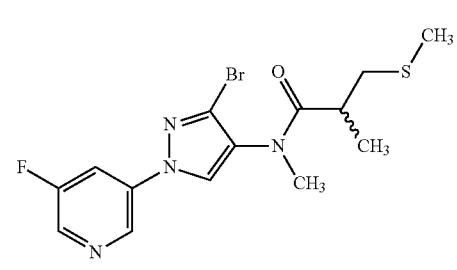 [SMILES: CSCC(C)C(=O)N(C)c1cn(-c2cncc(F)c2)nc1Br] | |
| 278 | White Solid | 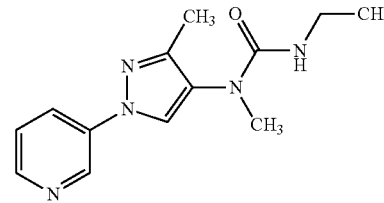 | |
| 279 | White Solid | 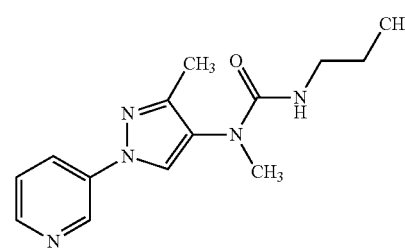 | |
| 280 | White Solid | 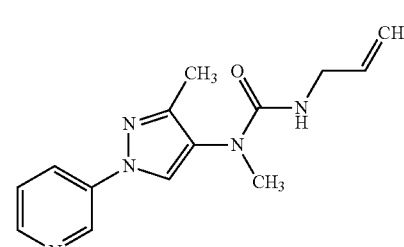 | |
| 281 | Orange Foam | 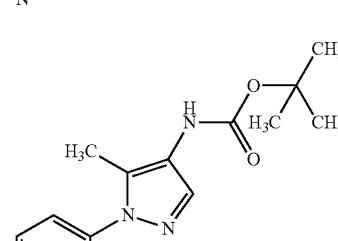 | |

TABLE 1-continued
Compound number, appearance, and structure
| Compound No. | Appearance | Structure | Prepared as in Example: |
|---|---|---|---|
| 282 | Colorless Oil | 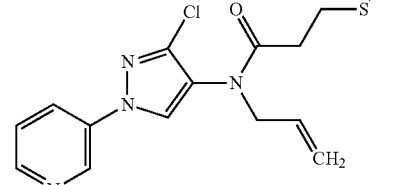 | |
| 283 | Colorless Oil | 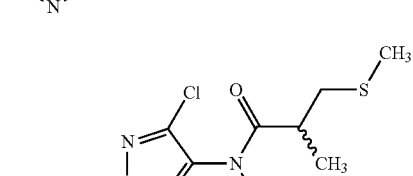 | |
| 284 | Colorless Oil | 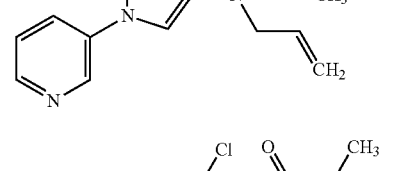 | |
| 285 | Clear Oil | 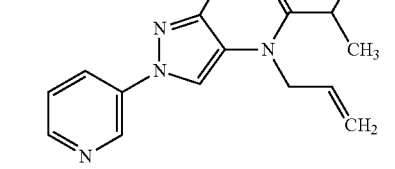 | |
| 286 | Yellow Oil | 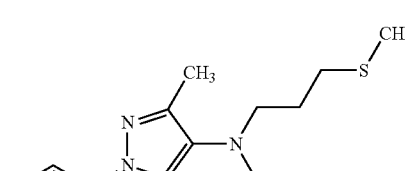 | |
| 287 | Yellow Oil | 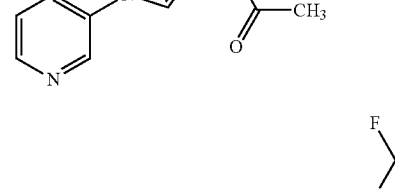 | |

TABLE 1-continued

| Compound No. | Appearance | Structure | Prepared as in Example: |
|---|---|---|---|
| 288 | Yellow Oil | ethyl N-(3-(methylthio)propyl)-N-(3-methyl-1-(pyridin-3-yl)-1H-pyrazol-4-yl)carbamate | |
| 289 | Dark Yellow Oil | 3-(methylthio)-N-(3-(methylthio)propyl)-N-(3-methyl-1-(pyridin-3-yl)-1H-pyrazol-4-yl)propanamide | |
| 290 | Yellow Oil | 2-methyl-3-(methylthio)-N-(3-(methylthio)propyl)-N-(3-methyl-1-(pyridin-3-yl)-1H-pyrazol-4-yl)propanamide | |
| 291 | Clear Oil | tert-butyl N-(3-chloro-1-(pyridin-3-yl)-1H-pyrazol-4-yl)-N-isopropylcarbamate | |
| 292 | Tan Solid | N-methyl-N-(3-methyl-1-(pyridin-3-yl)-1H-pyrazol-4-yl)-2-(2-(methylthio)ethoxy)propanamide | |
| 293 | Clear Oil | 2-(2-methoxyethoxy)-N-methyl-N-(3-methyl-1-(pyridin-3-yl)-1H-pyrazol-4-yl)propanamide | |

TABLE 1-continued

Compound number, appearance, and structure

| Compound No. | Appearance | Structure | Prepared as in Example: |
|---|---|---|---|
| 294 | Yellow Oil | ![structure] | |
| 295 | White Semi-Solid | ![structure] | |
| 296 | Colorless Oil | ![structure] | |
| 297 | White Solid | ![structure] | |
| 298 | White Solid | ![structure] | |
| 299 | White Solid | ![structure] | |

TABLE 1-continued

Compound number, appearance, and structure

| Compound No. | Appearance | Structure | Prepared as in Example: |
|---|---|---|---|
| 300 | White Solid | 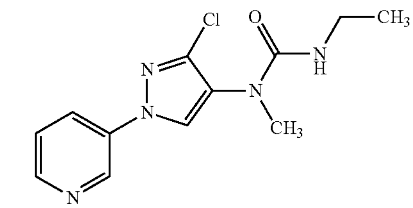 [SMILES: CCNC(=O)N(C)c1cn(-c2cccnc2)nc1Cl] | |
| 301 | White Solid | 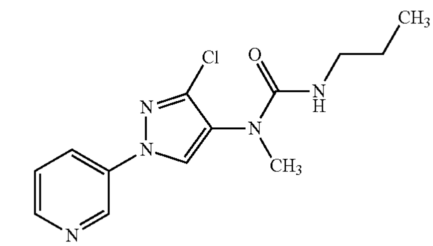 [SMILES: CCCNC(=O)N(C)c1cn(-c2cccnc2)nc1Cl] | |
| 302 | White Solid | 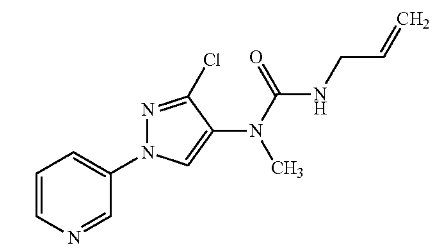 [SMILES: C=CCNC(=O)N(C)c1cn(-c2cccnc2)nc1Cl] | |
| 303 | Colorless Oil | 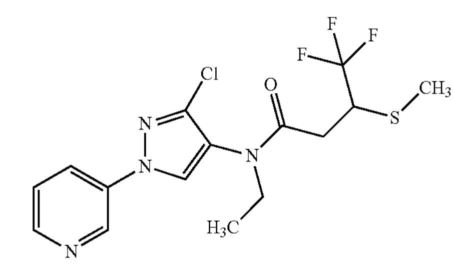 [SMILES: CCN(C(=O)CC(SC)C(F)(F)F)c1cn(-c2cccnc2)nc1Cl] | |
| 304 | Light Yellow Oil | 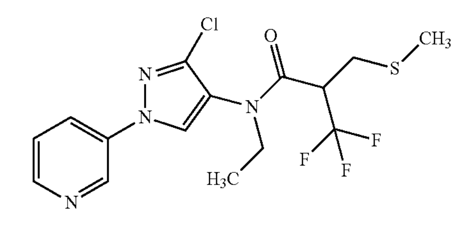 [SMILES: CCN(C(=O)C(CSC)C(F)(F)F)c1cn(-c2cccnc2)nc1Cl] | |
| 305 | White Solid | 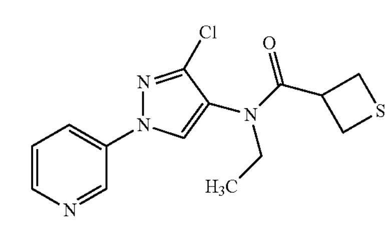 [SMILES: CCN(C(=O)C1CSC1)c1cn(-c2cccnc2)nc1Cl] | |

TABLE 1-continued

Compound number, appearance, and structure

| Compound No. | Appearance | Structure | Prepared as in Example: |
|---|---|---|---|
| 306 | Grey Solid | 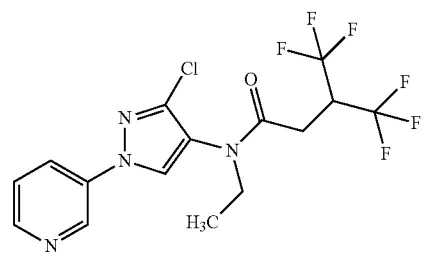 [SMILES: CCN(C(=O)CC(C(F)(F)F)C(F)(F)F)c1cn(-c2cccnc2)nc1Cl] | |
| 307 | Colorless Oil | 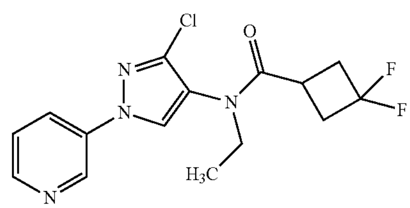 [SMILES: CCN(C(=O)C1CC(F)(F)C1)c1cn(-c2cccnc2)nc1Cl] | |
| 308 | Colorless Oil | 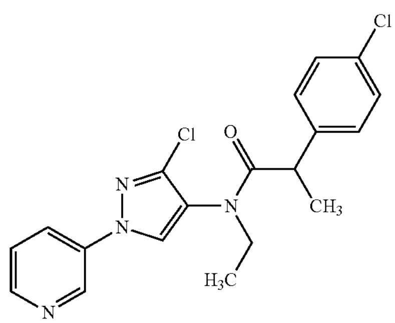 [SMILES: CCN(C(=O)C(C)c1ccc(Cl)cc1)c1cn(-c2cccnc2)nc1Cl] | |
| 309 | Colorless Oil | 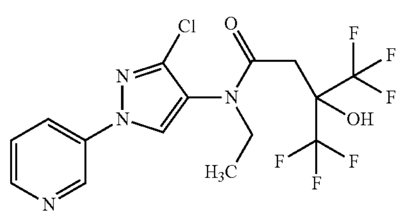 [SMILES: CCN(C(=O)CC(O)(C(F)(F)F)C(F)(F)F)c1cn(-c2cccnc2)nc1Cl] | |
| 310 | Light Yellow Semi-Solid | 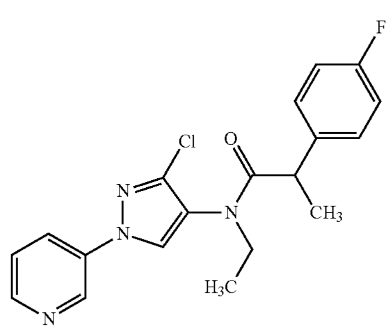 [SMILES: CCN(C(=O)C(C)c1ccc(F)cc1)c1cn(-c2cccnc2)nc1Cl] | |

TABLE 1-continued

Compound number, appearance, and structure

| Compound No. | Appearance | Structure | Prepared as in Example: |
|---|---|---|---|
| 311 | Colorless Oil | 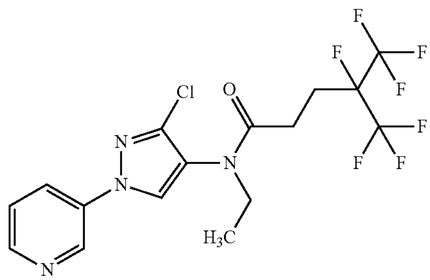 [SMILES: CCN(C(=O)CCC(F)(C(F)(F)F)C(F)(F)F)c1cn(-c2cccnc2)nc1Cl] | |
| 312 | White Solid | 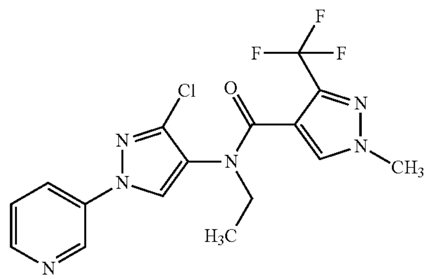 [SMILES: CCN(C(=O)c1cn(C)nc1C(F)(F)F)c1cn(-c2cccnc2)nc1Cl] | |
| 313 | Light Yellow Solid | 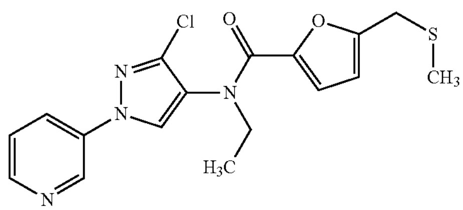 [SMILES: CCN(C(=O)c1ccc(CSC)o1)c1cn(-c2cccnc2)nc1Cl] | |
| 314 | Faint Yellow Oil | 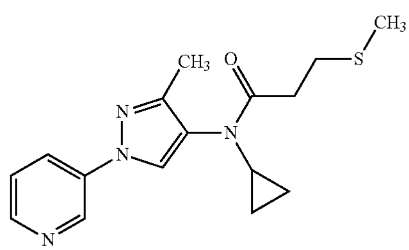 [SMILES: CSCCC(=O)N(c1cn(-c2cccnc2)nc1C)C1CC1] | |
| 315 | Faint Yellow Oil | 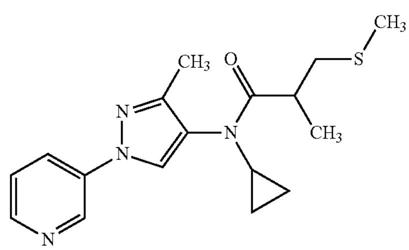 [SMILES: CSCC(C)C(=O)N(c1cn(-c2cccnc2)nc1C)C1CC1] | |
| 316 | Faint Yellow Solid | 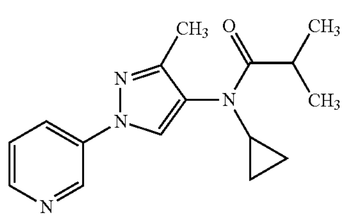 [SMILES: Cc1nn(-c2cccnc2)cc1N(C(=O)C(C)C)C1CC1] | |

TABLE 1-continued

Compound number, appearance, and structure

| Compound No. | Appearance | Structure | Prepared as in Example: |
|---|---|---|---|
| 317 | White Solid | *tert-butyl (3-bromo-1-(pyridin-3-yl)-1H-pyrazol-4-yl)carbamate* | |
| 318 | Brown Solid | *1-(3-chloro-1-(5-fluoropyridin-3-yl)-1H-pyrazol-4-yl)-3-propylurea* | |
| 319 | Brown Solid | *1-allyl-3-(3-chloro-1-(5-fluoropyridin-3-yl)-1H-pyrazol-4-yl)urea* | |
| 320 | Yellow Solid | *1-(3-chloro-1-(pyridin-3-yl)-1H-pyrazol-4-yl)-1,3-diethylurea* | |
| 321 | Yellow Solid | *1-(3-chloro-1-(pyridin-3-yl)-1H-pyrazol-4-yl)-1-ethyl-3-propylurea* | |
| 322 | Yellow Solid | *3-allyl-1-(3-chloro-1-(pyridin-3-yl)-1H-pyrazol-4-yl)-1-ethylurea* | |

TABLE 1-continued

Compound number, appearance, and structure

| Compound No. | Appearance | Structure | Prepared as in Example: |
|---|---|---|---|
| 323 | Colorless Oil | 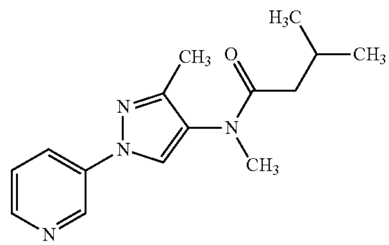 [SMILES: Cc1nn(-c2cccnc2)cc1N(C)C(=O)CC(C)C] | |
| 324 | White Solid | 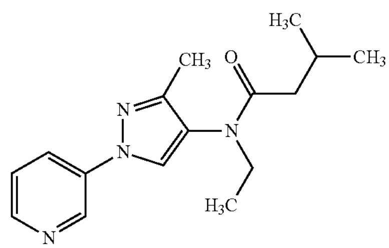 [SMILES: CCN(C(=O)CC(C)C)c1cn(-c2cccnc2)nc1C] | |
| 325 | White Solid | 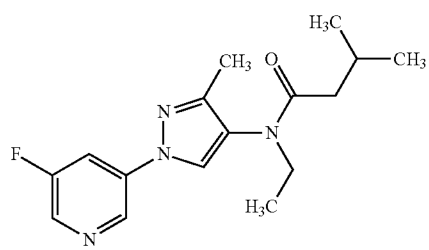 [SMILES: CCN(C(=O)CC(C)C)c1cn(-c2cncc(F)c2)nc1C] | |
| 326 | Colorless Oil | 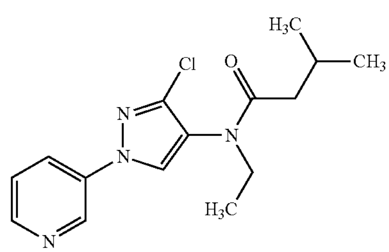 [SMILES: CCN(C(=O)CC(C)C)c1cn(-c2cccnc2)nc1Cl] | |
| 327 | White Solid | 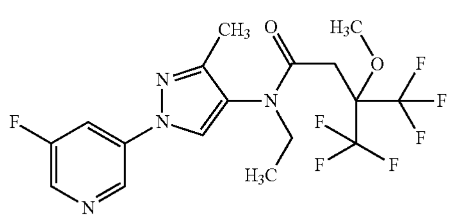 [SMILES: CCN(C(=O)CC(OC)(C(F)(F)F)C(F)(F)F)c1cn(-c2cncc(F)c2)nc1C] | |
| 328 | White Foam | 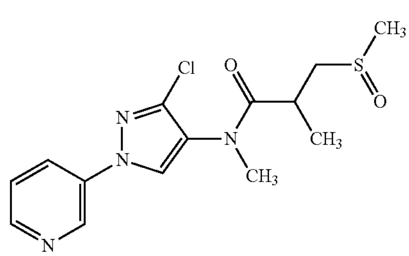 [SMILES: CC(CS(C)=O)C(=O)N(C)c1cn(-c2cccnc2)nc1Cl] | |

TABLE 1-continued
Compound number, appearance, and structure
| Compound No. | Appearance | Structure | Prepared as in Example: |
|---|---|---|---|
| 329 | White Foam | 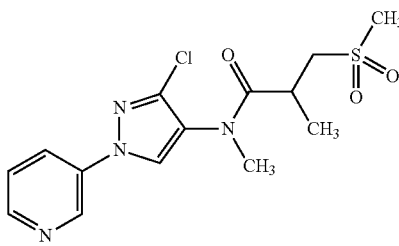 [SMILES: CC(CS(C)(=O)=O)C(=O)N(C)c1cn(-c2cccnc2)nc1Cl] | |
| 330 | White Foam | 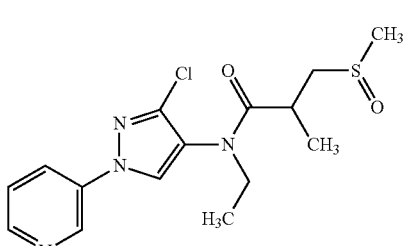 | |
| 331 | White Foam | 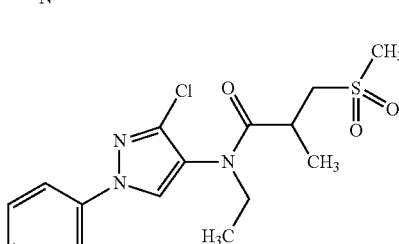 | |
| 332 | Clear Yellow Oil | 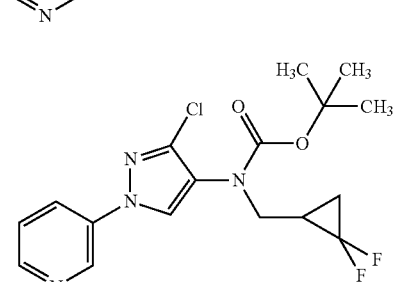 | |
| 333 | Clear Oil | 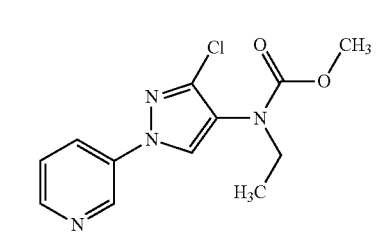 | |
| 334 | Light Brown Solid | 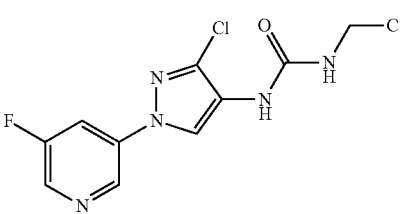 | |

TABLE 1-continued

Compound number, appearance, and structure

| Compound No. | Appearance | Structure | Prepared as in Example: |
|---|---|---|---|
| 335 | White Solid | 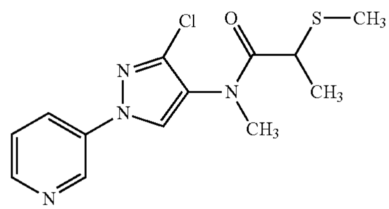 | |
| 336 | White Solid | 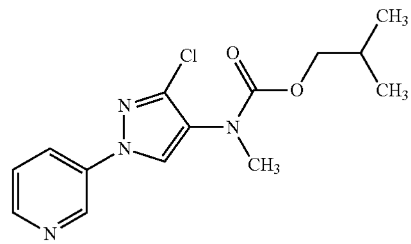 [SMILES: CC(C)COC(=O)N(C)c1cn(-c2cccnc2)nc1Cl] | |
| 337 | Pale Yellow Oil | 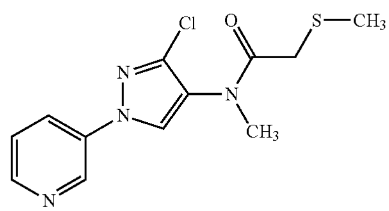 [SMILES: CSCC(=O)N(C)c1cn(-c2cccnc2)nc1Cl] | |
| 338 | Clear Oil | 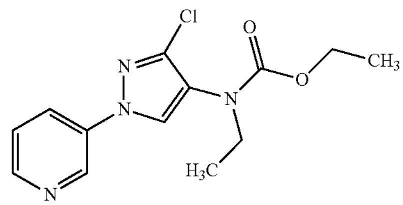 | |
| 339 | Clear Oil | 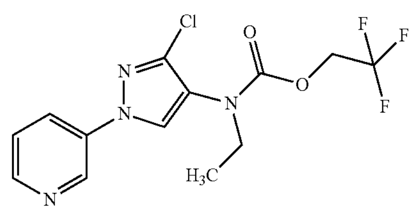 [SMILES: CCN(C(=O)OCC(F)(F)F)c1cn(-c2cccnc2)nc1Cl] | |
| 340 | White Solid | 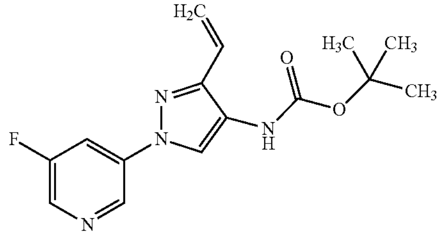 [SMILES: C=Cc1nn(-c2cncc(F)c2)cc1NC(=O)OC(C)(C)C] | |

TABLE 1-continued

Compound number, appearance, and structure

| Compound No. | Appearance | Structure | Prepared as in Example: |
|---|---|---|---|
| 341 | Yellow Oil | 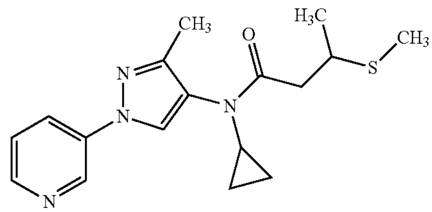 [SMILES: CSC(C)CC(=O)N(c1cn(-c2cccnc2)nc1C)C1CC1] | |
| 342 | Yellow Oil | 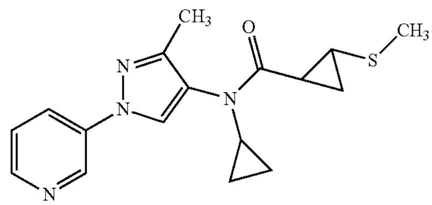 [SMILES: CSC1CC1C(=O)N(c1cn(-c2cccnc2)nc1C)C1CC1] | |
| 343 | Yellow Oil | 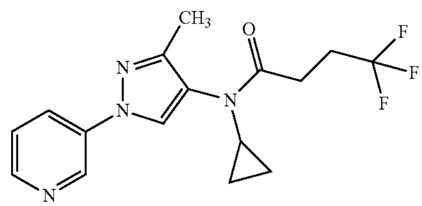 [SMILES: Cc1nn(-c2cccnc2)cc1N(C(=O)CCC(F)(F)F)C1CC1] | |
| 344 | Yellow Oil | 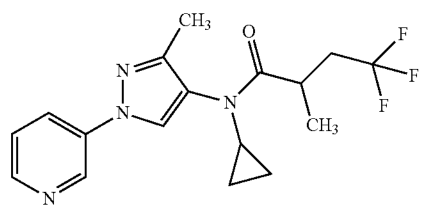 [SMILES: Cc1nn(-c2cccnc2)cc1N(C(=O)C(C)CC(F)(F)F)C1CC1] | |
| 345 | Yellow Solid | 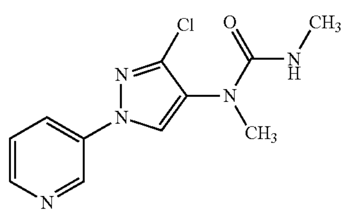 [SMILES: CNC(=O)N(C)c1cn(-c2cccnc2)nc1Cl] | |
| 346 | White Solid | 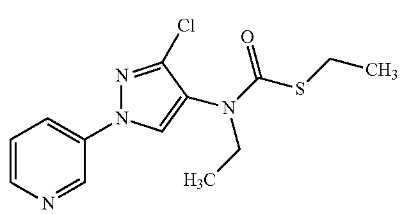 [SMILES: CCSC(=O)N(CC)c1cn(-c2cccnc2)nc1Cl] | |
| 347 | Pale Yellow Oil | 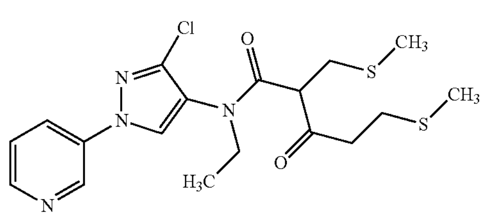 [SMILES: CCN(C(=O)C(CSC)C(=O)CCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 348 | Brown Solid | 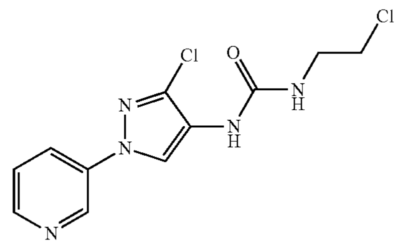 [SMILES: O=C(NCCCl)Nc1cn(-c2cccnc2)nc1Cl] | |
| 349 | Beige Solid | 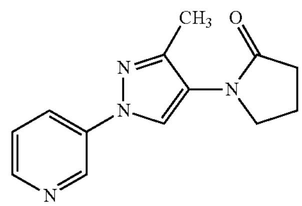 | |
| 350 | Colorless Oil | 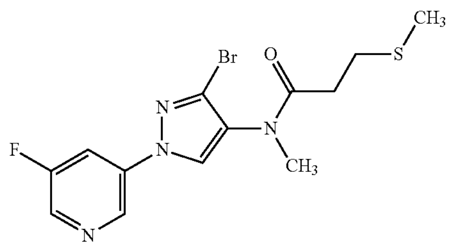 [SMILES: CSCCC(=O)N(C)c1cn(-c2cncc(F)c2)nc1Br] | |
| 351 | White Solid | 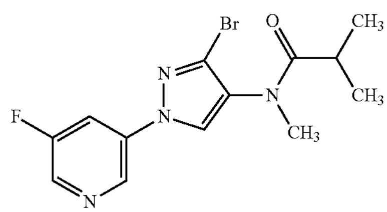 [SMILES: CC(C)C(=O)N(C)c1cn(-c2cncc(F)c2)nc1Br] | |
| 352 | Yellow Solid | 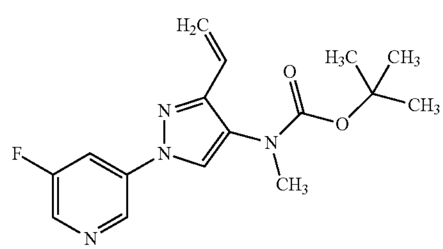 [SMILES: C=Cc1nn(-c2cncc(F)c2)cc1N(C)C(=O)OC(C)(C)C] | |
| 353 | Yellow Oil | 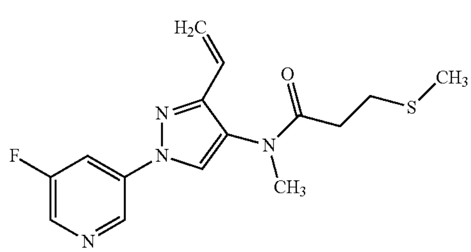 [SMILES: C=Cc1nn(-c2cncc(F)c2)cc1N(C)C(=O)CCSC] | |

TABLE 1-continued
Compound number, appearance, and structure
| Compound No. | Appearance | Structure | Prepared as in Example: |
|---|---|---|---|
| 354 | Yellow Oil | 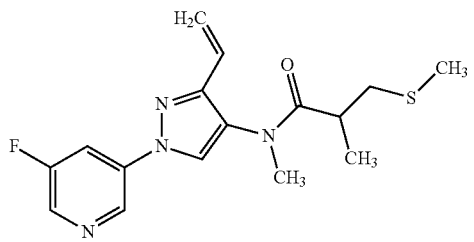 [SMILES: C=Cc1nn(-c2cncc(F)c2)cc1N(C)C(=O)C(C)CSC] | |
| 355 | Yellow Solid | 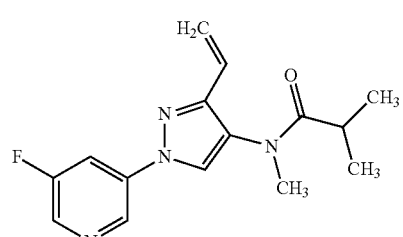 | |
| 356 | Yellow Oil | 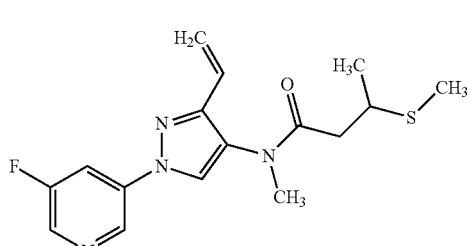 | |
| 357 | Yellow Oil | 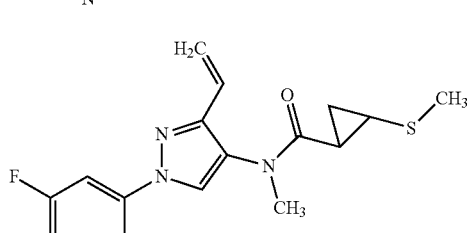 | |
| 358 | Off-White Solid | 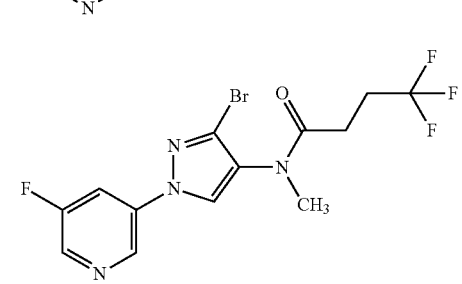 | |
| 359 | Off White Solid | 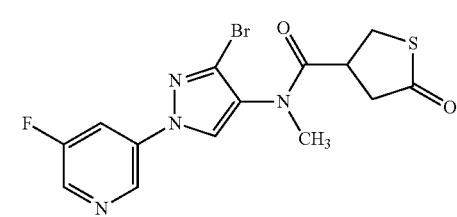 [SMILES: CN(C(=O)C1CSC(=O)C1)c1cn(-c2cncc(F)c2)nc1Br] | |

US 9,708,288 B2
315                                                                                         316
TABLE 1-continued
Compound number, appearance, and structure
| Compound No. | Appearance | Structure | Prepared as in Example: |
|---|---|---|---|
| 360 | White Solid | 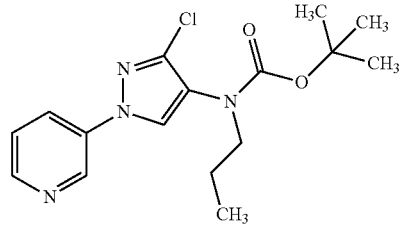 [SMILES: CCCN(C(=O)OC(C)(C)C)c1cn(-c2cccnc2)nc1Cl] | |
| 361 | Tan Solid | 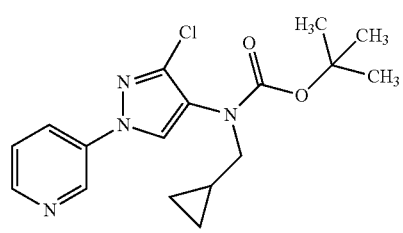 [SMILES: CC(C)(C)OC(=O)N(CC1CC1)c1cn(-c2cccnc2)nc1Cl] | |
| 362 | Clear Oil | 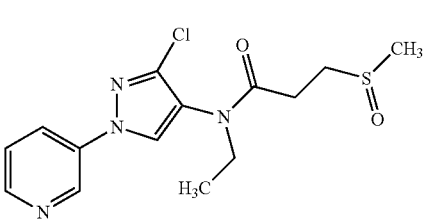 | |
| 363 | Clear Oil | 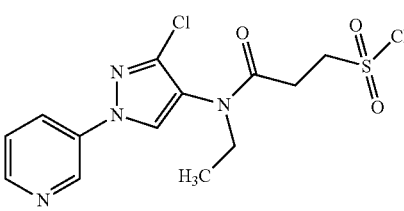 | |
| 364 | Yellow Oil | 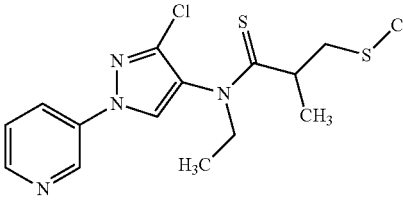 | |
| 365 | Yellow Oil | 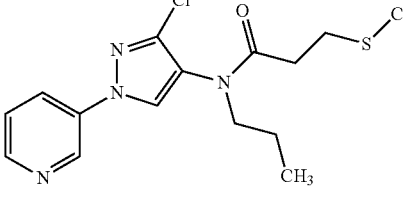 | |
| 366 | Yellow Oil | 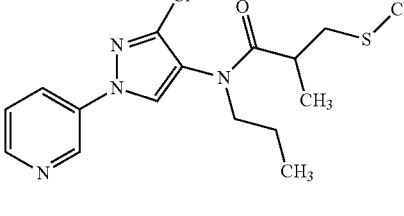 | |

TABLE 1-continued

Compound number, appearance, and structure

| Compound No. | Appearance | Structure | Prepared as in Example: |
|---|---|---|---|
| 367 | Clear Oil | 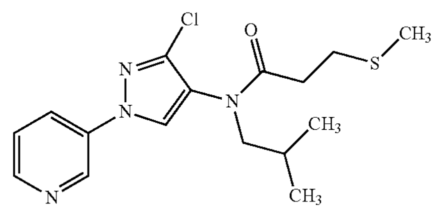 [SMILES: CSCCC(=O)N(CC(C)C)c1cn(-c2cccnc2)nc1Cl] | |
| 368 | White Solid | 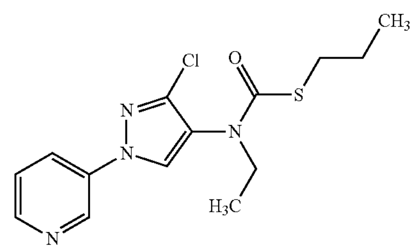 [SMILES: CCCSC(=O)N(CC)c1cn(-c2cccnc2)nc1Cl] | |
| 369 | Light Brown Oil | 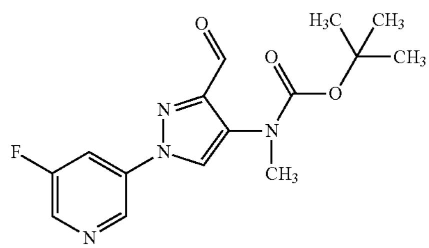 [SMILES: CN(C(=O)OC(C)(C)C)c1cn(-c2cncc(F)c2)nc1C=O] | |
| 370 | Colorless Gum | 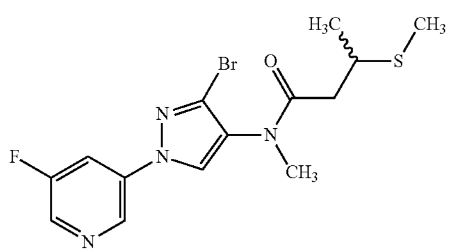 [SMILES: CSC(C)CC(=O)N(C)c1cn(-c2cncc(F)c2)nc1Br] | |
| 371 | Colorless Gum | 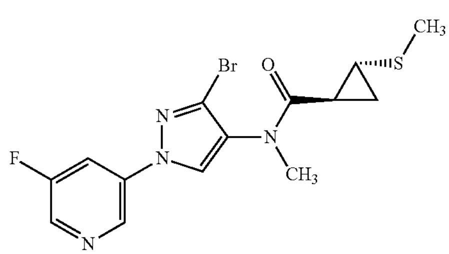 [SMILES: CS[C@@H]1C[C@H]1C(=O)N(C)c1cn(-c2cncc(F)c2)nc1Br] | |
| 372 | Yellow Oil | 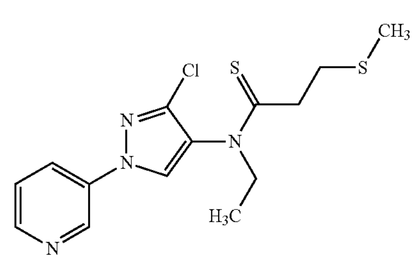 [SMILES: CCN(C(=S)CCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 373 | White Solid | 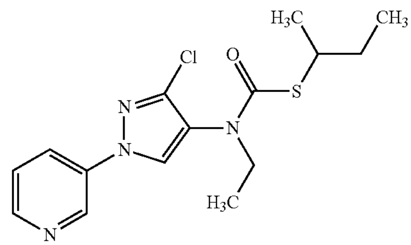 [SMILES: CCC(C)SC(=O)N(CC)c1cn(-c2cccnc2)nc1Cl] | |
| 374 | Beige Solid | 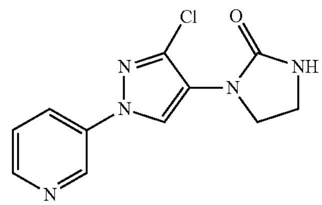 [SMILES: O=C1NCCN1c1cn(-c2cccnc2)nc1Cl] | |
| 375 | White Solid | 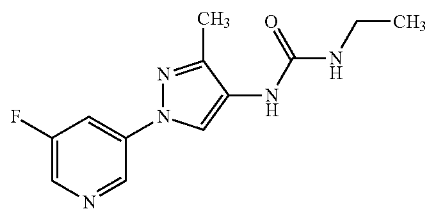 [SMILES: CCNC(=O)Nc1cn(-c2cncc(F)c2)nc1C] | |
| 376 | White Solid | 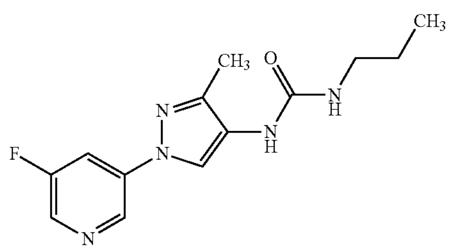 [SMILES: CCCNC(=O)Nc1cn(-c2cncc(F)c2)nc1C] | |
| 377 | White Solid | 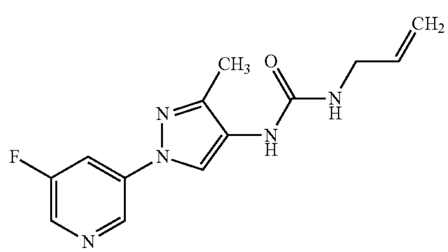 [SMILES: C=CCNC(=O)Nc1cn(-c2cncc(F)c2)nc1C] | |
| 378 | White Solid | 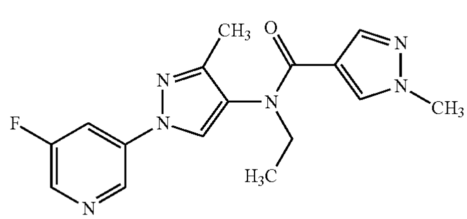 [SMILES: CCN(C(=O)c1cnn(C)c1)c1cn(-c2cncc(F)c2)nc1C] | |

TABLE 1-continued

Compound number, appearance, and structure

| Compound No. | Appearance | Structure | Prepared as in Example: |
|---|---|---|---|
| 379 | White Solid | 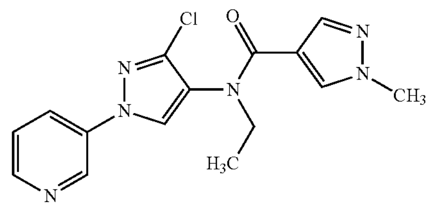 [SMILES: CCN(C(=O)c1cnn(C)c1)c1cn(-c2cccnc2)nc1Cl] | |
| 380 | White Solid | 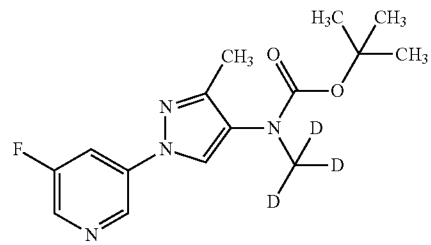 [SMILES: [2H]C([2H])([2H])N(C(=O)OC(C)(C)C)c1cn(-c2cncc(F)c2)nc1C] | |
| 381 | White Solid | 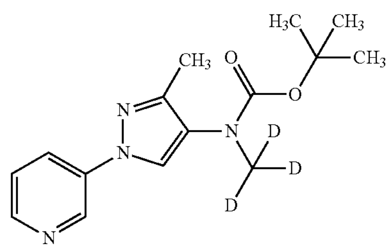 [SMILES: [2H]C([2H])([2H])N(C(=O)OC(C)(C)C)c1cn(-c2cccnc2)nc1C] | |
| 382 | Clear Oil | 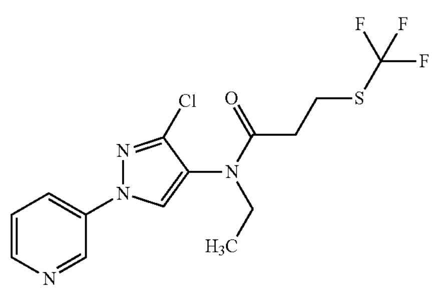 [SMILES: CCN(C(=O)CCSC(F)(F)F)c1cn(-c2cccnc2)nc1Cl] | |
| 383 | Pale Yellow Oil | 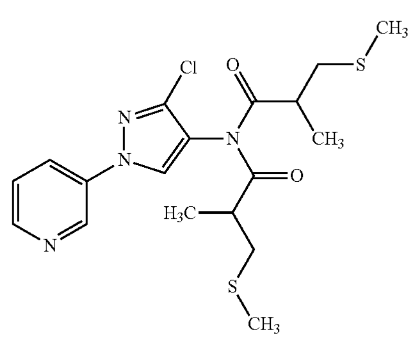 [SMILES: CSCC(C)C(=O)N(C(=O)C(C)CSC)c1cn(-c2cccnc2)nc1Cl] | |

TABLE 1-continued

Compound number, appearance, and structure

| Compound No. | Appearance | Structure | Prepared as in Example: |
|---|---|---|---|
| 384 | Colorless Oil | 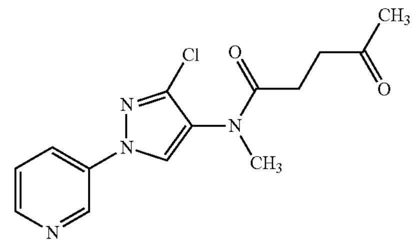 [SMILES: CC(=O)CCC(=O)N(C)c1cn(-c2cccnc2)nc1Cl] | |
| 385 | White Solid | 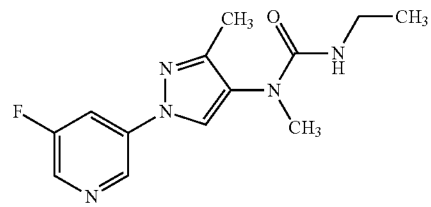 [SMILES: CCNC(=O)N(C)c1cn(-c2cncc(F)c2)nc1C] | |
| 386 | White Solid | 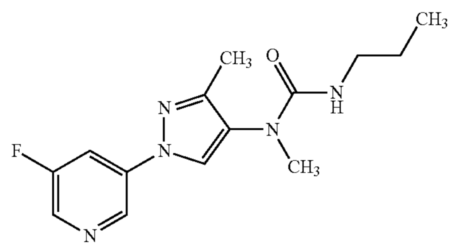 [SMILES: CCCNC(=O)N(C)c1cn(-c2cncc(F)c2)nc1C] | |
| 387 | White Solid | 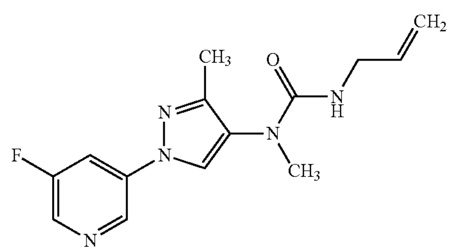 [SMILES: C=CCNC(=O)N(C)c1cn(-c2cncc(F)c2)nc1C] | |
| 388 | White Solid | 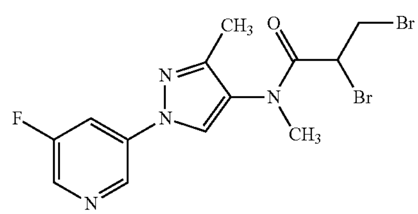 [SMILES: Cc1nn(-c2cncc(F)c2)cc1N(C)C(=O)C(Br)CBr] | |
| 389 | Colorless Oil | 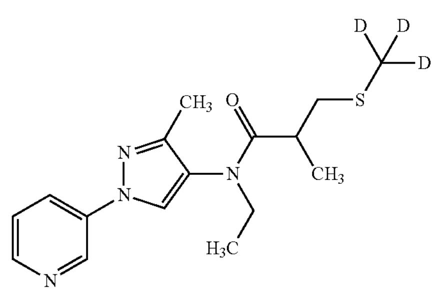 [SMILES: [2H]C([2H])([2H])SCC(C)C(=O)N(CC)c1cn(-c2cccnc2)nc1C] | |

TABLE 1-continued

Compound number, appearance, and structure

| Compound No. | Appearance | Structure | Prepared as in Example: |
|---|---|---|---|
| 390 | Off-White Solid | *(5-fluoropyridin-3-yl)-3-methylpyrazol-4-yl N-ethyl 2-methyl-3-(S-CD3)thio propanamide* | |
| 391 | Colorless Oil | *3-chloro-1-(pyridin-3-yl)pyrazol-4-yl N-methyl 2-methyl-3-(S-CD3)thio propanamide* | |
| 392 | Colorless Oil | *3-chloro-1-(pyridin-3-yl)pyrazol-4-yl N-ethyl 2-methyl-3-(S-CD3)thio propanamide* | |
| 393 | Colorless Oil | *3-chloro-1-(pyridin-3-yl)pyrazol-4-yl N-ethyl 2,2-dideutero-3-(methylthio) propanamide* | |
| 394 | Colorless Oil | *1-(5-fluoropyridin-3-yl)-3-methylpyrazol-4-yl N-ethyl 2,2-dideutero-3-(methylthio) propanamide* | |

TABLE 1-continued

Compound number, appearance, and structure

| Compound No. | Appearance | Structure | Prepared as in Example: |
|---|---|---|---|
| 395 | Pink Solid | 3-chloro-1-(pyridin-3-yl)-pyrazol-4-yl with N(CH₃)C(O)CHBrCH₂Br | |
| 396 | Colorless Oil | 3-chloro-1-(pyridin-3-yl)-pyrazol-4-yl with N(CH₃)C(O)CD₂CH₂SCH₃ | |
| 397 | Colorless Oil | 3-methyl-1-(5-fluoropyridin-3-yl)-pyrazol-4-yl with N(CD₃)C(O)CH₂CH₂SCH₃ | |
| 398 | White Solid | 3-methyl-1-(5-fluoropyridin-3-yl)-pyrazol-4-yl with N(CD₃)C(O)CH(CH₃)CH₂SCH₃ | |
| 399 | White Solid | 3-bromo-1-(5-fluoropyridin-3-yl)-pyrazol-4-yl with NHC(O)CH(CH₃)₂ | |
| 400 | Yellow Oil | 3-methyl-1-(pyridin-3-yl)-pyrazol-4-yl with N[CH₂CH(CH₃)CH₂SCH₃]C(O)CH₂CH₂SCH₃ | |

TABLE 1-continued

Compound number, appearance, and structure

| Compound No. | Appearance | Structure | Prepared as in Example: |
|---|---|---|---|
| 401 | Yellow Oil | 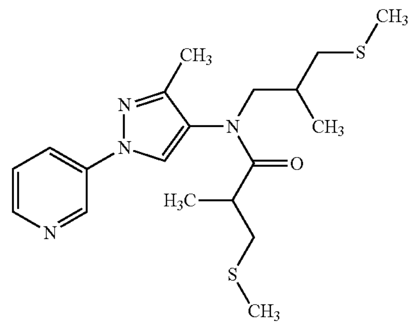 [SMILES: CSCC(C)CN(C(=O)C(C)CSC)c1cn(-c2cccnc2)nc1C] | |
| 402 | Yellow Oil | 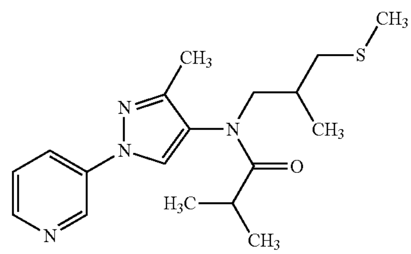 [SMILES: CSCC(C)CN(C(=O)C(C)C)c1cn(-c2cccnc2)nc1C] | |
| 403 | Yellow Oil | 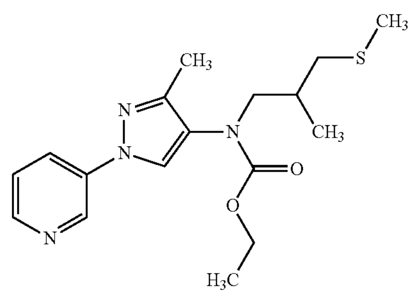 [SMILES: CCOC(=O)N(CC(C)CSC)c1cn(-c2cccnc2)nc1C] | |
| 404 | Yellow Solid | 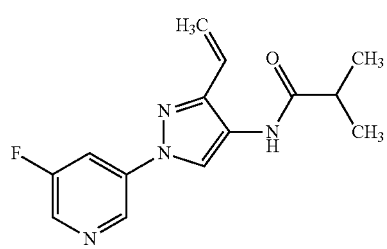 [SMILES: C=Cc1nn(-c2cncc(F)c2)cc1NC(=O)C(C)C] | |
| 405 | Colorless Oil | 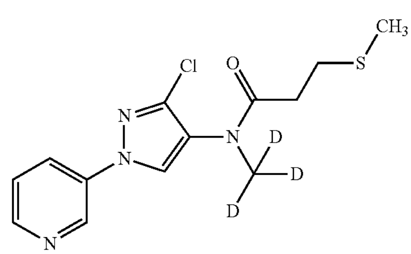 [SMILES: [2H]C([2H])([2H])N(C(=O)CCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 406 | Colorless Oil | 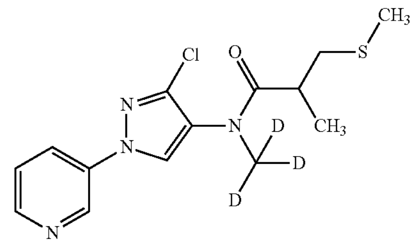 [SMILES: [2H]C([2H])([2H])N(C(=O)C(C)CSC)c1cn(-c2cccnc2)nc1Cl] | |
| 407 | Pale Yellow Oil | 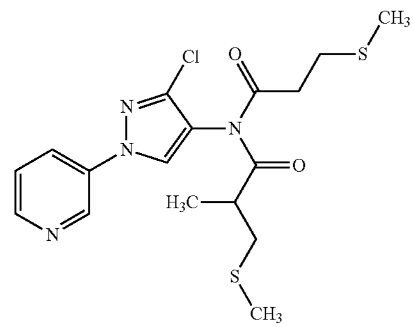 [SMILES: CSCCC(=O)N(C(=O)C(C)CSC)c1cn(-c2cccnc2)nc1Cl] | |
| 408 | Yellow Oil | 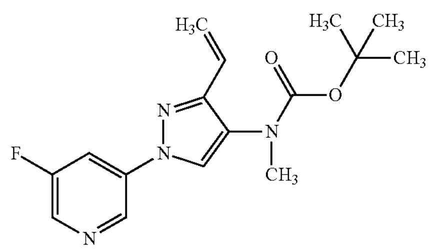 [SMILES: C=Cc1nn(-c2cncc(F)c2)cc1N(C)C(=O)OC(C)(C)C] | |
| 409 | White Solid | 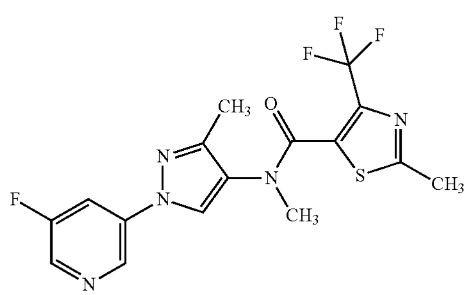 [SMILES: Cc1nc(C(F)(F)F)c(C(=O)N(C)c2cn(-c3cncc(F)c3)nc2C)s1] | |
| 410 | Orange Oil | 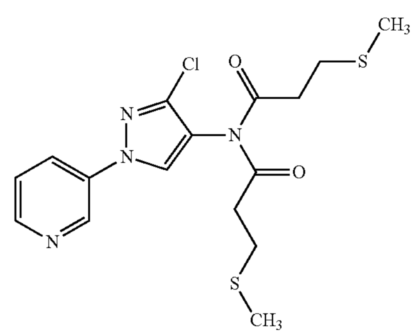 [SMILES: CSCCC(=O)N(C(=O)CCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 411 | Beige Solid | 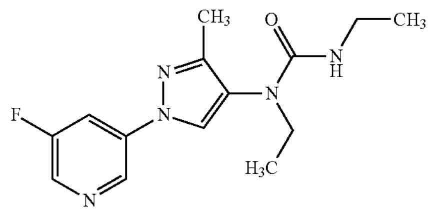 [SMILES: CCNC(=O)N(CC)c1cn(-c2cncc(F)c2)nc1C] | |
| 412 | White Solid | 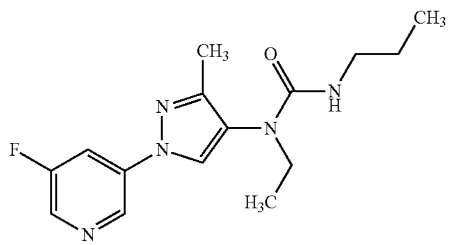 [SMILES: CCCNC(=O)N(CC)c1cn(-c2cncc(F)c2)nc1C] | |
| 413 | White Solid | 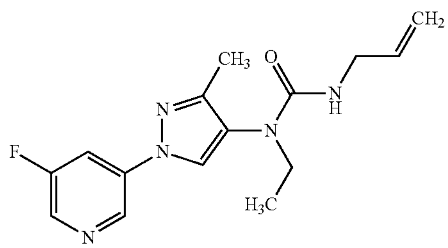 [SMILES: C=CCNC(=O)N(CC)c1cn(-c2cncc(F)c2)nc1C] | |
| 414 | Yellow Oil | 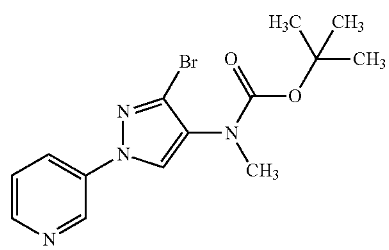 [SMILES: CN(C(=O)OC(C)(C)C)c1cn(-c2cccnc2)nc1Br] | |
| 415 | Off-White Solid | 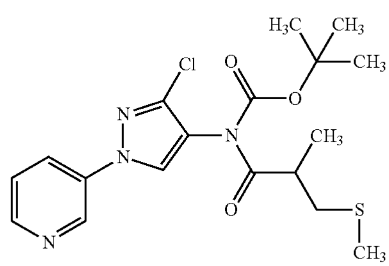 [SMILES: CSCC(C)C(=O)N(C(=O)OC(C)(C)C)c1cn(-c2cccnc2)nc1Cl] | |
| 416 | Yellow Oil | 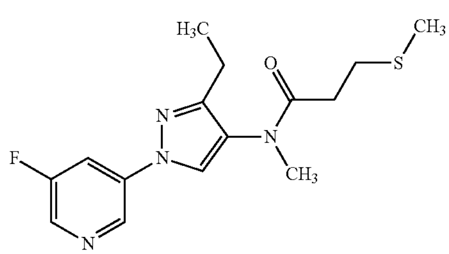 [SMILES: CCc1nn(-c2cncc(F)c2)cc1N(C)C(=O)CCSC] | |

TABLE 1-continued

Compound number, appearance, and structure

| Compound No. | Appearance | Structure | Prepared as in Example: |
|---|---|---|---|
| 417 | Yellow Oil | 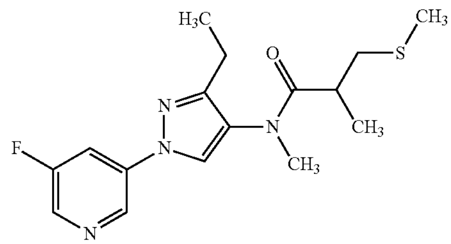 [SMILES: CCc1nn(-c2cncc(F)c2)cc1N(C)C(=O)C(C)CSC] | |
| 418 | Yellow Solid | 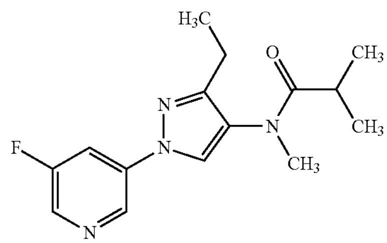 [SMILES: CCc1nn(-c2cncc(F)c2)cc1N(C)C(=O)C(C)C] | |
| 419 | Yellow Oil | 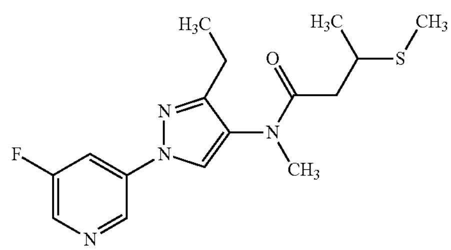 [SMILES: CCc1nn(-c2cncc(F)c2)cc1N(C)C(=O)CC(C)SC] | |
| 420 | Yellow Oil | 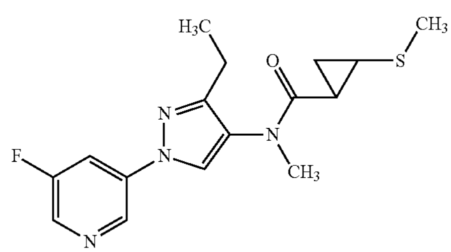 [SMILES: CCc1nn(-c2cncc(F)c2)cc1N(C)C(=O)C1CC1SC] | |
| 421 | Light Yellow Oil | 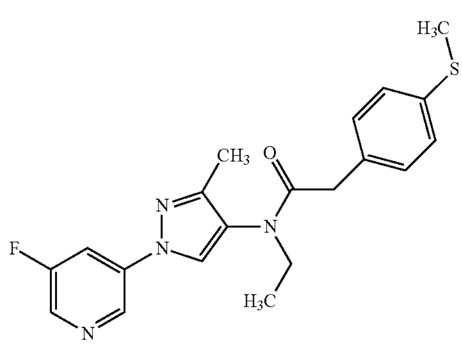 [SMILES: CCN(C(=O)Cc1ccc(SC)cc1)c1cn(-c2cncc(F)c2)nc1C] | |

TABLE 1-continued

Compound number, appearance, and structure

| Compound No. | Appearance | Structure | Prepared as in Example: |
|---|---|---|---|
| 422 | Light Yellow Oil | 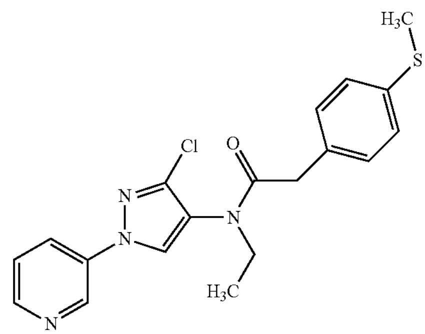 [SMILES: CCN(C(=O)Cc1ccc(SC)cc1)c1cn(-c2cccnc2)nc1Cl] | |
| 423 | Light Yellow Oil | 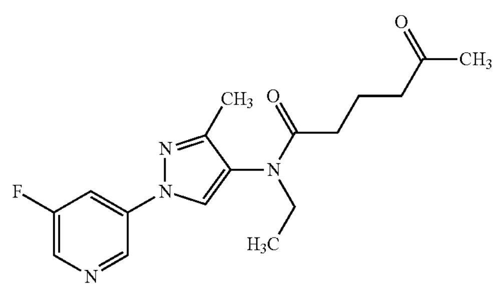 [SMILES: CCN(C(=O)CCCC(C)=O)c1cn(-c2cncc(F)c2)nc1C] | |
| 424 | Tan Solid | 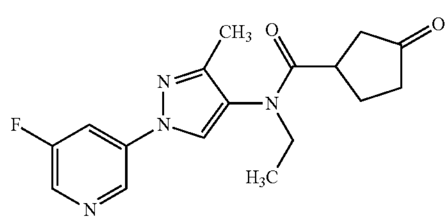 [SMILES: CCN(C(=O)C1CCC(=O)C1)c1cn(-c2cncc(F)c2)nc1C] | |
| 425 | Colorless Oil | 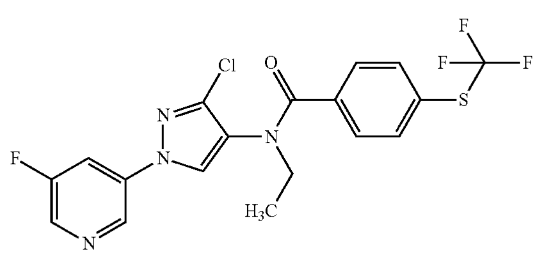 [SMILES: CCN(C(=O)c1ccc(SC(F)(F)F)cc1)c1cn(-c2cncc(F)c2)nc1Cl] | |
| 426 | Colorless Oil | 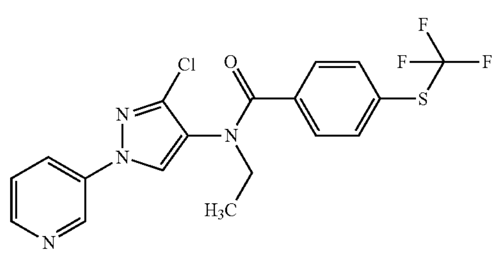 [SMILES: CCN(C(=O)c1ccc(SC(F)(F)F)cc1)c1cn(-c2cccnc2)nc1Cl] | |

TABLE 1-continued

Compound number, appearance, and structure

| Compound No. | Appearance | Structure | Prepared as in Example: |
|---|---|---|---|
| 427 | Yellow Oil | 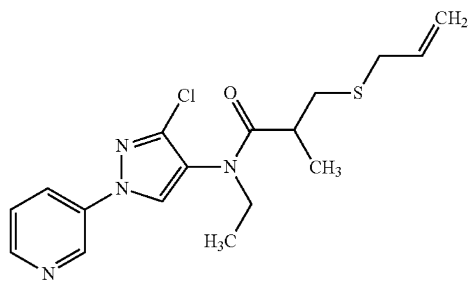 [SMILES: C=CCSCC(C)C(=O)N(CC)c1cn(-c2cccnc2)nc1Cl] | |
| 428 | Yellow Oil | 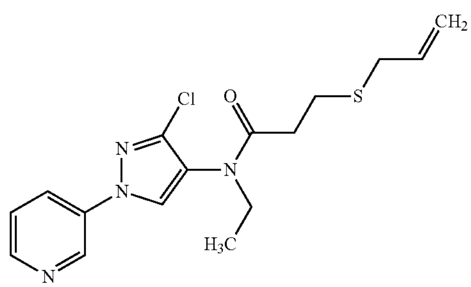 [SMILES: C=CCSCCC(=O)N(CC)c1cn(-c2cccnc2)nc1Cl] | |
| 429 | Yellow Oil | 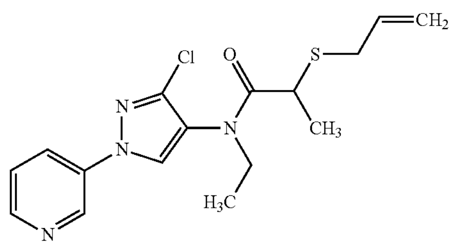 [SMILES: C=CCSC(C)C(=O)N(CC)c1cn(-c2cccnc2)nc1Cl] | |
| 430 | Light Yellow Oil | 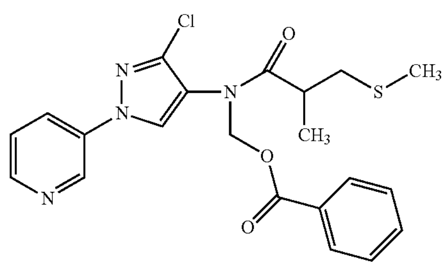 [SMILES: CSCC(C)C(=O)N(COC(=O)c1ccccc1)c1cn(-c2cccnc2)nc1Cl] | |
| 431 | White Solid | 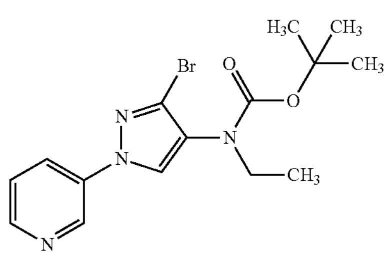 [SMILES: CCN(C(=O)OC(C)(C)C)c1cn(-c2cccnc2)nc1Br] | |

TABLE 1-continued

| Compound No. | Appearance | Structure | Prepared as in Example: |
|---|---|---|---|
| 432 | Yellow Oil | (3-chloro-1-(pyridin-3-yl)-1H-pyrazol-4-yl)-N-ethyl-2-(methylthio)acetamide structure | |
| 433 | Yellow Oil | N-(3-chloro-1-(pyridin-3-yl)-1H-pyrazol-4-yl)-N-acetyl-2-methyl-3-(methylthio)propanamide structure | |
| 434 | White Solid | tert-butyl (3-cyclopropyl-1-(5-fluoropyridin-3-yl)-1H-pyrazol-4-yl)carbamate structure | |
| 435 | White Solid | N-(1-(5-fluoropyridin-3-yl)-3-(hydroxymethyl)-1H-pyrazol-4-yl)isobutyramide structure | |
| 436 | White Solid | N-(1-(5-fluoropyridin-3-yl)-1H-pyrazol-4-yl)isobutyramide structure | |
| 437 | Yellow Oil | N-(3-chloro-1-(pyridin-3-yl)-1H-pyrazol-4-yl)-N-isobutyryl-2-methyl-3-(methylthio)propanamide structure | |

TABLE 1-continued
Compound number, appearance, and structure
| Compound No. | Appearance | Structure | Prepared as in Example: |
|---|---|---|---|
| 438 | Yellow Oil | 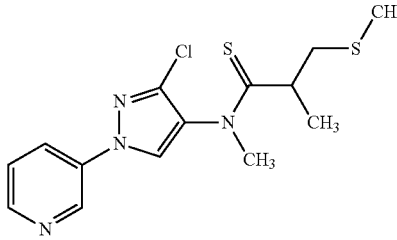 | |
| 439 | White Solid | 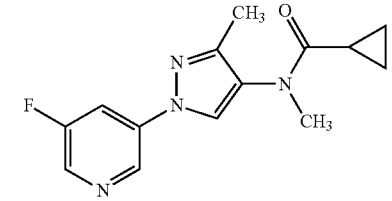 [SMILES: Cc1nn(-c2cncc(F)c2)cc1N(C)C(=O)C1CC1] | |
| 440 | White Solid | 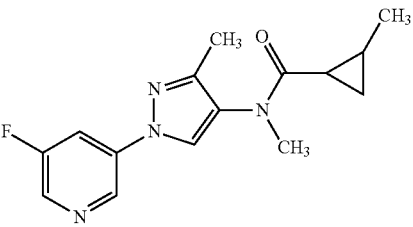 [SMILES: Cc1nn(-c2cncc(F)c2)cc1N(C)C(=O)C1CC1C] | |
| 441 | Yellow Solid | 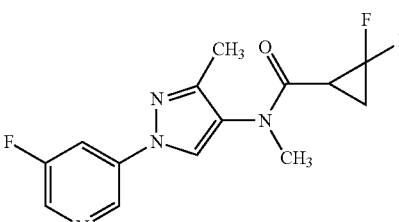 | |
| 442 | White Solid | 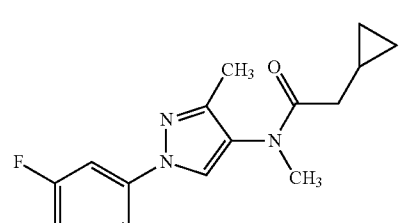 | |
| 443 | White Solid | 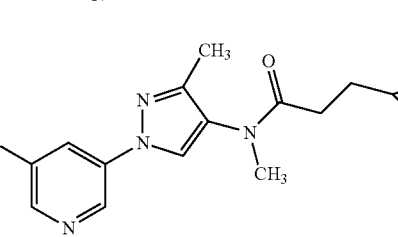 | |

TABLE 1-continued

Compound number, appearance, and structure

| Compound No. | Appearance | Structure | Prepared as in Example: |
|---|---|---|---|
| 444 | Brown Solid | 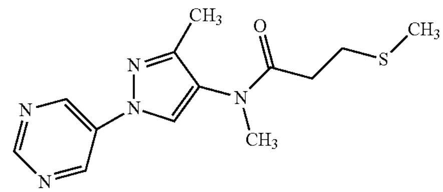 [SMILES: CSCCC(=O)N(C)c1cn(-c2cncnc2)nc1C] | |
| 445 | Brown Solid | 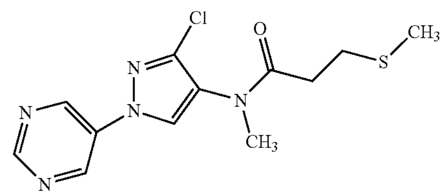 [SMILES: CSCCC(=O)N(C)c1cn(-c2cncnc2)nc1Cl] | |
| 446 | Yellow Oil | 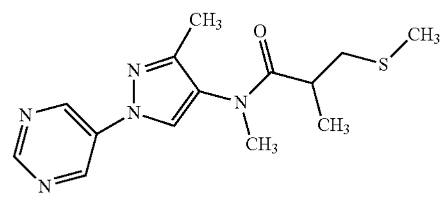 | |
| 447 | Dark Oil | 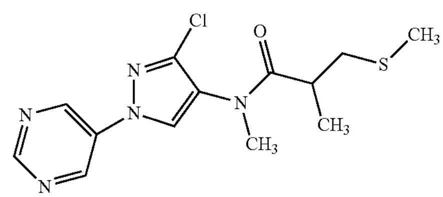 [SMILES: CSCC(C)C(=O)N(C)c1cn(-c2cncnc2)nc1Cl] | |
| 448 | Brown Solid | 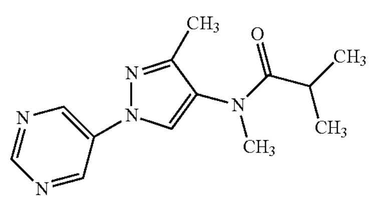 [SMILES: Cc1nn(-c2cncnc2)cc1N(C)C(=O)C(C)C] | |
| 449 | Tan Solid | 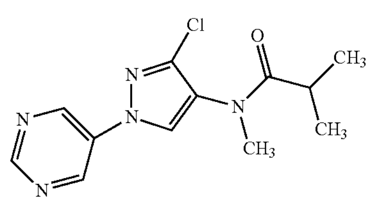 [SMILES: CC(C)C(=O)N(C)c1cn(-c2cncnc2)nc1Cl] | |
| 450 | White Oil | 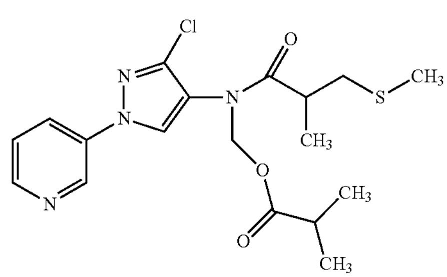 [SMILES: CSCC(C)C(=O)N(COC(=O)C(C)C)c1cn(-c2cccnc2)nc1Cl] | |

TABLE 1-continued

Compound number, appearance, and structure

| Compound No. | Appearance | Structure | Prepared as in Example: |
|---|---|---|---|
| 451 | Yellow Oil | 3-chloro-1-(pyridin-3-yl)-1H-pyrazol-4-yl with N-(ethoxycarbonyl)-2-methyl-3-(methylthio)propanamide | |
| 452 | Colorless Oil | 3-bromo-1-(pyridin-3-yl)-1H-pyrazol-4-yl with N-methyl-3-(methylthio)propanamide | |
| 453 | White Solid | 3-bromo-1-(pyridin-3-yl)-1H-pyrazol-4-yl with N-methyl-2-methyl-3-(methylthio)propanamide (racemic) | |
| 454 | White Solid | 3-bromo-1-(pyridin-3-yl)-1H-pyrazol-4-yl with N-methyl-isobutyramide | |
| 455 | Colorless Gum | 3-bromo-1-(pyridin-3-yl)-1H-pyrazol-4-yl with N-methyl-4,4,4-trifluorobutanamide | |
| 456 | Yellow Oil | 3-chloro-1-(pyridin-3-yl)-1H-pyrazol-4-yl with N-methyl-oxirane-2-carboxamide | |

TABLE 1-continued

Compound number, appearance, and structure

| Compound No. | Appearance | Structure | Prepared as in Example: |
|---|---|---|---|
| 457 | White Oil | 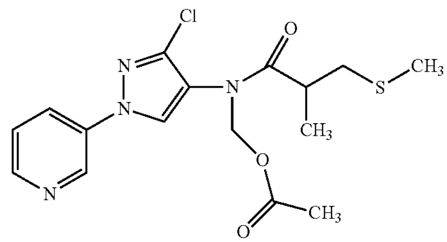 [SMILES: CSCC(C)C(=O)N(COC(C)=O)c1cn(-c2cccnc2)nc1Cl] | |
| 458 | White Solid | AND Enantimoer | |
| 459 | Colorless Oil | 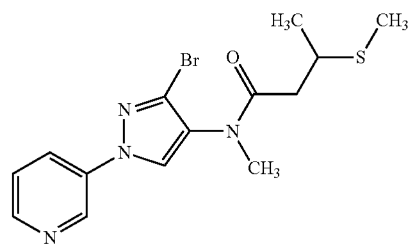 [SMILES: CSC(C)CC(=O)N(C)c1cn(-c2cccnc2)nc1Br] | |
| 460 | White Solid | 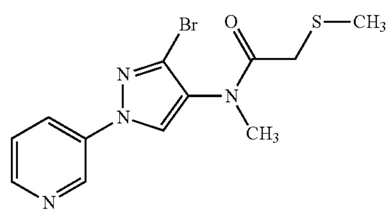 [SMILES: CSCC(=O)N(C)c1cn(-c2cccnc2)nc1Br] | |
| 461 | Colorless Gum | 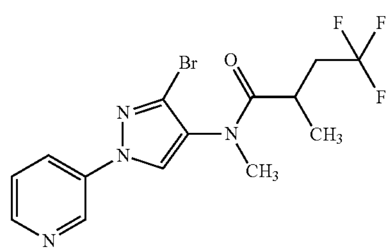 [SMILES: CC(CC(F)(F)F)C(=O)N(C)c1cn(-c2cccnc2)nc1Br] | |
| 462 | White Solid | 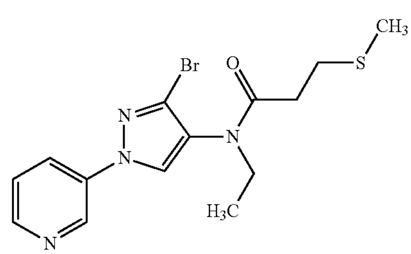 [SMILES: CCN(C(=O)CCSC)c1cn(-c2cccnc2)nc1Br] | |

TABLE 1-continued

Compound number, appearance, and structure

| Compound No. | Appearance | Structure | Prepared as in Example: |
|---|---|---|---|
| 463 | White Solid | 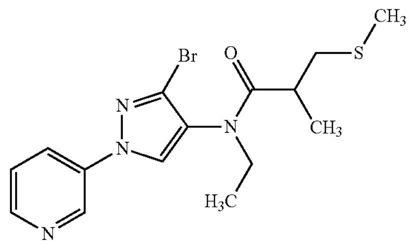 [SMILES: CCN(C(=O)C(C)CSC)c1cn(-c2cccnc2)nc1Br] | |
| 464 | Colorless Gum | 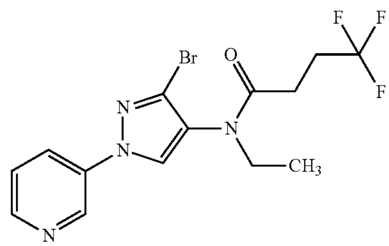 [SMILES: CCN(C(=O)CCC(F)(F)F)c1cn(-c2cccnc2)nc1Br] | |
| 465 | White Solid | 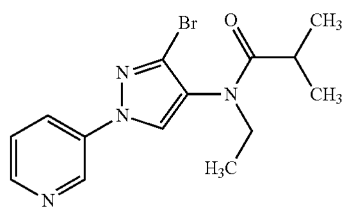 [SMILES: CCN(C(=O)C(C)C)c1cn(-c2cccnc2)nc1Br] | |
| 466 | White Solid | (AND Enantiomer) | |
| 467 | Colorless Gum | 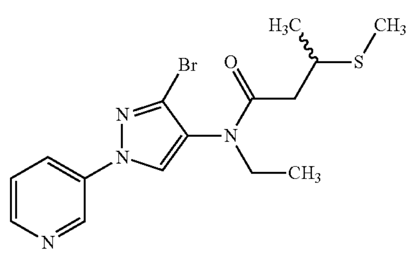 [SMILES: CCN(C(=O)CC(C)SC)c1cn(-c2cccnc2)nc1Br] | |
| 468 | Light Yellow Solid | 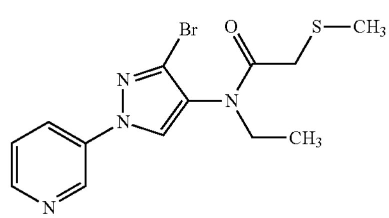 [SMILES: CCN(C(=O)CSC)c1cn(-c2cccnc2)nc1Br] | |

TABLE 1-continued
Compound number, appearance, and structure
| Compound No. | Appearance | Structure | Prepared as in Example: |
|---|---|---|---|
| 469 | White Solid | 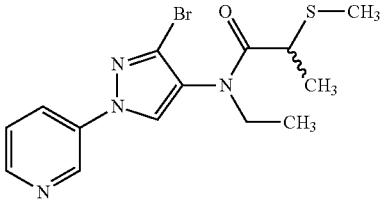 [SMILES: CCN(C(=O)C(C)SC)c1cn(-c2cccnc2)nc1Br] | |
| 470 | Light Yellow Oil | 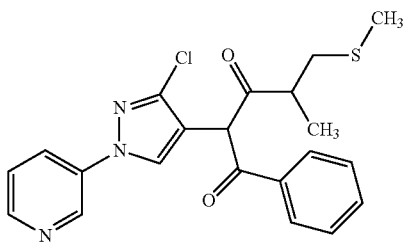 [SMILES: CSCC(C)C(=O)C(C(=O)c1ccccc1)c1cn(-c2cccnc2)nc1Cl] | |
| 471 | Light Yellow Oil | 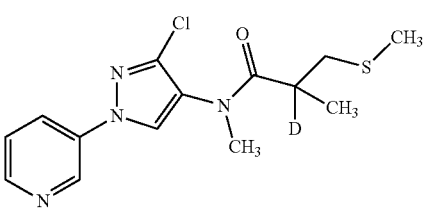 [SMILES: [2H]C(C)(CSC)C(=O)N(C)c1cn(-c2cccnc2)nc1Cl] | |
| 472 | Light Yellow Oil | 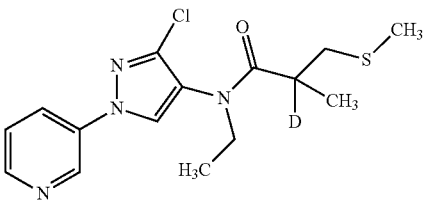 [SMILES: [2H]C(C)(CSC)C(=O)N(CC)c1cn(-c2cccnc2)nc1Cl] | |
| 473 | Light Purple Solid | 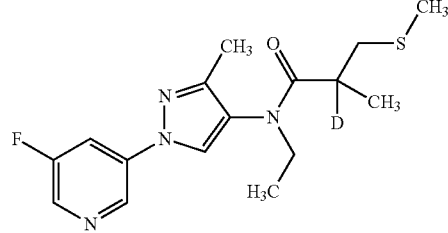 [SMILES: [2H]C(C)(CSC)C(=O)N(CC)c1cn(-c2cncc(F)c2)nc1C] | |
| 474 | Yellow Oil | 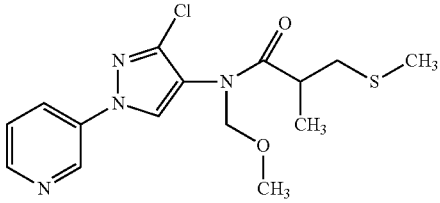 [SMILES: COCN(C(=O)C(C)CSC)c1cn(-c2cccnc2)nc1Cl] | |

TABLE 1-continued
Compound number, appearance, and structure
| Compound No. | Appearance | Structure | Prepared as in Example: |
|---|---|---|---|
| 475 | Light Yellow Oil | 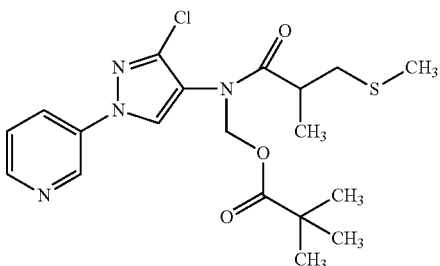 | |
| 476 | White Solid | 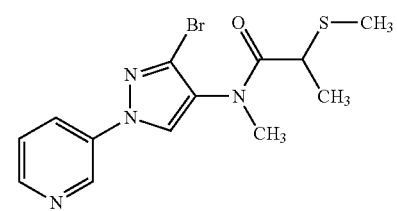 [SMILES: CSC(C)C(=O)N(C)c1cn(-c2cccnc2)nc1Br] | |
| 477 | Off-white Solid | 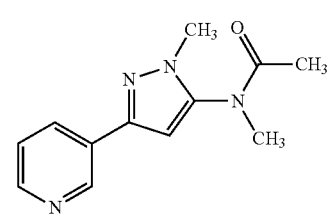 [SMILES: CC(=O)N(C)c1cc(-c2cccnc2)nn1C] | |
| 478 | Clear Oil | 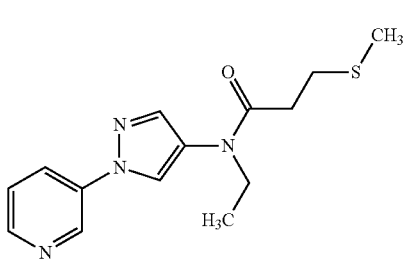 [SMILES: CCN(C(=O)CCSC)c1cnn(-c2cccnc2)c1] | |
| 479 | Beige Solid | 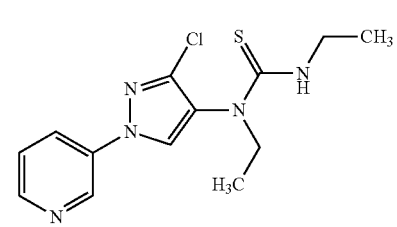 [SMILES: CCNC(=S)N(CC)c1cn(-c2cccnc2)nc1Cl] | |
| 480 | White Solid | 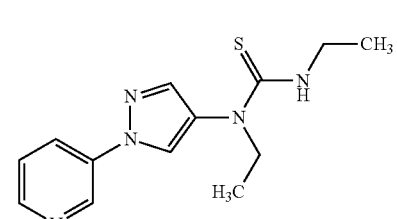 | |

TABLE 1-continued

Compound number, appearance, and structure

| Compound No. | Appearance | Structure | Prepared as in Example: |
|---|---|---|---|
| 481 | Light Yellow Oil | 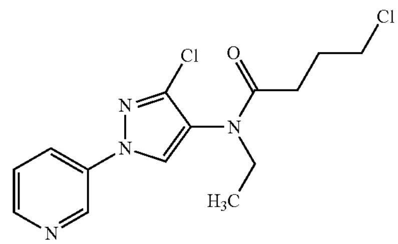 [SMILES: CCN(C(=O)CCCCl)c1cn(-c2cccnc2)nc1Cl] | |
| 482 | Beige Solid | 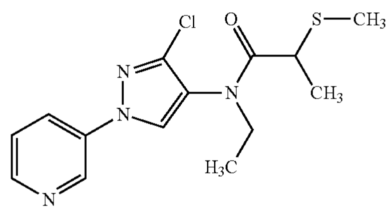 | |
| 483 | Clear Viscous Oil | 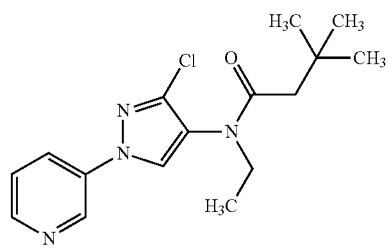 [SMILES: CCN(C(=O)CC(C)(C)C)c1cn(-c2cccnc2)nc1Cl] | |
| 484 | Clear Viscous Oil | 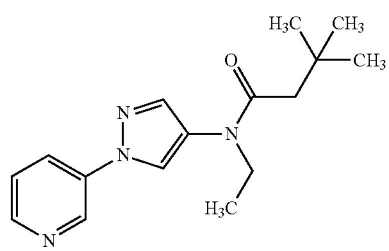 [SMILES: CCN(C(=O)CC(C)(C)C)c1cnn(-c2cccnc2)c1] | |
| 485 | White Oil | 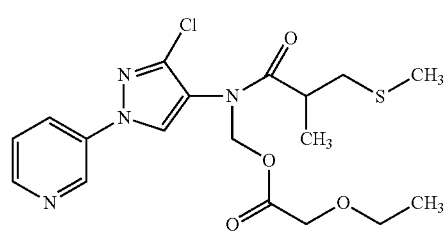 [SMILES: CCOCC(=O)OCN(C(=O)C(C)CSC)c1cn(-c2cccnc2)nc1Cl] | |
| 486 | Off White Solid | 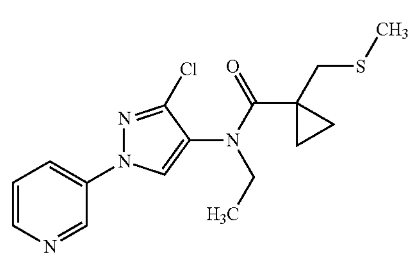 [SMILES: CCN(C(=O)C1(CSC)CC1)c1cn(-c2cccnc2)nc1Cl] | |

TABLE 1-continued

Compound number, appearance, and structure

| Compound No. | Appearance | Structure | Prepared as in Example: |
|---|---|---|---|
| 487 | Off-white Gum | 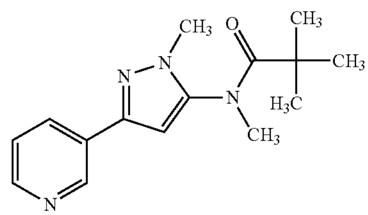 [SMILES: CN(C(=O)C(C)(C)C)c1cc(-c2cccnc2)nn1C] | |
| 488 | Light Yellow Solid | 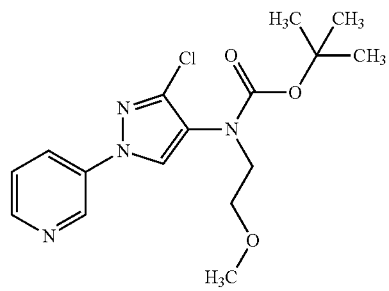 [SMILES: COCCN(C(=O)OC(C)(C)C)c1cn(-c2cccnc2)nc1Cl] | |
| 489 | Yellow Solid | 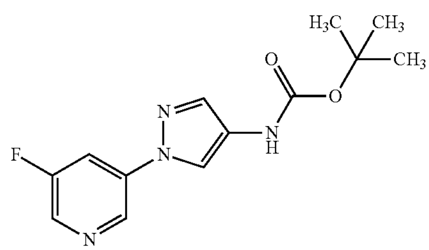 [SMILES: CC(C)(C)OC(=O)Nc1cnn(-c2cncc(F)c2)c1] | |
| 490 | Light Yellow Oil | 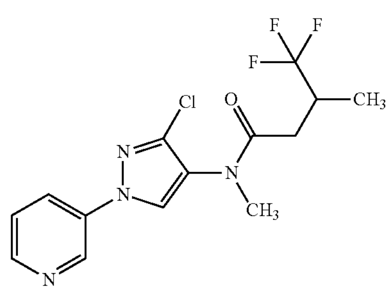 [SMILES: CC(CC(=O)N(C)c1cn(-c2cccnc2)nc1Cl)C(F)(F)F] | |
| 491 | Light Yellow Oil | 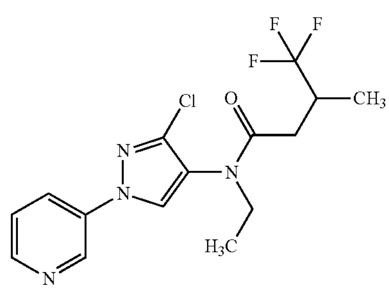 [SMILES: CCN(C(=O)CC(C)C(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 492 | White Solid | 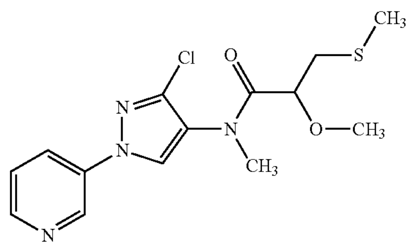 [SMILES: COC(CSC)C(=O)N(C)c1cn(-c2cccnc2)nc1Cl] | |
| 493 | Light Orange Oil | 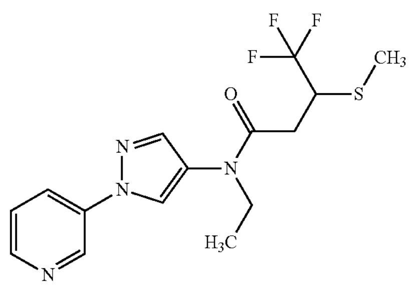 [SMILES: CCN(C(=O)CC(SC)C(F)(F)F)c1cnn(-c2cccnc2)c1] | |
| 494 | Yellow Oil | 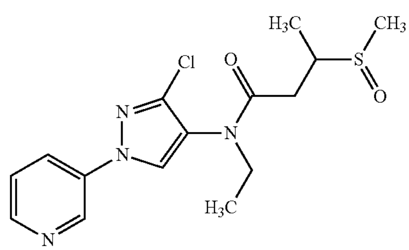 [SMILES: CCN(C(=O)CC(C)S(C)=O)c1cn(-c2cccnc2)nc1Cl] | |
| 495 | Clear Oil | 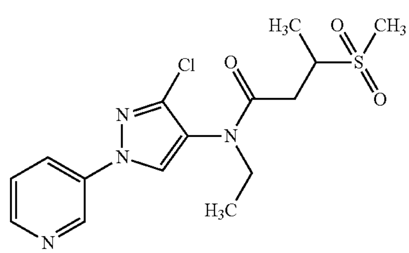 [SMILES: CCN(C(=O)CC(C)S(C)(=O)=O)c1cn(-c2cccnc2)nc1Cl] | |
| 496 | Light Yellow Oil | 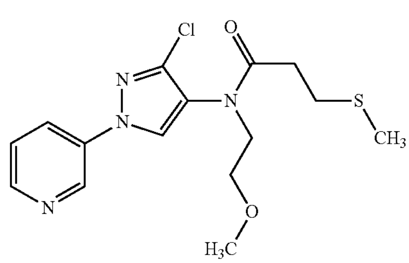 [SMILES: COCCN(C(=O)CCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 497 | Light Yellow Oil | 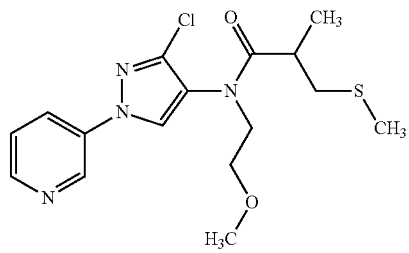 [SMILES: COCCN(C(=O)C(C)CSC)c1cn(-c2cccnc2)nc1Cl] | |
| 498 | Light Yellow Oil | 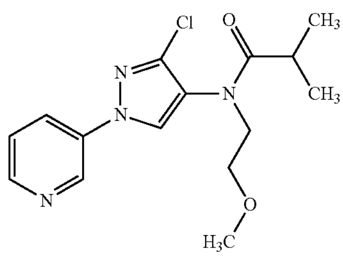 [SMILES: COCCN(C(=O)C(C)C)c1cn(-c2cccnc2)nc1Cl] | |
| 499 | Colorless Oil | 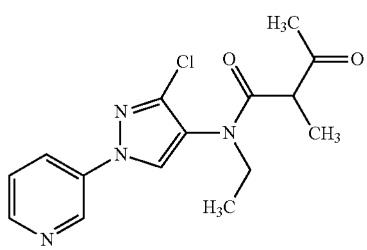 [SMILES: CCN(C(=O)C(C)C(C)=O)c1cn(-c2cccnc2)nc1Cl] | |
| 500 | Beige Solid | 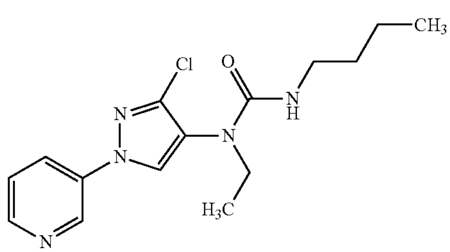 [SMILES: CCCCNC(=O)N(CC)c1cn(-c2cccnc2)nc1Cl] | |
| 501 | White Solid | 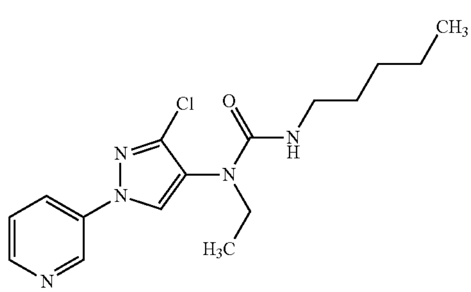 [SMILES: CCCCCNC(=O)N(CC)c1cn(-c2cccnc2)nc1Cl] | |

TABLE 1-continued

Compound number, appearance, and structure

| Compound No. | Appearance | Structure | Prepared as in Example: |
|---|---|---|---|
| 502 | Thick Yellow Oil | (3-pyridyl)-pyrazol-4-yl with N(ethyl)-C(=O)-NH-pentyl urea | |
| 503 | Beige Solid | 3-chloro-1-(3-pyridyl)-pyrazol-4-yl with N(ethyl)-C(=O)-NH-(sec-butyl) urea | |
| 504 | Beige Solid | 1-(3-pyridyl)-pyrazol-4-yl with N(ethyl)-C(=O)-NH-(sec-butyl) urea | |
| 505 | Colorless Gum | 3-bromo-1-(3-pyridyl)-pyrazol-4-yl with N(methyl)-C(=O)-CH₂-CF₂-CH(SCH₃)CH₃ | |
| 506 | Clear Colorless Oil | 3-chloro-1-(3-pyridyl)-pyrazol-4-yl with N(cyclopropylmethyl)-C(=O)-CH₂CH₂-SCH₃ | |
| 507 | Clear Colorless Oil | 3-chloro-1-(3-pyridyl)-pyrazol-4-yl with N(cyclopropylmethyl)-C(=O)-CH(CH₃)-CH₂-SCH₃ | |

TABLE 1-continued

Compound number, appearance, and structure

| Compound No. | Appearance | Structure | Prepared as in Example: |
|---|---|---|---|
| 508 | Clear Colorless Oil | 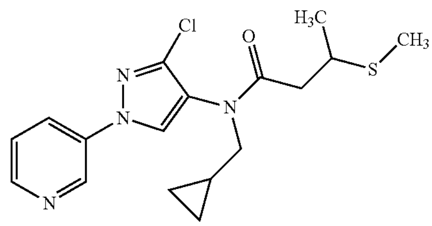 [SMILES: CSC(C)CC(=O)N(CC1CC1)c1cn(-c2cccnc2)nc1Cl] | |
| 509 | Pale Yellow Gum | 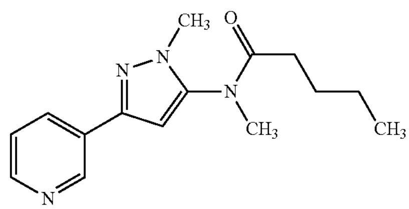 [SMILES: CCCCC(=O)N(C)c1cc(-c2cccnc2)nn1C] | |
| 510 | Yellow Oil | 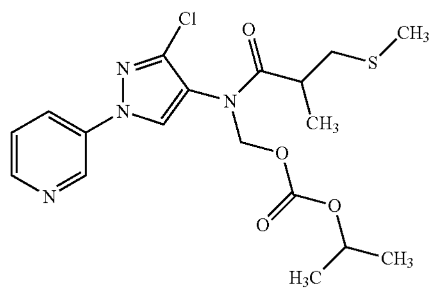 [SMILES: CSCC(C)C(=O)N(COC(=O)OC(C)C)c1cn(-c2cccnc2)nc1Cl] | |
| 511 | White Oil | 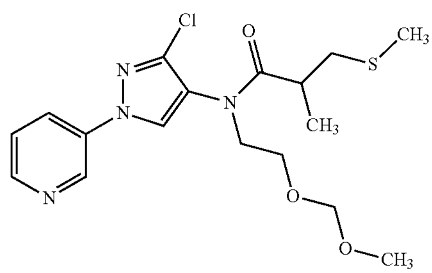 [SMILES: COCOCCN(C(=O)C(C)CSC)c1cn(-c2cccnc2)nc1Cl] | |
| 512 | Pale Yellow Oil | 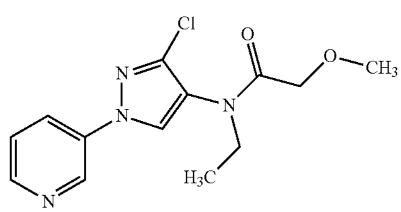 [SMILES: CCN(C(=O)COC)c1cn(-c2cccnc2)nc1Cl] | |
| 513 | Thick Clear Oil | 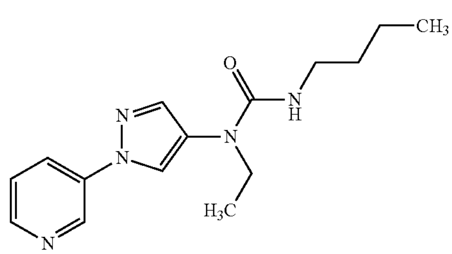 [SMILES: CCCCNC(=O)N(CC)c1cnn(-c2cccnc2)c1] | |

TABLE 1-continued

Compound number, appearance, and structure

| Compound No. | Appearance | Structure | Prepared as in Example: |
|---|---|---|---|
| 514 | White Solid | 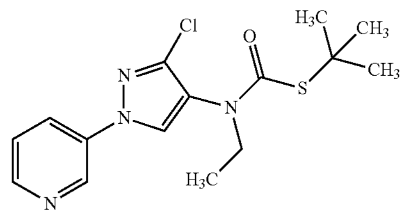 [SMILES: CCN(C(=O)SC(C)(C)C)c1cn(-c2cccnc2)nc1Cl] | |
| 515 | White Oil | 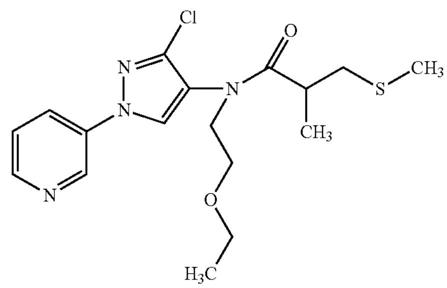 [SMILES: CCOCCN(C(=O)C(C)CSC)c1cn(-c2cccnc2)nc1Cl] | |
| 516 | Dark Brown Oil | 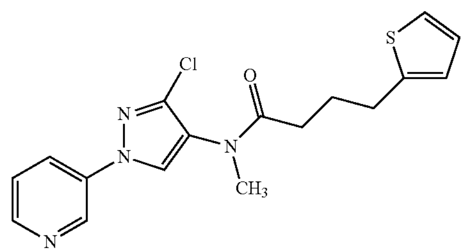 [SMILES: CN(C(=O)CCCc1cccs1)c1cn(-c2cccnc2)nc1Cl] | |
| 517 | White Solid | 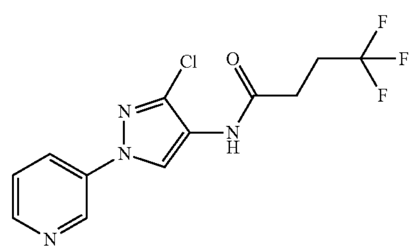 [SMILES: O=C(CCC(F)(F)F)Nc1cn(-c2cccnc2)nc1Cl] | |
| 518 | White Solid | 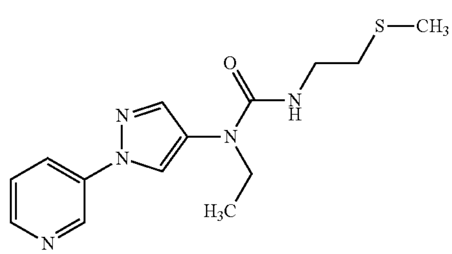 | |
| 519 | White Solid | 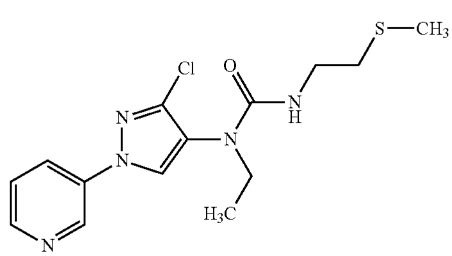 [SMILES: CCN(C(=O)NCCSC)c1cn(-c2cccnc2)nc1Cl] | |

TABLE 1-continued

Compound number, appearance, and structure

| Compound No. | Appearance | Structure | Prepared as in Example: |
|---|---|---|---|
| 520 | Brown Gum | 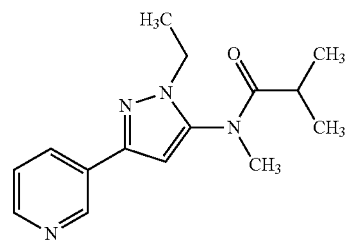 [SMILES: CCn1nc(-c2cccnc2)cc1N(C)C(=O)C(C)C] | |
| 521 | Beige Solid | 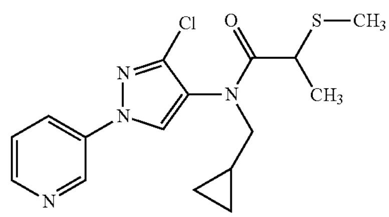 [SMILES: CSC(C)C(=O)N(CC1CC1)c1cn(-c2cccnc2)nc1Cl] | |
| 522 | White Solid | 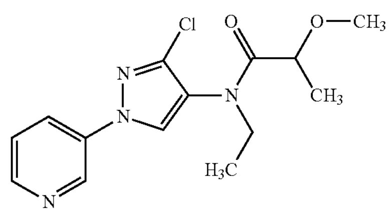 [SMILES: CCN(C(=O)C(C)OC)c1cn(-c2cccnc2)nc1Cl] | |
| 523 | Yellow Solid | 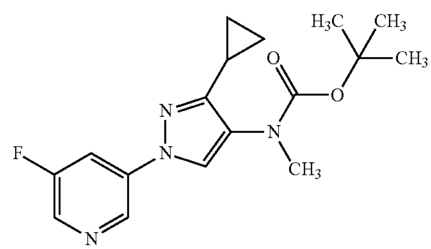 [SMILES: CN(C(=O)OC(C)(C)C)c1cn(-c2cncc(F)c2)nc1C1CC1] | |
| 524 | Light Brown Solid | 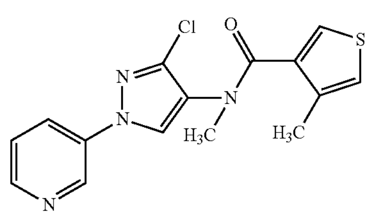 [SMILES: Cc1cscc1C(=O)N(C)c1cn(-c2cccnc2)nc1Cl] | |
| 525 | Faint Yellow Solid | 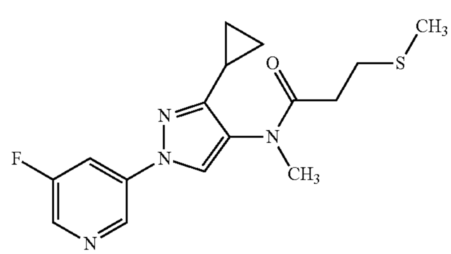 [SMILES: CSCCC(=O)N(C)c1cn(-c2cncc(F)c2)nc1C1CC1] | |

TABLE 1-continued

Compound number, appearance, and structure

| Compound No. | Appearance | Structure | Prepared as in Example: |
|---|---|---|---|
| 526 | Faint Yellow Solid | 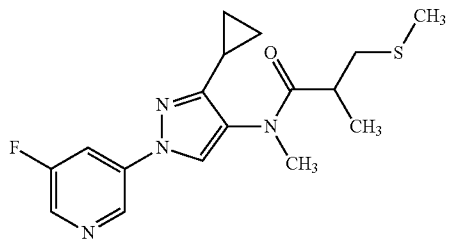 [SMILES: CSCC(C)C(=O)N(C)c1cn(-c2cncc(F)c2)nc1C1CC1] | |
| 527 | Yellow Oil | 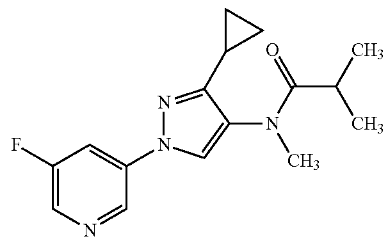 [SMILES: CC(C)C(=O)N(C)c1cn(-c2cncc(F)c2)nc1C1CC1] | |
| 528 | Light Brown Oil | 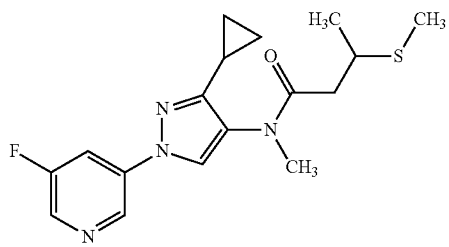 [SMILES: CSC(C)CC(=O)N(C)c1cn(-c2cncc(F)c2)nc1C1CC1] | |
| 529 | Faint Yellow Solid | 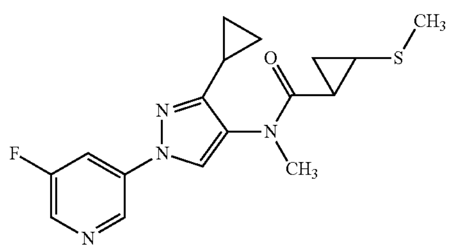 [SMILES: CSC1CC1C(=O)N(C)c1cn(-c2cncc(F)c2)nc1C1CC1] | |
| 530 | Clear Oil | 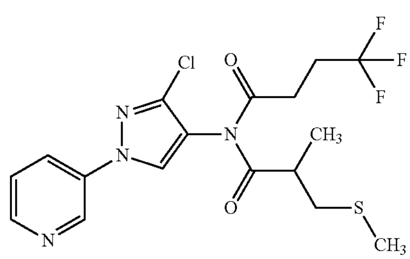 [SMILES: CSCC(C)C(=O)N(C(=O)CCC(F)(F)F)c1cn(-c2cccnc2)nc1Cl] | |
| 531 | Yellow Oil | 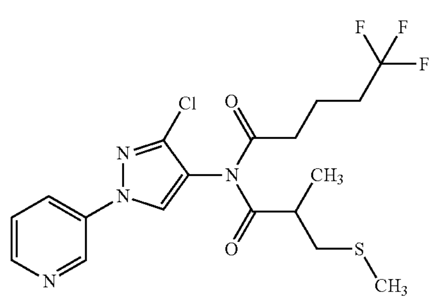 [SMILES: CSCC(C)C(=O)N(C(=O)CCCC(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 532 | White Solid | 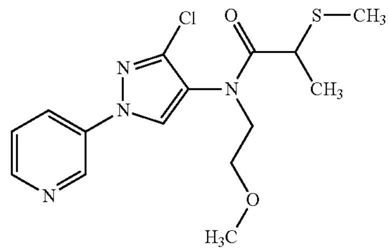 [SMILES: COCCN(C(=O)C(C)SC)c1cn(-c2cccnc2)nc1Cl] | |
| 533 | Orange Oil | 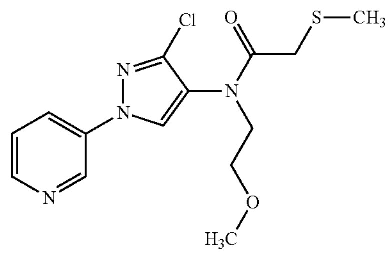 [SMILES: COCCN(C(=O)CSC)c1cn(-c2cccnc2)nc1Cl] | |
| 534 | Red Oil | 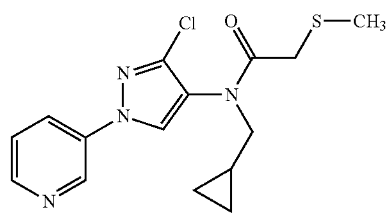 [SMILES: CSCC(=O)N(CC1CC1)c1cn(-c2cccnc2)nc1Cl] | |
| 535 | White Oil | 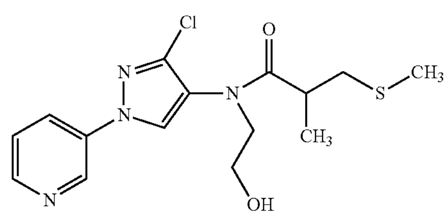 [SMILES: CSCC(C)C(=O)N(CCO)c1cn(-c2cccnc2)nc1Cl] | |
| 536 | White Solid | 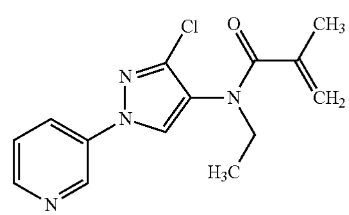 [SMILES: C=C(C)C(=O)N(CC)c1cn(-c2cccnc2)nc1Cl] | |
| 537 | Clear Oil | 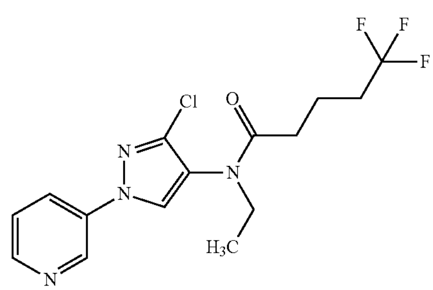 [SMILES: CCN(C(=O)CCCC(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 538 | White Solid | 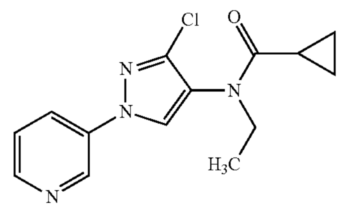 [SMILES: CCN(C(=O)C1CC1)c1cn(-c2cccnc2)nc1Cl] | |
| 539 | Clear Oil | 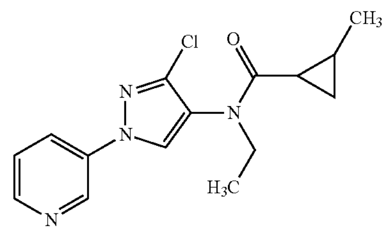 [SMILES: CCN(C(=O)C1CC1C)c1cn(-c2cccnc2)nc1Cl] | |
| 540 | Clear Oil | 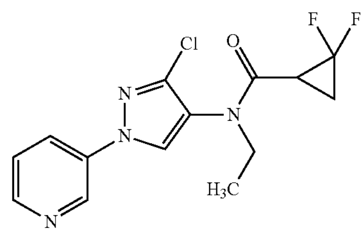 [SMILES: CCN(C(=O)C1CC1(F)F)c1cn(-c2cccnc2)nc1Cl] | |
| 541 | Light Yellow Oil | 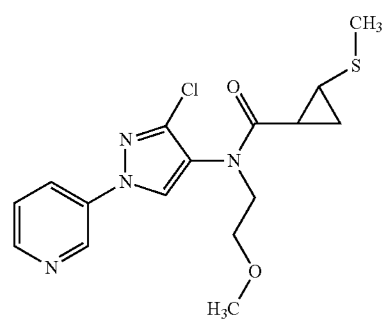 [SMILES: COCCN(C(=O)C1CC1SC)c1cn(-c2cccnc2)nc1Cl] | |
| 542 | Colorless Oil | 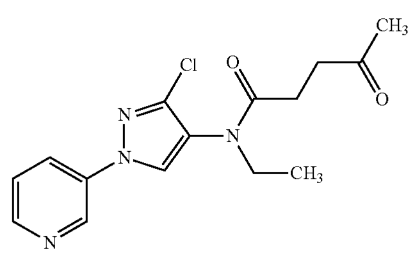 [SMILES: CCN(C(=O)CCC(C)=O)c1cn(-c2cccnc2)nc1Cl] | |
| 543 | White Solid | 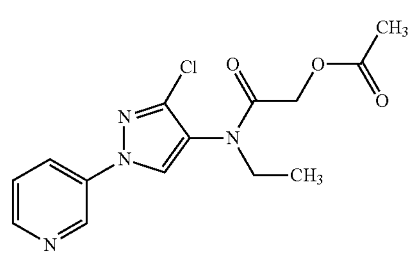 [SMILES: CCN(C(=O)COC(C)=O)c1cn(-c2cccnc2)nc1Cl] | |

TABLE 1-continued

Compound number, appearance, and structure

| Compound No. | Appearance | Structure | Prepared as in Example: |
|---|---|---|---|
| 544 | White Solid | 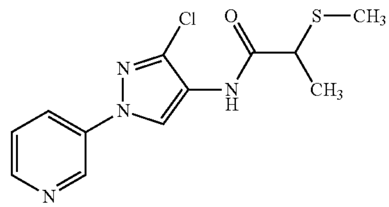 [SMILES: CSC(C)C(=O)Nc1cn(-c2cccnc2)nc1Cl] | |
| 545 | White Fluffy Solid | 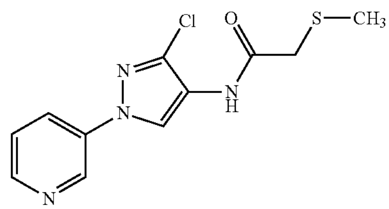 [SMILES: CSCC(=O)Nc1cn(-c2cccnc2)nc1Cl] | |
| 546 | Brown Solid | 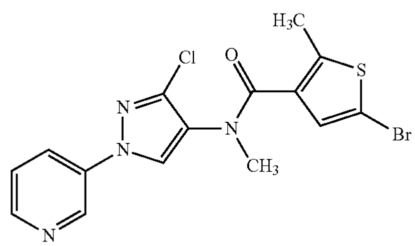 [SMILES: Cc1sc(Br)cc1C(=O)N(C)c1cn(-c2cccnc2)nc1Cl] | |
| 547 | Yellow Oil | 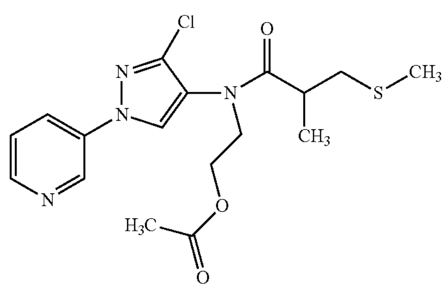 [SMILES: CSCC(C)C(=O)N(CCOC(C)=O)c1cn(-c2cccnc2)nc1Cl] | |
| 548 | White-Yellow Oil | 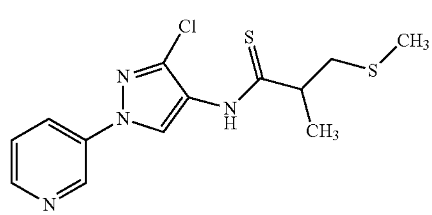 [SMILES: CSCC(C)C(=S)Nc1cn(-c2cccnc2)nc1Cl] | |
| 549 | Colorless Oil | 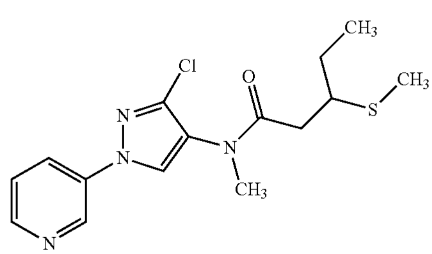 [SMILES: CCC(CC(=O)N(C)c1cn(-c2cccnc2)nc1Cl)SC] | |

TABLE 1-continued

Compound number, appearance, and structure

| Compound No. | Appearance | Structure | Prepared as in Example: |
|---|---|---|---|
| 550 | Colorless Oil | 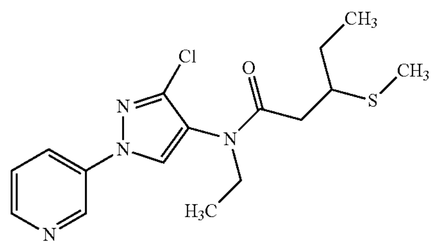 [SMILES: CCC(CC(=O)N(CC)c1cn(-c2cccnc2)nc1Cl)SC] | |
| 551 | Colorless Oil | 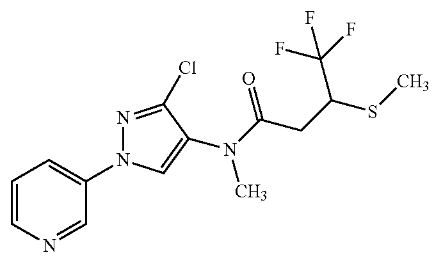 [SMILES: CSC(CC(=O)N(C)c1cn(-c2cccnc2)nc1Cl)C(F)(F)F] | |
| 552 | Colorless Oil | 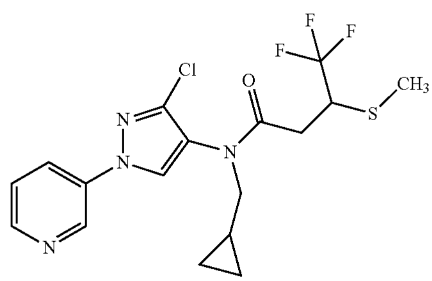 [SMILES: CSC(CC(=O)N(CC1CC1)c1cn(-c2cccnc2)nc1Cl)C(F)(F)F] | |
| 553 | Colorless Oil | 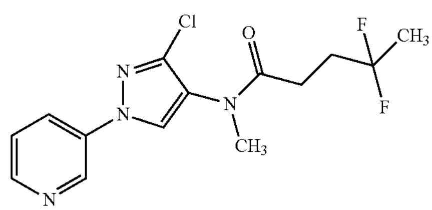 [SMILES: CN(C(=O)CCC(C)(F)F)c1cn(-c2cccnc2)nc1Cl] | |
| 554 | Colorless Oil | 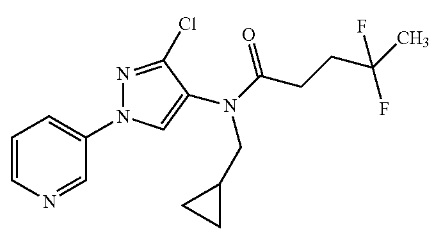 [SMILES: CC(F)(F)CCC(=O)N(CC1CC1)c1cn(-c2cccnc2)nc1Cl] | |
| 555 | Yellow Oil | 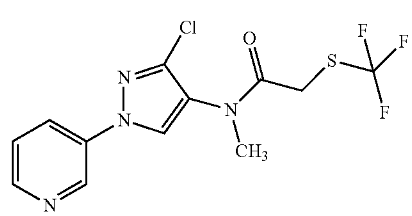 [SMILES: CN(C(=O)CSC(F)(F)F)c1cn(-c2cccnc2)nc1Cl] | |

TABLE 1-continued
Compound number, appearance, and structure
| Compound No. | Appearance | Structure | Prepared as in Example: |
|---|---|---|---|
| 556 | Pale Yellow Gum | 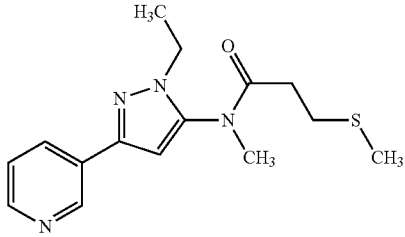 [SMILES: CCn1nc(-c2cccnc2)cc1N(C)C(=O)CCSC] | |
| 557 | Pale Yellow Gum | 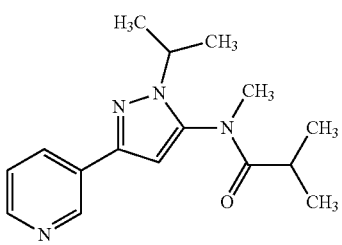 [SMILES: CC(C)C(=O)N(C)c1cc(-c2cccnc2)nn1C(C)C] | |
| 558 | Faint Yellow Oil | 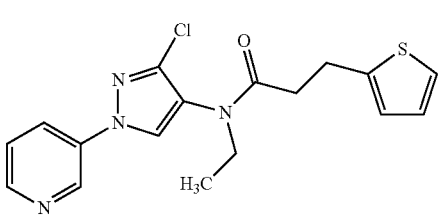 [SMILES: CCN(C(=O)CCc1cccs1)c1cn(-c2cccnc2)nc1Cl] | |
| 559 | Faint Yellow Oil | 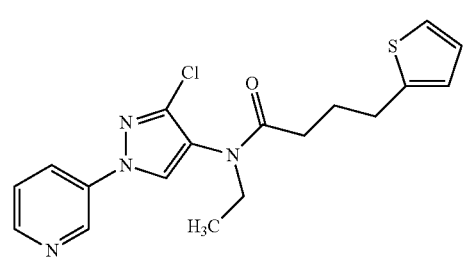 [SMILES: CCN(C(=O)CCCc1cccs1)c1cn(-c2cccnc2)nc1Cl] | |
| 560 | Yellow Solid | 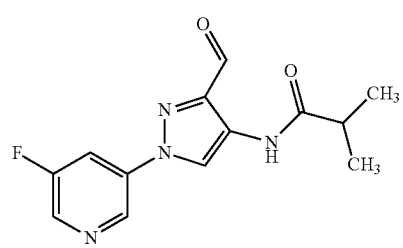 [SMILES: CC(C)C(=O)Nc1cn(-c2cncc(F)c2)nc1C=O] | |
| 561 | White Solid | 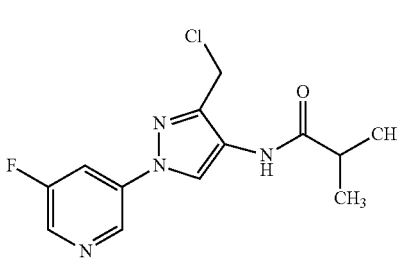 | |

TABLE 1-continued

Compound number, appearance, and structure

| Compound No. | Appearance | Structure | Prepared as in Example: |
|---|---|---|---|
| 562 | Brown Gum | 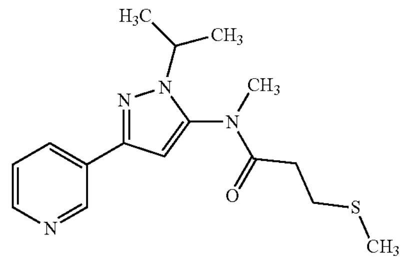 [SMILES: CSCCC(=O)N(C)c1cc(-c2cccnc2)nn1C(C)C] | |
| 563 | Pale Yellow Gum | 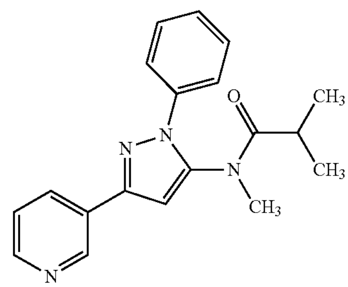 [SMILES: CC(C)C(=O)N(C)c1cc(-c2cccnc2)nn1-c1ccccc1] | |
| 564 | Pale Yellow Gum | 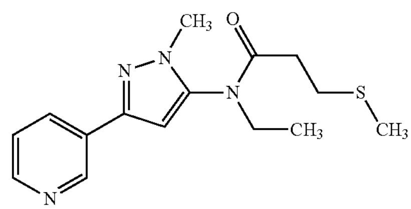 [SMILES: CCN(C(=O)CCSC)c1cc(-c2cccnc2)nn1C] | |
| 565 | Pale Yellow Gum | 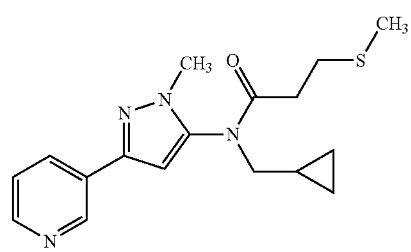 [SMILES: CSCCC(=O)N(CC1CC1)c1cc(-c2cccnc2)nn1C] | |
| 566 | Pale Yellow Gum | 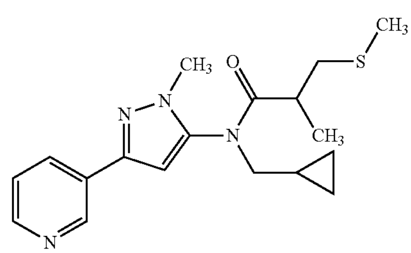 [SMILES: CSCC(C)C(=O)N(CC1CC1)c1cc(-c2cccnc2)nn1C] | |
| 567 | Off-white Solid | 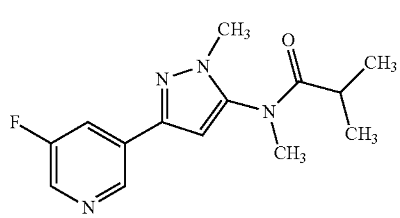 [SMILES: CC(C)C(=O)N(C)c1cc(-c2cncc(F)c2)nn1C] | |

TABLE 1-continued

| Compound No. | Appearance | Structure | Prepared as in Example: |
|---|---|---|---|
| 568 | Pale Yellow Gum | 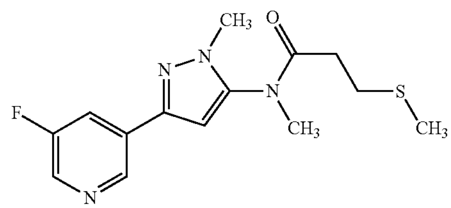 [SMILES: CSCCC(=O)N(C)c1cc(-c2cncc(F)c2)nn1C] | |
| 569 | Colorless Oil | 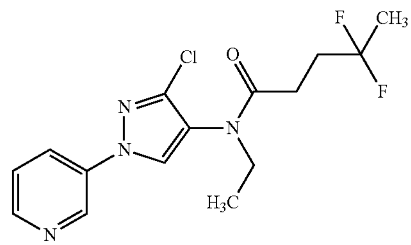 [SMILES: CCN(C(=O)CCC(C)(F)F)c1cn(-c2cccnc2)nc1Cl] | |
| 570 | White Semi-Solid | 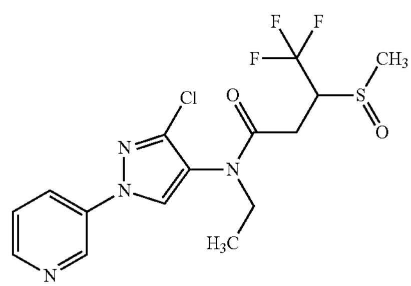 [SMILES: CCN(C(=O)CC(S(C)=O)C(F)(F)F)c1cn(-c2cccnc2)nc1Cl] | |
| 571 | White Semi-Solid | 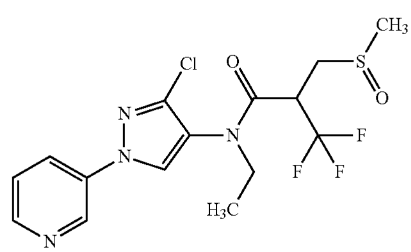 [SMILES: CCN(C(=O)C(CS(C)=O)C(F)(F)F)c1cn(-c2cccnc2)nc1Cl] | |
| 572 | Colorless Oil | 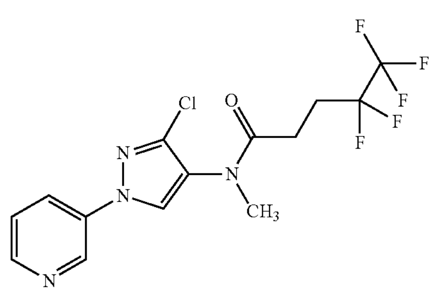 [SMILES: CN(C(=O)CCC(F)(F)C(F)(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 573 | Colorless Oil | 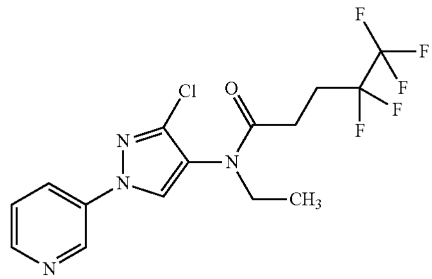 [SMILES: CCN(C(=O)CCC(F)(F)C(F)(F)F)c1cn(-c2cccnc2)nc1Cl] | |
| 574 | Colorless Oil | 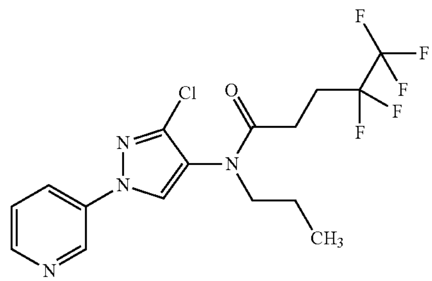 [SMILES: CCCN(C(=O)CCC(F)(F)C(F)(F)F)c1cn(-c2cccnc2)nc1Cl] | |
| 575 | Colorless Oil | 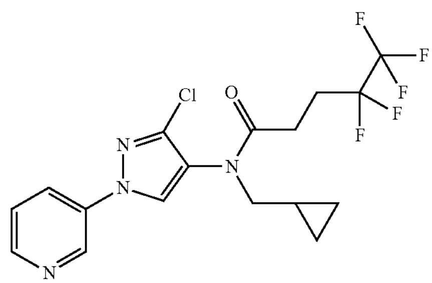 [SMILES: O=C(CCC(F)(F)C(F)(F)F)N(CC1CC1)c1cn(-c2cccnc2)nc1Cl] | |
| 576 | Colorless Oil | 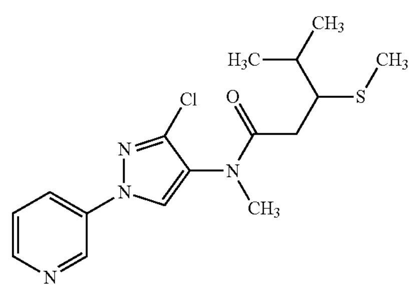 [SMILES: CSC(CC(=O)N(C)c1cn(-c2cccnc2)nc1Cl)C(C)C] | |
| 577 | Colorless Oil | 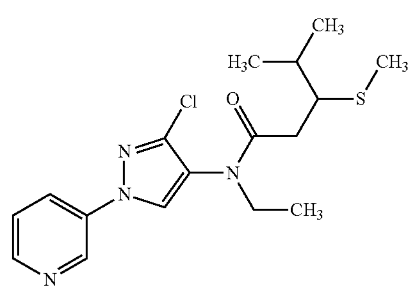 [SMILES: CCN(C(=O)CC(SC)C(C)C)c1cn(-c2cccnc2)nc1Cl] | |

TABLE 1-continued
Compound number, appearance, and structure
| Compound No. | Appearance | Structure | Prepared as in Example: |
|---|---|---|---|
| 578 | Colorless Oil | 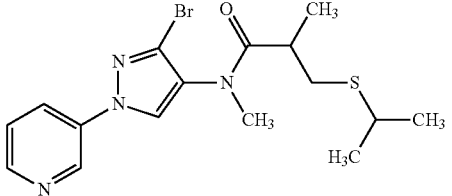 [SMILES: CC(C)SCC(C)C(=O)N(C)c1cn(-c2cccnc2)nc1Br] | |
| 579 | Colorless Oil | 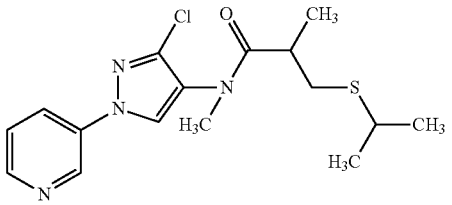 [SMILES: CC(C)SCC(C)C(=O)N(C)c1cn(-c2cccnc2)nc1Cl] | |
| 580 | Colorless Oil | 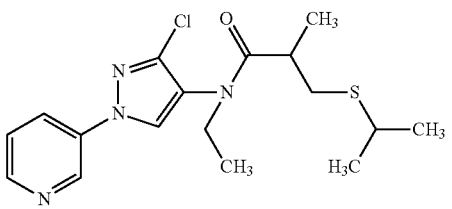 [SMILES: CCN(C(=O)C(C)CSC(C)C)c1cn(-c2cccnc2)nc1Cl] | |
| 581 | Colorless Solid | 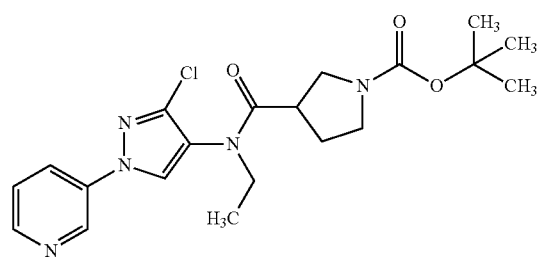 [SMILES: CCN(C(=O)C1CCN(C(=O)OC(C)(C)C)C1)c1cn(-c2cccnc2)nc1Cl] | |
| 582 | Clear Oil | 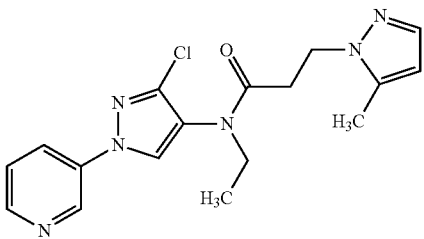 [SMILES: CCN(C(=O)CCn1nccc1C)c1cn(-c2cccnc2)nc1Cl] | |
| 583 | Brown Oil | 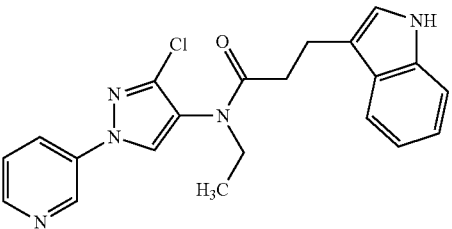 [SMILES: CCN(C(=O)CCc1c[nH]c2ccccc12)c1cn(-c2cccnc2)nc1Cl] | |

TABLE 1-continued

Compound number, appearance, and structure

| Compound No. | Appearance | Structure | Prepared as in Example: |
|---|---|---|---|
| 584 | Dark Yellow Oil | 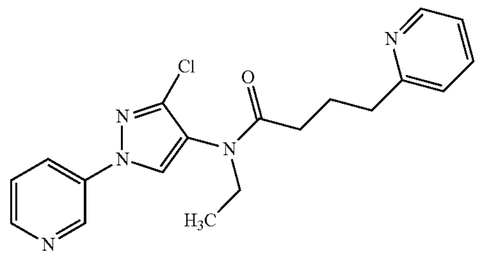 [SMILES: CCN(C(=O)CCCc1ccccn1)c1cn(-c2cccnc2)nc1Cl] | |
| 585 | White Solid | 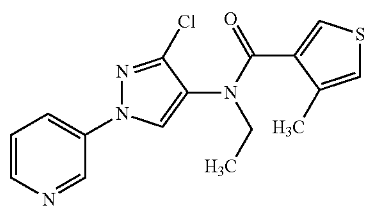 [SMILES: CCN(C(=O)c1cscc1C)c1cn(-c2cccnc2)nc1Cl] | |
| 586 | Yellow Solid | 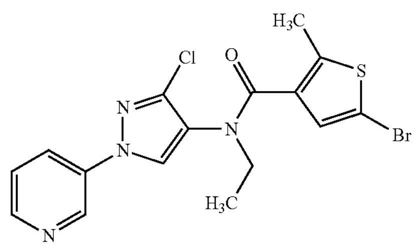 [SMILES: CCN(C(=O)c1cc(Br)sc1C)c1cn(-c2cccnc2)nc1Cl] | |
| 587 | Purple Solid | 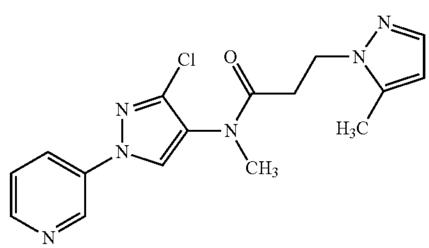 [SMILES: Cc1ccnn1CCC(=O)N(C)c1cn(-c2cccnc2)nc1Cl] | |
| 588 | Dark Yellow Oil | 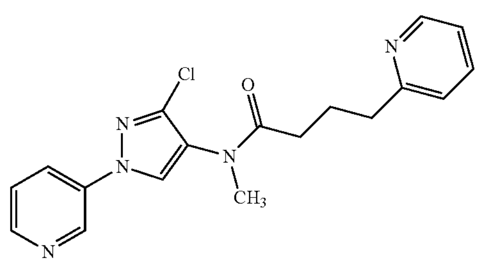 [SMILES: CN(C(=O)CCCc1ccccn1)c1cn(-c2cccnc2)nc1Cl] | |
| 589 | Colorless Solid | 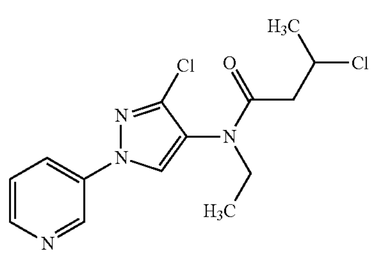 [SMILES: CCN(C(=O)CC(C)Cl)c1cn(-c2cccnc2)nc1Cl] | |

TABLE 1-continued

Compound number, appearance, and structure

| Compound No. | Appearance | Structure | Prepared as in Example: |
|---|---|---|---|
| 590 | Brown Solid | 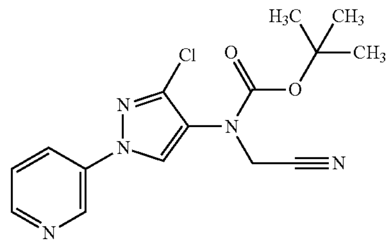 [SMILES: CC(C)(C)OC(=O)N(CC#N)c1cn(-c2cccnc2)nc1Cl] | |
| 591 | Light Yellow Solid | 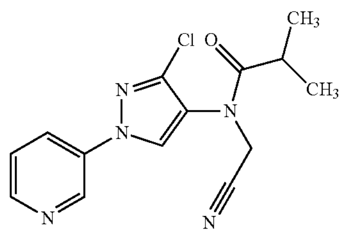 [SMILES: CC(C)C(=O)N(CC#N)c1cn(-c2cccnc2)nc1Cl] | |
| 592 | Brown Oil | 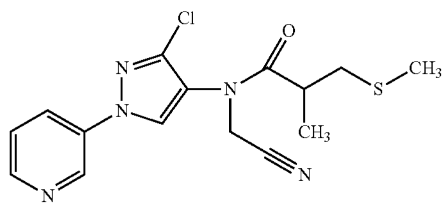 [SMILES: CSCC(C)C(=O)N(CC#N)c1cn(-c2cccnc2)nc1Cl] | |
| 593 | Brown Oil | 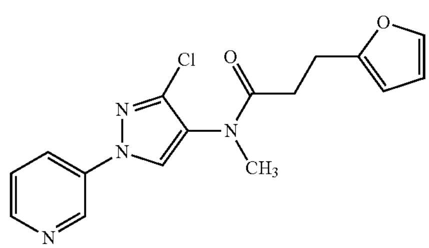 [SMILES: CN(C(=O)CCc1ccco1)c1cn(-c2cccnc2)nc1Cl] | |
| 594 | Faint Yellow Solid | 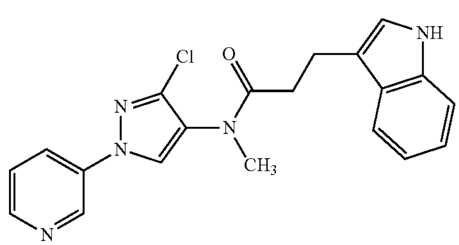 [SMILES: CN(C(=O)CCc1c[nH]c2ccccc12)c1cn(-c2cccnc2)nc1Cl] | |
| 595 | White solid | 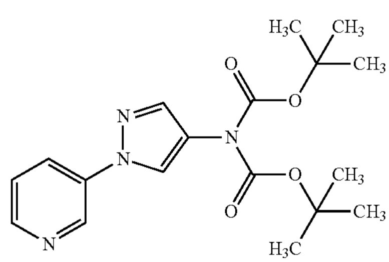 [SMILES: CC(C)(C)OC(=O)N(C(=O)OC(C)(C)C)c1cnn(-c2cccnc2)c1] | |

TABLE 1-continued
Compound number, appearance, and structure
| Compound No. | Appearance | Structure | Prepared as in Example: |
|---|---|---|---|
| 596 | Brown Solid | 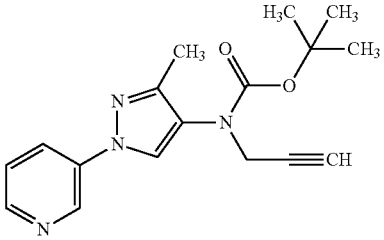 [SMILES: C#CCN(C(=O)OC(C)(C)C)c1cn(-c2cccnc2)nc1C] | |
| 597 | Colorless Oil | 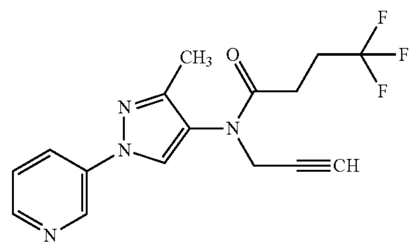 [SMILES: C#CCN(C(=O)CCC(F)(F)F)c1cn(-c2cccnc2)nc1C] | |
| 598 | Colorless Oil | 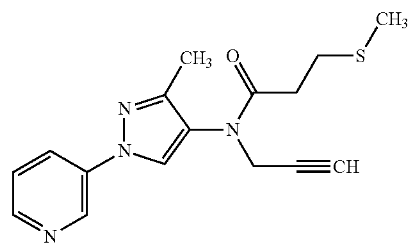 [SMILES: C#CCN(C(=O)CCSC)c1cn(-c2cccnc2)nc1C] | |
| 599 | Colorless Oil | 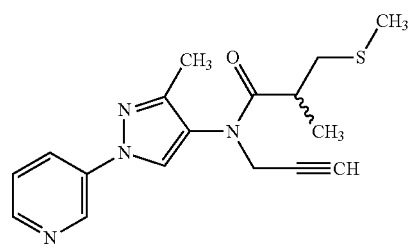 [SMILES: C#CCN(C(=O)C(C)CSC)c1cn(-c2cccnc2)nc1C] | |
| 600 | White Solid | 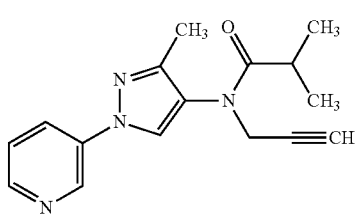 [SMILES: C#CCN(C(=O)C(C)C)c1cn(-c2cccnc2)nc1C] | |
| 601 | Yellow Solid | 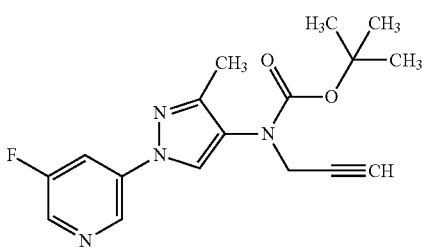 [SMILES: C#CCN(C(=O)OC(C)(C)C)c1cn(-c2cncc(F)c2)nc1C] | |

TABLE 1-continued

Compound number, appearance, and structure

| Compound No. | Appearance | Structure | Prepared as in Example: |
|---|---|---|---|
| 602 | Colorless Oil | 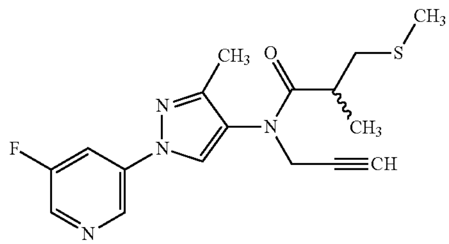 [SMILES: C#CCN(C(=O)C(C)CSC)c1cn(-c2cncc(F)c2)nc1C] | |
| 603 | Light Brown Solid | 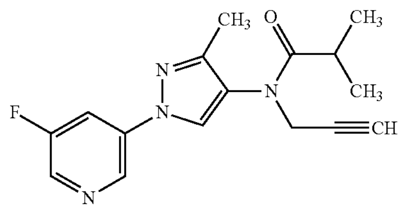 [SMILES: C#CCN(C(=O)C(C)C)c1cn(-c2cncc(F)c2)nc1C] | |
| 604 | Brown Gum | 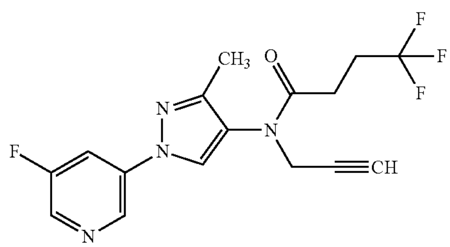 [SMILES: C#CCN(C(=O)CCC(F)(F)F)c1cn(-c2cncc(F)c2)nc1C] | |
| 605 | Light Brown Oil | 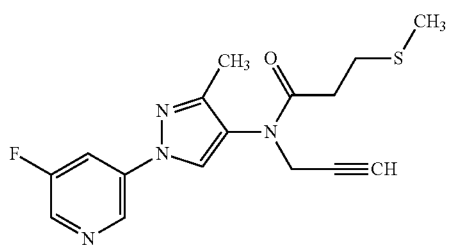 [SMILES: C#CCN(C(=O)CCSC)c1cn(-c2cncc(F)c2)nc1C] | |
| 606 | Light Brown Oil | 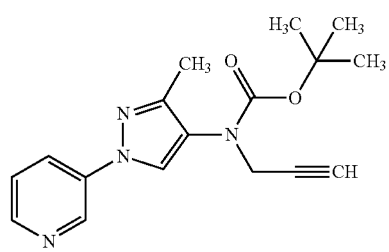 [SMILES: C#CCN(C(=O)OC(C)(C)C)c1cn(-c2cccnc2)nc1C] | |
| 607 | Colorless Oil | 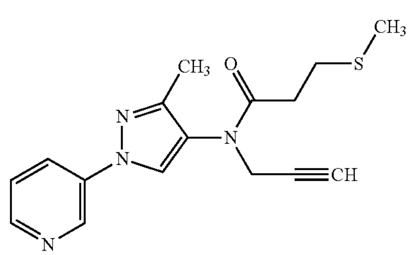 [SMILES: C#CCN(C(=O)CCSC)c1cn(-c2cccnc2)nc1C] | |

TABLE 1-continued

Compound number, appearance, and structure

| Compound No. | Appearance | Structure | Prepared as in Example: |
|---|---|---|---|
| 608 | Colorless Oil | *3-chloro-1-(pyridin-3-yl)-1H-pyrazol-4-yl N-(prop-2-yn-1-yl) 2-(methylthiomethyl)propanamide* | |
| 609 | Colorless Oil | *3-chloro-1-(pyridin-3-yl)-1H-pyrazol-4-yl N-(prop-2-yn-1-yl) 4,4,4-trifluorobutanamide* | |
| 610 | Yellow Solid | *3-chloro-1-(pyridin-3-yl)-1H-pyrazol-4-yl N-(prop-2-yn-1-yl) isobutyramide* | |
| 611 | Yellow Oil | *3-chloro-1-(pyridin-3-yl)-1H-pyrazol-4-yl N-(prop-2-yn-1-yl) 2-(methylthio)propanamide* | |
| 612 | Beige Solid | *3-chloro-1-(pyridin-3-yl)-1H-pyrazol-4-yl N-(prop-2-yn-1-yl) 2-(methylthio)acetamide* | |
| 613 | Brown Oil | *3-chloro-1-(pyridin-3-yl)-1H-pyrazol-4-yl N-(prop-2-yn-1-yl) 4,4,4-trifluoro-3-(methylthio)butanamide* | |

TABLE 1-continued

Compound number, appearance, and structure

| Compound No. | Appearance | Structure | Prepared as in Example: |
|---|---|---|---|
| 614 | Colorless Oil | 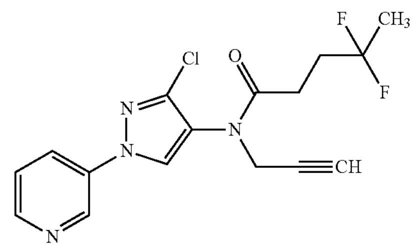 [SMILES: C#CCN(C(=O)CCC(C)(F)F)c1cn(-c2cccnc2)nc1Cl] | |
| 615 | Colorless Oil | 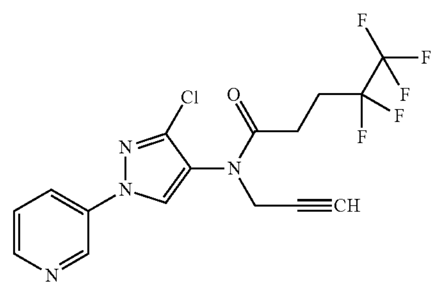 [SMILES: C#CCN(C(=O)CCC(F)(F)C(F)(F)F)c1cn(-c2cccnc2)nc1Cl] | |
| 616 | White Solid | 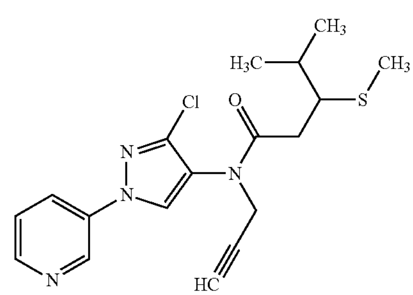 [SMILES: C#CCN(C(=O)CC(SC)C(C)C)c1cn(-c2cccnc2)nc1Cl] | |
| 617 | Off-White Foam | 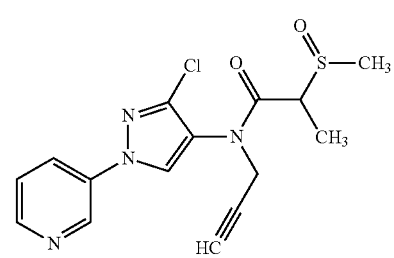 [SMILES: C#CCN(C(=O)C(C)S(C)=O)c1cn(-c2cccnc2)nc1Cl] | |
| 618 | Yellow Foam | 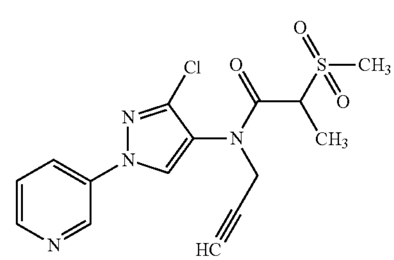 [SMILES: C#CCN(C(=O)C(C)S(C)(=O)=O)c1cn(-c2cccnc2)nc1Cl] | |

TABLE 1-continued

Compound number, appearance, and structure

| Compound No. | Appearance | Structure | Prepared as in Example: |
|---|---|---|---|
| 619 | Colorless Oil | 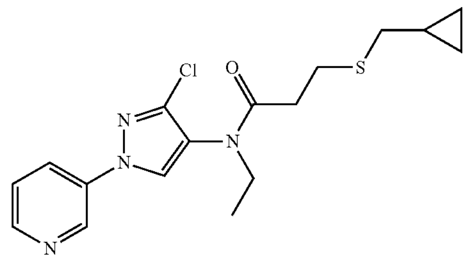 [SMILES: CCN(C(=O)CCSCC1CC1)c1cn(-c2cccnc2)nc1Cl] | |
| 620 | Colorless Gum | 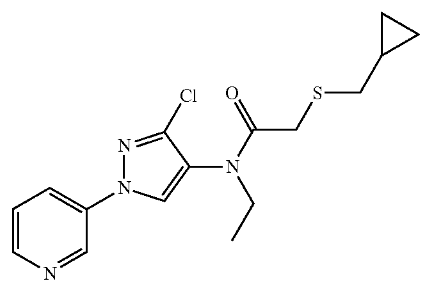 [SMILES: CCN(C(=O)CSCC1CC1)c1cn(-c2cccnc2)nc1Cl] | |
| 621 | Colorless Gum | 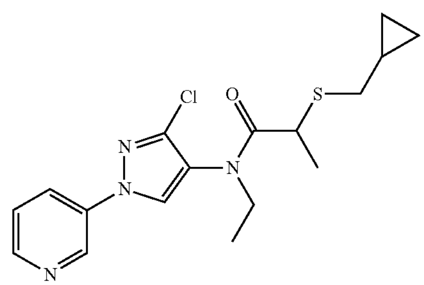 [SMILES: CCN(C(=O)C(C)SCC1CC1)c1cn(-c2cccnc2)nc1Cl] | |
| 622 | Colorless Oil | 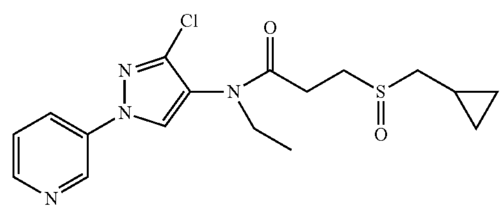 [SMILES: CCN(C(=O)CCS(=O)CC1CC1)c1cn(-c2cccnc2)nc1Cl] | |
| 623 | Colorless Gum | 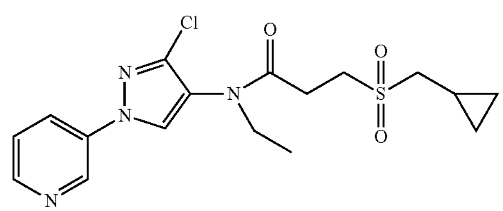 [SMILES: CCN(C(=O)CCS(=O)(=O)CC1CC1)c1cn(-c2cccnc2)nc1Cl] | |
| 624 | Colorless Gum | 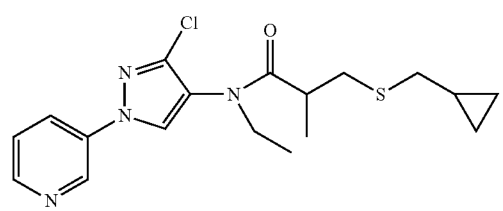 [SMILES: CCN(C(=O)C(C)CSCC1CC1)c1cn(-c2cccnc2)nc1Cl] | |

TABLE 1-continued

Compound number, appearance, and structure

| Compound No. | Appearance | Structure | Prepared as in Example: |
|---|---|---|---|
| 625 | Colorless Oil | 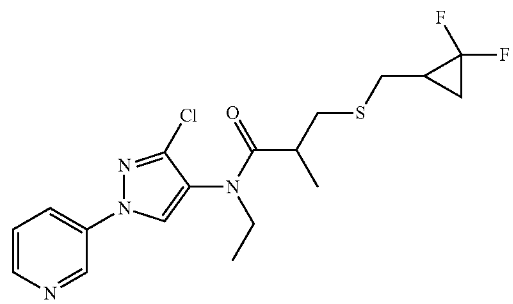 [SMILES: CCN(C(=O)C(C)CSCC1CC1(F)F)c1cn(-c2cccnc2)nc1Cl] | |
| 626 | White Solid | 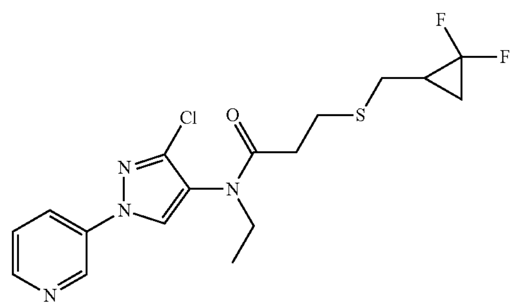 [SMILES: CCN(C(=O)CCSCC1CC1(F)F)c1cn(-c2cccnc2)nc1Cl] | |
| 627 | Colorless Gum | 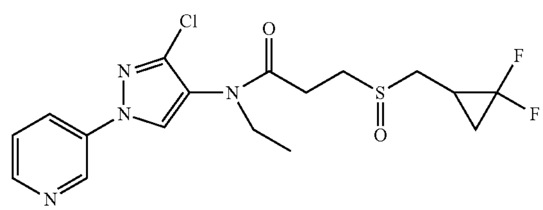 [SMILES: CCN(C(=O)CCS(=O)CC1CC1(F)F)c1cn(-c2cccnc2)nc1Cl] | |
| 628 | Colorless Gum | 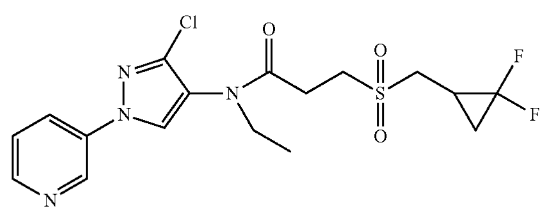 [SMILES: CCN(C(=O)CCS(=O)(=O)CC1CC1(F)F)c1cn(-c2cccnc2)nc1Cl] | |
| 629 | Colorless Oil | 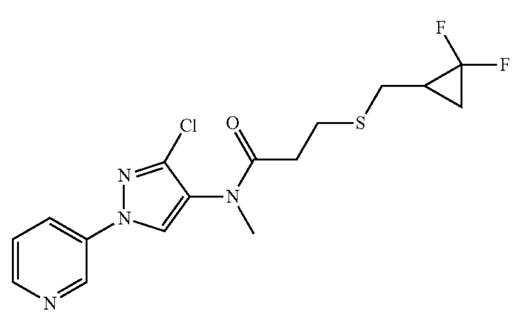 [SMILES: CN(C(=O)CCSCC1CC1(F)F)c1cn(-c2cccnc2)nc1Cl] | |

TABLE 1-continued

Compound number, appearance, and structure

| Compound No. | Appearance | Structure | Prepared as in Example: |
|---|---|---|---|
| 630 | Colorless Oil | 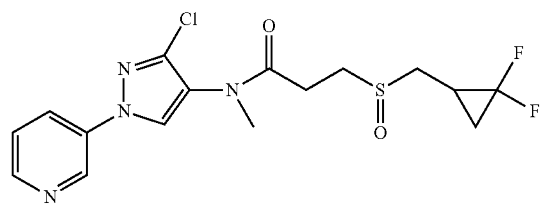 [SMILES: CN(C(=O)CCS(=O)CC1CC1(F)F)c1cn(-c2cccnc2)nc1Cl] | |
| 631 | Colorless Oil | 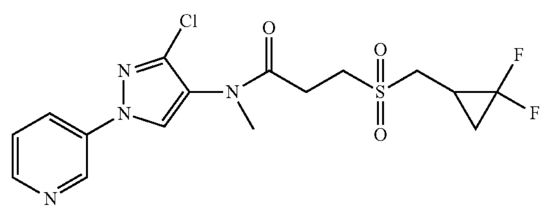 [SMILES: CN(C(=O)CCS(=O)(=O)CC1CC1(F)F)c1cn(-c2cccnc2)nc1Cl] | |
| 632 | Colorless Oil | 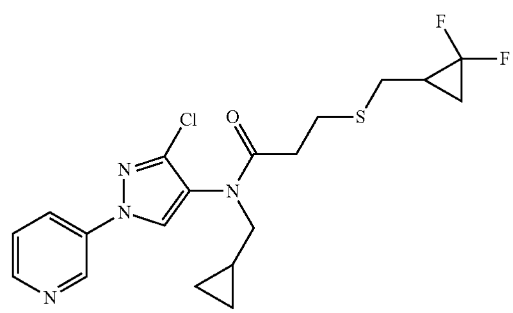 [SMILES: O=C(CCSCC1CC1(F)F)N(CC1CC1)c1cn(-c2cccnc2)nc1Cl] | |
| 633 | Colorless Gum | 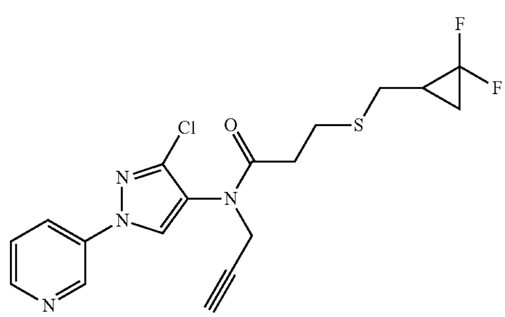 [SMILES: C#CCN(C(=O)CCSCC1CC1(F)F)c1cn(-c2cccnc2)nc1Cl] | |
| 634 | Brown Oil | 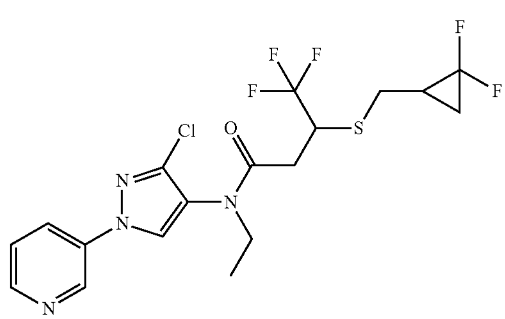 [SMILES: CCN(C(=O)CC(SCC1CC1(F)F)C(F)(F)F)c1cn(-c2cccnc2)nc1Cl] | |

TABLE 1-continued
Compound number, appearance, and structure
| Compound No. | Appearance | Structure | Prepared as in Example: |
|---|---|---|---|
| 635 | Clear Oil | 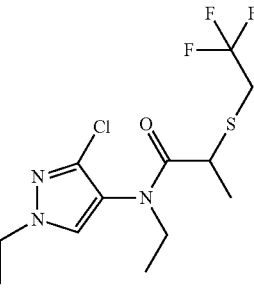 | |
| 636 | Colorless Oil | 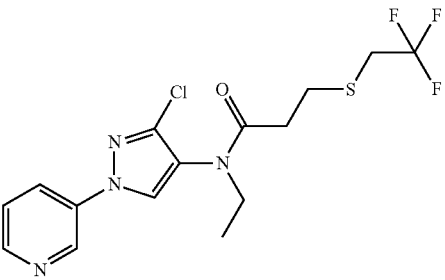 [SMILES: CCN(C(=O)CCSCC(F)(F)F)c1cn(-c2cccnc2)nc1Cl] | |
| 637 | Pale Yellow, Viscous Oil | 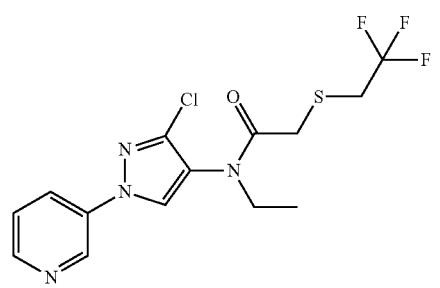 [SMILES: CCN(C(=O)CSCC(F)(F)F)c1cn(-c2cccnc2)nc1Cl] | |
| 638 | Viscous Brown Oil. | 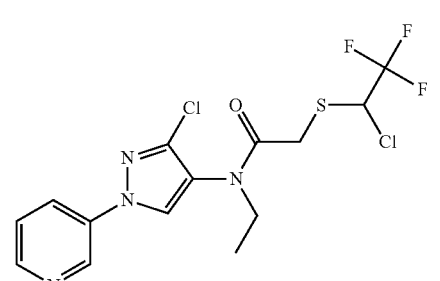 | |
| 639 | Pale Yellow, Viscous Oil | 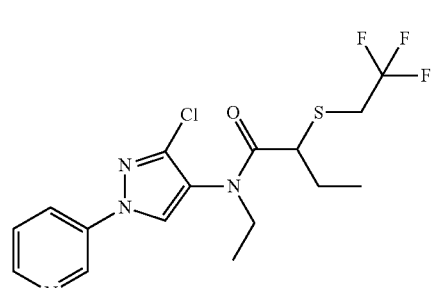 | |

TABLE 1-continued
Compound number, appearance, and structure
| Compound No. | Appearance | Structure | Prepared as in Example: |
|---|---|---|---|
| 640 | Opaque Viscous Oil. | 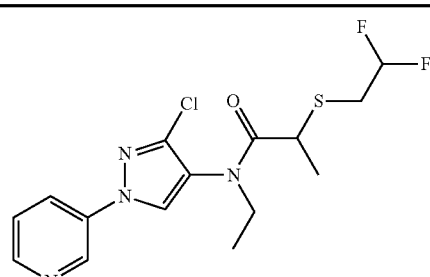 | |
| 641 | Opaque, Viscous Oil. | 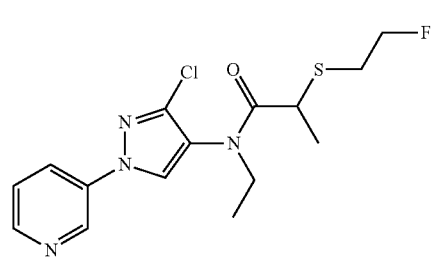 [SMILES: CCN(C(=O)C(C)SCCF)c1cn(-c2cccnc2)nc1Cl] | |
| 642 | Opaque, Viscous Oil. | 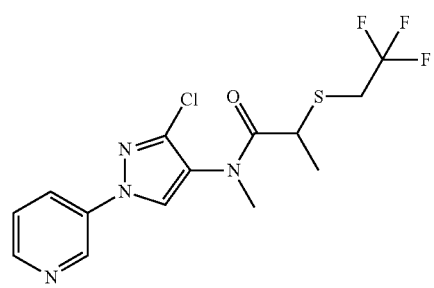 [SMILES: CC(SCC(F)(F)F)C(=O)N(C)c1cn(-c2cccnc2)nc1Cl] | |
| 643 | Oil | 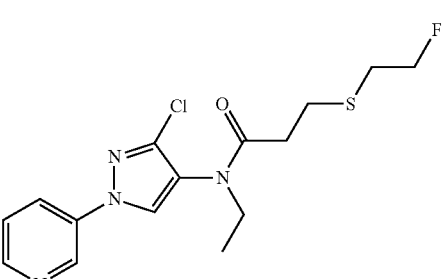 | |
| 644 | White Semi-Solid. | 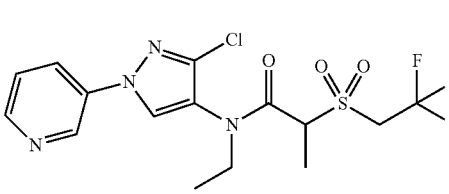 | |
| 645 | White semi-solid. | 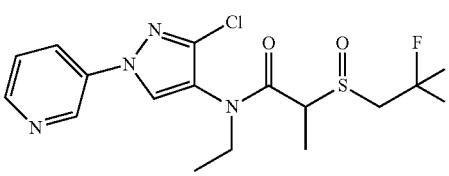 | |

TABLE 1-continued
Compound number, appearance, and structure
| Compound No. | Appearance | Structure | Prepared as in Example: |
|---|---|---|---|
| 646 | White Solid | 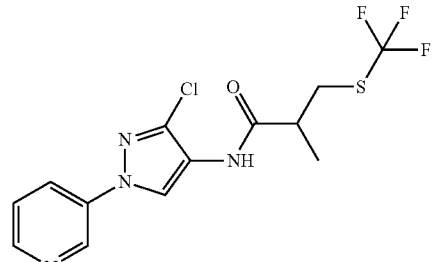 | |
| 647 | Yellow Oil | 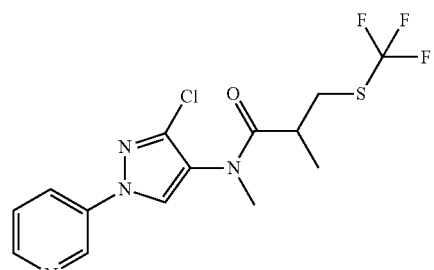 | |
| 648 | Yellow Oil | 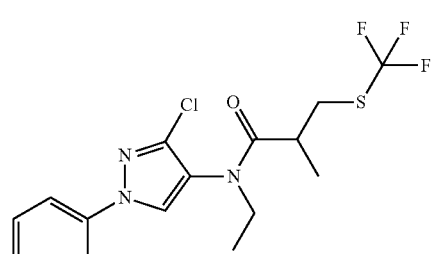 | |
| 649 | Colorless Oil | 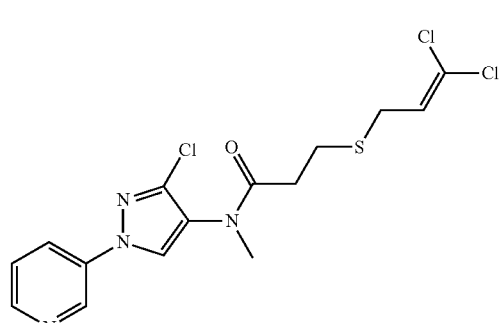 | |
| 650 | Colorless Gum | 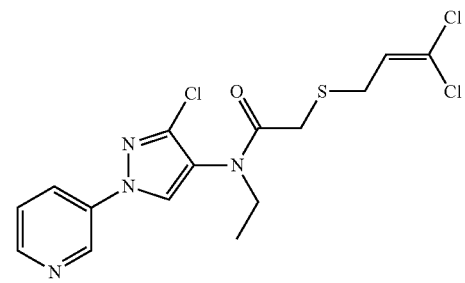 [SMILES: CCN(C(=O)CSCC=C(Cl)Cl)c1cn(-c2cccnc2)nc1Cl] | |

TABLE 1-continued

Compound number, appearance, and structure

| Compound No. | Appearance | Structure | Prepared as in Example: |
|---|---|---|---|
| 651 | Colorless Gum | 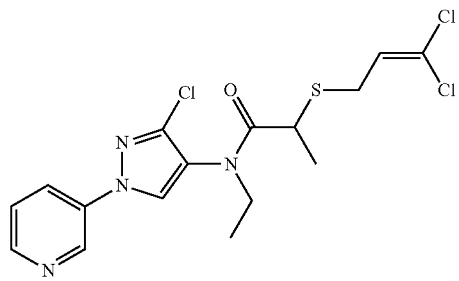 [SMILES: CCN(C(=O)C(C)SCC=C(Cl)Cl)c1cn(-c2cccnc2)nc1Cl] | |
| 652 | Opaque Viscous Oil. | 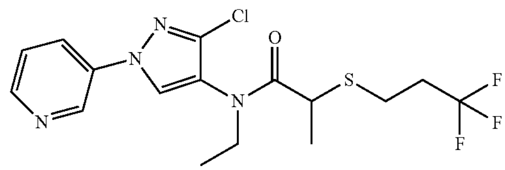 [SMILES: CCN(C(=O)C(C)SCCC(F)(F)F)c1cn(-c2cccnc2)nc1Cl] | |
| 653 | Oil | 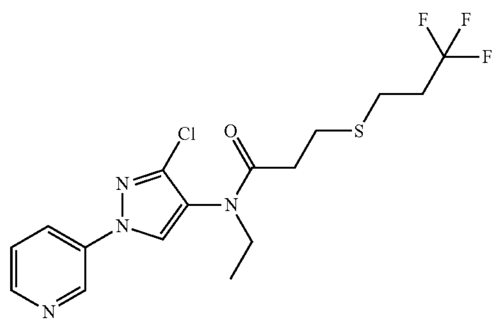 [SMILES: CCN(C(=O)CCSCCC(F)(F)F)c1cn(-c2cccnc2)nc1Cl] | |
| 654 | Opaque Viscous Oil. | 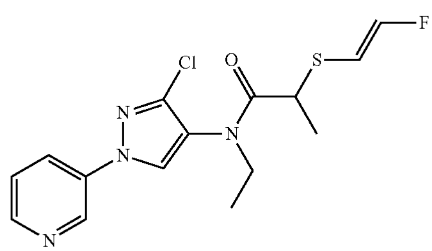 [SMILES: CCN(C(=O)C(C)S/C=C/F)c1cn(-c2cccnc2)nc1Cl] | |
| 655 | Colorless Oil | 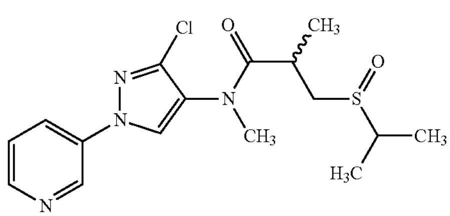 [SMILES: CC(CS(=O)C(C)C)C(=O)N(C)c1cn(-c2cccnc2)nc1Cl] | 51 |
| 656 | Light Brown Gum | 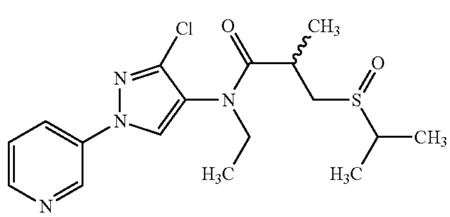 [SMILES: CCN(C(=O)C(C)CS(=O)C(C)C)c1cn(-c2cccnc2)nc1Cl] | 51 |

TABLE 1-continued

Compound number, appearance, and structure

| Compound No. | Appearance | Structure | Prepared as in Example: |
|---|---|---|---|
| 657 | Colorless Gum | 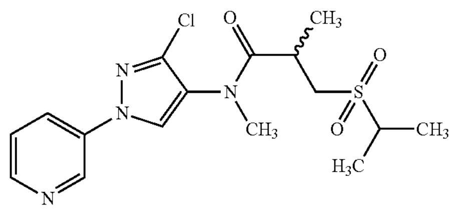 [SMILES: CC(CS(=O)(=O)C(C)C)C(=O)N(C)c1cn(-c2cccnc2)nc1Cl] | 52 |
| 658 | Colorless Oil | 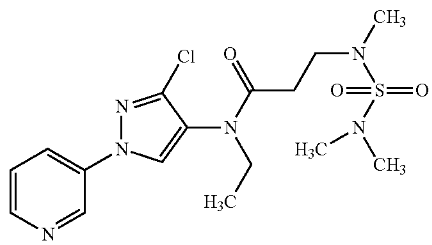 [SMILES: CCN(C(=O)CCN(C)S(=O)(=O)N(C)C)c1cn(-c2cccnc2)nc1Cl] | 149 |
| 659 | Faint Yellow Solid | 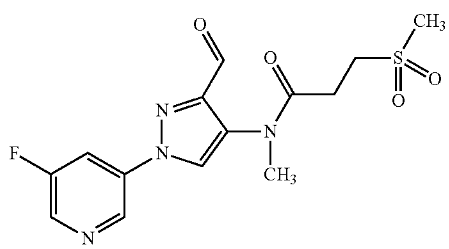 [SMILES: CN(C(=O)CCS(C)(=O)=O)c1cn(-c2cncc(F)c2)nc1C=O] | 35 |
| 660 | Yellow Oil | 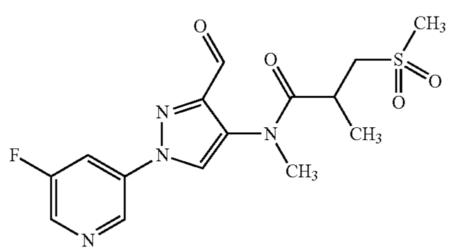 [SMILES: CC(CS(C)(=O)=O)C(=O)N(C)c1cn(-c2cncc(F)c2)nc1C=O] | 35 |
| 661 | Clear Oil | 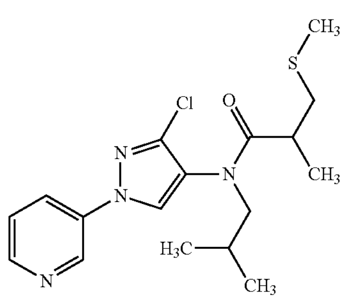 [SMILES: CSCC(C)C(=O)N(CC(C)C)c1cn(-c2cccnc2)nc1Cl] | 11 |
| 662 | Clear Oil | 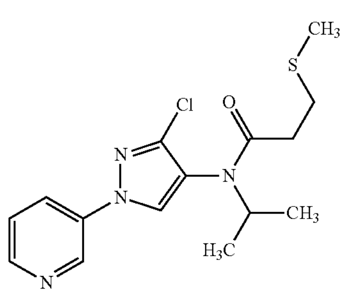 [SMILES: CSCCC(=O)N(c1cn(-c2cccnc2)nc1Cl)C(C)C] | 11 |

TABLE 1-continued
Compound number, appearance, and structure
| Compound No. | Appearance | Structure | Prepared as in Example: |
|---|---|---|---|
| 663 | Clear Oil | 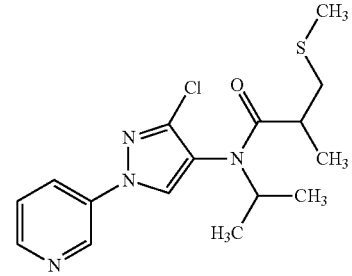 [SMILES: CSCC(C)C(=O)N(c1cn(-c2cccnc2)nc1Cl)C(C)C] | 11 |
| 664 | Clear Oil | 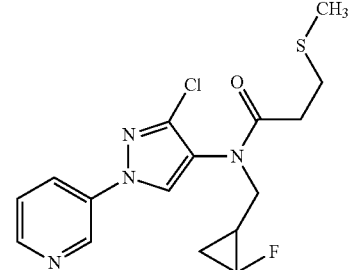 | 11 |
| 665 | Clear Oil | 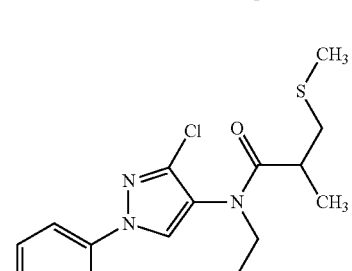 | 11 |
| 666 | Clear Oil | 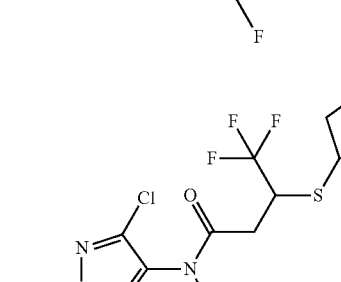 | 12 |

TABLE 1-continued

Compound number, appearance, and structure

| Compound No. | Appearance | Structure | Prepared as in Example: |
|---|---|---|---|
| 667 | White Solid | 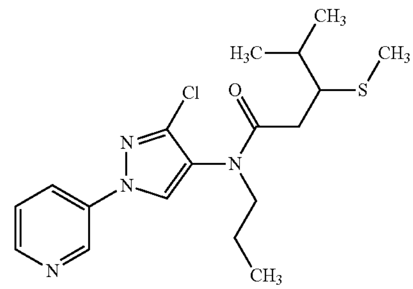 [SMILES: CCCN(C(=O)CC(SC)C(C)C)c1cn(-c2cccnc2)nc1Cl] | 12 |
| 668 | White Solid | 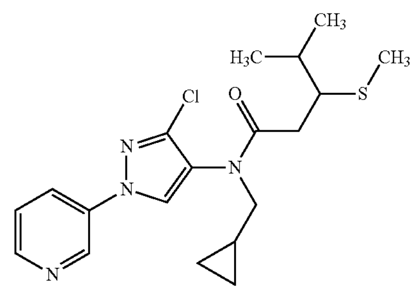 [SMILES: CSC(CC(=O)N(CC1CC1)c1cn(-c2cccnc2)nc1Cl)C(C)C] | 12 |
| 669 | White Solid | 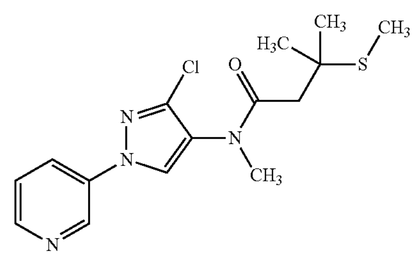 [SMILES: CSC(C)(C)CC(=O)N(C)c1cn(-c2cccnc2)nc1Cl] | 12 |
| 670 | White Solid | 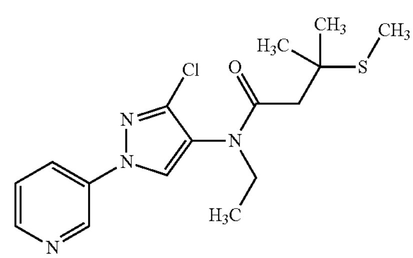 [SMILES: CCN(C(=O)CC(C)(C)SC)c1cn(-c2cccnc2)nc1Cl] | 12 |
| 671 | Colorless Gum | 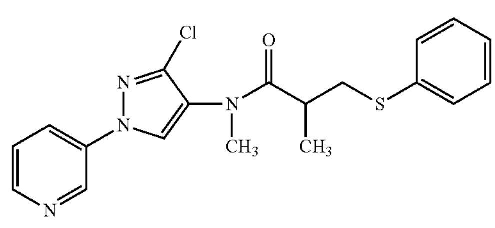 [SMILES: CC(CSc1ccccc1)C(=O)N(C)c1cn(-c2cccnc2)nc1Cl] | 106 |
| 672 | Colorless Gum | 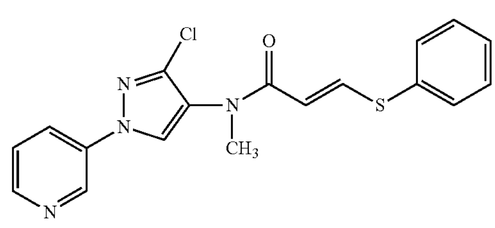 [SMILES: CN(C(=O)/C=C/Sc1ccccc1)c1cn(-c2cccnc2)nc1Cl] | 106 |

TABLE 1-continued
Compound number, appearance, and structure
| Compound No. | Appearance | Structure | Prepared as in Example: |
|---|---|---|---|
| 673 | Colorless Gum | 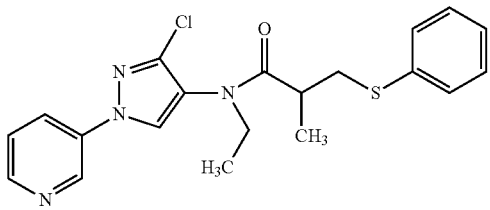 [SMILES: CCN(C(=O)C(C)CSc1ccccc1)c1cn(-c2cccnc2)nc1Cl] | 106 |
| 674 | Colorless Gum | 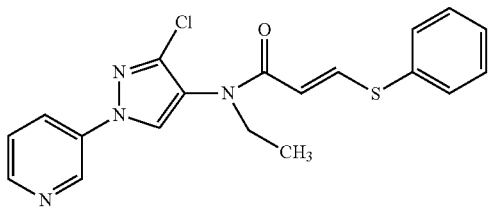 [SMILES: CCN(C(=O)/C=C/Sc1ccccc1)c1cn(-c2cccnc2)nc1Cl] | 106 |
| 675 | Light Brown Gum | 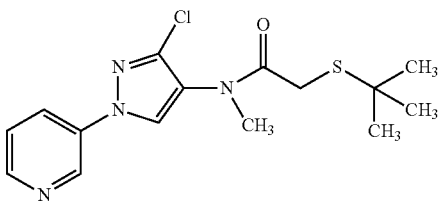 [SMILES: CN(C(=O)CSC(C)(C)C)c1cn(-c2cccnc2)nc1Cl] | 101 |
| 676 | Light Brown Gum | 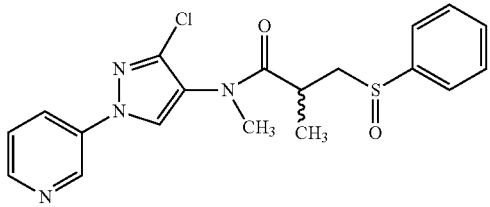 [SMILES: CC(CS(=O)c1ccccc1)C(=O)N(C)c1cn(-c2cccnc2)nc1Cl] | 51 |
| 677 | Colorless Oil | 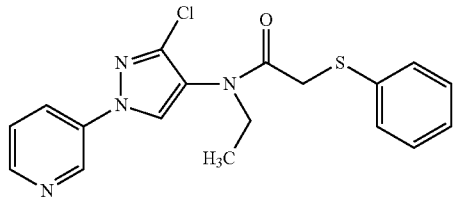 [SMILES: CCN(C(=O)CSc1ccccc1)c1cn(-c2cccnc2)nc1Cl] | 101 |
| 678 | White Foam | 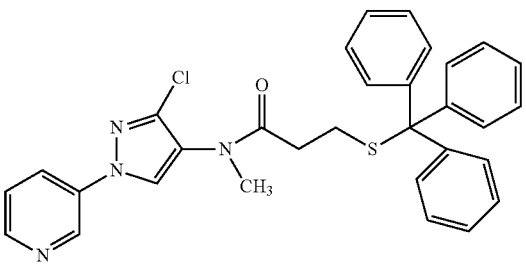 [SMILES: CN(C(=O)CCSC(c1ccccc1)(c1ccccc1)c1ccccc1)c1cn(-c2cccnc2)nc1Cl] | 106 |

TABLE 1-continued
Compound number, appearance, and structure
| Compound No. | Appearance | Structure | Prepared as in Example: |
|---|---|---|---|
| 679 | Colorless Oil | 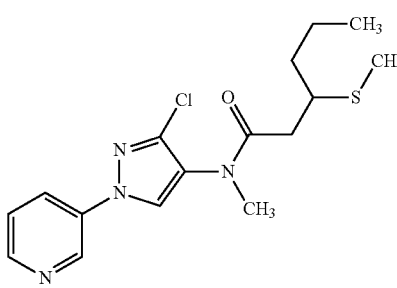 | 12 |
| 680 | Colorless Oil | 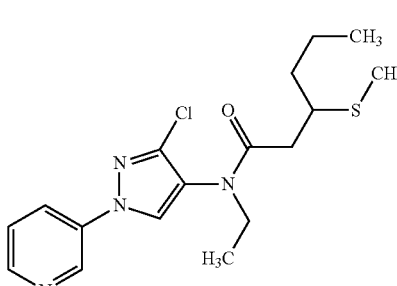 | 12 |
| 681 | Colorless Oil | 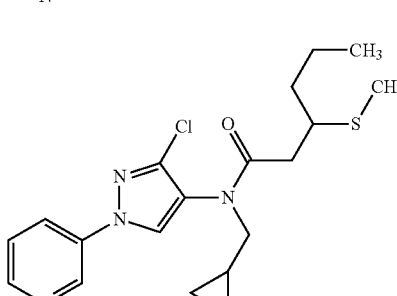 | 12 |
| 682 | Colorless Oil | 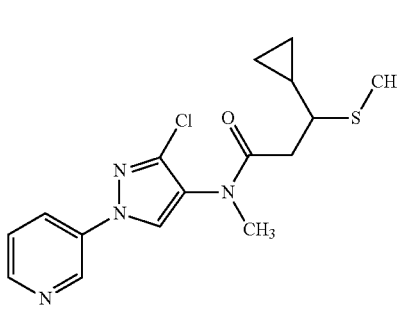 | 12 |
| 683 | Colorless Oil | 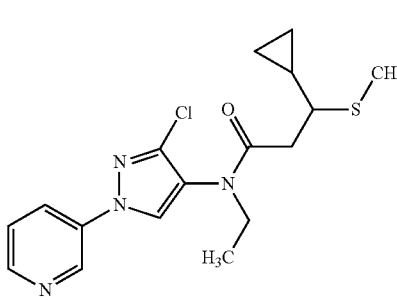 | 12 |

TABLE 1-continued

Compound number, appearance, and structure

| Compound No. | Appearance | Structure | Prepared as in Example: |
|---|---|---|---|
| 684 | Colorless Oil | 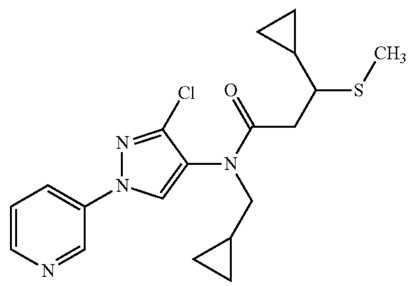 [SMILES: CSC(CC(=O)N(CC1CC1)c1cn(-c2cccnc2)nc1Cl)C1CC1] | 12 |
| 685 | Tan Solid | 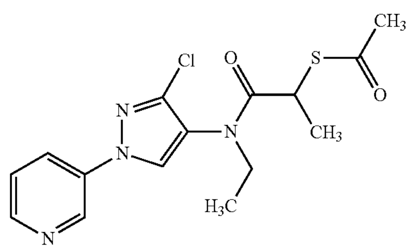 [SMILES: CCN(C(=O)C(C)SC(C)=O)c1cn(-c2cccnc2)nc1Cl] | 101 |
| 686 | Colorless Oil | 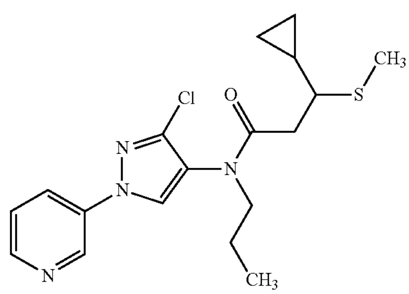 [SMILES: CCCN(C(=O)CC(SC)C1CC1)c1cn(-c2cccnc2)nc1Cl] | 12 |
| 687 | White Solid | 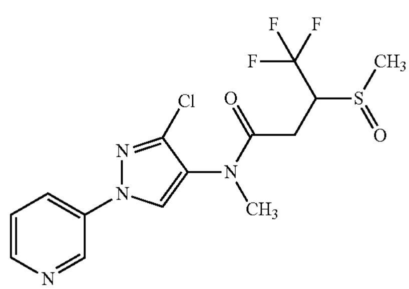 [SMILES: CN(C(=O)CC(S(C)=O)C(F)(F)F)c1cn(-c2cccnc2)nc1Cl] | 50 |
| 688 | Light Yellow Oil | 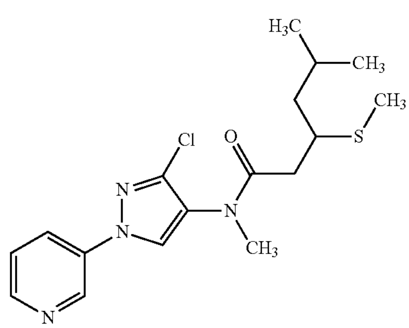 [SMILES: CSC(CC(=O)N(C)c1cn(-c2cccnc2)nc1Cl)CC(C)C] | 12 |

TABLE 1-continued
Compound number, appearance, and structure
| Compound No. | Appearance | Structure | Prepared as in Example: |
|---|---|---|---|
| 689 | Light Brown Oil | 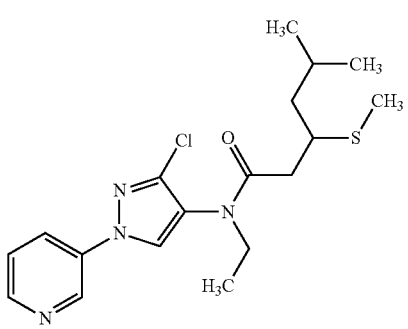 [SMILES: CCN(C(=O)CC(CC(C)C)SC)c1cn(-c2cccnc2)nc1Cl] | 12 |
| 690 | Colorless Oil | 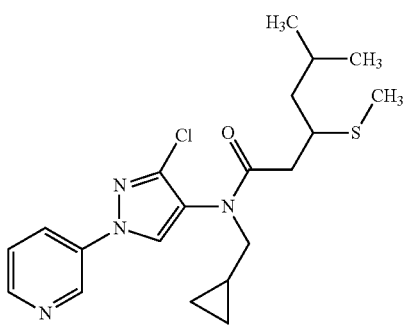 [SMILES: CSC(CC(=O)N(CC1CC1)c1cn(-c2cccnc2)nc1Cl)CC(C)C] | 12 |
| 691 | White Solid | 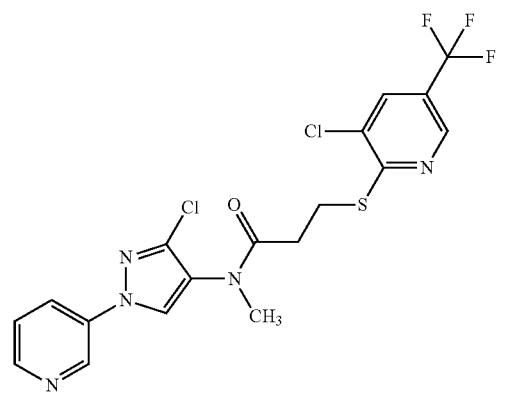 [SMILES: CN(C(=O)CCSc1ncc(C(F)(F)F)cc1Cl)c1cn(-c2cccnc2)nc1Cl] | 89 |
| 692 | Light Brown Oil | 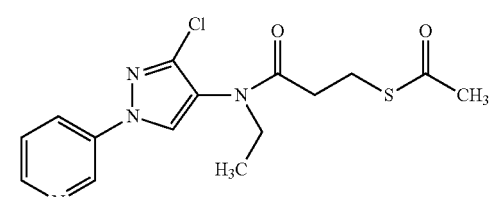 | 101 |

TABLE 1-continued

Compound number, appearance, and structure

| Compound No. | Appearance | Structure | Prepared as in Example: |
|---|---|---|---|
| 693 | Light Brown Oil | 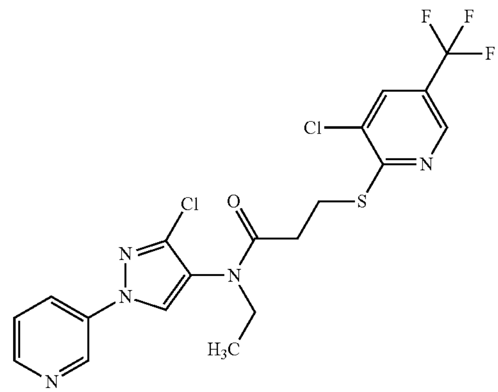 [SMILES: CCN(C(=O)CCSc1ncc(C(F)(F)F)cc1Cl)c1cn(-c2cccnc2)nc1Cl] | 89 |
| 694 | Tan Solid | 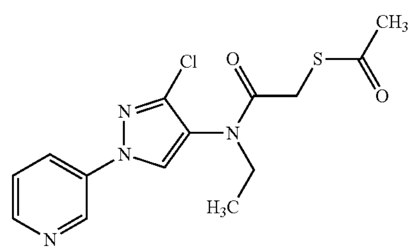 [SMILES: CCN(C(=O)CSC(C)=O)c1cn(-c2cccnc2)nc1Cl] | 101 |
| 695 | Light Brown Oil | 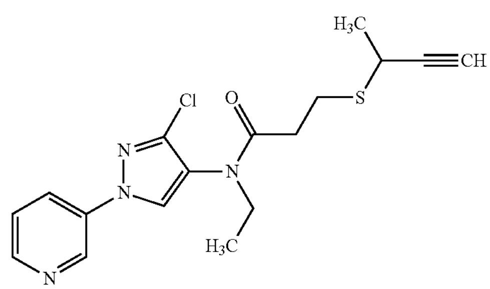 [SMILES: C#CC(C)SCCC(=O)N(CC)c1cn(-c2cccnc2)nc1Cl] | 89 |
| 696 | Faint Yellow Oil | 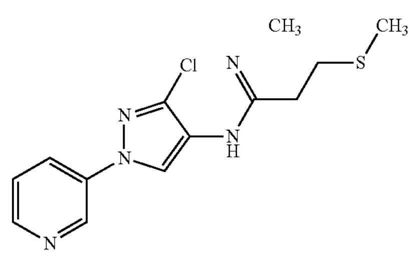 | 175 |
| 697 | Beige Solid | 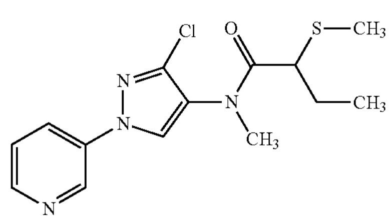 [SMILES: CCC(SC)C(=O)N(C)c1cn(-c2cccnc2)nc1Cl] | 39 |

TABLE 1-continued

Compound number, appearance, and structure

| Compound No. | Appearance | Structure | Prepared as in Example: |
|---|---|---|---|
| 698 | White Solid | 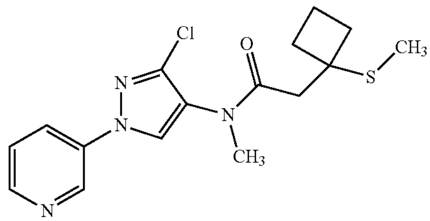 [SMILES: CSC1(CC(=O)N(C)c2cn(-c3cccnc3)nc2Cl)CCC1] | 12 |
| 699 | White Solid | 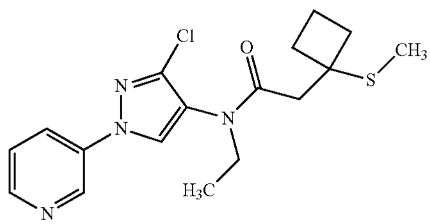 [SMILES: CCN(C(=O)CC1(SC)CCC1)c1cn(-c2cccnc2)nc1Cl] | 12 |
| 700 | White Solid | 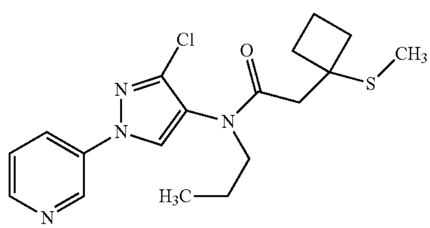 [SMILES: CCCN(C(=O)CC1(SC)CCC1)c1cn(-c2cccnc2)nc1Cl] | 12 |
| 701 | White Solid | 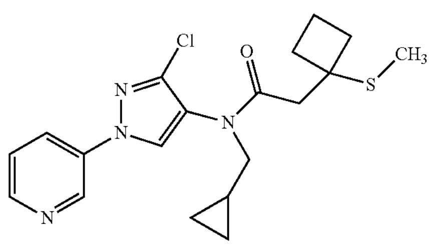 [SMILES: CSC1(CC(=O)N(CC2CC2)c2cn(-c3cccnc3)nc2Cl)CCC1] | 12 |
| 702 | Pale Yellow Oil | 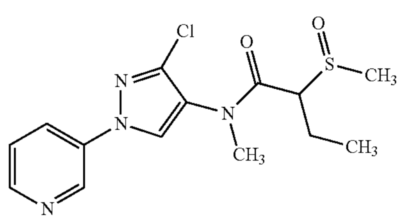 [SMILES: CCC(C(=O)N(C)c1cn(-c2cccnc2)nc1Cl)S(C)=O] | 51 |
| 703 | White Foam | 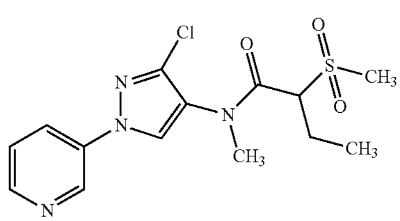 [SMILES: CCC(C(=O)N(C)c1cn(-c2cccnc2)nc1Cl)S(C)(=O)=O] | 52 |

TABLE 1-continued

Compound number, appearance, and structure

| Compound No. | Appearance | Structure | Prepared as in Example: |
|---|---|---|---|
| 704 | Orange Oil | 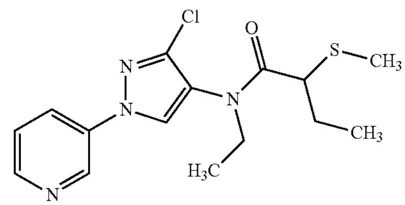 [SMILES: CCC(SC)C(=O)N(CC)c1cn(-c2cccnc2)nc1Cl] | 39 |
| 705 | Clear Thick Oil | 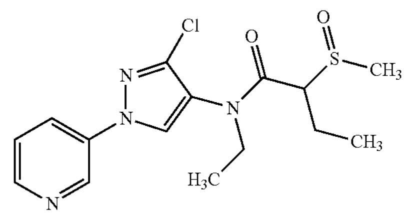 [SMILES: CCC(C(=O)N(CC)c1cn(-c2cccnc2)nc1Cl)S(C)=O] | 51 |
| 706 | Light Brown Solid | 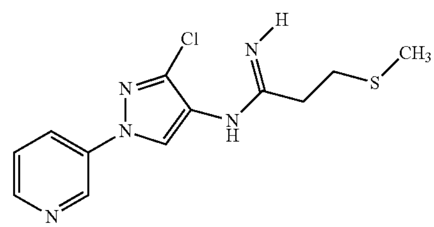 [SMILES: [H]/N=C(\CCSC)Nc1cn(-c2cccnc2)nc1Cl] | 175 |
| 707 | Light Brown Oil | 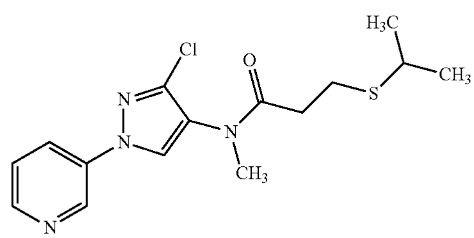 [SMILES: CC(C)SCCC(=O)N(C)c1cn(-c2cccnc2)nc1Cl] | 97 |
| 708 | Colorless Gum | 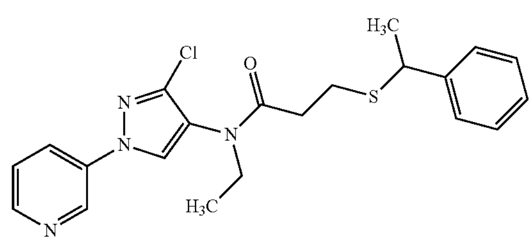 [SMILES: CCN(C(=O)CCSC(C)c1ccccc1)c1cn(-c2cccnc2)nc1Cl] | 97 |
| 709 | Colorless Gum | 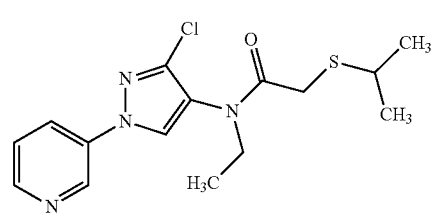 [SMILES: CCN(C(=O)CSC(C)C)c1cn(-c2cccnc2)nc1Cl] | 97 |

TABLE 1-continued

Compound number, appearance, and structure

| Compound No. | Appearance | Structure | Prepared as in Example: |
|---|---|---|---|
| 710 | Colorless Gum | 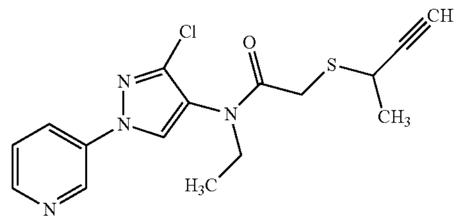 [SMILES: C#CC(C)SCC(=O)N(CC)c1cn(-c2cccnc2)nc1Cl] | 97 |
| 711 | Colorless Gum | 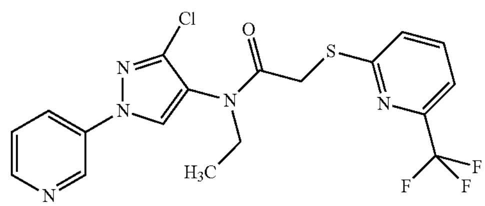 [SMILES: CCN(C(=O)CSc1cccc(C(F)(F)F)n1)c1cn(-c2cccnc2)nc1Cl] | 97 |
| 712 | Colorless Oil | 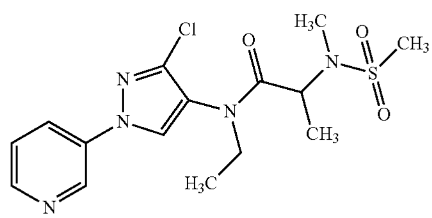 [SMILES: CCN(C(=O)C(C)N(C)S(C)(=O)=O)c1cn(-c2cccnc2)nc1Cl] | 149 |
| 713 | Colorless Oil | 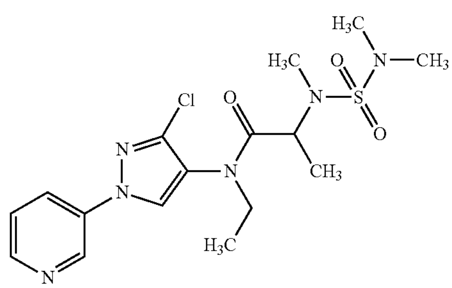 [SMILES: CCN(C(=O)C(C)N(C)S(=O)(=O)N(C)C)c1cn(-c2cccnc2)nc1Cl] | 149 |
| 714 | White Solid | 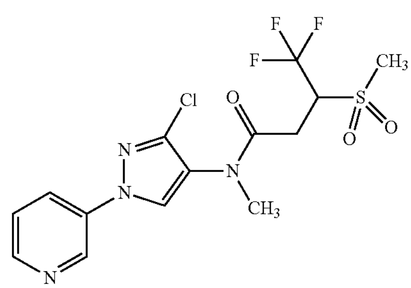 [SMILES: CN(C(=O)CC(C(F)(F)F)S(C)(=O)=O)c1cn(-c2cccnc2)nc1Cl] | 182 |
| 715 | White Solid | 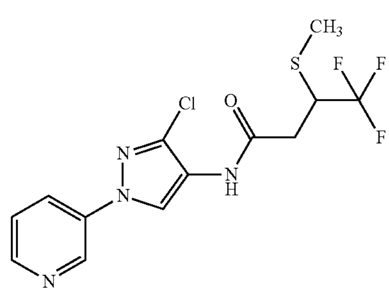 [SMILES: CSC(CC(=O)Nc1cn(-c2cccnc2)nc1Cl)C(F)(F)F] | 12 |

TABLE 1-continued

Compound number, appearance, and structure

| Compound No. | Appearance | Structure | Prepared as in Example: |
|---|---|---|---|
| 716 | Colorless Clear Gum | 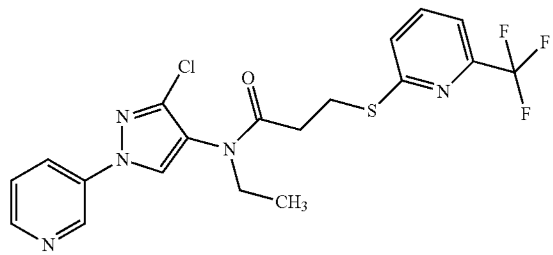 [SMILES: CCN(C(=O)CCSc1cccc(C(F)(F)F)n1)c1cn(-c2cccnc2)nc1Cl] | 97 |
| 717 | Colorless Gum | 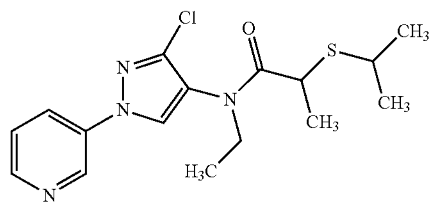 [SMILES: CCN(C(=O)C(C)SC(C)C)c1cn(-c2cccnc2)nc1Cl] | 97 |
| 718 | Colorless Gum | 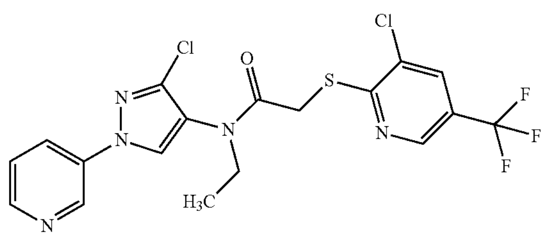 [SMILES: CCN(C(=O)CSc1ncc(C(F)(F)F)cc1Cl)c1cn(-c2cccnc2)nc1Cl] | 97 |
| 719 | Colorless Gum | 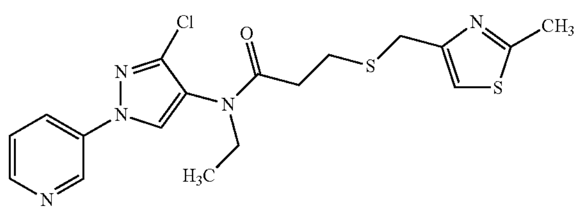 [SMILES: CCN(C(=O)CCSCc1csc(C)n1)c1cn(-c2cccnc2)nc1Cl] | 97 |
| 720 | Colorless Gum | 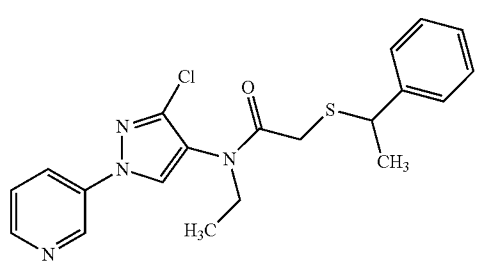 [SMILES: CCN(C(=O)CSC(C)c1ccccc1)c1cn(-c2cccnc2)nc1Cl] | 97 |
| 721 | Colorless Gum | 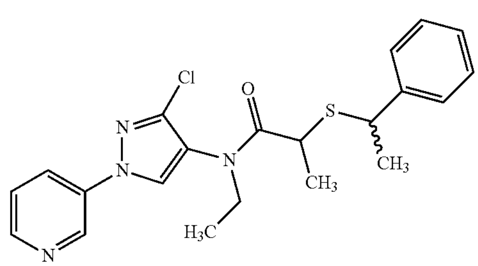 [SMILES: CCN(C(=O)C(C)SC(C)c1ccccc1)c1cn(-c2cccnc2)nc1Cl] | 97 |

TABLE 1-continued

Compound number, appearance, and structure

| Compound No. | Appearance | Structure | Prepared as in Example: |
|---|---|---|---|
| 722 | Colorless Gum | 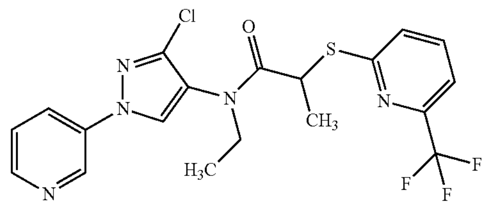 [SMILES: CCN(C(=O)C(C)Sc1cccc(C(F)(F)F)n1)c1cn(-c2cccnc2)nc1Cl] | 97 |
| 723 | Colorless Gum | 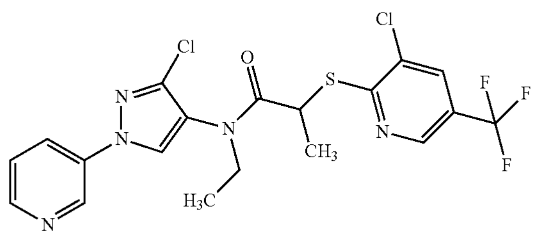 [SMILES: CCN(C(=O)C(C)Sc1ncc(C(F)(F)F)cc1Cl)c1cn(-c2cccnc2)nc1Cl] | 97 |
| 724 | Clear Oil | 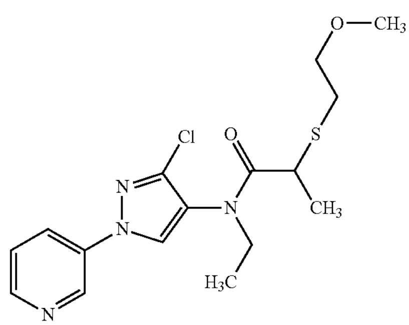 [SMILES: CCN(C(=O)C(C)SCCOC)c1cn(-c2cccnc2)nc1Cl] | 102 |
| 725 | Clear Oil | 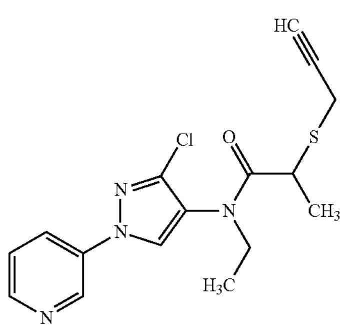 [SMILES: C#CCSC(C)C(=O)N(CC)c1cn(-c2cccnc2)nc1Cl] | 102 |
| 726 | Clear Oil | 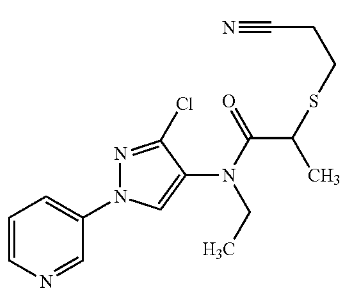 [SMILES: CCN(C(=O)C(C)SCCC#N)c1cn(-c2cccnc2)nc1Cl] | 102 |

TABLE 1-continued

Compound number, appearance, and structure

| Compound No. | Appearance | Structure | Prepared as in Example: |
|---|---|---|---|
| 727 | Clear Oil | 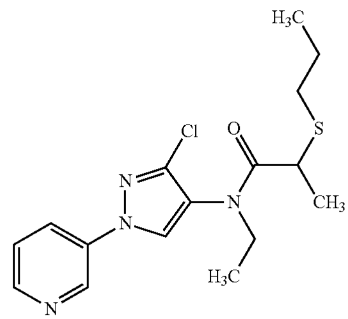 [SMILES: CCCSC(C)C(=O)N(CC)c1cn(-c2cccnc2)nc1Cl] | 102 |
| 728 | Clear Oil | 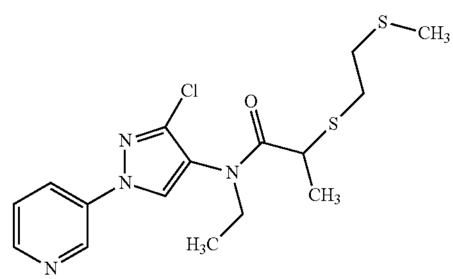 [SMILES: CCN(C(=O)C(C)SCCSC)c1cn(-c2cccnc2)nc1Cl] | 102 |
| 729 | Clear Oil | 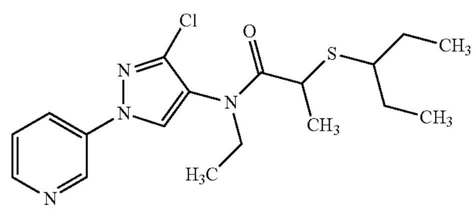 [SMILES: CCC(CC)SC(C)C(=O)N(CC)c1cn(-c2cccnc2)nc1Cl] | 102 |
| 730 | Clear Oil | 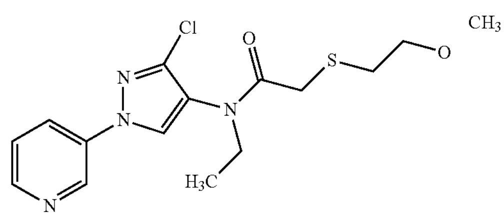 | 102 |
| 731 | Brown Oil | 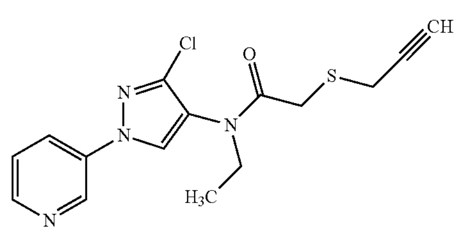 [SMILES: C#CCSCC(=O)N(CC)c1cn(-c2cccnc2)nc1Cl] | 102 |
| 732 | Clear Oil | 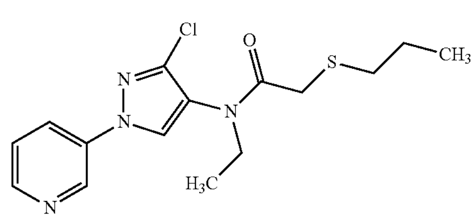 [SMILES: CCCSCC(=O)N(CC)c1cn(-c2cccnc2)nc1Cl] | 102 |

TABLE 1-continued
| Compound No. | Appearance | Structure | Prepared as in Example: |
|---|---|---|---|
| 733 | Clear Oil | 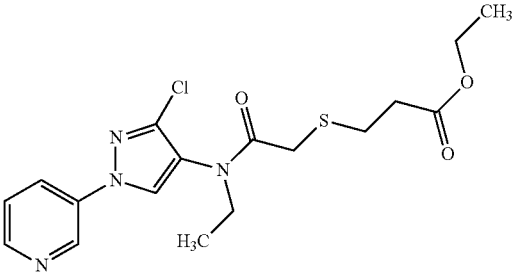 [SMILES: CCOC(=O)CCSCC(=O)N(CC)c1cn(-c2cccnc2)nc1Cl] | 102 |
| 734 | Clear Oil | 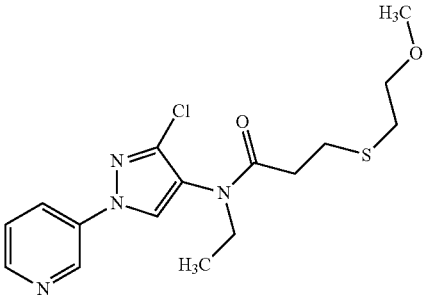 [SMILES: CCN(C(=O)CCSCCOC)c1cn(-c2cccnc2)nc1Cl] | 102 |
| 735 | Brown Oil | 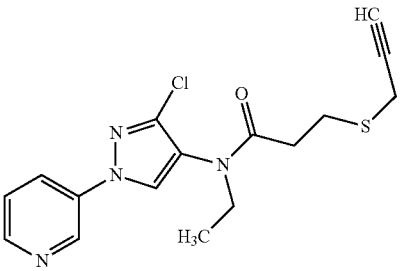 [SMILES: C#CCSCCC(=O)N(CC)c1cn(-c2cccnc2)nc1Cl] | 102 |
| 736 | Clear Oil | 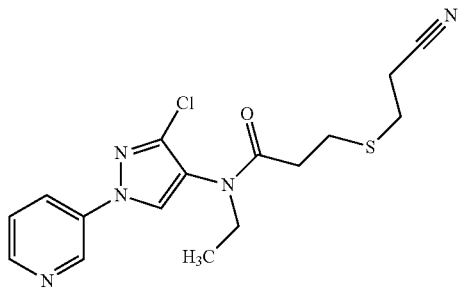 [SMILES: CCN(C(=O)CCSCCC#N)c1cn(-c2cccnc2)nc1Cl] | 102 |
| 737 | Clear Oil | 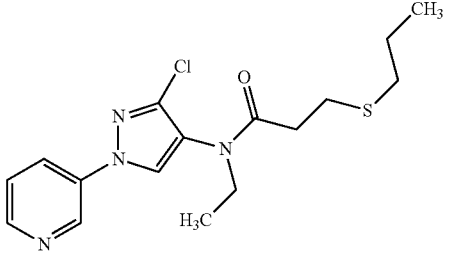 [SMILES: CCCSCCC(=O)N(CC)c1cn(-c2cccnc2)nc1Cl] | 102 |

TABLE 1-continued

Compound number, appearance, and structure

| Compound No. | Appearance | Structure | Prepared as in Example: |
|---|---|---|---|
| 738 | Clear Oil | 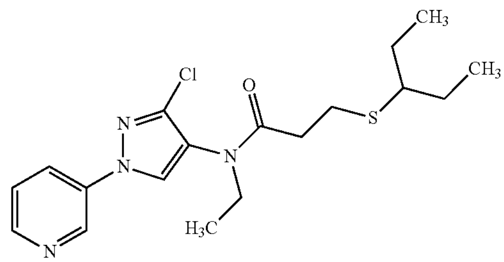 [SMILES: CCC(CC)SCCC(=O)N(CC)c1cn(-c2cccnc2)nc1Cl] | 102 |
| 739 | Clear Oil | 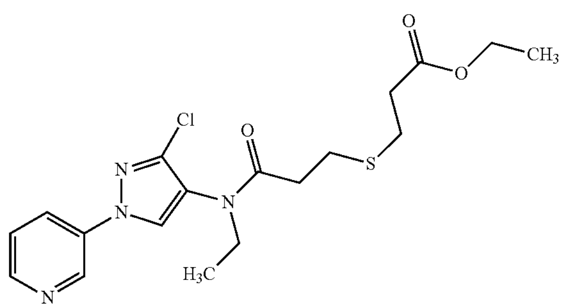 [SMILES: CCOC(=O)CCSCCC(=O)N(CC)c1cn(-c2cccnc2)nc1Cl] | 102 |
| 740 | Pink Solid | 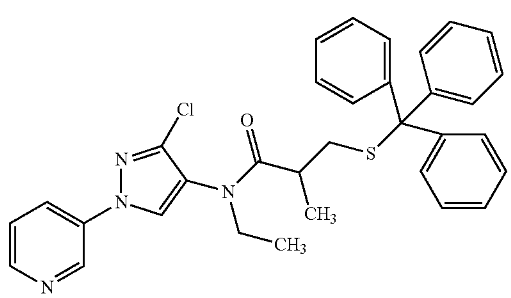 [SMILES: CCN(C(=O)C(C)CSC(c1ccccc1)(c1ccccc1)c1ccccc1)c1cn(-c2cccnc2)nc1Cl] | 42 |
| 741 | Colorless Gum | 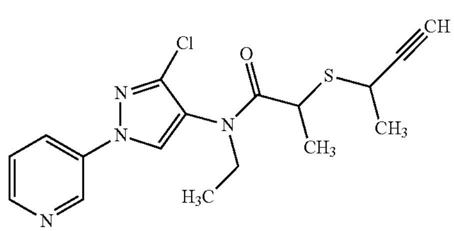 [SMILES: C#CC(C)SC(C)C(=O)N(CC)c1cn(-c2cccnc2)nc1Cl] | 97 |
| 742 | Colorless Gum | 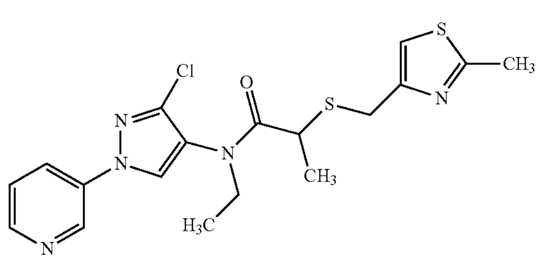 [SMILES: CCN(C(=O)C(C)SCc1csc(C)n1)c1cn(-c2cccnc2)nc1Cl] | 97 |

TABLE 1-continued

Compound number, appearance, and structure

| Compound No. | Appearance | Structure | Prepared as in Example: |
|---|---|---|---|
| 743 | Light Brown Oil | 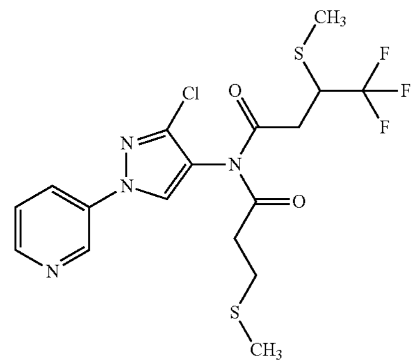 [SMILES: CSCCC(=O)N(C(=O)CC(SC)C(F)(F)F)c1cn(-c2cccnc2)nc1Cl] | 11 |
| 744 | Light Yellow Oil | 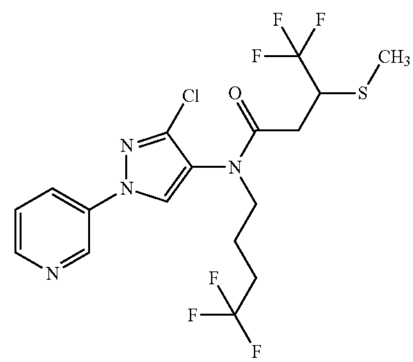 [SMILES: CSC(CC(=O)N(CCCC(F)(F)F)c1cn(-c2cccnc2)nc1Cl)C(F)(F)F] | 12 |
| 745 | Light Yellow Oil | 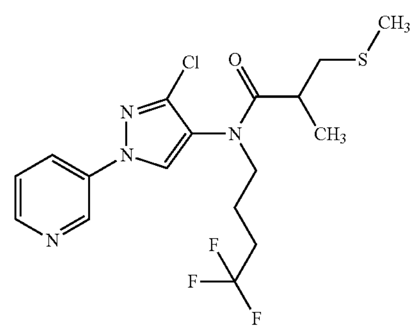 [SMILES: CSCC(C)C(=O)N(CCCC(F)(F)F)c1cn(-c2cccnc2)nc1Cl] | 11 |
| 746 | Light Yellow Oil | 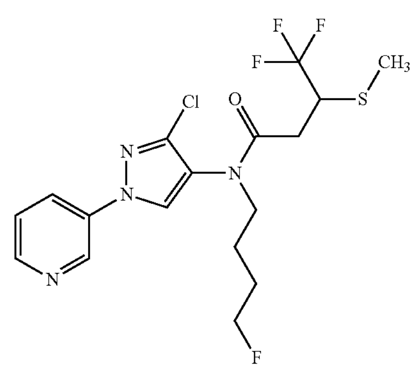 [SMILES: CSC(CC(=O)N(CCCCF)c1cn(-c2cccnc2)nc1Cl)C(F)(F)F] | 12 |

TABLE 1-continued

Compound number, appearance, and structure

| Compound No. | Appearance | Structure | Prepared as in Example: |
|---|---|---|---|
| 747 | Light Yellow Oil | 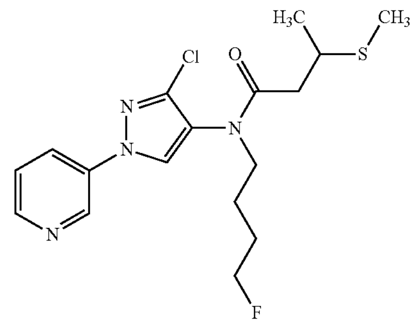 [SMILES: CSC(C)CC(=O)N(CCCCF)c1cn(-c2cccnc2)nc1Cl] | 12 |
| 748 | Colorless Oil | 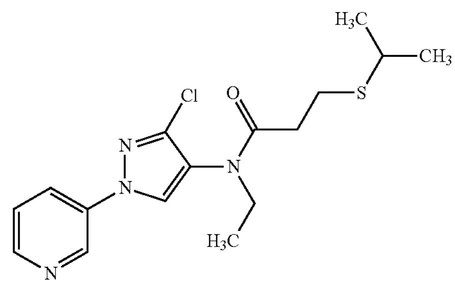 [SMILES: CCN(C(=O)CCSC(C)C)c1cn(-c2cccnc2)nc1Cl] | 97 |
| 749 | Light Yellow Oil | 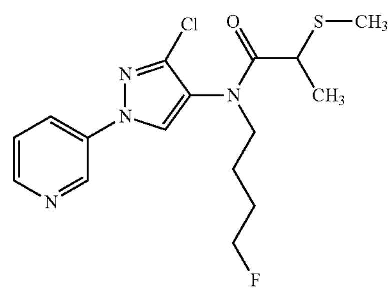 [SMILES: CSC(C)C(=O)N(CCCCF)c1cn(-c2cccnc2)nc1Cl] | 12 |
| 750 | Light Yellow Oil | 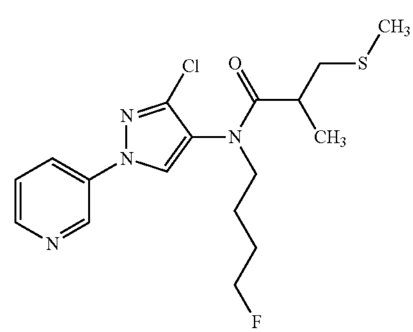 [SMILES: CSCC(C)C(=O)N(CCCCF)c1cn(-c2cccnc2)nc1Cl] | 11 |
| 751 | Brown Solid | 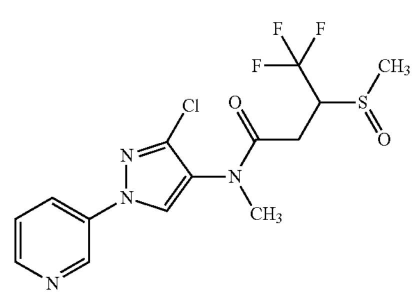 [SMILES: CN(C(=O)CC(S(C)=O)C(F)(F)F)c1cn(-c2cccnc2)nc1Cl] | 50 |

TABLE 1-continued

Compound number, appearance, and structure

| Compound No. | Appearance | Structure | Prepared as in Example: |
|---|---|---|---|
| 752 | Light Yellow Oil | 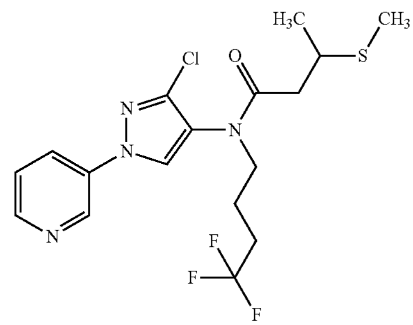 [SMILES: CSC(C)CC(=O)N(CCCC(F)(F)F)c1cn(-c2cccnc2)nc1Cl] | 11 |
| 753 | Colorless Gum | 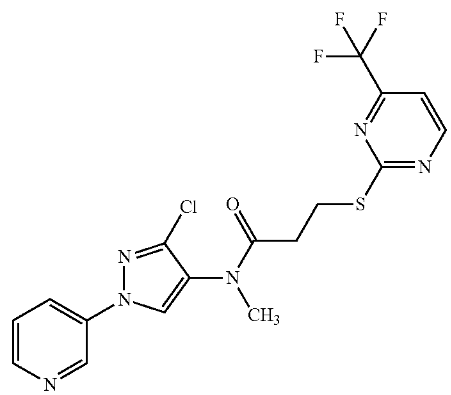 [SMILES: CN(C(=O)CCSc1nccc(C(F)(F)F)n1)c1cn(-c2cccnc2)nc1Cl] | 89 |
| 754 | Colorless Gum | 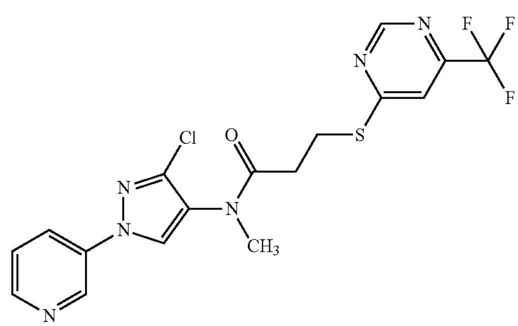 [SMILES: CN(C(=O)CCSc1cc(C(F)(F)F)ncn1)c1cn(-c2cccnc2)nc1Cl] | 89 |
| 755 | Light Yellow Oil | 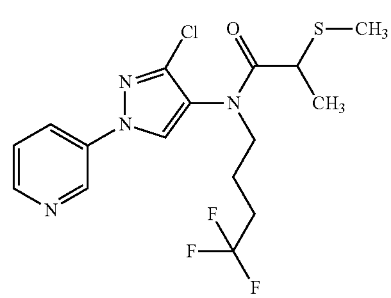 [SMILES: CSC(C)C(=O)N(CCCC(F)(F)F)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 756 | Light Yellow Oil | 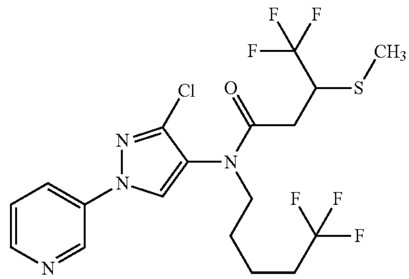 [SMILES: CSC(CC(=O)N(CCCCC(F)(F)F)c1cn(-c2cccnc2)nc1Cl)C(F)(F)F] | 12 |
| 757 | Light Yellow Oil | 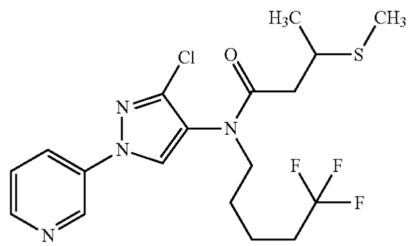 [SMILES: CSC(C)CC(=O)N(CCCCC(F)(F)F)c1cn(-c2cccnc2)nc1Cl] | 12 |
| 758 | Light Yellow Oil | 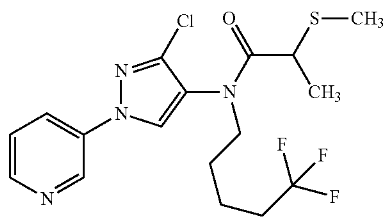 [SMILES: CSC(C)C(=O)N(CCCCC(F)(F)F)c1cn(-c2cccnc2)nc1Cl] | 12 |
| 759 | Light Yellow Oil | 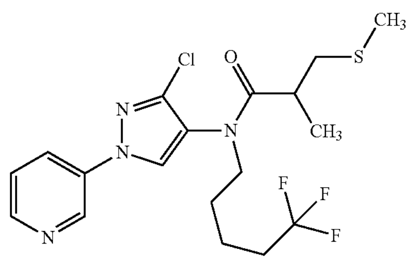 [SMILES: CSCC(C)C(=O)N(CCCCC(F)(F)F)c1cn(-c2cccnc2)nc1Cl] | 11 |
| 760 | Colorless Gum | 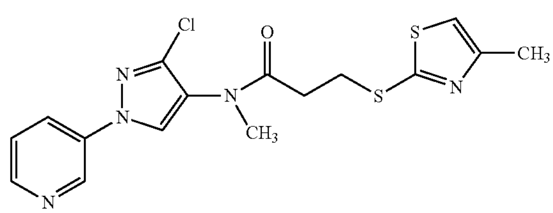 [SMILES: Cc1csc(SCCC(=O)N(C)c2cn(-c3cccnc3)nc2Cl)n1] | 101 |
| 761 | Colorless Gum | 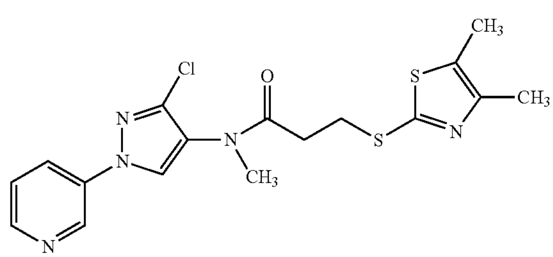 [SMILES: Cc1nc(SCCC(=O)N(C)c2cn(-c3cccnc3)nc2Cl)sc1C] | 101 |

TABLE 1-continued

Compound number, appearance, and structure

| Compound No. | Appearance | Structure | Prepared as in Example: |
|---|---|---|---|
| 762 | Colorless Gum | 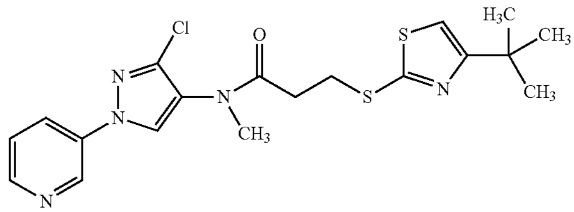 [SMILES: CN(C(=O)CCSc1nc(C(C)(C)C)cs1)c1cn(-c2cccnc2)nc1Cl] | 101 |
| 763 | Clear Oil | 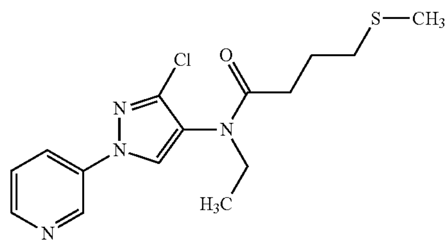 [SMILES: CCN(C(=O)CCCSC)c1cn(-c2cccnc2)nc1Cl] | 12 |
| 764 | Colorless Oil | 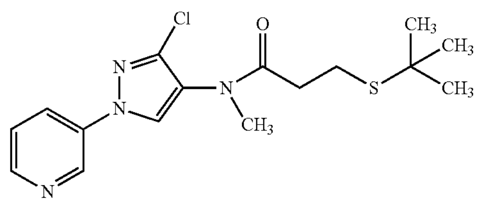 [SMILES: CN(C(=O)CCSC(C)(C)C)c1cn(-c2cccnc2)nc1Cl] | 101 |
| 765 | Amorphous Solid | 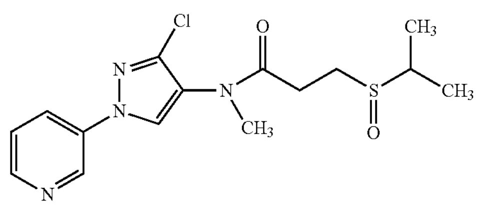 [SMILES: CC(C)S(=O)CCC(=O)N(C)c1cn(-c2cccnc2)nc1Cl] | 91 |
| 766 | Colorless Amorphous Solid | 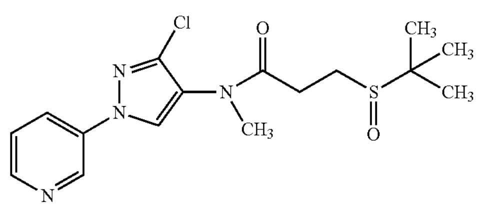 [SMILES: CN(C(=O)CCS(=O)C(C)(C)C)c1cn(-c2cccnc2)nc1Cl] | 91 |
| 767 | Colorless Amorphous Solid | 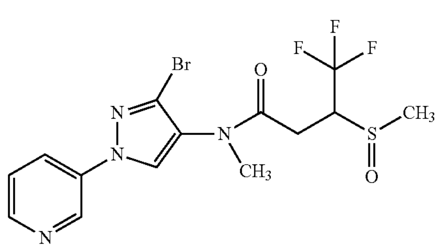 [SMILES: CN(C(=O)CC(S(C)=O)C(F)(F)F)c1cn(-c2cccnc2)nc1Br] | 91 |

TABLE 1-continued

Compound number, appearance, and structure

| Compound No. | Appearance | Structure | Prepared as in Example: |
|---|---|---|---|
| 768 | Light Yellow Oil | 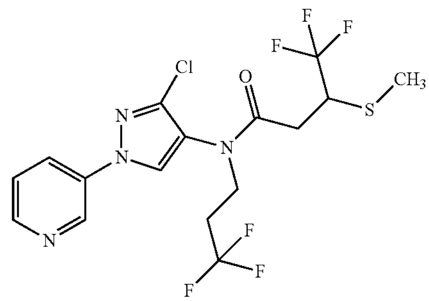 [SMILES: CSC(CC(=O)N(CCC(F)(F)F)c1cn(-c2cccnc2)nc1Cl)C(F)(F)F] | 12 |
| 769 | Off-White Solid | 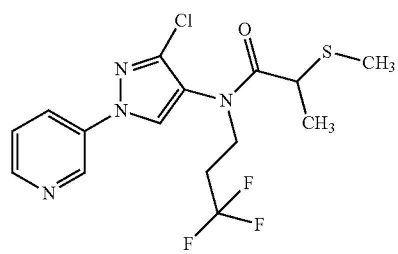 [SMILES: CSC(C)C(=O)N(CCC(F)(F)F)c1cn(-c2cccnc2)nc1Cl] | 12 |
| 770 | Light Yellow Oil | 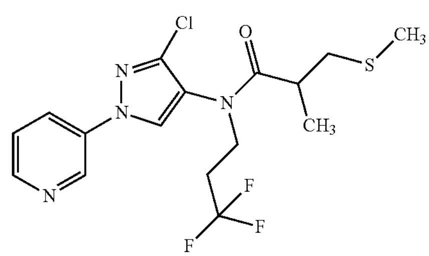 [SMILES: CSCC(C)C(=O)N(CCC(F)(F)F)c1cn(-c2cccnc2)nc1Cl] | 11 |
| 771 | Light Yellow Oil | 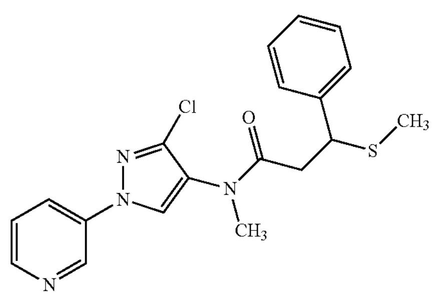 [SMILES: CSC(CC(=O)N(C)c1cn(-c2cccnc2)nc1Cl)c1ccccc1] | 12 |
| 772 | Light Yellow Oil | 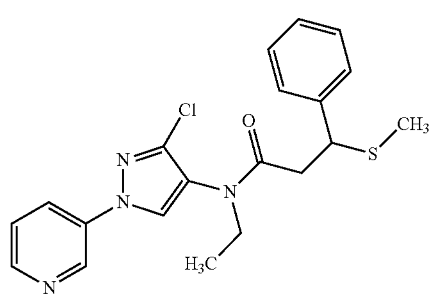 [SMILES: CCN(C(=O)CC(SC)c1ccccc1)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 773 | Light Yellow Oil | 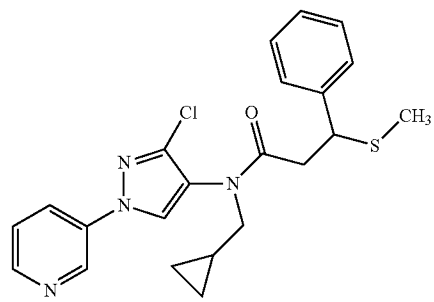 [SMILES: CSC(CC(=O)N(CC1CC1)c1cn(-c2cccnc2)nc1Cl)c1ccccc1] | 12 |
| 774 | Light Yellow Oil | 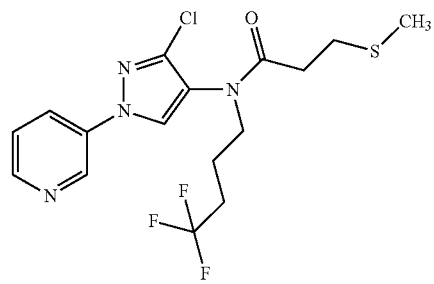 [SMILES: CSCCC(=O)N(CCCC(F)(F)F)c1cn(-c2cccnc2)nc1Cl] | 12 |
| 775 | Light Yellow Oil | 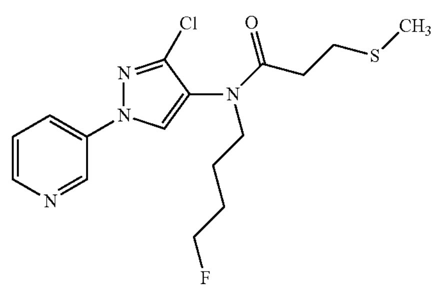 [SMILES: CSCCC(=O)N(CCCCF)c1cn(-c2cccnc2)nc1Cl] | 12 |
| 776 | Light Yellow Oil | 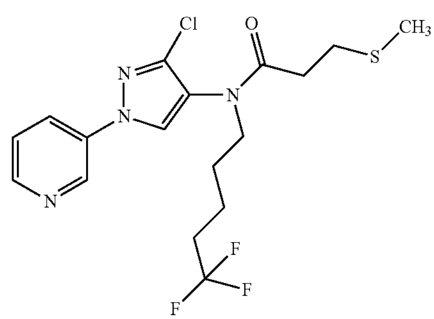 [SMILES: CSCCC(=O)N(CCCCC(F)(F)F)c1cn(-c2cccnc2)nc1Cl] | 12 |
| 777 | White Solid | 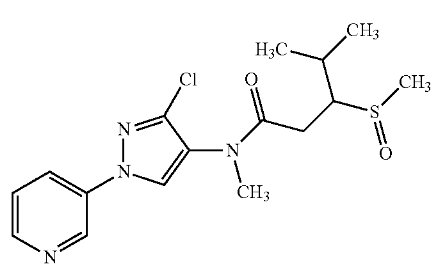 [SMILES: CC(C)C(CC(=O)N(C)c1cn(-c2cccnc2)nc1Cl)S(C)=O] | 50 |

TABLE 1-continued

Compound number, appearance, and structure

| Compound No. | Appearance | Structure | Prepared as in Example: |
|---|---|---|---|
| 778 | White Semi-Solid | 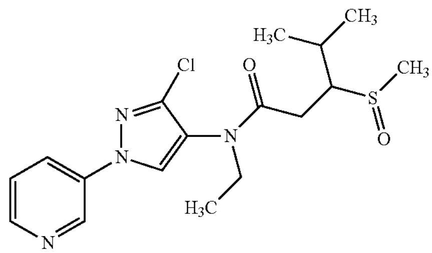 [SMILES: CCN(C(=O)CC(C(C)C)S(C)=O)c1cn(-c2cccnc2)nc1Cl] | 50 |
| 779 | Tan Solid | 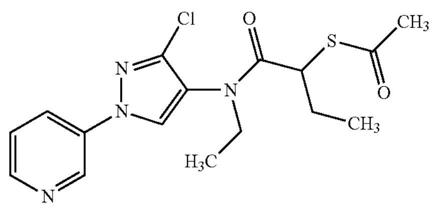 [SMILES: CCC(SC(C)=O)C(=O)N(CC)c1cn(-c2cccnc2)nc1Cl] | 101 |
| 780 | Light Yellow Oil | 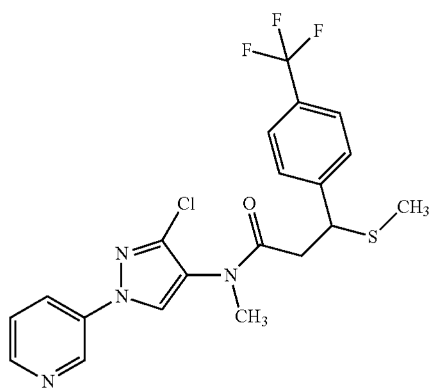 [SMILES: CSC(CC(=O)N(C)c1cn(-c2cccnc2)nc1Cl)c1ccc(C(F)(F)F)cc1] | 12 |
| 781 | Light Yellow Oil | 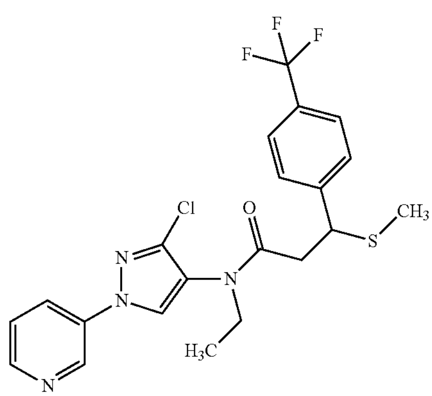 [SMILES: CCN(C(=O)CC(SC)c1ccc(C(F)(F)F)cc1)c1cn(-c2cccnc2)nc1Cl] | 12 |
| 782 | White Solid | 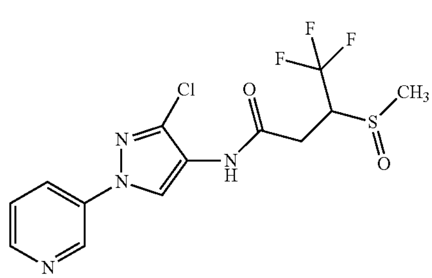 [SMILES: CS(=O)C(CC(=O)Nc1cn(-c2cccnc2)nc1Cl)C(F)(F)F] | 50 |

TABLE 1-continued
Compound number, appearance, and structure
| Compound No. | Appearance | Structure | Prepared as in Example: |
|---|---|---|---|
| 783 | Yellow Oil | 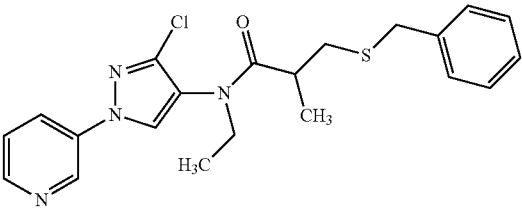 [SMILES: CCN(C(=O)C(C)CSCc1ccccc1)c1cn(-c2cccnc2)nc1Cl] | 89 |
| 784 | Clear Colorless Oil | 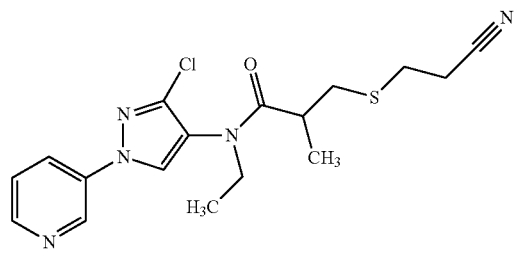 [SMILES: CCN(C(=O)C(C)CSCCC#N)c1cn(-c2cccnc2)nc1Cl] | 89 |
| 785 | Clear Colorless Oil | 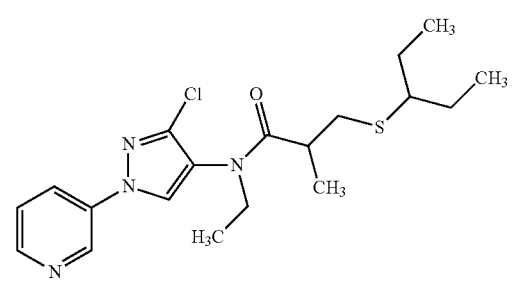 [SMILES: CCC(CC)SCC(C)C(=O)N(CC)c1cn(-c2cccnc2)nc1Cl] | 89 |
| 786 | Clear Colorless Oil | 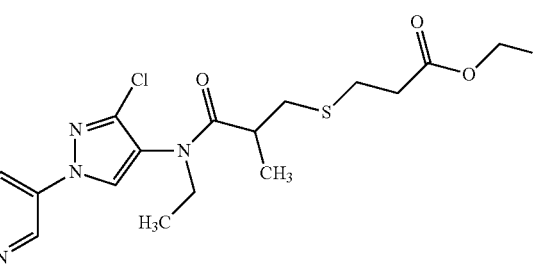 | 89 |
| 787 | Opaque Viscous Oil | 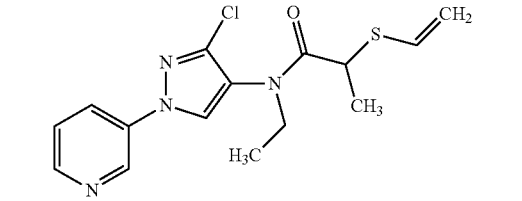 [SMILES: C=CSC(C)C(=O)N(CC)c1cn(-c2cccnc2)nc1Cl] | 144 |
| 788 | White Solid | 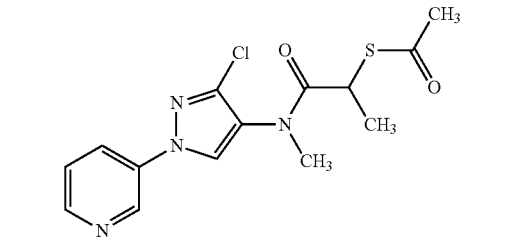 [SMILES: CC(=O)SC(C)C(=O)N(C)c1cn(-c2cccnc2)nc1Cl] | 101 |

TABLE 1-continued

Compound number, appearance, and structure

| Compound No. | Appearance | Structure | Prepared as in Example: |
|---|---|---|---|
| 789 | Orange Oil | 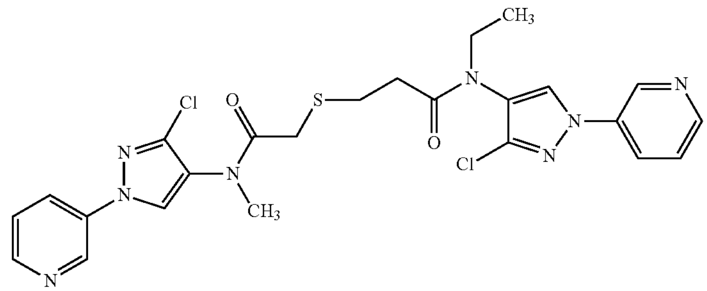 [SMILES: CCN(C(=O)CCSCC(=O)N(C)c1cn(-c2cccnc2)nc1Cl)c1cn(-c2cccnc2)nc1Cl] | 137 |
| 790 | Pale Yellow Oil | 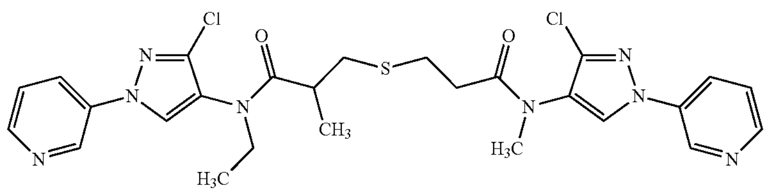 [SMILES: CCN(C(=O)C(C)CSCCC(=O)N(C)c1cn(-c2cccnc2)nc1Cl)c1cn(-c2cccnc2)nc1Cl] | 136 |
| 791 | Light Yellow Oil | 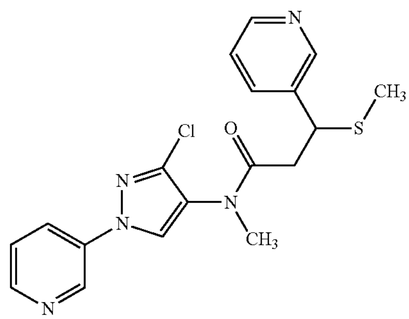 [SMILES: CSC(CC(=O)N(C)c1cn(-c2cccnc2)nc1Cl)c1cccnc1] | 12 |
| 792 | Light Yellow Oil | 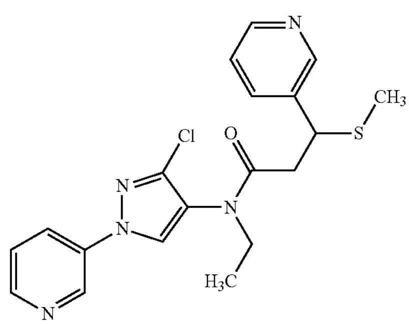 [SMILES: CCN(C(=O)CC(SC)c1cccnc1)c1cn(-c2cccnc2)nc1Cl] | 12 |
| 793 | Light Yellow Oil | 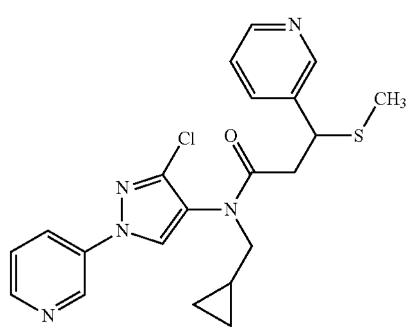 [SMILES: CSC(CC(=O)N(CC1CC1)c1cn(-c2cccnc2)nc1Cl)c1cccnc1] | 12 |

TABLE 1-continued

Compound number, appearance, and structure

| Compound No. | Appearance | Structure | Prepared as in Example: |
|---|---|---|---|
| 794 | Light Yellow Oil | 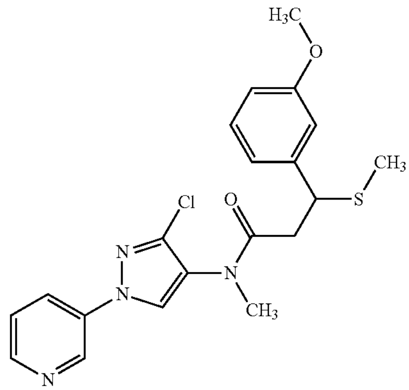 [SMILES: COc1cccc(C(CC(=O)N(C)c2cn(-c3cccnc3)nc2Cl)SC)c1] | 12 |
| 795 | Light Yellow Oil | 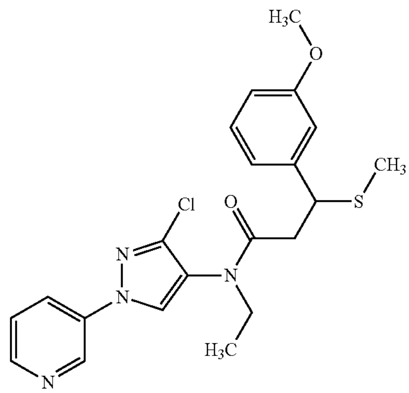 [SMILES: CCN(C(=O)CC(SC)c1cccc(OC)c1)c1cn(-c2cccnc2)nc1Cl] | 12 |
| 796 | Light Yellow Oil | 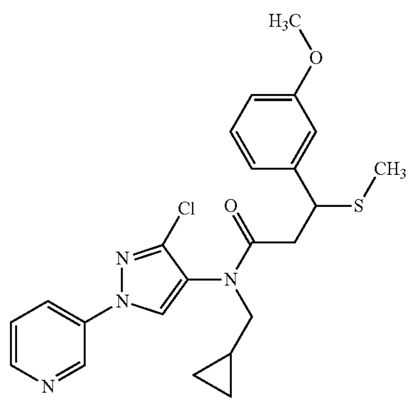 [SMILES: COc1cccc(C(CC(=O)N(CC2CC2)c2cn(-c3cccnc3)nc2Cl)SC)c1] | 12 |
| 787 | Yellow Solid | 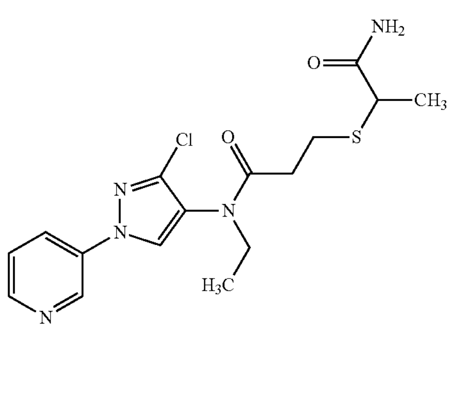 [SMILES: CCN(C(=O)CCSC(C)C(N)=O)c1cn(-c2cccnc2)nc1Cl] | 89 |

TABLE 1-continued

| Compound No. | Appearance | Structure | Prepared as in Example: |
|---|---|---|---|
| 798 | Colorless Gum | 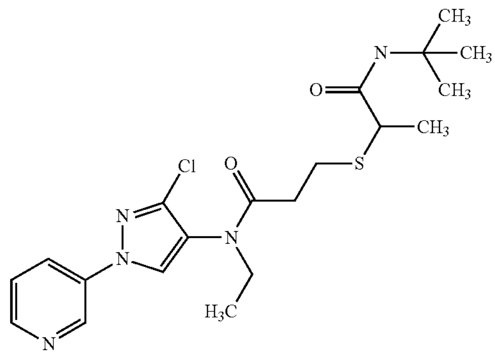 [SMILES: CCN(C(=O)CCSC(C)C(=O)NC(C)(C)C)c1cn(-c2cccnc2)nc1Cl] | 89 |
| 799 | Oil | 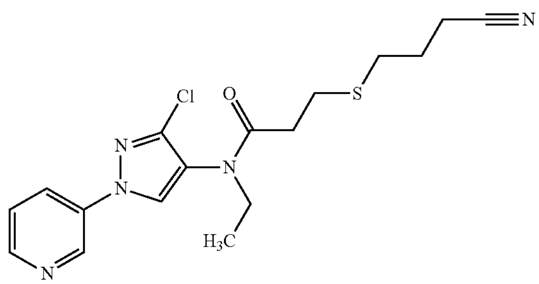 [SMILES: CCN(C(=O)CCSCCCC#N)c1cn(-c2cccnc2)nc1Cl] | 89 |
| 800 | White Semi Solid | 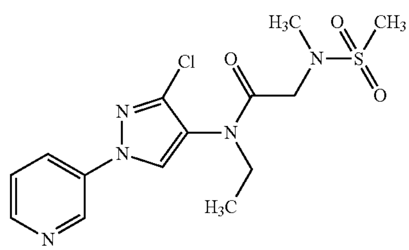 | 170 |
| 801 | White Solid | 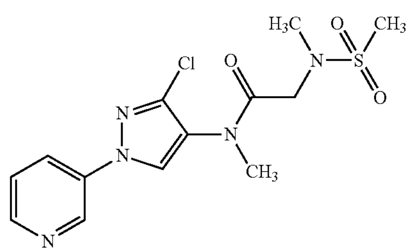 [SMILES: CN(C(=O)CN(C)S(C)(=O)=O)c1cn(-c2cccnc2)nc1Cl] | 170 |
| 802 | White Semi Solid | 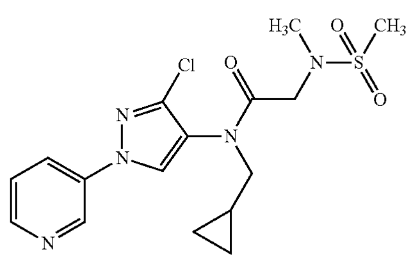 [SMILES: CN(CC(=O)N(CC1CC1)c1cn(-c2cccnc2)nc1Cl)S(C)(=O)=O] | 170 |

TABLE 1-continued
Compound number, appearance, and structure
| Compound No. | Appearance | Structure | Prepared as in Example: |
|---|---|---|---|
| 803 | Pale Yellow Foam | 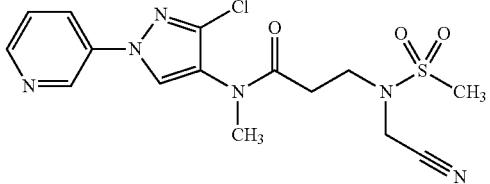 [SMILES: CN(C(=O)CCN(CC#N)S(C)(=O)=O)c1cn(-c2cccnc2)nc1Cl] | 147 |
| 804 | Colorless Gummy Liquid | 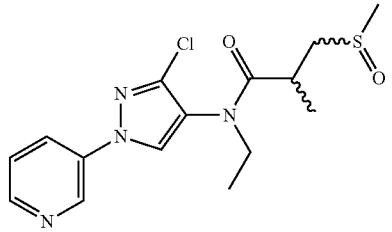 [SMILES: CCN(C(=O)C(C)CS(C)=O)c1cn(-c2cccnc2)nc1Cl] | 183 |
| 805 | Colorless Gummy Liquid | 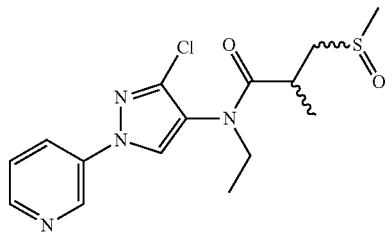 [SMILES: CCN(C(=O)C(C)CS(C)=O)c1cn(-c2cccnc2)nc1Cl] | 183 |
| 806 | Colorless Gummy Liquid | 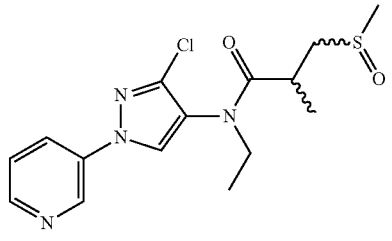 [SMILES: CCN(C(=O)C(C)CS(C)=O)c1cn(-c2cccnc2)nc1Cl] | 183 |
| 807 | Colorless Gummy Liquid | 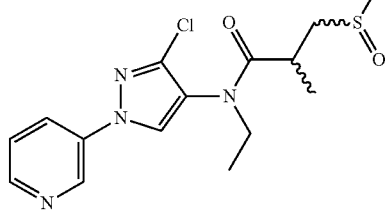 | 183 |
| 808 | Brown Solid | 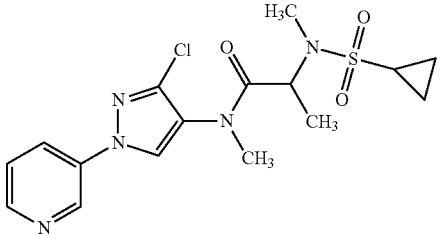 [SMILES: CC(C(=O)N(C)c1cn(-c2cccnc2)nc1Cl)N(C)S(=O)(=O)C1CC1] | 149 |

TABLE 1-continued

Compound number, appearance, and structure

| Compound No. | Appearance | Structure | Prepared as in Example: |
|---|---|---|---|
| 809 | White Solid | 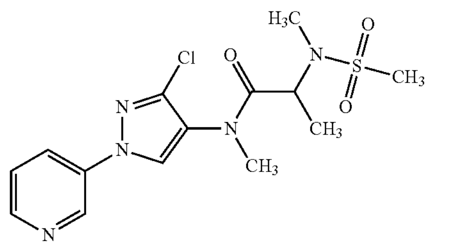 [SMILES: CC(C(=O)N(C)c1cn(-c2cccnc2)nc1Cl)N(C)S(C)(=O)=O] | 149 |
| 810 | White Solid | 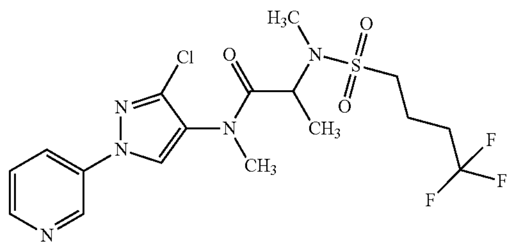 [SMILES: CC(C(=O)N(C)c1cn(-c2cccnc2)nc1Cl)N(C)S(=O)(=O)CCCC(F)(F)F] | 149 |
| 811 | Yellow Oil | 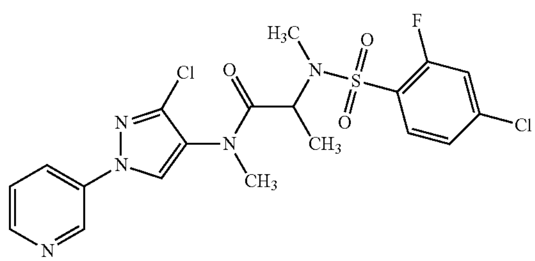 [SMILES: CC(C(=O)N(C)c1cn(-c2cccnc2)nc1Cl)N(C)S(=O)(=O)c1ccc(Cl)cc1F] | 149 |
| 812 | Light Yellow Semi-solid | 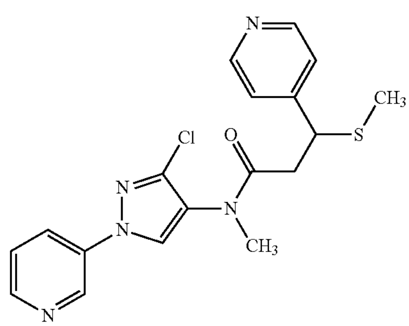 [SMILES: CSC(CC(=O)N(C)c1cn(-c2cccnc2)nc1Cl)c1ccncc1] | 12 |
| 813 | Light Yellow Semi-Solid | 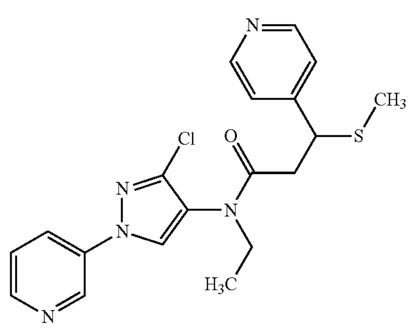 [SMILES: CCN(C(=O)CC(SC)c1ccncc1)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 814 | Light Yellow Semi-Solid | 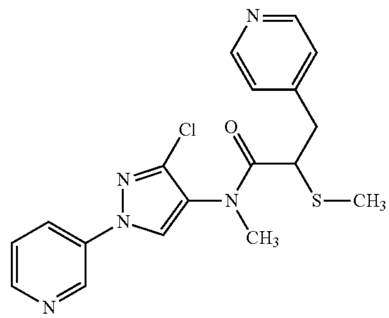 [SMILES: CSC(Cc1ccncc1)C(=O)N(C)c1cn(-c2cccnc2)nc1Cl] | 12 |
| 815 | Pale Orange Foam | 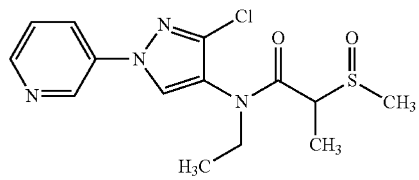 [SMILES: CCN(C(=O)C(C)S(C)=O)c1cn(-c2cccnc2)nc1Cl] | 51 |
| 816 | Pale Orange Solid | 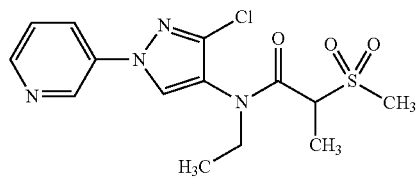 [SMILES: CCN(C(=O)C(C)S(C)(=O)=O)c1cn(-c2cccnc2)nc1Cl] | 52 |
| 817 | Brown Gum | 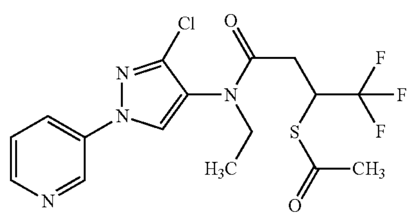 [SMILES: CCN(C(=O)CC(SC(C)=O)C(F)(F)F)c1cn(-c2cccnc2)nc1Cl] | 94 |
| 818 | Opaque, Viscous Oil | 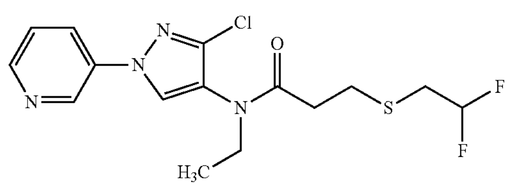 [SMILES: CCN(C(=O)CCSCC(F)F)c1cn(-c2cccnc2)nc1Cl] | 102 |
| 819 | Pale Yellow, Viscous Oil | 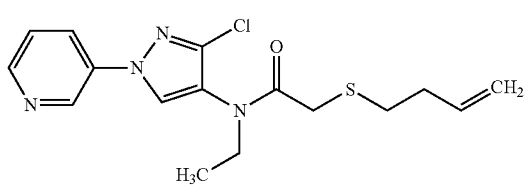 [SMILES: C=CCCSCC(=O)N(CC)c1cn(-c2cccnc2)nc1Cl] | 102 |
| 820 | Opaque, Viscous Oil | 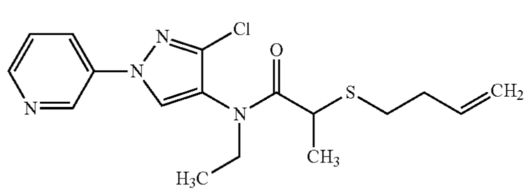 [SMILES: C=CCCSC(C)C(=O)N(CC)c1cn(-c2cccnc2)nc1Cl] | 102 |

TABLE 1-continued

Compound number, appearance, and structure

| Compound No. | Appearance | Structure | Prepared as in Example: |
|---|---|---|---|
| 821 | Opaque, Viscous Oil | 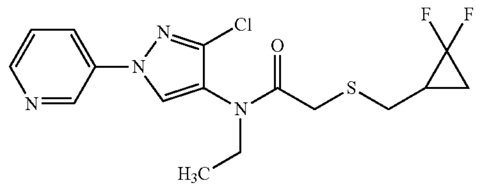 [SMILES: CCN(C(=O)CSCC1CC1(F)F)c1cn(-c2cccnc2)nc1Cl] | 102 |
| 822 | Opaque, Viscous Oil | 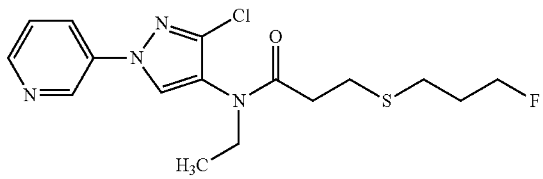 [SMILES: CCN(C(=O)CCSCCCF)c1cn(-c2cccnc2)nc1Cl] | 102 |
| 823 | Opaque Film | 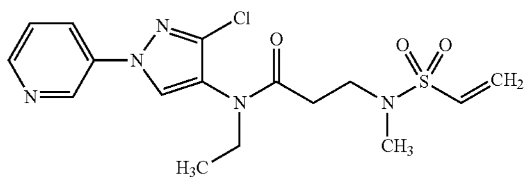 [SMILES: C=CS(=O)(=O)N(C)CCC(=O)N(CC)c1cn(-c2cccnc2)nc1Cl] | 149 |
| 824 | Opaque, Viscous Oil | 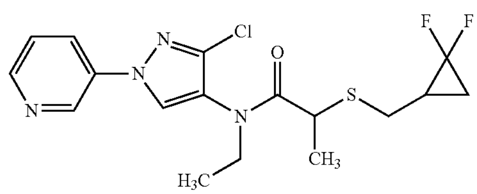 [SMILES: CCN(C(=O)C(C)SCC1CC1(F)F)c1cn(-c2cccnc2)nc1Cl] | 102 |
| 825 | Opaque, Viscous Oil | 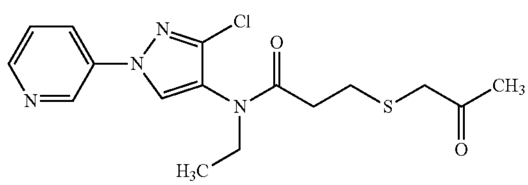 [SMILES: CCN(C(=O)CCSCC(C)=O)c1cn(-c2cccnc2)nc1Cl] | 96 |
| 826 | Yellow, Viscous Oil | 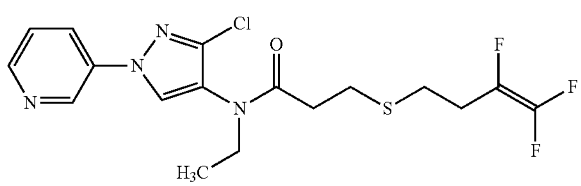 [SMILES: CCN(C(=O)CCSCCC(F)=C(F)F)c1cn(-c2cccnc2)nc1Cl] | 102 |
| 827 | Opaque, Viscous Oil | 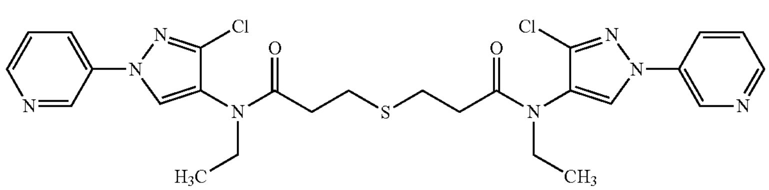 [SMILES: CCN(C(=O)CCSCCC(=O)N(CC)c1cn(-c2cccnc2)nc1Cl)c1cn(-c2cccnc2)nc1Cl] | 102 |
| 828 | Pale Yellow Oil | 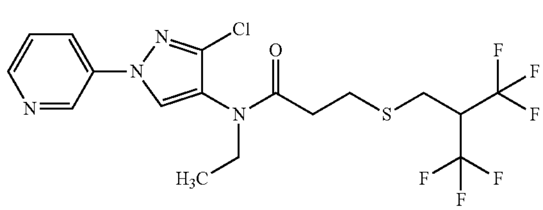 [SMILES: CCN(C(=O)CCSCC(C(F)(F)F)C(F)(F)F)c1cn(-c2cccnc2)nc1Cl] | 102 |

TABLE 1-continued
Compound number, appearance, and structure
| Compound No. | Appearance | Structure | Prepared as in Example: |
|---|---|---|---|
| 829 | Opaque, Viscous Oil | 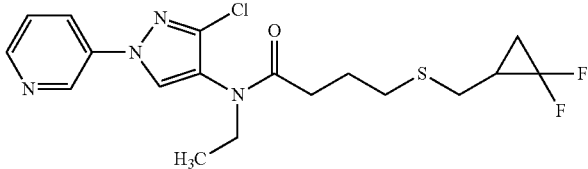 [SMILES: CCN(C(=O)CCCSCC1CC1(F)F)c1cn(-c2cccnc2)nc1Cl] | 12 |
| 830 | White Solid | 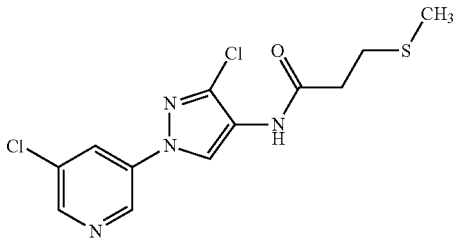 [SMILES: CSCCC(=O)Nc1cn(-c2cncc(Cl)c2)nc1Cl] | 11 |
| 831 | Off White Solid | 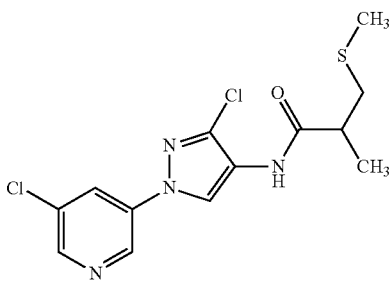 [SMILES: CSCC(C)C(=O)Nc1cn(-c2cncc(Cl)c2)nc1Cl] | 11 |
| 832 | Off White Solid | 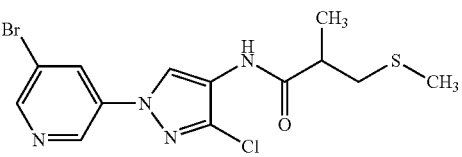 [SMILES: CSCC(C)C(=O)Nc1cn(-c2cncc(Br)c2)nc1Cl] | 11 |
| 833 | Off White Solid | 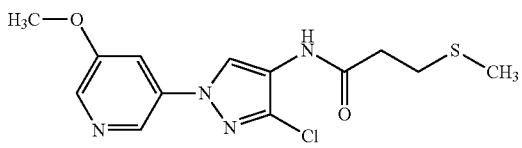 | 11 |
| 834 | Off White Solid | 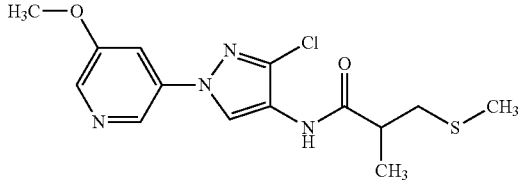 | 11 |
| 835 | Off White Solid | 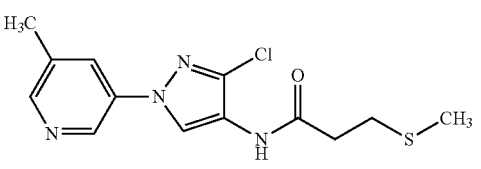 [SMILES: CSCCC(=O)Nc1cn(-c2cncc(C)c2)nc1Cl] | 11 |

TABLE 1-continued

Compound number, appearance, and structure

| Compound No. | Appearance | Structure | Prepared as in Example: |
|---|---|---|---|
| 836 | Off White Solid | 5-methylpyridin-3-yl linked to 3-chloro-pyrazol-1-yl, pyrazole-4-NH-C(=O)-CH(CH3)-CH2-S-CH3 | 11 |
| 837 | Yellow Liquid | 5-chloropyridin-3-yl linked to 3-chloro-pyrazol-1-yl, pyrazole-4-N(CH3)-C(=O)-CH2-CH2-S-CH3 | 79 |
| 838 | Yellow Liquid | 5-chloropyridin-3-yl linked to 3-chloro-pyrazol-1-yl, pyrazole-4-N(CH3)-C(=O)-CH(CH3)-CH2-S-CH3 | 79 |
| 839 | Yellow Liquid | 5-methoxypyridin-3-yl linked to 3-chloro-pyrazol-1-yl, pyrazole-4-N(CH3)-C(=O)-CH2-CH2-S-CH3 | 79 |
| 840 | Brown Gummy | 5-methoxypyridin-3-yl linked to 3-chloro-pyrazol-1-yl, pyrazole-4-N(CH3)-C(=O)-CH(CH3)-CH2-S-CH3 | 79 |
| 841 | Pale Yellow, Viscous Oil | pyridin-3-yl linked to 3-chloro-pyrazol-1-yl, pyrazole-4-N(CH2CH3)-C(=O)-CH2-CH2-S-CH2-CF2-CHF2 | 89 |
| 842 | White Solid | pyridin-3-yl linked to 3-chloro-pyrazol-1-yl, pyrazole-4-N(CH2CH3)-C(=O)-CH2-CH2-S-C(phenyl)3 | 12 |

TABLE 1-continued

Compound number, appearance, and structure

| Compound No. | Appearance | Structure | Prepared as in Example: |
|---|---|---|---|
| 843 | White Solid | 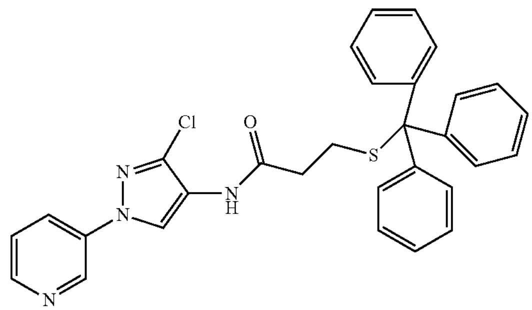 [SMILES: O=C(CCSC(c1ccccc1)(c1ccccc1)c1ccccc1)Nc1cn(-c2cccnc2)nc1Cl] | 42 |
| 844 | White Solid | 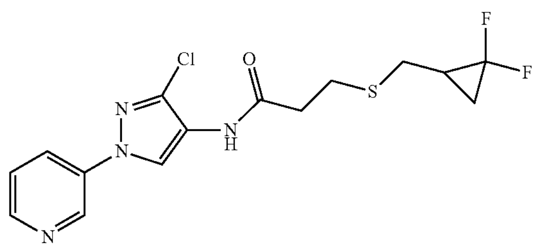 [SMILES: O=C(CCSCC1CC1(F)F)Nc1cn(-c2cccnc2)nc1Cl] | 42 |
| 845 | Colorless Oil | 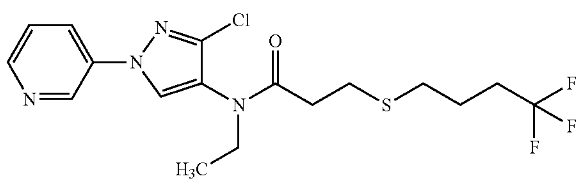 [SMILES: CCN(C(=O)CCSCCCC(F)(F)F)c1cn(-c2cccnc2)nc1Cl] | 89 |
| 846 | Opaque, Viscous Oil | 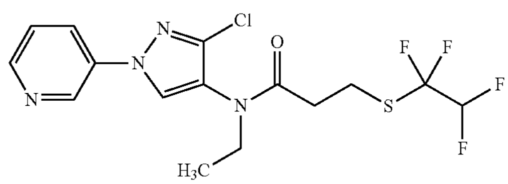 [SMILES: CCN(C(=O)CCSC(F)(F)C(F)F)c1cn(-c2cccnc2)nc1Cl] | 89 |
| 847 | Clear, Viscous Oil | 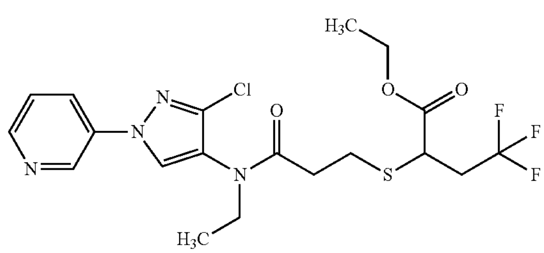 [SMILES: CCOC(=O)C(CC(F)(F)F)SCCC(=O)N(CC)c1cn(-c2cccnc2)nc1Cl] | 89 |
| 848 | White Solid | 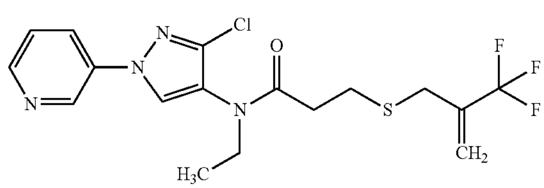 | 89 |

TABLE 1-continued

Compound number, appearance, and structure

| Compound No. | Appearance | Structure | Prepared as in Example: |
|---|---|---|---|
| 849 | Clear, Viscous Oil | (structure) | 89 |
| 850 | Opaque Film | (structure) | 89 |
| 851 | Light Yellow Oil | (structure) | 12 |
| 852 | Light Yellow Oil | (structure) | 12 |
| 853 | Light Yellow Oil | (structure) | 12 |
| 854 | Light Yellow Oil | (structure) | 12 |

TABLE 1-continued

Compound number, appearance, and structure

| Compound No. | Appearance | Structure | Prepared as in Example: |
|---|---|---|---|
| 855 | Light Yellow Oil | 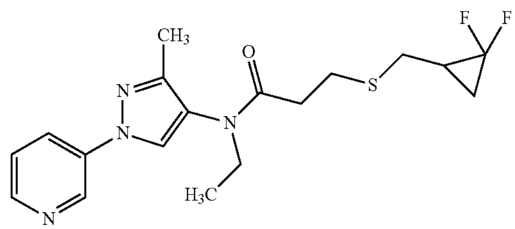 [SMILES: CCN(C(=O)CCSCC1CC1(F)F)c1cn(-c2cccnc2)nc1C] | 12 |
| 856 | Light Yellow Oil | 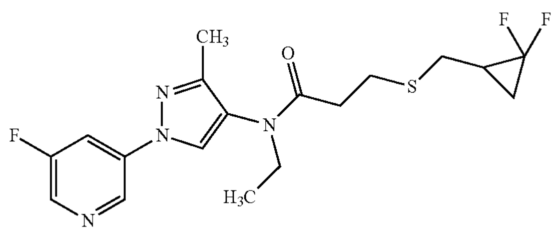 [SMILES: CCN(C(=O)CCSCC1CC1(F)F)c1cn(-c2cncc(F)c2)nc1C] | 12 |
| 857 | Brown Oil | 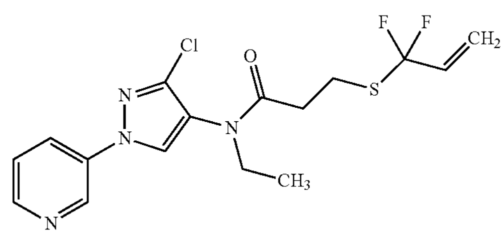 [SMILES: C=CC(F)(F)SCCC(=O)N(CC)c1cn(-c2cccnc2)nc1Cl] | 89 |
| 858 | Opaque, Viscous Oil | 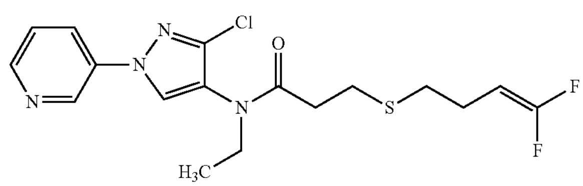 [SMILES: CCN(C(=O)CCSCCC=C(F)F)c1cn(-c2cccnc2)nc1Cl] | 89 |
| 859 | Clear, Viscous Oil | 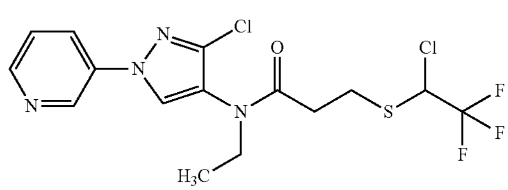 [SMILES: CCN(C(=O)CCSC(Cl)C(F)(F)F)c1cn(-c2cccnc2)nc1Cl] | 179 |
| 860 | Yellow Oil | 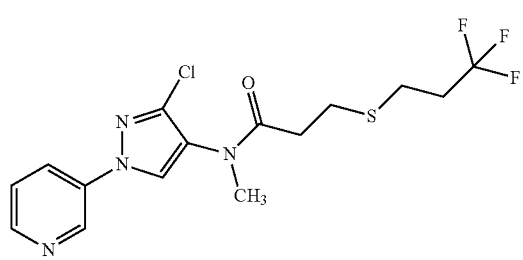 [SMILES: CN(C(=O)CCSCCC(F)(F)F)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 861 | Dark Oil | 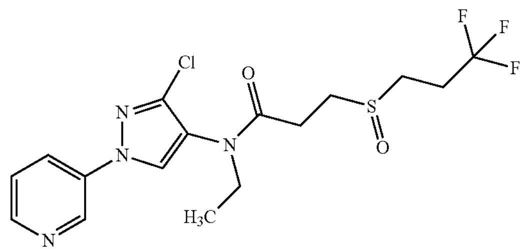 [SMILES: CCN(C(=O)CCS(=O)CCC(F)(F)F)c1cn(-c2cccnc2)nc1Cl] | 171 |
| 862 | Yellow Oil | 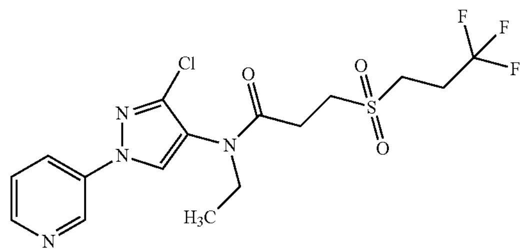 [SMILES: CCN(C(=O)CCS(=O)(=O)CCC(F)(F)F)c1cn(-c2cccnc2)nc1Cl] | 91 |
| 863 | Light Yellow Oil | 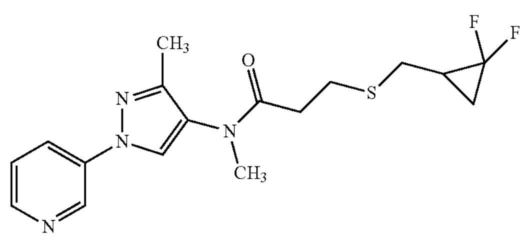 [SMILES: Cc1nn(-c2cccnc2)cc1N(C)C(=O)CCSCC1CC1(F)F] | 12 |
| 864 | Yellow Oil | 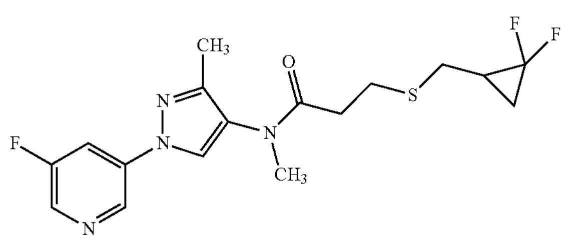 [SMILES: Cc1nn(-c2cncc(F)c2)cc1N(C)C(=O)CCSCC1CC1(F)F] | 12 |
| 865 | White Solid | 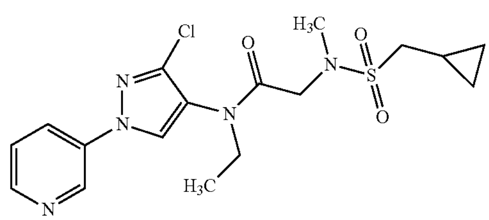 [SMILES: CCN(C(=O)CN(C)S(=O)(=O)CC1CC1)c1cn(-c2cccnc2)nc1Cl] | 170 |
| 866 | Clear Yellow Oil | 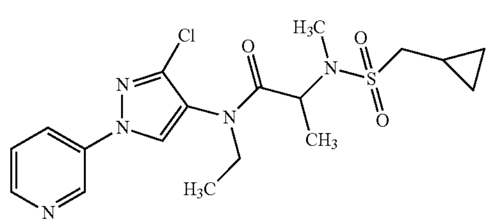 [SMILES: CCN(C(=O)C(C)N(C)S(=O)(=O)CC1CC1)c1cn(-c2cccnc2)nc1Cl] | 170 |

TABLE 1-continued

Compound number, appearance, and structure

| Compound No. | Appearance | Structure | Prepared as in Example: |
|---|---|---|---|
| 867 | Brown Oil | 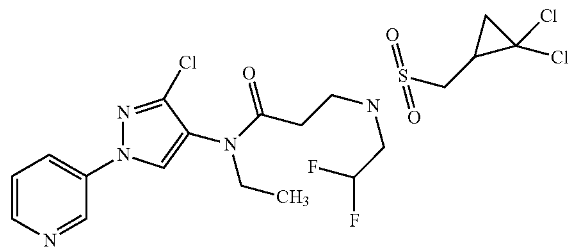 | 149 |
| 868 | Liquid | 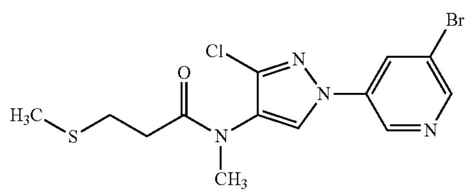 [SMILES: CSCCC(=O)N(C)c1cn(-c2cncc(Br)c2)nc1Cl] | 11 |
| 869 | Pale Brown Solid | 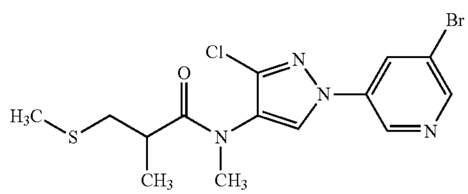 [SMILES: CSCC(C)C(=O)N(C)c1cn(-c2cncc(Br)c2)nc1Cl] | 11 |
| 870 | White Solid | 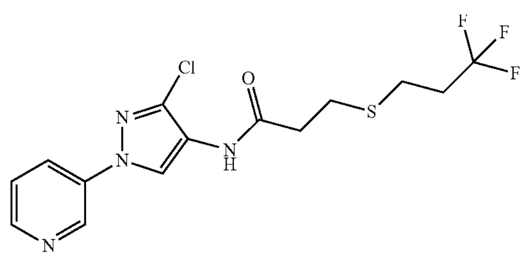 [SMILES: O=C(CCSCCC(F)(F)F)Nc1cn(-c2cccnc2)nc1Cl] | 12 |
| 871 | Yellow Oil | 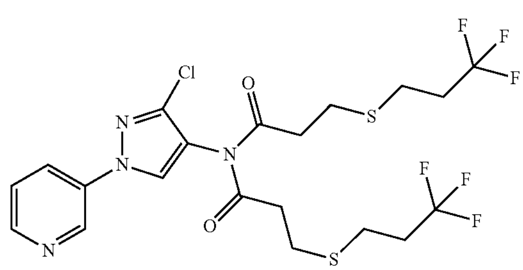 [SMILES: O=C(CCSCCC(F)(F)F)N(C(=O)CCSCCC(F)(F)F)c1cn(-c2cccnc2)nc1Cl] | 12 |
| 872 | White Solid | 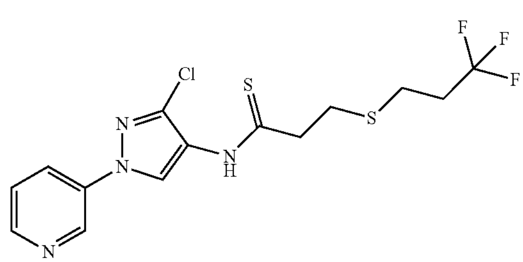 [SMILES: FC(F)(F)CCSCCC(=S)Nc1cn(-c2cccnc2)nc1Cl] | 49 |

TABLE 1-continued

Compound number, appearance, and structure

| Compound No. | Appearance | Structure | Prepared as in Example: |
|---|---|---|---|
| 873 | Viscous Clear Oil | 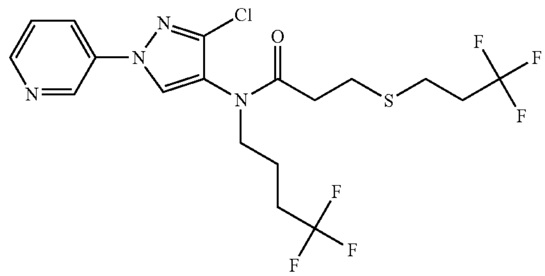 [SMILES: O=C(CCSCCC(F)(F)F)N(CCCC(F)(F)F)c1cn(-c2cccnc2)nc1Cl] | 12 |
| 874 | Clear Viscous Oil | 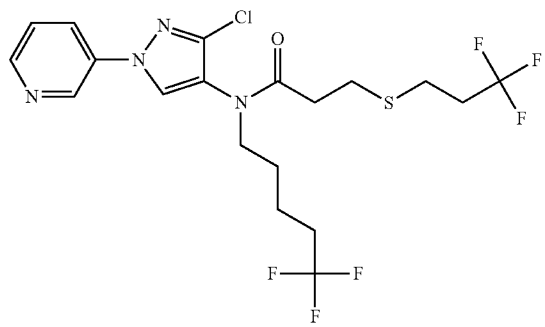 [SMILES: O=C(CCSCCC(F)(F)F)N(CCCCC(F)(F)F)c1cn(-c2cccnc2)nc1Cl] | 12 |
| 875 | White Foam | 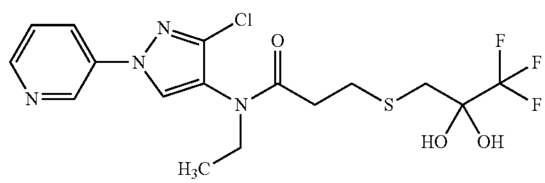 [SMILES: CCN(C(=O)CCSCC(O)(O)C(F)(F)F)c1cn(-c2cccnc2)nc1Cl] | 89 |
| 876 | White Cloudy Viscous Oil | 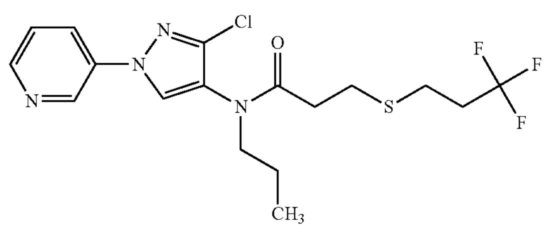 [SMILES: CCCN(C(=O)CCSCCC(F)(F)F)c1cn(-c2cccnc2)nc1Cl] | 12 |
| 877 | Orange Oil | 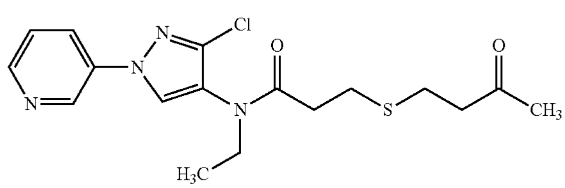 [SMILES: CCN(C(=O)CCSCCC(C)=O)c1cn(-c2cccnc2)nc1Cl] | 151 |
| 878 | White Solid | 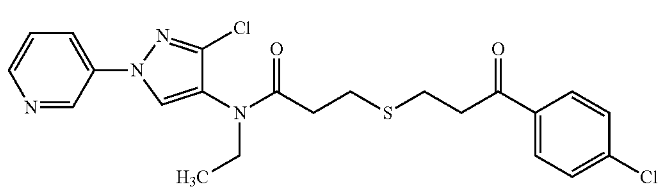 [SMILES: CCN(C(=O)CCSCCC(=O)c1ccc(Cl)cc1)c1cn(-c2cccnc2)nc1Cl] | 89 |

TABLE 1-continued

Compound number, appearance, and structure

| Compound No. | Appearance | Structure | Prepared as in Example: |
|---|---|---|---|
| 879 | Cloudy White Viscous Oil | 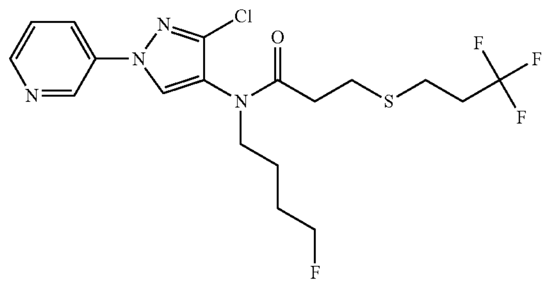 [SMILES: O=C(CCSCCC(F)(F)F)N(CCCCF)c1cn(-c2cccnc2)nc1Cl] | 12 |
| 880 | Clear Yellow Viscous Oil | 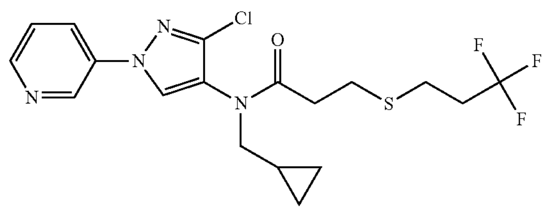 [SMILES: O=C(CCSCCC(F)(F)F)N(CC1CC1)c1cn(-c2cccnc2)nc1Cl] | 12 |
| 881 | Light Yellow Solid | 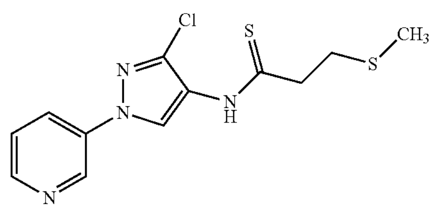 [SMILES: CSCCC(=S)Nc1cn(-c2cccnc2)nc1Cl] | 49 |
| 882 | Brown Oil | 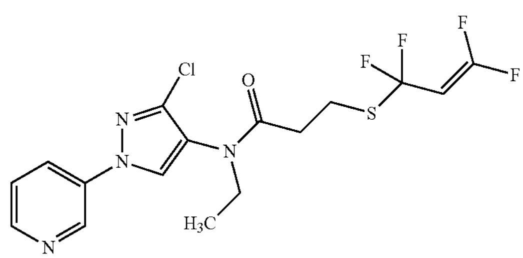 [SMILES: CCN(C(=O)CCSC(F)(F)C=C(F)F)c1cn(-c2cccnc2)nc1Cl] | 89 |
| 883 | Light Yellow Oil | 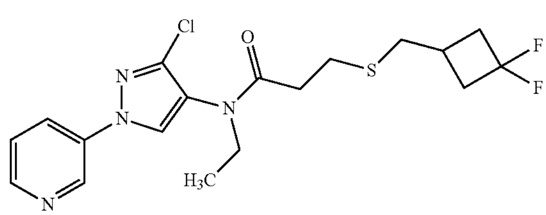 [SMILES: CCN(C(=O)CCSCC1CC(F)(F)C1)c1cn(-c2cccnc2)nc1Cl] | 89 |
| 884 | Yellow Viscous Oil | 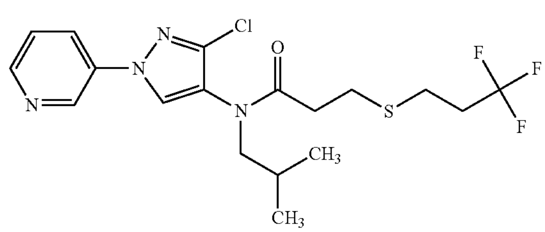 [SMILES: CC(C)CN(C(=O)CCSCCC(F)(F)F)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 885 | White Solid | 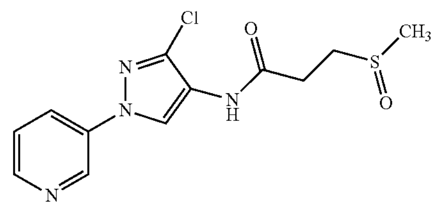 [SMILES: CS(=O)CCC(=O)Nc1cn(-c2cccnc2)nc1Cl] | 51 |
| 886 | White Solid | 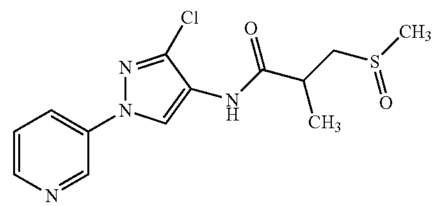 [SMILES: CC(CS(C)=O)C(=O)Nc1cn(-c2cccnc2)nc1Cl] | 51 |
| 887 | Yellow Viscous Oil | 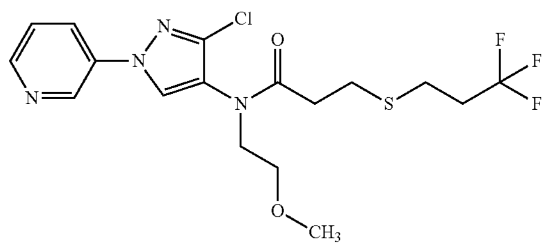 [SMILES: COCCN(C(=O)CCSCCC(F)(F)F)c1cn(-c2cccnc2)nc1Cl] | 12 |
| 888 | Clear, Viscous Oil | 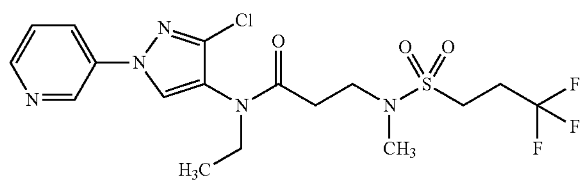 [SMILES: CCN(C(=O)CCN(C)S(=O)(=O)CCC(F)(F)F)c1cn(-c2cccnc2)nc1Cl] | 149 |
| 889 | Pale Yellow Oil | 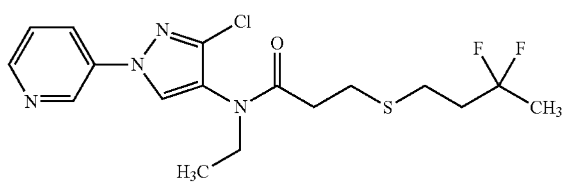 [SMILES: CCN(C(=O)CCSCCC(C)(F)F)c1cn(-c2cccnc2)nc1Cl] | 152 |
| 890 | Pale Yellow Oil | 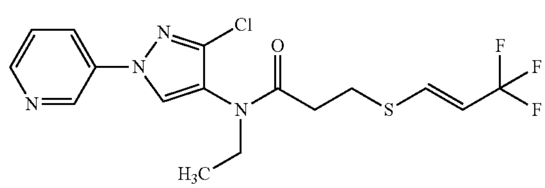 [SMILES: CCN(C(=O)CCS/C=C/C(F)(F)F)c1cn(-c2cccnc2)nc1Cl] | 145 |
| 891 | Yellow Viscous Oil | 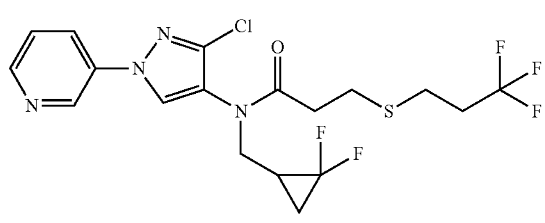 [SMILES: O=C(CCSCCC(F)(F)F)N(CC1CC1(F)F)c1cn(-c2cccnc2)nc1Cl] | 12 |

TABLE 1-continued

Compound number, appearance, and structure

| Compound No. | Appearance | Structure | Prepared as in Example: |
|---|---|---|---|
| 892 | Light Yellow Viscous Oil | 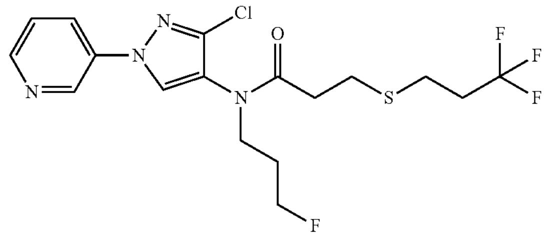 [SMILES: O=C(CCSCCC(F)(F)F)N(CCCF)c1cn(-c2cccnc2)nc1Cl] | 12 |
| 893 | Clear Oil | 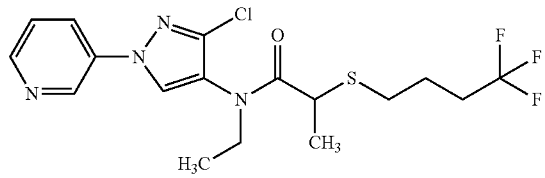 [SMILES: CCN(C(=O)C(C)SCCCC(F)(F)F)c1cn(-c2cccnc2)nc1Cl] | 102 |
| 894 | White Solid | 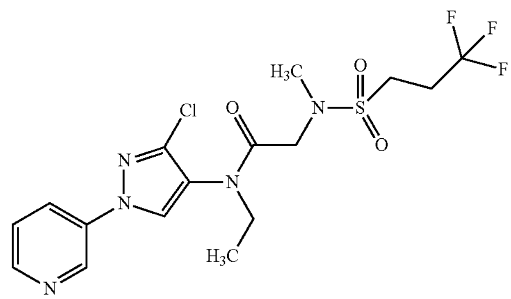 [SMILES: CCN(C(=O)CN(C)S(=O)(=O)CCC(F)(F)F)c1cn(-c2cccnc2)nc1Cl] | 170 |
| 895 | Clear Oil | 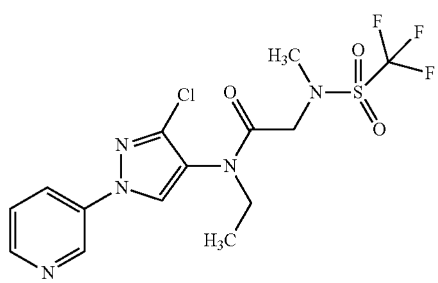 [SMILES: CCN(C(=O)CN(C)S(=O)(=O)C(F)(F)F)c1cn(-c2cccnc2)nc1Cl] | 170 |
| 896 | Yellow Viscous Oil | 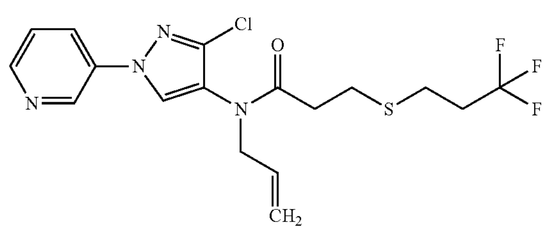 [SMILES: C=CCN(C(=O)CCSCCC(F)(F)F)c1cn(-c2cccnc2)nc1Cl] | 106 |
| 897 | Light Orange Viscous Oil | 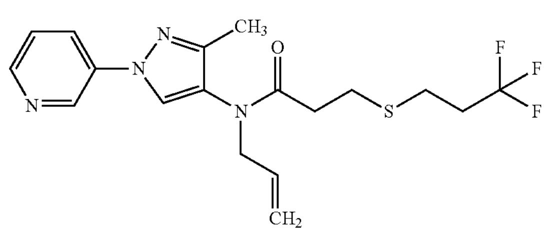 | 106 |

TABLE 1-continued

Compound number, appearance, and structure

| Compound No. | Appearance | Structure | Prepared as in Example: |
|---|---|---|---|
| 898 | Clear Oil | 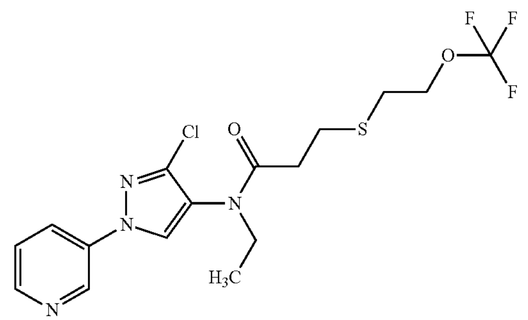 [SMILES: CCN(C(=O)CCSCCOC(F)(F)F)c1cn(-c2cccnc2)nc1Cl] | 89 |
| 899 | Pink Semi Solid | 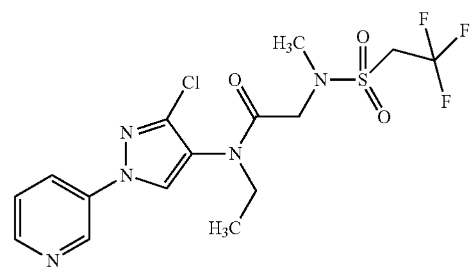 [SMILES: CCN(C(=O)CN(C)S(=O)(=O)CC(F)(F)F)c1cn(-c2cccnc2)nc1Cl] | 170 |
| 900 | Clear Viscous Oil | 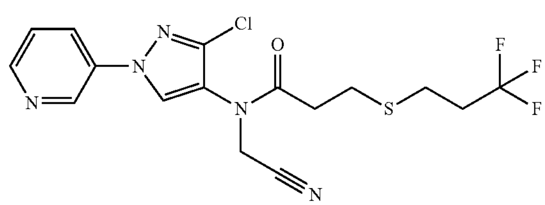 [SMILES: N#CCN(C(=O)CCSCCC(F)(F)F)c1cn(-c2cccnc2)nc1Cl] | 106 |
| 901 | Clear Oil | 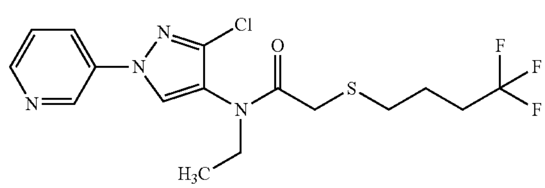 [SMILES: CCN(C(=O)CSCCCC(F)(F)F)c1cn(-c2cccnc2)nc1Cl] | 102 |
| 902 | Pale Orange Oil | 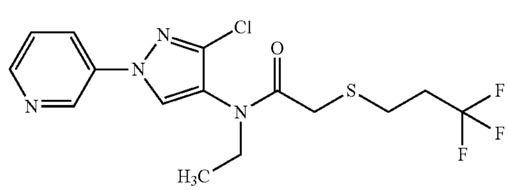 [SMILES: CCN(C(=O)CSCCC(F)(F)F)c1cn(-c2cccnc2)nc1Cl] | 102 |
| 903 | Clear Oil | 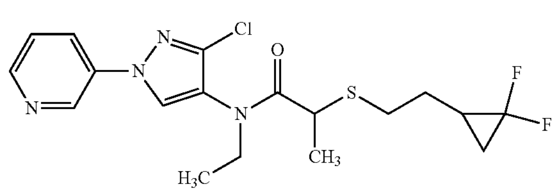 [SMILES: CCN(C(=O)C(C)SCCC1CC1(F)F)c1cn(-c2cccnc2)nc1Cl] | 102 |

TABLE 1-continued

Compound number, appearance, and structure

| Compound No. | Appearance | Structure | Prepared as in Example: |
|---|---|---|---|
| 904 | White Solid | 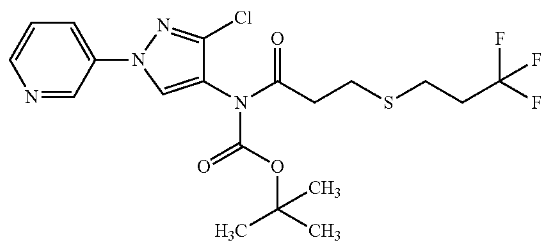 [SMILES: CC(C)(C)OC(=O)N(C(=O)CCSCCC(F)(F)F)c1cn(-c2cccnc2)nc1Cl] | 106 |
| 905 | Light Brown Oil | 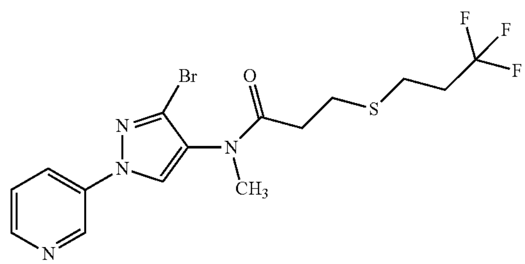 [SMILES: CN(C(=O)CCSCCC(F)(F)F)c1cn(-c2cccnc2)nc1Br] | 79 |
| 906 | Clear Colorless Oil | 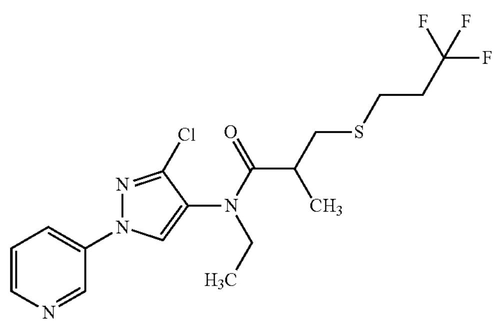 [SMILES: CCN(C(=O)C(C)CSCCC(F)(F)F)c1cn(-c2cccnc2)nc1Cl] | 89 |
| 907 | Clear Oil | 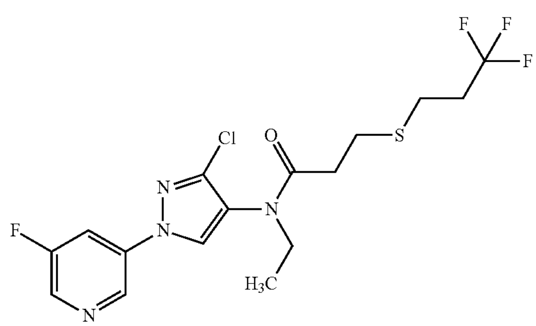 [SMILES: CCN(C(=O)CCSCCC(F)(F)F)c1cn(-c2cncc(F)c2)nc1Cl] | 11 |
| 908 | Light Yellow Oil | 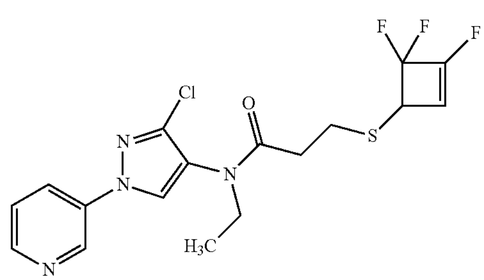 [SMILES: CCN(C(=O)CCSC1C=C(F)C1(F)F)c1cn(-c2cccnc2)nc1Cl] | 89 |

TABLE 1-continued
Compound number, appearance, and structure
| Compound No. | Appearance | Structure | Prepared as in Example: |
|---|---|---|---|
| 909 | Light Yellow Oil | 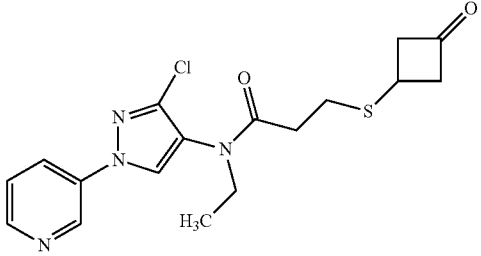 [SMILES: CCN(C(=O)CCSC1CC(=O)C1)c1cn(-c2cccnc2)nc1Cl] | 89 |
| 910 | Light Orange Oil | 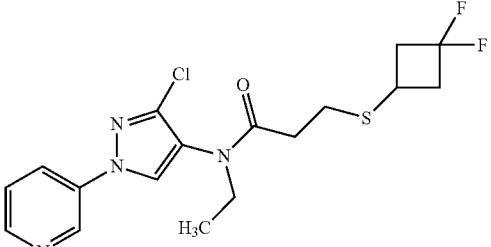 | 126 |
| 911 | | 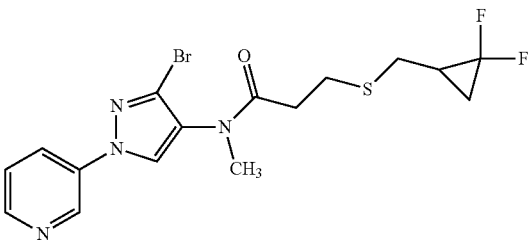 [SMILES: CN(C(=O)CCSCC1CC1(F)F)c1cn(-c2cccnc2)nc1Br] | 42 |
| 912 | Clear Oil | 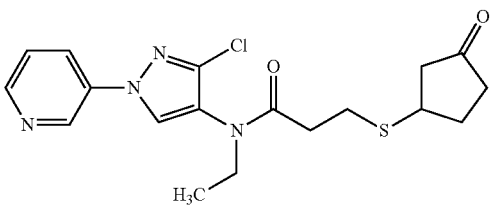 [SMILES: CCN(C(=O)CCSC1CCC(=O)C1)c1cn(-c2cccnc2)nc1Cl] | 151 |
| 913 | Clear Oil | 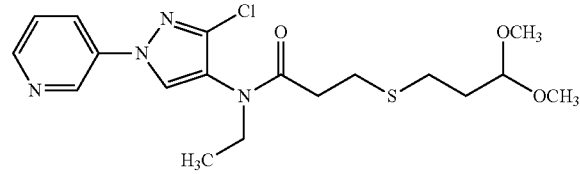 [SMILES: CCN(C(=O)CCSCCC(OC)OC)c1cn(-c2cccnc2)nc1Cl] | 89 |
| 914 | Light Yellow Oil | 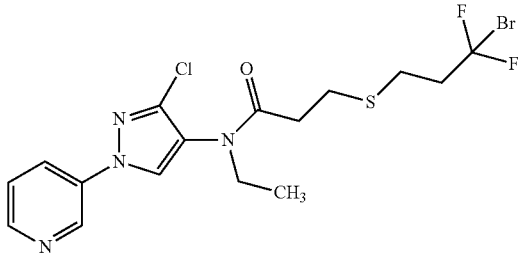 [SMILES: CCN(C(=O)CCSCCC(F)(F)Br)c1cn(-c2cccnc2)nc1Cl] | 89 |

TABLE 1-continued
Compound number, appearance, and structure
| Compound No. | Appearance | Structure | Prepared as in Example: |
|---|---|---|---|
| 915 | Clear Yellow Oil | 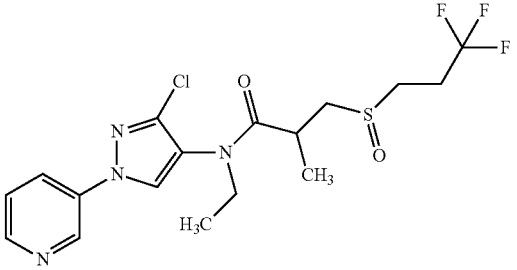 [SMILES: CCN(C(=O)C(C)CS(=O)CCC(F)(F)F)c1cn(-c2cccnc2)nc1Cl] | 51 |
| 916 | Colorless Gum | 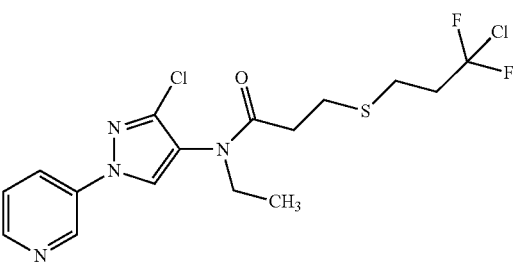 [SMILES: CCN(C(=O)CCSCCC(F)(F)Cl)c1cn(-c2cccnc2)nc1Cl] | 89 |
| 917 | Light Yellow Oil | 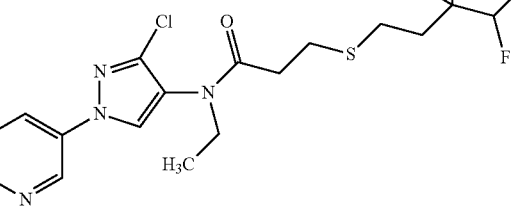 | 89 |
| 918 | Light Yellow Oil | 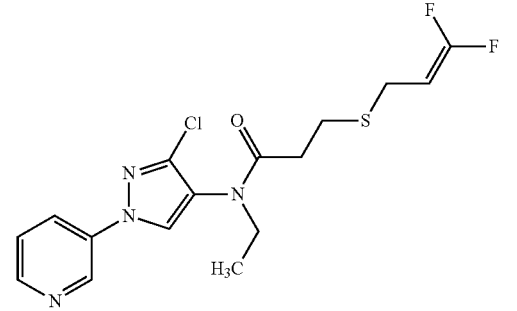 [SMILES: CCN(C(=O)CCSCC=C(F)F)c1cn(-c2cccnc2)nc1Cl] | 194 |
| 919 | Pale Yellow Oil | 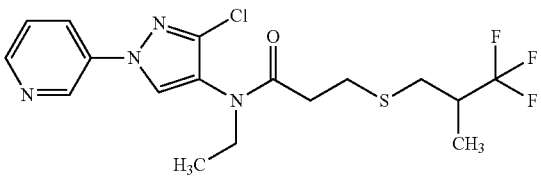 [SMILES: CCN(C(=O)CCSCC(C)C(F)(F)F)c1cn(-c2cccnc2)nc1Cl] | 143 |
| 920 | White Solid | 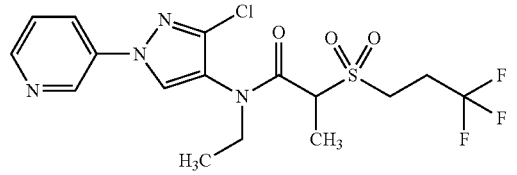 [SMILES: CCN(C(=O)C(C)S(=O)(=O)CCC(F)(F)F)c1cn(-c2cccnc2)nc1Cl] | 52 |

TABLE 1-continued

Compound number, appearance, and structure

| Compound No. | Appearance | Structure | Prepared as in Example: |
|---|---|---|---|
| 921 | Tacky, colorless solid | (structure) | 51 |
| 922 | Colorless Oil | (structure) | 43 |
| 923 | Clear Oil | (structure) | 89 |
| 924 | Clear Colorless Oil | (structure) | 51 |
| 925 | Viscous Slightly Yellow Oil | (structure) | 106 |
| 926 | Pale Yellow Oil | (structure) | 152 |

TABLE 1-continued

Compound number, appearance, and structure

| Compound No. | Appearance | Structure | Prepared as in Example: |
|---|---|---|---|
| 927 | Pale Yellow Oil | 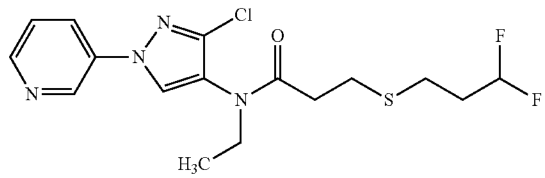 [SMILES: CCN(C(=O)CCSCCC(F)F)c1cn(-c2cccnc2)nc1Cl] | 153 |
| 928 | Yellow Viscous Oil | 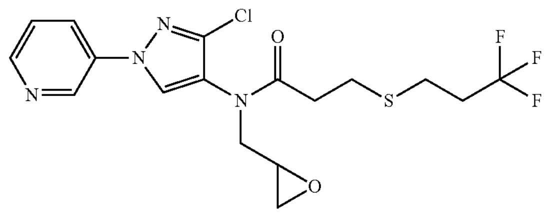 [SMILES: O=C(CCSCCC(F)(F)F)N(CC1CO1)c1cn(-c2cccnc2)nc1Cl] | 110 |
| 929 | Clear Oil | 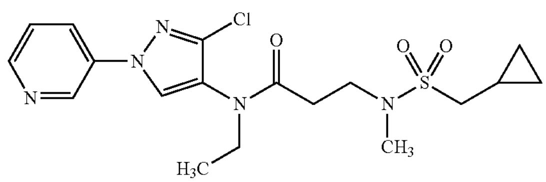 [SMILES: CCN(C(=O)CCN(C)S(=O)(=O)CC1CC1)c1cn(-c2cccnc2)nc1Cl] | 149 |
| 930 | Yellow Viscous Oil | 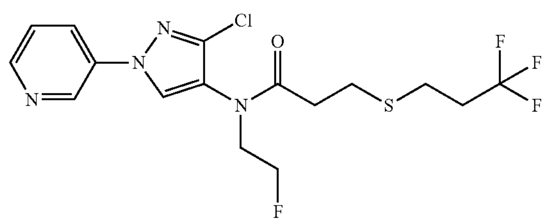 [SMILES: O=C(CCSCCC(F)(F)F)N(CCF)c1cn(-c2cccnc2)nc1Cl] | 106 |
| 931 | Slightly Yellow Oil | 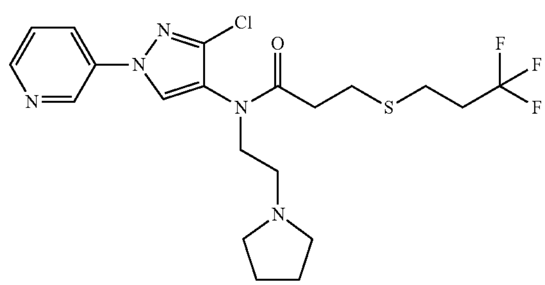 [SMILES: O=C(CCSCCC(F)(F)F)N(CCN1CCCC1)c1cn(-c2cccnc2)nc1Cl] | 106 |
| 932 | White Solid | 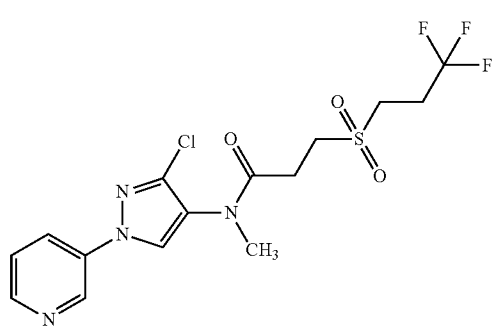 [SMILES: CN(C(=O)CCS(=O)(=O)CCC(F)(F)F)c1cn(-c2cccnc2)nc1Cl] | 91 |

TABLE 1-continued
Compound number, appearance, and structure
| Compound No. | Appearance | Structure | Prepared as in Example: |
|---|---|---|---|
| 933 | Clear Oil | 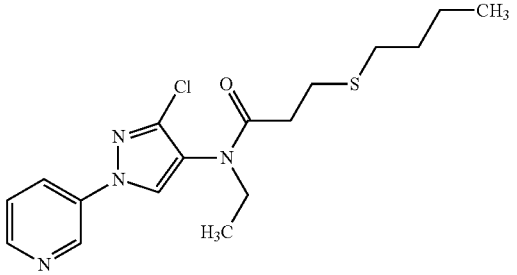 [SMILES: CCCCSCCC(=O)N(CC)c1cn(-c2cccnc2)nc1Cl] | 89 |
| 934 | Clear Yellow Oil | 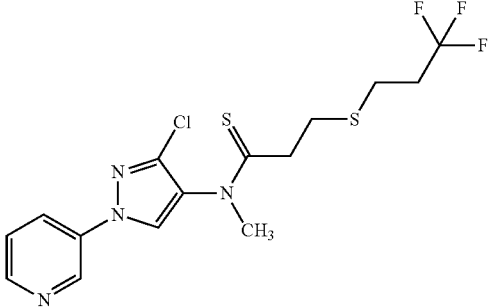 [SMILES: CN(C(=S)CCSCCC(F)(F)F)c1cn(-c2cccnc2)nc1Cl] | 49 |
| 935 | Clear Yellow Oil | 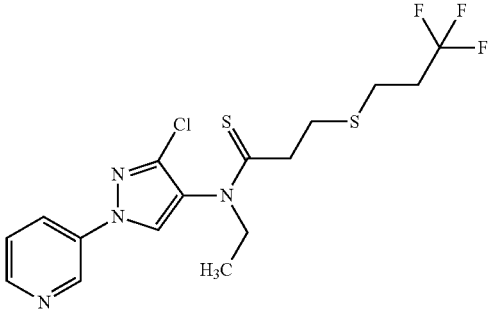 [SMILES: CCN(C(=S)CCSCCC(F)(F)F)c1cn(-c2cccnc2)nc1Cl] | 49 |
| 936 | Pale Red Oil | 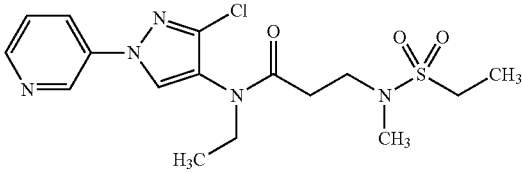 [SMILES: CCN(C(=O)CCN(C)S(=O)(=O)CC)c1cn(-c2cccnc2)nc1Cl] | 149 |
| 937 | Opaque Film | 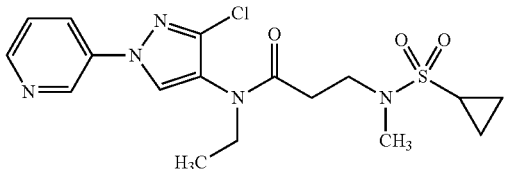 | 149 |
| 938 | Opaque Film | 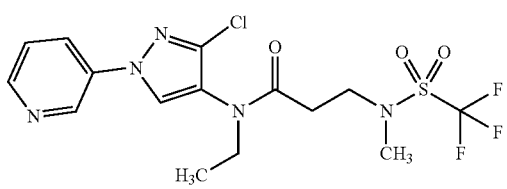 [SMILES: CCN(C(=O)CCN(C)S(=O)(=O)C(F)(F)F)c1cn(-c2cccnc2)nc1Cl] | 149 |

TABLE 1-continued

Compound number, appearance, and structure

| Compound No. | Appearance | Structure | Prepared as in Example: |
|---|---|---|---|
| 939 | Clear Oil | (3-pyridyl)-pyrazole(Cl)-N(Et)-C(O)-CH2CH2-N(CH3)-SO2-(4-CF3-phenyl) | 149 |
| 940 | Clear Oil | (3-pyridyl)-pyrazole(Cl)-N(Et)-C(O)-CH2CH2-N(CH3)-SO2-(2-Cl-phenyl) | 149 |
| 941 | Clear Oil | (3-pyridyl)-pyrazole(Cl)-N(Et)-C(O)-CH2CH2-N(CH3)-SO2-(3-CN-phenyl) | 149 |
| 942 | Clear Oil | (3-pyridyl)-pyrazole(Cl)-N(Et)-C(O)-CH2CH2-N(CH3)-SO2-(3-NO2-phenyl) | 149 |
| 943 | Clear Oil | (3-pyridyl)-pyrazole(Cl)-N(Et)-C(O)-CH2CH2-N(CH3)-SO2-CH2-(3-CF3-phenyl) | 149 |
| 944 | Opaque Oil | (3-pyridyl)-pyrazole(Cl)-N(Et)-C(O)-CH2CH2-N(CH3)-SO2-(1-methylimidazol-4-yl) | 149 |
| 945 | White Solid | (3-pyridyl)-pyrazole(Cl)-N(Et)-C(O)-CH2CH2-N(CH3)-SO2-(4-methylsulfonyl-phenyl) | 149 |

TABLE 1-continued

Compound number, appearance, and structure

| Compound No. | Appearance | Structure | Prepared as in Example: |
|---|---|---|---|
| 946 | Clear Glass | 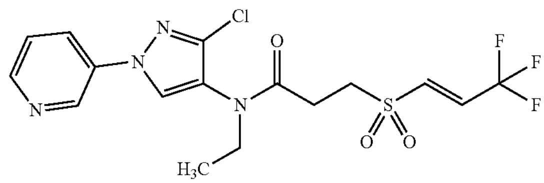 [SMILES: CCN(C(=O)CCS(=O)(=O)/C=C/C(F)(F)F)c1cn(-c2cccnc2)nc1Cl] | 52 |
| 947 | Clear Glass | 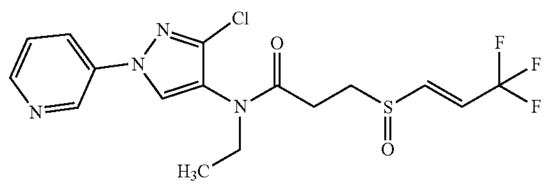 [SMILES: CCN(C(=O)CCS(=O)/C=C/C(F)(F)F)c1cn(-c2cccnc2)nc1Cl] | 51 |
| 948 | Yellow Oil | 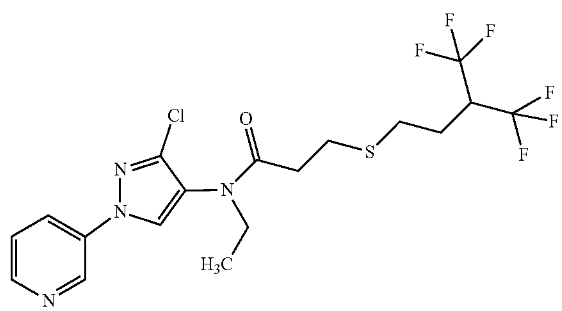 [SMILES: CCN(C(=O)CCSCCC(C(F)(F)F)C(F)(F)F)c1cn(-c2cccnc2)nc1Cl] | 89 |
| 949 | Colorless Oil | 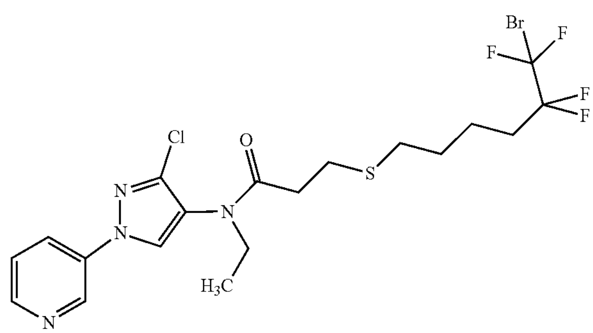 [SMILES: CCN(C(=O)CCSCCCCC(F)(F)C(F)(F)Br)c1cn(-c2cccnc2)nc1Cl] | 89 |
| 950 | Yellow Oil | 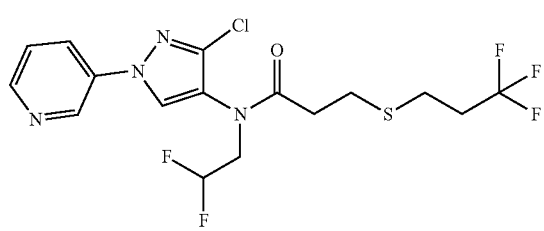 [SMILES: O=C(CCSCCC(F)(F)F)N(CC(F)F)c1cn(-c2cccnc2)nc1Cl] | 106 |

TABLE 1-continued
Compound number, appearance, and structure
| Compound No. | Appearance | Structure | Prepared as in Example: |
|---|---|---|---|
| 951 | Light Yellow Oil | 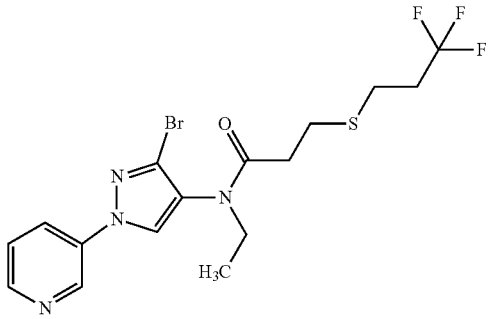 [SMILES: CCN(C(=O)CCSCCC(F)(F)F)c1cn(-c2cccnc2)nc1Br] | 79 |
| 952 | Orange Oil | 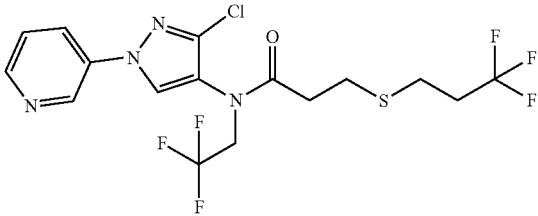 [SMILES: O=C(CCSCCC(F)(F)F)N(CC(F)(F)F)c1cn(-c2cccnc2)nc1Cl] | 106 |
| 953 | Yellow Oil | 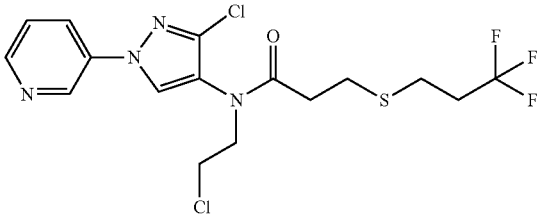 [SMILES: O=C(CCSCCC(F)(F)F)N(CCCl)c1cn(-c2cccnc2)nc1Cl] | 106 |
| 954 | Yellow Oil | 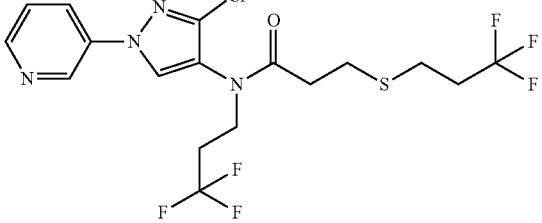 | 106 |
| 955 | White Solid | 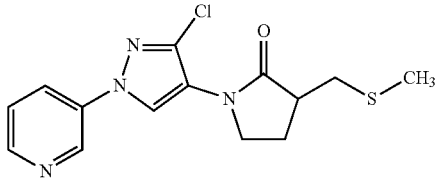 [SMILES: CSCC1CCN(c2cn(-c3cccnc3)nc2Cl)C1=O] | 132 |
| 956 | White Solid | 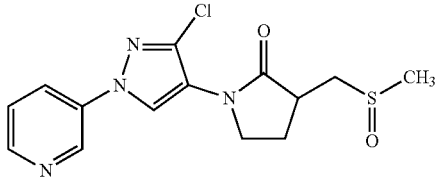 [SMILES: CS(=O)CC1CCN(c2cn(-c3cccnc3)nc2Cl)C1=O] | 50 |

TABLE 1-continued

Compound number, appearance, and structure

| Compound No. | Appearance | Structure | Prepared as in Example: |
|---|---|---|---|
| 957 | Colorless Oil | 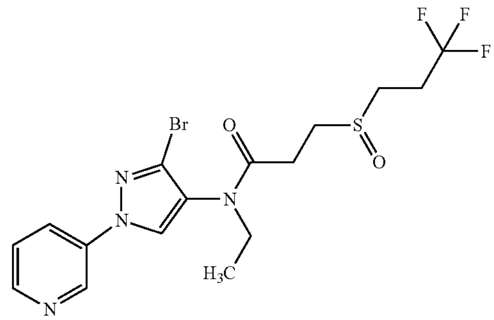 [SMILES: CCN(C(=O)CCS(=O)CCC(F)(F)F)c1cn(-c2cccnc2)nc1Br] | 51 |
| 958 | White Solid | 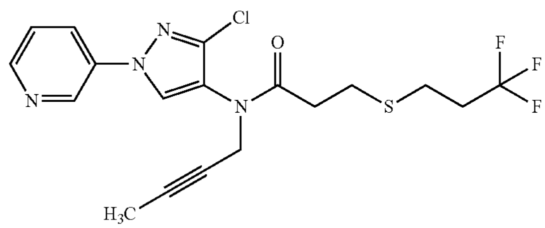 [SMILES: CC#CCN(C(=O)CCSCCC(F)(F)F)c1cn(-c2cccnc2)nc1Cl] | 106 |
| 959 | Yellow Oil | 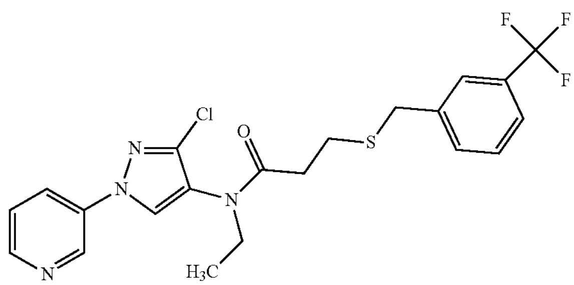 [SMILES: CCN(C(=O)CCSCc1cccc(C(F)(F)F)c1)c1cn(-c2cccnc2)nc1Cl] | 89 |
| 960 | Clear Yellow Oil | 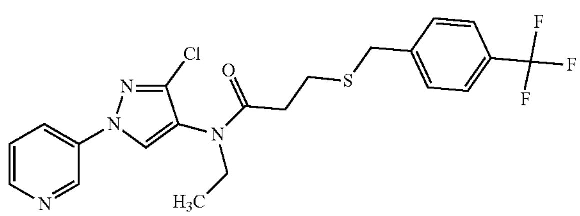 [SMILES: CCN(C(=O)CCSCc1ccc(C(F)(F)F)cc1)c1cn(-c2cccnc2)nc1Cl] | 89 |
| 961 | Clear Yellow Oil | 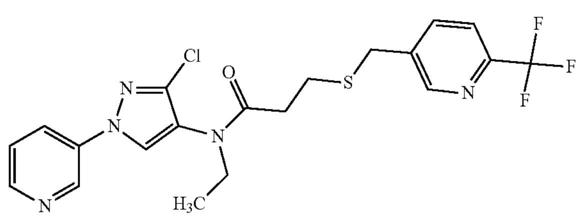 [SMILES: CCN(C(=O)CCSCc1ccc(C(F)(F)F)nc1)c1cn(-c2cccnc2)nc1Cl] | 89 |
| 962 | Colorless Oil | 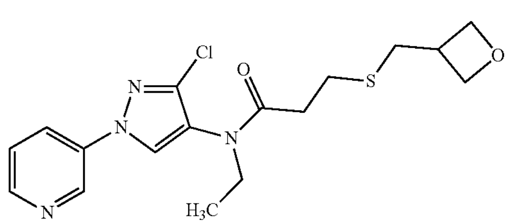 [SMILES: CCN(C(=O)CCSCC1COC1)c1cn(-c2cccnc2)nc1Cl] | 89 |

TABLE 1-continued

Compound number, appearance, and structure

| Compound No. | Appearance | Structure | Prepared as in Example: |
|---|---|---|---|
| 963 | Light Yellow Oil | 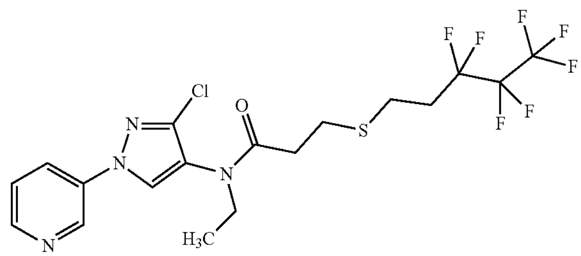 [SMILES: CCN(C(=O)CCSCCC(F)(F)C(F)(F)C(F)(F)F)c1cn(-c2cccnc2)nc1Cl] | 89 |
| 964 | Opaque Oil | 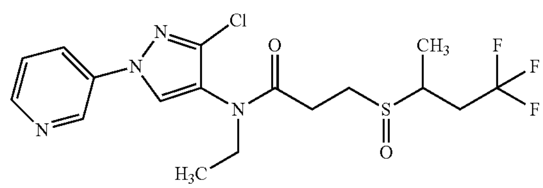 [SMILES: CCN(C(=O)CCS(=O)C(C)CC(F)(F)F)c1cn(-c2cccnc2)nc1Cl] | 51 |
| 965 | Off White Gum | 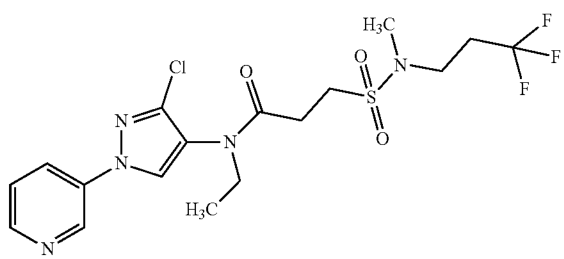 [SMILES: CCN(C(=O)CCS(=O)(=O)N(C)CCC(F)(F)F)c1cn(-c2cccnc2)nc1Cl] | 178 |
| 966 | Colorless Oil | 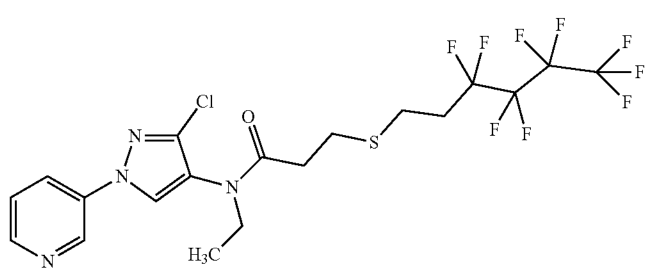 [SMILES: CCN(C(=O)CCSCCC(F)(F)C(F)(F)C(F)(F)C(F)(F)F)c1cn(-c2cccnc2)nc1Cl] | 89 |
| 967 | Colorless Oil | 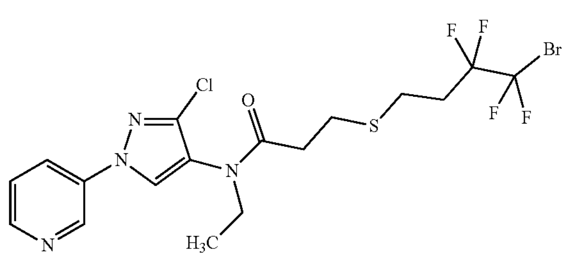 [SMILES: CCN(C(=O)CCSCCC(F)(F)C(F)(F)Br)c1cn(-c2cccnc2)nc1Cl] | 89 |
| 968 | Clear Viscous Oil | 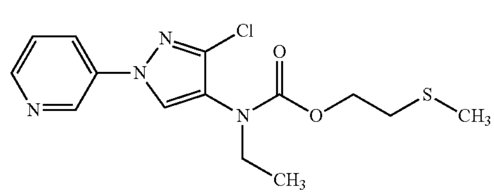 [SMILES: CCN(C(=O)OCCSC)c1cn(-c2cccnc2)nc1Cl] | 115 |

TABLE 1-continued
Compound number, appearance, and structure
| Compound No. | Appearance | Structure | Prepared as in Example: |
|---|---|---|---|
| 969 | Clear Yellow Oil | 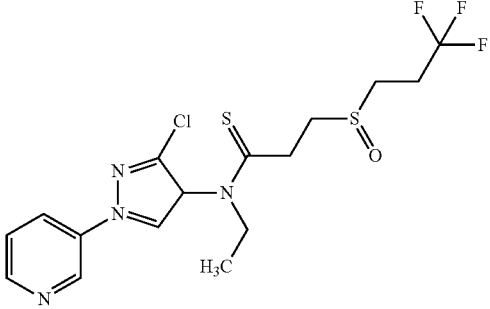 | 51 |
| 970 | Cloudy White Oil | 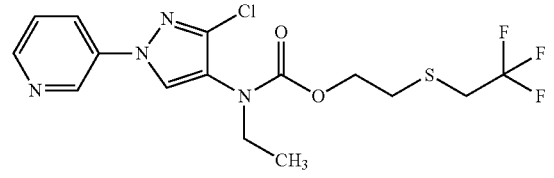 [SMILES: CCN(C(=O)OCCSCC(F)(F)F)c1cn(-c2cccnc2)nc1Cl] | 115 |
| 971 | Opaque Viscous Oil | 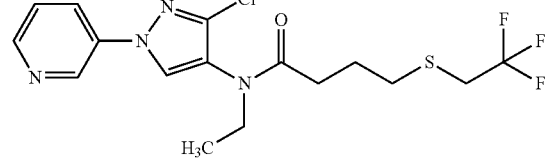 | 12 |
| 972 | Light Yellow Clear Viscous Oil | 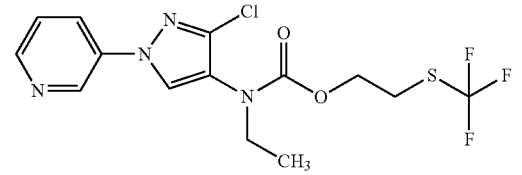 [SMILES: CCN(C(=O)OCCSC(F)(F)F)c1cn(-c2cccnc2)nc1Cl] | 115 |
| 973 | Clear Colorless Oil | 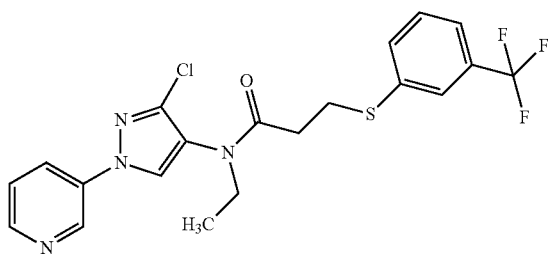 [SMILES: CCN(C(=O)CCSc1cccc(C(F)(F)F)c1)c1cn(-c2cccnc2)nc1Cl] | 12 |
| 974 | Off-White Solid | 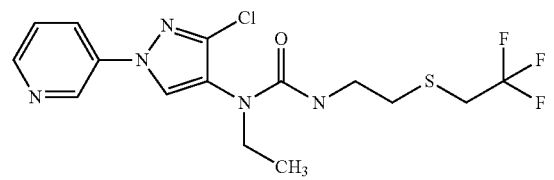 [SMILES: CCN(C(=O)NCCSCC(F)(F)F)c1cn(-c2cccnc2)nc1Cl] | 115 |

TABLE 1-continued

Compound number, appearance, and structure

| Compound No. | Appearance | Structure | Prepared as in Example: |
|---|---|---|---|
| 975 | Colorless Oil | 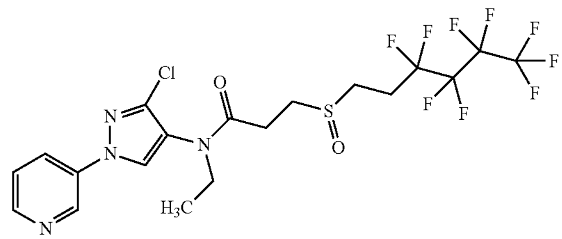 [SMILES: CCN(C(=O)CCS(=O)CCC(F)(F)C(F)(F)C(F)(F)C(F)(F)F)c1cn(-c2cccnc2)nc1Cl] | 50 |
| 976 | Colorless Oil | 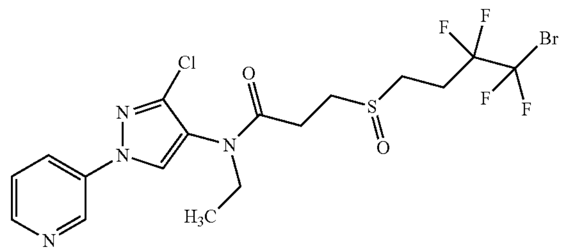 [SMILES: CCN(C(=O)CCS(=O)CCC(F)(F)C(F)(F)Br)c1cn(-c2cccnc2)nc1Cl] | 50 |
| 977 | Slightly Orange Clear Viscous Oil | 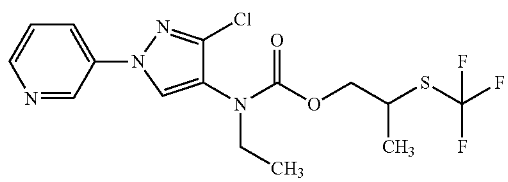 [SMILES: CCN(C(=O)OCC(C)SC(F)(F)F)c1cn(-c2cccnc2)nc1Cl] | 115 |
| 978 | Pale Yellow, Viscous Oil | 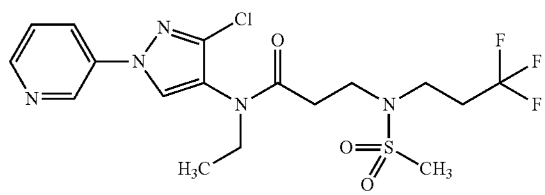 [SMILES: CCN(C(=O)CCN(CCC(F)(F)F)S(C)(=O)=O)c1cn(-c2cccnc2)nc1Cl] | 149 |
| 979 | Slightly Yellow Clear Viscous Semi-Solid | 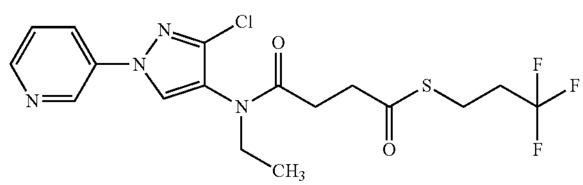 | 113 |
| 980 | Colorless Oil | 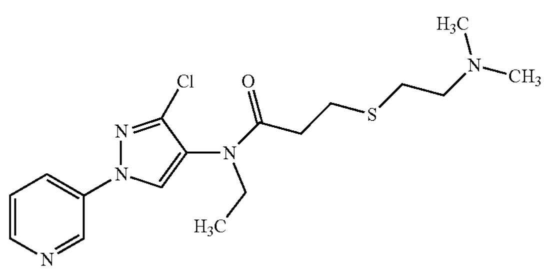 [SMILES: CCN(C(=O)CCSCCN(C)C)c1cn(-c2cccnc2)nc1Cl] | 89 |
| 981 | Opaque, Viscous Oil | 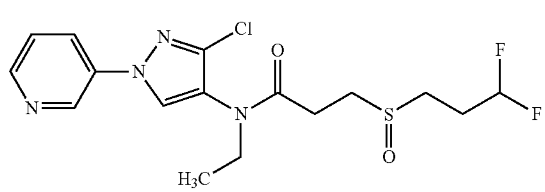 [SMILES: CCN(C(=O)CCS(=O)CCC(F)F)c1cn(-c2cccnc2)nc1Cl] | 51 |

TABLE 1-continued

Compound number, appearance, and structure

| Compound No. | Appearance | Structure | Prepared as in Example: |
|---|---|---|---|
| 982 | Clear Viscous Oil | 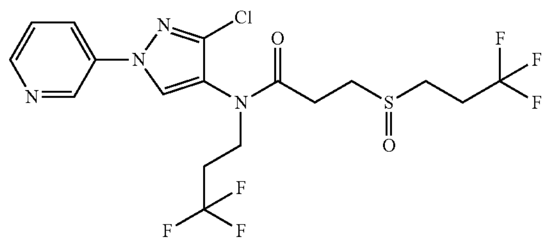 [SMILES: O=C(CCS(=O)CCC(F)(F)F)N(CCC(F)(F)F)c1cn(-c2cccnc2)nc1Cl] | 83 |
| 983 | Dark Orange Oil | 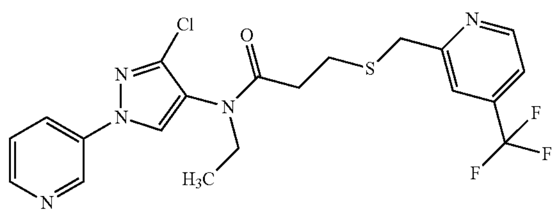 [SMILES: CCN(C(=O)CCSCc1cc(C(F)(F)F)ccn1)c1cn(-c2cccnc2)nc1Cl] | 89 |
| 984 | Light Yellow Solid | 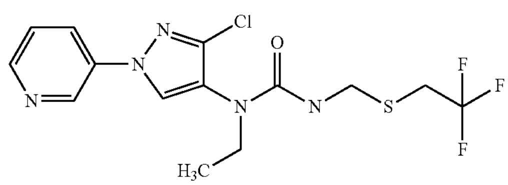 [SMILES: CCN(C(=O)NCSCC(F)(F)F)c1cn(-c2cccnc2)nc1Cl] | 116 |
| 985 | Colorless Oil | 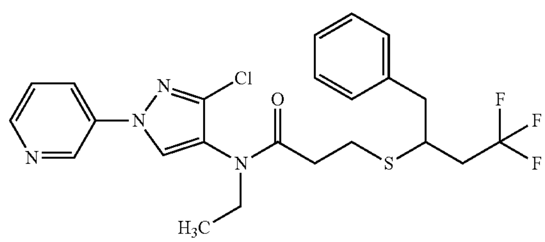 [SMILES: CCN(C(=O)CCSC(Cc1ccccc1)CC(F)(F)F)c1cn(-c2cccnc2)nc1Cl] | 156 |
| 986 | Colorless Oil | 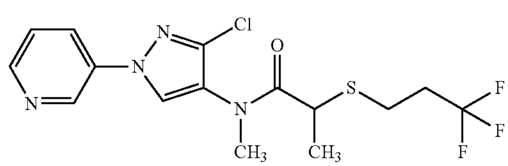 [SMILES: CC(SCCC(F)(F)F)C(=O)N(C)c1cn(-c2cccnc2)nc1Cl] | 102 |
| 987 | Clear Oil | 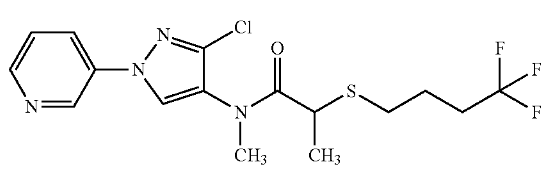 [SMILES: CC(SCCCC(F)(F)F)C(=O)N(C)c1cn(-c2cccnc2)nc1Cl] | 102 |
| 988 | White Solid | 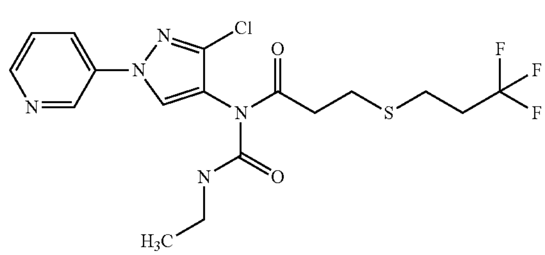 [SMILES: CCNC(=O)N(C(=O)CCSCCC(F)(F)F)c1cn(-c2cccnc2)nc1Cl] | 111 |

TABLE 1-continued

Compound number, appearance, and structure

| Compound No. | Appearance | Structure | Prepared as in Example: |
|---|---|---|---|
| 989 | Light Brown Solid | 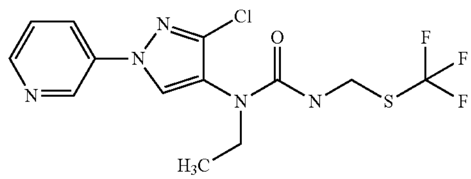 [SMILES: CCN(C(=O)NCSC(F)(F)F)c1cn(-c2cccnc2)nc1Cl] | 116 |
| 990 | Light Brown Solid | 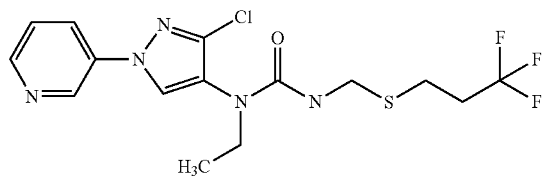 [SMILES: CCN(C(=O)NCSCCC(F)(F)F)c1cn(-c2cccnc2)nc1Cl] | 116 |
| 991 | Yellow Oil | 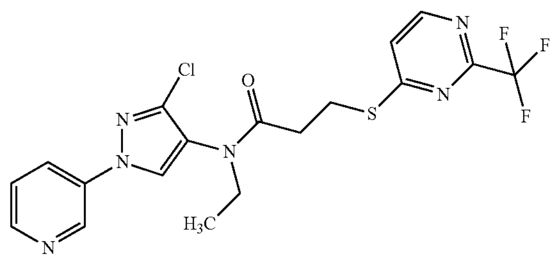 [SMILES: CCN(C(=O)CCSc1ccnc(C(F)(F)F)n1)c1cn(-c2cccnc2)nc1Cl] | 89 |
| 992 | White Solid | 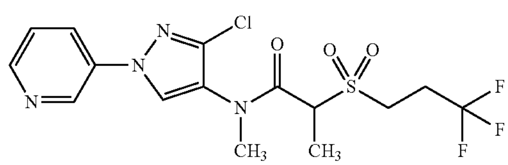 [SMILES: CC(C(=O)N(C)c1cn(-c2cccnc2)nc1Cl)S(=O)(=O)CCC(F)(F)F] | 52 |
| 993 | White Solid | 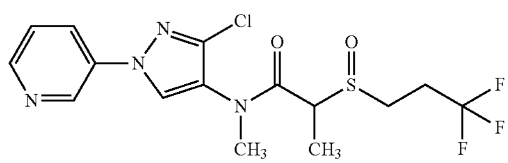 [SMILES: CC(C(=O)N(C)c1cn(-c2cccnc2)nc1Cl)S(=O)CCC(F)(F)F] | 51 |
| 994 | White Solid | 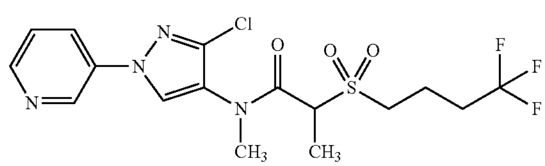 [SMILES: CC(C(=O)N(C)c1cn(-c2cccnc2)nc1Cl)S(=O)(=O)CCCC(F)(F)F] | 52 |
| 995 | White Solid | 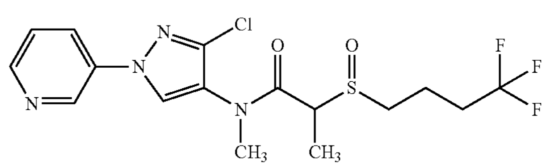 [SMILES: CC(C(=O)N(C)c1cn(-c2cccnc2)nc1Cl)S(=O)CCCC(F)(F)F] | 51 |
| 996 | Light Yellow Semi-Solid | 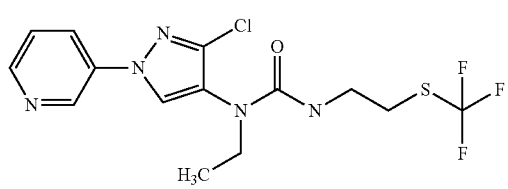 [SMILES: CCN(C(=O)NCCSC(F)(F)F)c1cn(-c2cccnc2)nc1Cl] | 116 |

TABLE 1-continued

Compound number, appearance, and structure

| Compound No. | Appearance | Structure | Prepared as in Example: |
|---|---|---|---|
| 997 | Light Yellow Semi-Solid | 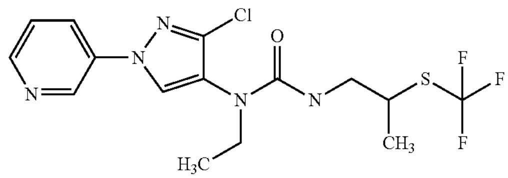 [SMILES: CCN(C(=O)NCC(C)SC(F)(F)F)c1cn(-c2cccnc2)nc1Cl] | 116 |
| 998 | Yellow Oil | 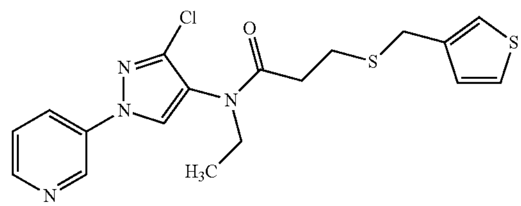 [SMILES: CCN(C(=O)CCSCc1ccsc1)c1cn(-c2cccnc2)nc1Cl] | 89 |
| 999 | Light Yellow Viscous Oil | 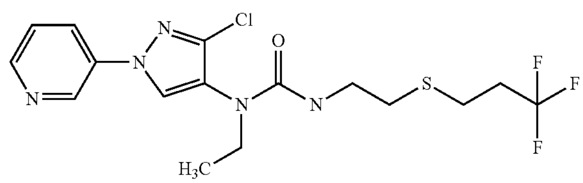 [SMILES: CCN(C(=O)NCCSCCC(F)(F)F)c1cn(-c2cccnc2)nc1Cl] | 116 |
| 1000 | Clear Oil | 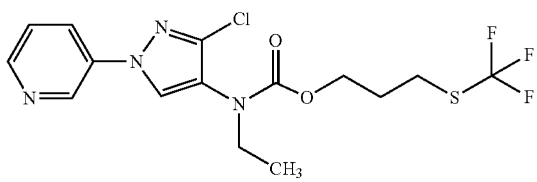 [SMILES: CCN(C(=O)OCCCSC(F)(F)F)c1cn(-c2cccnc2)nc1Cl] | 115 |
| 1001 | Colorless Gum | 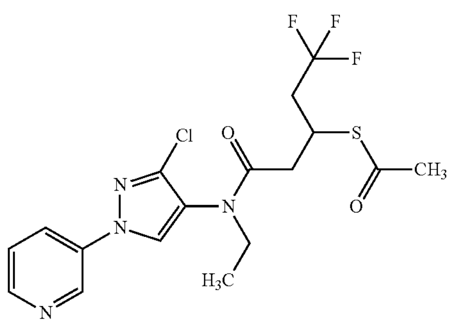 [SMILES: CCN(C(=O)CC(CC(F)(F)F)SC(C)=O)c1cn(-c2cccnc2)nc1Cl] | 89 |
| 1002 | Colorless Oil | 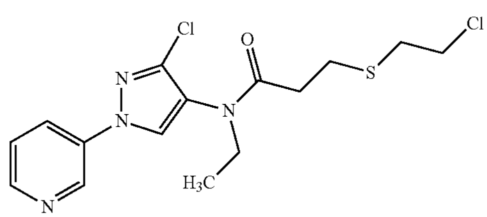 [SMILES: CCN(C(=O)CCSCCCl)c1cn(-c2cccnc2)nc1Cl] | 180 |
| 1003 | White Semi-Solid | 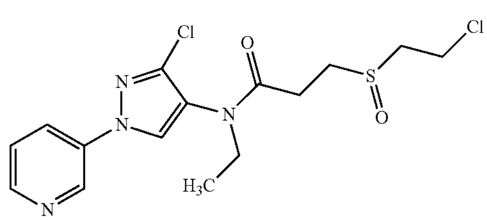 [SMILES: CCN(C(=O)CCS(=O)CCCl)c1cn(-c2cccnc2)nc1Cl] | 50 |

TABLE 1-continued

Compound number, appearance, and structure

| Compound No. | Appearance | Structure | Prepared as in Example: |
|---|---|---|---|
| 1004 | Brown Oil | 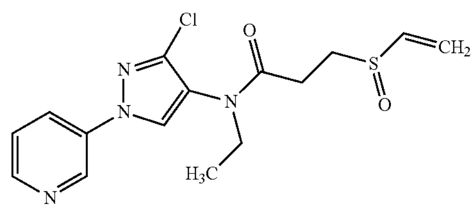 [SMILES: C=CS(=O)CCC(=O)N(CC)c1cn(-c2cccnc2)nc1Cl] | 127 |
| 1005 | Light Yellow Gum | 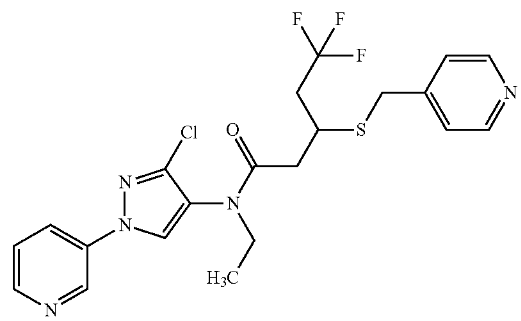 [SMILES: CCN(C(=O)CC(CC(F)(F)F)SCc1ccncc1)c1cn(-c2cccnc2)nc1Cl] | 89 |
| 1006 | Opaque, Viscous Oil | 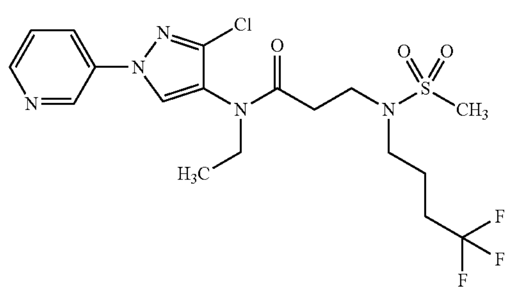 [SMILES: CCN(C(=O)CCN(CCCC(F)(F)F)S(C)(=O)=O)c1cn(-c2cccnc2)nc1Cl] | 149 |
| 1007 | Orange, Viscous Oil | 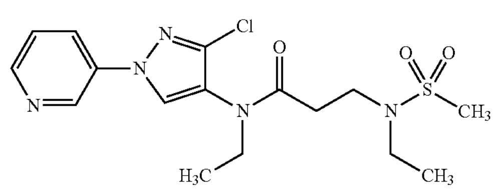 [SMILES: CCN(C(=O)CCN(CC)S(C)(=O)=O)c1cn(-c2cccnc2)nc1Cl] | 149 |
| 1008 | Light Yellow Gum | 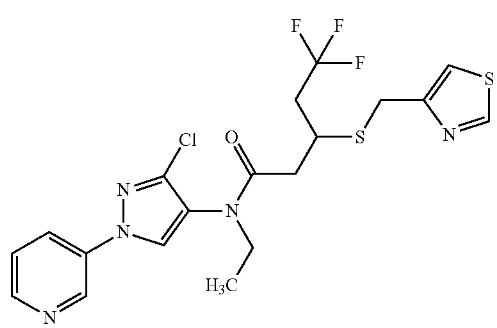 [SMILES: CCN(C(=O)CC(CC(F)(F)F)SCc1cscn1)c1cn(-c2cccnc2)nc1Cl] | 89 |

TABLE 1-continued

Compound number, appearance, and structure

| Compound No. | Appearance | Structure | Prepared as in Example: |
|---|---|---|---|
| 1009 | Light Yellow Oil | 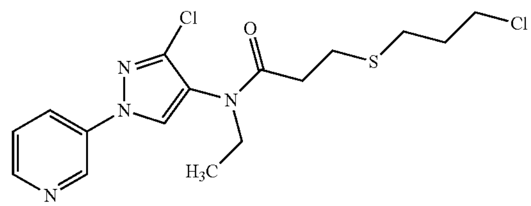 [SMILES: CCN(C(=O)CCSCCCCl)c1cn(-c2cccnc2)nc1Cl] | 89 |
| 1010 | Colorless Oil | 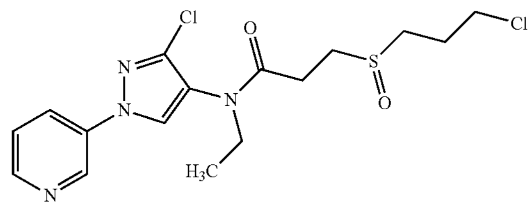 [SMILES: CCN(C(=O)CCS(=O)CCCCl)c1cn(-c2cccnc2)nc1Cl] | 50 |
| 1011 | Clear Oil | 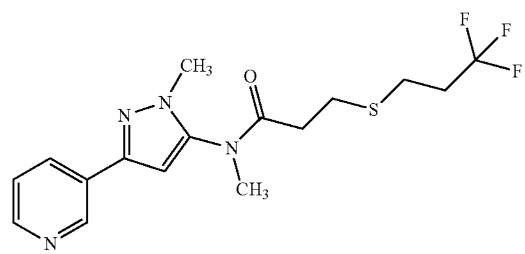 [SMILES: CN(C(=O)CCSCCC(F)(F)F)c1cc(-c2cccnc2)nn1C] | 106 |
| 1012 | Colorless, Tacky Semi-Solid | 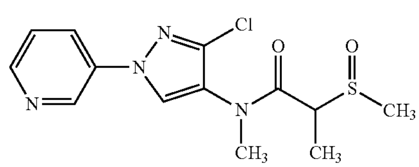 [SMILES: CC(C(=O)N(C)c1cn(-c2cccnc2)nc1Cl)S(C)=O] | 51 |
| 1013 | Yellow Viscous Oil/Semi Solid | 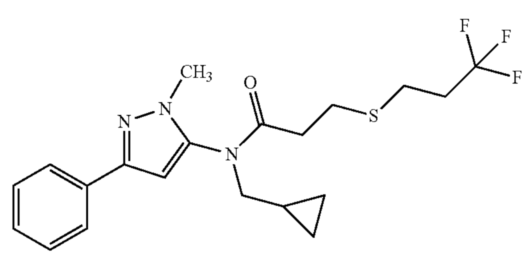 [SMILES: Cn1nc(-c2ccccc2)cc1N(CC1CC1)C(=O)CCSCCC(F)(F)F] | 106 |
| 1014 | Orange Oil | 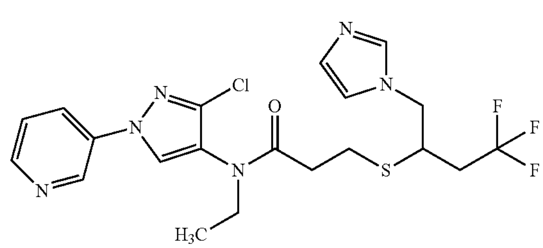 [SMILES: CCN(C(=O)CCSC(Cn1ccnc1)CC(F)(F)F)c1cn(-c2cccnc2)nc1Cl] | 156 |

TABLE 1-continued

Compound number, appearance, and structure

| Compound No. | Appearance | Structure | Prepared as in Example: |
|---|---|---|---|
| 1015 | Light Brown Gum | 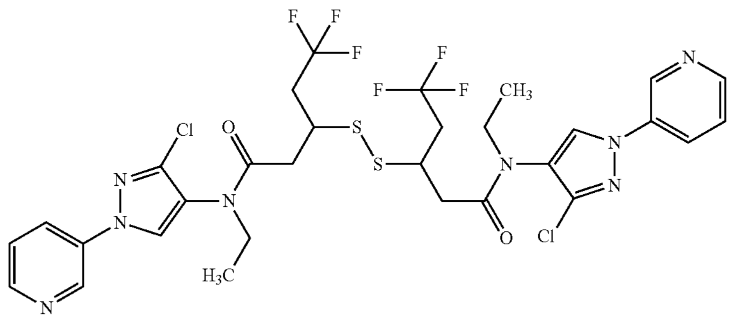 [SMILES: CCN(C(=O)CC(CC(F)(F)F)SSC(CC(=O)N(CC)c1cn(-c2cccnc2)nc1Cl)CC(F)(F)F)c1cn(-c2cccnc2)nc1Cl] | 136 |
| 1016 | Light Yellow Oil | 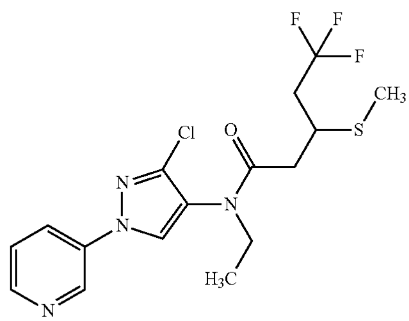 [SMILES: CCN(C(=O)CC(CC(F)(F)F)SC)c1cn(-c2cccnc2)nc1Cl] | 136 |
| 1017 | Yellow Oil | 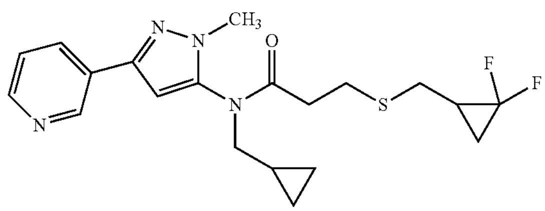 [SMILES: Cn1nc(-c2cccnc2)cc1N(CC1CC1)C(=O)CCSCC1CC1(F)F] | 106 |
| 1018 | Clear Colorless Oil | 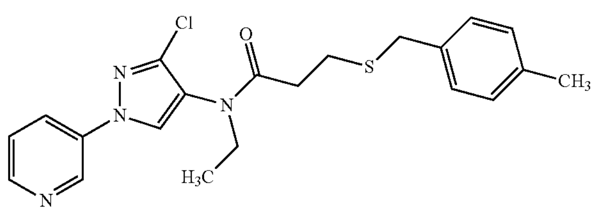 [SMILES: CCN(C(=O)CCSCc1ccc(C)cc1)c1cn(-c2cccnc2)nc1Cl] | 89 |
| 1019 | Yellow Oil | 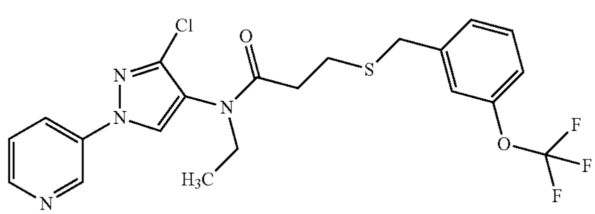 [SMILES: CCN(C(=O)CCSCc1cccc(OC(F)(F)F)c1)c1cn(-c2cccnc2)nc1Cl] | 89 |
| 1020 | Clear Viscous Oil | 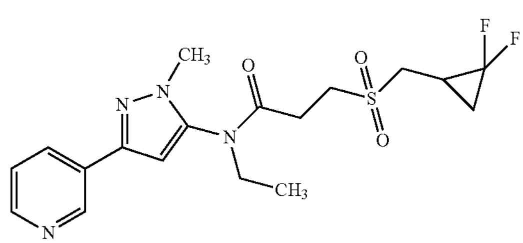 [SMILES: CCN(C(=O)CCS(=O)(=O)CC1CC1(F)F)c1cc(-c2cccnc2)nn1C] | 84 |

TABLE 1-continued

Compound number, appearance, and structure

| Compound No. | Appearance | Structure | Prepared as in Example: |
|---|---|---|---|
| 1021 | Yellow Oil | 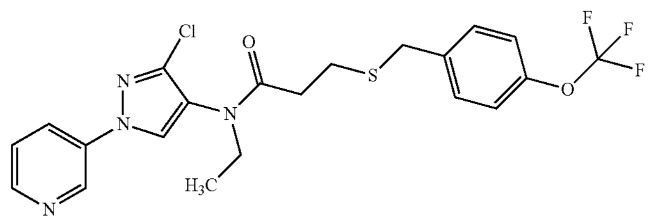 [SMILES: CCN(C(=O)CCSCc1ccc(OC(F)(F)F)cc1)c1cn(-c2cccnc2)nc1Cl] | 89 |
| 1022 | Yellow Oil | 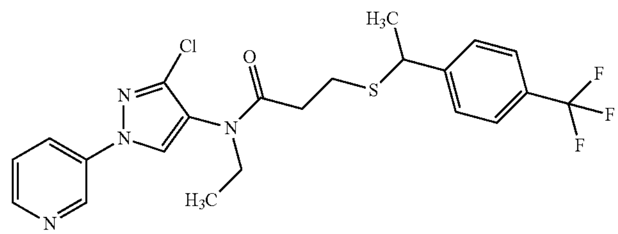 [SMILES: CCN(C(=O)CCSC(C)c1ccc(C(F)(F)F)cc1)c1cn(-c2cccnc2)nc1Cl] | 89 |
| 1023 | Clear Colorless Semi Solid | 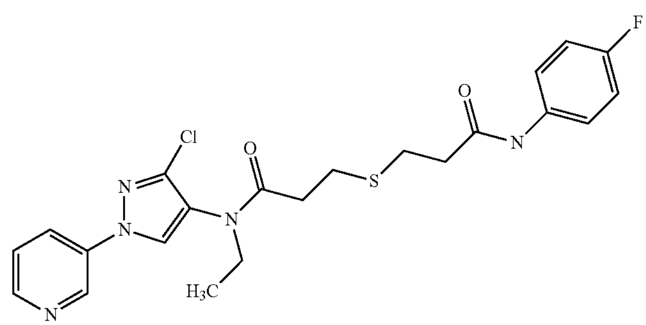 [SMILES: CCN(C(=O)CCSCCC(=O)Nc1ccc(F)cc1)c1cn(-c2cccnc2)nc1Cl] | 180 |
| 1024 | White Semi Solid | 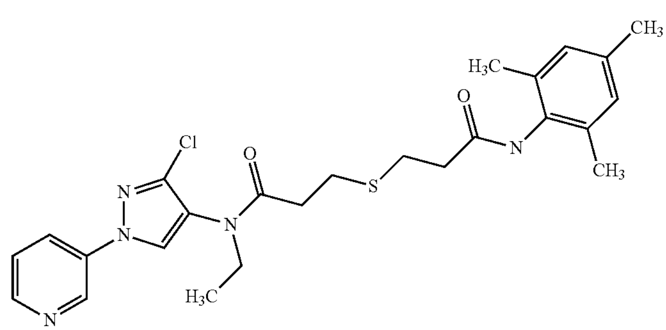 [SMILES: CCN(C(=O)CCSCCC(=O)Nc1c(C)cc(C)cc1C)c1cn(-c2cccnc2)nc1Cl] | 180 |
| 1025 | Clear Colorless Oil | 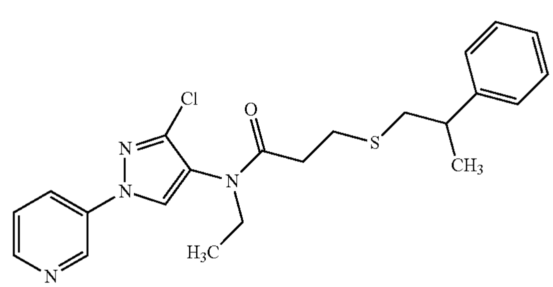 [SMILES: CCN(C(=O)CCSCC(C)c1ccccc1)c1cn(-c2cccnc2)nc1Cl] | 180 |

US 9,708,288 B2
547                                                                                                       548
TABLE 1-continued
Compound number, appearance, and structure
| Compound No. | Appearance | Structure | Prepared as in Example: |
|---|---|---|---|
| 1026 | Clear Colorless Oil | 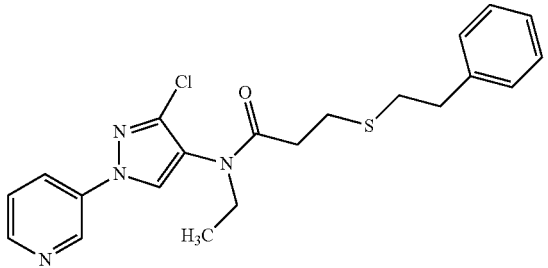 [SMILES: CCN(C(=O)CCSCCc1ccccc1)c1cn(-c2cccnc2)nc1Cl] | 180 |
| 1027 | Orange Oil | 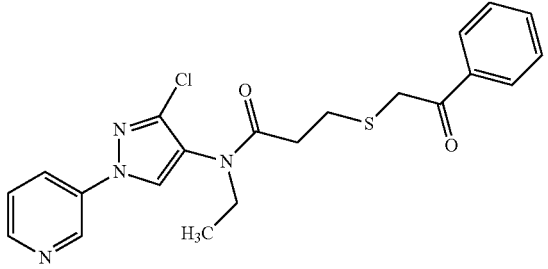 [SMILES: CCN(C(=O)CCSCC(=O)c1ccccc1)c1cn(-c2cccnc2)nc1Cl] | 180 |
| 1028 | White Solid | (+)- 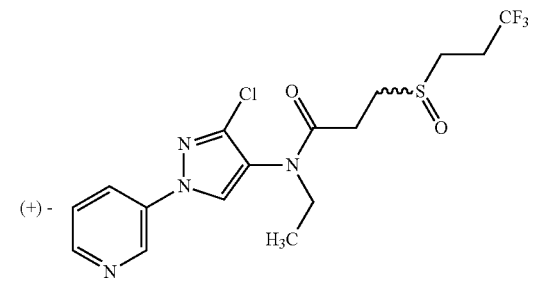 [SMILES: CCN(C(=O)CCS(=O)CCC(F)(F)F)c1cn(-c2cccnc2)nc1Cl] | 181 |
| 1029 | White Semi-Solid | (-)- 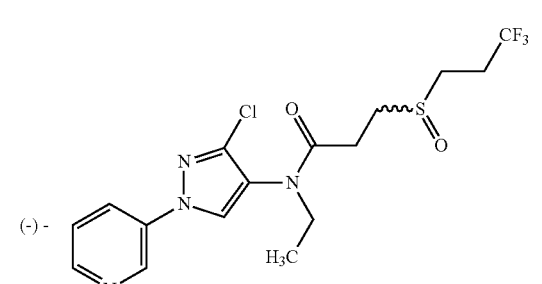 | 181 |
| 1030 | Colorless Oil | 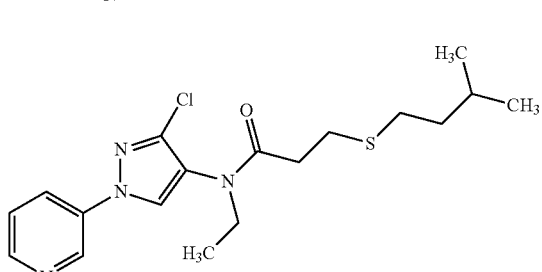 | 180 |

TABLE 1-continued
| Compound No. | Appearance | Structure | Prepared as in Example: |
|---|---|---|---|
| 1031 | Colorless Oil | 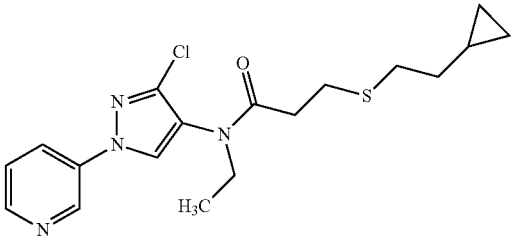 [SMILES: CCN(C(=O)CCSCCC1CC1)c1cn(-c2cccnc2)nc1Cl] | 180 |
| 1032 | Colorless Oil | 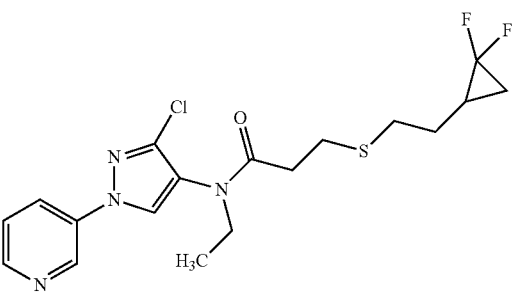 [SMILES: CCN(C(=O)CCSCCC1CC1(F)F)c1cn(-c2cccnc2)nc1Cl] | 180 |
| 1033 | Off-White Solid | 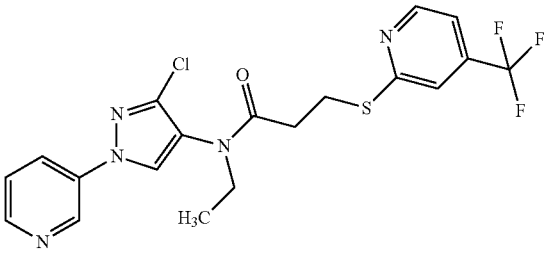 [SMILES: CCN(C(=O)CCSc1cc(C(F)(F)F)ccn1)c1cn(-c2cccnc2)nc1Cl] | 180 |
| 1034 | Colorless Oil | 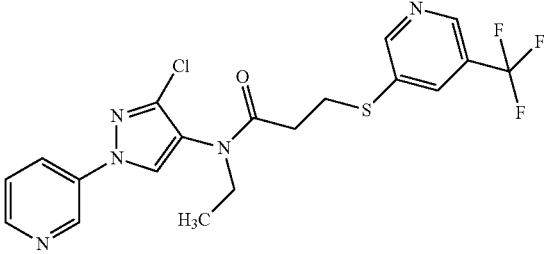 [SMILES: CCN(C(=O)CCSc1cncc(C(F)(F)F)c1)c1cn(-c2cccnc2)nc1Cl] | 180 |
| 1035 | Colorless Oil | 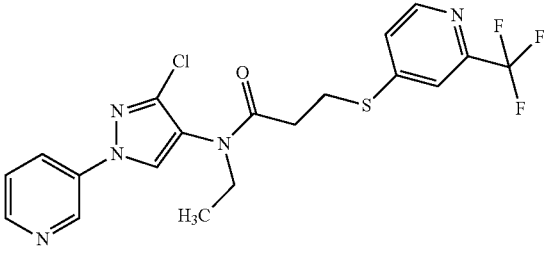 [SMILES: CCN(C(=O)CCSc1ccnc(C(F)(F)F)c1)c1cn(-c2cccnc2)nc1Cl] | 180 |

TABLE 1-continued

Compound number, appearance, and structure

| Compound No. | Appearance | Structure | Prepared as in Example: |
|---|---|---|---|
| 1036 | Yellow Oil | 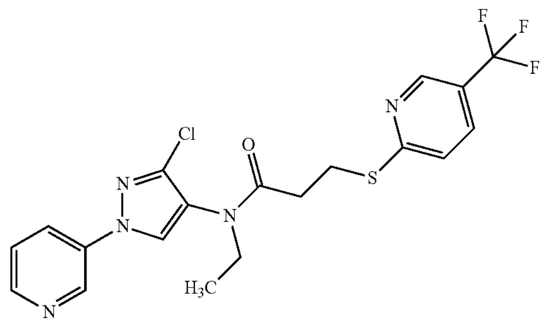 [SMILES: CCN(C(=O)CCSc1ccc(C(F)(F)F)cn1)c1cn(-c2cccnc2)nc1Cl] | 180 |
| 1037 | Colorless Oil | 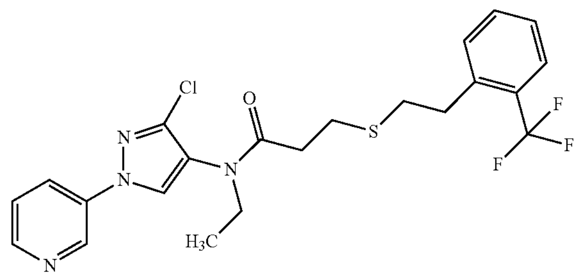 [SMILES: CCN(C(=O)CCSCCc1ccccc1C(F)(F)F)c1cn(-c2cccnc2)nc1Cl] | 180 |
| 1038 | Colorless Oil | 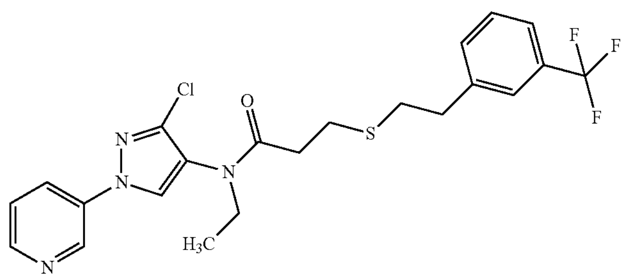 [SMILES: CCN(C(=O)CCSCCc1cccc(C(F)(F)F)c1)c1cn(-c2cccnc2)nc1Cl] | 180 |
| 1039 | Colorless Oil | 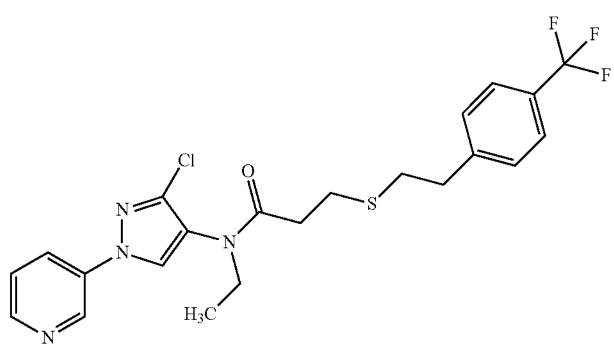 [SMILES: CCN(C(=O)CCSCCc1ccc(C(F)(F)F)cc1)c1cn(-c2cccnc2)nc1Cl] | 180 |
| 1040 | Colorless Oil | 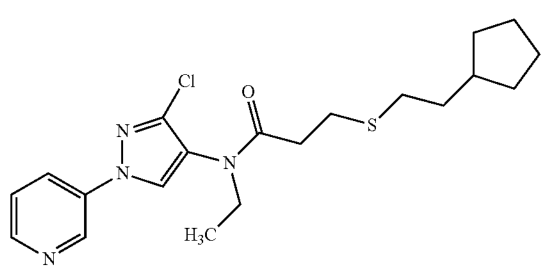 [SMILES: CCN(C(=O)CCSCCC1CCCC1)c1cn(-c2cccnc2)nc1Cl] | 180 |

TABLE 1-continued

| Compound No. | Appearance | Structure | Prepared as in Example: |
|---|---|---|---|
| 1041 | Colorless Oil | 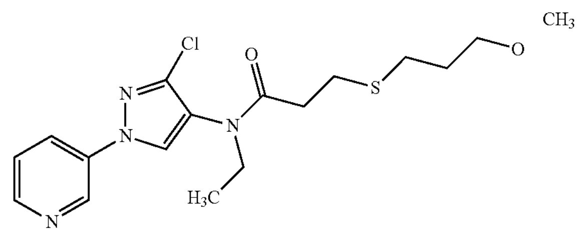 | 180 |
| 1042 | Colorless Oil | 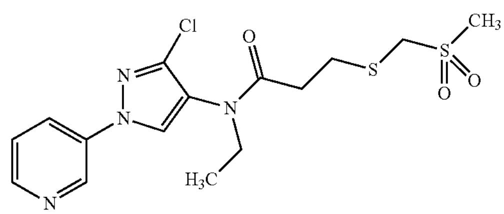 [SMILES: CCN(C(=O)CCSCS(C)(=O)=O)c1cn(-c2cccnc2)nc1Cl] | 180 |
| 1043 | Light Yellow Oil | 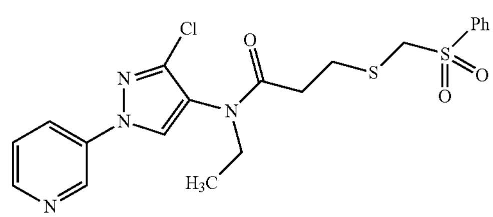 [SMILES: CCN(C(=O)CCSCS(=O)(=O)c1ccccc1)c1cn(-c2cccnc2)nc1Cl] | 180 |
| 1044 | Colorless Oil | 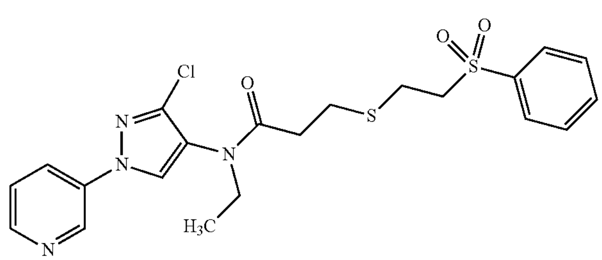 [SMILES: CCN(C(=O)CCSCCS(=O)(=O)c1ccccc1)c1cn(-c2cccnc2)nc1Cl] | 180 |
| 1045 | Colorless Oil | 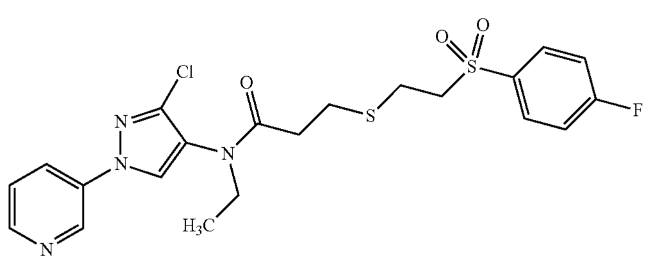 [SMILES: CCN(C(=O)CCSCCS(=O)(=O)c1ccc(F)cc1)c1cn(-c2cccnc2)nc1Cl] | 180 |
| 1046 | Colorless Oil | 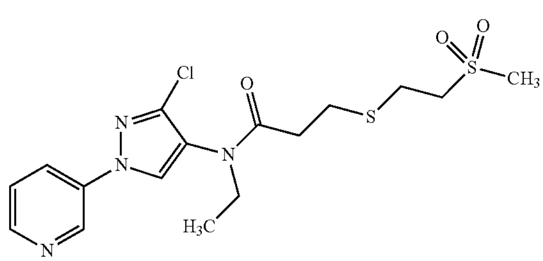 [SMILES: CCN(C(=O)CCSCCS(C)(=O)=O)c1cn(-c2cccnc2)nc1Cl] | 180 |

TABLE 1-continued

Compound number, appearance, and structure

| Compound No. | Appearance | Structure | Prepared as in Example: |
|---|---|---|---|
| 1047 | Colorless Oil | 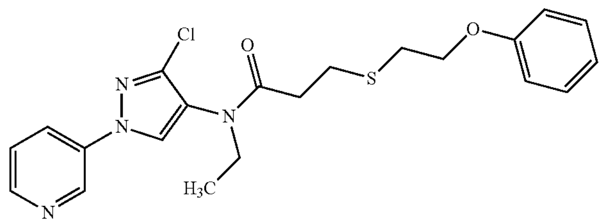 [SMILES: CCN(C(=O)CCSCCOc1ccccc1)c1cn(-c2cccnc2)nc1Cl] | 180 |
| 1048 | Light Yellow Oil | 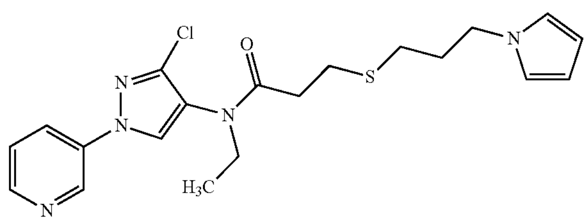 [SMILES: CCN(C(=O)CCSCCCn1cccc1)c1cn(-c2cccnc2)nc1Cl] | 180 |
| 1049 | Colorless Oil | 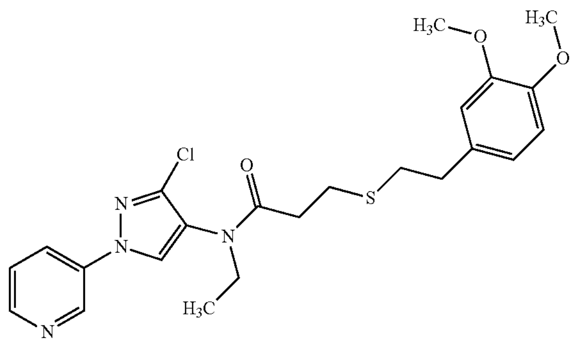 [SMILES: CCN(C(=O)CCSCCc1ccc(OC)c(OC)c1)c1cn(-c2cccnc2)nc1Cl] | 180 |
| 1050 | Light Yellow Oil | 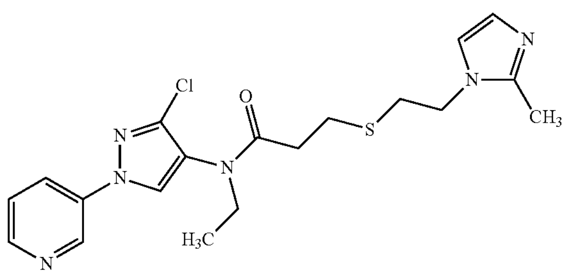 [SMILES: CCN(C(=O)CCSCCn1ccnc1C)c1cn(-c2cccnc2)nc1Cl] | 180 |
| 1051 | Colorless Oil | 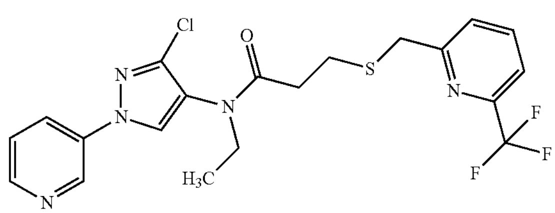 [SMILES: CCN(C(=O)CCSCc1cccc(C(F)(F)F)n1)c1cn(-c2cccnc2)nc1Cl] | 180 |
| 1052 | Colorless Oil | 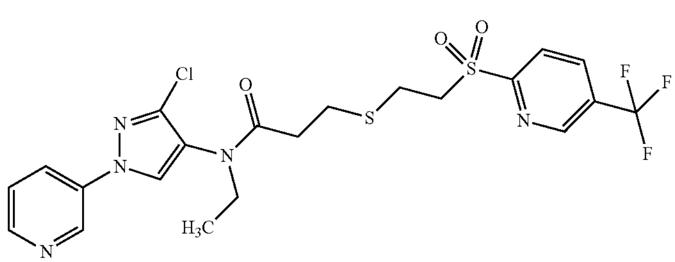 [SMILES: CCN(C(=O)CCSCCS(=O)(=O)c1ccc(C(F)(F)F)cn1)c1cn(-c2cccnc2)nc1Cl] | 180 |

TABLE 1-continued

Compound number, appearance, and structure

| Compound No. | Appearance | Structure | Prepared as in Example: |
|---|---|---|---|
| 1053 | Pale Yellow Oil | 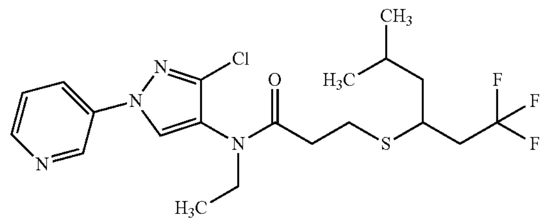 [SMILES: CCN(C(=O)CCSC(CC(C)C)CC(F)(F)F)c1cn(-c2cccnc2)nc1Cl] | 156 |
| 1054 | Light Yellow Oil | 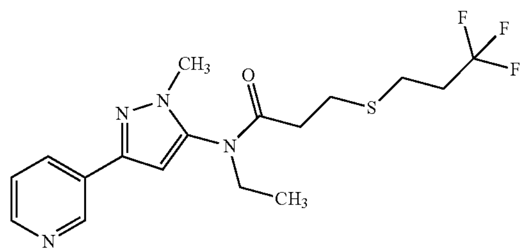 [SMILES: CCN(C(=O)CCSCCC(F)(F)F)c1cc(-c2cccnc2)nn1C] | 106 |
| 1055 | Pale Orange Oil | 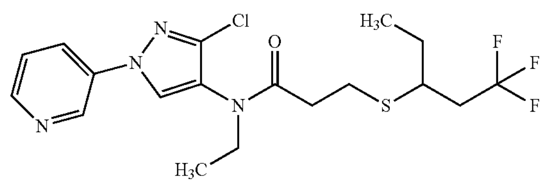 [SMILES: CCC(CC(F)(F)F)SCCC(=O)N(CC)c1cn(-c2cccnc2)nc1Cl] | 156 |
| 1056 | Clear Really Viscous Oil | 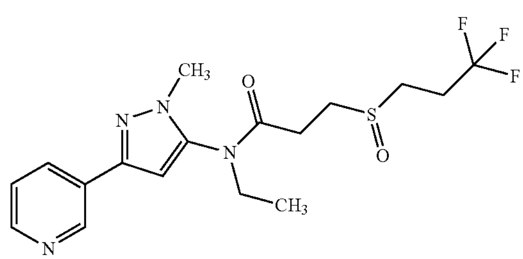 [SMILES: CCN(C(=O)CCS(=O)CCC(F)(F)F)c1cc(-c2cccnc2)nn1C] | 83 |
| 1057 | Clear/White Viscous Semi-Solid | 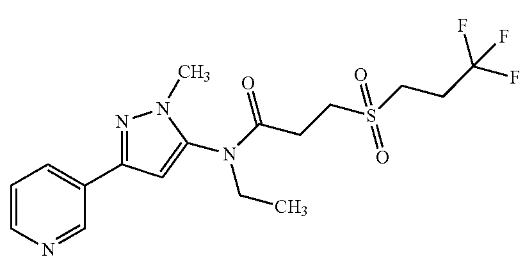 [SMILES: CCN(C(=O)CCS(=O)(=O)CCC(F)(F)F)c1cc(-c2cccnc2)nn1C] | 84 |
| 1058 | Clear Semi-Solid | 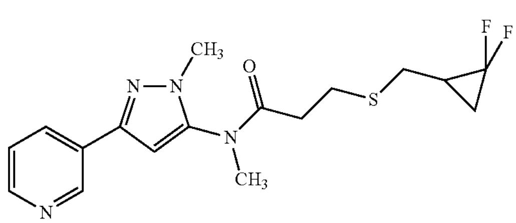 [SMILES: CN(C(=O)CCSCC1CC1(F)F)c1cc(-c2cccnc2)nn1C] | 106 |

TABLE 1-continued

Compound number, appearance, and structure

| Compound No. | Appearance | Structure | Prepared as in Example: |
|---|---|---|---|
| 1059 | Light Yellow Gum | 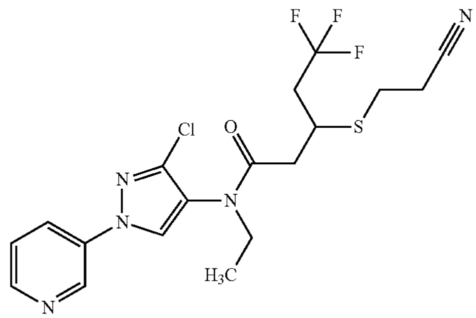 [SMILES: CCN(C(=O)CC(CC(F)(F)F)SCCC#N)c1cn(-c2cccnc2)nc1Cl] | 89 |
| 1060 | Yellow Viscous Oil | 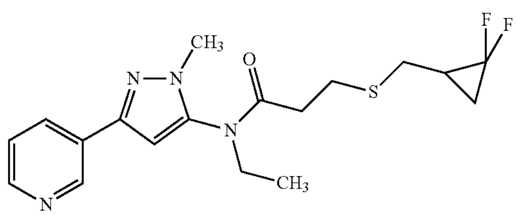 [SMILES: CCN(C(=O)CCSCC1CC1(F)F)c1cc(-c2cccnc2)nn1C] | 106 |
| 1061 | Clear Viscous Oil | 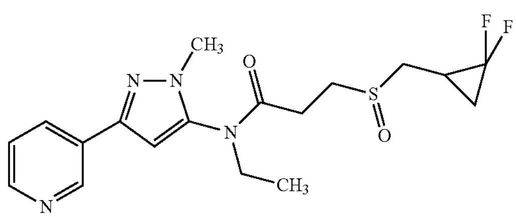 [SMILES: CCN(C(=O)CCS(=O)CC1CC1(F)F)c1cc(-c2cccnc2)nn1C] | 83 |
| 1062 | Orange Oil | 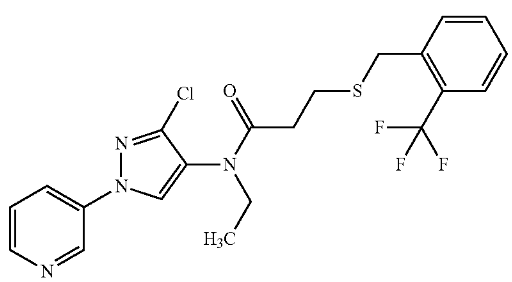 [SMILES: CCN(C(=O)CCSCc1ccccc1C(F)(F)F)c1cn(-c2cccnc2)nc1Cl] | 89 |
| 1063 | Yellow Solid | 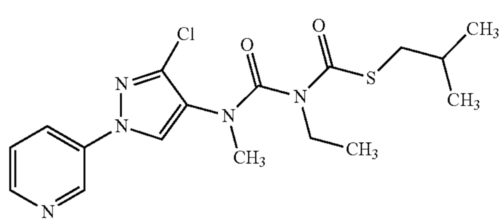 [SMILES: CCN(C(=O)SCC(C)C)C(=O)N(C)c1cn(-c2cccnc2)nc1Cl] | 174 |
| 1064 | Faint Yellow Oil | 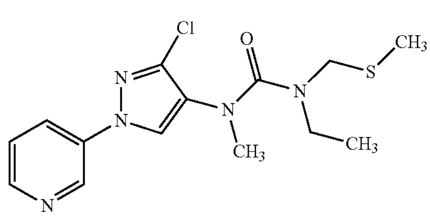 [SMILES: CCN(CSC)C(=O)N(C)c1cn(-c2cccnc2)nc1Cl] | 174 |

TABLE 1-continued

Compound number, appearance, and structure

| Compound No. | Appearance | Structure | Prepared as in Example: |
|---|---|---|---|
| Y2000 | Colorless Solid | (structure) | 100 |
| Y2001 | White Solid | (structure) | 196 |
| Y2002 | Gummy White Solid | (structure) | 12 |
| Y2003 | White Solid | (structure) | 124 |
| Y2004 | Yellow Oil | (structure) | 11 |
| Y2005 | Yellow Oil | (structure) | 31 |

TABLE 1-continued
Compound number, appearance, and structure
| Compound No. | Appearance | Structure | Prepared as in Example: |
|---|---|---|---|
| Y2006 | Yellow Oil | 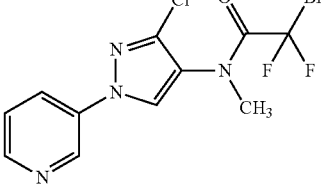 | 100 |
| Y2007 | Light Yellow Gum | 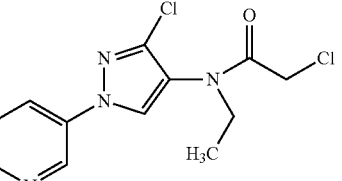 | 100 |
| Y2008 | Light Yellow Oil | 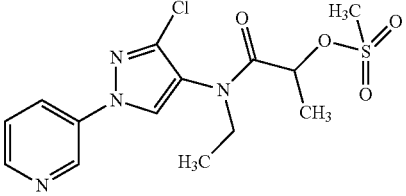 [SMILES: CCN(C(=O)C(C)OS(C)(=O)=O)c1cn(-c2cccnc2)nc1Cl] | 125 |
| Y2009 | White Solid | 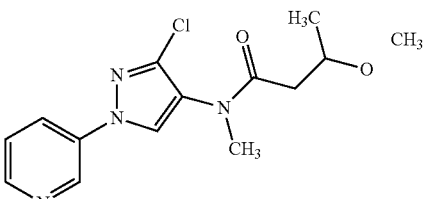 | 12 |
| Y2010 | Faint Yellow Solid | 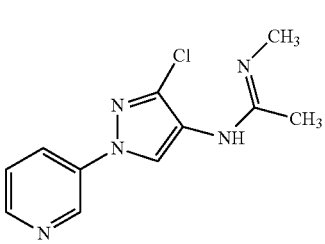 [SMILES: C/N=C(\C)Nc1cn(-c2cccnc2)nc1Cl] | 175 |
| Y2011 | White Solid | 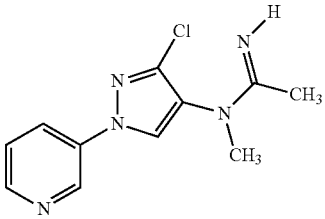 [SMILES: [H]/N=C(\C)N(C)c1cn(-c2cccnc2)nc1Cl] | 175 |
| Y2012 | Yellow Oil | 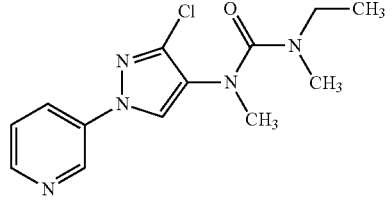 [SMILES: CCN(C)C(=O)N(C)c1cn(-c2cccnc2)nc1Cl] | 195 |

TABLE 1-continued

Compound number, appearance, and structure

| Compound No. | Appearance | Structure | Prepared as in Example: |
|---|---|---|---|
| Y2013 | Brown Solid | 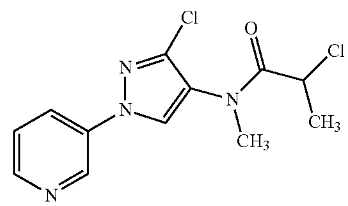 [SMILES: CC(Cl)C(=O)N(C)c1cn(-c2cccnc2)nc1Cl] | 100 |
| Y2014 | Yellow Solid | 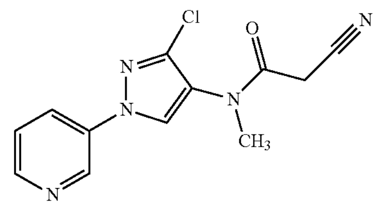 [SMILES: CN(C(=O)CC#N)c1cn(-c2cccnc2)nc1Cl] | 12 |
| Y2015 | Light Yellow Solid | 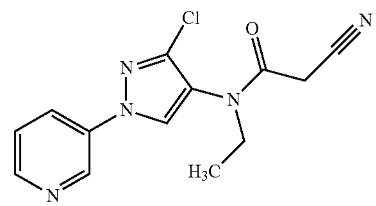 [SMILES: CCN(C(=O)CC#N)c1cn(-c2cccnc2)nc1Cl] | 12 |
| Y2016 | Light Yellow Semi-Solid | 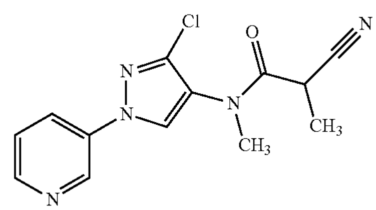 [SMILES: CC(C#N)C(=O)N(C)c1cn(-c2cccnc2)nc1Cl] | 12 |
| Y2017 | Light Yellow Semi-Solid | 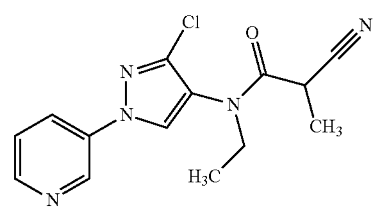 [SMILES: CCN(C(=O)C(C)C#N)c1cn(-c2cccnc2)nc1Cl] | 12 |
| Y2018 | Light Yellow Oil | 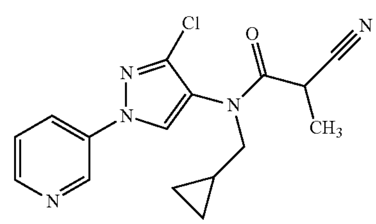 [SMILES: CC(C#N)C(=O)N(CC1CC1)c1cn(-c2cccnc2)nc1Cl] | 12 |
| Y2019 | Colorless Oil | 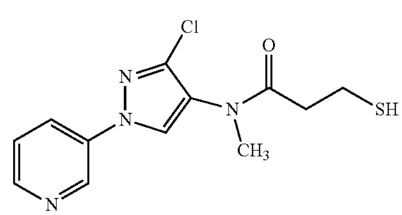 [SMILES: CN(C(=O)CCS)c1cn(-c2cccnc2)nc1Cl] | 87 |

TABLE 1-continued

| Compound No. | Appearance | Structure | Prepared as in Example: |
|---|---|---|---|
| Y2021 | Light Brown Oil | 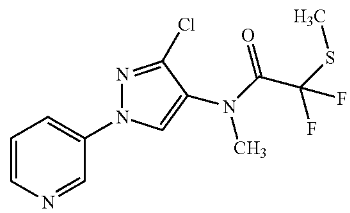 [SMILES: CSC(F)(F)C(=O)N(C)c1cn(-c2cccnc2)nc1Cl] | 198 |
| Y2022 | Yellow Oil | 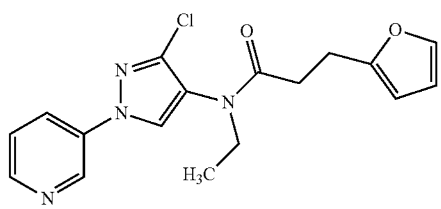 [SMILES: CCN(C(=O)CCc1ccco1)c1cn(-c2cccnc2)nc1Cl] | 42 |
| Y2023 | Yellow Oil | 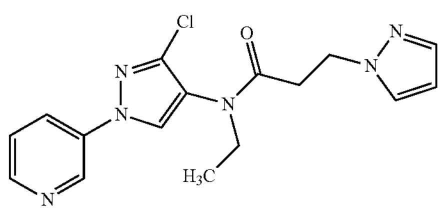 [SMILES: CCN(C(=O)CCn1cccn1)c1cn(-c2cccnc2)nc1Cl] | 42 |
| Y2024 | Off-White Solid | 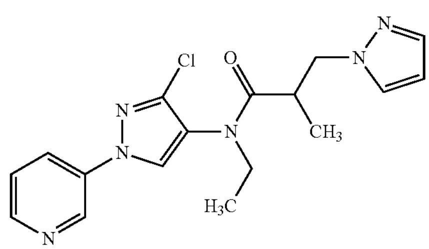 [SMILES: CCN(C(=O)C(C)Cn1cccn1)c1cn(-c2cccnc2)nc1Cl] | 42 |
| Y2025 | Yellow Oil | 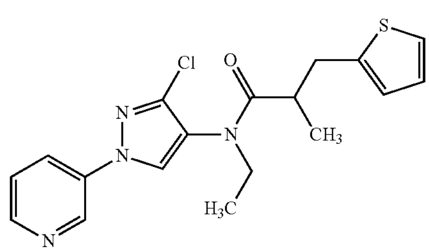 [SMILES: CCN(C(=O)C(C)Cc1cccs1)c1cn(-c2cccnc2)nc1Cl] | 42 |
| Y2026 | Off-White Semisolid | 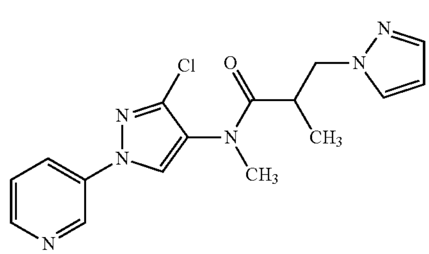 [SMILES: CC(Cn1cccn1)C(=O)N(C)c1cn(-c2cccnc2)nc1Cl] | 42 |

TABLE 1-continued

Compound number, appearance, and structure

| Compound No. | Appearance | Structure | Prepared as in Example: |
|---|---|---|---|
| Y2027 | Off-White Solid | 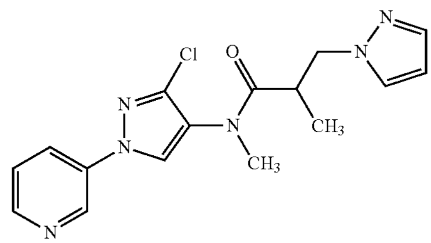 [SMILES: CC(Cn1cccn1)C(=O)N(C)c1cn(-c2cccnc2)nc1Cl] | 42 |
| Y2028 | Light Brown Semisolid | 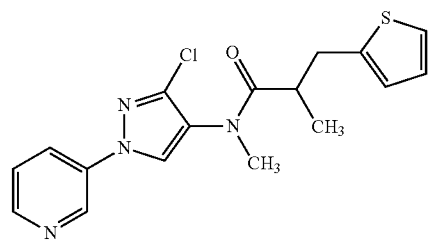 [SMILES: CC(Cc1cccs1)C(=O)N(C)c1cn(-c2cccnc2)nc1Cl] | 42 |
| Y2029 | Yellow Oil | 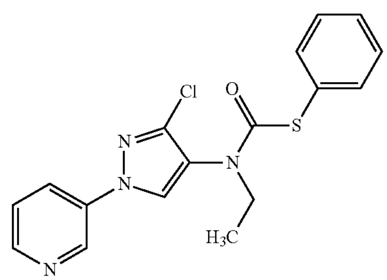 [SMILES: CCN(C(=O)Sc1ccccc1)c1cn(-c2cccnc2)nc1Cl] | 11 |
| Y2030 | White Solid | 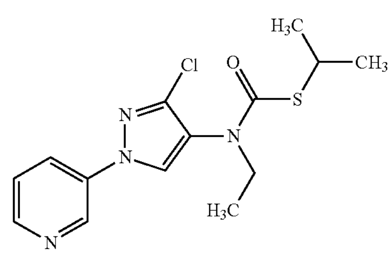 [SMILES: CCN(C(=O)SC(C)C)c1cn(-c2cccnc2)nc1Cl] | 11 |
| Y2031 | White Solid | 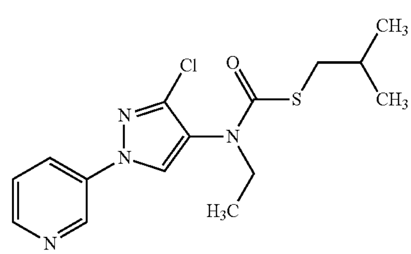 [SMILES: CCN(C(=O)SCC(C)C)c1cn(-c2cccnc2)nc1Cl] | 11 |
| Y2032 | White Solid | 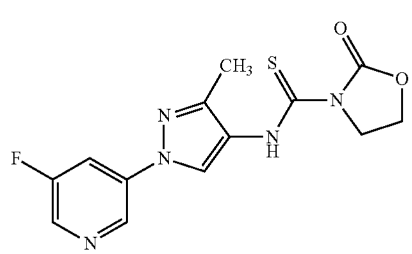 [SMILES: Cc1nn(-c2cncc(F)c2)cc1NC(=S)N1CCOC1=O] | 163 |

TABLE 1-continued

Compound number, appearance, and structure

| Compound No. | Appearance | Structure | Prepared as in Example: |
|---|---|---|---|
| Y2033 | Brown Solid | 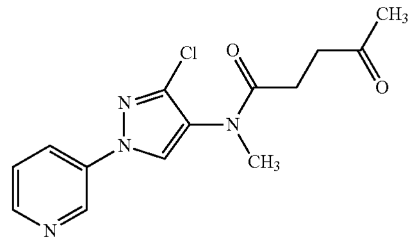 [SMILES: CC(=O)CCC(=O)N(C)c1cn(-c2cccnc2)nc1Cl] | 40 |
| Y2034 | White Solid | 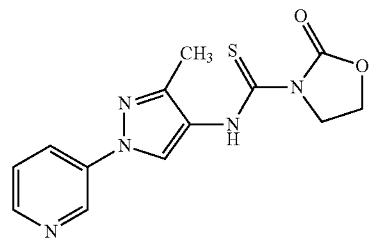 [SMILES: Cc1nn(-c2cccnc2)cc1NC(=S)N1CCOC1=O] | 163 |
| Y2035 | Light Yellow Solid | 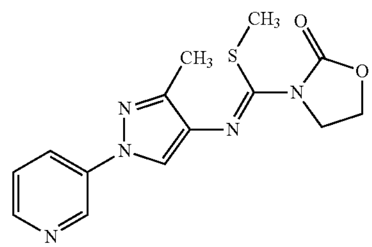 [SMILES: CS/C(=N\c1cn(-c2cccnc2)nc1C)N1CCOC1=O] | 164 |
| Y2036 | White Solid | 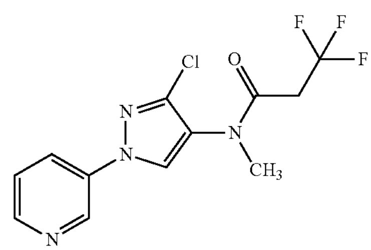 [SMILES: CN(C(=O)CC(F)(F)F)c1cn(-c2cccnc2)nc1Cl] | 12 |
| Y2037 | White Solid | 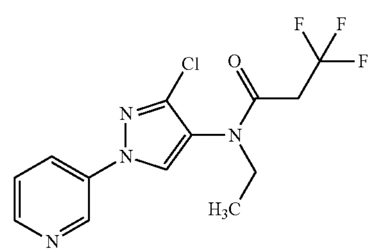 [SMILES: CCN(C(=O)CC(F)(F)F)c1cn(-c2cccnc2)nc1Cl] | 12 |
| Y2038 | Colorless Oil | 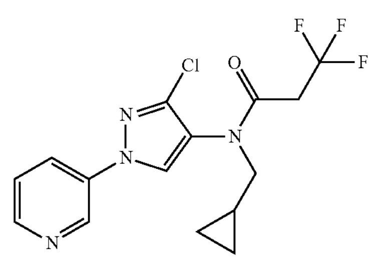 [SMILES: O=C(CC(F)(F)F)N(CC1CC1)c1cn(-c2cccnc2)nc1Cl] | 12 |

TABLE 1-continued

Compound number, appearance, and structure

| Compound No. | Appearance | Structure | Prepared as in Example: |
|---|---|---|---|
| Y2039 | White Solid | 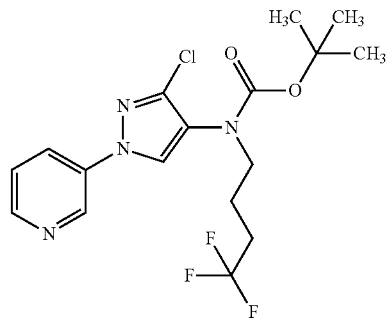 [SMILES: CC(C)(C)OC(=O)N(CCCC(F)(F)F)c1cn(-c2cccnc2)nc1Cl] | 14 |
| Y2040 | White Solid | 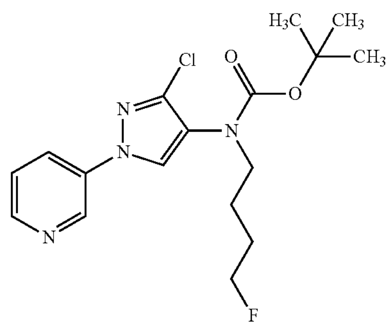 [SMILES: CC(C)(C)OC(=O)N(CCCCF)c1cn(-c2cccnc2)nc1Cl] | 14 |
| Y2041 | Light Brown Solid | 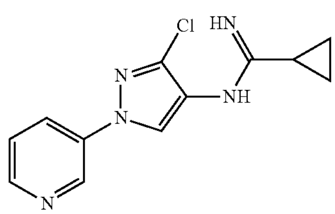 [SMILES: N=C(Nc1cn(-c2cccnc2)nc1Cl)C1CC1] | 175 |
| Y2042 | White Solid | 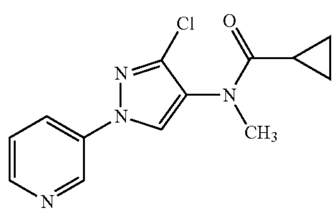 [SMILES: CN(C(=O)C1CC1)c1cn(-c2cccnc2)nc1Cl] | 12 |
| Y2043 | Clear Oil | 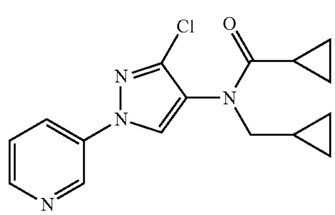 [SMILES: O=C(C1CC1)N(CC1CC1)c1cn(-c2cccnc2)nc1Cl] | 12 |
| Y2044 | Yellow Oil | 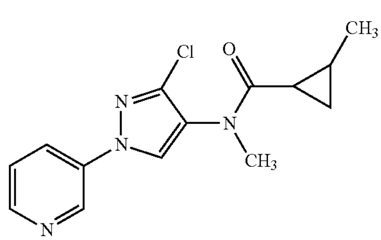 [SMILES: CC1CC1C(=O)N(C)c1cn(-c2cccnc2)nc1Cl] | 12 |

TABLE 1-continued
Compound number, appearance, and structure
| Compound No. | Appearance | Structure | Prepared as in Example: |
|---|---|---|---|
| Y2045 | Clear Oil | 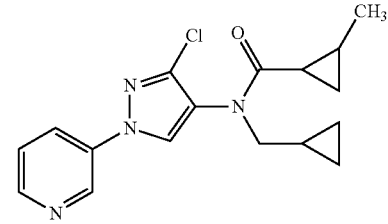 [SMILES: CC1CC1C(=O)N(CC1CC1)c1cn(-c2cccnc2)nc1Cl] | 12 |
| Y2046 | Yellow Oil | 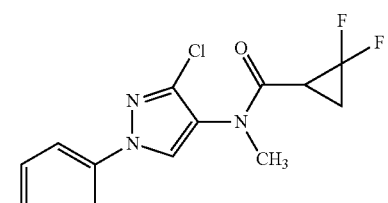 | 12 |
| Y2047 | Clear Oil | 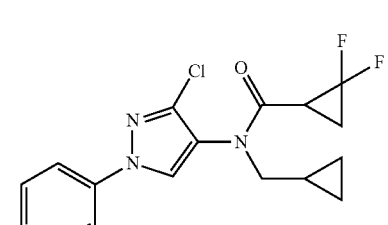 | 12 |
| Y2048 | White Solid | 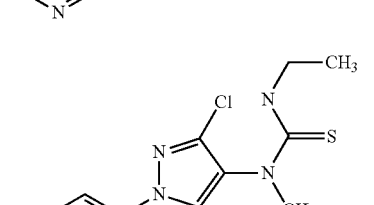 | 45 |
| Y2049 | Yellow Oil | 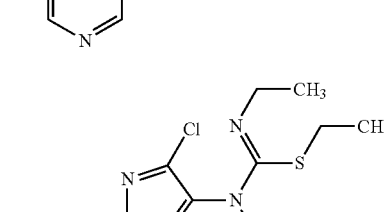 | 177 |
| Y2050 | Yellow Solid | 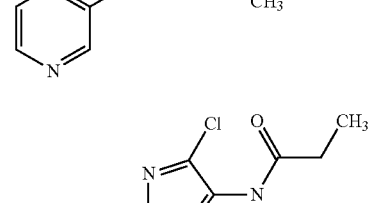 | 11 |

TABLE 1-continued

Compound number, appearance, and structure

| Compound No. | Appearance | Structure | Prepared as in Example: |
|---|---|---|---|
| Y2051 | White Solid | 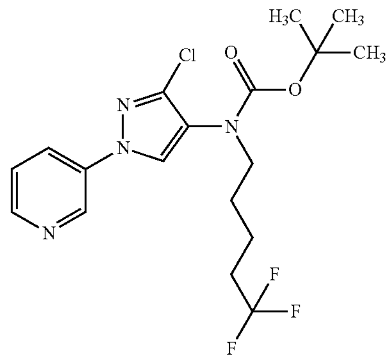 [SMILES: CC(C)(C)OC(=O)N(CCCCC(F)(F)F)c1cn(-c2cccnc2)nc1Cl] | 14 |
| Y2052 | White Solid | 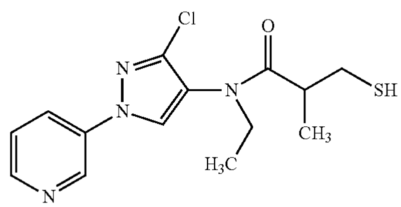 [SMILES: CCN(C(=O)C(C)CS)c1cn(-c2cccnc2)nc1Cl] | 87 |
| Y2053 | Salmon Colored Foam | 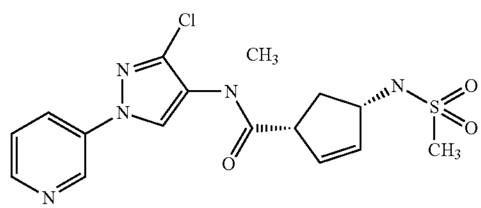 | 140 |
| Y2054 | White Foam | 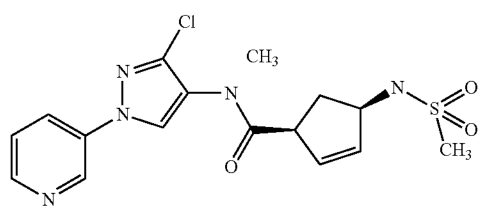 | 140 |
| Y2055 | Light Yellow Oil | 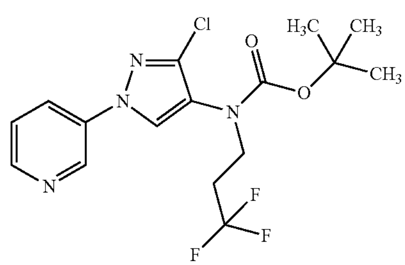 [SMILES: CC(C)(C)OC(=O)N(CCC(F)(F)F)c1cn(-c2cccnc2)nc1Cl] | 14 |
| Y2056 | White Solid | 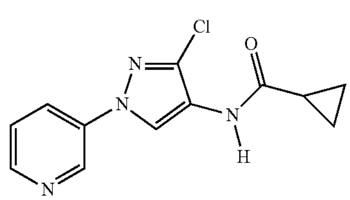 [SMILES: O=C(Nc1cn(-c2cccnc2)nc1Cl)C1CC1] | 11 |

TABLE 1-continued

Compound number, appearance, and structure

| Compound No. | Appearance | Structure | Prepared as in Example: |
|---|---|---|---|
| Y2057 | Yellow Oil | 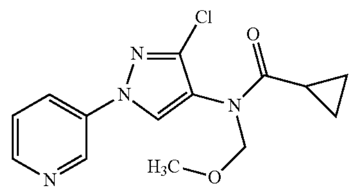 [SMILES: COCN(C(=O)C1CC1)c1cn(-c2cccnc2)nc1Cl] | 14 |
| Y2058 | Yellow Oil | 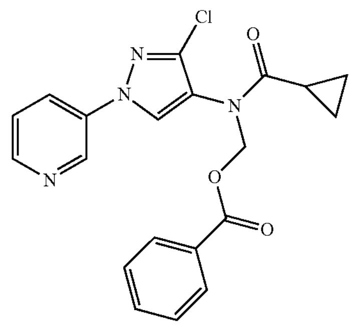 [SMILES: O=C(OCN(C(=O)C1CC1)c1cn(-c2cccnc2)nc1Cl)c1ccccc1] | 14 |
| Y2059 | Yellow Oil | 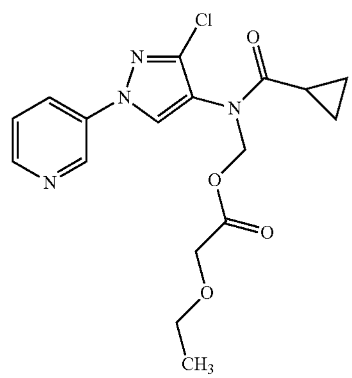 [SMILES: CCOCC(=O)OCN(C(=O)C1CC1)c1cn(-c2cccnc2)nc1Cl] | 14 |
| Y2060 | White Solid | 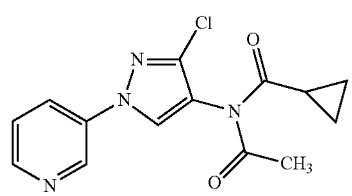 [SMILES: CC(=O)N(C(=O)C1CC1)c1cn(-c2cccnc2)nc1Cl] | 14 |
| Y2061 | White Solid | 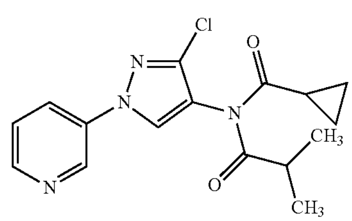 [SMILES: CC(C)C(=O)N(C(=O)C1CC1)c1cn(-c2cccnc2)nc1Cl] | 14 |
| Y2062 | Faint Orange Oil | 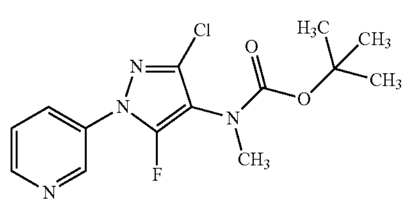 [SMILES: CN(C(=O)OC(C)(C)C)c1c(Cl)nn(-c2cccnc2)c1F] | 31 |

TABLE 1-continued

| Compound No. | Appearance | Structure | Prepared as in Example: |
|---|---|---|---|
| Y2063 | Faint Yellow Oil | 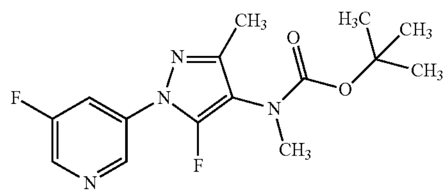 [SMILES: Cc1nn(-c2cncc(F)c2)c(F)c1N(C)C(=O)OC(C)(C)C] | 31 |
| Y2064 | White Semi Solid | 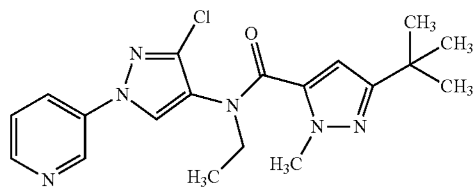 [SMILES: CCN(C(=O)c1cc(C(C)(C)C)nn1C)c1cn(-c2cccnc2)nc1Cl] | 11 |
| Y2065 | Yellow Semi Solid | 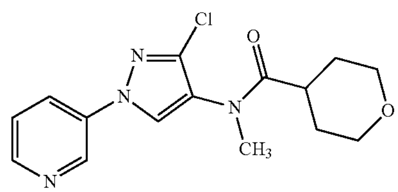 [SMILES: CN(C(=O)C1CCOCC1)c1cn(-c2cccnc2)nc1Cl] | 11 |
| Y2066 | Yellow Oil | 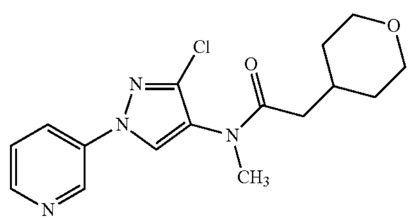 [SMILES: CN(C(=O)CC1CCOCC1)c1cn(-c2cccnc2)nc1Cl] | 11 |
| Y2067 | Clear Oil | 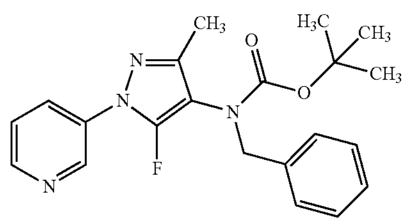 [SMILES: Cc1nn(-c2cccnc2)c(F)c1N(Cc1ccccc1)C(=O)OC(C)(C)C] | 31 |
| Y2068 | Yellow Oil | 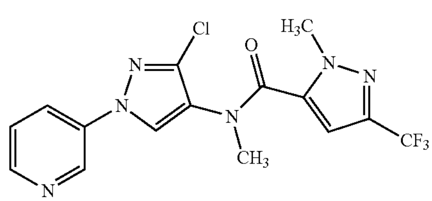 [SMILES: CN(C(=O)c1cc(C(F)(F)F)nn1C)c1cn(-c2cccnc2)nc1Cl] | 11 |
| Y2069 | White Solid | 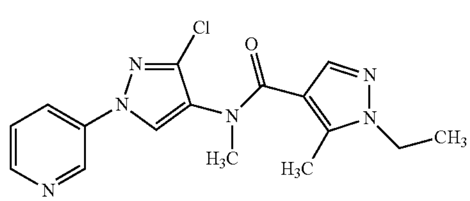 [SMILES: CCn1ncc(C(=O)N(C)c2cn(-c3cccnc3)nc2Cl)c1C] | 11 |

TABLE 1-continued

Compound number, appearance, and structure

| Compound No. | Appearance | Structure | Prepared as in Example: |
|---|---|---|---|
| Y2070 | Yellow Oil | 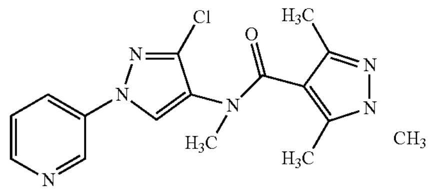 | 11 |
| Y2071 | Light Brown Gum | 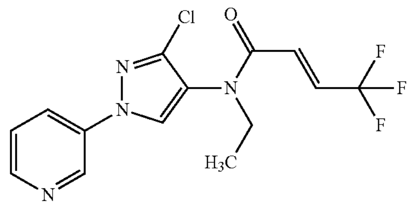 [SMILES: CCN(C(=O)/C=C/C(F)(F)F)c1cn(-c2cccnc2)nc1Cl] | 42 |
| Y2072 | Brown Gum | 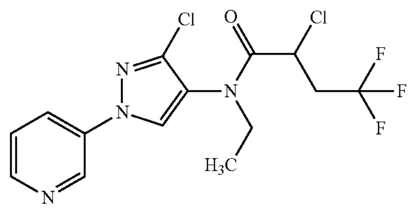 [SMILES: CCN(C(=O)C(Cl)CC(F)(F)F)c1cn(-c2cccnc2)nc1Cl] | 42 |
| Y2073 | White Semi-Solid | 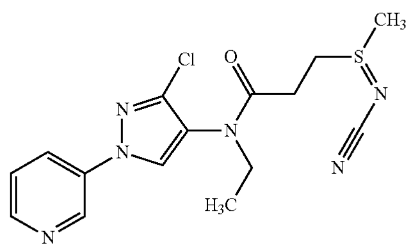 [SMILES: CCN(C(=O)CC/S(C)=N\C#N)c1cn(-c2cccnc2)nc1Cl] | 53 |
| Y2074 | Yellow Oil | 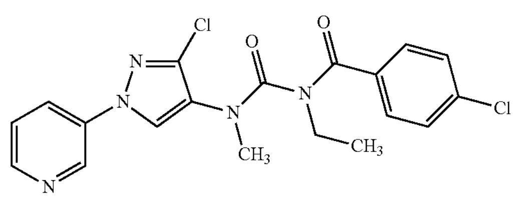 [SMILES: CCN(C(=O)c1ccc(Cl)cc1)C(=O)N(C)c1cn(-c2cccnc2)nc1Cl] | 174 |
| Y2075 | Clear Oil | 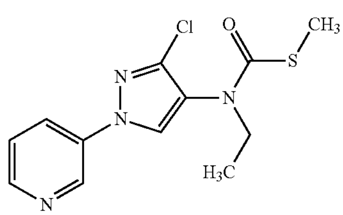 [SMILES: CCN(C(=O)SC)c1cn(-c2cccnc2)nc1Cl] | 11 |
| Y2076 | Clear Oil | 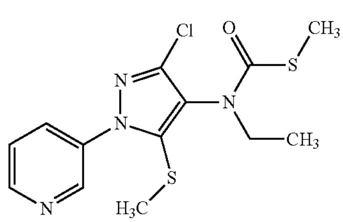 [SMILES: CCN(C(=O)SC)c1c(Cl)nn(-c2cccnc2)c1SC] | 166 |

TABLE 1-continued

Compound number, appearance, and structure

| Compound No. | Appearance | Structure | Prepared as in Example: |
|---|---|---|---|
| Y2077 | White Solid | 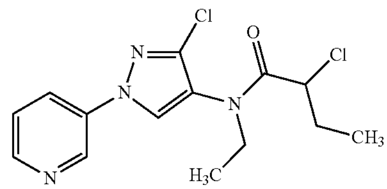 [SMILES: CCC(Cl)C(=O)N(CC)c1cn(-c2cccnc2)nc1Cl] | 100 |
| Y2078 | White Solid | 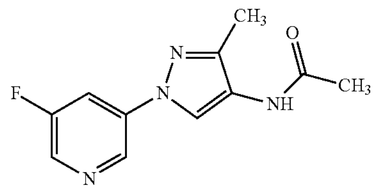 [SMILES: CC(=O)Nc1cn(-c2cncc(F)c2)nc1C] | 11 |
| Y2079 | Yellow Oil | 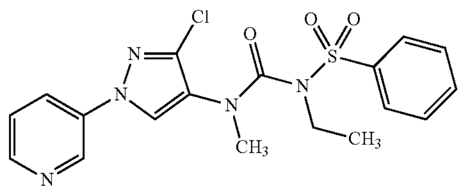 [SMILES: CCN(C(=O)N(C)c1cn(-c2cccnc2)nc1Cl)S(=O)(=O)c1ccccc1] | 174 |
| Y2080 | Yellow Oil | 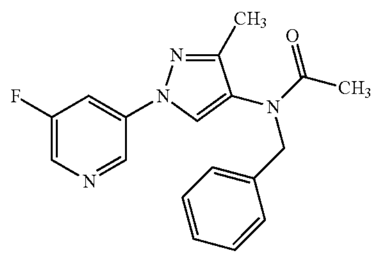 [SMILES: CC(=O)N(Cc1ccccc1)c1cn(-c2cncc(F)c2)nc1C] | 14 |
| Y2081 | Yellow Oil | 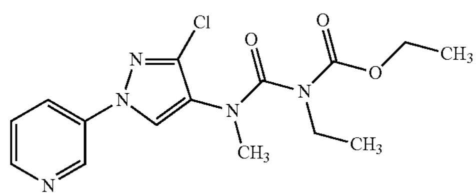 [SMILES: CCOC(=O)N(CC)C(=O)N(C)c1cn(-c2cccnc2)nc1Cl] | 174 |
| Y2082 | Yellow Oil | 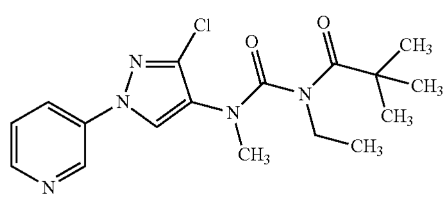 [SMILES: CCN(C(=O)N(C)c1cn(-c2cccnc2)nc1Cl)C(=O)C(C)(C)C] | 174 |
| Y2083 | Off-White Solid | 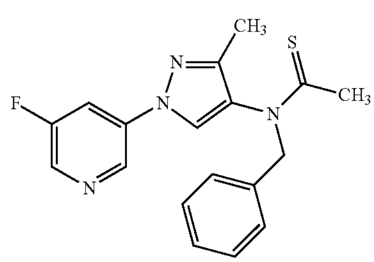 | 49 |

TABLE 1-continued

Compound number, appearance, and structure

| Compound No. | Appearance | Structure | Prepared as in Example: |
|---|---|---|---|
| Y2084 | White Solid | 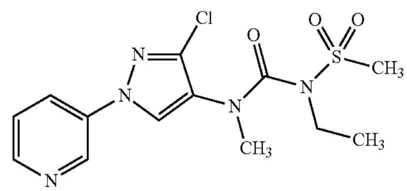 [SMILES: CCN(C(=O)N(C)c1cn(-c2cccnc2)nc1Cl)S(C)(=O)=O] | 174 |
| Y2085 | White Semi-Solid | 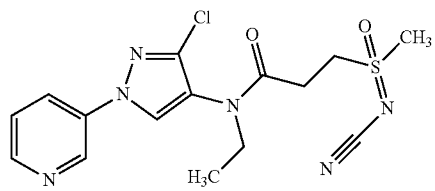 [SMILES: CCN(C(=O)CCS(C)(=O)=NC#N)c1cn(-c2cccnc2)nc1Cl] | 53 |
| Y2088 | Yellow Solid | 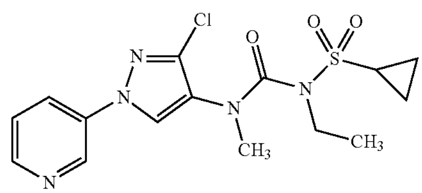 [SMILES: CCN(C(=O)N(C)c1cn(-c2cccnc2)nc1Cl)S(=O)(=O)C1CC1] | 174 |
| Y2089 | Dark Yellow Oil | 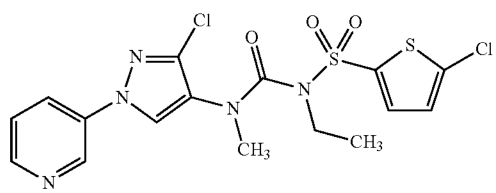 [SMILES: CCN(C(=O)N(C)c1cn(-c2cccnc2)nc1Cl)S(=O)(=O)c1ccc(Cl)s1] | 174 |
| Y2090 | Brown Gum | 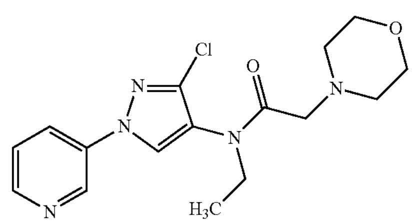 [SMILES: CCN(C(=O)CN1CCOCC1)c1cn(-c2cccnc2)nc1Cl] | 148 |
| Y2091 | Light Brown Gum | 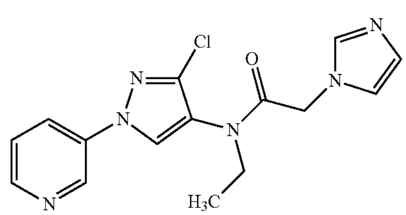 [SMILES: CCN(C(=O)Cn1ccnc1)c1cn(-c2cccnc2)nc1Cl] | 148 |
| Y2092 | White Solid | 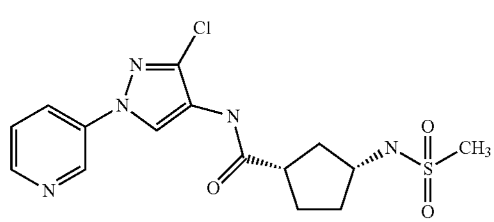 [SMILES: CS(=O)(=O)N[C@@H]1CC[C@H](C(=O)Nc2cn(-c3cccnc3)nc2Cl)C1] | 141 |

TABLE 1-continued

Compound number, appearance, and structure

| Compound No. | Appearance | Structure | Prepared as in Example: |
|---|---|---|---|
| Y2093 | Light Brown Solid | 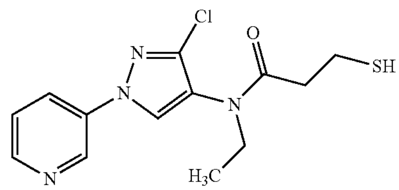 [SMILES: CCN(C(=O)CCS)c1cn(-c2cccnc2)nc1Cl] | 87 |
| Y2094 | Opaque, Waxy Solid | 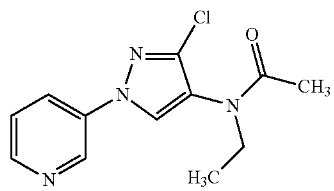 [SMILES: CCN(C(C)=O)c1cn(-c2cccnc2)nc1Cl] | 159 |
| Y2097 | Opaque, Viscous Oil | 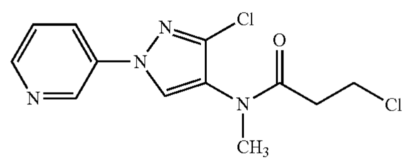 [SMILES: CN(C(=O)CCCl)c1cn(-c2cccnc2)nc1Cl] | 100 |
| Y2098 | Bright Yellow Solid | 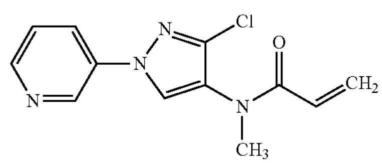 [SMILES: C=CC(=O)N(C)c1cn(-c2cccnc2)nc1Cl] | 159 |
| Y2099 | White Solid | 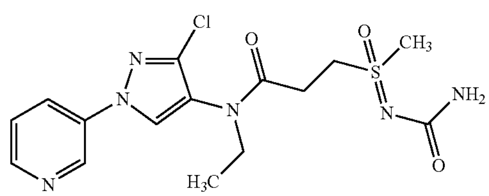 [SMILES: CCN(C(=O)CCS(C)(=O)=NC(N)=O)c1cn(-c2cccnc2)nc1Cl] | 128 |
| Y2102 | Colorless, Viscous Oil | 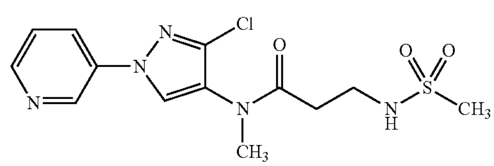 [SMILES: CN(C(=O)CCNS(C)(=O)=O)c1cn(-c2cccnc2)nc1Cl] | 146 |
| Y2104 | Light Yellow Semi-Solid | 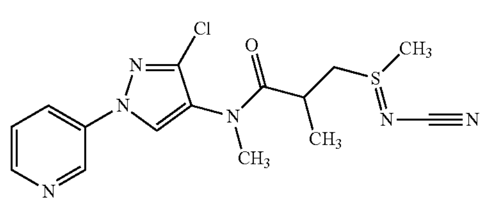 [SMILES: CC(C/S(C)=N/C#N)C(=O)N(C)c1cn(-c2cccnc2)nc1Cl] | 53 |
| Y2105 | Light Yellow Semi-Solid | 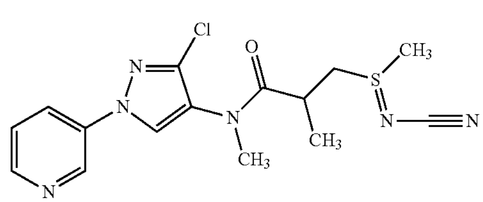 [SMILES: CC(C/S(C)=N/C#N)C(=O)N(C)c1cn(-c2cccnc2)nc1Cl] | 53 |

TABLE 1-continued

Compound number, appearance, and structure

| Compound No. | Appearance | Structure | Prepared as in Example: |
|---|---|---|---|
| Y2106 | White Solid | 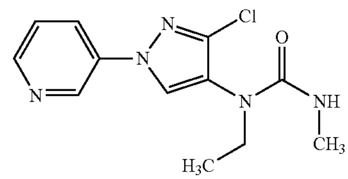 [SMILES: CCN(C(=O)NC)c1cn(-c2cccnc2)nc1Cl] | 45 |
| Y2107 | Faint Yellow Oil | 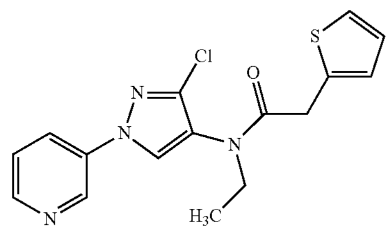 [SMILES: CCN(C(=O)Cc1cccs1)c1cn(-c2cccnc2)nc1Cl] | 42 |
| Y2108 | Yellow Oil | 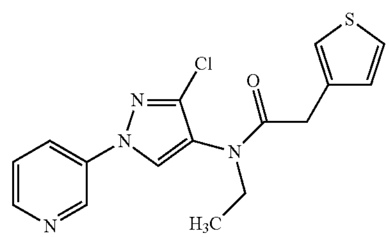 [SMILES: CCN(C(=O)Cc1ccsc1)c1cn(-c2cccnc2)nc1Cl] | 42 |
| Y2109 | Yellow Oil | 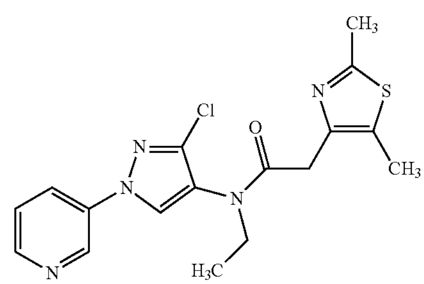 [SMILES: CCN(C(=O)Cc1nc(C)sc1C)c1cn(-c2cccnc2)nc1Cl] | 42 |
| Y2110 | Yellow Oil | 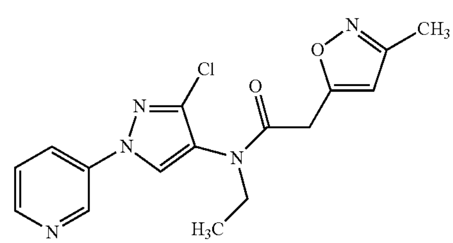 [SMILES: CCN(C(=O)Cc1cc(C)no1)c1cn(-c2cccnc2)nc1Cl] | 42 |
| Y2111 | Yellow Oil | 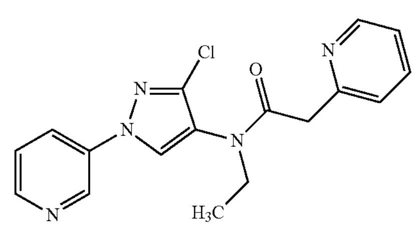 [SMILES: CCN(C(=O)Cc1ccccn1)c1cn(-c2cccnc2)nc1Cl] | 425 |

TABLE 1-continued

| Compound No. | Appearance | Structure | Prepared as in Example: |
|---|---|---|---|
| Y2112 | Faint Yellow Oil | 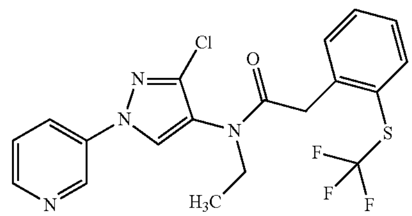 [SMILES: CCN(C(=O)Cc1ccccc1SC(F)(F)F)c1cn(-c2cccnc2)nc1Cl] | 42 |
| Y2113 | White Semi-Solid | 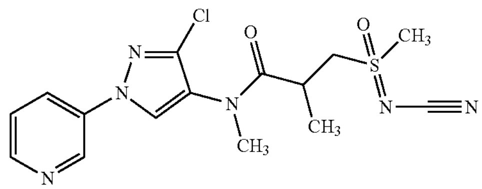 [SMILES: CC(CS(C)(=O)=NC#N)C(=O)N(C)c1cn(-c2cccnc2)nc1Cl] | 53 |
| Y2114 | White Solid | 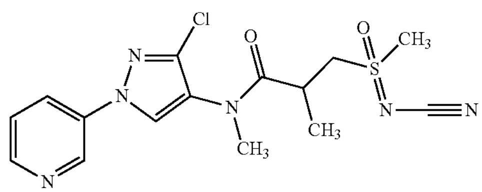 [SMILES: CC(CS(C)(=O)=NC#N)C(=O)N(C)c1cn(-c2cccnc2)nc1Cl] | 53 |
| Y2115 | Pale Orange Oil | 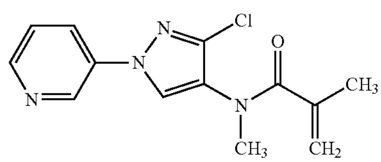 [SMILES: C=C(C)C(=O)N(C)c1cn(-c2cccnc2)nc1Cl] | 159 |
| Y2116 | White Foam | 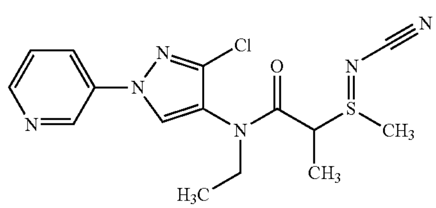 [SMILES: CCN(C(=O)C(C)/S(C)=N/C#N)c1cn(-c2cccnc2)nc1Cl] | 53 |
| Y2117 | White Solid | 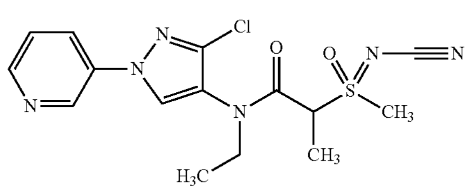 [SMILES: CCN(C(=O)C(C)S(C)(=O)=NC#N)c1cn(-c2cccnc2)nc1Cl] | 53 |
| Y2118 | White Solid | 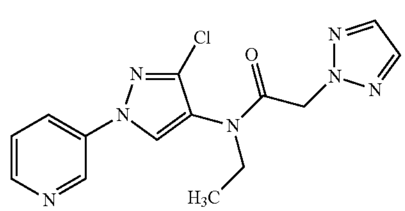 [SMILES: CCN(C(=O)Cn1nccn1)c1cn(-c2cccnc2)nc1Cl] | 12 |

TABLE 1-continued

Compound number, appearance, and structure

| Compound No. | Appearance | Structure | Prepared as in Example: |
|---|---|---|---|
| Y2119 | Colorless Oil | 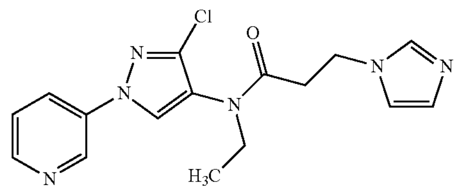 [SMILES: CCN(C(=O)CCn1ccnc1)c1cn(-c2cccnc2)nc1Cl] | 12 |
| Y2120 | White Solid | 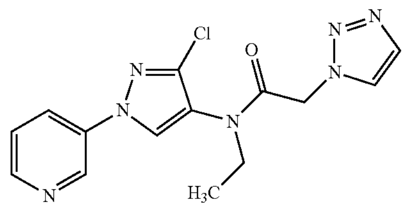 [SMILES: CCN(C(=O)Cn1ccnn1)c1cn(-c2cccnc2)nc1Cl] | 12 |
| Y2121 | White Solid | 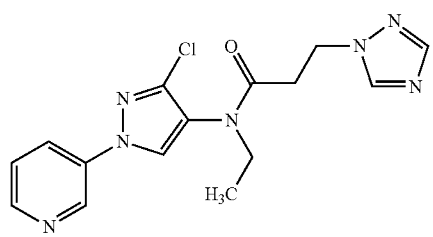 [SMILES: CCN(C(=O)CCn1cncn1)c1cn(-c2cccnc2)nc1Cl] | 12 |
| Y2122 | White Solid | 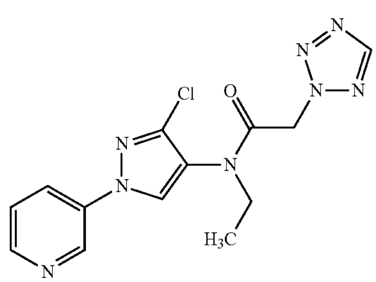 [SMILES: CCN(C(=O)Cn1ncnn1)c1cn(-c2cccnc2)nc1Cl] | 12 |
| Y2123 | Colorless Oil | 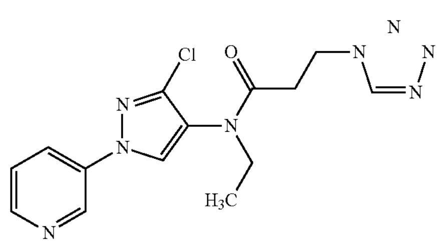 | 12 |
| Y2124 | White Solid | 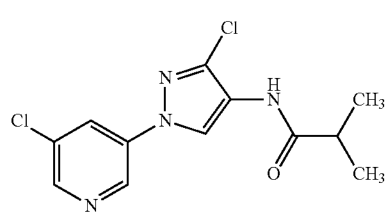 [SMILES: CC(C)C(=O)Nc1cn(-c2cncc(Cl)c2)nc1Cl] | 11 |

TABLE 1-continued
Compound number, appearance, and structure
| Compound No. | Appearance | Structure | Prepared as in Example: |
|---|---|---|---|
| Y2125 | Off White Solid | 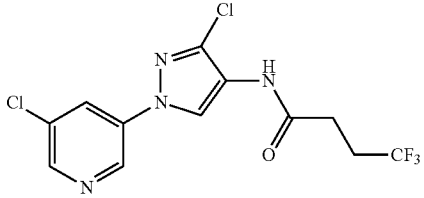 [SMILES: O=C(CCC(F)(F)F)Nc1cn(-c2cncc(Cl)c2)nc1Cl] | 11 |
| Y2126 | Off White Solid | 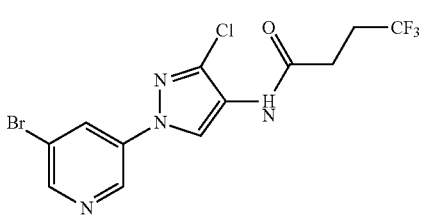 [SMILES: O=C(CCC(F)(F)F)Nc1cn(-c2cncc(Br)c2)nc1Cl] | 11 |
| Y2127 | Yellow Solid | 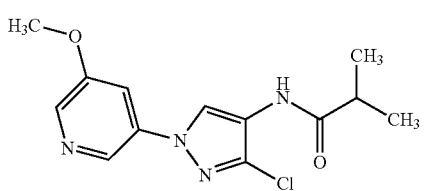 [SMILES: COc1cncc(-n2cc(NC(=O)C(C)C)c(Cl)n2)c1] | 11 |
| Y2128 | Off White Solid | 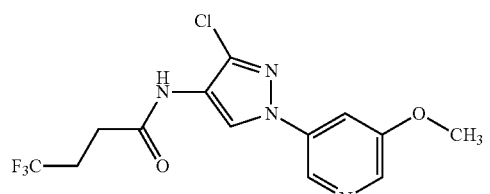 | 11 |
| Y2129 | Ash White Solid | 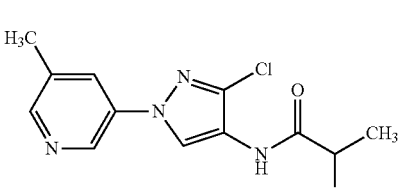 | 11 |
| Y2130 | Yellow Solid | 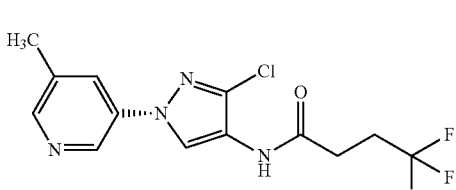 | 11 |
| Y2131 | Dark Brown Solid | 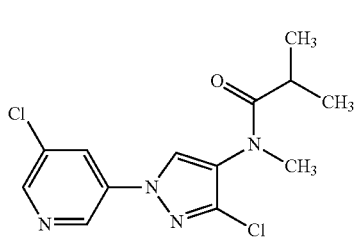 [SMILES: CC(C)C(=O)N(C)c1cn(-c2cncc(Cl)c2)nc1Cl] | 79 |

TABLE 1-continued

Compound number, appearance, and structure

| Compound No. | Appearance | Structure | Prepared as in Example: |
|---|---|---|---|
| Y2132 | Off White Solid | 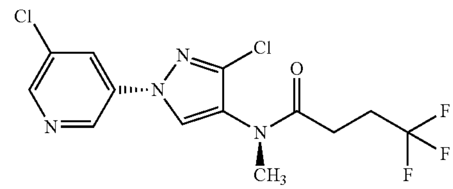 | 79 |
| Y2133 | Brown Solid | 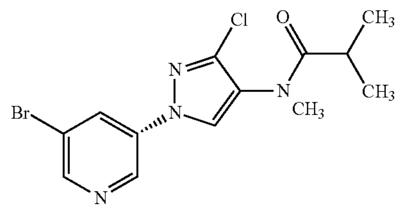 | 79 |
| Y2134 | Off White Solid | 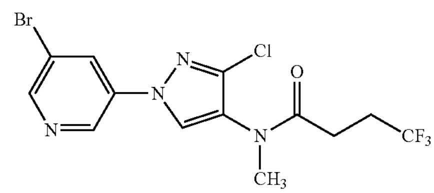 [SMILES: CN(C(=O)CCC(F)(F)F)c1cn(-c2cncc(Br)c2)nc1Cl] | 79 |
| Y2135 | Off White Solid | 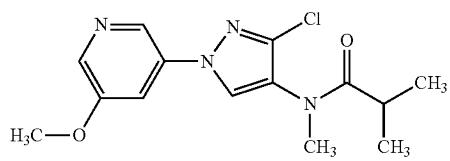 [SMILES: COc1cncc(-n2cc(N(C)C(=O)C(C)C)c(Cl)n2)c1] | 79 |
| Y2136 | Brown Liquid | 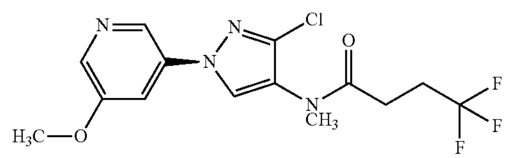 | 79 |
| Y2137 | Brown Solid | 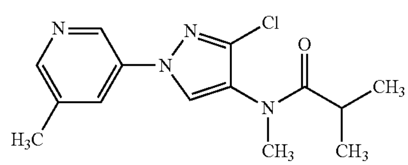 [SMILES: Cc1cncc(-n2cc(N(C)C(=O)C(C)C)c(Cl)n2)c1] | 79 |
| Y2138 | Brown solid | 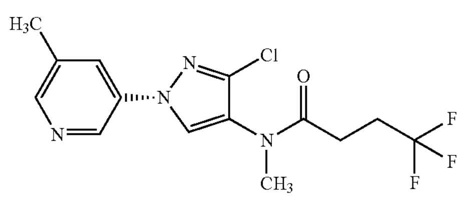 | 79 |
| Y2139 | White Solid | 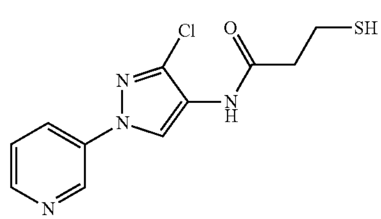 [SMILES: O=C(CCS)Nc1cn(-c2cccnc2)nc1Cl] | 87 |

TABLE 1-continued

Compound number, appearance, and structure

| Compound No. | Appearance | Structure | Prepared as in Example: |
|---|---|---|---|
| Y2140 | Off White Solid | 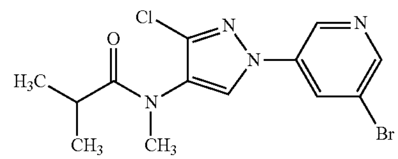 [SMILES: CC(C)C(=O)N(C)c1cn(-c2cncc(Br)c2)nc1Cl] | 79 |
| Y2141 | Off White Solid | 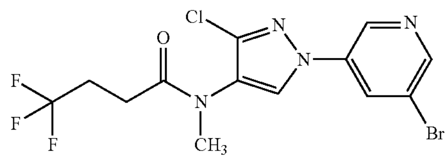 [SMILES: CN(C(=O)CCC(F)(F)F)c1cn(-c2cncc(Br)c2)nc1Cl] | 79 |
| Y2142 | White Solid | 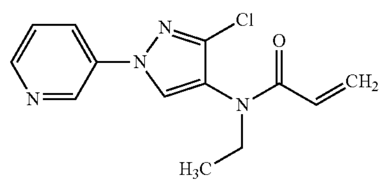 [SMILES: C=CC(=O)N(CC)c1cn(-c2cccnc2)nc1Cl] | 159 |
| Y2143 | Clear Hard Oil | 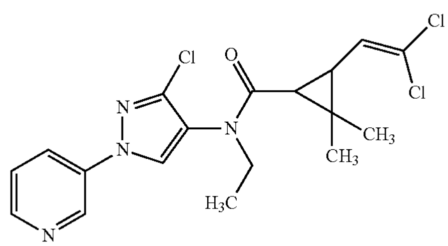 [SMILES: CCN(C(=O)C1C(C=C(Cl)Cl)C1(C)C)c1cn(-c2cccnc2)nc1Cl] | 12 |
| Y2144 | White Solid | 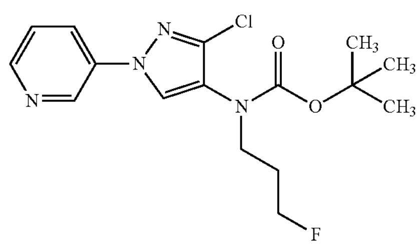 [SMILES: CC(C)(C)OC(=O)N(CCCF)c1cn(-c2cccnc2)nc1Cl] | 14 |
| Y2145 | Clear Semi-Solid | 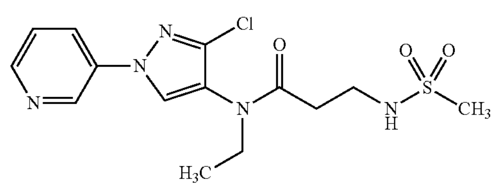 [SMILES: CCN(C(=O)CCNS(C)(=O)=O)c1cn(-c2cccnc2)nc1Cl] | 146 |
| Y2146 | Clear Oil | 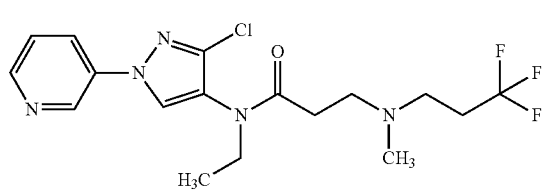 [SMILES: CCN(C(=O)CCN(C)CCC(F)(F)F)c1cn(-c2cccnc2)nc1Cl] | 150 |

TABLE 1-continued

Compound number, appearance, and structure

| Compound No. | Appearance | Structure | Prepared as in Example: |
|---|---|---|---|
| Y2147 | Viscous Clear Light Yellow Oil | 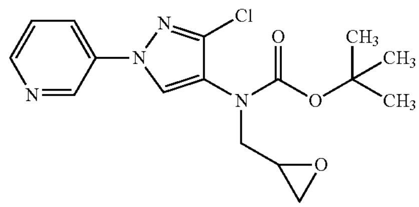 [SMILES: CC(C)(C)OC(=O)N(CC1CO1)c1cn(-c2cccnc2)nc1Cl] | 14 |
| Y2148 | Light Yellow Solid | 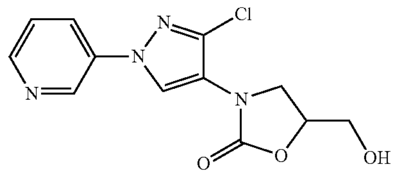 [SMILES: O=C1OC(CO)CN1c1cn(-c2cccnc2)nc1Cl] | 117 |
| Y2149 | Slightly Yellow Clear Oil | 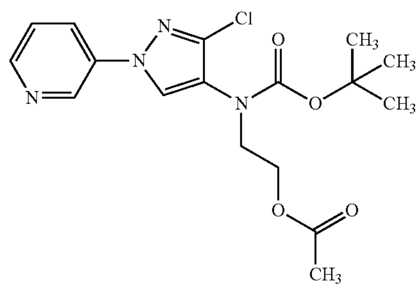 [SMILES: CC(=O)OCCN(C(=O)OC(C)(C)C)c1cn(-c2cccnc2)nc1Cl] | 14 |
| Y2150 | Clear Oil | 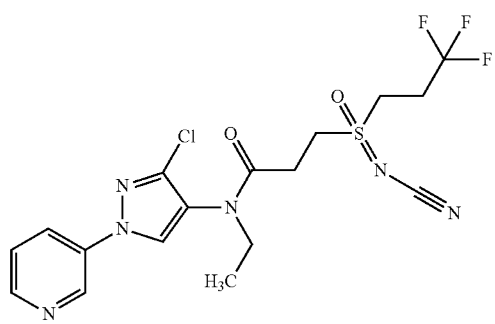 [SMILES: CCN(C(=O)CCS(=O)(CCC(F)(F)F)=NC#N)c1cn(-c2cccnc2)nc1Cl] | 53 |
| Y2151 | Clear Viscous Oil | 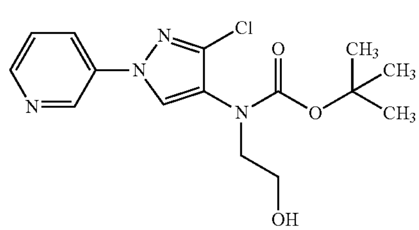 [SMILES: CC(C)(C)OC(=O)N(CCO)c1cn(-c2cccnc2)nc1Cl] | 107 |
| Y2152 | Off-White Solid | 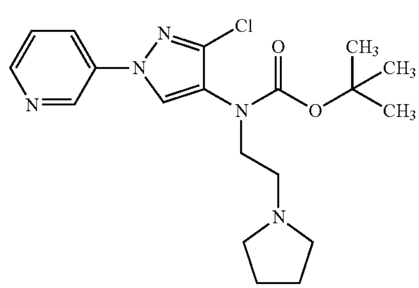 [SMILES: CC(C)(C)OC(=O)N(CCN1CCCC1)c1cn(-c2cccnc2)nc1Cl] | 109 |

TABLE 1-continued

Compound number, appearance, and structure

| Compound No. | Appearance | Structure | Prepared as in Example: |
|---|---|---|---|
| Y2153 | Clear Light Yellow Oil | 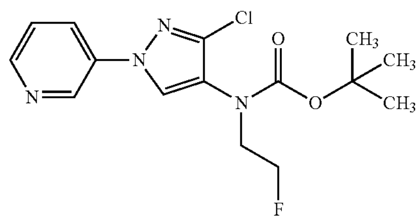 [SMILES: CC(C)(C)OC(=O)N(CCF)c1cn(-c2cccnc2)nc1Cl] | 14 |
| Y2154 | Clear Viscous Oil | 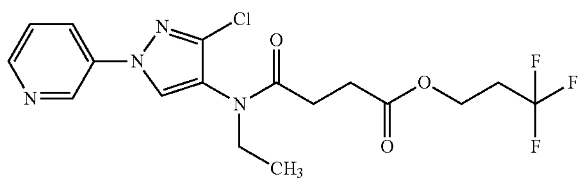 [SMILES: CCN(C(=O)CCC(=O)OCCC(F)(F)F)c1cn(-c2cccnc2)nc1Cl] | 114 |
| Y2155 | Light Brown Oil | 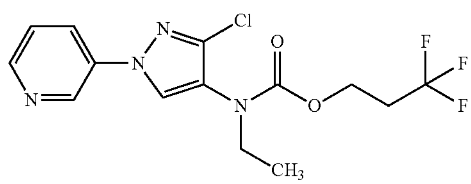 [SMILES: CCN(C(=O)OCCC(F)(F)F)c1cn(-c2cccnc2)nc1Cl] | 115 |
| Y2156 | Light Brown Oil | 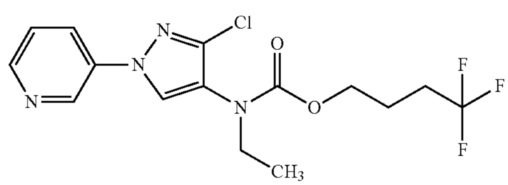 [SMILES: CCN(C(=O)OCCCC(F)(F)F)c1cn(-c2cccnc2)nc1Cl] | 115 |
| Y2157 | Light Yellow Oil | 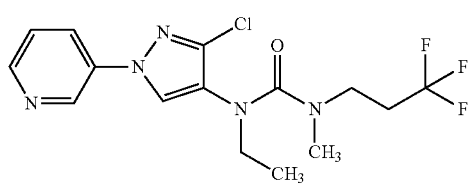 [SMILES: CCN(C(=O)N(C)CCC(F)(F)F)c1cn(-c2cccnc2)nc1Cl] | 115 |
| Y2158 | White Solid | 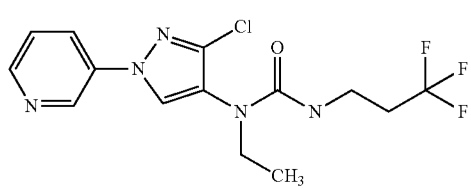 [SMILES: CCN(C(=O)NCCC(F)(F)F)c1cn(-c2cccnc2)nc1Cl] | 115 |
| Y2159 | Light Pink Viscous Oil | 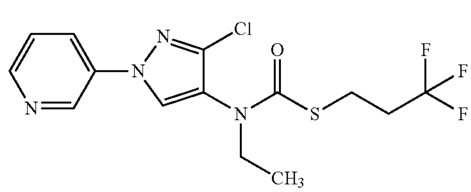 [SMILES: CCN(C(=O)SCCC(F)(F)F)c1cn(-c2cccnc2)nc1Cl] | 115 |

TABLE 1-continued

Compound number, appearance, and structure

| Compound No. | Appearance | Structure | Prepared as in Example: |
|---|---|---|---|
| Y2160 | White Foamy Solid | 3-chloro-1-(pyridin-3-yl)pyrazol-4-yl; N-ethyl; urea linker to N-CH2CH2CH2CF3 | 115 |
| Y2161 | Light Yellow Oil | 3-chloro-1-(pyridin-3-yl)pyrazol-4-yl; N(CH2CHF2)-C(O)-O-C(CH3)3 | 14 |
| Y2162 | Clear Yellow Oil | 3-chloro-1-(pyridin-3-yl)pyrazol-4-yl; N(CH2CF3)-C(O)-O-C(CH3)3 | 14 |
| Y2163 | Clear Yellow Oil | 3-chloro-1-(pyridin-3-yl)pyrazol-4-yl; N(CH2CH2Cl)-C(O)-O-C(CH3)3 | 14 |
| Y2164 | Clear Oil | 3-chloro-1-(pyridin-3-yl)pyrazol-4-yl; N-ethyl; urea linker to N(CH3)-CH2CF3 | 115 |
| Y2165 | White Solid | 3-chloro-1-(pyridin-3-yl)pyrazol-4-yl; N-ethyl; urea linker to NH-CH2CF3 | 115 |
| Y2166 | White Solid | 3-chloro-1-(pyridin-3-yl)pyrazol-4-yl-NH-C(O)-CH2CH2CH2Cl | 129 |

TABLE 1-continued

Compound number, appearance, and structure

| Compound No. | Appearance | Structure | Prepared as in Example: |
|---|---|---|---|
| Y2167 | Yellow Solid | 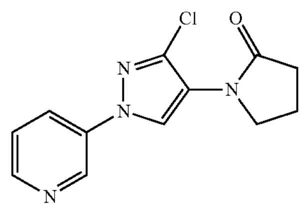 [SMILES: O=C1CCCN1c1cn(-c2cccnc2)nc1Cl] | 130 |
| Y2168 | Light Yellow Solid | 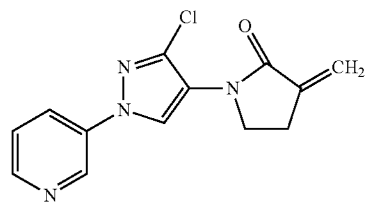 [SMILES: C=C1CCN(c2cn(-c3cccnc3)nc2Cl)C1=O] | 131 |
| Y2169 | Light Brown Solid | 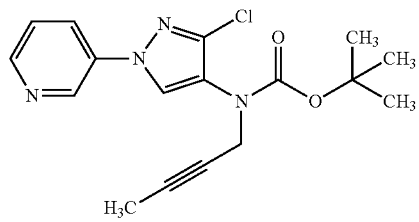 [SMILES: CC#CCN(C(=O)OC(C)(C)C)c1cn(-c2cccnc2)nc1Cl] | 14 |
| Y2170 | Light Yellow Clear Oil | 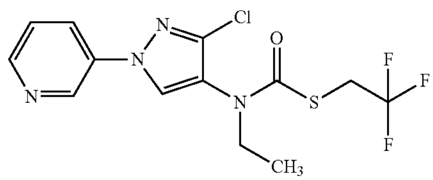 | 115 |
| Y2171 | Light Yellow Oil | 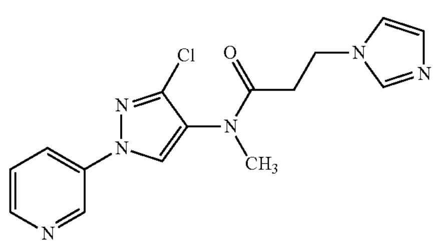 [SMILES: CN(C(=O)CCn1ccnc1)c1cn(-c2cccnc2)nc1Cl] | 12 |
| Y2172 | White Solid | 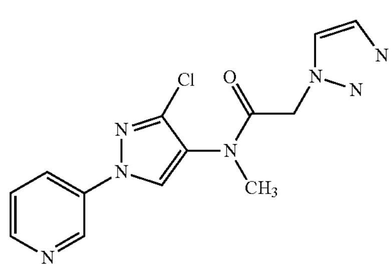 [SMILES: CN(C(=O)CN(N)/C=C\N)c1cn(-c2cccnc2)nc1Cl] | 12 |

TABLE 1-continued

Compound number, appearance, and structure

| Compound No. | Appearance | Structure | Prepared as in Example: |
|---|---|---|---|
| Y2173 | Colorless Oil | 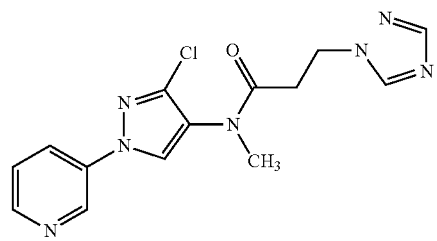 [SMILES: CN(C(=O)CCN/C=N\C=N)c1cn(-c2cccnc2)nc1Cl] | 12 |
| Y2174 | Colorless Oil | 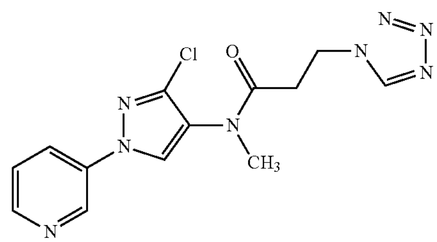 [SMILES: CN(C(=O)CCN/C=N\N=N)c1cn(-c2cccnc2)nc1Cl] | 12 |
| Y2175 | Off-White Solid | 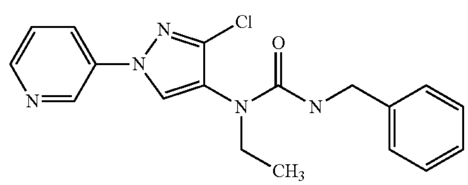 [SMILES: CCN(C(=O)NCc1ccccc1)c1cn(-c2cccnc2)nc1Cl] | 45 |
| Y2176 | White Solid | 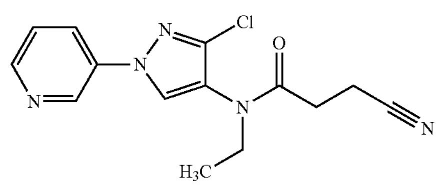 [SMILES: CCN(C(=O)CCC#N)c1cn(-c2cccnc2)nc1Cl] | 42 |
| Y2177 | Light Yellow Gum | 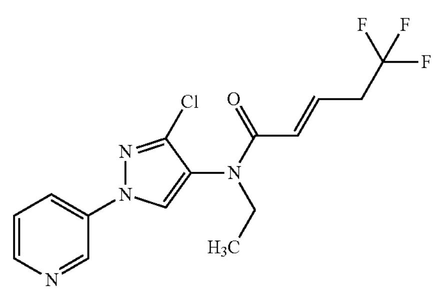 [SMILES: CCN(C(=O)/C=C/CC(F)(F)F)c1cn(-c2cccnc2)nc1Cl] | 193 |
| Y2178 | Pale Brown, Glassy Solid | 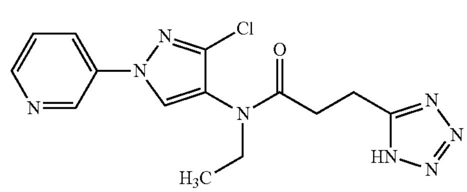 [SMILES: CCN(C(=O)CCc1nnn[nH]1)c1cn(-c2cccnc2)nc1Cl] | 142 |

TABLE 1-continued

Compound number, appearance, and structure

| Compound No. | Appearance | Structure | Prepared as in Example: |
|---|---|---|---|
| Y2179 | Light Yellow Oil | 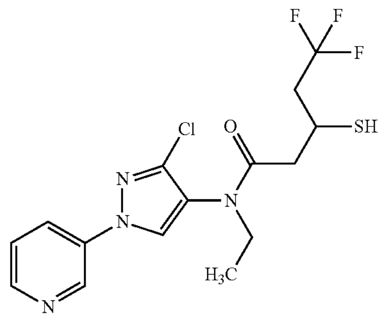 [SMILES: CCN(C(=O)CC(S)CC(F)(F)F)c1cn(-c2cccnc2)nc1Cl] | 87 |
| Y2180 | Pale Yellow, Viscous Oil | 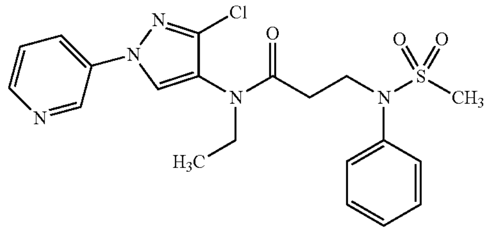 [SMILES: CCN(C(=O)CCN(c1ccccc1)S(C)(=O)=O)c1cn(-c2cccnc2)nc1Cl] | 149 |
| Y2181 | White Solid | 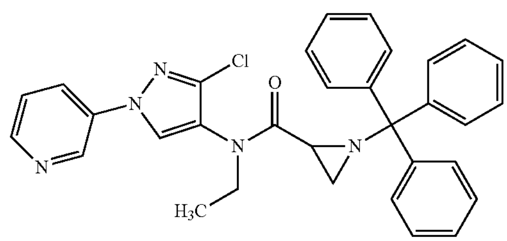 [SMILES: CCN(C(=O)C1CN1C(c1ccccc1)(c1ccccc1)c1ccccc1)c1cn(-c2cccnc2)nc1Cl] | 42 |
| Y2182 | Clear Oil | 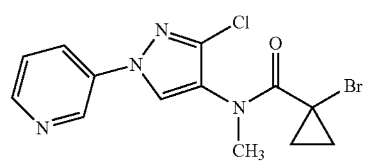 [SMILES: CN(C(=O)C1(Br)CC1)c1cn(-c2cccnc2)nc1Cl] | 42 |
| Y2184 | Light Yellow Solid | 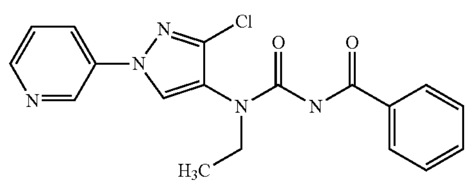 [SMILES: CCN(C(=O)NC(=O)c1ccccc1)c1cn(-c2cccnc2)nc1Cl] | 45 |
| Y2185 | Clear Oil | 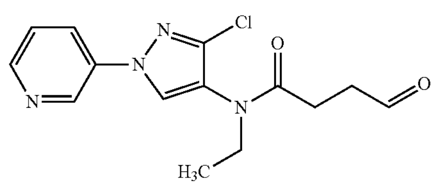 [SMILES: CCN(C(=O)CCC=O)c1cn(-c2cccnc2)nc1Cl] | 120 |
| Y2186 | Off-White Solid | 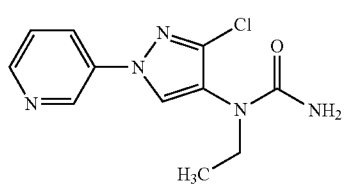 [SMILES: CCN(C(N)=O)c1cn(-c2cccnc2)nc1Cl] | 119 |

TABLE 1-continued

Compound number, appearance, and structure

| Compound No. | Appearance | Structure | Prepared as in Example: |
|---|---|---|---|
| Y2187 | Light Brown Solid | 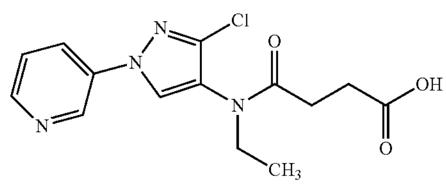 [SMILES: CCN(C(=O)CCC(=O)O)c1cn(-c2cccnc2)nc1Cl] | 112 |
| Y2188 | Brown Viscous Oil | 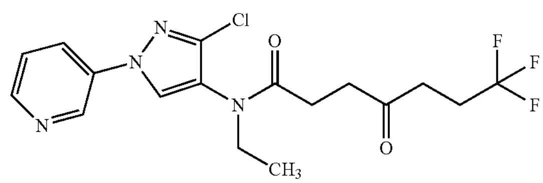 [SMILES: CCN(C(=O)CCC(=O)CCC(F)(F)F)c1cn(-c2cccnc2)nc1Cl] | 123 |
| Y2189 | White Solid | 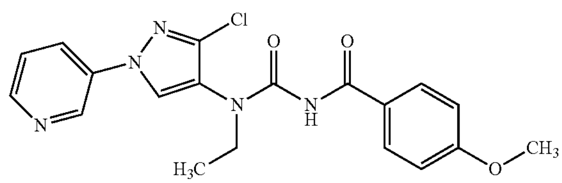 [SMILES: CCN(C(=O)NC(=O)c1ccc(OC)cc1)c1cn(-c2cccnc2)nc1Cl] | 118 |
| Y2190 | Off-White Solid | 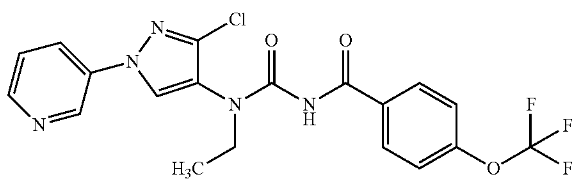 [SMILES: CCN(C(=O)NC(=O)c1ccc(OC(F)(F)F)cc1)c1cn(-c2cccnc2)nc1Cl] | 118 |
| Y2191 | White Solid | 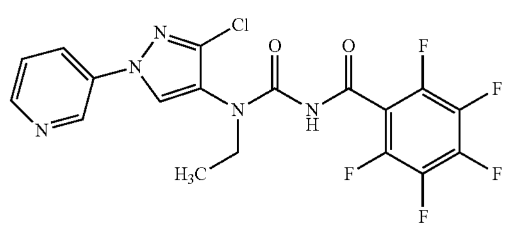 [SMILES: CCN(C(=O)NC(=O)c1c(F)c(F)c(F)c(F)c1F)c1cn(-c2cccnc2)nc1Cl] | 118 |
| Y2192 | White Solid | 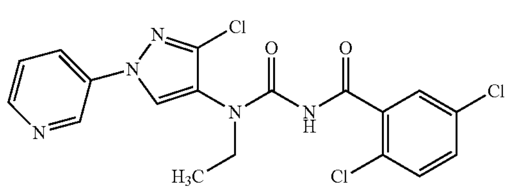 [SMILES: CCN(C(=O)NC(=O)c1cc(Cl)ccc1Cl)c1cn(-c2cccnc2)nc1Cl] | 118 |

TABLE 1-continued
Compound number, appearance, and structure
| Compound No. | Appearance | Structure | Prepared as in Example: |
|---|---|---|---|
| Y2193 | Slightly Yellow Solid | 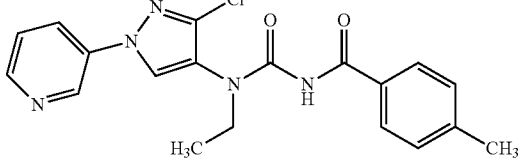 | 118 |
| Y2194 | White Solid | 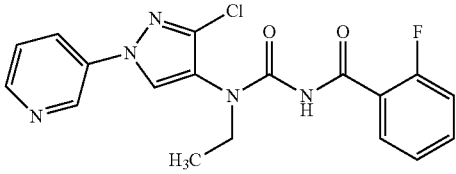 [SMILES: CCN(C(=O)NC(=O)c1ccccc1F)c1cn(-c2cccnc2)nc1Cl] | 118 |
| Y2195 | Tan Solid | 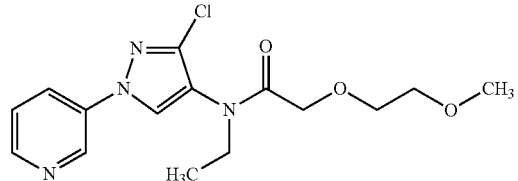 | 173 |
| Y2196 | White Solid | 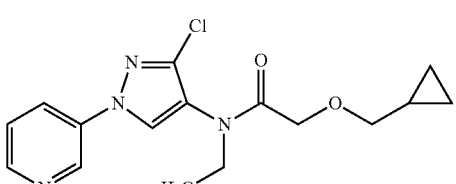 | 12 |
| Y2197 | Yellow Oil | 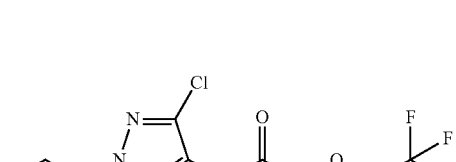 | 173 |
| Y2198 | Yellow Oil | 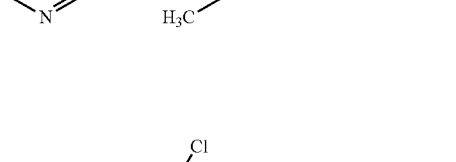 | 173 |

TABLE 1-continued

Compound number, appearance, and structure

| Compound No. | Appearance | Structure | Prepared as in Example: |
|---|---|---|---|
| Y2199 | Off White Solid | 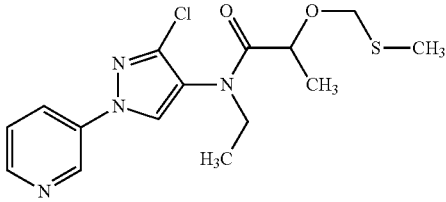 [SMILES: CCN(C(=O)C(C)OCSC)c1cn(-c2cccnc2)nc1Cl] | 197 |
| Y2200 | White Solid | 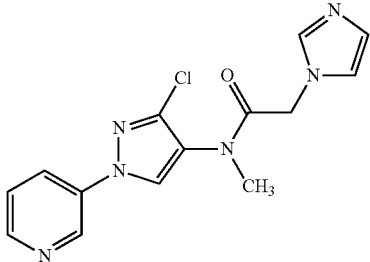 [SMILES: CN(C(=O)Cn1ccnc1)c1cn(-c2cccnc2)nc1Cl] | 12 |
| Y2201 | White Solid | 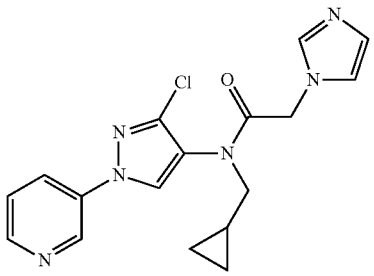 [SMILES: O=C(Cn1ccnc1)N(CC1CC1)c1cn(-c2cccnc2)nc1Cl] | 12 |

Lengthy table referenced here

US09708288-20170718-T00001

Please refer to the end of the specification for access instructions.

Lengthy table referenced here

US09708288-20170718-T00002

Please refer to the end of the specification for access instructions.

Lengthy table referenced here

US09708288-20170718-T00003

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09708288B2). An electronic copy of the table will also be available from the USPTO upon request and payment of the fee set forth in 37 CFR 1.19(b)(3).

We claim:

1. A formulation comprising a carrier and a molecule having the following structure

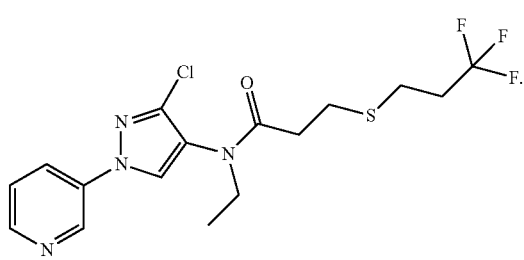

653

2. A formulation according to claim 1 wherein said formulation is encapsulated inside, or placed on the surface of, a capsule, wherein said capsule has a diameter of about 100-900 nanometers.

3. A formulation according to claim 1 wherein said formulation is encapsulated inside, or placed on the surface of, a capsule, wherein said capsule has a diameter of about 10-900 microns.

4. The formulation according to claim 1 further comprising:
   (a) one or more compounds having acaricidal, algicidal, avicidal, bactericidal, fungicidal, herbicidal, insecticidal, molluscicidal, nematicidal, rodenticidal, or virucidal properties; or
   (b) one or more compounds that are antifeedants, bird repellents, chemosterilants, herbicide safeners, insect attractants, insect repellents, mammal repellents, mating disrupters, plant activators, plant growth regulators, or synergists; or
   (c) both (a) and (b).

5. The formulation according to claim 1 wherein further comprising one or more compounds selected from the group consisting of: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl) ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethoethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

6. The formulation according to claim 1 comprising an agriculturally acceptable carrier.

7. The formulation according to claim 1 wherein said molecule is in a form of a pesticidally acceptable acid addition salt.

8. The formulation according to claim 1 wherein said molecule is in a form of a salt derivative.

9. The formulation according to claim 1 wherein said molecule is in a form a hydrate.

10. The formulation according to claim 1 wherein said molecule has a $^2H$ in place of $^1H$.

11. The formulation according to claim 1 wherein said molecule has a $^{13}C$ in place of a $^{12}C$.

12. The formulation according to claim 1 further comprising a biopesticide.

13. The formulation according to claim 1 further comprising one or more of the following compounds:
   (a) 3-(4-chloro-2,6-dimethylphenyl)-4-hydroxy-8-oxa-1-azaspiro[4,5]dec-3-en-2-one;
   (b) 3-(4'-chloro-2,4-dimethyl[1,1'-biphenyl]-3-yl)-4-hydroxy-8-oxa-1-azaspiro[4,5]dec-3-en-2-one;
   (c) 4-[[(6-chloro-3-pyridinyl)methyl]methylamino]-2(5H)-furanone;
   (d) 4-[[(6-chloro-3-pyridinyl)methyl]cyclopropylamino]-2(5H)-furanone;
   (e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
   (f) 2-cyano-N-ethyl-4-fluoro-3-methoxy-benzenesulfonamide;
   (g) 2-cyano-N-ethyl-3-methoxy-benzenesulfonamide;
   (h) 2-cyano-3-difluoromethoxy-N-ethyl-4-fluoro-benzenesulfonamide;
   (i) 2-cyano-3-fluoromethoxy-N-ethyl-benzenesulfonamide;
   (j) 2-cyano-6-fluoro-3-methoxy-N,N-dimethyl-benzenesulfonamide;
   (k) 2-cyano-N-ethyl-6-fluoro-3-methoxy-N-methyl-benzenesulfonamide;
   (l) 2-cyano-3-difluoromethoxy-N,N-dimethylbenzenesulfon-amide;
   (m) 3-(difluoromethyl)-N-[2-(3,3-dimethylbutyl)phenyl]-1-methyl-1H-pyrazole-4-carboxamide;
   (n) N-ethyl-2,2-dimethylpropionamide-2-(2,6-dichloro-α,α,α-trifluoro-p-tolyl) hydrazone;
   (o) N-ethyl-2,2-dichloro-1-methylcyclopropane-carboxamide-2-(2,6-dichloro-α,α,α-trifluoro-p-tolyl) hydrazone nicotine;
   (p) O-{(E–)-[2-(4-chloro-phenyl)-2-cyano-1-(2-trifluoromethylphenyl)-vinyl]} S-methyl thiocarbonate;
   (q) (E)-N1-[(2-chloro-1,3-thiazol-5-ylmethyl)]-N2-cyano-N1-methylacetamidine;
   (r) 1-(6-chloropyridin-3-ylmethyl)-7-methyl-8-nitro-1,2,3,5,6,7-hexahydro-imidazo[1,2-a]pyridin-5-ol;
   (s) 4-[4-chlorophenyl-(2-butylidine-hydrazono)methyl)]phenyl mesylate; and
   (t) N-Ethyl-2,2-dichloro-1-methylcyclopropanecarboxamide-2-(2,6-dichloro-alpha,alpha,alpha-trifluoro-p-tolyl)hydrazone.

14. The formulation according to claim 1 further comprising a compound having one or more of the following modes of action: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs).

15. The formulation according to claim 1 further comprising a seed.

16. The formulation according to claim 1 further comprising a seed that has been genetically modified to express one or more specialized traits.

17. The formulation according to claim 1 wherein said formulation is encapsulated inside, or placed on the surface of, a capsule.

18. A process comprising applying a formulation according to claim 1, to an area to control a pest, in an amount sufficient to control said pest.

19. The process according to claim 18 wherein said pest is selected from beetles, earwigs, cockroaches, flies, aphids, scales, whiteflies, leafhoppers, ants, wasps, termites, moths, lice, grasshoppers, locusts, crickets, fleas, *thrips*, bristletails, mites, ticks, nematodes, and symphylans.

20. The process according to claim 18 wherein said pest is from the Phyla Nematoda or Arthropoda.

21. The process according to claim 18 wherein said pest is from the Subphyla Chelicerata, Myriapoda, or Hexapoda.

22. The process according to claim 18 wherein said pest is from the Class of Arachnida, Symphyla, or Insecta.

23. The process according to claim 18 wherein said pest is from the Order Anoplura, Order Coleoptera, Order Dermaptera, Order Blattaria, Order Diptera, Order Hemiptera, Order Hymenoptera, Order Isoptera, Order Lepidoptera, Order Mallophaga, Order Orthoptera, Order Siphonaptera, Order Thysanoptera, Order Thysanura, Order Acarina, or Order Symphyla.

24. The process according to claim 18 wherein said pest is MYZUPE.

25. The process according to claim 18 wherein said amount is from about 0.01 grams per hectare to about 5000 grams per hectare.

26. The process according to claim 18 wherein said amount is from about 0.1 grams per hectare to about 500 grams per hectare.

27. The process according to claim 18 wherein said amount is from about 1 gram per hectare to about 50 grams per hectare.

28. The process according to claim 18 wherein said area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

29. The process according to claim 18 further comprising applying said formulation to a genetically modified plant that has been genetically modified to express one or more specialized traits.

30. The formulation according to claim 1 further comprising ammonium sulfate.

31. A process comprising: orally administering; or topically applying; a formulation according to claim 1, to a non-human animal, to control endoparasites, ectoparasites, or both.

32. A process comprising applying the formulation according to claim 1 to a plant to enhance the plant's health, yield, vigor, quality, or tolerance, at a time when pest activity is low.

* * * * *